US012653860B2

(12) United States Patent
D'Souza et al.

(10) Patent No.: US 12,653,860 B2
(45) Date of Patent: Jun. 16, 2026

(54) COMPOSITIONS AND METHODS FOR EDITING BETA-GLOBIN FOR TREATMENT OF HEMAGLOBINOPATHIES

(71) Applicant: Vertex Pharmaceuticals Incorporated, Boston, MA (US)

(72) Inventors: Sanjay D'Souza, Cambridge, MA (US); Jason West, Lexington, MA (US); Brenda K. Eustace, Brookline, MA (US); Sudipta Mahajan, Boston, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 1200 days.

(21) Appl. No.: 17/619,949

(22) PCT Filed: Jun. 17, 2020

(86) PCT No.: PCT/US2020/038203

§ 371 (c)(1),
(2) Date: Dec. 16, 2021

(87) PCT Pub. No.: WO2020/257325

PCT Pub. Date: Dec. 24, 2020

(65) Prior Publication Data

US 2023/0022146 A1 Jan. 26, 2023

Related U.S. Application Data

(60) Provisional application No. 62/862,539, filed on Jun. 17, 2019.

(51) Int. Cl.

| | |
|---|---|
| ***C12N 15/113*** | (2010.01) |
| ***A61K 35/28*** | (2015.01) |
| ***A61K 38/17*** | (2006.01) |
| ***A61K 40/10*** | (2025.01) |
| ***A61K 40/40*** | (2025.01) |
| ***A61P 7/06*** | (2006.01) |
| ***A61P 37/06*** | (2006.01) |
| ***C12N 5/0783*** | (2010.01) |
| ***C12N 5/0789*** | (2010.01) |
| ***C12N 7/00*** | (2006.01) |
| ***C12N 9/22*** | (2006.01) |
| ***C12N 15/11*** | (2006.01) |
| ***C12N 15/86*** | (2006.01) |
| ***C12N 15/90*** | (2006.01) |
| *A61K 48/00* | (2006.01) |

(52) U.S. Cl.

CPC .......... *A61K 38/1709* (2013.01); *A61K 35/28* (2013.01); *A61K 40/10* (2025.01); *A61K 40/40* (2025.01); *A61P 7/06* (2018.01); *A61P 37/06* (2018.01); *C12N 5/0636* (2013.01); *C12N 5/0647* (2013.01); *C12N 7/00* (2013.01); *C12N 9/22* (2013.01); *C12N 15/11* (2013.01); *C12N 15/86* (2013.01); *C12N 15/907* (2013.01); *A61K 48/00* (2013.01); *A61K 2239/31* (2023.05); *A61K 2239/38* (2023.05); *C12N 2310/20* (2017.05); *C12N 2500/02* (2013.01); *C12N 2501/125* (2013.01); *C12N 2501/145* (2013.01); *C12N 2501/2303* (2013.01); *C12N 2501/26* (2013.01); *C12N 2750/14143* (2013.01); *C12N 2800/80* (2013.01)

(58) Field of Classification Search

CPC ........ A61K 35/28; A61K 40/10; A61K 48/00; A61K 2239/31; A61K 2239/38; C12N 5/0647; C12N 9/22; C12N 15/11; C12N 15/86; C12N 15/907; C12N 2310/20; C12N 2501/145; C12N 2750/14143; C12N 2800/80

See application file for complete search history.

(56) References Cited

U.S. PATENT DOCUMENTS

| | | | |
|---|---|---|---|
| 3,687,808 | A | 8/1972 | Merigan et al. |
| 4,469,863 | A | 9/1984 | Ts'o et al. |
| 4,476,301 | A | 10/1984 | Imbach et al. |
| 5,023,243 | A | 6/1991 | Tullis |
| 5,034,506 | A | 7/1991 | Summerton et al. |
| 5,087,570 | A | 2/1992 | Weissman et al. |
| 5,166,315 | A | 11/1992 | Summerton et al. |
| 5,177,196 | A | 1/1993 | Meyer, Jr. et al. |

(Continued)

FOREIGN PATENT DOCUMENTS

| | | | |
|---|---|---|---|
| WO | WO-03024949 | A1 | 3/2003 |
| WO | 2005012487 | A2 | 2/2005 |

(Continued)

OTHER PUBLICATIONS

Vakulskas, (2018). A high-fidelity Cas9 mutant delivered as a ribonucleoprotein complex enables efficient gene editing in human hematopoietic stem and progenitor cells. Nature medicine, 24(8), 1216-1224. https://doi.org/10.1038/s41591-018-0137-0 (Year: 2018).*

(Continued)

*Primary Examiner* — Maria G Leavitt

(74) *Attorney, Agent, or Firm* — McNeill PLLC

(57) ABSTRACT

The disclosure features methods of correcting a mutation in the human beta-globin (HBB) gene in a cell or population of cells. The disclosure also features methods of increasing repair of a DNA double stranded break (DSB) in an HBB gene by the homology-directed repair (HDR) pathway. The disclosure also features compositions for use in the methods.

23 Claims, 52 Drawing Sheets

Specification includes a Sequence Listing.

(56) References Cited

U.S. PATENT DOCUMENTS

| | | | |
|---|---|---|---|
| 5,185,444 | A | 2/1993 | Summerton et al. |
| 5,188,897 | A | 2/1993 | Suhadolnik et al. |
| 5,214,134 | A | 5/1993 | Weis et al. |
| 5,216,141 | A | 6/1993 | Benner |
| 5,235,033 | A | 8/1993 | Summerton et al. |
| 5,264,423 | A | 11/1993 | Cohen et al. |
| 5,264,562 | A | 11/1993 | Matteucci |
| 5,264,564 | A | 11/1993 | Matteucci |
| 5,276,019 | A | 1/1994 | Cohen et al. |
| 5,278,302 | A | 1/1994 | Caruthers et al. |
| 5,286,717 | A | 2/1994 | Cohen et al. |
| 5,321,131 | A | 6/1994 | Agrawal et al. |
| 5,399,676 | A | 3/1995 | Froehler |
| 5,405,938 | A | 4/1995 | Summerton et al. |
| 5,405,939 | A | 4/1995 | Suhadolnik et al. |
| 5,434,257 | A | 7/1995 | Matteucci et al. |
| 5,453,496 | A | 9/1995 | Caruthers et al. |
| 5,455,233 | A | 10/1995 | Spielvogel et al. |
| 5,466,677 | A | 11/1995 | Baxter et al. |
| 5,470,967 | A | 11/1995 | Huie et al. |
| 5,476,925 | A | 12/1995 | Letsinger et al. |
| 5,489,677 | A | 2/1996 | Sanghvi et al. |
| 5,519,126 | A | 5/1996 | Hecht |
| 5,536,821 | A | 7/1996 | Agrawal et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,561,225 | A | 10/1996 | Maddry et al. |
| 5,563,253 | A | 10/1996 | Agrawal et al. |
| 5,571,799 | A | 11/1996 | Tkachuk et al. |
| 5,587,361 | A | 12/1996 | Cook et al. |
| 5,596,086 | A | 1/1997 | Matteucci et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,633,360 | A | 5/1997 | Bischofberger et al. |
| 5,643,741 | A | 7/1997 | Tsukamoto et al. |
| 5,663,312 | A | 9/1997 | Chaturvedula |
| 5,670,351 | A | 9/1997 | Emerson et al. |
| 5,677,136 | A | 10/1997 | Simmons et al. |
| 5,677,437 | A | 10/1997 | Teng et al. |
| 5,677,439 | A | 10/1997 | Weis et al. |
| 5,817,491 | A | 10/1998 | Yee et al. |
| 5,817,773 | A | 10/1998 | Wilson et al. |
| 5,851,984 | A | 12/1998 | Matthews et al. |
| 5,858,358 | A | 1/1999 | June et al. |
| 5,883,223 | A | 3/1999 | Gray |
| 6,030,836 | A | 2/2000 | Thiede et al. |
| 6,352,694 | B1 | 3/2002 | June et al. |
| 6,534,055 | B1 | 3/2003 | June et al. |
| 6,692,964 | B1 | 2/2004 | June et al. |
| 6,797,514 | B2 | 9/2004 | Berenson et al. |
| 6,825,351 | B2 | 11/2004 | Mceachern et al. |
| 6,835,731 | B2 | 12/2004 | Bridger et al. |
| 6,867,041 | B2 | 3/2005 | Berenson et al. |
| 6,887,466 | B2 | 5/2005 | June et al. |
| 6,893,821 | B2 | 5/2005 | Raz et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 7,402,607 | B2 | 7/2008 | Smith et al. |
| 7,790,458 | B2 | 9/2010 | Xu et al. |
| 7,939,057 | B2 | 5/2011 | Battista et al. |
| 8,895,299 | B2 | 11/2014 | Riordan |
| 9,592,232 | B2 | 3/2017 | Charifson et al. |
| 9,943,545 | B2 | 4/2018 | Rezner |
| 9,944,912 | B2 | 4/2018 | Joung et al. |
| 10,006,004 | B2 | 6/2018 | Furcht et al. |
| 10,058,573 | B1 | 8/2018 | Morrow et al. |
| 10,086,045 | B2 | 10/2018 | Cameron |
| 10,526,591 | B2 | 1/2020 | Joung et al. |
| 12,497,614 | B2 * | 12/2025 | D'Souza ................ C12N 15/11 |
| 2011/0281361 | A1 | 11/2011 | DeKelver et al. |
| 2015/0111871 | A1 * | 4/2015 | Charifson et al. ... C07D 401/14 514/210.18 |
| 2018/0021413 | A1 | 1/2018 | Porteus |
| 2018/0030438 | A1 | 2/2018 | Porteus et al. |
| 2018/0100148 | A1 | 4/2018 | Vakulskas et al. |
| 2018/0142222 | A1 | 5/2018 | Sternberg et al. |
| 2018/0194782 | A1 | 7/2018 | Finlay et al. |
| 2018/0200387 | A1 | 7/2018 | Porteus |
| 2019/0010196 | A1 * | 1/2019 | Durocher et al. ..... C12N 15/00 |
| 2019/0010471 | A1 | 1/2019 | Zhang et al. |
| 2019/0038771 | A1 | 2/2019 | Cradick et al. |
| 2019/0177710 | A1 | 6/2019 | Lee |
| 2020/0149020 | A1 | 5/2020 | Cereseto et al. |
| 2022/0025409 | A1 * | 1/2022 | Dever et al. ....... C12N 15/8645 |
| 2022/0228142 | A1 | 7/2022 | D'Souza et al. |

FOREIGN PATENT DOCUMENTS

| | | | |
|---|---|---|---|
| WO | 2011125054 | A2 | 10/2011 |
| WO | 2011130749 | A2 | 10/2011 |
| WO | 2013052523 | A1 | 4/2013 |
| WO | 2013103659 | A1 | 7/2013 |
| WO | 2013151666 | A2 | 10/2013 |
| WO | 2014135998 | A1 | 9/2014 |
| WO | 2015009952 | A1 | 1/2015 |
| WO | WO-2015148863 | A2 | 10/2015 |
| WO | WO-2016073990 | A2 | 5/2016 |
| WO | WO-2016154579 | A2 | 9/2016 |
| WO | WO-2017053729 | A1 | 3/2017 |
| WO | WO-2018149888 | A1 | 8/2018 |
| WO | 2019097305 | A2 | 5/2019 |
| WO | WO-2019138082 | A1 | 7/2019 |
| WO | WO-2019185920 | A1 | 10/2019 |
| WO | WO-2020057481 | A1 | 3/2020 |
| WO | WO-2020257325 | A1 | 12/2020 |
| WO | WO-2022133246 | A1 | 6/2022 |

OTHER PUBLICATIONS

Altschul, et al. "Gapped BLAST and PSI-BLAST: a new generation of protein database search programs." Nucleic Acids Research 1997, 25(17), 3389-3402.

Altschul, et al., "Basic local alignment search tool," Journal of Molecular Biology 1990, 215(3), 403-410.

Bak, Rasmus O., et al., "CRISPR/Cas 9 genome editing in human hematopoietic stem cells," Nat. Protoc., Feb. 2018, vol. 13(2), pp. 358-376.

Baldwin, Kismet, et al., "Enrichment of Human Hematopoietic Stem/Progenitor Cells Facilitates Transduction for Stem Cell Gene Therapy," Stem Cells, vol. 33, 2015, pp. 1532-1542.

Lidonnici, Maria Rosa, et al., "The Challenge of HSCs Procurement for gene Therapy: Exploring Plerixafor As Mobilization Agent," Blood, vol. 122 (21) 2901, 2013.

Miyaoka, Yuichiro, et al., "Systematic quantification fo HDR and NHEJ reveals effects of locus, nuclease, and cell type on genome-editing," Scientific Reports, 2016, pp. 1-12.

Oki, Toshihiko, et al., "A novel cell-cycle-indicator, mVenus-p27k-, Identified quiescent cells and visualizes G0-G1 transition," Scientific Reports, vol. 4, 4012, pp. 1-10.

Zonari, Erika, et al., "Genetic Engineering and Transplantation of Highly Purified Hematopoietic Stem Cells (HSC) for Improved Ex Vivo Gene Therapy," Stem Cell Engineering and Therapies I, Molecular Therapy, vol. 22, Supplement 1, May 2014, S13.

Anzalone, A. et al. "Search-and-replace genome editing without double-strand breaks or donor DNA". Nature (Dec. 2019); 576(7785): 149-157. Epub Oct. 21, 2019.

Arnoult, N. et al. "Regulation of DNA repair pathway choice in S and G2 phases by the NHEJ inhibitor CYREN". Nature (Sep. 2017); 549(7673): 548-552. Epub Sep. 28, 2017.

(56) References Cited

OTHER PUBLICATIONS

Botuyan, M. et al. "Structural basis for the methylation state-specific recognition of histone H4-K20 by 53BP1 and Crb2 in DNA repair". Cell (Dec. 29, 2006); 127(7): 1361-1373.
Broxmeyer, H.E. et al. "Rapid mobilization of murine and human hematopoietic stem and progenitor cells with AMD3100, a CXCR4 antagonist". The Journal of Experimental Medicine (Apr. 18, 2005); 201(8): 1307-1318.
Calsou, P. et al. "The DNA-dependent protein kinase catalytic activity regulates DNA end processing by means of Ku entry into DNA". Journal of Biological Chemistry (Mar. 19, 1999); 274(12): 7848-7856.
Canny, M.D. et al. "Inhibition of 53BP1 favors homology-dependent DNA repair and increases CRISPR-Cas9 genome-editing efficiency". Nature Biotechnology (Jan. 2018); 36(1): 95-102. Epub Nov. 27, 2017.
CAS 1169562-71-3 RN, STN, "Benzofuro[3,2-d]pyrimidin-4(3H)-one, 8-chloro-2-(2S)-2-pyrrolidinyl-, hydrochloride (1:?) (CA Index Name)"; entered Jul. 27, 2009, received Oct. 27, 2022, 1 page.
CAS 159182-43-1 RN, STN, "Benzenesulfonamide, 4-[[(hexylamino)carbonyl]amino]-N-[4-[2-[[(2S)-2-hydroxy-3-(4-hydroxyphenoxy)propyl]amino]ethyl]phenyl]—(CA Index Name)"; entered Nov. 24, 1994, 1 page.
CAS 312756-74-4 RN, STN, "Benzamide, 4-bromo-N-(4-bromophenyl)-3-[[(phenylmethyl)amino]sulfonyl]—(CA Index Name)"; entered Jan. 4, 2001, 1 page.
CAS 503468-95-9 RN, STN, "4H-1-Benzopyran-4-one, 8-(4-dibenzothienyl)-2-(4-morpholinyl)—(CA Index Name)"; entered Apr. 18, 2003, 1 page.
CAS 912444-00-9 RN, STN, "1H-Benzimidazole-7-carboxamide, 2-[(2R)-2-methyl-2-pyrrolidinyl]—(CA Index Name)"; entered Nov. 5, 2006, 1 page.
Chapman, J.R. et al. "Playing the end game: DNA double-strand break repair pathway choice". Molecular Cell (Aug. 24, 2012); 47(4): 497-510.
Cox, D.B. et al. "Therapeutic genome editing: prospects and challenges". Nature Medicine (Feb. 2015); 21(2): 121-131. Epub Feb. 5, 2015.
De Montalembert, M. "Management of sickle cell disease". Bmj. (Sep. 8, 2008); 337.
Dever, D.P. et al. "CRISPR/Cas9 β-globin gene targeting in human haematopoietic stem cells". Nature (Nov. 2016); 539(7629): 384-389. Epub Nov. 7, 2016.
Devine, S. et al. "Rapid mobilization of functional donor hematopoietic cells without G-CSF using AMD3100, an antagonist of the CXCR4/SDF-1 interaction". Blood, The Journal of the American Society of Hematology (Aug. 15, 2008); 112(4): 990-998.
Escribano-Diaz, C. et al. "A cell cycle-dependent regulatory circuit composed of 53BP1-RIF1 and BRCA1-CtIP controls DNA repair pathway choice". Molecular Cell (Mar. 7, 2013); 49(5): 872-883.
Feng, L. et al. "RIF1 counteracts BRCA1-mediated end resection during DNA repair". Journal of Biological Chemistry (Apr. 19, 2013); 288(16): 11135-11143.
Fradet-Turcotte, A. et al. "53BP1 is a reader of the DNA-damage-induced H2A Lys 15 ubiquitin mark". Nature (Jul. 2013); 499(7456): 50-54. Epub Jun. 12, 2013.
Gene ID 3043 "HBB hemoglobin subunit beta [ *Homo sapiens* (human) ]" updated Oct. 22, 2022, 13 pages.
Gottlieb, T.M. et al. "The DNA-dependent protein kinase: requirement for DNA ends and association with Ku antigen". Cell (Jan. 15, 1993); 72(1): 131-142.
Guo, X. et al. "Acetylation of 53BP1 dictates the DNA double strand break repair pathway". Nucleic Acids Research (Jan. 25, 2018); 46(2): 689-703.
Hoban, M.D. et al. "CRISPR/Cas9-mediated correction of the sickle mutation in human CD34+ cells". Molecular Therapy (Sep. 1, 2016); 24(9): 1561-1569.
International Preliminary Report on Patentability for International Application No. PCT/US2020/038203, dated Dec. 21, 2021, 13 pages.
International Search Report and Written Opinion for International Application No. PCT/US2020/038203, mailed Nov. 17, 2020, 22 pages.
International Search Report and Written Opinion for International Application No. PCT/US2021/064085, mailed Apr. 11, 2020, 12 pages.
Invitation to Pay Additional Fees for International Application No. PCT/US2020/038203, mailed Sep. 22, 2020, 17 pages.
Ismail, I.H. et al. "SU11752 inhibits the DNA-dependent protein kinase and DNA double-strand break repair resulting in ionizing radiation sensitization". Oncogene (Jan. 2004); 23(4): 873-882. Epub Aug. 8, 2003.
Iwabuchi, K. et al. "Two cellular proteins that bind to wild-type but not mutant p53". Proceedings of the National Academy of Sciences (Jun. 21, 1994); 91(13): 6098-6102.
Izzard, R.A. et al. "Competitive and noncompetitive inhibition of the DNA-dependent protein kinase". Cancer Research (Jun. 1, 1999); 59(11): 2581-2586.
Kashishian, A. et al. "DNA-dependent protein kinase inhibitors as drug candidates for the treatment of cancer". Molecular Cancer Therapeutics (Dec. 2003); 2(12): 1257-1264. Epub Jan. 5, 2004.
Leahy, J.J. et al. "Identification of a highly potent and selective DNA-dependent protein kinase (DNA-PK) inhibitor (NU7441) by screening of chromenone libraries". Bioorganic & Medicinal Chemistry Letters (Dec. 20, 2004); 14(24): 6083-6087.
Martin, R.M. et al. "Highly efficient and marker-free genome editing of human pluripotent stem cells by CRISPR-Cas9 RNP and AAV6 donor-mediated homologous recombination". Cell Stem Cell (May 2, 2019); 24(5): 821-828.
Morton, J. et al. "Granulocyte-colony-stimulating factor (G-CSF)-primed allogeneic bone marrow: significantly less graft-versus-host disease and comparable engraftment to G-CSF-mobilized peripheral blood stem cells". Blood, The Journal of the American Society of Hematology (Dec. 1, 2001); 98(12): 3186-3191.
Noon, A.T. et al. "53BP1-dependent robust localized KAP-1 phosphorylation is essential for heterochromatic DNA double-strand break repair". Nature Cell Biology (Feb. 2010); 12(2): 177-184.
Paulsen, B.S. et al. "Ectopic expression of RAD52 and dn53BP1 improves homology-directed repair during CRISPR-Cas9 genome editing". Nature Biomedical Engineering (Nov. 2017); 1(11): 878-888. Epub Oct. 9, 2017.
Sheth, S. et al. "Sickle cell disease: time for a closer look at treatment options?". British Journal of Haematology (Aug. 2013); 162(4): 455-464.
Smith, T. et al. "Economic analysis of a randomized clinical trial to compare filgrastim-mobilized peripheral-blood progenitor-cell transplantation and autologous bone marrow transplantation in patients with Hodgkin's and non-Hodgkin's lymphoma". Journal of Clinical Oncology (Jan. 1997); 15(1): 5-10.
Tasan, I. et al. "Use of genome-editing tools to treat sickle cell disease". Human Genetics (Sep. 2016); 135(9): 1011-28. Epub Jun. 1, 2016.
Vakulskas, C.A. et al. "A high-fidelity Cas9 mutant delivered as a ribonucleoprotein complex enables efficient gene editing in human hematopoietic stem and progenitor cells". Nature Medicine (Aug. 2018); 24(8): 1216-1224; including Supplementary Information.
Weinert, B. et al. "Timed inhibition of CDC7 increases CRISPR-Cas9 mediated templated repair". Nature Communications (Apr. 30, 2020); 11(1): 1-5. Epub.
Wilson, A. et al. "Hematopoietic stem cells reversibly switch from dormancy to self-renewal during homeostasis and repair". Cell (Dec. 12, 2008); 135(6): 1118-1129.
Yoo, S. et al. "Geometry of a complex formed by double strand break repair proteins at a single DNA end: recruitment of DNA-PKcs induces inward translocation of Ku protein". Nucleic Acids Research (Dec. 1, 1999); 27(24): 4679-4686.
Yu, C. et al. "Small molecules enhance CRISPR genome editing in pluripotent stem cells". Cell Stem Cell (Feb. 5, 2015); 16(2): 142-147.

(56) References Cited

OTHER PUBLICATIONS

Zimmermann, M. et al. "53BP1: pro choice in DNA repair". Trends in Cell Biology (Feb. 1, 2014); 24(2): 108-117. Epub Oct. 4, 2013.

* cited by examiner

| | H3-95-30 + DMSO | N1-95-30 + DMSO | No Donor + DMSO | Mock + DMSO | H3-95-30 + NU7441 | N1-95-30 + NU7441 | No Donor + NU7441 | Mock + NU7441 |
|---|---|---|---|---|---|---|---|---|
| 0 bp indel | 56.5 | 44.3 | 66.8 | 96.4 | 15.0 | 4.8 | 13.7 | 99.0 |
| −1, +1 bp indel | 12.2 | 13.3 | 10.2 | 0.4 | 2.6 | 1.5 | 2.6 | 0.1 |
| < −3 bp deletion | 23.3 | 31.4 | 18.4 | 0.1 | 46.8 | 63.6 | 75.6 | 0.2 |
| +3bp insertion | 3.2 | 5.7 | 0.0 | 0.0 | 28.4 | 22.1 | 0.3 | 0.0 |

SEQUENCE LISTING

<160> NUMBER OF SEQ ID NOS: 124

<210> SEQ ID NO 1
<211> LENGTH: 114
<212> TYPE: RNA
<213> ORGANISM: Artificial Sequence
<220> FEATURE:
<223> OTHER INFORMATION: Synthetic: gRNA-related, sgRNA1
<220> FEATURE:
<221> NAME/KEY: misc_feature
<222> LOCATION: (1)..(30)
<223> OTHER INFORMATION: n is any ribonucleotide
<220> FEATURE:
<221> NAME/KEY: misc_feature
<222> LOCATION: (18)..(30)
<223> OTHER INFORMATION: individual ribonucleotides may be absent
<220> FEATURE:
<221> NAME/KEY: misc_feature
<222> LOCATION: (108)..(114)
<223> OTHER INFORMATION: individual ribonucleotides may be absent

<400> SEQUENCE: 1
nnnnnnnnnn nnnnnnnnnn nnnnnnnnnn guuuuagagc uagaaauagc aaguuaaaau 60
aaggcuaguc cguuaucaac uugaaaaagu ggcaccgagu cggugcuuuu uuuu 114

<210> SEQ ID NO 2
<211> LENGTH: 113
<212> TYPE: RNA
<213> ORGANISM: Artificial Sequence
<220> FEATURE:
<223> OTHER INFORMATION: Synthetic: gRNA-related, SpCas9 sgRNA
<220> FEATURE:
<221> NAME/KEY: misc_feature
<222> LOCATION: (1)..(4)
<223> OTHER INFORMATION: linked via phosphorothioate bond
<220> FEATURE:
<221> NAME/KEY: modified_base
<222> LOCATION: (1)..(3)
<223> OTHER INFORMATION: 2' O-methyl phosphorothioate nucleotides
<220> FEATURE:
<221> NAME/KEY: misc_feature
<222> LOCATION: (4)..(33)
<223> OTHER INFORMATION: n is any ribonucleotide
<220> FEATURE:
<221> NAME/KEY: misc_feature
<222> LOCATION: (21)..(33)
<223> OTHER INFORMATION: individual ribonucleotides may be absent
<220> FEATURE:
<221> NAME/KEY: modified_base
<222> LOCATION: (110)..(112)
<223> OTHER INFORMATION: 2' O-methyl phosphorothioate nucleotides
<220> FEATURE:
<221> NAME/KEY: misc_feature
<222> LOCATION: (110)..(113)
<223> OTHER INFORMATION: linked via phosphorothioate bond

<400> SEQUENCE: 2
cuunnnnnnn nnnnnnnnnn nnnnnnnnnn nnnguuuuag agcuagaaau agcaaguuaa 60
aauaaggcua guccguuauc aacuugaaaa aguggcaccg agucggugcu uuu 113

<210> SEQ ID NO 3
<211> LENGTH: 20
<212> TYPE: DNA
<213> ORGANISM: Artificial Sequence
<220> FEATURE:
<223> OTHER INFORMATION: Synthetic: gRNA-related, AAVS1 target sequence A

<400> SEQUENCE: 3
ggggccacta gggacaggat 20

<210> SEQ ID NO 4
<211> LENGTH: 20
<212> TYPE: RNA
<213> ORGANISM: Artificial Sequence
<220> FEATURE:
<223> OTHER INFORMATION: Synthetic: gRNA-related, AAVS1 sgRNA spacer A

<400> SEQUENCE: 4
ggggccacua gggacaggau 20

<210> SEQ ID NO 5
<211> LENGTH: 20
<212> TYPE: DNA
<213> ORGANISM: Artificial Sequence
<220> FEATURE:
<223> OTHER INFORMATION: Synthetic: gRNA-related, AAVS1 target sequence B

<400> SEQUENCE: 5
gccagtagcc agccccgtcc 20

<210> SEQ ID NO 6
<211> LENGTH: 20
<212> TYPE: RNA
<213> ORGANISM: Artificial Sequence
<220> FEATURE:
<223> OTHER INFORMATION: Synthetic: gRNA-related, AAVS1 sgRNA spacer B

<400> SEQUENCE: 6
gccaguagcc agccccgucc 20

<210> SEQ ID NO 7
<211> LENGTH: 18
<212> TYPE: DNA
<213> ORGANISM: Artificial Sequence
<220> FEATURE:
<223> OTHER INFORMATION: Synthetic: gRNA-related, BFP target sequence

<400> SEQUENCE: 7
tgaagcactg cacgccat 18

<210> SEQ ID NO 8
<211> LENGTH: 18
<212> TYPE: RNA
<213> ORGANISM: Artificial Sequence
<220> FEATURE:
<223> OTHER INFORMATION: Synthetic: gRNA-related, BFP sgRNA spacer

<400> SEQUENCE: 8
ugaagcacug cacgccau 18

<210> SEQ ID NO 9
<211> LENGTH: 20
<212> TYPE: DNA
<213> ORGANISM: Artificial Sequence
<220> FEATURE:
<223> OTHER INFORMATION: Synthetic: gRNA-related, GFP target sequence A

<400> SEQUENCE: 9
gctgaagcac tgcacgccgt 20

<210> SEQ ID NO 10
<211> LENGTH: 20
<212> TYPE: RNA
<213> ORGANISM: Artificial Sequence
<220> FEATURE:
<223> OTHER INFORMATION: Synthetic: gRNA-related, GFP sgRNA spacer A

<400> SEQUENCE: 10
gcugaagcac ugcacgccgu 20

<210> SEQ ID NO 11
<211> LENGTH: 20
<212> TYPE: DNA
<213> ORGANISM: Artificial Sequence
<220> FEATURE:
<223> OTHER INFORMATION: Synthetic: gRNA-related, GFP target sequence B

<400> SEQUENCE: 11
ctcgtgacca ccctgaccta 20

<210> SEQ ID NO 12
<211> LENGTH: 20
<212> TYPE: RNA
<213> ORGANISM: Artificial Sequence

```
<220> FEATURE:
<223> OTHER INFORMATION: Synthetic: gRNA-related, GFP sgRNA spacer B

<400> SEQUENCE: 12

cucgugacca cccugaccua                                                        20

<210> SEQ ID NO 13
<211> LENGTH: 20
<212> TYPE: DNA
<213> ORGANISM: Artificial Sequence
<220> FEATURE:
<223> OTHER INFORMATION: Synthetic: gRNA-related, GSD1a target sequence

<400> SEQUENCE: 13

tctttggaca gcgtccatac                                                        20

<210> SEQ ID NO 14
<211> LENGTH: 20
<212> TYPE: RNA
<213> ORGANISM: Artificial Sequence
<220> FEATURE:
<223> OTHER INFORMATION: Synthetic: gRNA-related, GSD1a Ch32 gRNA spacer

<400> SEQUENCE: 14

ucuuuggaca gcguccauac                                                        20

<210> SEQ ID NO 15
<211> LENGTH: 20
<212> TYPE: DNA
<213> ORGANISM: Artificial Sequence
<220> FEATURE:
<223> OTHER INFORMATION: Synthetic: gRNA-related, HBB target sequence

<400> SEQUENCE: 15

cttgccccac agggcagtaa                                                        20

<210> SEQ ID NO 16
<211> LENGTH: 20
<212> TYPE: RNA
<213> ORGANISM: Artificial Sequence
<220> FEATURE:
<223> OTHER INFORMATION: Synthetic: gRNA-related, HBB RO2 sgRNA spacer

<400> SEQUENCE: 16

cuugccccac agggcaguaa                                                        20

<210> SEQ ID NO 17
<211> LENGTH: 100
<212> TYPE: RNA
<213> ORGANISM: Artificial Sequence
<220> FEATURE:
<223> OTHER INFORMATION: Synthetic: gRNA-related, HBB sgRNA
<220> FEATURE:
<221> NAME/KEY: modified_base
<222> LOCATION: (1)..(3)
<223> OTHER INFORMATION: 2' O-methyl phosphorothioate nucleotides
<220> FEATURE:
<221> NAME/KEY: misc_feature
<222> LOCATION: (1)..(4)
<223> OTHER INFORMATION: linked via phosphorothioate bond
<220> FEATURE:
<221> NAME/KEY: misc_feature
<222> LOCATION: (97)..(100)
<223> OTHER INFORMATION: linked via phosphorothioate bond
<220> FEATURE:
<221> NAME/KEY: modified_base
<222> LOCATION: (97)..(99)
<223> OTHER INFORMATION: 2' O-methyl phosphorothioate nucleotides
```

<400> SEQUENCE: 17
cuugccccac agggcaguaa guuuuagagc uagaaauagc aaguuaaaau aaggcuaguc 60
cguuaucaac uugaaaaagu ggcaccgagu cggugcuuuu 100

<210> SEQ ID NO 18
<211> LENGTH: 20
<212> TYPE: DNA
<213> ORGANISM: Artificial Sequence
<220> FEATURE:
<223> OTHER INFORMATION: Synthetic: gRNA-related, CFTR target sequence

<400> SEQUENCE: 18
tctgtatcta tattcatcat 20

<210> SEQ ID NO 19
<211> LENGTH: 20
<212> TYPE: RNA
<213> ORGANISM: Artificial Sequence
<220> FEATURE:
<223> OTHER INFORMATION: Synthetic: gRNA-related, CFTR sgRNA spacer

<400> SEQUENCE: 19
ucuguaucua uauucaucau 20

<210> SEQ ID NO 20
<211> LENGTH: 23
<212> TYPE: DNA
<213> ORGANISM: Artificial Sequence
<220> FEATURE:
<223> OTHER INFORMATION: Synthetic: gRNA-related, HBB Target Sequence

<400> SEQUENCE: 20
cttgccccac agggcagtaa cgg 23

<210> SEQ ID NO 21
<211> LENGTH: 127
<212> TYPE: DNA
<213> ORGANISM: Artificial Sequence
<220> FEATURE:
<223> OTHER INFORMATION: Synthetic: Donor DNA, ssODN1 (Ht-CR282)

<400> SEQUENCE: 21
gccacctacg gcaagctgac cctgaagttc atctgcacca ccggcaagct gcccgtgccc 60
tggcccaccc tcgtgaccac cctgacgtac ggcgtgcagt gcttcagccg ctaccccgac 120
cacatga 127

<210> SEQ ID NO 22
<211> LENGTH: 127
<212> TYPE: DNA
<213> ORGANISM: Artificial Sequence
<220> FEATURE:
<223> OTHER INFORMATION: Synthetic: Donor DNA, ssODN2 (Hn-CR283)

<400> SEQUENCE: 22
tcatgtggtc ggggtagcgg ctgaagcact gcacgccgta cgtcagggtg gtcacgaggg 60
tgggccaggg cacgggcagc ttgccggtgg tgcagatgaa cttcagggtc agcttgccgt 120
aggtggc 127

<210> SEQ ID NO 23
<211> LENGTH: 127
<212> TYPE: DNA
<213> ORGANISM: Artificial Sequence
<220> FEATURE:
<223> OTHER INFORMATION: Synthetic: Donor DNA, ssODN3 (Hn-39-88)

<400> SEQUENCE: 23
cgctcctgga cgtagccttc gggcatggcg gacttgaaga agtcgtgctg cttcatgtgg 60
tcggggtagc ggctgaagca ctgcacgccg tacgtcaggg tggtcacgag ggtgggccag 120
ggcacgg 127

<210> SEQ ID NO 24
<211> LENGTH: 152
<212> TYPE: DNA
<213> ORGANISM: Artificial Sequence
<220> FEATURE:
<223> OTHER INFORMATION: Synthetic: Donor DNA, ssODN4 (Ht-91-61)

<400> SEQUENCE: 24
gccacctacg gcaagctgac cctgaagttc atctgcacca ccggcaagct gcccgtgccc 60
tggcccaccc tcgtgaccac cctgacgtac ggcgtgcagt gcttcagccg ctaccccgac 120
cacatgaagc agcacgactt cttcaagtcc gc 152

<210> SEQ ID NO 25
<211> LENGTH: 152
<212> TYPE: DNA
<213> ORGANISM: Artificial Sequence
<220> FEATURE:
<223> OTHER INFORMATION: Synthetic: Donor DNA, ssODN (Hn-91-61)

<400> SEQUENCE: 25
gcggacttga agaagtcgtg ctgcttcatg tggtcggggt agcggctgaa gcactgcacg 60
ccgtacgtca gggtggtcac gagggtgggc cagggcacgg gcagcttgcc ggtggtgcag 120
atgaacttca gggtcagctt gccgtaggtg gc 152

<210> SEQ ID NO 26
<211> LENGTH: 127
<212> TYPE: DNA
<213> ORGANISM: Artificial Sequence
<220> FEATURE:
<223> OTHER INFORMATION: Synthetic: Donor DNA, ssODN (Hn-91-36)

<400> SEQUENCE: 26
tcatgtggtc ggggtagcgg ctgaagcact gcacgccgta cgtcagggtg gtcacgaggg 60
tgggccaggg cacgggcagc ttgccggtgg tgcagatgaa cttcagggtc agcttgccgt 120
aggtggc 127

<210> SEQ ID NO 27
<211> LENGTH: 152
<212> TYPE: DNA
<213> ORGANISM: Artificial Sequence
<220> FEATURE:
<223> OTHER INFORMATION: Synthetic: Donor DNA, ssODN (Ht-91-61)

<400> SEQUENCE: 27
gccacctacg gcaagctgac cctgaagttc atctgcacca ccggcaagct gcccgtgccc 60
tggcccaccc tcgtgaccac cctgacgtac ggcgtgcagt gcttcagccg ctaccccgac 120
cacatgaagc agcacgactt cttcaagtcc gc 152

<210> SEQ ID NO 28
<211> LENGTH: 127
<212> TYPE: DNA

-continued

<213> ORGANISM: Artificial Sequence
<220> FEATURE:
<223> OTHER INFORMATION: Synthetic: Donor DNA, ssODN (Ht-39-88)

<400> SEQUENCE: 28
cgctcctgga cgtagccttc gggcatggcg gacttgaaga agtcgtgctg cttcatgtgg 60
tcggggtagc ggctgaagca ctgcacgccg tacgtcaggg tggtcacgag ggtgggccag 120
ggcacgg 127

<210> SEQ ID NO 29
<211> LENGTH: 127
<212> TYPE: DNA
<213> ORGANISM: Artificial Sequence
<220> FEATURE:
<223> OTHER INFORMATION: Synthetic: Donor DNA, ssODN 1067

<400> SEQUENCE: 29
gccacctacg gcaagctgac cctgaagttc atctgcacca ccggcaagct gcccgtgccc 60
tggcccaccc tcgtgaccac cctgagccac ggggtgcagt gcttcagccg ctaccccgac 120
cacatga 127

<210> SEQ ID NO 30
<211> LENGTH: 127
<212> TYPE: DNA
<213> ORGANISM: Artificial Sequence
<220> FEATURE:
<223> OTHER INFORMATION: Synthetic: Donor DNA, ssODN 1068

<400> SEQUENCE: 30
tcatgtggtc ggggtagcgg ctgaagcact gcaccccgtg gctcagggtg gtcacgaggg 60
tgggccaggg cacgggcagc ttgccggtgg tgcagatgaa cttcagggtc agcttgccgt 120
aggtggc 127

<210> SEQ ID NO 31
<211> LENGTH: 127
<212> TYPE: DNA
<213> ORGANISM: Artificial Sequence
<220> FEATURE:
<223> OTHER INFORMATION: Synthetic: Donor DNA, ssODN 1069

<400> SEQUENCE: 31
tcatctgcac caccggcaag ctgcccgtgc cctggcccac cctcgtgacc accctgagcc 60
acggggtgca gtgcttcagc cgctaccccg accacatgaa gcagcacgac ttcttcaagt 120
ccgccat 127

<210> SEQ ID NO 32
<211> LENGTH: 127
<212> TYPE: DNA
<213> ORGANISM: Artificial Sequence
<220> FEATURE:
<223> OTHER INFORMATION: Synthetic: Donor DNA, ssODN 1070

<400> SEQUENCE: 32
atggcggact tgaagaagtc gtgctgcttc atgtggtcgg ggtagcggct gaagcactgc 60
accccgtggc tcagggtggt cacgagggtg ggccagggca cgggcagctt gccggtggtg 120
cagatga 127

<210> SEQ ID NO 33
<211> LENGTH: 127

<212> TYPE: DNA
<213> ORGANISM: Artificial Sequence
<220> FEATURE:
<223> OTHER INFORMATION: Synthetic: Donor DNA, ssODN 1061

<400> SEQUENCE: 33
ctcctggacg tagccttcgg gcatggcgga cttgaagaag tcgtgctgct tcatgtggtc 60
ggggtagcgg ctgaagcact gcaccccgtg gctcagggtg gtcacgaggg tgggccaggg 120
cacgggc 127

<210> SEQ ID NO 34
<211> LENGTH: 127
<212> TYPE: DNA
<213> ORGANISM: Artificial Sequence
<220> FEATURE:
<223> OTHER INFORMATION: Synthetic: Donor DNA, ssODN 1062

<400> SEQUENCE: 34
gcccgtgccc tggcccaccc tcgtgaccac cctgagccac ggggtgcagt gcttcagccg 60
ctaccccgac cacatgaagc agcacgactt cttcaagtcc gccatgcccg aaggctacgt 120
ccaggag 127

<210> SEQ ID NO 35
<211> LENGTH: 127
<212> TYPE: DNA
<213> ORGANISM: Artificial Sequence
<220> FEATURE:
<223> OTHER INFORMATION: Synthetic: Donor DNA, ssODN 1063

<400> SEQUENCE: 35
gacttgaaga agtcgtgctg cttcatgtgg tcggggtagc ggctgaagca ctgcaccccg 60
tggctcaggg tggtcacgag ggtgggccag ggcacgggca gcttgccggt ggtgcagatg 120
aacttca 127

<210> SEQ ID NO 36
<211> LENGTH: 127
<212> TYPE: DNA
<213> ORGANISM: Artificial Sequence
<220> FEATURE:
<223> OTHER INFORMATION: Synthetic: Donor DNA, ssODN 1064

<400> SEQUENCE: 36
tgaagttcat ctgcaccacc ggcaagctgc ccgtgccctg gcccaccctc gtgaccaccc 60
tgagccacgg ggtgcagtgc ttcagccgct accccgacca catgaagcag cacgacttct 120
tcaagtc 127

<210> SEQ ID NO 37
<211> LENGTH: 50
<212> TYPE: DNA
<213> ORGANISM: Artificial Sequence
<220> FEATURE:
<223> OTHER INFORMATION: Synthetic: Donor DNA, 50-0 dsDNA

<400> SEQUENCE: 37
cccagaaact tgttctgttt ttccatagga ttctctttgg acagtgccct 50

<210> SEQ ID NO 38
<211> LENGTH: 150
<212> TYPE: DNA
<213> ORGANISM: Artificial Sequence
<220> FEATURE:

-continued

<223> OTHER INFORMATION: Synthetic: Donor DNA, 150-0 dsDNA

<400> SEQUENCE: 38
agggcactgt ccaaagagaa tcctatggaa aaacagaaca agtttctggg gttactgaat 60
gaatgctttt gcccaaagcc tacaccttca agaagagtgt agcctgagaa ggatttcaca 120
tgttgcctct agaagggaga actgggtggc 150

<210> SEQ ID NO 39
<211> LENGTH: 142
<212> TYPE: DNA
<213> ORGANISM: Artificial Sequence
<220> FEATURE:
<223> OTHER INFORMATION: Synthetic: Donor DNA, 93-50 ssODN

<400> SEQUENCE: 39
tcttgaaggt gtaggctttg ggcaaaagca ttcattcagt aaccccagaa acttgttctg 60
tttttccata ggattctctt tggacagtgc ccttactggt gggtcctgga tactgactac 120
tacagcaaca cttccgtgcc ct 142

<210> SEQ ID NO 40
<211> LENGTH: 125
<212> TYPE: DNA
<213> ORGANISM: Artificial Sequence
<220> FEATURE:
<223> OTHER INFORMATION: Synthetic: Donor DNA, 25-100 ssODN

<400> SEQUENCE: 40
taggattctc tttggacagt gcccttactg gtgggtcctg gatactgact actacagcaa 60
cacttccgtg cccctgataa agcagttccc tgtaacctgt gagactggac caggtaagcg 120
tccca 125

<210> SEQ ID NO 41
<211> LENGTH: 125
<212> TYPE: DNA
<213> ORGANISM: Artificial Sequence
<220> FEATURE:
<223> OTHER INFORMATION: Synthetic: Donor DNA, H3-95-30 ssODN

<400> SEQUENCE: 41
taagcacagt ggaagaattt cattctgttc tcagttttcc tggattatgc ctggcaccat 60
taaagaaaat atcataagct ttggtgtttg ctatgatgaa tatagataca gaagcgtcat 120
caaag 125

<210> SEQ ID NO 42
<211> LENGTH: 125
<212> TYPE: DNA
<213> ORGANISM: Artificial Sequence
<220> FEATURE:
<223> OTHER INFORMATION: Synthetic: Donor DNA, N1-95-30 ssODN

<400> SEQUENCE: 42
aattaagcac agtggaagaa tttcattctg ttctcagttt tcctggatta tgcctggcac 60
cattaaagaa aatatcatct ttggtgtttg ctagcatgat gaatatagat acagaagcgt 120
catca 125

<210> SEQ ID NO 43
<211> LENGTH: 1000
<212> TYPE: DNA
<213> ORGANISM: Artificial Sequence
<220> FEATURE:
<223> OTHER INFORMATION: Synthetic: Donor DNA, AAVS1 locus LHA (used
for BFP donor)

<400> SEQUENCE: 43

```
ccccagctct tctctgttca gccctaagaa tcctggctcc agcccctcct actctagccc     60
ccaaccccct agccactaag gcaattgggg tgcaggaatg ggggcagggt accagcctca    120
ccaagtggtt gataaaccca cgtggggtac cctaagaact tgggaacagc cacagcaggg    180
gggcgatgct tggggacctg cctggagaag gatgcaggac gagaaacaca gccccaggtg    240
gagaaactgg ccgggaatca agagtcaccc agagacagtg accaaccatc cctgttttcc    300
taggactgag ggtttcagtg ctaaaactag gctgtcctgg gcaaacagca taagctggtc    360
accccacacc cagacctgac ccaaacccag ctcccctgct tcttggccac gtaacctgag    420
aagggaatcc ctcctctctg aaccccagcc caccccaatg ctccaggcct cctgggatac    480
cccgaagagt gagtttgcca agcagtcacc ccacagttgg aggagaatcc acccaaaagg    540
cagcctggta gacagggctg gggtggcctc tcgtggggtc caggccaagt aggtggcctg    600
gggcctctgg gggatgcagg ggaaggggga tgcaggggaa cggggatgca ggggaacggg    660
gctcagtctg aagagcagag ccaggaaccc ctgtagggaa ggggcaggag agccaggggc    720
atgagatggt ggacgaggaa gggggacagg gaagcctgag cgcctctcct gggcttgcca    780
aggactcaaa cccagaagcc cagagcaggg ccttagggaa gcgggaccct gctctgggcg    840
gaggaatatg tcccagatag cactggggac tctttaagga aagaaggatg gagaaagaga    900
aagggagtag aggcggccac gacctggtga acacctagga cgcaccattc tcacaaaggg    960
agttttccac acggacaccc ccctcctcac cacagccctg                         1000
```

<210> SEQ ID NO 44
<211> LENGTH: 717
<212> TYPE: DNA
<213> ORGANISM: Artificial Sequence
<220> FEATURE:
<223> OTHER INFORMATION: Synthetic: Donor DNA, BFP locus donor

<400> SEQUENCE: 44

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccca tggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccaa gctgagcaaa gaccccaacg agaagcgcga tcacatggtc    660
ctgctggagt tcgtgaccgc cgccgggatc actctcggca tggacgagct gtacaag       717
```

<210> SEQ ID NO 45
<211> LENGTH: 1000
<212> TYPE: DNA
<213> ORGANISM: Artificial Sequence
<220> FEATURE:
<223> OTHER INFORMATION: Synthetic: Donor DNA, AAVS1 locus RHA (used for BFP donor)

<400> SEQUENCE: 45
actgtggggt ggaggggaca gataaaagta cccagaacca gagccacatt aaccggccct 60
gggaatataa ggtggtccca gctcggggac acaggatccc tggaggcagc aaacatgctg 120
tcctgaagtg gacatagggg cccgggttgg aggaagaaga ctagctgagc tctcggaccc 180
ctggaagatg ccatgacagg gggctggaag agctagcaca gactagagag gtaagggggg 240
taggggagct gcccaaatga aaggagtgag aggtgacccg aatccacagg agaacggggt 300
gtccaggcaa agaaagcaag aggatggaga ggtggctaaa gccagggaga cggggtactt 360
tggggttgtc cagaaaaacg gtgatgatgc aggcctacaa gaaggggagg cgggacgcaa 420
gggagacatc cgtcggagaa ggccatccta agaaacgaga gatggcacag gccccagaag 480
gagaaggaaa agggaaccca gcgagtgaag acggcatggg gttgggtgag ggaggagaga 540
tgcccggaga ggacccagac acggggagga tccgctcaga ggacatcacg tggtgcagcg 600
ccgagaagga agtgctccgg aaagagcatc cttgggcagc aacacagcag agagcaaggg 660
gaagagggag tggaggaaga cggaacctga aggaggcggc agggaaggat ctgggccagc 720
cgtagaggtg acccaggcca caagctgcag acagaaagcg gcacaggccc aggggagaga 780
atgcaggtca gagaaagcag gacctgcctg ggaaggggaa acagtgggcc agaggcggcg 840
cagaagccag tagagctcaa agtggtccgg actcaggaga gagacggcag cgttagaggg 900
cagagttccg gcggcacagc aagggcactc gggggcgaga ggagggcagc gcaaagtgac 960
aatggccagg gccaggcaga tagaccagac tgagctatgg 1000

<210> SEQ ID NO 46
<211> LENGTH: 1000
<212> TYPE: DNA
<213> ORGANISM: Artificial Sequence
<220> FEATURE:
<223> OTHER INFORMATION: Synthetic: Donor DNA, AAVS1 locus LHA (used for GFP donor)

<400> SEQUENCE: 46
ccccagctct tctctgttca gccctaagaa tcctggctcc agcccctcct actctagccc 60 ccaacccccct agccactaag gcaattgggg tgcaggaatg ggggcagggt accagcctca 120
ccaagtggtt gataaaccca cgtggggtac cctaagaact tgggaacagc cacagcaggg 180
gggcgatgct tggggacctg cctggagaag gatgcaggac gagaaacaca gccccaggtg 240
gagaaactgg ccgggaatca agagtcaccc agagacagtg accaaccatc cctgttttcc 300
taggactgag ggtttcagtg ctaaaactag gctgtcctgg gcaaacagca taagctggtc 360
accccacacc cagacctgac ccaaacccag ctcccctgct tcttggccac gtaacctgag 420
aagggaatcc ctcctctctg aaccccagcc caccccaatg ctccaggcct cctgggatac 480
cccgaagagt gagtttgcca agcagtcacc ccacagttgg aggagaatcc acccaaaagg 540
cagcctggta gacagggctg gggtggcctc tcgtggggtc caggccaagt aggtggcctg 600
gggcctctgg gggatgcagg ggaaggggga tgcaggggaa cggggatgca ggggaacggg 660
gctcagtctg aagagcagag ccaggaaccc ctgtagggaa ggggcaggag agccaggggc 720
atgagatggt ggacgaggaa gggggacagg gaagcctgag cgcctctcct gggcttgcca 780
aggactcaaa cccagaagcc cagagcaggg ccttagggaa gcgggaccct gctctgggcg 840

```
gaggaatatg tcccagatag cactggggac tctttaagga aagaaggatg gagaaagaga    900

aagggagtag aggcggccac gacctggtga acacctagga cgcaccattc tcacaaaggg    960

agttttccac acggacaccc ccctcctcac cacagccctg                          1000


<210> SEQ ID NO 47
<211> LENGTH: 720
<212> TYPE: DNA
<213> ORGANISM: Artificial Sequence
<220> FEATURE:
<223> OTHER INFORMATION: Synthetic: Donor DNA, GFP donor to AAVS1 locus

<400> SEQUENCE: 47

atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaagtaa    720


<210> SEQ ID NO 48
<211> LENGTH: 1000
<212> TYPE: DNA
<213> ORGANISM: Artificial Sequence
<220> FEATURE:
<223> OTHER INFORMATION: Synthetic: Donor DNA, AAVS1 locus RHA (used for
      GFP donor)

<400> SEQUENCE: 48

actgtggggt ggaggggaca gataaaagta cccagaacca gagccacatt aaccggccct     60

gggaatataa ggtggtccca gctcggggac acaggatccc tggaggcagc aaacatgctg    120

tcctgaagtg gacatagggg cccgggttgg aggaagaaga ctagctgagc tctcggaccc    180

ctggaagatg ccatgacagg gggctggaag agctagcaca gactagagag gtaagggggg    240

taggggagct gcccaaatga aaggagtgag aggtgacccg aatccacagg agaacggggt    300

gtccaggcaa agaaagcaag aggatggaga ggtggctaaa gccagggaga cggggtactt    360

tggggttgtc cagaaaaacg gtgatgatgc aggcctacaa gaaggggagg cgggacgcaa    420

gggagacatc cgtcggagaa ggccatccta agaaacgaga gatggcacag gccccagaag    480

gagaaggaaa agggaaccca gcgagtgaag acggcatggg gttgggtgag ggaggagaga    540

tgcccggaga ggacccagac acggggagga tccgctcaga ggacatcacg tggtgcagcg    600

ccgagaagga agtgctccgg aaagagcatc cttgggcagc aacacagcag agagcaaggg    660

gaagagggag tggaggaaga cggaacctga aggaggcggc agggaaggat ctgggccagc    720

cgtagaggtg acccaggcca caagctgcag acagaaagcg gcacaggccc aggggagaga    780

atgcaggtca gagaaagcag gacctgcctg ggaaggggaa acagtgggcc agaggcggcg    840
```

```
cagaagccag tagagctcaa agtggtccgg actcaggaga gagacggcag cgttagaggg    900

cagagttccg gcggcacagc aagggcactc gggggcgaga ggagggcagc gcaaagtgac    960

aatggccagg gccaggcaga tagaccagac tgagctatgg                         1000


<210> SEQ ID NO 49
<211> LENGTH: 2189
<212> TYPE: DNA
<213> ORGANISM: Artificial Sequence
<220> FEATURE:
<223> OTHER INFORMATION: Synthetic: Donor DNA, HBB locus LHA (used for
      E7 to E7V AAV.304)

<400> SEQUENCE: 49

cttgctttga caattttggt ctttcagaat actataaata taacctatat tataatttca     60

taaagtctgt gcattttctt tgacccagga tatttgcaaa agacatattc aaacttccgc    120

agaacacttt atttcacata tacatgcctc ttatatcagg gatgtgaaac agggtcttga    180

aaactgtcta aatctaaaac aatgctaatg caggtttaaa tttaataaaa taaaatccaa    240

aatctaacag ccaagtcaaa tctgcatgtt ttaacattta aaatatttta aagacgtctt    300

ttcccaggat tcaacatgtg aaatcttttc tcagggatac acgtgtgcct agatcctcat    360

tgctttagtt ttttacagag gaatgaatat aaaaagaaaa tacttaaatt ttatccctct    420

tacctctata atcatacata ggcataattt tttaacctag gctccagata gccatagaag    480

aaccaaacac tttctgcgtg tgtgagaata atcagagtga gatttttca caagtacctg    540

atgagggttg agacaggtag aaaaagtgag agatctctat ttatttagca ataatagaga    600

aagcatttaa gagaataaag caatggaaat aagaaatttg taaatttcct tctgataact    660

agaaatagag gatccagttt cttttggtta acctaaattt tatttcattt tattgtttta    720

ttttatttta ttttatttta ttttgtgtaa tcgtagtttc agagtgttag agctgaaagg    780

aagaagtagg agaaacatgc aaagtaaaag tataacactt tccttactaa accgacatgg    840

gtttccaggt aggggcagga ttcaggatga ctgacagggc ccttagggaa cactgagacc    900

ctacgctgac ctcataaatg cttgctacct ttgctgtttt aattacatct tttaatagca    960

ggaagcagaa ctctgcactt caaaagtttt tcctcacctg aggagttaat ttagtacaag   1020

gggaaaaagt acagggggat gggagaaagg cgatcacgtt gggaagctat agagaaagaa   1080

gagtaaattt tagtaaagga ggtttaaaca aacaaaatat aaagagaaat aggaacttga   1140

atcaaggaaa tgattttaaa acgcagtatt cttagtggac tagaggaaaa aaataatctg   1200

agccaagtag aagacctttt cccctcctac ccctactttc taagtcacag aggctttttg   1260

ttcccccaga cactcttgca gattagtcca ggcagaaaca gttagatgtc cccagttaac   1320

ctcctatttg acaccactga ttaccccatt gatagtcaca ctttgggttg taagtgactt   1380

tttatttatt tgtatttttg actgcattaa gaggtctcta gtttttttatc tcttgtttcc   1440

caaaacctaa taagtaacta atgcacagag cacattgatt tgtatttatt ctatttttag   1500

acataattta ttagcatgca tgagcaaatt aagaaaaaca acaacaaatg aatgcatata   1560

tatgtatatg tatgtgtgta tatatacaca catatatata tatatttttt cttttcttac   1620

cagaaggttt taatccaaat aaggagaaga tatgcttaga accgaggtag agttttcatc   1680

cattctgtcc tgtaagtatt ttgcatattc tggagacgca ggaagagatc catctacata   1740

tcccaaagct gaattatggt agacaaaact cttccacttt tagtgcatca acttcttatt   1800

tgtgtaataa gaaaattggg aaaacgatct tcaatatgct taccaagctg tgattccaaa   1860
```

tattacgtaa atacacttgc aaaggaggat gtttttagta gcaatttgta ctgatggtat 1920
ggggccaaga gatatatctt agagggaggg ctgagggttt gaagtccaac tcctaagcca 1980
gtgccagaag agccaaggac aggtacggct gtcatcactt agacctcacc ctgtggagcc 2040
acaccctagg gttggccaat ctactcccag gagcagggag ggcaggagcc agggctgggc 2100
ataaaagtca gggcagagcc atctattgct tacatttgct tctgacacaa ctgtgttcac 2160
tagcaacctc aaacagacac catggtgca 2189

<210> SEQ ID NO 50
<211> LENGTH: 46
<212> TYPE: DNA
<213> ORGANISM: Artificial Sequence
<220> FEATURE:
<223> OTHER INFORMATION: Synthetic: Donor DNA, E7 to E7V AAV.304

<400> SEQUENCE: 50
tctgactcct gtcgagaagt ctgcagtcac tgctctatgg gggaaa 46

<210> SEQ ID NO 51
<211> LENGTH: 2200
<212> TYPE: DNA
<213> ORGANISM: Artificial Sequence
<220> FEATURE:
<223> OTHER INFORMATION: Synthetic: Donor DNA, HBB locus RHA (used for
E7 to E7V AAV.304)

<400> SEQUENCE: 51
gtgaacgtgg atgaagttgg tggtgaggcc ctgggcaggt tggtatcaag gttacaagac 60
aggtttaagg agaccaatag aaactgggca tgtggagaca gagaagactc ttgggtttct 120
gataggcact gactctctct gcctattggt ctattttccc acccttaggc tgctggtggt 180
ctacccttgg acccagaggt tctttgagtc ctttggggat ctgtccactc ctgatgctgt 240
tatgggcaac cctaaggtga aggctcatgg caagaaagtg ctcggtgcct ttagtgatgg 300
cctggctcac ctggacaacc tcaagggcac ctttgccaca ctgagtgagc tgcactgtga 360
caagctgcac gtggatcctg agaacttcag ggtgagtcta tgggacgctt gatgttttct 420
ttccccttct tttctatggt taagttcatg tcataggaag gggataagta acagggtaca 480
gtttagaatg ggaaacagac gaatgattgc atcagtgtgg aagtctcagg atcgttttag 540
tttcttttat ttgctgttca taacaattgt tttcttttgt ttaattcttg ctttcttttt 600
ttttcttctc cgcaattttt actattatac ttaatgcctt aacattgtgt ataacaaaag 660
gaaatatctc tgagatacat taagtaactt aaaaaaaaac tttacacagt ctgcctagta 720
cattactatt tggaatatat gtgtgcttat ttgcatattc ataatctccc tactttattt 780
tcttttattt ttaattgata cataatcatt atacatattt atgggttaaa gtgtaatgtt 840
ttaatatgtg tacacatatt gaccaaatca gggtaatttt gcatttgtaa ttttaaaaaa 900
tgctttcttc ttttaatata ctttttttgtt tatcttattt ctaatacttt ccctaatctc 960
tttctttcag ggcaataatg atacaatgta tcatgcctct ttgcaccatt ctaaagaata 1020
acagtgataa tttctgggtt aaggcaatag caatatctct gcatataaat atttctgcat 1080
ataaattgta actgatgtaa gaggtttcat attgctaata gcagctacaa tccagctacc 1140
attctgcttt tattttatgg ttgggataag gctggattat tctgagtcca agctaggccc 1200
ttttgctaat catgttcata cctcttatct tcctcccaca gctcctgggc aacgtgctgg 1260
tctgtgtgct ggcccatcac tttggcaaag aattcacccc accagtgcag gctgcctatc 1320
agaaagtggt ggctggtgtg gctaatgccc tggcccacaa gtatcactaa gctcgctttc 1380
ttgctgtcca atttctatta aaggttcctt tgttccctaa gtccaactac taaactgggg 1440
gatattatga agggccttga gcatctggat tctgcctaat aaaaaacatt tattttcatt 1500
gcaatgatgt atttaaatta tttctgaata ttttactaaa aagggaatgt gggaggtcag 1560
tgcatttaaa acataaagaa atgaagagct agttcaaacc ttgggaaaat acactatatc 1620
ttaaactcca tgaaagaagg tgaggctgca aacagctaat gcacattggc aacagcccct 1680
gatgcatatg ccttattcat ccctcagaaa aggattcaag tagaggcttg atttggaggt 1740
taaagttttg ctatgctgta ttttacatta cttattgttt tagctgtcct catgaatgtc 1800
ttttcactac ccatttgctt atcctgcatc tctcagcctt gactccactc agttctcttg 1860
cttagagata ccacctttcc cctgaagtgt tccttccatg ttttacggcg agatggtttc 1920
tcctcgcctg gccactcagc cttagttgtc tctgttgtct tatagaggtc tacttgaaga 1980
aggaaaaaca ggggtcatgg tttgactgtc ctgtgagccc ttcttccctg cctcccccac 2040
tcacagtgac ccggaatctg cagtgctagt ctcccggaac tatcactctt tcacagtctg 2100
ctttggaagg actgggctta gtatgaaaag ttaggactga gaagaatttg aaaggcggct 2160
ttttgtagct tgatattcac tactgtctta ttaccctgtc 2200

<210> SEQ ID NO 52
<211> LENGTH: 2189
<212> TYPE: DNA
<213> ORGANISM: Artificial Sequence
<220> FEATURE:
<223> OTHER INFORMATION: Synthetic: Donor DNA, HBB locus LHA (used for E7 to E7V AAV.307)

<400> SEQUENCE: 52
cttgctttga caattttggt ctttcagaat actataaata taacctatat tataatttca 60
taaagtctgt gcattttctt tgacccagga tatttgcaaa agacatattc aaacttccgc 120
agaacacttt atttcacata tacatgcctc ttatatcagg gatgtgaaac agggtcttga 180
aaactgtcta aatctaaaac aatgctaatg caggtttaaa tttaataaaa taaaatccaa 240
aatctaacag ccaagtcaaa tctgcatgtt ttaacattta aaatatttta aagacgtctt 300
ttcccaggat tcaacatgtg aaatcttttc tcagggatac acgtgtgcct agatcctcat 360
tgctttagtt ttttacagag gaatgaatat aaaaagaaaa tacttaaatt ttatccctct 420
tacctctata atcatacata ggcataattt tttaacctag gctccagata gccatagaag 480
aaccaaacac tttctgcgtg tgtgagaata atcagagtga gatttttca caagtacctg 540 atgagggttg agacaggtag aaaaagtgag agatctctat ttatttagca ataatagaga 600
aagcatttaa gagaataaag caatggaaat aagaaatttg taaatttcct tctgataact 660
agaaatagag gatccagttt cttttggtta acctaaattt tatttcattt tattgtttta 720
ttttatttta ttttatttta ttttgtgtaa tcgtagtttc agagtgttag agctgaaagg 780
aagaagtagg agaaacatgc aaagtaaaag tataacactt tccttactaa accgacatgg 840
gtttccaggt aggggcagga ttcaggatga ctgacagggc ccttagggaa cactgagacc 900
ctacgctgac ctcataaatg cttgctacct ttgctgtttt aattacatct tttaatagca 960
ggaagcagaa ctctgcactt caaaagtttt tcctcacctg aggagttaat ttagtacaag 1020
gggaaaaagt acagggggat gggagaaagg cgatcacgtt gggaagctat agagaaagaa 1080
gagtaaattt tagtaaagga ggtttaaaca aacaaaatat aaagagaaat aggaacttga 1140
atcaaggaaa tgattttaaa acgcagtatt cttagtggac tagaggaaaa aaataatctg 1200
agccaagtag aagacctttt cccctcctac ccctactttc taagtcacag aggctttttg 1260
ttcccccaga cactcttgca gattagtcca ggcagaaaca gttagatgtc cccagttaac 1320
ctcctatttg acaccactga ttaccccatt gatagtcaca ctttgggttg taagtgactt 1380
tttatttatt tgtatttttg actgcattaa gaggtctcta gtttttttatc tcttgtttcc 1440 caaaacctaa taagtaacta atgcacagag cacattgatt tgtatttatt ctatttttag 1500
acataattta ttagcatgca tgagcaaatt aagaaaaaca acaacaaatg aatgcatata 1560
tatgtatatg tatgtgtgta tatatacaca catatatata tatatttttt cttttcttac 1620
cagaaggttt taatccaaat aaggagaaga tatgcttaga accgaggtag agttttcatc 1680
cattctgtcc tgtaagtatt ttgcatattc tggagacgca ggaagagatc catctacata 1740
tcccaaagct gaattatggt agacaaaact cttccacttt tagtgcatca acttcttatt 1800
tgtgtaataa gaaaattggg aaaacgatct tcaatatgct taccaagctg tgattccaaa 1860
tattacgtaa atacacttgc aaaggaggat gtttttagta gcaatttgta ctgatggtat 1920
ggggccaaga gatatatctt agagggaggg ctgagggttt gaagtccaac tcctaagcca 1980
gtgccagaag agccaaggac aggtacggct gtcatcactt agacctcacc ctgtggagcc 2040
acaccctagg gttggccaat ctactcccag gagcagggag ggcaggagcc agggctgggc 2100
ataaaagtca gggcagagcc atctattgct tacatttgct tctgacacaa ctgtgttcac 2160
tagcaacctc aaacagacac catggtgca 2189

<210> SEQ ID NO 53
<211> LENGTH: 46
<212> TYPE: DNA
<213> ORGANISM: Artificial Sequence
<220> FEATURE:
<223> OTHER INFORMATION: Synthetic: Donor DNA, E7 to E7V AAV.307

<400> SEQUENCE: 53
tctgactcct gtcgaaaaat ccgctgtcac cgccctctgg ggcaag 46

<210> SEQ ID NO 54
<211> LENGTH: 2200
<212> TYPE: DNA
<213> ORGANISM: Artificial Sequence
<220> FEATURE:
<223> OTHER INFORMATION: Synthetic: Donor DNA, HBB locus RHA (used for
E7 to E7V AAV.307)

<400> SEQUENCE: 54
gtgaacgtgg atgaagttgg tggtgaggcc ctgggcaggt tggtatcaag gttacaagac 60
aggtttaagg agaccaatag aaactgggca tgtggagaca gagaagactc ttgggtttct 120
gataggcact gactctctct gcctattggt ctattttccc acccttaggc tgctggtggt 180
ctacccttgg acccagaggt tctttgagtc ctttggggat ctgtccactc ctgatgctgt 240
tatgggcaac cctaaggtga aggctcatgg caagaaagtg ctcggtgcct ttagtgatgg 300
cctggctcac ctggacaacc tcaagggcac ctttgccaca ctgagtgagc tgcactgtga 360
caagctgcac gtggatcctg agaacttcag ggtgagtcta tgggacgctt gatgttttct 420
ttccccttct tttctatggt taagttcatg tcataggaag gggataagta acagggtaca 480
gtttagaatg ggaaacagac gaatgattgc atcagtgtgg aagtctcagg atcgttttag 540
tttcttttat ttgctgttca taacaattgt tttcttttgt ttaattcttg ctttcttttt 600

-continued

```
ttttcttctc cgcaattttt actattatac ttaatgcctt aacattgtgt ataacaaaag    660

gaaatatctc tgagatacat taagtaactt aaaaaaaaac tttacacagt ctgcctagta    720

cattactatt tggaatatat gtgtgcttat ttgcatattc ataatctccc tactttattt    780

tcttttattt ttaattgata cataatcatt atacatattt atgggttaaa gtgtaatgtt    840

ttaatatgtg tacacatatt gaccaaatca gggtaatttt gcatttgtaa ttttaaaaaa    900

tgctttcttc ttttaatata cttttttgtt tatcttattt ctaatacttt ccctaatctc    960

tttctttcag ggcaataatg atacaatgta tcatgcctct ttgcaccatt ctaaagaata   1020

acagtgataa tttctgggtt aaggcaatag caatatctct gcatataaat atttctgcat   1080

ataaattgta actgatgtaa gaggtttcat attgctaata gcagctacaa tccagctacc   1140

attctgcttt tattttatgg ttgggataag gctggattat tctgagtcca agctaggccc   1200

ttttgctaat catgttcata cctcttatct tcctcccaca gctcctgggc aacgtgctgg   1260

tctgtgtgct ggcccatcac tttggcaaag aattcacccc accagtgcag gctgcctatc   1320

agaaagtggt ggctggtgtg gctaatgccc tggcccacaa gtatcactaa gctcgctttc   1380

ttgctgtcca atttctatta aaggttcctt tgttccctaa gtccaactac taaactgggg   1440

gatattatga agggccttga gcatctggat tctgcctaat aaaaaacatt tattttcatt   1500

gcaatgatgt atttaaatta tttctgaata ttttactaaa aagggaatgt gggaggtcag   1560

tgcatttaaa acataaagaa atgaagagct agttcaaacc ttgggaaaat acactatatc   1620

ttaaactcca tgaaagaagg tgaggctgca aacagctaat gcacattggc aacagcccct   1680

gatgcatatg ccttattcat ccctcagaaa aggattcaag tagaggcttg atttggaggt   1740

taaagttttg ctatgctgta ttttacatta cttattgttt tagctgtcct catgaatgtc   1800

ttttcactac ccatttgctt atcctgcatc tctcagcctt gactccactc agttctcttg   1860

cttagagata ccacctttcc cctgaagtgt tccttccatg ttttacggcg agatggtttc   1920

tcctcgcctg gccactcagc cttagttgtc tctgttgtct tatagaggtc tacttgaaga   1980

aggaaaaaca ggggtcatgg tttgactgtc ctgtgagccc ttcttccctg cctcccccac   2040

tcacagtgac ccggaatctg cagtgctagt ctcccggaac tatcactctt tcacagtctg   2100

ctttggaagg actgggctta gtatgaaaag ttaggactga gaagaatttg aaaggcggct   2160

ttttgtagct tgatattcac tactgtctta ttaccctgtc                         2200
```

<210> SEQ ID NO 55
<211> LENGTH: 803
<212> TYPE: DNA
<213> ORGANISM: Artificial Sequence
<220> FEATURE:
<223> OTHER INFORMATION: Synthetic: Donor DNA, HBB locus LHA (used for GFP AAV)

<400> SEQUENCE: 55

```
gactgcatta agaggtctct agttttttac ctcttgtttc ccaaaaccta ataagtaact     60

aatgcacaga gcacattgat ttgtatttat tctattttta gacataattt attagcatgc    120

atgagcaaat taagaaaaac aacaacaaat gaatgcatat atatgtatat gtatgtgtgt    180

acatatacac atatatatat atttttttc ttttcttacc agaaggtttt aatccaaata    240

aggagaagat atgcttagaa ctgaggtaga gttttcatcc attctgtcct gtaagtattt    300

tgcatattct ggagacgcag gaagagatcc atctacatat cccaaagctg aattatggta    360

gacaaaactc ttccactttt agtgcatcaa tttcttattt gtgtaataag aaaattggga    420
```

-continued

```
aaacgatctt caatatgctt accaagctgt gattccaaat attacgtaaa tacacttgca    480

aaggaggatg tttttagtag caatttgtac tgatggtatg gggccaagag atatatctta    540

gagggagggc tgagggtttg aagtccaact cctaagccag tgccagaaga gccaaggaca    600

ggtacggctg tcatcactta gacctcaccc tgtggagcca caccctaggg ttggccaatc    660

tactcccagg agcagggagg gcaggagcca gggctgggca taaaagtcag ggcagagcca    720

tctattgctt acatttgctt ctgacacaac tgtgttcact agcaacctca aacagacacc    780

atggtgcatc tgactcctga gga                                            803
```

<210> SEQ ID NO 56
<211> LENGTH: 720
<212> TYPE: DNA
<213> ORGANISM: Artificial Sequence
<220> FEATURE:
<223> OTHER INFORMATION: Synthetic: Donor DNA, GFP

<400> SEQUENCE: 56

```
atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaagtaa    720
```

<210> SEQ ID NO 57
<211> LENGTH: 920
<212> TYPE: DNA
<213> ORGANISM: Artificial Sequence
<220> FEATURE:
<223> OTHER INFORMATION: Synthetic: Donor DNA, HBB locus RHA (used for GFP AAV)

<400> SEQUENCE: 57

```
ctgccctgtg ggcaaggtg aacgtggatg aagttggtgg tgaggccctg ggcaggttgg     60

tatcaaggtt acaagacagg tttaaggaga ccaatagaaa ctgggcatgt ggagacagag    120

aagactcttg ggtttctgat aggcactgac tctctctgcc tattggtcta ttttcccacc    180

cttaggctgc tggtggtcta cccttggacc cagaggttct ttgagtcctt tggggatctg    240

tccactcctg atgctgttat gggcaaccct aaggtgaagg ctcatggcaa gaaagtgctc    300

ggtgccttta gtgatggcct ggctcacctg gacaacctca agggcacctt tgccacactg    360

agtgagctgc actgtgacaa gctgcacgtg gatcctgaga acttcagggt gagtctatgg    420

gacgcttgat gttttctttc cccttctttt ctatggttaa gttcatgtca taggaagggg    480

ataagtaaca gggtacagtt tagaatggga aacagacgaa tgattgcatc agtgtggaag    540

tctcaggatc gttttagttt cttttatttg ctgttcataa caattgtttt cttttgttta    600
```

attcttgctt tctttttttt tcttctccgc aatttttact attatactta atgccttaac 660
attgtgtata acaaaaggaa atatctctga gatacattaa gtaacttaaa aaaaaacttt 720
acacagtctg cctagtacat tactatttgg aatatatgtg tgcttatttg catattcata 780
atctccctac tttattttct tttattttta attgatacat aatcattata catatttatg 840
ggttaaagtg taatgtttta atatgtgtac acatattgac caaatcaggg taattttgca 900
tttgtaattt taaaaaatgc 920

<210> SEQ ID NO 58
<211> LENGTH: 451
<212> TYPE: DNA
<213> ORGANISM: Artificial Sequence
<220> FEATURE:
<223> OTHER INFORMATION: Synthetic: MND promoter

<400> SEQUENCE: 58
ggccgccagt gtgatggata tctgcagaat tcgcccttat ggggatccga acagagagac 60
agcagaatat gggccaaaca ggatatctgt ggtaagcagt tcctgccccg gctcagggcc 120
aagaacagtt ggaacagcag aatatgggcc aaacaggata tctgtggtaa gcagttcctg 180
ccccggctca gggccaagaa cagatggtcc ccagatgcgg tcccgccctc agcagtttct 240
agagaaccat cagatgtttc cagggtgccc caaggacctg aaatgaccct gtgccttatt 300
tgaactaacc aatcagttcg cttctcgctt ctgttcgcgc gcttctgctc cccgagctct 360
atataagcag agctcgttta gtgaaccgtc agatcgcctg gagacgccat ccacgctgtt 420
ttgacctcca tagaagacac cgactctaga g 451

<210> SEQ ID NO 59
<211> LENGTH: 1178
<212> TYPE: DNA
<213> ORGANISM: Artificial Sequence
<220> FEATURE:
<223> OTHER INFORMATION: Synthetic: EF1 promoter

<400> SEQUENCE: 59
ggctccggtg cccgtcagtg ggcagagcgc acatcgccca cagtccccga gaagttgggg 60
ggaggggtcg gcaattgaac cggtgcctag agaaggtggc gcggggtaaa ctgggaaagt 120
gatgtcgtgt actggctccg cctttttccc gagggtgggg gagaaccgta tataagtgca 180
gtagtcgccg tgaacgttct ttttcgcaac gggtttgccg ccagaacaca ggtaagtgcc 240
gtgtgtggtt cccgcgggcc tggcctcttt acgggttatg gcccttgcgt gccttgaatt 300
acttccactg gctgcagtac gtgattcttg atcccgagct tcgggttgga agtgggtggg 360
agagttcgag gccttgcgct taaggagccc cttcgcctcg tgcttgagtt gaggcctggc 420
ctgggcgctg gggccgccgc gtgcgaatct ggtggcacct tcgcgcctgt ctcgctgctt 480
tcgataagtc tctagccatt taaaattttt gatgacctgc tgcgacgctt tttttctggc 540
aagatagtct tgtaaatgcg ggccaagatc tgcacactgg tatttcggtt tttggggccg 600
cgggcggcga cggggcccgt gcgtcccagc gcacatgttc ggcgaggcgg ggcctgcgag 660
cgcggccacc gagaatcgga cgggggtagt ctcaagctgg ccggcctgct ctggtgcctg 720
gcctcgcgcc gccgtgtatc gccccgccct gggcggcaag gctggcccgg tcggcaccag 780
ttgcgtgagc ggaaagatgg ccgcttcccg gccctgctgc agggagctca aaatggagga 840
cgcggcgctc gggagagcgg gcgggtgagt cacccacaca aaggaaaagg gcctttccgt 900
cctcagccgt cgcttcatgt gactccacgg agtaccgggc gccgtccagg cacctcgatt 960
agttctcgag cttttggagt acgtcgtctt taggttgggg ggaggggttt tatgcgatgg 1020
agtttcccca cactgagtgg gtggagactg aagttaggcc agcttggcac ttgatgtaat 1080
tctccttgga atttgccctt tttgagtttg gatcttggtt cattctcaag cctcagacag 1140
tggttcaaag tttttttctt ccatttcagg tgtcgtga 1178

<210> SEQ ID NO 60
<211> LENGTH: 402
<212> TYPE: DNA
<213> ORGANISM: Artificial Sequence
<220> FEATURE:
<223> OTHER INFORMATION: Synthetic: SFFV promoter

<400> SEQUENCE: 60
gtaacgccat tttgcaaggc atggaaaaat accaaaccaa gaatagagaa gttcagatca 60
agggcgggta catgaaaata gctaacgttg ggccaaacag gatatctgcg gtgagcagtt 120
tcggccccgg cccggggcca agaacagatg gtcaccgcag tttcggcccc ggcccgaggc 180
caagaacaga tggtccccag atatggccca accctcagca gtttcttaag acccatcaga 240
tgtttccagg ctcccccaag gacctgaaat gaccctgcgc cttatttgaa ttaaccaatc 300
agcctgcttc tcgcttctgt tcgcgcgctt ctgcttcccg agctctataa aagagctcac 360
aacccctcac tcggcgcgcc agtcctccga cagactgagt cg 402

<210> SEQ ID NO 61
<211> LENGTH: 57
<212> TYPE: DNA
<213> ORGANISM: Unknown
<220> FEATURE:
<223> OTHER INFORMATION: Teschovirus sp.
<220> FEATURE:
<221> NAME/KEY: misc_feature
<222> LOCATION: (1)..(57)
<223> OTHER INFORMATION: 2A peptide from porcine teschovirus

<400> SEQUENCE: 61
gccacgaact tctctctgtt aaagcaagca ggagacgtgg aagaaaaccc cggtcct 57

<210> SEQ ID NO 62
<211> LENGTH: 49
<212> TYPE: DNA
<213> ORGANISM: Artificial Sequence
<220> FEATURE:
<223> OTHER INFORMATION: Synthetic: Synthetic poly(A) signal

<400> SEQUENCE: 62
aataaaatcg ctatccatcg aagatggatg tgtgttggtt ttttgtgtg 49

<210> SEQ ID NO 63
<211> LENGTH: 24
<212> TYPE: DNA
<213> ORGANISM: Artificial Sequence
<220> FEATURE:
<223> OTHER INFORMATION: Synthetic: PAM, Canonical PAM
<220> FEATURE:
<221> NAME/KEY: misc_feature
<222> LOCATION: (1)..(22)
<223> OTHER INFORMATION: n is a, c, g, or t
<220> FEATURE:
<221> NAME/KEY: misc_feature
<222> LOCATION: (20)..(21)
<223> OTHER INFORMATION: each individual residue may be absent

<400> SEQUENCE: 63
nnnnnnnnnn nnnnnnnnnn nnrg 24

<210> SEQ ID NO 64
<211> LENGTH: 3
<212> TYPE: DNA
<213> ORGANISM: Artificial Sequence
<220> FEATURE:
<223> OTHER INFORMATION: Synthetic: PAM, SpCas9 PAM
<220> FEATURE:
<221> NAME/KEY: misc_feature
<222> LOCATION: (1)..(1)
<223> OTHER INFORMATION: n is a, c, g, or t

<400> SEQUENCE: 64 nrg 3

<210> SEQ ID NO 65
<211> LENGTH: 7
<212> TYPE: PRT
<213> ORGANISM: Artificial Sequence
<220> FEATURE:
<223> OTHER INFORMATION: Synthetic: Nuclear localization signal (NLS), SV40 NLS 1

<400> SEQUENCE: 65

Pro Lys Lys Lys Arg Lys Val
1 5

<210> SEQ ID NO 66
<211> LENGTH: 7
<212> TYPE: PRT
<213> ORGANISM: Artificial Sequence
<220> FEATURE:
<223> OTHER INFORMATION: Synthetic: NLS, SV40 NLS 2

<400> SEQUENCE: 66

Pro Lys Lys Lys Arg Arg Val
1 5

<210> SEQ ID NO 67
<211> LENGTH: 16
<212> TYPE: PRT
<213> ORGANISM: Artificial Sequence
<220> FEATURE:
<223> OTHER INFORMATION: Synthetic: NLS, Nucleoplasmin NLS

<400> SEQUENCE: 67

Lys Arg Pro Ala Ala Thr Lys Lys Ala Gly Gln Ala Lys Lys Lys Lys
1 5 10 15

<210> SEQ ID NO 68
<211> LENGTH: 225
<212> TYPE: DNA
<213> ORGANISM: Artificial Sequence
<220> FEATURE:
<223> OTHER INFORMATION: Synthetic: I53, i53 (DNA)

<400> SEQUENCE: 68
atgctgatct tcgtgaagac cctgaccggc aagaccatca ccctggaggt ggagcccagc 60
gacaccatcg agaacgtgaa ggccaagatc caggacaagg agggcatccc ccccgaccag 120
cagaggctgg ccttcgccgg caagagcctg gaggacggca ggaccctgag cgactacaac 180
atcctgaagg acagcaagct gcaccccctg ctgaggctga ggtga 225

<210> SEQ ID NO 69
<211> LENGTH: 225

<212> TYPE: RNA
<213> ORGANISM: Artificial Sequence
<220> FEATURE:
<223> OTHER INFORMATION: Synthetic: I53 mRNA, i53 (RNA)

<400> SEQUENCE: 69
augcugaucu ucgugaagac ccugaccggc aagaccauca cccuggaggu ggagcccagc      60
gacaccaucg agaacgugaa ggccaagauc caggacaagg agggcauccc ccccgaccag     120
cagaggcugg ccuucgccgg caagagccug gaggacggca ggacccugag cgacuacaac     180
auccugaagg acagcaagcu gcacccccug cugaggcuga gguga                     225

<210> SEQ ID NO 70
<211> LENGTH: 74
<212> TYPE: PRT
<213> ORGANISM: Artificial Sequence
<220> FEATURE:
<223> OTHER INFORMATION: Synthetic: I53, i53 (aa)

<400> SEQUENCE: 70

Met Leu Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ala Phe Ala Gly Lys
        35                  40                  45

Ser Leu Glu Asp Gly Arg Thr Leu Ser Asp Tyr Asn Ile Leu Lys Asp
    50                  55                  60

Ser Lys Leu His Pro Leu Leu Arg Leu Arg
65                  70

<210> SEQ ID NO 71
<211> LENGTH: 222
<212> TYPE: RNA
<213> ORGANISM: Artificial Sequence
<220> FEATURE:
<223> OTHER INFORMATION: Synthetic: DM mRNA, I53-DM (RNA)

<400> SEQUENCE: 71
auguugauuu ucgugaaaac ccuuaccggg aaaaccauca cccucgaggu ugaacccucg      60
gauacgauag aaaauguaaa ggccaagauc caggauaagg aaggaauucc uccugaucag     120
cagagacugg ccuuugcugg caaaucgcug gaagauggac guacuuuguc ugacuacaau     180
auucuaaagg acucuaaacu ucaucuagug uugagacuuc gu                       222

<210> SEQ ID NO 72
<211> LENGTH: 228
<212> TYPE: DNA
<213> ORGANISM: Artificial Sequence
<220> FEATURE:
<223> OTHER INFORMATION: Synthetic: A10 (DNA)

<400> SEQUENCE: 72
atgcagattt acgtgaagac ctttgcccgg aagcccatca ccctcgaggt tgaaccctcg      60
gatacgatag aaaatgtaaa ggccaagatc caggataagg aaggaattcc tcctgatcag     120
cagcgactga tctttgctga aatgcggctg gaagatggac gtactttgtc tgactacaat     180
attaaaaacg actctactct ttttcttgtg ttgaaaaata gtgttact                 228

<210> SEQ ID NO 73
<211> LENGTH: 228

<212> TYPE: RNA
<213> ORGANISM: Artificial Sequence
<220> FEATURE:
<223> OTHER INFORMATION: Synthetic: A10 (RNA)

<400> SEQUENCE: 73
augcagauuu acgugaagac cuuugcccgg aagcccauca cccucgaggu ugaacccucg 60
gauacgauag aaaauguaaa ggccaagauc caggauaagg aaggaauucc uccugaucag 120
cagcgacuga ucuuugcuga aaugcggcug gaagauggac guacuuuguc ugacuacaau 180
auuaaaaacg acucuacucu uuuucuugug uugaaaaaua guguuacu 228

<210> SEQ ID NO 74
<211> LENGTH: 76
<212> TYPE: PRT
<213> ORGANISM: Artificial Sequence
<220> FEATURE:
<223> OTHER INFORMATION: Synthetic: A10 (aa)

<400> SEQUENCE: 74

Met Gln Ile Tyr Val Lys Thr Phe Ala Arg Lys Pro Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Phe Ala Glu Met
35 40 45

Arg Leu Glu Asp Gly Arg Thr Leu Ser Asp Tyr Asn Ile Lys Asn Asp
50 55 60

Ser Thr Leu Phe Leu Val Leu Lys Asn Ser Val Thr
65 70 75

<210> SEQ ID NO 75
<211> LENGTH: 228
<212> TYPE: DNA
<213> ORGANISM: Artificial Sequence
<220> FEATURE:
<223> OTHER INFORMATION: Synthetic: A11 (DNA)

<400> SEQUENCE: 75
atgctgattt tcgtgaccac cgatatgggg atgacaatct cactcgaggt tgaaccctcg 60
gatacgatag aaaatgtaaa ggccaagatc caggataagg aaggaattcc tcctgatcag 120
cagagactga tctttggtga caaggatctg gaagatggac gtactttgtc tgactacaat 180
attcaaaagg agtctagcct taatcttgtg ctgaaacttc gtggtggt 228

<210> SEQ ID NO 76
<211> LENGTH: 228
<212> TYPE: RNA
<213> ORGANISM: Artificial Sequence
<220> FEATURE:
<223> OTHER INFORMATION: Synthetic: A11 (RNA)

<400> SEQUENCE: 76
augcugauuu ucgugaccac cgauaugggg augacaaucu cacucgaggu ugaacccucg 60
gauacgauag aaaauguaaa ggccaagauc caggauaagg aaggaauucc uccugaucag 120
cagagacuga ucuuugguga caaggaucug gaagauggac guacuuuguc ugacuacaau 180
auucaaaagg agucuagccu uaaucuugug cugaaacuuc gugguggu 228

<210> SEQ ID NO 77
<211> LENGTH: 76

<212> TYPE: PRT
<213> ORGANISM: Artificial Sequence
<220> FEATURE:
<223> OTHER INFORMATION: Synthetic: A11 (aa)

<400> SEQUENCE: 77

```
Met Leu Ile Phe Val Thr Thr Asp Met Gly Met Thr Ile Ser Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Gly Asp Lys
        35                  40                  45

Asp Leu Glu Asp Gly Arg Thr Leu Ser Asp Tyr Asn Ile Gln Lys Glu
    50                  55                  60

Ser Ser Leu Asn Leu Val Leu Lys Leu Arg Gly Gly
65                  70                  75
```

<210> SEQ ID NO 78
<211> LENGTH: 228
<212> TYPE: DNA
<213> ORGANISM: Artificial Sequence
<220> FEATURE:
<223> OTHER INFORMATION: Synthetic: C08 (DNA)

<400> SEQUENCE: 78

```
atgcagattt tcgtgaccac cgatatgtgg atgagaatct cactcgaggt tgaaccctcg     60

gatacgatag aaaatgtaaa ggccaagatc caggataagg aaggaattcc tcctgatcag    120

cagagactga tctttggtga caaggatctg gaagatggac gtactttgtc tgactacaat    180

attcaaaagg agtctagcct taatcttgtg ctgaaccttc gtggtggt                 228
```

<210> SEQ ID NO 79
<211> LENGTH: 228
<212> TYPE: RNA
<213> ORGANISM: Artificial Sequence
<220> FEATURE:
<223> OTHER INFORMATION: Synthetic: C08 (RNA)

<400> SEQUENCE: 79

```
augcagauuu ucgugaccac cgauaugugg augagaaucu cacucgaggu ugaacccucg     60

gauacgauag aaaauguaaa ggccaagauc caggauaagg aaggaauucc uccugaucag    120

cagagacuga ucuuugguga caaggaucug gaagauggac guacuuuguc ugacuacaau    180

auucaaaagg agucuagccu uaaucuugug cugaaccuuc gugguggu                 228
```

<210> SEQ ID NO 80
<211> LENGTH: 76
<212> TYPE: PRT
<213> ORGANISM: Artificial Sequence
<220> FEATURE:
<223> OTHER INFORMATION: Synthetic: C08 (aa)

<400> SEQUENCE: 80

```
Met Gln Ile Phe Val Thr Thr Asp Met Trp Met Arg Ile Ser Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Gly Asp Lys
        35                  40                  45

Asp Leu Glu Asp Gly Arg Thr Leu Ser Asp Tyr Asn Ile Gln Lys Glu
    50                  55                  60
```

-continued

Ser Ser Leu Asn Leu Val Leu Asn Leu Arg Gly Gly
65 70 75

<210> SEQ ID NO 81
<211> LENGTH: 228
<212> TYPE: DNA
<213> ORGANISM: Artificial Sequence
<220> FEATURE:
<223> OTHER INFORMATION: Synthetic: G08 (DNA)

<400> SEQUENCE: 81
atgttgattt tcgtgaaaac ccttaccggg aaaaccatca ccctcgaggt tgaaccctcg 60
gatacgatag aaaatgtaaa ggccaagatc caggataagg aaggaattcc tcctgatcag 120
cagagactga tctttgctgg caaatcgctg gaagatggac gtactttgtc tgactacaat 180
attctaaagg actctaaact tcatcctctg ttgagacttc gtggtggt 228

<210> SEQ ID NO 82
<211> LENGTH: 228
<212> TYPE: RNA
<213> ORGANISM: Artificial Sequence
<220> FEATURE:
<223> OTHER INFORMATION: Synthetic: G08 (RNA)

<400> SEQUENCE: 82
auguugauuu ucgugaaaac ccuuaccggg aaaaccauca cccucgaggu ugaacccucg 60
gauacgauag aaaauguaaa ggccaagauc caggauaagg aaggaauucc uccugaucag 120
cagagacuga ucuuugcugg caaaucgcug gaagauggac guacuuuguc ugacuacaau 180
auucuaaagg acucuaaacu ucauccucug uugagacuuc gugguggu 228

<210> SEQ ID NO 83
<211> LENGTH: 76
<212> TYPE: PRT
<213> ORGANISM: Artificial Sequence
<220> FEATURE:
<223> OTHER INFORMATION: Synthetic: G08 (aa)

<400> SEQUENCE: 83

Met Leu Ile Phe Val Lys Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Phe Ala Gly Lys
35 40 45

Ser Leu Glu Asp Gly Arg Thr Leu Ser Asp Tyr Asn Ile Leu Lys Asp
50 55 60

Ser Lys Leu His Pro Leu Leu Arg Leu Arg Gly Gly
65 70 75

<210> SEQ ID NO 84
<211> LENGTH: 228
<212> TYPE: DNA
<213> ORGANISM: Artificial Sequence
<220> FEATURE:
<223> OTHER INFORMATION: Synthetic: H04 (DNA)

<400> SEQUENCE: 84
atgcgaatta tcgtgaaaac ctttatgcgg aagccgatca cgctcgaggt tgaaccctcg 60
gatacgatag aaaatgtaaa ggccaagatc caggataagg aaggaattcc tcctgatcag 120
cagagactgt attttgcggc cagtcagctg gaagatggac gtactttgtc tgactacaat 180
attcaaaagg agtctactct tcttcttgtg gtaaggctgc tccgcgtt 228

<210> SEQ ID NO 85
<211> LENGTH: 228
<212> TYPE: RNA
<213> ORGANISM: Artificial Sequence
<220> FEATURE:
<223> OTHER INFORMATION: Synthetic: H04 (RNA)

<400> SEQUENCE: 85
augcgaauua ucgugaaaac cuuuaugcgg aagccgauca cgcucgaggu ugaacccucg 60
gauacgauag aaaauguaaa ggccaagauc caggauaagg aaggaauucc uccugaucag 120
cagagacugu auuuugcggc cagucagcug gaagauggac guacuuuguc ugacuacaau 180
auucaaaagg agucuacucu ucuucuugug guaaggcugc uccgcguu 228

<210> SEQ ID NO 86
<211> LENGTH: 76
<212> TYPE: PRT
<213> ORGANISM: Artificial Sequence
<220> FEATURE:
<223> OTHER INFORMATION: Synthetic: H04 (aa)

<400> SEQUENCE: 86

Met Arg Ile Ile Val Lys Thr Phe Met Arg Lys Pro Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Tyr Phe Ala Ala Ser
35 40 45

Gln Leu Glu Asp Gly Arg Thr Leu Ser Asp Tyr Asn Ile Gln Lys Glu
50 55 60

Ser Thr Leu Leu Leu Val Val Arg Leu Leu Arg Val
65 70 75

<210> SEQ ID NO 87
<211> LENGTH: 222
<212> TYPE: DNA
<213> ORGANISM: Artificial Sequence
<220> FEATURE:
<223> OTHER INFORMATION: Synthetic: I53 alt (DNA)

<400> SEQUENCE: 87
atgttgattt tcgtgaaaac ccttaccggg aaaaccatca ccctcgaggt tgaaccctcg 60
gatacgatag aaaatgtaaa ggccaagatc caggataagg aaggaattcc tcctgatcag 120
cagagactgg cctttgctgg caaatcgctg gaagatggac gtactttgtc tgactacaat 180
attctaaagg actctaaact tcatcctctg ttgagacttc gt 222

<210> SEQ ID NO 88
<211> LENGTH: 222
<212> TYPE: RNA
<213> ORGANISM: Artificial Sequence
<220> FEATURE:
<223> OTHER INFORMATION: Synthetic: I53 alt (RNA)

<400> SEQUENCE: 88
auguugauuu ucgugaaaac ccuuaccggg aaaaccauca cccucgaggu ugaacccucg 60
gauacgauag aaaauguaaa ggccaagauc caggauaagg aaggaauucc uccugaucag 120
cagagacugg ccuuugcugg caaaucgcug gaagauggac guacuuuguc ugacuacaau 180
auucuaaagg acucuaaacu ucauccucug uugagacuuc gu 222

<210> SEQ ID NO 89
<211> LENGTH: 291
<212> TYPE: DNA
<213> ORGANISM: Artificial Sequence
<220> FEATURE:
<223> OTHER INFORMATION: Synthetic: FLAG-tagged i53 DNA

<400> SEQUENCE: 89
atggactaca aagacgatga cgataaagcc gccagtttaa acggcgcgcc attaattaag 60
gatccaatgt tgattttcgt gaaaaccctt accgggaaaa ccatcaccct cgaggttgaa 120
ccctcggata cgatagaaaa tgtaaaggcc aagatccagg ataaggaagg aattcctcct 180
gatcagcaga gactggcctt tgctggcaaa tcgctggaag atggacgtac tttgtctgac 240
tacaatattc taaaggactc taaacttcat cctctgttga gacttcgttg a 291

<210> SEQ ID NO 90
<211> LENGTH: 291
<212> TYPE: RNA
<213> ORGANISM: Artificial Sequence
<220> FEATURE:
<223> OTHER INFORMATION: Synthetic: FLAG-tagged i53 RNA

<400> SEQUENCE: 90
auggacuaca aagacgauga cgauaaagcc gccaguuuaa acggcgcgcc auuaauuaag 60
gauccaaugu ugauuuucgu gaaaacccuu accgggaaaa ccaucacccu cgagguugaa 120
cccucggaua cgauagaaaa uguaaaggcc aagauccagg auaaggaagg aauuccuccu 180
gaucagcaga gacuggccuu ugcuggcaaa ucgcuggaag auggacguac uuugucugac 240
uacaauauuc uaaaggacuc uaaacuucau ccucuguuga gacuucguug a 291

<210> SEQ ID NO 91
<211> LENGTH: 39
<212> TYPE: DNA
<213> ORGANISM: Artificial Sequence
<220> FEATURE:
<223> OTHER INFORMATION: Synthetic: Linker (DNA)

<400> SEQUENCE: 91
gccgccagtt taaacggcgc gccattaatt aaggatcca 39

<210> SEQ ID NO 92
<211> LENGTH: 39
<212> TYPE: RNA
<213> ORGANISM: Artificial Sequence
<220> FEATURE:
<223> OTHER INFORMATION: Synthetic: Linker (RNA)

<400> SEQUENCE: 92
gccgccaguu uaaacggcgc gccauuaauu aaggaucca 39

<210> SEQ ID NO 93
<211> LENGTH: 13
<212> TYPE: PRT
<213> ORGANISM: Artificial Sequence
<220> FEATURE:
<223> OTHER INFORMATION: Synthetic: Linker

<400> SEQUENCE: 93

Ala Ala Ser Leu Asn Gly Ala Pro Leu Ile Lys Asp Pro

-continued 1 5 10

<210> SEQ ID NO 94
<211> LENGTH: 6
<212> TYPE: PRT
<213> ORGANISM: Artificial Sequence
<220> FEATURE:
<223> OTHER INFORMATION: Synthetic: Protein tag, 6xHis

<400> SEQUENCE: 94

His His His His His His
1 5

<210> SEQ ID NO 95
<211> LENGTH: 9
<212> TYPE: PRT
<213> ORGANISM: Artificial Sequence
<220> FEATURE:
<223> OTHER INFORMATION: Synthetic: Protein tag, Flag

<400> SEQUENCE: 95

Met Asp Tyr Lys Asp Asp Asp Asp Lys
1 5

<210> SEQ ID NO 96
<211> LENGTH: 24
<212> TYPE: DNA
<213> ORGANISM: Artificial Sequence
<220> FEATURE:
<223> OTHER INFORMATION: Synthetic: Protein tag, FLAG (DNA)

<400> SEQUENCE: 96
gactacaaag acgatgacga taaa 24

<210> SEQ ID NO 97
<211> LENGTH: 24
<212> TYPE: RNA
<213> ORGANISM: Artificial Sequence
<220> FEATURE:
<223> OTHER INFORMATION: Synthetic: Protein tag, FLAG (RNA)

<400> SEQUENCE: 97
gacuacaaag acgaugacga uaaa 24

<210> SEQ ID NO 98
<211> LENGTH: 4435
<212> TYPE: DNA
<213> ORGANISM: Artificial Sequence
<220> FEATURE:
<223> OTHER INFORMATION: Synthetic: Donor DNA, HBB locus LHA to RHA
(used for E6V to E6, AAV.323)

<400> SEQUENCE: 98
cttgctttga caattttggt ctttcagaat actataaata taacctatat tataatttca 60
taaagtctgt gcattttctt tgacccagga tatttgcaaa agacatattc aaacttccgc 120
agaacacttt atttcacata tacatgcctc ttatatcagg gatgtgaaac agggtcttga 180
aaactgtcta aatctaaaac aatgctaatg caggtttaaa tttaataaaa taaaatccaa 240
aatctaacag ccaagtcaaa tctgcatgtt ttaacattta aaatatttta aagacgtctt 300
ttcccaggat tcaacatgtg aaatcttttc tcagggatac acgtgtgcct agatcctcat 360
tgctttagtt ttttacagag gaatgaatat aaaaagaaaa tacttaaatt ttatccctct 420
tacctctata atcatacata ggcataattt tttaacctag gctccagata gccatagaag 480

-continued

```
aaccaaacac tttctgcgtg tgtgagaata atcagagtga gatttttca caagtacctg    540
atgagggttg agacaggtag aaaaagtgag agatctctat ttatttagca ataatagaga    600
aagcatttaa gagaataaag caatggaaat aagaaatttg taaatttcct tctgataact    660
agaaatagag gatccagttt cttttggtta acctaaattt tatttcattt tattgtttta    720
ttttatttta ttttatttta ttttgtgtaa tcgtagtttc agagtgttag agctgaaagg    780
aagaagtagg agaaacatgc aaagtaaaag tataacactt tccttactaa accgacatgg    840
gtttccaggt aggggcagga ttcaggatga ctgacagggc ccttagggaa cactgagacc    900
ctacgctgac ctcataaatg cttgctacct ttgctgtttt aattacatct tttaatagca    960
ggaagcagaa ctctgcactt caaaagtttt tcctcacctg aggagttaat ttagtacaag   1020
gggaaaaagt acagggggat gggagaaagg cgatcacgtt gggaagctat agagaaagaa   1080
gagtaaattt tagtaaagga ggtttaaaca aacaaaatat aaagagaaat aggaacttga   1140
atcaaggaaa tgattttaaa acgcagtatt cttagtggac tagaggaaaa aaataatctg   1200
agccaagtag aagacctttt cccctcctac ccctactttc taagtcacag aggcttttg    1260
ttcccccaga cactcttgca gattagtcca ggcagaaaca gttagatgtc cccagttaac   1320
ctcctatttg acaccactga ttaccccatt gatagtcaca ctttgggttg taagtgactt   1380
tttatttatt tgtattttg actgcattaa gaggtctcta gttttttatc tcttgtttcc    1440
caaaacctaa taagtaacta atgcacagag cacattgatt tgtatttatt ctatttttag   1500
acataattta ttagcatgca tgagcaaatt aagaaaaaca acaacaaatg aatgcatata   1560
tatgtatatg tatgtgtgta tatatacaca catatatata tatattttt cttttcttac    1620
cagaaggttt taatccaaat aaggagaaga tatgcttaga accgaggtag agttttcatc   1680
cattctgtcc tgtaagtatt ttgcatattc tggagacgca ggaagagatc catctacata   1740
tcccaaagct gaattatggt agacaaaact cttccacttt tagtgcatca acttcttatt   1800
tgtgtaataa gaaaattggg aaaacgatct tcaatatgct taccaagctg tgattccaaa   1860
tattacgtaa atacacttgc aaaggaggat gtttttagta gcaatttgta ctgatggtat   1920
ggggccaaga gatatatctt agagggaggg ctgagggttt gaagtccaac tcctaagcca   1980
gtgccagaag agccaaggac aggtacggct gtcatcactt agacctcacc ctgtggagcc   2040
acaccctagg gttggccaat ctactcccag gagcagggag ggcaggagcc agggctgggc   2100
ataaaagtca gggcagagcc atctattgct tacatttgct tctgacacaa ctgtgttcac   2160
tagcaacctc aaacagacac catggtgcat ctgactcctg aagaaaaatc cgctgtcact   2220
gccctgtggg gcaaggtgaa cgtggatgaa gttggtggtg aggccctggg caggttggta   2280
tcaaggttac aagacaggtt taaggagacc aatagaaact gggcatgtgg agacagagaa   2340
gactcttggg tttctgatag gcactgactc tctctgccta ttggtctatt ttcccaccct   2400
taggctgctg gtggtctacc cttggaccca gaggttcttt gagtcctttg gggatctgtc   2460
cactcctgat gctgttatgg gcaaccctaa ggtgaaggct catggcaaga aagtgctcgg   2520
tgcctttagt gatggcctgg ctcacctgga caacctcaag ggcacctttg ccacactgag   2580
tgagctgcac tgtgacaagc tgcacgtgga tcctgagaac ttcagggtga gtctatggga   2640
cgcttgatgt tttctttccc cttcttttct atggttaagt tcatgtcata ggaaggggat   2700
aagtaacagg gtacagttta gaatgggaaa cagacgaatg attgcatcag tgtggaagtc   2760
tcaggatcgt ttagtttct tttatttgct gttcataaca attgttttct tttgtttaat    2820
tcttgctttc ttttttttc ttctccgcaa tttttactat tatacttaat gccttaacat    2880
```

```
tgtgtataac aaaaggaaat atctctgaga tacattaagt aacttaaaaa aaaactttac   2940
acagtctgcc tagtacatta ctatttggaa tatatgtgtg cttatttgca tattcataat   3000
ctccctactt tattttcttt tatttttaat tgatacataa tcattataca tatttatggg   3060
ttaaagtgta atgttttaat atgtgtacac atattgacca aatcagggta attttgcatt   3120
tgtaatttta aaaaatgctt tcttctttta atatactttt ttgtttatct tatttctaat   3180
actttcccta atctctttct ttcagggcaa taatgataca atgtatcatg cctctttgca   3240
ccattctaaa gaataacagt gataatttct gggttaaggc aatagcaata tctctgcata   3300
taaatatttc tgcatataaa ttgtaactga tgtaagaggt ttcatattgc taatagcagc   3360
tacaatccag ctaccattct gcttttattt tatggttggg ataaggctgg attattctga   3420
gtccaagcta ggcccttttg ctaatcatgt tcatacctct tatcttcctc ccacagctcc   3480
tgggcaacgt gctggtctgt gtgctggccc atcactttgg caaagaattc accccaccag   3540
tgcaggctgc ctatcagaaa gtggtggctg gtgtggctaa tgccctggcc cacaagtatc   3600
actaagctcg ctttcttgct gtccaatttc tattaaaggt tcctttgttc cctaagtcca   3660
actactaaac tgggggatat tatgaagggc cttgagcatc tggattctgc ctaataaaaa   3720
acatttattt tcattgcaat gatgtattta aattatttct gaatatttta ctaaaaaggg   3780
aatgtgggag gtcagtgcat ttaaaacata aagaaatgaa gagctagttc aaaccttggg   3840
aaaatacact atatcttaaa ctccatgaaa gaaggtgagg ctgcaaacag ctaatgcaca   3900
ttggcaacag cccctgatgc atatgcctta ttcatccctc agaaaaggat tcaagtagag   3960
gcttgatttg gaggttaaag ttttgctatg ctgtatttta cattacttat tgttttagct   4020
gtcctcatga atgtcttttc actacccatt tgcttatcct gcatctctca gccttgactc   4080
cactcagttc tcttgcttag agataccacc tttcccctga agtgttcctt ccatgtttta   4140
cggcgagatg gtttctcctc gcctggccac tcagccttag ttgtctctgt tgtcttatag   4200
aggtctactt gaagaaggaa aaacaggggt catggtttga ctgtcctgtg agcccttctt   4260
ccctgcctcc cccactcaca gtgacccgga atctgcagtg ctagtctccc ggaactatca   4320
ctctttcaca gtctgctttg gaaggactgg gcttagtatg aaaagttagg actgagaaga   4380
atttgaaagg cggctttttg tagcttgata ttcactactg tcttattacc ctgtc        4435
```

<210> SEQ ID NO 99
<211> LENGTH: 2199
<212> TYPE: DNA
<213> ORGANISM: Artificial Sequence
<220> FEATURE:
<223> OTHER INFORMATION: Synthetic: Donor DNA, HBB locus LHA (used for
E6V to E6, AAV.323)

<400> SEQUENCE: 99

```
cttgctttga caattttggt ctttcagaat actataaata taacctatat tataatttca     60
taaagtctgt gcattttctt tgacccagga tatttgcaaa agacatattc aaacttccgc    120
agaacacttt atttcacata tacatgcctc ttatatcagg gatgtgaaac agggtcttga    180
aaactgtcta aatctaaaac aatgctaatg caggtttaaa tttaataaaa taaaatccaa    240
aatctaacag ccaagtcaaa tctgcatgtt ttaacattta aaatatttta aagacgtctt    300
ttcccaggat tcaacatgtg aaatcttttc tcagggatac acgtgtgcct agatcctcat    360
tgctttagtt ttttacagag gaatgaatat aaaaagaaaa tacttaaatt ttatccctct    420
tacctctata atcatacata ggcataattt tttaacctag gctccagata gccatagaag    480
```

aaccaaacac tttctgcgtg tgtgagaata atcagagtga gattttttca caagtacctg 540
atgagggttg agacaggtag aaaaagtgag agatctctat ttatttagca ataatagaga 600
aagcatttaa gagaataaag caatggaaat aagaaatttg taaatttcct tctgataact 660
agaaatagag gatccagttt cttttggtta acctaaattt tatttcattt tattgtttta 720
ttttatttta ttttatttta ttttgtgtaa tcgtagtttc agagtgttag agctgaaagg 780
aagaagtagg agaaacatgc aaagtaaaag tataacactt tccttactaa accgacatgg 840
gtttccaggt aggggcagga ttcaggatga ctgacagggc ccttagggaa cactgagacc 900
ctacgctgac ctcataaatg cttgctacct ttgctgtttt aattacatct tttaatagca 960
ggaagcagaa ctctgcactt caaaagtttt tcctcacctg aggagttaat ttagtacaag 1020
gggaaaaagt acagggggat gggagaaagg cgatcacgtt gggaagctat agagaaagaa 1080
gagtaaattt tagtaaagga ggtttaaaca aacaaaatat aaagagaaat aggaacttga 1140
atcaaggaaa tgattttaaa acgcagtatt cttagtggac tagaggaaaa aaataatctg 1200
agccaagtag aagacctttt cccctcctac ccctactttc taagtcacag aggctttttg 1260
ttcccccaga cactcttgca gattagtcca ggcagaaaca gttagatgtc cccagttaac 1320
ctcctatttg acaccactga ttaccccatt gatagtcaca ctttgggttg taagtgactt 1380
tttatttatt tgtatttttg actgcattaa gaggtctcta gtttttttatc tcttgtttcc 1440 caaaacctaa taagtaacta atgcacagag cacattgatt tgtatttatt ctatttttag 1500
acataattta ttagcatgca tgagcaaatt aagaaaaaca acaacaaatg aatgcatata 1560
tatgtatatg tatgtgtgta tatatacaca catatatata tatatttttt cttttcttac 1620
cagaaggttt taatccaaat aaggagaaga tatgcttaga accgaggtag agttttcatc 1680
cattctgtcc tgtaagtatt ttgcatattc tggagacgca ggaagagatc catctacata 1740
tcccaaagct gaattatggt agacaaaact cttccacttt tagtgcatca acttcttatt 1800
tgtgtaataa gaaaattggg aaaacgatct tcaatatgct taccaagctg tgattccaaa 1860
tattacgtaa atacacttgc aaaggaggat gtttttagta gcaatttgta ctgatggtat 1920
ggggccaaga gatatatctt agagggaggg ctgagggttt gaagtccaac tcctaagcca 1980
gtgccagaag agccaaggac aggtacggct gtcatcactt agacctcacc ctgtggagcc 2040
acaccctagg gttggccaat ctactcccag gagcagggag ggcaggagcc agggctgggc 2100
ataaaagtca gggcagagcc atctattgct tacatttgct tctgacacaa ctgtgttcac 2160
tagcaacctc aaacagacac catggtgcat ctgactcct 2199

<210> SEQ ID NO 100
<211> LENGTH: 2218
<212> TYPE: DNA
<213> ORGANISM: Artificial Sequence
<220> FEATURE:
<223> OTHER INFORMATION: Synthetic: Donor DNA, HBB locus RHA (used for E6V to E6, AAV.323)

<400> SEQUENCE: 100
actgccctgt ggggcaaggt gaacgtggat gaagttggtg gtgaggccct gggcaggttg 60
gtatcaaggt tacaagacag gtttaaggag accaatagaa actgggcatg tggagacaga 120
gaagactctt gggtttctga taggcactga ctctctctgc ctattggtct attttcccac 180
ccttaggctg ctggtggtct acccttggac ccagaggttc tttgagtcct ttggggatct 240
gtccactcct gatgctgtta tgggcaaccc taaggtgaag gctcatggca agaaagtgct 300

-continued

```
cggtgccttt agtgatggcc tggctcacct ggacaacctc aagggcacct ttgccacact    360

gagtgagctg cactgtgaca agctgcacgt ggatcctgag aacttcaggg tgagtctatg    420

ggacgcttga tgttttcttt ccccttcttt tctatggtta agttcatgtc ataggaaggg    480

gataagtaac agggtacagt ttagaatggg aaacagacga atgattgcat cagtgtggaa    540

gtctcaggat cgttttagtt tcttttattt gctgttcata acaattgttt tcttttgttt    600

aattcttgct ttcttttttt ttcttctccg caatttttac tattatactt aatgccttaa    660

cattgtgtat aacaaaagga aatatctctg agatacatta agtaacttaa aaaaaaactt    720

tacacagtct gcctagtaca ttactatttg gaatatatgt gtgcttattt gcatattcat    780

aatctcccta ctttatttc ttttatttt aattgataca taatcattat acatatttat    840

gggttaaagt gtaatgtttt aatatgtgta cacatattga ccaaatcagg gtaattttgc    900

atttgtaatt ttaaaaaatg ctttcttctt ttaatatact tttttgttta tcttatttct    960

aatactttcc ctaatctctt tctttcaggg caataatgat acaatgtatc atgcctcttt   1020

gcaccattct aaagaataac agtgataatt tctgggttaa ggcaatagca atatctctgc   1080

atataaatat ttctgcatat aaattgtaac tgatgtaaga ggtttcatat tgctaatagc   1140

agctacaatc cagctaccat tctgctttta ttttatggtt gggataaggc tggattattc   1200

tgagtccaag ctaggccctt ttgctaatca tgttcatacc tcttatcttc ctcccacagc   1260

tcctgggcaa cgtgctggtc tgtgtgctgg cccatcactt tggcaaagaa ttcaccccac   1320

cagtgcaggc tgcctatcag aaagtggtgg ctggtgtggc taatgccctg gcccacaagt   1380

atcactaagc tcgctttctt gctgtccaat ttctattaaa ggttcctttg ttccctaagt   1440

ccaactacta aactggggga tattatgaag ggccttgagc atctggattc tgcctaataa   1500

aaaacattta ttttcattgc aatgatgtat ttaaattatt tctgaatatt ttactaaaaa   1560

gggaatgtgg gaggtcagtg catttaaaac ataaagaaat gaagagctag ttcaaacctt   1620

gggaaaatac actatatctt aaactccatg aaagaaggtg aggctgcaaa cagctaatgc   1680

acattggcaa cagcccctga tgcatatgcc ttattcatcc ctcagaaaag gattcaagta   1740

gaggcttgat ttggaggtta aagttttgct atgctgtatt ttacattact tattgtttta   1800

gctgtcctca tgaatgtctt ttcactaccc atttgcttat cctgcatctc tcagccttga   1860

ctccactcag ttctcttgct tagagatacc acctttcccc tgaagtgttc cttccatgtt   1920

ttacggcgag atggtttctc ctcgcctggc cactcagcct tagttgtctc tgttgtctta   1980

tagaggtcta cttgaagaag gaaaaacagg ggtcatggtt tgactgtcct gtgagccctt   2040

cttccctgcc tcccccactc acagtgaccc ggaatctgca gtgctagtct cccggaacta   2100

tcactctttc acagtctgct ttggaaggac tgggcttagt atgaaaagtt aggactgaga   2160

agaatttgaa aggcggcttt ttgtagcttg atattcacta ctgtcttatt accctgtc     2218
```

<210> SEQ ID NO 101
<211> LENGTH: 1421
<212> TYPE: DNA
<213> ORGANISM: Artificial Sequence
<220> FEATURE:
<223> OTHER INFORMATION: Synthetic: Donor DNA, HBB exons 1-3

<400> SEQUENCE: 101

```
atggtgcatc tgactcctga agaaaaatcc gctgtcactg ccctgtgggg caaggtgaac     60

gtggatgaag ttggtggtga ggccctgggc aggttggtat caaggttaca agacaggttt    120
```

-continued

```
aaggagacca atagaaactg ggcatgtgga gacagagaag actcttgggt ttctgatagg    180

cactgactct ctctgcctat tggtctattt tcccaccctt aggctgctgg tggtctaccc    240

ttggacccag aggttctttg agtcctttgg ggatctgtcc actcctgatg ctgttatggg    300

caaccctaag gtgaaggctc atggcaagaa agtgctcggt gcctttagtg atggcctggc    360

tcacctggac aacctcaagg gcacctttgc cacactgagt gagctgcact gtgacaagct    420

gcacgtggat cctgagaact tcagggtgag tctatgggac gcttgatgtt ttctttcccc    480

ttcttttcta tggttaagtt catgtcatag gaaggggata agtaacaggg tacagtttag    540

aatgggaaac agacgaatga ttgcatcagt gtggaagtct caggatcgtt ttagtttctt    600

ttatttgctg ttcataacaa ttgttttctt ttgtttaatt cttgctttct ttttttttct    660

tctccgcaat ttttactatt atacttaatg ccttaacatt gtgtataaca aaaggaaata    720

tctctgagat acattaagta acttaaaaaa aaactttaca cagtctgcct agtacattac    780

tatttggaat atatgtgtgc ttatttgcat attcataatc tccctacttt attttctttt    840

atttttaatt gatacataat cattatacat atttatgggt taaagtgtaa tgttttaata    900

tgtgtacaca tattgaccaa atcagggtaa ttttgcattt gtaattttaa aaaatgcttt    960

cttcttttaa tatacttttt tgtttatctt atttctaata ctttccctaa tctctttctt   1020

tcagggcaat aatgatacaa tgtatcatgc ctctttgcac cattctaaag aataacagtg   1080

ataatttctg ggttaaggca atagcaatat ctctgcatat aaatatttct gcatataaat   1140

tgtaactgat gtaagaggtt tcatattgct aatagcagct acaatccagc taccattctg   1200

cttttatttt atggttggga taaggctgga ttattctgag tccaagctag gcccttttgc   1260

taatcatgtt catacctctt atcttcctcc cacagctcct gggcaacgtg ctggtctgtg   1320

tgctggccca tcactttggc aaagaattca ccccaccagt gcaggctgcc tatcagaaag   1380

tggtggctgg tgtggctaat gccctggccc acaagtatca c                        1421
```

<210> SEQ ID NO 102
<211> LENGTH: 18
<212> TYPE: DNA
<213> ORGANISM: Artificial Sequence
<220> FEATURE:
<223> OTHER INFORMATION: Synthetic: Donor DNA, E6V to E6 Insert

<400> SEQUENCE: 102

```
gaagaaaaat ccgctgtc                                                    18
```

<210> SEQ ID NO 103
<211> LENGTH: 1404
<212> TYPE: PRT
<213> ORGANISM: Streptococcus pyogenes
<220> FEATURE:
<221> NAME/KEY: misc_feature
<222> LOCATION: (1)..(1404)
<223> OTHER INFORMATION: Wild-type S. pyogenes Cas9

<400> SEQUENCE: 103

```
Met Ala Pro Lys Lys Lys Arg Lys Val Gly Ser Gly Gly Ser Gly Gly
1               5                   10                  15

Ser Gly Asp Lys Lys Tyr Ser Ile Gly Leu Asp Ile Gly Thr Asn Ser
            20                  25                  30

Val Gly Trp Ala Val Ile Thr Asp Glu Tyr Lys Val Pro Ser Lys Lys
        35                  40                  45

Phe Lys Val Leu Gly Asn Thr Asp Arg His Ser Ile Lys Lys Asn Leu
    50                  55                  60
```

```
Ile Gly Ala Leu Leu Phe Asp Ser Gly Glu Thr Ala Glu Ala Thr Arg
65                  70                  75                  80

Leu Lys Arg Thr Ala Arg Arg Arg Tyr Thr Arg Arg Lys Asn Arg Ile
                85                  90                  95

Cys Tyr Leu Gln Glu Ile Phe Ser Asn Glu Met Ala Lys Val Asp Asp
            100                 105                 110

Ser Phe Phe His Arg Leu Glu Glu Ser Phe Leu Val Glu Glu Asp Lys
        115                 120                 125

Lys His Glu Arg His Pro Ile Phe Gly Asn Ile Val Asp Glu Val Ala
    130                 135                 140

Tyr His Glu Lys Tyr Pro Thr Ile Tyr His Leu Arg Lys Lys Leu Val
145                 150                 155                 160

Asp Ser Thr Asp Lys Ala Asp Leu Arg Leu Ile Tyr Leu Ala Leu Ala
                165                 170                 175

His Met Ile Lys Phe Arg Gly His Phe Leu Ile Glu Gly Asp Leu Asn
            180                 185                 190

Pro Asp Asn Ser Asp Val Asp Lys Leu Phe Ile Gln Leu Val Gln Thr
        195                 200                 205

Tyr Asn Gln Leu Phe Glu Glu Asn Pro Ile Asn Ala Ser Gly Val Asp
    210                 215                 220

Ala Lys Ala Ile Leu Ser Ala Arg Leu Ser Lys Ser Arg Arg Leu Glu
225                 230                 235                 240

Asn Leu Ile Ala Gln Leu Pro Gly Glu Lys Lys Asn Gly Leu Phe Gly
                245                 250                 255

Asn Leu Ile Ala Leu Ser Leu Gly Leu Thr Pro Asn Phe Lys Ser Asn
            260                 265                 270

Phe Asp Leu Ala Glu Asp Ala Lys Leu Gln Leu Ser Lys Asp Thr Tyr
        275                 280                 285

Asp Asp Asp Leu Asp Asn Leu Leu Ala Gln Ile Gly Asp Gln Tyr Ala
    290                 295                 300

Asp Leu Phe Leu Ala Ala Lys Asn Leu Ser Asp Ala Ile Leu Leu Ser
305                 310                 315                 320

Asp Ile Leu Arg Val Asn Thr Glu Ile Thr Lys Ala Pro Leu Ser Ala
                325                 330                 335

Ser Met Ile Lys Arg Tyr Asp Glu His His Gln Asp Leu Thr Leu Leu
            340                 345                 350

Lys Ala Leu Val Arg Gln Gln Leu Pro Glu Lys Tyr Lys Glu Ile Phe
        355                 360                 365

Phe Asp Gln Ser Lys Asn Gly Tyr Ala Gly Tyr Ile Asp Gly Gly Ala
    370                 375                 380

Ser Gln Glu Glu Phe Tyr Lys Phe Ile Lys Pro Ile Leu Glu Lys Met
385                 390                 395                 400

Asp Gly Thr Glu Glu Leu Leu Val Lys Leu Asn Arg Glu Asp Leu Leu
                405                 410                 415

Arg Lys Gln Arg Thr Phe Asp Asn Gly Ser Ile Pro His Gln Ile His
            420                 425                 430

Leu Gly Glu Leu His Ala Ile Leu Arg Arg Gln Glu Asp Phe Tyr Pro
        435                 440                 445

Phe Leu Lys Asp Asn Arg Glu Lys Ile Glu Lys Ile Leu Thr Phe Arg
    450                 455                 460

Ile Pro Tyr Tyr Val Gly Pro Leu Ala Arg Gly Asn Ser Arg Phe Ala
465                 470                 475                 480
```

-continued

```
Trp Met Thr Arg Lys Ser Glu Glu Thr Ile Thr Pro Trp Asn Phe Glu
                485                 490                 495

Glu Val Val Asp Lys Gly Ala Ser Ala Gln Ser Phe Ile Glu Arg Met
            500                 505                 510

Thr Asn Phe Asp Lys Asn Leu Pro Asn Glu Lys Val Leu Pro Lys His
        515                 520                 525

Ser Leu Leu Tyr Glu Tyr Phe Thr Val Tyr Asn Glu Leu Thr Lys Val
    530                 535                 540

Lys Tyr Val Thr Glu Gly Met Arg Lys Pro Ala Phe Leu Ser Gly Glu
545                 550                 555                 560

Gln Lys Lys Ala Ile Val Asp Leu Leu Phe Lys Thr Asn Arg Lys Val
                565                 570                 575

Thr Val Lys Gln Leu Lys Glu Asp Tyr Phe Lys Lys Ile Glu Cys Phe
            580                 585                 590

Asp Ser Val Glu Ile Ser Gly Val Glu Asp Arg Phe Asn Ala Ser Leu
        595                 600                 605

Gly Thr Tyr His Asp Leu Leu Lys Ile Ile Lys Asp Lys Asp Phe Leu
    610                 615                 620

Asp Asn Glu Glu Asn Glu Asp Ile Leu Glu Asp Ile Val Leu Thr Leu
625                 630                 635                 640

Thr Leu Phe Glu Asp Arg Glu Met Ile Glu Glu Arg Leu Lys Thr Tyr
                645                 650                 655

Ala His Leu Phe Asp Asp Lys Val Met Lys Gln Leu Lys Arg Arg Arg
            660                 665                 670

Tyr Thr Gly Trp Gly Arg Leu Ser Arg Lys Leu Ile Asn Gly Ile Arg
        675                 680                 685

Asp Lys Gln Ser Gly Lys Thr Ile Leu Asp Phe Leu Lys Ser Asp Gly
    690                 695                 700

Phe Ala Asn Arg Asn Phe Met Gln Leu Ile His Asp Asp Ser Leu Thr
705                 710                 715                 720

Phe Lys Glu Asp Ile Gln Lys Ala Gln Val Ser Gly Gln Gly Asp Ser
                725                 730                 735

Leu His Glu His Ile Ala Asn Leu Ala Gly Ser Pro Ala Ile Lys Lys
            740                 745                 750

Gly Ile Leu Gln Thr Val Lys Val Val Asp Glu Leu Val Lys Val Met
        755                 760                 765

Gly Arg His Lys Pro Glu Asn Ile Val Ile Glu Met Ala Arg Glu Asn
    770                 775                 780

Gln Thr Thr Gln Lys Gly Gln Lys Asn Ser Arg Glu Arg Met Lys Arg
785                 790                 795                 800

Ile Glu Glu Gly Ile Lys Glu Leu Gly Ser Gln Ile Leu Lys Glu His
                805                 810                 815

Pro Val Glu Asn Thr Gln Leu Gln Asn Glu Lys Leu Tyr Leu Tyr Tyr
            820                 825                 830

Leu Gln Asn Gly Arg Asp Met Tyr Val Asp Gln Glu Leu Asp Ile Asn
        835                 840                 845

Arg Leu Ser Asp Tyr Asp Val Asp His Ile Val Pro Gln Ser Phe Leu
    850                 855                 860

Lys Asp Asp Ser Ile Asp Asn Lys Val Leu Thr Arg Ser Asp Lys Asn
865                 870                 875                 880

Arg Gly Lys Ser Asp Asn Val Pro Ser Glu Glu Val Val Lys Lys Met
                885                 890                 895

Lys Asn Tyr Trp Arg Gln Leu Leu Asn Ala Lys Leu Ile Thr Gln Arg
```

```
            900                 905                 910

Lys Phe Asp Asn Leu Thr Lys Ala Glu Arg Gly Gly Leu Ser Glu Leu
        915                 920                 925

Asp Lys Ala Gly Phe Ile Lys Arg Gln Leu Val Glu Thr Arg Gln Ile
    930                 935                 940

Thr Lys His Val Ala Gln Ile Leu Asp Ser Arg Met Asn Thr Lys Tyr
945                 950                 955                 960

Asp Glu Asn Asp Lys Leu Ile Arg Glu Val Lys Val Ile Thr Leu Lys
                965                 970                 975

Ser Lys Leu Val Ser Asp Phe Arg Lys Asp Phe Gln Phe Tyr Lys Val
            980                 985                 990

Arg Glu Ile Asn Asn Tyr His His  Ala His Asp Ala Tyr  Leu Asn Ala
        995                 1000                1005

Val Val  Gly Thr Ala Leu Ile  Lys Lys Tyr Pro Lys  Leu Glu Ser
    1010                 1015                 1020

Glu Phe  Val Tyr Gly Asp Tyr  Lys Val Tyr Asp Val  Arg Lys Met
    1025                 1030                 1035

Ile Ala  Lys Ser Glu Gln Glu  Ile Gly Lys Ala Thr  Ala Lys Tyr
    1040                 1045                 1050

Phe Phe  Tyr Ser Asn Ile Met  Asn Phe Phe Lys Thr  Glu Ile Thr
    1055                 1060                 1065

Leu Ala  Asn Gly Glu Ile Arg  Lys Arg Pro Leu Ile  Glu Thr Asn
    1070                 1075                 1080

Gly Glu  Thr Gly Glu Ile Val  Trp Asp Lys Gly Arg  Asp Phe Ala
    1085                 1090                 1095

Thr Val  Arg Lys Val Leu Ser  Met Pro Gln Val Asn  Ile Val Lys
    1100                 1105                 1110

Lys Thr  Glu Val Gln Thr Gly  Gly Phe Ser Lys Glu  Ser Ile Leu
    1115                 1120                 1125

Pro Lys  Arg Asn Ser Asp Lys  Leu Ile Ala Arg Lys  Lys Asp Trp
    1130                 1135                 1140

Asp Pro  Lys Lys Tyr Gly Gly  Phe Asp Ser Pro Thr  Val Ala Tyr
    1145                 1150                 1155

Ser Val  Leu Val Val Ala Lys  Val Glu Lys Gly Lys  Ser Lys Lys
    1160                 1165                 1170

Leu Lys  Ser Val Lys Glu Leu  Leu Gly Ile Thr Ile  Met Glu Arg
    1175                 1180                 1185

Ser Ser  Phe Glu Lys Asn Pro  Ile Asp Phe Leu Glu  Ala Lys Gly
    1190                 1195                 1200

Tyr Lys  Glu Val Lys Lys Asp  Leu Ile Ile Lys Leu  Pro Lys Tyr
    1205                 1210                 1215

Ser Leu  Phe Glu Leu Glu Asn  Gly Arg Lys Arg Met  Leu Ala Ser
    1220                 1225                 1230

Ala Gly  Glu Leu Gln Lys Gly  Asn Glu Leu Ala Leu  Pro Ser Lys
    1235                 1240                 1245

Tyr Val  Asn Phe Leu Tyr Leu  Ala Ser His Tyr Glu  Lys Leu Lys
    1250                 1255                 1260

Gly Ser  Pro Glu Asp Asn Glu  Gln Lys Gln Leu Phe  Val Glu Gln
    1265                 1270                 1275

His Lys  His Tyr Leu Asp Glu  Ile Ile Glu Gln Ile  Ser Glu Phe
    1280                 1285                 1290

Ser Lys  Arg Val Ile Leu Ala  Asp Ala Asn Leu Asp  Lys Val Leu
    1295                 1300                 1305
```

Ser Ala Tyr Asn Lys His Arg Asp Lys Pro Ile Arg Glu Gln Ala
1310 1315 1320

Glu Asn Ile Ile His Leu Phe Thr Leu Thr Asn Leu Gly Ala Pro
1325 1330 1335

Ala Ala Phe Lys Tyr Phe Asp Thr Thr Ile Asp Arg Lys Arg Tyr
1340 1345 1350

Thr Ser Thr Lys Glu Val Leu Asp Ala Thr Leu Ile His Gln Ser
1355 1360 1365

Ile Thr Gly Leu Tyr Glu Thr Arg Ile Asp Leu Ser Gln Leu Gly
1370 1375 1380

Gly Asp Gly Ser Ala Gly Ser Gly Gly Ser Gly Gly Ser Gly Pro
1385 1390 1395

Lys Lys Lys Arg Lys Val
1400

<210> SEQ ID NO 104
<211> LENGTH: 1105
<212> TYPE: PRT
<213> ORGANISM: Staphylococcus aureus
<220> FEATURE:
<221> NAME/KEY: misc_feature
<222> LOCATION: (1)..(1105)
<223> OTHER INFORMATION: Wild-type S. aureus Cas9

<400> SEQUENCE: 104

Met His His His His His His His His Gly Ser Gly Gly Ser Gly Gly
1 5 10 15

Ser Gly Pro Lys Lys Lys Arg Lys Val Gly Ser Gly Gly Ser Gly Gly
20 25 30

Ser Gly Lys Arg Asn Tyr Ile Leu Gly Leu Asp Ile Gly Ile Thr Ser
35 40 45

Val Gly Tyr Gly Ile Ile Asp Tyr Glu Thr Arg Asp Val Ile Asp Ala
50 55 60

Gly Val Arg Leu Phe Lys Glu Ala Asn Val Glu Asn Asn Glu Gly Arg
65 70 75 80

Arg Ser Lys Arg Gly Ala Arg Arg Leu Lys Arg Arg Arg Arg His Arg
85 90 95

Ile Gln Arg Val Lys Lys Leu Leu Phe Asp Tyr Asn Leu Leu Thr Asp
100 105 110

His Ser Glu Leu Ser Gly Ile Asn Pro Tyr Glu Ala Arg Val Lys Gly
115 120 125

Leu Ser Gln Lys Leu Ser Glu Glu Glu Phe Ser Ala Ala Leu Leu His
130 135 140

Leu Ala Lys Arg Arg Gly Val His Asn Val Asn Glu Val Glu Glu Asp
145 150 155 160

Thr Gly Asn Glu Leu Ser Thr Lys Glu Gln Ile Ser Arg Asn Ser Lys
165 170 175

Ala Leu Glu Glu Lys Tyr Val Ala Glu Leu Gln Leu Glu Arg Leu Lys
180 185 190

Lys Asp Gly Glu Val Arg Gly Ser Ile Asn Arg Phe Lys Thr Ser Asp
195 200 205

Tyr Val Lys Glu Ala Lys Gln Leu Leu Lys Val Gln Lys Ala Tyr His
210 215 220

Gln Leu Asp Gln Ser Phe Ile Asp Thr Tyr Ile Asp Leu Leu Glu Thr
225 230 235 240

-continued

```
Arg Arg Thr Tyr Tyr Glu Gly Pro Gly Glu Gly Ser Pro Phe Gly Trp
                245                 250                 255

Lys Asp Ile Lys Glu Trp Tyr Glu Met Leu Met Gly His Cys Thr Tyr
            260                 265                 270

Phe Pro Glu Glu Leu Arg Ser Val Lys Tyr Ala Tyr Asn Ala Asp Leu
        275                 280                 285

Tyr Asn Ala Leu Asn Asp Leu Asn Asn Leu Val Ile Thr Arg Asp Glu
    290                 295                 300

Asn Glu Lys Leu Glu Tyr Tyr Glu Lys Phe Gln Ile Ile Glu Asn Val
305                 310                 315                 320

Phe Lys Gln Lys Lys Lys Pro Thr Leu Lys Gln Ile Ala Lys Glu Ile
                325                 330                 335

Leu Val Asn Glu Glu Asp Ile Lys Gly Tyr Arg Val Thr Ser Thr Gly
            340                 345                 350

Lys Pro Glu Phe Thr Asn Leu Lys Val Tyr His Asp Ile Lys Asp Ile
        355                 360                 365

Thr Ala Arg Lys Glu Ile Ile Glu Asn Ala Glu Leu Leu Asp Gln Ile
    370                 375                 380

Ala Lys Ile Leu Thr Ile Tyr Gln Ser Ser Glu Asp Ile Gln Glu Glu
385                 390                 395                 400

Leu Thr Asn Leu Asn Ser Glu Leu Thr Gln Glu Glu Ile Glu Gln Ile
                405                 410                 415

Ser Asn Leu Lys Gly Tyr Thr Gly Thr His Asn Leu Ser Leu Lys Ala
            420                 425                 430

Ile Asn Leu Ile Leu Asp Glu Leu Trp His Thr Asn Asp Asn Gln Ile
        435                 440                 445

Ala Ile Phe Asn Arg Leu Lys Leu Val Pro Lys Lys Val Asp Leu Ser
    450                 455                 460

Gln Gln Lys Glu Ile Pro Thr Thr Leu Val Asp Asp Phe Ile Leu Ser
465                 470                 475                 480

Pro Val Val Lys Arg Ser Phe Ile Gln Ser Ile Lys Val Ile Asn Ala
                485                 490                 495

Ile Ile Lys Lys Tyr Gly Leu Pro Asn Asp Ile Ile Ile Glu Leu Ala
            500                 505                 510

Arg Glu Lys Asn Ser Lys Asp Ala Gln Lys Met Ile Asn Glu Met Gln
        515                 520                 525

Lys Arg Asn Arg Gln Thr Asn Glu Arg Ile Glu Glu Ile Ile Arg Thr
    530                 535                 540

Thr Gly Lys Glu Asn Ala Lys Tyr Leu Ile Glu Lys Ile Lys Leu His
545                 550                 555                 560

Asp Met Gln Glu Gly Lys Cys Leu Tyr Ser Leu Glu Ala Ile Pro Leu
                565                 570                 575

Glu Asp Leu Leu Asn Asn Pro Phe Asn Tyr Glu Val Asp His Ile Ile
            580                 585                 590

Pro Arg Ser Val Ser Phe Asp Asn Ser Phe Asn Asn Lys Val Leu Val
        595                 600                 605

Lys Gln Glu Glu Asn Ser Lys Lys Gly Asn Arg Thr Pro Phe Gln Tyr
    610                 615                 620

Leu Ser Ser Ser Asp Ser Lys Ile Ser Tyr Glu Thr Phe Lys Lys His
625                 630                 635                 640

Ile Leu Asn Leu Ala Lys Gly Lys Gly Arg Ile Ser Lys Thr Lys Lys
                645                 650                 655

Glu Tyr Leu Leu Glu Glu Arg Asp Ile Asn Arg Phe Ser Val Gln Lys
```

```
            660                 665                 670

Asp Phe Ile Asn Arg Asn Leu Val Asp Thr Arg Tyr Ala Thr Arg Gly
        675                 680                 685

Leu Met Asn Leu Leu Arg Ser Tyr Phe Arg Val Asn Asn Leu Asp Val
    690                 695                 700

Lys Val Lys Ser Ile Asn Gly Gly Phe Thr Ser Phe Leu Arg Arg Lys
705                 710                 715                 720

Trp Lys Phe Lys Lys Glu Arg Asn Lys Gly Tyr Lys His His Ala Glu
                725                 730                 735

Asp Ala Leu Ile Ile Ala Asn Ala Asp Phe Ile Phe Lys Glu Trp Lys
            740                 745                 750

Lys Leu Asp Lys Ala Lys Lys Val Met Glu Asn Gln Met Phe Glu Glu
        755                 760                 765

Lys Gln Ala Glu Ser Met Pro Glu Ile Glu Thr Glu Gln Glu Tyr Lys
    770                 775                 780

Glu Ile Phe Ile Thr Pro His Gln Ile Lys His Ile Lys Asp Phe Lys
785                 790                 795                 800

Asp Tyr Lys Tyr Ser His Arg Val Asp Lys Lys Pro Asn Arg Glu Leu
                805                 810                 815

Ile Asn Asp Thr Leu Tyr Ser Thr Arg Lys Asp Asp Lys Gly Asn Thr
            820                 825                 830

Leu Ile Val Asn Asn Leu Asn Gly Leu Tyr Asp Lys Asp Asn Asp Lys
        835                 840                 845

Leu Lys Lys Leu Ile Asn Lys Ser Pro Glu Lys Leu Leu Met Tyr His
    850                 855                 860

His Asp Pro Gln Thr Tyr Gln Lys Leu Lys Leu Ile Met Glu Gln Tyr
865                 870                 875                 880

Gly Asp Glu Lys Asn Pro Leu Tyr Lys Tyr Tyr Glu Glu Thr Gly Asn
                885                 890                 895

Tyr Leu Thr Lys Tyr Ser Lys Lys Asp Asn Gly Pro Val Ile Lys Lys
            900                 905                 910

Ile Lys Tyr Tyr Gly Asn Lys Leu Asn Ala His Leu Asp Ile Thr Asp
        915                 920                 925

Asp Tyr Pro Asn Ser Arg Asn Lys Val Val Lys Leu Ser Leu Lys Pro
    930                 935                 940

Tyr Arg Phe Asp Val Tyr Leu Asp Asn Gly Val Tyr Lys Phe Val Thr
945                 950                 955                 960

Val Lys Asn Leu Asp Val Ile Lys Lys Glu Asn Tyr Tyr Glu Val Asn
                965                 970                 975

Ser Lys Cys Tyr Glu Glu Ala Lys Lys Leu Lys Lys Ile Ser Asn Gln
            980                 985                 990

Ala Glu Phe Ile Ala Ser Phe Tyr  Asn Asn Asp Leu Ile  Lys Ile Asn
        995                 1000                 1005

Gly Glu  Leu Tyr Arg Val Ile  Gly Val Asn Asn Asp  Leu Leu Asn
    1010                 1015                 1020

Arg Ile  Glu Val Asn Met Ile  Asp Ile Thr Tyr Arg  Glu Tyr Leu
    1025                 1030                 1035

Glu Asn  Met Asn Asp Lys Arg  Pro Pro Arg Ile Ile  Lys Thr Ile
    1040                 1045                 1050

Ala Ser  Lys Thr Gln Ser Ile  Lys Lys Tyr Ser Thr  Asp Ile Leu
    1055                 1060                 1065

Gly Asn  Leu Tyr Glu Val Lys  Ser Lys Lys His Pro  Gln Ile Ile
    1070                 1075                 1080
```

```
Lys Lys Gly Gly Ser Ala Gly Ser Gly Gly Ser Gly Gly Ser Gly
    1085                1090                1095

Pro Lys Lys Lys Arg Lys Val
    1100                1105


<210> SEQ ID NO 105
<211> LENGTH: 7107
<212> TYPE: DNA
<213> ORGANISM: Artificial Sequence
<220> FEATURE:
<223> OTHER INFORMATION: Synthetic: Donor template, Full AAV-323

<400> SEQUENCE: 105

cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcac gcgtcttgct ttgacaattt tggtctttca gaatactata    180

aatataacct atattataat ttcataaagt ctgtgcattt tctttgaccc aggatatttg    240

caaaagacat attcaaactt ccgcagaaca ctttatttca catatacatg cctcttatat    300

cagggatgtg aaacagggtc ttgaaaactg tctaaatcta aaacaatgct aatgcaggtt    360

taaatttaat aaaataaaat ccaaaatcta acagccaagt caaatctgca tgttttaaca    420

tttaaaatat tttaaagacg tcttttccca ggattcaaca tgtgaaatct tttctcaggg    480

atacacgtgt gcctagatcc tcattgcttt agttttttac agaggaatga atataaaaag    540

aaaatactta aattttatcc ctcttacctc tataatcata cataggcata attttttaac    600

ctaggctcca gatagccata gaagaaccaa acactttctg cgtgtgtgag aataatcaga    660

gtgagatttt ttcacaagta cctgatgagg gttgagacag gtagaaaaag tgagagatct    720

ctatttattt agcaataata gagaaagcat ttaagagaat aaagcaatgg aaataagaaa    780

tttgtaaatt tccttctgat aactagaaat agaggatcca gtttcttttg gttaacctaa    840

attttatttc attttattgt tttattttat tttattttat tttattttgt gtaatcgtag    900

tttcagagtg ttagagctga aaggaagaag taggagaaac atgcaaagta aaagtataac    960

actttcctta ctaaaccgac atgggtttcc aggtaggggc aggattcagg atgactgaca   1020

gggcccttag ggaacactga gaccctacgc tgacctcata aatgcttgct acctttgctg   1080

ttttaattac atcttttaat agcaggaagc agaactctgc acttcaaaag tttttcctca   1140

cctgaggagt taatttagta caaggggaaa aagtacaggg ggatgggaga aaggcgatca   1200

cgttgggaag ctatagagaa agaagagtaa attttagtaa aggaggttta aacaaacaaa   1260

atataaagag aaataggaac ttgaatcaag gaaatgattt taaaacgcag tattcttagt   1320

ggactagagg aaaaaaataa tctgagccaa gtagaagacc ttttcccctc ctacccctac   1380

tttctaagtc acagaggctt tttgttcccc cagacactct tgcagattag tccaggcaga   1440

aacagttaga tgtccccagt taacctccta tttgacacca ctgattaccc cattgatagt   1500

cacactttgg gttgtaagtg actttttatt tatttgtatt tttgactgca ttaagaggtc   1560

tctagttttt tatctcttgt ttcccaaaac ctaataagta actaatgcac agagcacatt   1620

gatttgtatt tattctattt ttagacataa tttattagca tgcatgagca aattaagaaa   1680

aacaacaaca aatgaatgca tatatatgta tatgtatgtg tgtatatata cacacatata   1740

tatatatatt ttttcttttc ttaccagaag gttttaatcc aaataaggag aagatatgct   1800

tagaaccgag gtagagtttt catccattct gtcctgtaag tattttgcat attctggaga   1860
```

-continued

```
cgcaggaaga gatccatcta catatcccaa agctgaatta tggtagacaa aactcttcca   1920
cttttagtgc atcaacttct tatttgtgta ataagaaaat tgggaaaacg atcttcaata   1980
tgcttaccaa gctgtgattc caaatattac gtaaatacac ttgcaaagga ggatgttttt   2040
agtagcaatt tgtactgatg gtatggggcc aagagatata tcttagaggg agggctgagg   2100
gtttgaagtc caactcctaa gccagtgcca gaagagccaa ggacaggtac ggctgtcatc   2160
acttagacct caccctgtgg agccacaccc tagggttggc caatctactc ccaggagcag   2220
ggagggcagg agccagggct gggcataaaa gtcagggcag agccatctat tgcttacatt   2280
tgcttctgac acaactgtgt tcactagcaa cctcaaacag acaccatggt gcatctgact   2340
cctgaagaaa aatccgctgt cactgccctg tggggcaagg tgaacgtgga tgaagttggt   2400
ggtgaggccc tgggcaggtt ggtatcaagg ttacaagaca ggtttaagga gaccaataga   2460
aactgggcat gtggagacag agaagactct tgggtttctg ataggcactg actctctctg   2520
cctattggtc tattttccca cccttaggct gctggtggtc tacccttgga cccagaggtt   2580
ctttgagtcc tttggggatc tgtccactcc tgatgctgtt atgggcaacc ctaaggtgaa   2640
ggctcatggc aagaaagtgc tcggtgcctt tagtgatggc ctggctcacc tggacaacct   2700
caagggcacc tttgccacac tgagtgagct gcactgtgac aagctgcacg tggatcctga   2760
gaacttcagg gtgagtctat gggacgcttg atgttttctt tccccttctt ttctatggtt   2820
aagttcatgt cataggaagg ggataagtaa cagggtacag tttagaatgg gaaacagacg   2880
aatgattgca tcagtgtgga agtctcagga tcgttttagt ttcttttatt tgctgttcat   2940
aacaattgtt ttcttttgtt taattcttgc tttctttttt tttcttctcc gcaattttta   3000
ctattatact taatgcctta acattgtgta taacaaaagg aaatatctct gagatacatt   3060
aagtaactta aaaaaaaact ttacacagtc tgcctagtac attactattt ggaatatatg   3120
tgtgcttatt tgcatattca taatctccct actttatttt cttttatttt taattgatac   3180
ataatcatta tacatattta tgggttaaag tgtaatgttt taatatgtgt acacatattg   3240
accaaatcag ggtaattttg catttgtaat tttaaaaaat gctttcttct tttaatatac   3300
ttttttgttt atcttatttc taatactttc cctaatctct ttctttcagg gcaataatga   3360
tacaatgtat catgcctctt tgcaccattc taaagaataa cagtgataat ttctgggtta   3420
aggcaatagc aatatctctg catataaata tttctgcata taaattgtaa ctgatgtaag   3480
aggtttcata ttgctaatag cagctacaat ccagctacca ttctgctttt attttatggt   3540
tgggataagg ctggattatt ctgagtccaa gctaggccct tttgctaatc atgttcatac   3600
ctcttatctt cctcccacag ctcctgggca acgtgctggt ctgtgtgctg gcccatcact   3660
ttggcaaaga attcacccca ccagtgcagg ctgcctatca gaaagtggtg gctggtgtgg   3720
ctaatgccct ggcccacaag tatcactaag ctcgctttct tgctgtccaa tttctattaa   3780
aggttccttt gttccctaag tccaactact aaactggggg atattatgaa gggccttgag   3840
catctggatt ctgcctaata aaaaacattt attttcattg caatgatgta tttaaattat   3900
ttctgaatat tttactaaaa agggaatgtg ggaggtcagt gcatttaaaa cataaagaaa   3960
tgaagagcta gttcaaacct tgggaaaata cactatatct taaactccat gaaagaaggt   4020
gaggctgcaa acagctaatg cacattggca acagcccctg atgcatatgc cttattcatc   4080
cctcagaaaa ggattcaagt agaggcttga tttggaggtt aaagttttgc tatgctgtat   4140
tttacattac ttattgtttt agctgtcctc atgaatgtct tttcactacc catttgctta   4200
tcctgcatct ctcagccttg actccactca gttctcttgc ttagagatac cacctttccc   4260
```

-continued ctgaagtgtt ccttccatgt tttacggcga gatggtttct cctcgcctgg ccactcagcc 4320
ttagttgtct ctgttgtctt atagaggtct acttgaagaa ggaaaaacag gggtcatggt 4380
ttgactgtcc tgtgagccct tcttccctgc ctcccccact cacagtgacc cggaatctgc 4440
agtgctagtc tcccggaact atcactcttt cacagtctgc tttggaagga ctgggcttag 4500
tatgaaaagt taggactgag aagaatttga aaggcggctt tttgtagctt gatattcact 4560
actgtcttat taccctgtcg gtaaccacgt gcggccgagg ctgcagcgtc gtcctcccta 4620
ggaaccccta gtgatggagt tggccactcc ctctctgcgc gctcgctcgc tcactgaggc 4680
cgggcgacca aaggtcgccc gacgcccggg ctttgcccgg gcggcctcag tgagcgagcg 4740
agcgcgcagc tgcctgcagg ggcgcctgat gcggtatttt ctccttacgc atctgtgcgg 4800
tatttcacac cgcatacgtc aaagcaacca tagtacgcgc cctgtagcgg cgcattaagc 4860
gcggcgggtg tggtggttac gcgcagcgtg accgctacac ttgccagcgc cctagcgccc 4920
gctcctttcg ctttcttccc ttcctttctc gccacgttcg ccggctttcc ccgtcaagct 4980
ctaaatcggg ggctcccttt agggttccga tttagtgctt tacggcacct cgaccccaaa 5040
aaacttgatt tgggtgatgg ttcacgtagt gggccatcgc cctgatagac ggtttttcgc 5100
cctttgacgt tggagtccac gttctttaat agtggactct tgttccaaac tggaacaaca 5160
ctcaacccta tctcgggcta ttcttttgat ttataaggga ttttgccgat ttcggcctat 5220
tggttaaaaa atgagctgat ttaacaaaaa tttaacgcga attttaacaa aatattaacg 5280
tttacaattt tatggtgcac tctcagtaca atctgctctg atgccgcata gttaagccag 5340
ccccgacacc cgccaacacc cgctgacgcg ccctgacggg cttgtctgct cccggcatcc 5400
gcttacagac aagctgtgac cgtctccggg agctgcatgt gtcagaggtt ttcaccgtca 5460
tcaccgaaac gcgcgagacg aaagggcctc gtgatacgcc tatttttata ggttaatgtc 5520
atgaacaata aaactgtctg cttacataaa cagtaataca aggggtgtta tgagccatat 5580
tcaacgggaa acgtcgaggc cgcgattaaa ttccaacatg gatgctgatt tatatgggta 5640
taaatgggct cgcgataatg tcgggcaatc aggtgcgaca atctatcgct tgtatgggaa 5700
gcccgatgcg ccagagttgt ttctgaaaca tggcaaaggt agcgttgcca atgatgttac 5760
agatgagatg gtcagactaa actggctgac ggaatttatg cctcttccga ccatcaagca 5820
ttttatccgt actcctgatg atgcatggtt actcaccact gcgatccccg gaaaaacagc 5880
attccaggta ttagaagaat atcctgattc aggtgaaaat attgttgatg cgctggcagt 5940
gttcctgcgc cggttgcatt cgattcctgt ttgtaattgt ccttttaaca gcgatcgcgt 6000
atttcgtctc gctcaggcgc aatcacgaat gaataacggt ttggttgatg cgagtgattt 6060
tgatgacgag cgtaatggct ggcctgttga acaagtctgg aaagaaatgc ataaactttt 6120
gccattctca ccggattcag tcgtcactca tggtgatttc tcacttgata accttatttt 6180
tgacgagggg aaattaatag gttgtattga tgttggacga gtcggaatcg cagaccgata 6240
ccaggatctt gccatcctat ggaactgcct cggtgagttt tctccttcat tacagaaacg 6300
gctttttcaa aaatatggta ttgataatcc tgatatgaat aaattgcagt ttcatttgat 6360
gctcgatgag tttttctaat ctcatgacca aaatccctta acgtgagttt tcgttccact 6420
gagcgtcaga ccccgtagaa aagatcaaag gatcttcttg agatcctttt tttctgcgcg 6480
taatctgctg cttgcaaaca aaaaaaccac cgctaccagc ggtggtttgt ttgccggatc 6540
aagagctacc aactcttttt ccgaaggtaa ctggcttcag cagagcgcag ataccaaata 6600

-continued

```
ctgtccttct agtgtagccg tagttaggcc accacttcaa gaactctgta gcaccgccta   6660

catacctcgc tctgctaatc ctgttaccag tggctgctgc cagtggcgat aagtcgtgtc   6720

ttaccgggtt ggactcaaga cgatagttac cggataaggc gcagcggtcg ggctgaacgg   6780

ggggttcgtg cacacagccc agcttggagc gaacgaccta caccgaactg agatacctac   6840

agcgtgagct atgagaaagc gccacgcttc ccgaagggag aaaggcggac aggtatccgg   6900

taagcggcag ggtcggaaca ggagagcgca cgagggagct tccaggggga aacgcctggt   6960

atctttatag tcctgtcggg tttcgccacc tctgacttga gcgtcgattt ttgtgatgct   7020

cgtcaggggg gcggagccta tggaaaaacg ccagcaacgc ggccttttta cggttcctgg   7080

ccttttgctg gccttttgct cacatgt                                       7107
```

<210> SEQ ID NO 106
<211> LENGTH: 130
<212> TYPE: DNA
<213> ORGANISM: Artificial Sequence
<220> FEATURE:
<223> OTHER INFORMATION: Synthetic: AAV2 ITR for LHA (AAV.323)

<400> SEQUENCE: 106

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct                                                           130
```

<210> SEQ ID NO 107
<211> LENGTH: 141
<212> TYPE: DNA
<213> ORGANISM: Artificial Sequence
<220> FEATURE:
<223> OTHER INFORMATION: Synthetic: AAV2 ITR for RHA (AAV.323)

<400> SEQUENCE: 107

```
aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag ctgcctgcag g                                              141
```

<210> SEQ ID NO 108
<211> LENGTH: 4435
<212> TYPE: DNA
<213> ORGANISM: Artificial Sequence
<220> FEATURE:
<223> OTHER INFORMATION: Synthetic: Donor template, HBB Locus LHA to RHA
      (AAV.304)

<400> SEQUENCE: 108

```
cttgctttga caattttggt ctttcagaat actataaata taacctatat tataatttca     60

taaagtctgt gcattttctt tgacccagga tatttgcaaa agacatattc aaacttccgc    120

agaacacttt atttcacata tacatgcctc ttatatcagg gatgtgaaac agggtcttga    180

aaactgtcta aatctaaaac aatgctaatg caggtttaaa tttaataaaa taaaatccaa    240

aatctaacag ccaagtcaaa tctgcatgtt ttaacattta aaatatttta aagacgtctt    300

ttcccaggat tcaacatgtg aaatcttttc tcagggatac acgtgtgcct agatcctcat    360

tgctttagtt ttttacagag gaatgaatat aaaaagaaaa tacttaaatt ttatccctct    420

tacctctata atcatacata ggcataattt tttaacctag gctccagata gccatagaag    480

aaccaaacac tttctgcgtg tgtgagaata atcagagtga gatttttca caagtacctg     540
```

-continued

```
atgagggttg agacaggtag aaaaagtgag agatctctat ttatttagca ataatagaga    600
aagcatttaa gagaataaag caatggaaat aagaaatttg taaatttcct tctgataact    660
agaaatagag gatccagttt cttttggtta acctaaattt tatttcattt tattgtttta    720
ttttatttta ttttatttta ttttgtgtaa tcgtagtttc agagtgttag agctgaaagg    780
aagaagtagg agaaacatgc aaagtaaaag tataacactt tccttactaa accgacatgg    840
gtttccaggt aggggcagga ttcaggatga ctgacagggc ccttagggaa cactgagacc    900
ctacgctgac ctcataaatg cttgctacct ttgctgtttt aattacatct tttaatagca    960
ggaagcagaa ctctgcactt caaaagtttt tcctcacctg aggagttaat ttagtacaag   1020
gggaaaaagt acagggggat gggagaaagg cgatcacgtt gggaagctat agagaaagaa   1080
gagtaaattt tagtaaagga ggtttaaaca aacaaaatat aaagagaaat aggaacttga   1140
atcaaggaaa tgattttaaa acgcagtatt cttagtggac tagaggaaaa aaataatctg   1200
agccaagtag aagacctttt cccctcctac ccctactttc taagtcacag aggctttttg   1260
ttcccccaga cactcttgca gattagtcca ggcagaaaca gttagatgtc cccagttaac   1320
ctcctatttg acaccactga ttaccccatt gatagtcaca ctttgggttg taagtgactt   1380
tttatttatt tgtattttg actgcattaa gaggtctcta gtttttatc tcttgtttcc   1440
caaaacctaa taagtaacta atgcacagag cacattgatt tgtatttatt ctatttttag   1500
acataattta ttagcatgca tgagcaaatt aagaaaaaca acaacaaatg aatgcatata   1560
tatgtatatg tatgtgtgta tatatacaca catatatata tatatttttt cttttcttac   1620
cagaaggttt taatccaaat aaggagaaga tatgcttaga accgaggtag agttttcatc   1680
cattctgtcc tgtaagtatt ttgcatattc tggagacgca ggaagagatc catctacata   1740
tcccaaagct gaattatggt agacaaaact cttccacttt tagtgcatca acttcttatt   1800
tgtgtaataa gaaaattggg aaaacgatct tcaatatgct taccaagctg tgattccaaa   1860
tattacgtaa atacacttgc aaaggaggat gtttttagta gcaatttgta ctgatggtat   1920
ggggccaaga gatatatctt agagggaggg ctgagggttt gaagtccaac tcctaagcca   1980
gtgccagaag agccaaggac aggtacggct gtcatcactt agacctcacc ctgtggagcc   2040
acaccctagg gttggccaat ctactcccag gagcagggag ggcaggagcc agggctgggc   2100
ataaaagtca gggcagagcc atctattgct tacatttgct tctgacacaa ctgtgttcac   2160
tagcaacctc aaacagacac catggtgcat ctgactcctg tcgagaagtc tgcagtcact   2220
gctctatggg ggaaagtgaa cgtggatgaa gttggtggtg aggccctggg caggttggta   2280
tcaaggttac aagacaggtt taaggagacc aatagaaact gggcatgtgg agacagagaa   2340
gactcttggg tttctgatag gcactgactc tctctgccta ttggtctatt ttcccaccct   2400
taggctgctg gtggtctacc cttggaccca gaggttcttt gagtcctttg gggatctgtc   2460
cactcctgat gctgttatgg gcaaccctaa ggtgaaggct catggcaaga aagtgctcgg   2520
tgcctttagt gatggcctgg ctcacctgga caacctcaag ggcacctttg ccacactgag   2580
tgagctgcac tgtgacaagc tgcacgtgga tcctgagaac ttcagggtga gtctatggga   2640
cgcttgatgt tttctttccc cttcttttct atggttaagt tcatgtcata ggaaggggat   2700
aagtaacagg gtacagttta gaatgggaaa cagacgaatg attgcatcag tgtggaagtc   2760
tcaggatcgt tttagtttct tttatttgct gttcataaca attgttttct tttgtttaat   2820
tcttgctttc tttttttttc ttctccgcaa tttttactat tatacttaat gccttaacat   2880
tgtgtataac aaaaggaaat atctctgaga tacattaagt aacttaaaaa aaaactttac   2940
```

acagtctgcc tagtacatta ctatttggaa tatatgtgtg cttatttgca tattcataat 3000
ctccctactt tattttcttt tatttttaat tgatacataa tcattataca tatttatggg 3060
ttaaagtgta atgttttaat atgtgtacac atattgacca aatcagggta attttgcatt 3120
tgtaatttta aaaaatgctt tcttctttta atatactttt ttgtttatct tatttctaat 3180
actttcccta atctctttct ttcagggcaa taatgataca atgtatcatg cctctttgca 3240
ccattctaaa gaataacagt gataatttct gggttaaggc aatagcaata tctctgcata 3300
taaatatttc tgcatataaa ttgtaactga tgtaagaggt ttcatattgc taatagcagc 3360
tacaatccag ctaccattct gcttttattt tatggttggg ataaggctgg attattctga 3420
gtccaagcta ggccctttttg ctaatcatgt tcatacctct tatcttcctc ccacagctcc 3480
tgggcaacgt gctggtctgt gtgctggccc atcactttgg caaagaattc accccaccag 3540
tgcaggctgc ctatcagaaa gtggtggctg gtgtggctaa tgccctggcc cacaagtatc 3600
actaagctcg ctttcttgct gtccaatttc tattaaaggt tcctttgttc cctaagtcca 3660
actactaaac tgggggatat tatgaagggc cttgagcatc tggattctgc ctaataaaaa 3720
acatttattt tcattgcaat gatgtattta aattatttct gaatatttta ctaaaaaggg 3780
aatgtgggag gtcagtgcat ttaaaacata aagaaatgaa gagctagttc aaaccttggg 3840
aaaatacact atatcttaaa ctccatgaaa gaaggtgagg ctgcaaacag ctaatgcaca 3900
ttggcaacag cccctgatgc atatgcctta ttcatccctc agaaaaggat tcaagtagag 3960
gcttgatttg gaggttaaag ttttgctatg ctgtatttta cattacttat tgttttagct 4020
gtcctcatga atgtcttttc actacccatt tgcttatcct gcatctctca gccttgactc 4080
cactcagttc tcttgcttag agataccacc tttcccctga agtgttcctt ccatgtttta 4140
cggcgagatg gtttctcctc gcctggccac tcagccttag ttgtctctgt tgtcttatag 4200
aggtctactt gaagaaggaa aaacaggggt catggtttga ctgtcctgtg agcccttctt 4260
ccctgcctcc cccactcaca gtgacccgga atctgcagtg ctagtctccc ggaactatca 4320
ctctttcaca gtctgctttg gaaggactgg gcttagtatg aaaagttagg actgagaaga 4380
atttgaaagg cggctttttg tagcttgata ttcactactg tcttattacc ctgtc 4435

<210> SEQ ID NO 109
<211> LENGTH: 7118
<212> TYPE: DNA
<213> ORGANISM: Artificial Sequence
<220> FEATURE:
<223> OTHER INFORMATION: Synthetic: Donor template, Full AAV (AAV.304)

<400> SEQUENCE: 109
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtcttgc tttgacaatt ttggtctttc 180
agaatactat aaatataacc tatattataa tttcataaag tctgtgcatt ttctttgacc 240
caggatattt gcaaaagaca tattcaaact tccgcagaac actttatttc acatatacat 300
gcctcttata tcagggatgt gaaacagggt cttgaaaact gtctaaatct aaaacaatgc 360
taatgcaggt ttaaatttaa taaaataaaa tccaaaatct aacagccaag tcaaatctgc 420
atgttttaac atttaaaata ttttaaagac gtcttttccc aggattcaac atgtgaaatc 480
ttttctcagg gatacacgtg tgcctagatc ctcattgctt tagtttttta cagaggaatg 540

```
aatataaaaa gaaaatactt aaattttatc cctcttacct ctataatcat acataggcat    600
aattttttaa cctaggctcc agatagccat agaagaacca aacactttct gcgtgtgtga    660
gaataatcag agtgagattt tttcacaagt acctgatgag ggttgagaca ggtagaaaaa    720
gtgagagatc tctatttatt tagcaataat agagaaagca tttaagagaa taaagcaatg    780
gaaataagaa atttgtaaat ttccttctga taactagaaa tagaggatcc agtttctttt    840
ggttaaccta aattttattt cattttattg ttttatttta ttttatttta ttttattttg    900
tgtaatcgta gtttcagagt gttagagctg aaaggaagaa gtaggagaaa catgcaaagt    960
aaaagtataa cactttcctt actaaaccga catgggtttc caggtagggg caggattcag   1020
gatgactgac agggccctta gggaacactg agaccctacg ctgacctcat aaatgcttgc   1080
tacctttgct gttttaatta catcttttaa tagcaggaag cagaactctg cacttcaaaa   1140
gtttttcctc acctgaggag ttaatttagt acaaggggaa aaagtacagg gggatgggag   1200
aaaggcgatc acgttgggaa gctatagaga aagaagagta aattttagta aaggaggttt   1260
aaacaaacaa aatataaaga gaaataggaa cttgaatcaa ggaaatgatt ttaaaacgca   1320
gtattcttag tggactagag gaaaaaaata atctgagcca agtagaagac cttttcccct   1380
cctaccccta ctttctaagt cacagaggct ttttgttccc ccagacactc ttgcagatta   1440
gtccaggcag aaacagttag atgtccccag ttaacctcct atttgacacc actgattacc   1500
ccattgatag tcacactttg ggttgtaagt gactttttat ttatttgtat ttttgactgc   1560
attaagaggt ctctagtttt ttatctcttg tttcccaaaa cctaataagt aactaatgca   1620
cagagcacat tgatttgtat ttattctatt tttagacata atttattagc atgcatgagc   1680
aaattaagaa aaacaacaac aaatgaatgc atatatatgt atatgtatgt gtgtatatat   1740
acacacatat atatatatat tttttctttt cttaccagaa ggttttaatc caaataagga   1800
gaagatatgc ttagaaccga ggtagagttt tcatccattc tgtcctgtaa gtattttgca   1860
tattctggag acgcaggaag agatccatct acatatccca aagctgaatt atggtagaca   1920
aaactcttcc acttttagtg catcaacttc ttatttgtgt aataagaaaa ttgggaaaac   1980
gatcttcaat atgcttacca agctgtgatt ccaaatatta cgtaaataca cttgcaaagg   2040
aggatgtttt tagtagcaat ttgtactgat ggtatggggc caagagatat atcttagagg   2100
gagggctgag ggtttgaagt ccaactccta agccagtgcc agaagagcca aggacaggta   2160
cggctgtcat cacttagacc tcaccctgtg gagccacacc ctagggttgg ccaatctact   2220
cccaggagca gggagggcag gagccagggc tgggcataaa agtcagggca gagccatcta   2280
ttgcttacat ttgcttctga cacaactgtg ttcactagca acctcaaaca gacaccatgg   2340
tgcatctgac tcctgtcgag aagtctgcag tcactgctct atgggggaaa gtgaacgtgg   2400
atgaagttgg tggtgaggcc ctgggcaggt tggtatcaag gttacaagac aggtttaagg   2460
agaccaatag aaactgggca tgtggagaca gagaagactc ttgggtttct gataggcact   2520
gactctctct gcctattggt ctattttccc acccttaggc tgctggtggt ctacccttgg   2580
acccagaggt tctttgagtc ctttggggat ctgtccactc ctgatgctgt tatgggcaac   2640
cctaaggtga aggctcatgg caagaaagtg ctcggtgcct ttagtgatgg cctggctcac   2700
ctggacaacc tcaagggcac ctttgccaca ctgagtgagc tgcactgtga caagctgcac   2760
gtggatcctg agaacttcag ggtgagtcta tgggacgctt gatgttttct ttccccttct   2820
tttctatggt taagttcatg tcataggaag gggataagta acagggtaca gtttagaatg   2880
ggaaacagac gaatgattgc atcagtgtgg aagtctcagg atcgttttag tttcttttat   2940
```

-continued

```
ttgctgttca taacaattgt tttcttttgt ttaattcttg ctttcttttt ttttcttctc   3000
cgcaattttt actattatac ttaatgcctt aacattgtgt ataacaaaag gaaatatctc   3060
tgagatacat taagtaactt aaaaaaaaac tttacacagt ctgcctagta cattactatt   3120
tggaatatat gtgtgcttat ttgcatattc ataatctccc tactttattt tcttttattt   3180
ttaattgata cataatcatt atacatattt atgggttaaa gtgtaatgtt ttaatatgtg   3240
tacacatatt gaccaaatca gggtaatttt gcatttgtaa ttttaaaaaa tgctttcttc   3300
ttttaatata cttttttgtt tatcttattt ctaatacttt ccctaatctc tttctttcag   3360
ggcaataatg atacaatgta tcatgcctct ttgcaccatt ctaaagaata acagtgataa   3420
tttctgggtt aaggcaatag caatatctct gcatataaat atttctgcat ataaattgta   3480
actgatgtaa gaggtttcat attgctaata gcagctacaa tccagctacc attctgcttt   3540
tattttatgg ttgggataag gctggattat tctgagtcca agctaggccc ttttgctaat   3600
catgttcata cctcttatct tcctcccaca gctcctgggc aacgtgctgg tctgtgtgct   3660
ggcccatcac tttggcaaag aattcacccc accagtgcag gctgcctatc agaaagtggt   3720
ggctggtgtg gctaatgccc tggcccacaa gtatcactaa gctcgctttc ttgctgtcca   3780
atttctatta aaggttcctt tgttccctaa gtccaactac taaactgggg gatattatga   3840
agggccttga gcatctggat tctgcctaat aaaaaacatt tattttcatt gcaatgatgt   3900
atttaaatta tttctgaata ttttactaaa aagggaatgt gggaggtcag tgcatttaaa   3960
acataaagaa atgaagagct agttcaaacc ttgggaaaat acactatatc ttaaactcca   4020
tgaaagaagg tgaggctgca aacagctaat gcacattggc aacagcccct gatgcatatg   4080
ccttattcat ccctcagaaa aggattcaag tagaggcttg atttggaggt taaagttttg   4140
ctatgctgta ttttacatta cttattgttt tagctgtcct catgaatgtc ttttcactac   4200
ccatttgctt atcctgcatc tctcagcctt gactccactc agttctcttg cttagagata   4260
ccacctttcc cctgaagtgt tccttccatg ttttacggcg agatggtttc tcctcgcctg   4320
gccactcagc cttagttgtc tctgttgtct tatagaggtc tacttgaaga aggaaaaaca   4380
ggggtcatgg tttgactgtc ctgtgagccc ttcttccctg cctcccccac tcacagtgac   4440
ccggaatctg cagtgctagt ctcccggaac tatcactctt tcacagtctg ctttggaagg   4500
actgggctta gtatgaaaag ttaggactga gaagaatttg aaaggcggct ttttgtagct   4560
tgatattcac tactgtctta ttaccctgtc ggtaaccacg tgcggccgag gctgcagcgt   4620
cgtcctccct aggaacccct agtgatggag ttggccactc cctctctgcg cgctcgctcg   4680
ctcactgagg ccgggcgacc aaaggtcgcc cgacgcccgg gctttgcccg ggcggcctca   4740
gtgagcgagc gagcgcgcag ctgcctgcag gggcgcctga tgcggtattt tctccttacg   4800
catctgtgcg gtatttcaca ccgcatacgt caaagcaacc atagtacgcg ccctgtagcg   4860
gcgcattaag cgcggcgggt gtggtggtta cgcgcagcgt gaccgctaca cttgccagcg   4920
ccctagcgcc cgctcctttc gctttcttcc cttcctttct cgccacgttc gccggctttc   4980
cccgtcaagc tctaaatcgg gggctccctt tagggttccg atttagtgct ttacggcacc   5040
tcgaccccaa aaaacttgat ttgggtgatg gttcacgtag tgggccatcg ccctgataga   5100
cggtttttcg ccctttgacg ttggagtcca cgttctttaa tagtggactc ttgttccaaa   5160
ctggaacaac actcaaccct atctcgggct attcttttga tttataaggg attttgccga   5220
tttcggccta ttggttaaaa aatgagctga tttaacaaaa atttaacgcg aattttaaca   5280
```

-continued aaatattaac gtttacaatt ttatggtgca ctctcagtac aatctgctct gatgccgcat 5340
agttaagcca gccccgacac ccgccaacac ccgctgacgc gccctgacgg gcttgtctgc 5400
tcccggcatc cgcttacaga caagctgtga ccgtctccgg gagctgcatg tgtcagaggt 5460
tttcaccgtc atcaccgaaa cgcgcgagac gaaagggcct cgtgatacgc ctatttttat 5520
aggttaatgt catgaacaat aaaactgtct gcttacataa acagtaatac aaggggtgtt 5580
atgagccata ttcaacggga aacgtcgagg ccgcgattaa attccaacat ggatgctgat 5640
ttatatgggt ataaatgggc tcgcgataat gtcgggcaat caggtgcgac aatctatcgc 5700
ttgtatggga agcccgatgc gccagagttg tttctgaaac atggcaaagg tagcgttgcc 5760
aatgatgtta cagatgagat ggtcagacta aactggctga cggaatttat gcctcttccg 5820
accatcaagc attttatccg tactcctgat gatgcatggt tactcaccac tgcgatcccc 5880
ggaaaaacag cattccaggt attagaagaa tatcctgatt caggtgaaaa tattgttgat 5940
gcgctggcag tgttcctgcg ccggttgcat tcgattcctg tttgtaattg tccttttaac 6000
agcgatcgcg tatttcgtct cgctcaggcg caatcacgaa tgaataacgg tttggttgat 6060
gcgagtgatt ttgatgacga gcgtaatggc tggcctgttg aacaagtctg gaaagaaatg 6120
cataaacttt tgccattctc accggattca gtcgtcactc atggtgattt ctcacttgat 6180
aaccttattt ttgacgaggg gaaattaata ggttgtattg atgttggacg agtcggaatc 6240
gcagaccgat accaggatct tgccatccta tggaactgcc tcggtgagtt ttctccttca 6300
ttacagaaac ggctttttca aaaatatggt attgataatc ctgatatgaa taaattgcag 6360
tttcatttga tgctcgatga gtttttctaa tctcatgacc aaaatccctt aacgtgagtt 6420
ttcgttccac tgagcgtcag accccgtaga aaagatcaaa ggatcttctt gagatccttt 6480
ttttctgcgc gtaatctgct gcttgcaaac aaaaaaacca ccgctaccag cggtggtttg 6540
tttgccggat caagagctac caactctttt tccgaaggta actggcttca gcagagcgca 6600
gataccaaat actgtccttc tagtgtagcc gtagttaggc caccacttca agaactctgt 6660
agcaccgcct acatacctcg ctctgctaat cctgttacca gtggctgctg ccagtggcga 6720
taagtcgtgt cttaccgggt tggactcaag acgatagtta ccggataagg cgcagcggtc 6780
gggctgaacg gggggttcgt gcacacagcc cagcttggag cgaacgacct acaccgaact 6840
gagataccta cagcgtgagc tatgagaaag cgccacgctt cccgaaggga gaaaggcgga 6900
caggtatccg gtaagcggca gggtcggaac aggagagcgc acgagggagc ttccaggggg 6960
aaacgcctgg tatctttata gtcctgtcgg gtttcgccac ctctgacttg agcgtcgatt 7020
tttgtgatgc tcgtcagggg ggcggagcct atggaaaaac gccagcaacg cggccttttt 7080
acggttcctg gccttttgct ggccttttgc tcacatgt 7118

<210> SEQ ID NO 110
<211> LENGTH: 4435
<212> TYPE: DNA
<213> ORGANISM: Artificial Sequence
<220> FEATURE:
<223> OTHER INFORMATION: Synthetic: Donor template, HBB Locus LHA to RHA (AAV.307)

<400> SEQUENCE: 110
cttgctttga caattttggt ctttcagaat actataaata taacctatat tataatttca 60
taaagtctgt gcattttctt tgacccagga tatttgcaaa agacatattc aaacttccgc 120
agaacacttt atttcacata tacatgcctc ttatatcagg gatgtgaaac agggtcttga 180

-continued aaactgtcta aatctaaaac aatgctaatg caggtttaaa tttaataaaa taaaatccaa 240
aatctaacag ccaagtcaaa tctgcatgtt ttaacattta aaatatttta aagacgtctt 300
ttcccaggat tcaacatgtg aaatcttttc tcagggatac acgtgtgcct agatcctcat 360
tgctttagtt ttttacagag gaatgaatat aaaaagaaaa tacttaaatt ttatccctct 420
tacctctata atcatacata ggcataattt tttaacctag gctccagata gccatagaag 480
aaccaaacac tttctgcgtg tgtgagaata atcagagtga gattttttca caagtacctg 540
atgagggttg agacaggtag aaaaagtgag agatctctat ttatttagca ataatagaga 600
aagcatttaa gagaataaag caatggaaat aagaaatttg taaatttcct tctgataact 660
agaaatagag gatccagttt cttttggtta acctaaattt tatttcattt tattgtttta 720
ttttatttta ttttatttta ttttgtgtaa tcgtagtttc agagtgttag agctgaaagg 780
aagaagtagg agaaacatgc aaagtaaaag tataacactt tccttactaa accgacatgg 840
gtttccaggt aggggcagga ttcaggatga ctgacagggc ccttagggaa cactgagacc 900
ctacgctgac ctcataaatg cttgctacct ttgctgtttt aattacatct tttaatagca 960
ggaagcagaa ctctgcactt caaaagtttt tcctcacctg aggagttaat ttagtacaag 1020
gggaaaaagt acagggggat gggagaaagg cgatcacgtt gggaagctat agagaaagaa 1080
gagtaaattt tagtaaagga ggtttaaaca aacaaaatat aaagagaaat aggaacttga 1140
atcaaggaaa tgattttaaa acgcagtatt cttagtggac tagaggaaaa aaataatctg 1200
agccaagtag aagacctttt cccctcctac ccctactttc taagtcacag aggctttttg 1260
ttcccccaga cactcttgca gattagtcca ggcagaaaca gttagatgtc cccagttaac 1320
ctcctatttg acaccactga ttaccccatt gatagtcaca ctttgggttg taagtgactt 1380
tttatttatt tgtattttttg actgcattaa gaggtctcta gtttttatc tcttgtttcc 1440 caaaacctaa taagtaacta atgcacagag cacattgatt tgtatttatt ctatttttag 1500
acataattta ttagcatgca tgagcaaatt aagaaaaaca acaacaaatg aatgcatata 1560
tatgtatatg tatgtgtgta tatatacaca catatatata tatatttttt cttttcttac 1620
cagaaggttt taatccaaat aaggagaaga tatgcttaga accgaggtag agttttcatc 1680
cattctgtcc tgtaagtatt ttgcatattc tggagacgca ggaagagatc catctacata 1740
tcccaaagct gaattatggt agacaaaact cttccacttt tagtgcatca acttcttatt 1800
tgtgtaataa gaaaattggg aaaacgatct tcaatatgct taccaagctg tgattccaaa 1860
tattacgtaa atacacttgc aaaggaggat gtttttagta gcaatttgta ctgatggtat 1920
ggggccaaga gatatatctt agagggaggg ctgagggttt gaagtccaac tcctaagcca 1980
gtgccagaag agccaaggac aggtacggct gtcatcactt agacctcacc ctgtggagcc 2040
acaccctagg gttggccaat ctactcccag gagcagggag ggcaggagcc agggctgggc 2100
ataaaagtca gggcagagcc atctattgct tacatttgct tctgacacaa ctgtgttcac 2160
tagcaacctc aaacagacac catggtgcat ctgactcctg tcgaaaaatc cgctgtcacc 2220
gccctctggg gcaaggtgaa cgtggatgaa gttggtggtg aggccctggg caggttggta 2280
tcaaggttac aagacaggtt taaggagacc aatagaaact gggcatgtgg agacagagaa 2340
gactcttggg tttctgatag gcactgactc tctctgccta ttggtctatt ttcccaccct 2400
taggctgctg gtggtctacc cttggaccca gaggttcttt gagtcctttg gggatctgtc 2460
cactcctgat gctgttatgg gcaaccctaa ggtgaaggct catggcaaga aagtgctcgg 2520
tgcctttagt gatggcctgg ctcacctgga caacctcaag ggcacctttg ccacactgag 2580
tgagctgcac tgtgacaagc tgcacgtgga tcctgagaac ttcagggtga gtctatggga 2640
cgcttgatgt tttctttccc cttcttttct atggttaagt tcatgtcata ggaaggggat 2700
aagtaacagg gtacagttta gaatgggaaa cagacgaatg attgcatcag tgtggaagtc 2760
tcaggatcgt tttagtttct tttatttgct gttcataaca attgttttct tttgtttaat 2820
tcttgctttc tttttttttc ttctccgcaa tttttactat tatacttaat gccttaacat 2880
tgtgtataac aaaaggaaat atctctgaga tacattaagt aacttaaaaa aaaactttac 2940
acagtctgcc tagtacatta ctatttggaa tatatgtgtg cttatttgca tattcataat 3000
ctccctactt tattttcttt tatttttaat tgatacataa tcattataca tatttatggg 3060
ttaaagtgta atgttttaat atgtgtacac atattgacca aatcagggta attttgcatt 3120
tgtaatttta aaaaatgctt tcttctttta atatactttt ttgtttatct tatttctaat 3180
actttcccta atctctttct ttcagggcaa taatgataca atgtatcatg cctctttgca 3240
ccattctaaa gaataacagt gataatttct gggttaaggc aatagcaata tctctgcata 3300
taaatatttc tgcatataaa ttgtaactga tgtaagaggt ttcatattgc taatagcagc 3360
tacaatccag ctaccattct gcttttattt tatggttggg ataaggctgg attattctga 3420
gtccaagcta ggcccttttg ctaatcatgt tcatacctct tatcttcctc ccacagctcc 3480
tgggcaacgt gctggtctgt gtgctggccc atcactttgg caaagaattc accccaccag 3540
tgcaggctgc ctatcagaaa gtggtggctg gtgtggctaa tgccctggcc cacaagtatc 3600
actaagctcg ctttcttgct gtccaatttc tattaaaggt tcctttgttc cctaagtcca 3660
actactaaac tgggggatat tatgaagggc cttgagcatc tggattctgc ctaataaaaa 3720
acatttattt tcattgcaat gatgtattta aattatttct gaatatttta ctaaaaaggg 3780
aatgtgggag gtcagtgcat ttaaaacata aagaaatgaa gagctagttc aaaccttggg 3840
aaaatacact atatcttaaa ctccatgaaa gaaggtgagg ctgcaaacag ctaatgcaca 3900
ttggcaacag cccctgatgc atatgcctta ttcatccctc agaaaaggat tcaagtagag 3960
gcttgatttg gaggttaaag ttttgctatg ctgtatttta cattacttat tgttttagct 4020
gtcctcatga atgtcttttc actacccatt tgcttatcct gcatctctca gccttgactc 4080
cactcagttc tcttgcttag agataccacc tttcccctga agtgttcctt ccatgtttta 4140
cggcgagatg gtttctcctc gcctggccac tcagccttag ttgtctctgt tgtcttatag 4200
aggtctactt gaagaaggaa aaacaggggt catggtttga ctgtcctgtg agcccttctt 4260
ccctgcctcc cccactcaca gtgacccgga atctgcagtg ctagtctccc ggaactatca 4320
ctctttcaca gtctgctttg gaaggactgg gcttagtatg aaaagttagg actgagaaga 4380
atttgaaagg cggctttttg tagcttgata ttcactactg tcttattacc ctgtc 4435

<210> SEQ ID NO 111
<211> LENGTH: 7118
<212> TYPE: DNA
<213> ORGANISM: Artificial Sequence
<220> FEATURE:
<223> OTHER INFORMATION: Synthetic: Donor template, Full AAV (AAV.307)

<400> SEQUENCE: 111
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtcttgc tttgacaatt ttggtctttc 180

-continued

```
agaatactat aaatataacc tatattataa tttcataaag tctgtgcatt ttctttgacc    240
caggatattt gcaaaagaca tattcaaact tccgcagaac actttatttc acatatacat    300
gcctcttata tcagggatgt gaaacagggt cttgaaaact gtctaaatct aaaacaatgc    360
taatgcaggt ttaaatttaa taaaataaaa tccaaaatct aacagccaag tcaaatctgc    420
atgttttaac atttaaaata ttttaaagac gtcttttccc aggattcaac atgtgaaatc    480
ttttctcagg gatacacgtg tgcctagatc ctcattgctt tagtttttta cagaggaatg    540
aatataaaaa gaaaatactt aaattttatc cctcttacct ctataatcat acataggcat    600
aatttttaa cctaggctcc agatagccat agaagaacca aacactttct gcgtgtgtga    660
gaataatcag agtgagattt tttcacaagt acctgatgag ggttgagaca ggtagaaaaa    720
gtgagagatc tctatttatt tagcaataat agagaaagca tttaagagaa taaagcaatg    780
gaaataagaa atttgtaaat ttccttctga taactagaaa tagaggatcc agtttctttt    840
ggttaaccta aattttattt cattttattg ttttatttta ttttatttta ttttattttg    900
tgtaatcgta gtttcagagt gttagagctg aaaggaagaa gtaggagaaa catgcaaagt    960
aaaagtataa cactttcctt actaaaccga catgggtttc caggtagggg caggattcag   1020
gatgactgac agggccctta gggaacactg agaccctacg ctgacctcat aaatgcttgc   1080
tacctttgct gttttaatta catcttttaa tagcaggaag cagaactctg cacttcaaaa   1140
gtttttcctc acctgaggag ttaatttagt acaaggggaa aaagtacagg gggatgggag   1200
aaaggcgatc acgttgggaa gctatagaga aagaagagta aattttagta aaggaggttt   1260
aaacaaacaa aatataaaga gaaataggaa cttgaatcaa ggaaatgatt ttaaaacgca   1320
gtattcttag tggactagag gaaaaaaata atctgagcca agtagaagac cttttcccct   1380
cctaccccta ctttctaagt cacagaggct ttttgttccc ccagacactc ttgcagatta   1440
gtccaggcag aaacagttag atgtccccag ttaacctcct atttgacacc actgattacc   1500
ccattgatag tcacactttg ggttgtaagt gactttttat ttatttgtat ttttgactgc   1560
attaagaggt ctctagtttt ttatctcttg tttcccaaaa cctaataagt aactaatgca   1620
cagagcacat tgatttgtat ttattctatt tttagacata atttattagc atgcatgagc   1680
aaattaagaa aaacaacaac aaatgaatgc atatatatgt atatgtatgt gtgtatatat   1740
acacacatat atatatatat tttttctttt cttaccagaa ggttttaatc caaataagga   1800
gaagatatgc ttagaaccga ggtagagttt tcatccattc tgtcctgtaa gtattttgca   1860
tattctggag acgcaggaag agatccatct acatatccca aagctgaatt atggtagaca   1920
aaactcttcc acttttagtg catcaacttc ttatttgtgt aataagaaaa ttgggaaaac   1980
gatcttcaat atgcttacca agctgtgatt ccaaatatta cgtaaataca cttgcaaagg   2040
aggatgtttt tagtagcaat ttgtactgat ggtatggggc caagagatat atcttagagg   2100
gagggctgag ggtttgaagt ccaactccta agccagtgcc agaagagcca aggacaggta   2160
cggctgtcat cacttagacc tcaccctgtg gagccacacc ctagggttgg ccaatctact   2220
cccaggagca gggagggcag gagccagggc tgggcataaa agtcagggca gagccatcta   2280
ttgcttacat ttgcttctga cacaactgtg ttcactagca acctcaaaca gacaccatgg   2340
tgcatctgac tcctgtcgaa aaatccgctg tcaccgccct ctggggcaag gtgaacgtgg   2400
atgaagttgg tggtgaggcc ctgggcaggt tggtatcaag gttacaagac aggtttaagg   2460
agaccaatag aaactgggca tgtggagaca gagaagactc ttgggtttct gataggcact   2520
gactctctct gcctattggt ctattttccc acccttaggc tgctggtggt ctacccttgg   2580
```

```
acccagaggt tctttgagtc ctttggggat ctgtccactc ctgatgctgt tatgggcaac   2640
cctaaggtga aggctcatgg caagaaagtg ctcggtgcct ttagtgatgg cctggctcac   2700
ctggacaacc tcaagggcac ctttgccaca ctgagtgagc tgcactgtga caagctgcac   2760
gtggatcctg agaacttcag ggtgagtcta tgggacgctt gatgttttct ttccccttct   2820
tttctatggt taagttcatg tcataggaag gggataagta acagggtaca gtttagaatg   2880
ggaaacagac gaatgattgc atcagtgtgg aagtctcagg atcgttttag tttcttttat   2940
ttgctgttca taacaattgt tttcttttgt ttaattcttg ctttcttttt ttttcttctc   3000
cgcaattttt actattatac ttaatgcctt aacattgtgt ataacaaaag gaaatatctc   3060
tgagatacat taagtaactt aaaaaaaaac tttacacagt ctgcctagta cattactatt   3120
tggaatatat gtgtgcttat ttgcatattc ataatctccc tactttattt tcttttattt   3180
ttaattgata cataatcatt atacatattt atgggttaaa gtgtaatgtt ttaatatgtg   3240
tacacatatt gaccaaatca gggtaatttt gcatttgtaa ttttaaaaaa tgctttcttc   3300
ttttaatata ctttttttgtt tatcttattt ctaatacttt ccctaatctc tttctttcag   3360
ggcaataatg atacaatgta tcatgcctct ttgcaccatt ctaaagaata acagtgataa   3420
tttctgggtt aaggcaatag caatatctct gcatataaat atttctgcat ataaattgta   3480
actgatgtaa gaggtttcat attgctaata gcagctacaa tccagctacc attctgcttt   3540
tattttatgg ttgggataag gctggattat tctgagtcca agctaggccc ttttgctaat   3600
catgttcata cctcttatct tcctcccaca gctcctgggc aacgtgctgg tctgtgtgct   3660
ggcccatcac tttggcaaag aattcacccc accagtgcag gctgcctatc agaaagtggt   3720
ggctggtgtg gctaatgccc tggcccacaa gtatcactaa gctcgctttc ttgctgtcca   3780
atttctatta aaggttcctt tgttccctaa gtccaactac taaactgggg gatattatga   3840
agggccttga gcatctggat tctgcctaat aaaaaacatt tattttcatt gcaatgatgt   3900
atttaaatta tttctgaata ttttactaaa aagggaatgt gggaggtcag tgcatttaaa   3960
acataaagaa atgaagagct agttcaaacc ttgggaaaat acactatatc ttaaactcca   4020
tgaaagaagg tgaggctgca aacagctaat gcacattggc aacagcccct gatgcatatg   4080
ccttattcat ccctcagaaa aggattcaag tagaggcttg atttggaggt taaagttttg   4140
ctatgctgta ttttacatta cttattgttt tagctgtcct catgaatgtc ttttcactac   4200
ccatttgctt atcctgcatc tctcagcctt gactccactc agttctcttg cttagagata   4260
ccacctttcc cctgaagtgt tccttccatg ttttacggcg agatggtttc tcctcgcctg   4320
gccactcagc cttagttgtc tctgttgtct tatagaggtc tacttgaaga aggaaaaaca   4380
ggggtcatgg tttgactgtc ctgtgagccc ttcttccctg cctcccccac tcacagtgac   4440
ccggaatctg cagtgctagt ctcccggaac tatcactctt tcacagtctg ctttggaagg   4500
actgggctta gtatgaaaag ttaggactga gaagaatttg aaaggcggct ttttgtagct   4560
tgatattcac tactgtctta ttaccctgtc ggtaaccacg tgcggccgag gctgcagcgt   4620
cgtcctccct aggaacccct agtgatggag ttggccactc cctctctgcg cgctcgctcg   4680
ctcactgagg ccgggcgacc aaaggtcgcc cgacgcccgg gctttgcccg ggcggcctca   4740
gtgagcgagc gagcgcgcag ctgcctgcag gggcgcctga tgcggtattt tctccttacg   4800
catctgtgcg gtatttcaca ccgcatacgt caaagcaacc atagtacgcg ccctgtagcg   4860
gcgcattaag cgcggcgggt gtggtggtta cgcgcagcgt gaccgctaca cttgccagcg   4920
```

-continued ccctagcgcc cgctcctttc gctttcttcc cttcctttct cgccacgttc gccggctttc 4980
cccgtcaagc tctaaatcgg gggctccctt tagggttccg atttagtgct ttacggcacc 5040
tcgaccccaa aaaacttgat ttgggtgatg gttcacgtag tgggccatcg ccctgataga 5100
cggtttttcg ccctttgacg ttggagtcca cgttctttaa tagtggactc ttgttccaaa 5160
ctggaacaac actcaaccct atctcgggct attcttttga tttataaggg attttgccga 5220
tttcggccta ttggttaaaa aatgagctga tttaacaaaa atttaacgcg aattttaaca 5280
aaatattaac gtttacaatt ttatggtgca ctctcagtac aatctgctct gatgccgcat 5340
agttaagcca gccccgacac ccgccaacac ccgctgacgc gccctgacgg gcttgtctgc 5400
tcccggcatc cgcttacaga caagctgtga ccgtctccgg gagctgcatg tgtcagaggt 5460
tttcaccgtc atcaccgaaa cgcgcgagac gaaagggcct cgtgatacgc ctatttttat 5520
aggttaatgt catgaacaat aaaactgtct gcttacataa acagtaatac aaggggtgtt 5580
atgagccata ttcaacggga aacgtcgagg ccgcgattaa attccaacat ggatgctgat 5640
ttatatgggt ataaatgggc tcgcgataat gtcgggcaat caggtgcgac aatctatcgc 5700
ttgtatggga agcccgatgc gccagagttg tttctgaaac atggcaaagg tagcgttgcc 5760
aatgatgtta cagatgagat ggtcagacta aactggctga cggaatttat gcctcttccg 5820
accatcaagc attttatccg tactcctgat gatgcatggt tactcaccac tgcgatcccc 5880
ggaaaaacag cattccaggt attagaagaa tatcctgatt caggtgaaaa tattgttgat 5940
gcgctggcag tgttcctgcg ccggttgcat tcgattcctg tttgtaattg tccttttaac 6000
agcgatcgcg tatttcgtct cgctcaggcg caatcacgaa tgaataacgg tttggttgat 6060
gcgagtgatt ttgatgacga gcgtaatggc tggcctgttg aacaagtctg gaaagaaatg 6120
cataaacttt tgccattctc accggattca gtcgtcactc atggtgattt ctcacttgat 6180
aaccttattt ttgacgaggg gaaattaata ggttgtattg atgttggacg agtcggaatc 6240
gcagaccgat accaggatct tgccatccta tggaactgcc tcggtgagtt ttctccttca 6300
ttacagaaac ggctttttca aaaatatggt attgataatc ctgatatgaa taaattgcag 6360
tttcatttga tgctcgatga gtttttctaa tctcatgacc aaaatccctt aacgtgagtt 6420
ttcgttccac tgagcgtcag accccgtaga aaagatcaaa ggatcttctt gagatccttt 6480
ttttctgcgc gtaatctgct gcttgcaaac aaaaaaacca ccgctaccag cggtggtttg 6540
tttgccggat caagagctac caactctttt tccgaaggta actggcttca gcagagcgca 6600
gataccaaat actgtccttc tagtgtagcc gtagttaggc caccacttca agaactctgt 6660
agcaccgcct acatacctcg ctctgctaat cctgttacca gtggctgctg ccagtggcga 6720
taagtcgtgt cttaccgggt tggactcaag acgatagtta ccggataagg cgcagcggtc 6780
gggctgaacg gggggttcgt gcacacagcc cagcttggag cgaacgacct acaccgaact 6840
gagataccta cagcgtgagc tatgagaaag cgccacgctt cccgaaggga gaaaggcgga 6900
caggtatccg gtaagcggca gggtcggaac aggagagcgc acgagggagc ttccaggggg 6960
aaacgcctgg tatctttata gtcctgtcgg gtttcgccac ctctgacttg agcgtcgatt 7020
tttgtgatgc tcgtcagggg ggcggagcct atggaaaaac gccagcaacg cggccttttt 7080
acggttcctg gccttttgct ggccttttgc tcacatgt 7118

<210> SEQ ID NO 112
<211> LENGTH: 141
<212> TYPE: DNA
<213> ORGANISM: Artificial Sequence -continued

```
<220> FEATURE:
<223> OTHER INFORMATION: Synthetic: Donor template, 5 ITR

<400> SEQUENCE: 112

cctgcaggca gctgcgcgct cgctcgctca ctgaggccgc ccgggcaaag cccgggcgtc      60

gggcgacctt tggtcgcccg gcctcagtga gcgagcgagc gcgcagagag ggagtggcca     120

actccatcac taggggttcc t                                               141

<210> SEQ ID NO 113
<211> LENGTH: 48
<212> TYPE: DNA
<213> ORGANISM: Artificial Sequence
<220> FEATURE:
<223> OTHER INFORMATION: Synthetic: Wild-type HBB gene region
<220> FEATURE:
<221> NAME/KEY: misc_feature
<222> LOCATION: (2)..(2)
<223> OTHER INFORMATION: n is c or t

<400> SEQUENCE: 113

anctgactcc tgaggagaag tctgccgtta ctgccctgtg gggcaagg                   48

<210> SEQ ID NO 114
<211> LENGTH: 48
<212> TYPE: DNA
<213> ORGANISM: Artificial Sequence
<220> FEATURE:
<223> OTHER INFORMATION: Synthetic: Sickle HBB gene region
<220> FEATURE:
<221> NAME/KEY: misc_feature
<222> LOCATION: (2)..(2)
<223> OTHER INFORMATION: n is c or t

<400> SEQUENCE: 114

anctgactcc tgtggagaag tctgccgtta ctgccctgtg gggcaagg                   48

<210> SEQ ID NO 115
<211> LENGTH: 20
<212> TYPE: DNA
<213> ORGANISM: Artificial Sequence
<220> FEATURE:
<223> OTHER INFORMATION: Synthetic: R02 gRNA

<400> SEQUENCE: 115

cttgccccac agggcagtaa                                                  20

<210> SEQ ID NO 116
<211> LENGTH: 48
<212> TYPE: DNA
<213> ORGANISM: Artificial Sequence
<220> FEATURE:
<223> OTHER INFORMATION: Synthetic: AAV.307

<400> SEQUENCE: 116

atctgactcc tgtcgaaaaa tccgctgtca ccgccctctg gggcaagg                   48

<210> SEQ ID NO 117
<211> LENGTH: 48
<212> TYPE: DNA
<213> ORGANISM: Artificial Sequence
<220> FEATURE:
<223> OTHER INFORMATION: Synthetic: AAV.304

<400> SEQUENCE: 117

atctgactcc tgtcgagaag tctgcagtca ctgctctatg ggggaaag                   48
```

<210> SEQ ID NO 118
<211> LENGTH: 48
<212> TYPE: DNA
<213> ORGANISM: Artificial Sequence
<220> FEATURE:
<223> OTHER INFORMATION: Synthetic: Beta-thal HBB gene region
<220> FEATURE:
<221> NAME/KEY: misc_feature
<222> LOCATION: (2)..(2)
<223> OTHER INFORMATION: n is c or t

<400> SEQUENCE: 118
anctgactcc tgaggagaag tctgcagtta ctgccctgtg gggcaagg 48

<210> SEQ ID NO 119
<211> LENGTH: 48
<212> TYPE: DNA
<213> ORGANISM: Artificial Sequence
<220> FEATURE:
<223> OTHER INFORMATION: Synthetic: AAV.323

<400> SEQUENCE: 119
atctgactcc tgaagaaaaa tccgctgtca ctgccctttg gggcaagg 48

<210> SEQ ID NO 120
<211> LENGTH: 51
<212> TYPE: DNA
<213> ORGANISM: Artificial Sequence
<220> FEATURE:
<223> OTHER INFORMATION: Synthetic: HBB -9 INDEL

<400> SEQUENCE: 120
acctgactcc tgaggagaag tctgccctgt ggggcaaggt gaacgtggat g 51

<210> SEQ ID NO 121
<211> LENGTH: 60
<212> TYPE: DNA
<213> ORGANISM: Artificial Sequence
<220> FEATURE:
<223> OTHER INFORMATION: Synthetic: HBB Wild-type Reference

<400> SEQUENCE: 121
acctgactcc tgaggagaag tctgccgtta ctgccctgtg gggcaaggtg aacgtggatg 60

<210> SEQ ID NO 122
<211> LENGTH: 5
<212> TYPE: PRT
<213> ORGANISM: Artificial Sequence
<220> FEATURE:
<223> OTHER INFORMATION: Synthetic: polypeptide sequence encoded by the
NGS and reference reads

<400> SEQUENCE: 122

Ser Ala Val Thr Ala
1 5

<210> SEQ ID NO 123
<211> LENGTH: 51
<212> TYPE: DNA
<213> ORGANISM: Artificial Sequence
<220> FEATURE:
<223> OTHER INFORMATION: Synthetic: HBB -9 INDEL with a 9nt deletion

<400> SEQUENCE: 123
acctgactcc tgtggagaag tctgccctgt ggggcaaggt gaacgtggat g 51

-continued

```
<210> SEQ ID NO 124
<211> LENGTH: 60
<212> TYPE: DNA
<213> ORGANISM: Artificial Sequence
<220> FEATURE:
<223> OTHER INFORMATION: Synthetic: HBB Sickle Cell Mutation

<400> SEQUENCE: 124

acctgactcc tgtggagaag tctgccgtta ctgccctgtg gggcaaggtg aacgtggatg     60
```

COMPOSITIONS AND METHODS FOR EDITING BETA-GLOBIN FOR TREATMENT OF HEMAGLOBINOPATHIES

RELATED APPLICATIONS

This application is a U.S. National Phase Application, filed under 35 U.S.C. § 371, of International Application No. PCT/US2020/038203, filed on Jun. 17, 2020, which claims the benefit of U.S. Provisional Application Ser. No. 62/862, 539, filed Jun. 17, 2019, which are hereby incorporated by reference in their entireties.

REFERENCE TO SEQUENCE LISTING

The instant application contains a Sequence Listing, which has been submitted electronically in ASCII format via EFS-Web and is hereby incorporated by reference in its entirety. Said ASCII copy, created on May 22, 2025, is named 2025-05-22_01245-0045-01US_ST25.txt and is 136, 825 bytes in size.

BACKGROUND

Hemoglobin (Hb) carries oxygen from the lungs to tissues in erythrocytes or red blood cells (RBCs). During prenatal development and until shortly after birth, hemoglobin is present in the form of fetal hemoglobin (HbF), a tetrameric protein composed of two alpha (a)-globin chains and two gamma (γ)-globin chains. HbF is largely replaced by adult hemoglobin (HbA), a tetrameric protein in which the γ-globin chains of HbF are replaced with beta (β)-globin chains, through a process known as globin switching. HbF is more efficient than HbA at carrying oxygen. The average adult makes less than 1% HbF out of total hemoglobin. The a-hemoglobin gene is located on chromosome 16, while the β-hemoglobin gene (HBB), A gamma ($\gamma^{A}$)-globin chain (HBG1, also known as gamma globin A), and G gamma (γˆ-globin chain (HBG2, also known as gamma globin G) are located on chromosome 11 within the globin gene cluster (i.e., globin locus).

Mutations in HBB can cause hemoglobin disorders (i.e., hemoglobinopathies) including sickle cell disease (SCD) and beta-thalassemia (β-Thal). Approximately 93,000 people in the United States are diagnosed with a hemoglobinopathy. Worldwide, 300,000 children are born with hemoglobinopathies every year (Angastiniotis & Modell, *Ann N Y Acad Sci,* 850:251-269 (1998)). Because these conditions are associated with HBB mutations, their symptoms typically do not manifest until after globin switching from HbF to HbA.

SCD is the most common inherited hematologic disease in the United States, affecting approximately 80,000 people (Brousseau, *Am J Hematol* 85(1):77-78 (2010)). SCD is most common in people of African ancestry, for whom the prevalence of SCD is 1 in 500. In Africa, the prevalence of SCD is 15 million (Aliyu et al. *Am J Hematol,* 83:63-70 (2008)). SCD is also more common in people of Indian, Saudi Arabian and Mediterranean descent.

SCD is caused by a single homozygous mutation in the HBB gene, c.20A>T (HbS mutation). The sickle mutation is a point mutation (GAG-GTG) on HBB that results in substitution of valine for glutamic acid at amino acid position 6 in exon 1 (E6V) in the protein. The mutation is also referred to as an E7V mutation because it occurs at the $7^{th}$ position in the gene coding exon, where the first amino acid is methionine. The valine at position 6 of the β-hemoglobin chain is hydrophobic and causes a change in conformation of the β-globin protein when it is not bound to oxygen. This change of conformation causes HbS proteins to polymerize in the absence of oxygen, leading to deformation (i.e., sickling) of RBCs. SCD is inherited in an autosomal recessive manner, so that only patients with two HbS alleles have the disease. Heterozygous subjects have sickle cell trait, and may suffer from anemia and/or painful crises if they are severely dehydrated or oxygen deprived.

Delivery of a corrected HBB gene via gene therapy is currently being investigated in clinical trials. However, the long-term efficacy and safety of this approach is unknown. Transplantation with hematopoietic stem cells from an HLA-matched allogeneic stem cell donor has been demonstrated to cure SCD, but this procedure involves risks including the possibility of graft vs. host disease after transplantation. In addition, matched allogeneic donors often cannot be identified. Thus, there is a need for improved methods of managing these and other hemoglobinopathies.

SUMMARY OF DISCLOSURE

In some aspects, the disclosure provides a method for homology directed repair (HDR) of a double-strand break (DSB) in a target region in a human beta-globin (HBB) gene in a cell or population of cells the method comprising contacting the cell or population of cells with:

(a) a *S. pyogenes* Cas9 endonuclease, an mRNA encoding the *S. pyogenes* Cas9 endonuclease, or a recombinant expression vector comprising a nucleotide sequence encoding the *S. pyogenes* Cas9 endonuclease, wherein the *S. pyogenes* Cas9 endonuclease is a high fidelity Cas9;

(b) a single guide RNA (sgRNA) targeting a target site in an HBB gene, the sgRNA comprising a spacer sequence corresponding to a target sequence consisting of SEQ ID NO: 15; and (c) a recombinant vector comprising a nucleic acid, the nucleic acid comprising from 5' to 3' (i) a nucleotide sequence homologous with a region located upstream of the target region in the HBB gene, (ii) a nucleotide sequence homologous with a region of the HBB gene comprising the target region, and (iii) a nucleotide sequence homologous with a region located downstream of the target region in the HBB gene;

wherein a double-strand break (DSB) occurs at the target site in the HBB gene and the nucleic acid is exchanged with a homologous nucleotide sequence of the HBB gene.

In other aspects, the disclosure provides a method for homology directed repair (HDR) of a double-strand break (DSB) in a target region in a human beta-globin (HBB) gene in a cell or population of cells the method comprising contacting the cell or population of cells with:

(a) a *S. pyogenes* Cas9 endonuclease, an mRNA encoding the *S. pyogenes* Cas9 endonuclease, or a recombinant expression vector comprising a nucleotide sequence encoding the *S. pyogenes* Cas9 endonuclease, wherein the *S. pyogenes* Cas9 endonuclease is a high fidelity Cas9;

(b) a single guide RNA (sgRNA) targeting a target site in an HBB gene, the sgRNA recognizes a target sequence consisting of SEQ ID NO: 20; and (c) a recombinant vector comprising a nucleic acid, the nucleic acid comprising from 5' to 3' (i) a nucleotide sequence homologous with a region located upstream of the target region in the HBB gene, (ii) a nucleotide sequence homologous with a region of the HBB gene comprising the target region, and (iii) a nucleotide sequence homologous with a region located downstream of the target region in the HBB gene;

wherein a double-strand break (DSB) occurs at the target site in the HBB gene and the nucleic acid is exchanged with a homologous nucleotide sequence of the HBB gene.

In any of the foregoing or related aspects, cleavage of one or more predicted off-target sites in the cell or population of cells is reduced relative to a cell or population of cells contacted with a wild-type *S. pyogenes* Cas9. In some aspects, cleavage of one or more predicted off-target sites is reduced by at least about 50%.

In any of the foregoing or related aspects, the nucleotide sequence of (c)(ii) corrects an E6V mutation in the HBB gene and is homologous with a region of the HBB gene encoding the E6V mutation. In some aspects, the nucleotide sequence of (c)(ii) comprises the sequence of SEQ ID NO: 102.

In any of the foregoing or related aspects, the nucleotide sequence of (c)(i) is homologous with a region located upstream of the E6V mutation in the HBB gene and the nucleotide sequence of (c)(iii) is homologous with a region located downstream of the E6V mutation.

In some aspects, the disclosure provides a method for correcting an E6V mutation in human beta-globin (HBB) in a cell or population of cells, the method comprising contacting the cell or population of cells comprising an HBB gene encoding the E6V mutation with:

(a) a DNA endonuclease, an mRNA encoding the DNA endonuclease, or a recombinant expression vector comprising a nucleotide sequence encoding the DNA endonuclease;

(b) a single guide RNA (sgRNA) targeting a target site in the HBB gene; and (c) a recombinant vector comprising a nucleic acid, the nucleic acid comprising from 5' to 3' (i) a nucleotide sequence homologous with a region located upstream of the E6V mutation in the HBB gene, (ii) a nucleotide sequence which corrects the E6V mutation and is homologous with a region of the HBB gene encoding the E6V mutation, the nucleotide sequence set forth in SEQ ID NO: 102, and (iii) a nucleotide sequence homologous with a region located downstream of the E6V mutation in the HBB gene, wherein a double-strand break (DSB) occurs at the target site in the HBB gene and the nucleic acid is exchanged with a homologous nucleotide sequence of HBB gene, thereby correcting the E6V mutation in the HBB gene in the cell or population of cells.

In any of the foregoing or related aspects, the DSB occurs 10-50 nucleotides upstream or downstream of the region of the HBB gene encoding the E6V mutation. In some aspects, the DSB occurs within exon 1 of the HBB gene.

In any of the foregoing or related aspects, the sgRNA comprises a spacer sequence corresponding to a target sequence consisting of SEQ ID NO: 15. In other aspects, the sgRNA recognizes a target sequence consisting of SEQ ID NO: 15. In other aspects, the sgRNA recognizes a target sequence consisting of SEQ ID NO: 20.

In any of the foregoing or related aspects, the DNA endonuclease is a Cas9 endonuclease. In some aspects, the Cas9 endonuclease is a *S. pyogenes* Cas9 endonuclease.

In some aspects, the disclosure provides a method for correcting an E6V mutation in human beta-globin (HBB) in a cell or population of cells, the method comprising contacting the cell or population of cells comprising an HBB gene encoding the E6V mutation with:

(a) a *S. pyogenes* Cas9 endonuclease, an mRNA encoding the *S. pyogenes* Cas9 endonuclease, or a recombinant expression vector comprising a nucleotide sequence encoding the *S. pyogenes* Cas9 endonuclease;

(b) a single guide RNA (sgRNA) targeting a target site in the HBB gene, the sgRNA comprising a spacer sequence corresponding to a target sequence consisting of SEQ ID NO: 15; and (c) a recombinant vector comprising a nucleic acid, the nucleic acid comprising from 5' to 3' (i) a nucleotide sequence homologous with a region located upstream of the E6V mutation in the HBB gene, (ii) a nucleotide sequence which corrects the E6V mutation and is homologous with a region of the HBB gene encoding the E6V mutation, the nucleotide sequence set forth in SEQ ID NO: 102, and (iii) a nucleotide sequence homologous with a region located downstream of the E6V mutation in the HBB gene, wherein a double-strand break (DSB) occurs at the target site in the HBB gene and the nucleic acid is exchanged with a homologous nucleotide sequence of the HBB gene, thereby correcting the E6V mutation in the HBB gene in the cell or population of cells.

In some aspects, the disclosure provides a method for correcting an E6V mutation in human beta-globin (HBB) in a cell or population of cells, the method comprising contacting the cell or population of cells comprising an HBB gene encoding the E6V mutation with:

(a) a *S. pyogenes* Cas9 endonuclease, an mRNA encoding the *S. pyogenes* Cas9 endonuclease, or a recombinant expression vector comprising a nucleotide sequence encoding the *S. pyogenes* Cas9 endonuclease;

(b) a single guide RNA (sgRNA) targeting a target site in the HBB gene, the sgRNA recognizes a target sequence consisting of SEQ ID NO: 20; and (c) a recombinant vector comprising a nucleic acid, the nucleic acid comprising from 5' to 3' (i) a nucleotide sequence homologous with a region located upstream of the E6V mutation in the HBB gene, (ii) a nucleotide sequence which corrects the E6V mutation and is homologous with a region of the HBB gene encoding the E6V mutation, the nucleotide sequence set forth in SEQ ID NO: 102, and (iii) a nucleotide sequence homologous with a region located downstream of the E6V mutation in the HBB gene, wherein a double-strand break (DSB) occurs at the target site in the HBB gene and the nucleic acid is exchanged with a homologous nucleotide sequence of the HBB gene, thereby correcting the E6V mutation in the HBB gene in the cell or population of cells.

In any of the foregoing or related aspects, the method further comprises contacting the cell with a 53BP1 inhibitor. In some aspects, the method further comprises contacting the cell with an inhibitor of DNA-PK. In other aspects, the method comprises contacting the cell with a 53BP1 inhibitor and an inhibitor of DNA-PK. In some aspects, the 53BP1 inhibitor and/or the inhibitor of DNA-PK increases HDR of the DSB, relative to HDR in a cell or population of cells without the 53BP1 inhibitor and/or inhibitor of DNA-PK.

In any of the foregoing or related aspects, the *S. pyogenes* Cas9 endonuclease is a high fidelity *S. pyogenes* Cas9 endonuclease. In some aspects, cleavage of one or more predicted off-target sites is reduced by at least about 50% relative to a cell or population of cells contacted with a wild-type *S. pyogenes* Cas9.

In some aspects, the disclosure provides a method for homology directed repair (HDR) of a double-strand break (DSB) in a target region in a human beta-globin (HBB) gene in a cell or population of cells, the method comprising contacting the cell or population of cells with:

(a) a DNA endonuclease, an mRNA encoding the DNA endonuclease, or a recombinant expression vector comprising a nucleotide sequence encoding the DNA endonuclease;

(b) a single guide RNA (sgRNA) targeting a target site in an HBB gene;

(c) a recombinant vector comprising a nucleic acid, the nucleic acid comprising from 5' to 3' (i) a nucleotide sequence homologous with a region located upstream of the target region in the HBB gene, (ii) a nucleotide sequence homologous with a region of the HBB gene comprising the target region, and (iii) a nucleotide sequence homologous with a region located downstream of the target region in the HBB gene; and (d) a 53BP1 inhibitor, wherein a double-strand break (DSB) occurs at the target site in the HBB gene and the nucleic acid is exchanged with a homologous nucleotide sequence of the HBB gene. In some aspects, the HDR of the DSB is increased relative to HDR in a cell or population of cells without the 53BP1 inhibitor.

In other aspects, the disclosure provides a method for homology directed repair (HDR) of a double-strand break (DSB) in a target region in a human beta-globin (HBB) gene in a cell or population of cells, the method comprising contacting the cell or population of cells with:

(a) a DNA endonuclease, an mRNA encoding the DNA endonuclease, or a recombinant expression vector comprising a nucleotide sequence encoding the DNA endonuclease;

(b) a single guide RNA (sgRNA) targeting a target site in an HBB gene;

(c) a recombinant vector comprising a nucleic acid, the nucleic acid comprising from 5' to 3' (i) a nucleotide sequence homologous with a region located upstream of the target region in the HBB gene, (ii) a nucleotide sequence homologous with a region of the HBB gene comprising the target region, and (iii) a nucleotide sequence homologous with a region located downstream of the target region in the HBB gene; and (d) a DNA-PK inhibitor, wherein a double-strand break (DSB) occurs at the target site in the HBB gene and the nucleic acid is exchanged with a homologous nucleotide sequence of the HBB gene. In some aspects, the HDR of the DSB is increased relative to HDR in a cell or population of cells without the DNA-PK inhibitor.

In other aspects, the disclosure provides a method for homology directed repair (HDR) of a double-strand break (DSB) in a target region in a human beta-globin (HBB) gene in a cell or population of cells, the method comprising contacting the cell or population of cells with:

(a) a DNA endonuclease, an mRNA encoding the DNA endonuclease, or a recombinant expression vector comprising a nucleotide sequence encoding the DNA endonuclease;

(b) a single guide RNA (sgRNA) targeting a target site in an HBB gene;

(c) a recombinant vector comprising a nucleic acid, the nucleic acid comprising from 5' to 3' (i) a nucleotide sequence homologous with a region located upstream of the target region in the HBB gene, (ii) a nucleotide sequence homologous with a region of the HBB gene comprising the target region, and (iii) a nucleotide sequence homologous with a region located downstream of the target region in the HBB gene;

(d) a 53BP1 inhibitor; and (e) a DNA-PK inhibitor, wherein a double-strand break (DSB) occurs at the target site in the HBB gene and the nucleic acid is exchanged with a homologous nucleotide sequence of the HBB gene. In some aspects, the HDR of the DSB with the exchange of the nucleic acid into the HBB gene in the cell or population of cells is increased relative to HDR in a cell or population of cells without the 53BP1 inhibitor and DNA-PK inhibitor.

In any of the foregoing or related aspects, the DSB occurs 10-50 nucleotides upstream or downstream of a region of the HBB gene encoding an E6V mutation. In some aspects, the DSB occurs within exon 1 of the HBB gene.

In any of the foregoing or related aspects, the sgRNA comprises a spacer sequence corresponding to a target sequence consisting of SEQ ID NO: 15. In other aspects, the sgRNA recognizes a target sequence consisting of SEQ ID NO: 15. In some aspects, the sgRNA recognizes a target sequence consisting of SEQ ID NO: 20.

In some aspects, the disclosure provides a method for homology directed repair (HDR) of a double-strand break (DSB) in a target region in a human beta-globin (HBB) gene in a cell or population of cells, the method comprising contacting the cell or population of cells with:

(a) a *S. pyogenes* Cas9 endonuclease, an mRNA encoding the *S. pyogenes* Cas9 endonuclease, or a recombinant expression vector comprising a nucleotide sequence encoding the *S. pyogenes* Cas9 endonuclease;

(b) a single guide RNA (sgRNA) targeting a target site in the HBB gene, the sgRNA comprising a spacer sequence corresponding to a target sequence consisting of SEQ ID NO: 15;

(c) a recombinant vector comprising a nucleic acid, the nucleic acid comprising from 5' to 3' (i) a nucleotide sequence homologous with a region located upstream of the target region in the HBB gene, (ii) a nucleotide sequence homologous with a region of the HBB gene comprising the target region, and (iii) a nucleotide sequence homologous with a region located downstream of the target region in the HBB gene; and (d) a 53BP1 inhibitor, wherein a double-strand break (DSB) occurs at the target site in the HBB gene and the nucleic acid is exchanged with a homologous nucleotide sequence of the HBB gene. In some aspects, the HDR of the DSB is increased relative to HDR in a cell or population of cells without the 53BP1 inhibitor.

In other aspects, the disclosure provides a method for homology directed repair (HDR) of a double-strand break (DSB) in a target region in a human beta-globin (HBB) gene in a cell or population of cells, the method comprising contacting the cell or population of cells with:

(a) a *S. pyogenes* Cas9 endonuclease, an mRNA encoding the *S. pyogenes* Cas9 endonuclease, or a recombinant expression vector comprising a nucleotide sequence encoding the *S. pyogenes* Cas9 endonuclease;

(b) a single guide RNA (sgRNA) targeting a target site in the HBB gene, the sgRNA comprising a spacer sequence corresponding to a target sequence consisting of SEQ ID NO: 15;

(c) a recombinant vector comprising a nucleic acid, the nucleic acid comprising from 5' to 3' (i) a nucleotide sequence homologous with a region located upstream of the target region in the HBB gene, (ii) a nucleotide sequence homologous with a region of the HBB gene comprising the target region, and (iii) a nucleotide sequence homologous with a region located downstream of the target region in the HBB gene; and (d) a DNA-PK inhibitor, wherein a double-strand break (DSB) occurs at the target site in the HBB gene and the nucleic acid is exchanged with a homologous nucleotide sequence of the HBB gene. In some aspects, the DSB is increased relative to HDR in a cell or population of cells without the DNA-PK inhibitor.

In other aspects, the disclosure provides a method for homology directed repair (HDR) of a double-strand break (DSB) in a target region in a human beta-globin (HBB) gene in a cell or population of cells, the method comprising contacting the cell or population of cells with:

(a) a *S. pyogenes* Cas9 endonuclease, an mRNA encoding the *S. pyogenes* Cas9 endonuclease, or a recombinant expression vector comprising a nucleotide sequence encoding the *S. pyogenes* Cas9 endonuclease;

(b) a single guide RNA (sgRNA) targeting a target site in the HBB gene, the sgRNA comprising a spacer sequence corresponding to a target sequence consisting of SEQ ID NO: 15;

(c) a recombinant vector comprising a nucleic acid, the nucleic acid comprising from 5' to 3' (i) a nucleotide sequence homologous with a region located upstream of the target region in the HBB gene, (ii) a nucleotide sequence homologous with a region of the HBB gene comprising the target region, and (iii) a nucleotide sequence homologous with a region located downstream of the target region in the HBB gene;

(d) a 53BP1 inhibitor; and (e) a DNA-PK inhibitor, wherein a double-strand break (DSB) occurs at the target site in the HBB gene and the nucleic acid is exchanged with a homologous nucleotide sequence of the HBB gene. In some aspects, the HDR of the DSB is increased relative to HDR in a cell or population of cells without the 53BP1 inhibitor and DNA-PK inhibitor.

In any of the foregoing or related aspects, the nucleotide sequence of (c)(ii) corrects an E6V mutation in the HBB gene and is homologous with a region of the HBB gene encoding an E6V mutation. In some aspects, the nucleotide sequence of (c)(ii) comprises the sequence of SEQ ID NO: 102.

In any of the foregoing or related aspects, the nucleotide sequence of (c)(i) is homologous with a region upstream of the region encoding an E6V mutation in the HBB gene and the nucleotide sequence of (c)(iii) is homologous to a region downstream of the E6V mutation.

In some aspects, the disclosure provides a method for correcting an E6V mutation in human beta-globin (HBB) by homology directed repair (HDR) in a cell or population of cells, the method comprising contacting the cell or population of cells comprising an HBB gene encoding the E6V mutation with:

(a) a DNA endonuclease, an mRNA encoding the DNA endonuclease, or a recombinant expression vector comprising a nucleotide sequence encoding the DNA endonuclease;

(b) a single guide RNA (sgRNA) targeting a target site in a HBB gene;

(c) a recombinant vector comprising a nucleic acid, the nucleic acid comprising from 5' to 3' (i) a nucleotide sequence homologous with a region located upstream of the E6V mutation in the HBB gene, (ii) a nucleotide sequence which corrects the E6V mutation and is homologous with a region of the HBB gene encoding the E6V mutation, the nucleotide sequence set forth in SEQ ID NO: 102, and (iii) a nucleotide sequence homologous with a region located downstream of the E6V mutation in the HBB gene; and (d) a 53BP1 inhibitor, wherein a double-strand break (DSB) occurs at the target site in the HBB gene and the nucleic acid is exchanged with a homologous nucleotide sequence of the HBB gene. In some aspects, correction of the E6V mutation is increased relative to a cell or population of cells without the 53BP1 inhibitor.

In other aspects, the disclosure provides a method for correcting an E6V mutation in human beta-globin (HBB) by homology directed repair (HDR) in a cell or population of cells, the method comprising contacting the cell or population of cells comprising an HBB gene encoding the E6V mutation with:

(a) a DNA endonuclease, an mRNA encoding the DNA endonuclease, or a recombinant expression vector comprising a nucleotide sequence encoding the DNA endonuclease;

(b) a single guide RNA (sgRNA) targeting a target site in a HBB gene;

(c) a recombinant vector comprising a nucleic acid, the nucleic acid comprising from 5' to 3' (i) a nucleotide sequence homologous with a region located upstream of the E6V mutation in the HBB gene, (ii) a nucleotide sequence which corrects the E6V mutation and is homologous with a region of the HBB gene encoding the E6V mutation, the nucleotide sequence set forth in SEQ ID NO: 102, and (iii) a nucleotide sequence homologous with a region located downstream of the E6V mutation in the HBB gene; and (d) a DNA-PK inhibitor, wherein a double-strand break (DSB) occurs at the target site in the HBB gene and the nucleic acid is exchanged with a homologous nucleotide sequence of the HBB gene. In some aspects, correction of the E6V mutation is increased relative to a cell or population of cells without the DNA-PK inhibitor.

In yet other aspects, the disclosure provides a method for correcting an E6V mutation in human beta-globin (HBB) by homology directed repair (HDR) in a cell or population of cells, the method comprising contacting the cell or population of cells comprising an HBB gene encoding the E6V mutation with:

(a) a DNA endonuclease, an mRNA encoding the DNA endonuclease, or a recombinant expression vector comprising a nucleotide sequence encoding the DNA endonuclease;

(b) a single guide RNA (sgRNA) targeting a target site in a HBB gene;

(c) a recombinant vector comprising a nucleic acid, the nucleic acid comprising from 5' to 3' (i) a nucleotide sequence homologous with a region located upstream of the E6V mutation in the HBB gene, (ii) a nucleotide sequence which corrects the E6V mutation and is homologous with a region of the HBB gene encoding the E6V mutation, the nucleotide sequence set forth in SEQ ID NO: 102, and (iii) a nucleotide sequence homologous with a region located downstream of the E6V mutation in the HBB gene;

(d) a 53BP1 inhibitor; and (e) a DNA-PK inhibitor, wherein a double-strand break (DSB) occurs at the target site in the HBB gene and the nucleic acid is exchanged with a homologous nucleotide sequence of the HBB gene. In some aspects, correction of the E6V mutation is increased relative to a cell or population of cells without the 53BP1 inhibitor and DNA-PK inhibitor.

In any of the foregoing or related aspects, the DSB occurs 10-50 nucleotides upstream or downstream of a region of the HBB gene encoding the E6V mutation. In some aspects, the DSB occurs within exon 1 of the HBB gene.

In any of the foregoing or related aspects, the sgRNA comprises a spacer sequence corresponding to a target sequence consisting of SEQ ID NO: 15. In other aspects, the sgRNA recognizes a target sequence consisting of SEQ ID NO: 15. In other aspects, the sgRNA recognizes a target sequence consisting of SEQ ID NO: 20.

In any of the foregoing or related aspects, the nucleotide sequence of (c)(i) is homologous with a region comprising the promoter of the HBB gene and/or upstream sequences of the coding region of the HBB gene.

In any of the foregoing or related aspects, the nucleotide sequence of (c)(iii) is homologous with a region comprising a portion of exon 1, intron 1-2, exon 2, and a portion of intron 2-3, inclusive, and, optionally all or a portion of exon 3, of the HBB gene. In some aspects, the nucleotide sequence of (c)(iii) spans the target site.

In any of the foregoing or related aspects, the DNA endonuclease is a Cas9 endonuclease.

In some aspects, the Cas9 endonuclease is a *S. pyogenes* Cas9 endonuclease. In some aspects, the *S. pyogenes* Cas9 endonuclease is a high fidelity *S. pyogenes* Cas9 endonuclease. In some aspects, cleavage of one or more predicted off-target sites is reduced by at least about 50% relative to a wild-type *S. pyogenes* Cas9 endonuclease. In any of the foregoing or related aspects, the high fidelity Cas9 endonuclease comprises a R691A mutation. In some aspects, the high fidelity Cas9 endonuclease comprises at least one NLS. In some aspects, the at least one NLS is an sv40 NLS.

In any of the foregoing or related aspects, the 53BP1 inhibitor and/or the inhibitor of DNA-PK increases HDR frequency in the cell population by at least 50% relative to a cell population without the 53BP1 inhibitor and/or the inhibitor of DNA-PK. In some aspects, the 53BP1 inhibitor and/or the inhibitor of DNA-PK decreases indel frequency by 1-2 fold, 1.1-2 fold, or 2-10 fold in the cell population.

In any of the foregoing or related aspects, the 53BP1 inhibitor is a 53BP1 binding polypeptide that inhibits 53BP1 recruitment to the DSB in the cell. In some aspects, the 53BP1 binding polypeptide comprises an amino acid sequence selected from a group consisting of: SEQ ID NOs: 70, 74, 77, 80, 83 and 86. In some aspects, the 53BP1 inhibitor comprises a nucleic acid comprising a nucleotide sequence encoding a 53BP1 binding polypeptide that inhibits 53BP1 recruitment to the DSB site in the cell. In some aspects, the nucleic acid comprises a nucleotide sequence selected from a group consisting of: SEQ ID NOs: 69, 73, 76, 79, 82, 85 and 88. In some aspects, the nucleic acid comprises a vector comprising a nucleotide sequence encoding the 53BP1 binding polypeptide. In some aspects, the vector comprises a nucleotide sequence selected from a group consisting of: SEQ ID NOs: 68, 72, 75, 78, 81, 84 and 87. In other aspects, the 53BP1 inhibitor comprises a small interfering ribonucleic acid (siRNA) targeting 53BP1.

In any of the foregoing or related aspects, the inhibitor of DNA-PK targets the catalytic subunit of DNA-PK (DNA-PKcs). In some aspects, the inhibitor of DNA-PK is Nu7441. In some aspects, the inhibitor of DNA-PK is Compound 984 or Compound 296.

In any of the foregoing or related aspects, the nucleotide sequence of (c)(i) is about 0.2 kb to about 3 kb in length. In any of the foregoing or related aspects, the nucleotide sequence of (c)(iii) is about 0.2 kb to about 3 kb in length. In any of the foregoing or related aspects, the nucleotide sequence of (c)(i) and/or the nucleotide sequence of (c)(iii) is about 0.2 kb-1 kb, about 1 kb-1.5 kb, 1.5 kb-2 kb, 2 kb-2.2 kb or 2.0 kb-2.3 kb in length. In any of the foregoing or related aspects, the nucleotide sequence of (c)(i) and/or the nucleotide sequence of (c)(iii) is about 2.2 kb each.

In any of the foregoing or related aspects, the recombinant vector comprises SEQ ID NO: 98. In some aspects, the recombinant vector is an AAV vector. In some aspects, the AAV vector is about 2.5 kb-4.6 kb in length. In some aspects, the AAV vector comprises AAV6. In some aspects, the AAV vector comprises 5' and 3' inverted terminal repeats (ITRs) derived from AAV2. In some aspects, the 5' ITR comprises SEQ ID NO: 106 and the 3' ITR comprises SEQ ID NO: 107. In some aspects, the AAV vector comprises SEQ ID NO: 105.

In any of the foregoing or related aspects, the cell or population of cells is a hematopoietic stem or progenitor cell (HSPC). In some aspects, the cell or population of cells is a long-term HSPC (LT-HSPC). In some aspects, the cell is a CD34 expressing cell.

In any of the foregoing or related aspects, the cell or population of cells is isolated from a tissue sample obtained from a human donor. In some aspects, the tissue sample is a peripheral blood sample. In some aspects, the human donor has a sickle cell disease.

In some aspects, the disclosure provides a cell or population of cells generated by any of the methods described herein In some aspects, the disclosure provides a method for treating a patient having a disease or disorder, comprising administering the cell or population of cells described herein, thereby treating the disease or disorder. In some aspects, the disease or disorder is sickle cell anemia.

BRIEF DESCRIPTION OF FIGURES

FIG. 1A shows HDR efficiency in the presence of Nu7441 (e.g., an inhibitor of DNA-PKcs), SCR7 (e.g., an inhibitor of DNA Ligase IV), and RS1 (e.g., an agonist of Rad51).

FIGS. 2A-2B show the efficiency of HDR repair to convert GFP to BFP. FIGS. 2C-2D show indel formation in the AAVS1 locus.

FIG. 6A shows HDR efficiency in the presence of different doses of mRNA encoding i53 (e.g., inhibitor of 53BP1) relative to negative controls that include mock electroporation (EP), AAV donor DNA alone or RNP-only (i.e., no AAV donor DNA). FIG. 6B shows HDR efficiency in the presence of different doses of mRNA encoding i53, Cyren1 (e.g., inhibitor of Ku70/80), or Cyren2 (e.g., inhibitor of Ku70/80) relative to negative controls that include AAV alone (i.e., no RNP). FIG. 6C shows HDR efficiency in the presence of varied doses of Nu7441 relative to a DMSO-only control, mRNA encoding i53, or a control mRNA (DM) (i.e., absence of a modulator of DNA repair).

FIG. 12A includes a bar graph showing HDR editing efficiency in CD34-expressing LT-HSPCs isolated following mobilization with a combination of Mozobil and GCSF. FIG. 12B includes a bar graph showing HDR editing efficiency in LT-HSPCs isolated following mobilization with Mozobil alone.

FIG. 22A shows a comparison of HDR efficiency for AAV given pre-EP or post-EP in combination with gRNA/Cas9 RNP.

FIG. 22B shows a comparison of HDR efficiency in the presence of i53 or Nu7441 relative to RNP+AAV-only.

FIG. 23A shows % chimerism for LT-HSPCs edited with gRNA/Cas9 RNP and AAV given either pre-EP or post-EP. FIG. 23B shows % chimerism for LT-HSPCs edited with AAV and gRNA/Cas9 RNP in the presence of i53 or Nu7441 compared to RNP+AAV-only.

FIG. 24A shows % chimerism for LT-HSPCs edited with gRNA/Cas9 RNP and AAV given either pre-EP or post-EP. FIG. 24B shows % chimerism for LT-HSPCs edited with AAV and gRNA/Cas9 RNP in the presence of i53 or Nu7441 compared to RNP+AAV-only.

FIG. 26A shows HDR editing efficiency for LT-HSPCs edited with gRNA/Cas9 RNP and AAV given either pre-EP or post-EP. FIG. 26B shows HDR editing efficiency for LT-HSPCs edited with AAV and gRNA/Cas9 RNP in the presence of i53 or Nu7441 compared to RNP+AAV-only.

FIG. 37A further provides a measure of the percentage of total cells that remained viable following editing. FIG. 37B further provides a comparison to cells edited with R02 RNP+AAV and mRNA encoding i53.

FIGS. 38A-38C represent data from independent experiments ("Experiment 1" or "Experiment 2"). FIG. 38C further provides a measure of the percentage of total cells that remained viable following editing.

DETAILED DESCRIPTION

Figure 1A:
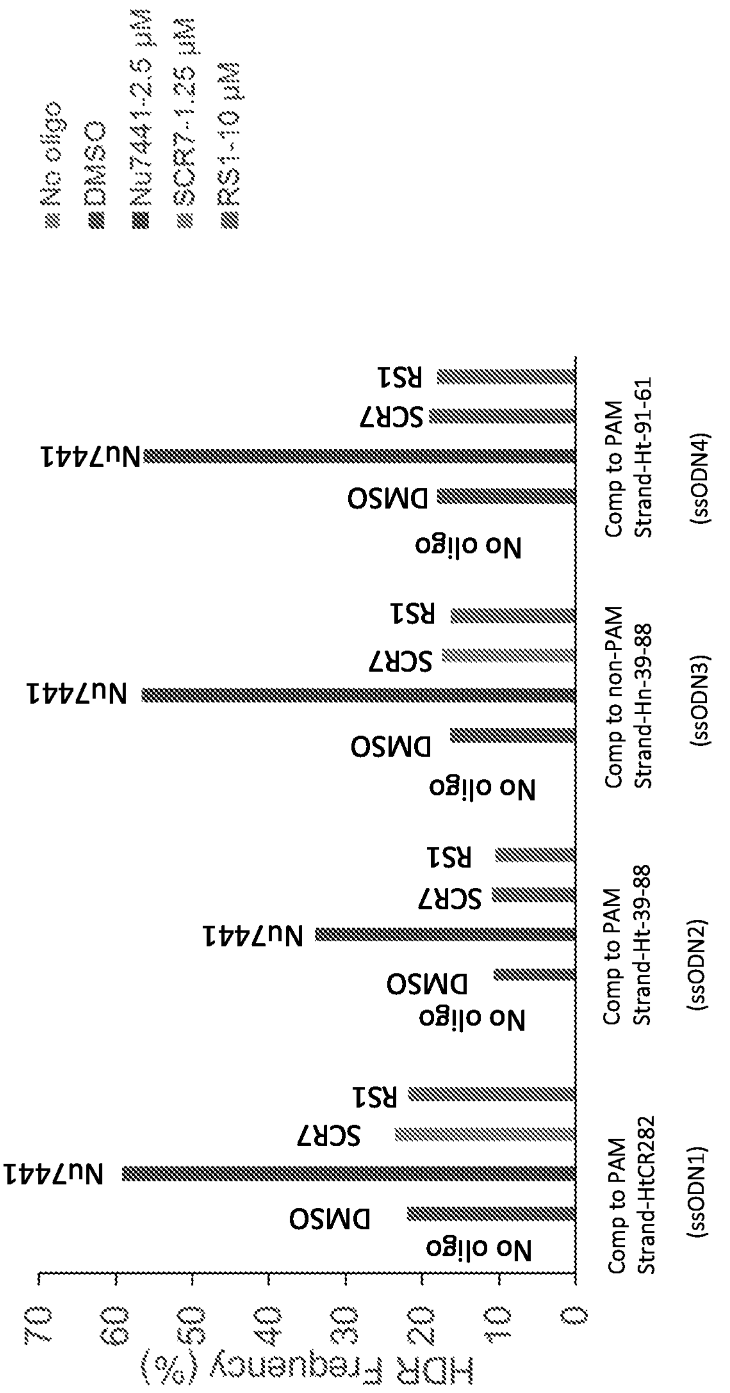
FIGS. 1A-ID include bar graphs showing efficiency of HDR repair in HEK293 T cells using single-stranded oligodeoxynucleotide (ssODN) donor DNA that converts a gene in the AAVS1 locus encoding a blue fluorescent protein (BFP) to a gene encoding green fluorescent protein (GFP).

The present disclosure is based, at least in part, on the use of an unique donor polynucleotide designed to correct a Glu6Val (E6V) mutation in exon 1 of the HBB gene in combination with an efficient gRNA and a site-directed nuclease (e.g., SpCas9) to generate a double-stranded break (DSB) at a target site in HBB to correct the mutation via homology directed repair (HDR), thereby treating sickle cell disease. The donor polynucleotide comprises a nucleotide sequence that corrects the E6V mutation and is homologous with a region of the HBB gene encoding the E6V mutation and all or part of target sequence for a site directed nuclease (e.g., an SpCas9 PAM site or complement thereof). For example, the donor polynucleotide can include a nucleotide sequence that is homologous with a region of the HBB gene that comprises a PAM recognition site, or complement thereof, that is recognized by the site directed nuclease. In some embodiments, a recombinant vector comprises the donor polynucleotide that corrects the E6V mutation located between two homology arms: a left homology arm (LHA) comprising a nucleotide sequence homologous to region in the HBB gene upstream of the E6V mutation; and a right homology arm (RHA) comprising a nucleotide sequence homologous to a region in the HBB gene downstream of the E6V mutation and spanning the target site. In some embodiments, the homology arms are each about 500 nucleotides or more. In some embodiments, the homology arms are each about 2.2 kb. In some aspects, the donor polynucleotide is codon optimized to increase HDR.

The present disclosure is also based, at least in part, on the discovery that CD34+ cells derived from sickle cell patients having the E6V mutation in an HBB gene, were successfully genetically edited with the unique donor polynucleotide to correct the E6V mutation. It has been demonstrated that such edited CD34+ cells differentiate into red blood cells having the same characteristics (e.g., enucleation) as unedited cells. It has also been shown that HDR of a DSB effected by the gRNA and DNA endonuclease was increased with a 53BP1 inhibitor and/or DNA-PK inhibitor. It has been further demonstrated that off-target activity of a Cas9 endonuclease in combination with a gRNA targeting a target site proximal to the E6V mutation is reduced by using a Cas9 endonuclease engineered to have high-fidelity.

Genome Editing

In some aspects, the disclosure provides methods for editing a cell to correct an E6V mutation in human beta-globin (HBB). In some embodiments, the E6V mutation is corrected by editing an HBB gene encoding the E6V mutation (i.e., genome editing). As is well known in the art and used herein, the term "E7V" refers to a single nucleotide polymorphism (SNP) in the HBB gene that occurs in the seventh codon downstream the transcription start site (i.e. the seventh codon of HBB if including the AUG start codon), wherein the SNP converts the wild-type codon encoding Glu to a codon encoding Val. Correspondingly, a beta-globin polypeptide with an "E7V" mutation refers to substitution of Glu to Val occurring in the seventh amino acid residue of the beta-globin polypeptide if including the initial methionine amino acid. As used herein, the term "E6V" refers to a SNP in the HBB gene that occurs in the sixth codon downstream the AUG start codon (i.e., the sixth codon of the HBB open reading frame downstream the start codon), wherein the SNP converts the wild-type encoding Glu to a codon encoding Val. Correspondingly, a beta-globin polypeptide with an "E6V" mutation refers to substitution of Glu to Val occurring at the sixth amino acid residue of the beta-globing polypeptide, not including the initial methionine amino acid. Accordingly, as readily understood by one of ordinary skill in the art, the terms "E7V" and "E6V" refer to the same mutation in the HBB gene, and are used interchangeably herein when used in reference to the sickle mutation.

Genome editing generally refers to the process of editing or changing the nucleotide sequence of a genome, preferably in a precise, desirable and/or pre-determined manner. Examples of compositions, systems, and methods of genome editing described herein use site-directed nucleases to cut or cleave DNA at precise target locations in the genome, thereby creating a double-strand break (DSB) in the DNA. Such breaks can be repaired by endogenous DNA repair pathways, such as homology directed repair (HDR) and/or non-homologous end-joining (NHEJ) repair (see e.g., Cox et al., (2015) Nature Medicine 21 (2):121-31). One of the major obstacles to efficient genome editing in non-dividing cells is lack of homology directed repair (HDR). Without HDR, non-dividing cells rely on non-homologous end joining (NHEJ) to repair double-strand breaks (DSB) that occur in the genome. The results of NHEJ-mediated DNA repair of DSBs can include correct repair of the DSB, or deletion or insertion of one or more nucleotides or polynucleotides.

In some embodiments, the disclosure provides improved methods for editing a cell to correct an E6V mutation encoded by the HBB gene. In some embodiments, the disclosure provides methods for improving HDR of a DSB in a target region in an HBB gene. In some embodiments, the methods disclosed herein utilize a donor polynucleotide or recombinant vector, a gRNA and a DNA endonuclease (e.g., SpCas9) to edit an HBB gene within a cell (e.g., correct an E6V mutation encoded by the HBB gene). In some embodiments, the method disclosed herein utilize a donor polynucleotide or recombinant vector, a gRNA, a DNA endonuclease (e.g., SpCas9), and a 53BP1 inhibitor and/or DNA- PKcs inhibitor, to improve genome editing of an HBB gene within a cell (e.g., correction of an E6V mutation encoded by the HBB gene).

In some embodiments, the disclosure provides a donor polynucleotide comprising SEQ ID NO: 102, a gRNA comprising a spacer sequence corresponding to a target sequence comprising SEQ ID NO: 15, and a Cas9 endonuclease (e.g., SpCas9). In some embodiments, the disclosure provides a recombinant vector comprising SEQ ID NO: 98, a gRNA comprising a spacer sequence corresponding to a target sequence comprising SEQ ID NO: 15, and a Cas9 endonuclease (e.g., SpCas9).

In some embodiments, the disclosure provides a donor polynucleotide comprising SEQ ID NO: 102, a gRNA that recognizes a target sequence comprising SEQ ID NO: 15, and a Cas9 endonuclease (e.g., SpCas9). In some embodiments, the disclosure provides a recombinant vector comprising SEQ ID NO: 98, a gRNA that recognizes a target sequence comprising SEQ ID NO: 15, and a Cas9 endonuclease (e.g., SpCas9).

In some embodiments, the disclosure provides a donor polynucleotide comprising SEQ ID NO: 102, a gRNA that recognizes a target sequence comprising SEQ ID NO: 20, and a Cas9 endonuclease (e.g., SpCas9). In some embodiments, the disclosure provides a recombinant vector comprising SEQ ID NO: 98, a gRNA that recognizes a target sequence comprising SEQ ID NO: 20, and a Cas9 endonuclease (e.g., SpCas9).

In some embodiments, the disclosure provides a donor polynucleotide comprising SEQ ID NO: 102, a gRNA comprising a spacer sequence comprising SEQ ID NO: 16, and a Cas9 endonuclease (e.g., SpCas9). In some embodiments, the disclosure provides a recombinant vector comprising SEQ ID NO: 98, a gRNA comprising a spacer sequence comprising SEQ ID NO: 16, and a Cas9 endonuclease (e.g., SpCas9).

In some embodiments, the disclosure provides a donor polynucleotide comprising SEQ ID NO: 102, a gRNA comprising SEQ ID NO: 17, and a Cas9 endonuclease (e.g., SpCas9). In some embodiments, the disclosure provides a recombinant vector comprising SEQ ID NO: 98, a gRNA comprising SEQ ID NO: 17, and a Cas9 endonuclease (e.g., SpCas9).

In some embodiments, the disclosure provides a donor polynucleotide or recombinant vector, a gRNA comprising a spacer sequence corresponding to a target sequence comprising SEQ ID NO: 15, and a high-fidelity Cas9 endonuclease (e.g., high-fidelity SpCas9). In some embodiments, the disclosure provides a donor polynucleotide or recombinant vector, a gRNA that recognizes a target sequence comprising SEQ ID NO: 15, and a high-fidelity Cas9 endonuclease (e.g., high-fidelity SpCas9). In some embodiments, the disclosure provides a donor polynucleotide or recombinant vector, a gRNA that recognizes a target sequence comprising SEQ ID NO: 20, and a high-fidelity Cas9 endonuclease (e.g., high-fidelity SpCas9). In some embodiments, the disclosure provides a donor polynucleotide or recombinant vector, a gRNA comprising a spacer sequence comprising SEQ ID NO: 16, and a high-fidelity Cas9 endonuclease (e.g., high-fidelity SpCas9). In some embodiments, the disclosure provides a donor polynucleotide or recombinant vector, a gRNA comprising SEQ ID NO: 17, and a high-fidelity Cas9 endonuclease (e.g., high-fidelity SpCas9).

In some embodiments, the disclosure provides a donor polynucleotide comprising SEQ ID NO: 102, a gRNA targeting a target site in an HBB gene, and a Cas9 endonuclease (e.g., SpCas9). In some embodiments, the disclosure provides a recombinant vector comprising SEQ ID NO: 98, a gRNA targeting a target site in an HBB gene, and a Cas9 endonuclease (e.g., SpCas9).

In some embodiments, the disclosure provides a donor polynucleotide or recombinant vector, a gRNA comprising a spacer sequence corresponding to a target sequence comprising SEQ ID NO: 15, a Cas9 endonuclease (e.g., SpCas9), and a 53BP1 inhibitor and/or DNA-PKcs inhibitor. In some embodiments, the disclosure provides a donor polynucleotide or recombinant vector, a gRNA that recognizes a target sequence comprising SEQ ID NO: 15, a Cas9 endonuclease (e.g., SpCas9), and a 53BP1 inhibitor and/or DNA-PKcs inhibitor. In some embodiments, the disclosure provides a donor polynucleotide or recombinant vector, a gRNA that recognizes a target sequence comprising SEQ ID NO: 20, a Cas9 endonuclease (e.g., SpCas9), and a 53BP1 inhibitor and/or DNA-PKcs inhibitor. In some embodiments, the disclosure provides a donor polynucleotide or recombinant vector, a gRNA comprising a spacer sequence comprising SEQ ID NO: 16, a Cas9 endonuclease (e.g., SpCas9), and a 53BP1 inhibitor and/or DNA-PKcs inhibitor. In some embodiments, the disclosure provides a donor polynucleotide or recombinant vector, a gRNA comprising SEQ ID NO: 17, a Cas9 endonuclease (e.g., SpCas9), and a 53BP1 inhibitor and/or DNA-PKcs inhibitor.

In some embodiments, the disclosure provides a donor polynucleotide or recombinant vector, a gRNA comprising a spacer sequence corresponding to a target sequence comprising SEQ ID NO: 15, a Cas9 endonuclease (e.g., SpCas9), and a 53BP1 inhibitor comprising a polypeptide sequence of SEQ ID NO: 70 and/or DNA-PKcs inhibitor. In some embodiments, the disclosure provides a donor polynucleotide or recombinant vector, a gRNA that recognizes a target sequence comprising SEQ ID NO: 15, a Cas9 endonuclease (e.g., SpCas9), and a 53BP1 inhibitor comprising a polypeptide sequence of SEQ ID NO: 70 and/or DNA-PKcs inhibitor. In some embodiments, the disclosure provides a donor polynucleotide or recombinant vector, a gRNA that recognizes a target sequence comprising SEQ ID NO: 20, a Cas9 endonuclease (e.g., SpCas9), and a 53BP1 inhibitor comprising a polypeptide sequence of SEQ ID NO: 70 and/or DNA-PKcs inhibitor. In some embodiments, the disclosure provides a donor polynucleotide or recombinant vector, a gRNA comprising a spacer sequence comprising SEQ ID NO: 16, a Cas9 endonuclease (e.g., SpCas9), and a 53BP1 inhibitor comprising a polypeptide sequence of SEQ ID NO: 70 and/or DNA-PKcs inhibitor. In some embodiments, the disclosure provides a donor polynucleotide or recombinant vector, a gRNA comprising SEQ ID NO: 17, a Cas9 endonuclease (e.g., SpCas9), and a 53BP1 inhibitor comprising a polypeptide sequence of SEQ ID NO: 70 and/or DNA-PKcs inhibitor.

In some embodiments, the disclosure provides a donor polynucleotide or recombinant vector, a gRNA comprising a spacer sequence corresponding to a target sequence comprising SEQ ID NO: 15, a Cas9 endonuclease (e.g., SpCas9), and a 53BP1 inhibitor and/or DNA-PKcs inhibitor selected from Compound 984 and Compound 296. In some embodiments, the disclosure provides a donor polynucleotide or recombinant vector, a gRNA that recognizes a target sequence comprising SEQ ID NO: 15, a Cas9 endonuclease (e.g., SpCas9), and a 53BP1 inhibitor and/or DNA-PKcs inhibitor selected from Compound 984 and Compound 296. In some embodiments, the disclosure provides a donor polynucleotide or recombinant vector, a gRNA that recognizes a target sequence comprising SEQ ID NO: 20, a Cas9 endonuclease (e.g., SpCas9), and a 53BP1 inhibitor and/or DNA-PKcs inhibitor selected from Compound 984 and Compound 296. In some embodiments, the disclosure provides a donor polynucleotide or recombinant vector, a gRNA comprising a spacer sequence comprising SEQ ID NO: 16, a Cas9 endonuclease (e.g., SpCas9), and a 53BP1 inhibitor and/or DNA-PKcs inhibitor selected from Compound 984 and Compound 296. In some embodiments, the disclosure provides a donor polynucleotide or recombinant vector, a gRNA comprising SEQ ID NO: 17, a Cas9 endonuclease (e.g., SpCas9), and a 53BP1 inhibitor and/or DNA-PKcs inhibitor selected from Compound 984 and Compound 296.

In some embodiments, the disclosure provides a donor polynucleotide or recombinant vector, a gRNA comprising a spacer sequence corresponding to a target sequence comprising SEQ ID NO: 15, a Cas9 endonuclease (e.g., SpCas9), and a 53BP1 inhibitor comprising a polypeptide sequence of SEQ ID NO: 70 and/or DNA-PKcs inhibitor selected from Compound 984 and Compound 296. In some embodiments, the disclosure provides a donor polynucleotide or recombinant vector, a gRNA that recognizes a target sequence comprising SEQ ID NO: 15, a Cas9 endonuclease (e.g., SpCas9), and a 53BP1 inhibitor comprising a polypeptide sequence of SEQ ID NO: 70 and/or DNA-PKcs inhibitor selected from Compound 984 and Compound 296. In some embodiments, the disclosure provides a donor polynucleotide or recombinant vector, a gRNA that recognizes a target sequence comprising SEQ ID NO: 20, a Cas9 endonuclease (e.g., SpCas9), and a 53BP1 inhibitor comprising a polypeptide sequence of SEQ ID NO: 70 and/or DNA-PKcs inhibitor selected from Compound 984 and Compound 296. In some embodiments, the disclosure provides a donor polynucleotide or recombinant vector, a gRNA comprising a spacer sequence comprising SEQ ID NO: 16, a Cas9 endonuclease (e.g., SpCas9), and a 53BP1 inhibitor comprising a polypeptide sequence of SEQ ID NO: 70 and/or DNA-PKcs inhibitor selected from Compound 984 and Compound 296. In some embodiments, the disclosure provides a donor polynucleotide or recombinant vector, a gRNA comprising SEQ ID NO: 17, a Cas9 endonuclease (e.g., SpCas9), and a 53BP1 inhibitor comprising a polypeptide sequence of SEQ ID NO: 70 and/or DNA-PKcs inhibitor selected from Compound 984 and Compound 296.

In some embodiments, the disclosure provides a donor polynucleotide comprising SEQ ID NO: 102, a gRNA targeting a target site in an HBB gene, a Cas9 endonuclease (e.g., SpCas9), and a 53BP1 inhibitor and/or DNA-PKcs inhibitor. In some embodiments, the disclosure provides a recombinant vector comprising SEQ ID NO: 98, a gRNA targeting a target site in an HBB gene, a Cas9 endonuclease (e.g., SpCas9), and a 53BP1 inhibitor and/or DNA-PKcs inhibitor.

In some embodiments, the disclosure provides a donor polynucleotide comprising SEQ ID NO: 102, a gRNA targeting a target site in an HBB gene, a Cas9 endonuclease (e.g., SpCas9), and a 53BP1 inhibitor comprising a polypeptide sequence of SEQ ID NO: 70 and/or DNA-PKcs inhibitor. In some embodiments, the disclosure provides a recombinant vector comprising SEQ ID NO: 98, a gRNA targeting a target site in an HBB gene, a Cas9 endonuclease (e.g., SpCas9), and a 53BP1 inhibitor comprising a polypeptide sequence of SEQ ID NO: 70 and/or DNA-PKcs inhibitor.

In some embodiments, the disclosure provides a donor polynucleotide comprising SEQ ID NO: 102, a gRNA targeting a target site in an HBB gene, a Cas9 endonuclease (e.g., SpCas9), and a 53BP1 inhibitor and/or DNA-PKcs inhibitor selected from Compound 984 and Compound 296. In some embodiments, the disclosure provides a recombinant vector comprising SEQ ID NO: 98, a gRNA targeting a target site in an HBB gene, a Cas9 endonuclease (e.g., SpCas9), and a 53BP1 inhibitor and/or DNA-PKcs inhibitor selected from Compound 984 and Compound 296.

In some embodiments, the disclosure provides a donor polynucleotide comprising SEQ ID NO: 102, a gRNA targeting a target site in an HBB gene, a Cas9 endonuclease (e.g., SpCas9), and a 53BP1 inhibitor comprising a polypeptide sequence of SEQ ID NO: 70 and/or DNA-PKcs inhibitor selected from Compound 984 and Compound 296. In some embodiments, the disclosure provides a recombinant vector comprising SEQ ID NO: 98, a gRNA targeting a target site in an HBB gene, a Cas9 endonuclease (e.g., SpCas9), and a 53BP1 inhibitor comprising a polypeptide sequence of SEQ ID NO: 70 and/or DNA-PKcs inhibitor selected from Compound 984 and Compound 296.

In some embodiments, the disclosure provides a donor polynucleotide comprising SEQ ID NO: 102, a gRNA comprising a spacer sequence corresponding to a target sequence comprising SEQ ID NO: 15, a Cas9 endonuclease (e.g., SpCas9) and a 53BP1 inhibitor. In some embodiments, the disclosure provides a donor polynucleotide comprising SEQ ID NO: 102, a gRNA comprising a spacer sequence corresponding to a target sequence comprising SEQ ID NO: 15, a Cas9 endonuclease (e.g., SpCas9) and a 53BP1 inhibitor comprising a polypeptide sequence of SEQ ID NO: 70. In some embodiments, the disclosure provides a donor polynucleotide comprising SEQ ID NO: 102, a gRNA that recognizes a target sequence comprising SEQ ID NO: 15, a Cas9 endonuclease (e.g., SpCas9) and a 53BP1 inhibitor. In some embodiments, the disclosure provides a donor polynucleotide comprising SEQ ID NO: 102, a gRNA that recognizes a target sequence comprising SEQ ID NO: 15, a Cas9 endonuclease (e.g., SpCas9) and a 53BP1 inhibitor comprising a polypeptide sequence of SEQ ID NO: 70. In some embodiments, the disclosure provides a donor polynucleotide comprising SEQ ID NO: 102, a gRNA that recognizes a target sequence comprising SEQ ID NO: 20, a Cas9 endonuclease (e.g., SpCas9) and a 53BP1 inhibitor. In some embodiments, the disclosure provides a donor polynucleotide comprising SEQ ID NO: 102, a gRNA that recognizes a target sequence comprising SEQ ID NO: 20, a Cas9 endonuclease (e.g., SpCas9) and a 53BP1 inhibitor comprising a polypeptide sequence of SEQ ID NO: 70. In some embodiments, the disclosure provides a recombinant vector comprising SEQ ID NO: 98 a gRNA comprising a spacer sequence corresponding to a target sequence comprising SEQ ID NO: 15, a Cas9 endonuclease (e.g., SpCas9) and a 53BP1 inhibitor. In some embodiments, the disclosure provides a recombinant vector comprising SEQ ID NO: 98, a gRNA comprising a spacer sequence corresponding to a target sequence comprising SEQ ID NO: 15, a Cas9 endonuclease (e.g., SpCas9) and a 53BP1 inhibitor comprising a polypeptide sequence of SEQ ID NO: 70. In some embodiments, the disclosure provides a recombinant vector comprising SEQ ID NO: 98 a gRNA that recognizes a target sequence comprising SEQ ID NO: 15, a Cas9 endonuclease (e.g., SpCas9) and a 53BP1 inhibitor. In some embodiments, the disclosure provides a recombinant vector comprising SEQ ID NO: 98, a gRNA that recognizes a target sequence comprising SEQ ID NO: 15, a Cas9 endonuclease (e.g., SpCas9) and a 53BP1 inhibitor comprising a polypeptide sequence of SEQ ID NO: 70. In some embodiments, the disclosure provides a recombinant vector comprising SEQ ID NO: 98 a gRNA that recognizes a target sequence comprising SEQ ID NO: 20, a Cas9 endonuclease (e.g., SpCas9) and a 53BP1 inhibitor. In some embodiments, the disclosure provides a recombinant vector comprising SEQ ID NO: 98, a gRNA that recognizes a target sequence comprising SEQ ID NO: 20, a Cas9 endonuclease (e.g., SpCas9) and a 53BP1 inhibitor comprising a polypeptide sequence of SEQ ID NO: 70.

In some embodiments, the disclosure provides a donor polynucleotide comprising SEQ ID NO: 102, a gRNA comprising a spacer sequence corresponding to a target sequence comprising SEQ ID NO: 15, a Cas9 endonuclease (e.g., SpCas9) and a DNA-PKcs inhibitor. In some embodiments, the disclosure provides a donor polynucleotide comprising SEQ ID NO: 102, a gRNA comprising a spacer sequence corresponding to a target sequence comprising SEQ ID NO: 15, a Cas9 endonuclease (e.g., SpCas9) and a DNA-PKcs inhibitor selected from Compound 984 and Compound 296. In some embodiments, the disclosure provides a donor polynucleotide comprising SEQ ID NO: 102, a gRNA that recognizes a target sequence comprising SEQ ID NO: 15, a Cas9 endonuclease (e.g., SpCas9) and a DNA-PKcs inhibitor. In some embodiments, the disclosure provides a donor polynucleotide comprising SEQ ID NO: 102, a gRNA that recognizes a target sequence comprising SEQ ID NO: 15, a Cas9 endonuclease (e.g., SpCas9) and a DNA-PKcs inhibitor selected from Compound 984 and Compound 296. In some embodiments, the disclosure provides a donor polynucleotide comprising SEQ ID NO: 102, a gRNA that recognizes a target sequence comprising SEQ ID NO: 20, a Cas9 endonuclease (e.g., SpCas9) and a DNA-PKcs inhibitor. In some embodiments, the disclosure provides a donor polynucleotide comprising SEQ ID NO: 102, a gRNA that recognizes a target sequence comprising SEQ ID NO: 20, a Cas9 endonuclease (e.g., SpCas9) and a DNA-PKcs inhibitor selected from Compound 984 and Compound 296. In some embodiments, the disclosure provides a recombinant vector comprising SEQ ID NO: 98, a gRNA comprising a spacer sequence corresponding to a target sequence comprising SEQ ID NO: 15, a Cas9 endonuclease (e.g., SpCas9) and a DNA-PKcs inhibitor. In some embodiments, the disclosure provides a recombinant vector comprising SEQ ID NO: 98, a gRNA comprising a spacer sequence corresponding to a target sequence comprising SEQ ID NO: 15, a Cas9 endonuclease (e.g., SpCas9) and a DNA-PKcs inhibitor selected from Compound 984 and Compound 296. In some embodiments, the disclosure provides a recombinant vector comprising SEQ ID NO: 98, a gRNA that recognizes a target sequence comprising SEQ ID NO: 15, a Cas9 endonuclease (e.g., SpCas9) and a DNA-PKcs inhibitor. In some embodiments, the disclosure provides a recombinant vector comprising SEQ ID NO: 98, a gRNA that recognizes a target sequence comprising SEQ ID NO: 15, a Cas9 endonuclease (e.g., SpCas9) and a DNA-PKcs inhibitor selected from Compound 984 and Compound 296. In some embodiments, the disclosure provides a recombinant vector comprising SEQ ID NO: 98, a gRNA that recognizes a target sequence comprising SEQ ID NO: 20, a Cas9 endonuclease (e.g., SpCas9) and a DNA-PKcs inhibitor. In some embodiments, the disclosure provides a recombinant vector comprising SEQ ID NO: 98, a gRNA that recognizes a target sequence comprising SEQ ID NO: 20, a Cas9 endonuclease (e.g., SpCas9) and a DNA-PKcs inhibitor selected from Compound 984 and Compound 296.

In some embodiments, the disclosure provides a donor polynucleotide comprising SEQ ID NO: 102, a gRNA comprising a spacer sequence corresponding to a target sequence comprising SEQ ID NO: 15, a Cas9 endonuclease (e.g., SpCas9), a 53BP1 inhibitor, and a DNA-PKcs inhibitor. In some embodiments, the disclosure provides a donor polynucleotide comprising SEQ ID NO: 102, a gRNA comprising a spacer sequence corresponding to a target sequence comprising SEQ ID NO: 15, a Cas9 endonuclease (e.g., SpCas9), a 53BP1 inhibitor comprising a polypeptide sequence of SEQ ID NO: 70 and a DNA-PKcs inhibitor selected from Compound 984 and Compound 296. In some embodiments, the disclosure provides a donor polynucleotide comprising SEQ ID NO: 102, a gRNA that recognizes a target sequence comprising SEQ ID NO: 15, a Cas9 endonuclease (e.g., SpCas9), a 53BP1 inhibitor, and a DNA-PKcs inhibitor. In some embodiments, the disclosure provides a donor polynucleotide comprising SEQ ID NO: 102, a gRNA that recognizes a target sequence comprising SEQ ID NO: 15, a Cas9 endonuclease (e.g., SpCas9), a 53BP1 inhibitor comprising a polypeptide sequence of SEQ ID NO: 70 and a DNA-PKcs inhibitor selected from Compound 984 and Compound 296. In some embodiments, the disclosure provides a donor polynucleotide comprising SEQ ID NO: 102, a gRNA that recognizes a target sequence comprising SEQ ID NO: 20, a Cas9 endonuclease (e.g., SpCas9), a 53BP1 inhibitor, and a DNA-PKcs inhibitor. In some embodiments, the disclosure provides a donor polynucleotide comprising SEQ ID NO: 102, a gRNA that recognizes a target sequence comprising SEQ ID NO: 20, a Cas9 endonuclease (e.g., SpCas9), a 53BP1 inhibitor comprising a polypeptide sequence of SEQ ID NO: 70 and a DNA-PKcs inhibitor selected from Compound 984 and Compound 296. In some embodiments, the disclosure provides a recombinant vector comprising SEQ ID NO: 98 a gRNA comprising a spacer sequence corresponding to a target sequence comprising SEQ ID NO: 15, a Cas9 endonuclease (e.g., SpCas9), a 53BP1 inhibitor and a DNA-PKcs inhibitor. In some embodiments, the disclosure provides a recombinant vector comprising SEQ ID NO: 98, a gRNA comprising a spacer sequence corresponding to a target sequence comprising SEQ ID NO: 15, a Cas9 endonuclease (e.g., SpCas9), a 53BP1 inhibitor comprising a polypeptide sequence of SEQ ID NO: 70 and a DNA-PKcs inhibitor selected from Compound 984 and Compound 296. In some embodiments, the disclosure provides a recombinant vector comprising SEQ ID NO: 98 a gRNA that recognizes a target sequence comprising SEQ ID NO: 15, a Cas9 endonuclease (e.g., SpCas9), a 53BP1 inhibitor and a DNA-PKcs inhibitor. In some embodiments, the disclosure provides a recombinant vector comprising SEQ ID NO: 98, a gRNA that recognizes a target sequence comprising SEQ ID NO: 15, a Cas9 endonuclease (e.g., SpCas9), a 53BP1 inhibitor comprising a polypeptide sequence of SEQ ID NO: 70 and a DNA-PKcs inhibitor selected from Compound 984 and Compound 296. In some embodiments, the disclosure provides a recombinant vector comprising SEQ ID NO: 98 a gRNA that recognizes a target sequence comprising SEQ ID NO: 20, a Cas9 endonuclease (e.g., SpCas9), a 53BP1 inhibitor and a DNA-PKcs inhibitor. In some embodiments, the disclosure provides a recombinant vector comprising SEQ ID NO: 98, a gRNA that recognizes a target sequence comprising SEQ ID NO: 20, a Cas9 endonuclease (e.g., SpCas9), a 53BP1 inhibitor comprising a polypeptide sequence of SEQ ID NO: 70 and a DNA-PKcs inhibitor selected from Compound 984 and Compound 296.

In some embodiments, the disclosure provides a donor polynucleotide comprising SEQ ID NO: 102, a gRNA comprising a spacer sequence comprising SEQ ID NO: 16, a Cas9 endonuclease (e.g., SpCas9) and a 53BP1 inhibitor.

In some embodiments, the disclosure provides a donor polynucleotide comprising SEQ ID NO: 102, a gRNA comprising a spacer sequence comprising SEQ ID NO: 16, a Cas9 endonuclease (e.g., SpCas9) and a 53BP1 inhibitor comprising a polypeptide sequence of SEQ ID NO: 70. In some embodiments, the disclosure provides a recombinant vector comprising SEQ ID NO: 98, a gRNA comprising a spacer sequence comprising SEQ ID NO: 16, a Cas9 endonuclease (e.g., SpCas9), and a 53BP1 inhibitor. In some embodiments, the disclosure provides a recombinant vector comprising SEQ ID NO: 98, a gRNA comprising a spacer sequence comprising SEQ ID NO: 16, a Cas9 endonuclease (e.g., SpCas9), and a 53BP1 inhibitor comprising a polypeptide sequence of SEQ ID NO: 70.

In some embodiments, the disclosure provides a donor polynucleotide comprising SEQ ID NO: 102, a gRNA comprising a spacer sequence comprising SEQ ID NO: 16, a Cas9 endonuclease (e.g., SpCas9) and a DNA-PKcs inhibitor. In some embodiments, the disclosure provides a donor polynucleotide comprising SEQ ID NO: 102, a gRNA comprising a spacer sequence comprising SEQ ID NO: 16, a Cas9 endonuclease (e.g., SpCas9) and a DNA-PKcs inhibitor selected from Compound 984 and Compound 296. In some embodiments, the disclosure provides a recombinant vector comprising SEQ ID NO: 98, a gRNA comprising a spacer sequence comprising SEQ ID NO: 16, a Cas9 endonuclease (e.g., SpCas9), and a DNA-PKcs inhibitor. In some embodiments, the disclosure provides a recombinant vector comprising SEQ ID NO: 98, a gRNA comprising a spacer sequence comprising SEQ ID NO: 16, a Cas9 endonuclease (e.g., SpCas9), and a DNA-PKcs inhibitor selected from Compound 984 and Compound 296.

In some embodiments, the disclosure provides a donor polynucleotide comprising SEQ ID NO: 102, a gRNA comprising a spacer sequence comprising SEQ ID NO: 16, a Cas9 endonuclease (e.g., SpCas9), a 53BP1 inhibitor and a DNA-PKcs inhibitor. In some embodiments, the disclosure provides a donor polynucleotide comprising SEQ ID NO: 102, a gRNA comprising a spacer sequence comprising SEQ ID NO: 16, a Cas9 endonuclease (e.g., SpCas9), a 53BP1 inhibitor comprising a polypeptide sequence of SEQ ID NO: 70 and a DNA-PKcs inhibitor selected from Compound 984 and Compound 296. In some embodiments, the disclosure provides a recombinant vector comprising SEQ ID NO: 98, a gRNA comprising a spacer sequence comprising SEQ ID NO: 16, a Cas9 endonuclease (e.g., SpCas9), a 53BP1 inhibitor and a DNA-PKcs inhibitor. In some embodiments, the disclosure provides a recombinant vector comprising SEQ ID NO: 98, a gRNA comprising a spacer sequence comprising SEQ ID NO: 16, a Cas9 endonuclease (e.g., SpCas9), a 53BP1 inhibitor comprising a polypeptide sequence of SEQ ID NO: 70, and a DNA-PKcs inhibitor selected from Compound 984 and Compound 296.

In some embodiments, the disclosure provides a donor polynucleotide comprising SEQ ID NO: 102, a gRNA comprising SEQ ID NO: 17, a Cas9 endonuclease (e.g., SpCas9) and a 53BP1 inhibitor. In some embodiments, the disclosure provides a donor polynucleotide comprising SEQ ID NO: 102, a gRNA comprising SEQ ID NO: 17, a Cas9 endonuclease (e.g., SpCas9) and a 53BP1 inhibitor comprising a polypeptide sequence of SEQ ID NO: 70. In some embodiments, the disclosure provides a recombinant vector comprising SEQ ID NO: 98, a gRNA comprising SEQ ID NO: 17, a Cas9 endonuclease (e.g., SpCas9), and a 53BP1 inhibitor. In some embodiments, the disclosure provides a recombinant vector comprising SEQ ID NO: 98, a gRNA comprising SEQ ID NO: 17, a Cas9 endonuclease (e.g., SpCas9), and a 53BP1 inhibitor comprising a polypeptide sequence of SEQ ID NO: 70.

In some embodiments, the disclosure provides a donor polynucleotide comprising SEQ ID NO: 102, a gRNA comprising SEQ ID NO: 17, a Cas9 endonuclease (e.g., SpCas9) and a DNA-PKcs inhibitor. In some embodiments, the disclosure provides a donor polynucleotide comprising SEQ ID NO: 102, a gRNA comprising SEQ ID NO: 17, a Cas9 endonuclease (e.g., SpCas9) and a DNA-PKcs inhibitor selected from Compound 984 and Compound 296. In some embodiments, the disclosure provides a recombinant vector comprising SEQ ID NO: 98, a gRNA comprising SEQ ID NO: 17, a Cas9 endonuclease (e.g., SpCas9), and a DNA-PKcs inhibitor. In some embodiments, the disclosure provides a recombinant vector comprising SEQ ID NO: 98, a gRNA comprising SEQ ID NO: 17, a Cas9 endonuclease (e.g., SpCas9), and a DNA-PKcs inhibitor selected from Compound 984 and Compound 296.

In some embodiments, the disclosure provides a donor polynucleotide comprising SEQ ID NO: 102, a gRNA comprising SEQ ID NO: 17, a Cas9 endonuclease (e.g., SpCas9), a 53BP1 inhibitor and a DNA-PKcs inhibitor. In some embodiments, the disclosure provides a donor polynucleotide comprising SEQ ID NO: 102, a gRNA comprising SEQ ID NO: 17, a Cas9 endonuclease (e.g., SpCas9), a 53BP1 inhibitor comprising a polypeptide sequence of SEQ ID NO: 70, and a DNA-PKcs inhibitor selected from Compound 984 and Compound 296. In some embodiments, the disclosure provides a recombinant vector comprising SEQ ID NO: 98, a gRNA comprising SEQ ID NO: 17, a Cas9 endonuclease (e.g., SpCas9), a 53BP1 inhibitor and a DNA-PKcs inhibitor. In some embodiments, the disclosure provides a recombinant vector comprising SEQ ID NO: 98, a gRNA comprising SEQ ID NO: 17, a Cas9 endonuclease (e.g., SpCas9), a 53BP1 inhibitor comprising a polypeptide sequence of SEQ ID NO: 70, and a DNA-PKcs inhibitor selected from Compound 984 and Compound 296.

In some embodiments, the donor polynucleotide comprises a nucleotide sequence complement to SEQ ID NO: 102. In some embodiments, the recombinant vector comprises a nucleotide sequence complement to SEQ ID NO: 98.

Donor Polynucleotides

The disclosure provides donor polynucleotides that, upon insertion into a DSB, correct or induce a mutation in a target nucleic acid (e.g., a genomic DNA). In some embodiments, the donor polynucleotides provided by the disclosure are recognized and used by the HDR machinery of a cell to repair a double strand break (DSB) introduced into a target nucleic acid by a site-directed nuclease, wherein repair of the DSB results in the insertion of the donor polynucleotide into the target nucleic acid. In some embodiments, the donor polynucleotides and/or recombinant vectors provided by the disclosure are recognized and used by the HDR machinery of a cell to repair a double strand break (DSB) introduced into a target nucleic acid (e.g., HBB gene) by a site-directed nuclease, wherein the region proximal to the DSB is exchanged for the corresponding region provided by the donor polynucleotide. Alternatively, a donor polynucleotide may have no regions of homology to the targeted location in the DNA and may be integrated by NHEJ-dependent end joining following cleavage at the target site.

In some embodiments, a donor template can be DNA or RNA, single-stranded and/or double-stranded, and can be introduced into a cell in linear or circular form. In some embodiments, the donor template can be a donor polynucleotide or a recombinant vector. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In some embodiments, a donor template can be introduced into a cell as part of a vector molecule having additional sequences such as, for example, replication origins, promoters and genes encoding antibiotic resistance. In some embodiments, a donor template can be introduced as naked nucleic acid or as nucleic acid complexed with an agent such as a liposome or poloxamer. In some embodiments, a donor template or can be delivered by a virus (e.g., adenovirus, AAV, herpesvirus, retrovirus, lentivirus and integrase defective lentivirus (IDLV)).

A donor template, in some embodiments, is inserted so that its expression is driven by the endogenous promoter at the integration site, namely the promoter that drives expression of the endogenous gene into which the donor is inserted. In some embodiments, a donor template is integrated so that its expression is driven by the endogenous promoter at the integration site, namely the promoter that drives expression of the endogenous gene into which the donor is exchanged. However, in some embodiments, the donor template comprises an exogenous promoter and/or enhancer, for example a constitutive promoter, an inducible promoter, or tissue-specific promoter. In some embodiments, the exogenous promoter is an EF1α promoter comprising a sequence of SEQ ID NO: 59. Other promoters known to those of skill in the art may also be used.

In some embodiments, exogenous sequences may also include transcriptional and/or translational regulatory sequences, for example, promoters, enhancers, insulators, internal ribosome entry sites, sequences encoding 2A peptides and/or polyadenylation signals.

In some embodiments, the donor polynucleotides comprise a nucleotide sequence which corrects or induces a mutation in a genomic DNA (gDNA) molecule in a cell, wherein when the donor polynucleotide is introduced into the cell in combination with a site-directed nuclease, a HDR DNA repair pathway inserts the donor polynucleotide into a double-stranded DNA break (DSB) introduced into the gDNA by the site-directed nuclease at a location proximal to the mutation, thereby correcting the mutation. In some embodiments, the donor polynucleotides and/or recombinant vectors comprise a nucleotide sequence which corrects or induces a mutation in a genomic DNA (gDNA) molecule in a cell, wherein when the donor polynucleotide is introduced into the cell in combination with a site-directed nuclease, a HDR DNA repair pathway exchanges a region proximal to a double-stranded DNA break (DSB) for the corresponding region provided by the donor polynucleotide and/or recombinant vectors, by the site-directed nuclease at a location proximal to the mutation, thereby correcting the mutation.

In some embodiments, the donor polynucleotide comprises a nucleotide sequence which corrects or induces a mutation, wherein the nucleotide sequence that corrects or induces a mutation comprises a single nucleotide. In some embodiments, the nucleotide sequence which corrects or induces a mutation comprises two or more nucleotides. In some embodiments, the nucleotide sequence which corrects or induces a mutation comprises a codon. In some embodiments, the nucleotide sequence which corrects or induces a mutation comprises one or more codons. In some embodiments, the nucleotide sequence which corrects or induces a mutation comprises an exonic sequence. In some embodiments, the nucleotide sequence which corrects or induces a mutation comprises an intronic sequence. In some embodiments, the nucleotide sequence which corrects or induces a mutation comprises all or a portion of an exonic sequence. In some embodiments, the nucleotide sequence which corrects or induces a mutation comprises all or a portion of an intronic sequence. In some embodiments, the nucleotide sequence which corrects or induces a mutation comprises all or a portion of an exonic sequence and all or a portion of an intronic sequence.

In some embodiments, the donor polynucleotide sequence is identical to or substantially identical to (having at least one nucleotide difference) an endogenous sequence of a target nucleic acid. In some embodiments, the endogenous sequence comprises a genomic sequence of the cell. In some embodiments, the endogenous sequence comprises a chromosomal or extrachromosomal sequence. In some embodiments, the donor polynucleotide sequence comprises a sequence that is substantially identical (comprises at least one nucleotide difference/change) to a portion of the endogenous sequence in a cell at or near the DSB. In some embodiments, repair of the target nucleic acid molecule with the donor polynucleotide results in an insertion, deletion, or substitution of one or more nucleotides of the target nucleic acid molecule. In some embodiments, the insertion, deletion, or substitution of one or more nucleotides results in one or more amino acid changes in a protein expressed from a gene comprising the target sequence. In some embodiments, the insertion, deletion, or substitution of one or more nucleotides results in one or more nucleotide changes in an RNA expressed from the target gene. In some embodiments, the insertion, deletion, or substitution of one or more nucleotides alters the expression level of the target gene. In some embodiments, the insertion, deletion, or substitution of one or more nucleotides results in increased or decreased expression of the target gene. In some embodiments, the insertion, deletion, or substitution of one or more nucleotides results in gene knockdown. In some embodiments, the insertion, deletion, or substitution of one or more nucleotides results in gene knockout. In some embodiments, the repair of the target nucleic acid molecule with the donor polynucleotide results in replacement of an exon sequence, an intron sequence, a transcriptional control sequence, a translational control sequence, a sequence comprising a splicing signal, or a non-coding sequence of the target gene.

In some embodiments, the donor polynucleotide is of a suitable length to correct or induce a mutation in a gDNA. In some embodiments, the donor polynucleotide comprises 10, 15, 20, 25, 50, 75, 100 or more nucleotides in length. In some embodiments, the donor polynucleotide comprises 18 nucleotides in length. In some embodiments, the donor polynucleotide comprises 10-30 nucleotides in length. In some embodiments, the donor polynucleotide comprises 10-20 nucleotides in length. In some embodiments, the donor polynucleotide comprises 15-25 nucleotides in length. In some embodiments, the donor polynucleotide comprises 20-30 nucleotides in length. In some embodiments, the donor polynucleotide comprises 10, 11, 12, 13, 14, 15, 16, 17, 18, 19, 20, 21, 22, 23, 24, 25, 26, 27, 28, 29 or 30 nucleotides in length.

In some embodiments, the donor polynucleotide comprises a nucleotide sequence homologous to a region in a target gene. In some embodiments, the nucleotide sequence homologous to a region in a target gene is 10-30, 10-20, 15-25 or 20-30 nucleotides in length.

In some embodiments (for example those described herein where a donor polynucleotide is incorporated into the cleaved nucleic acid as an insertion mediated by non-homologous end joining) the donor polynucleotide has no homology arms. In some embodiments, to facilitate HDR repair of a DSB, the donor polynucleotide has flanking homology arms (for example those described herein where a donor polynucleotide is incorporated into the cleaved nucleic acid as an insertion mediated by HDR repair). In some embodiments, the donor polynucleotide is about 10-100, about 20-80, about 30-70, or about 40-60 nucleotides in length. In some embodiments, the donor polynucleotide is about 10-100 nucleotides in length. In some embodiments, the donor polynucleotide is about 20-80 nucleotides in length. In some embodiments, the donor polynucleotide is about 30-70 nucleotides in length. In some embodiments, the donor polynucleotide is about 40-60 nucleotides in length. In some embodiments, the donor polynucleotide is 40, 41, 42, 43, 44, 45, 46, 46, 48, 49, 50, 51, 52, 53, 54, 55, 56, 57, 58, 59 or 60 nucleotides in length. In some embodiments, the donor polynucleotide is 40 nucleotides in length. In some embodiments, the donor polynucleotide is 41 nucleotides in length. In some embodiments, the donor polynucleotide is 42 nucleotides in length. In some embodiments, the donor polynucleotide is 43 nucleotides in length. In some embodiments, the donor polynucleotide is 44 nucleotides in length. In some embodiments, the donor polynucleotide is 45 nucleotides in length. In some embodiments, the donor polynucleotide is 46 nucleotides in length. In some embodiments, the donor polynucleotide is 47 nucleotides in length. In some embodiments, the donor polynucleotide is 48 nucleotides in length. In some embodiments, the donor polynucleotide is 49 nucleotides in length. In some embodiments, the donor polynucleotide is 50 nucleotides in length. In some embodiments, the donor polynucleotide is 51 nucleotides in length. In some embodiments, the donor polynucleotide is 52 nucleotides in length. In some embodiments, the donor polynucleotide is 53 nucleotides in length. In some embodiments, the donor polynucleotide is 54 nucleotides in length. In some embodiments, the donor polynucleotide is 55 nucleotides in length. In some embodiments, the donor polynucleotide is 56 nucleotides in length. In some embodiments, the donor polynucleotide is 57 nucleotides in length. In some embodiments, the donor polynucleotide is 58 nucleotides in length. In some embodiments, the donor polynucleotide is 59 nucleotides in length. In some embodiments, the donor polynucleotide is 60 nucleotides in length.

In some embodiments, a donor polynucleotide comprising exogenous genetic material is flanked by homology arms to allow integration of the exogenous genetic material by HDR repair of a DSB in a target gene. The homology arms are designed to anneal to regions of gDNA that flank a DSB in a target gene. Methods of designing homology arms that allow HDR repair of a DSB site in a target gene are taught in the art. See for example US 20110281361 which is incorporated by reference herein.

In some embodiments, for HDR repair of a DSB, a donor polynucleotide comprises a left and right flanking homology arms (LHA and RHA) that allow annealing to gDNA. In some embodiments, the homology arms flank the mutation or correction being introduced at the site of a DSB. In some embodiments, a recombinant vector comprises the donor polynucleotide flanked by a LHA and a RHA. In some embodiments, the homology arms are at least 30-100, at least 50-200, at least 100-300, at least 100-500, at least 250-1000, at least 500-1500 nucleotides in length. In some embodiments, the homology arms are at least 100 nucleotides in length. In some embodiments, the homology arms are at least 200-500, at least 450-1000, at least 500-1500, at least 1000-2000, at least 1500-2500, at least 2000-3000, or at least 2500-3500 nucleotides in length In some embodiments, the homology arms are at least 200 nucleotides in length. In some embodiments, the homology arms are at least 300 nucleotides in length. In some embodiments, the homology arms are at least 400 nucleotides in length. In some embodiments, the homology arms are at least 500 nucleotides in length. In some embodiments, the homology arms are at least 600 nucleotides in length. In some embodiments, the homology arms are at least 700 nucleotides in length. In some embodiments, the homology arms are at least 800 nucleotides in length. In some embodiments, the homology arms are at least 900 nucleotides in length. In some embodiments, the homology arms are at least 1000 nucleotides in length. In some embodiments, the homology arms are at least 1500 nucleotides in length. In some embodiments, the homology arms are at least 2000 nucleotides in length. In some embodiments, the homology arms are at least 2500 nucleotides in length. In some embodiments, the homology arms are at least 3000 nucleotides in length. In some embodiments, the homology arms are at least 3500 nucleotides in length.

In some embodiments, the LHA is at least 200-500, at least 450-1000, at least 500-1500, at least 1000-2000, at least 1500-2500, at least 2000-3000, or at least 2500-3500 nucleotides in length. In some embodiments, the LHA is about 500 to about 2500 nucleotides in length. In some embodiments, the LHA is about 2.2 kb. In some embodiments, the RHA is at least 200-500, at least 450-1000, at least 500-1500, at least 1000-2000, at least 1500-2500, at least 2000-3000, or at least 2500-3500 nucleotides in length. In some embodiments, the RHA is about 500 to about 2500 nucleotides in length. In some embodiments, the RHA is about 2.2 kb.

In some embodiments, the LHA and the RHA are the same length. In some embodiments, the LHA and the RHA are different lengths. In some embodiments, the LHA and the RHA have a combined length of about 400 to about 5000, about 500 to about 4500, about 1000 to about 4400 nucleotides. In some embodiments, the LHA and the RHA have a combined length of about 4400 nucleotides. In some embodiments, the LHA is about 500 to about 2500 nucleotides in length and the RHA is about 500 to about 2500 nucleotides in length. In some embodiments, the LHA is about 2.2 kb in length and the RHA is about 2.2 kb in length. The rate of HDR is a function of the distance between the mutation at the DSB cut site. Thus, in some embodiments, the homology arms are designed to anneal to gDNA directly adjacent to the site of a DSB. In some embodiments, a left or right homology arm is designed to anneal to gDNA no more than 1-10 nucleotides, 5-15, 10-30, 15-40, or 15-50 nucleotides from the DSB site in a target gene. In some embodiments, a left or right homology arm is designed to anneal to gDNA no more than 1 nucleotide from the DSB site in a target gene. In some embodiments, a left or right homology arm is designed to anneal to gDNA no more than 2 nucleotides from the DSB site in a target gene. In some embodiments, a left or right homology arm is designed to anneal to gDNA no more than 3 nucleotides from the DSB site in a target gene. In some embodiments, a left or right homology arm is designed to anneal to gDNA no more than 4 nucleotides from the DSB site in a target gene. In some embodiments, a left or right homology arm is designed to anneal to gDNA no more than 5 nucleotides from the DSB site in a target gene. In some embodiments, a left or right homology arm is designed to anneal to gDNA no more than 6 nucleotides from the DSB site in a target gene. In some embodiments, a left or right homology arm is designed to anneal to gDNA no more than 7 nucleotides from the DSB site in a target gene. In some embodiments, a left or right homology arm is designed to anneal to gDNA no more than 8 nucleotides from the DSB site in a target gene. In some embodiments, a left or right homology arm is designed to anneal to gDNA no more than 9 nucleotides from the DSB site in a target gene. In some embodiments, a left or right homology arm is designed to anneal to gDNA no more than 10 nucleotides from the DSB site in a target gene.

In some embodiments, the homology arms of a donor polynucleotide are fully complementary to gDNA flanking a DSB site in a target gene. In some embodiments, the homology arms of a donor polynucleotide have sufficient complementary to gDNA flanking a DSB site in a target gene to allow HDR repair. In some embodiments, the homology arms within a recombinant vector are fully complementary to gDNA flanking a DSB site in a target gene. In some embodiments, the homology arms within a recombinant vector have sufficient complementary to gDNA flanking a DSB site in a target gene to allow HDR repair.

In some embodiments, a donor polynucleotide provided by the disclosure comprises an intronic sequence. In some embodiments, the donor polynucleotide comprises an intronic sequence which corrects or induces a mutation in a gDNA. In some embodiments, the donor polynucleotide comprises an exonic sequence. In some embodiments, the donor polynucleotide comprises an exonic sequence which corrects or induces a mutation in a gDNA.

Donor Polynucleotide Correcting SCD Mutation

In some embodiments, the disclosure provides a donor polynucleotide and/or recombinant vector that corrects an SCD mutation (e.g., E6V/E7V in exon 1 of the HBB gene) in a cell. In some embodiments, the donor polynucleotide comprises GAG or GAA to correct the GTG codon that leads to the E6V mutation. In some embodiments, the donor polynucleotide comprises a polynucleotide sequence having at least about 90% identify to the nucleotide sequence set forth in SEQ ID NO: 102, or a complement thereof. In some embodiments, the disclosure provides a donor polynucleotide can include a nucleotide sequence that is homologous with a region of the HBB gene that comprises a PAM recognition site, or complement thereof, that is recognized by the site directed nuclease. In some embodiments, the disclosure provides a donor polynucleotide and/or recombinant vector that mutates the PAM recognition site in the target sequence to ensure that the site directed nuclease does not cleave the donor polynucleotide after it is exchanged. In some embodiments, the PAM recognition site is mutated to a polynucleotide sequence without introducing a single nucleotide polymorphism (SNP) associated with β-thalassemia. In some embodiments, the donor polynucleotide comprises the nucleotide sequence set forth in SEQ ID NO: 102, or a complement thereof. In some embodiments, the donor polynucleotide is codon optimized to improve HDR.

In some embodiments, the donor polynucleotide is 10-20 bases, 15-25 bases, 20-30 bases, 25-35 bases, or 30-40 bases in length. In some embodiments, the donor polynucleotide is 10, 11, 12, 13, 14, 15, 16, 17, 18, 19 or 20 bases in length.

In some embodiments, the donor polynucleotide is located between two homology arms (LHA and RHA). In some embodiments, the LHA and RHA are the same length. In some embodiments, the LHA and RHA are different lengths. In some embodiments, the homology arms are each about 500 bases, about 600 bases, about 700 bases, about 800 bases, about 900 bases, about 1 kb, about 1.5 kb, about 2 kb, about 2.5 kb, or about 3 kb in length. In some embodiments, the homology arms are each about 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb or 3 kb in length. In some embodiments, the LHA is about 0.5 kb to about 3 kb in length, and the RHA is about 0.5 kb to about 3 kb in length, wherein the LHA and RHA are different lengths. In some embodiments, the LHA is about 0.5 kb to about 3 kb in length, and the RHA is about 0.5 kb to about 3 kb in length, wherein the LHA and RHA are the same length. In some embodiments, the LHA is about 0.5 kb to about 1.5 kb, about 1.0 kb to about 2.0 kb, about 1.5 kb to about 2.5 kb, or about 2.0 kb to about 3.0 kb, and the RHA is about 0.5 kb to about 1.5 kb, about 1.0 kb to about 2.0 kb, about 1.5 kb to about 2.5 kb, or about 2.0 kb to about 3.0 kb, wherein the LHA and RHA are different lengths. In some embodiments, the LHA is about 0.5 kb to about 1.5 kb, about 1.0 kb to about 2.0 kb, about 1.5 kb to about 2.5 kb, or about 2.0 kb to about 3.0 kb, and the RHA is about 0.5 kb to about 1.5 kb, about 1.0 kb to about 2.0 kb, about 1.5 kb to about 2.5 kb, or about 2.0 kb to about 3.0 kb, wherein the LHA and RHA are the same length. In some embodiments, the LHA is about 2.2 kb and the RHA is about 2.2 kb. In some embodiments, the length of each homology arm is determined based on the capacity of the delivery system used to provide the donor polynucleotide.

In some embodiments, the LHA comprises a nucleotide sequence homologous or substantially homologous to exon 1 of the HBB gene. In some embodiments, the LHA comprises a nucleotide sequence homologous or substantially homologous to a region upstream of an E6V mutation in exon 1 of the HBB gene. In some embodiments, the LHA comprises a nucleotide sequence homologous or substantially homologous to the promoter for the HBB gene. In some embodiments, the LHA comprises a nucleotide sequence homologous or substantially homologous to regions upstream of the HBB gene. In some embodiments, the LHA comprises a nucleotide sequence homologous or substantially homologous to a region of exon 1 of the HBB gene upstream of an E6V mutation, along with the promoter and regions upstream of the HBB gene. In some embodiments, the LHA comprises the nucleotide sequence set forth in SEQ ID NO: 99. In some embodiments, the LHA comprises a nucleotide sequence having at least 80%, 85%, 90%, 95%, 96%, 97%, 98% or 99% identity to SEQ ID NO: 99.

In some embodiments, the LHA comprises a nucleotide sequence homologous or substantially homologous to exon 1 of the HBB gene and is about 0.5 kb to about 3.0 kb. In some embodiments, the LHA comprises a nucleotide sequence homologous or substantially homologous to a region upstream of an E6V mutation in exon 1 of the HBB gene and is about 0.5 kb to about 3.0 kb. In some embodiments, the LHA comprises a nucleotide sequence homologous or substantially homologous to the promoter for the HBB gene and is about 0.5 kb to about 3.0 kb. In some embodiments, the LHA comprises a nucleotide sequence homologous or substantially homologous to regions upstream of the HBB gene and is about 0.5 kb to about 3.0 kb. In some embodiments, the LHA comprises a nucleotide sequence homologous or substantially homologous to a region of exon 1 of the HBB gene upstream of an E6V mutation, along with the promoter and regions upstream of the HBB gene and is about 0.5 kb to about 3.0 kb. In some embodiments, the LHA comprises the nucleotide sequence set forth in SEQ ID NO: 99. In some embodiments, the LHA comprises a nucleotide sequence having at least 80%, 85%, 90%, 95%, 96%, 97%, 98% or 99% identity to SEQ ID NO: 99.

In some embodiments, the RHA comprises a nucleotide sequence homologous or substantially homologous to exon 1 of the HBB gene. In some embodiments, the RHA comprises a nucleotide sequence homologous or substantially homologous to a region downstream of an E6V mutation in exon 1 of the HBB gene. In some embodiments, the RHA comprises a nucleotide sequence homologous or substantially homologous to a region downstream of a double-strand break (DSB) effected by a gRNA and endonuclease. In some embodiments, the RHA comprises a nucleotide sequence that spans the target site. In some embodiments, the RHA comprises a nucleotide sequence homologous or substantially homologous to all or a portion of intron 1-2 of the HBB gene. In some embodiments, the RHA comprises a nucleotide sequence homologous or substantially homologous to all or a portion of exon 2 of the HBB gene. In some embodiments, the RHA comprises a nucleotide sequence homologous or substantially homologous to all or a portion of intron 2-3 of the HBB gene. In some embodiments, the RHA comprises a nucleotide sequence homologous or substantially homologous to all or a portion of exon 3 of the HBB gene. In some embodiments, the RHA comprises a nucleotide sequence homologous or substantially homologous to a region downstream of the DSB in exon 1, intron 1-2, exon 2, and a portion of intron 2-3, inclusive. In some embodiments, the RHA comprises a nucleotide sequence homologous or substantially homologous to a region downstream of the DSB in exon 1, intron 1-2, exon 2, intron 2-3, and a portion of exon 3, inclusive. In some embodiments, the RHA comprises a nucleotide sequence homologous or substantially homologous to a region downstream of the DSB in exon 1, intron 1-2, exon 2, intron 2-3, and exon 3 inclusive. In some embodiments, the RHA comprises the nucleotide sequence set forth in SEQ ID NO: 100. In some embodiments, the RHA comprises a nucleotide sequence having at least 80%, 85%, 90%, 95%, 96%, 97%, 98% or 99% identity to SEQ ID NO: 100.

In some embodiments, the RHA comprises a nucleotide sequence homologous or substantially homologous to exon 1 of the HBB gene and is about 0.5 kb to about 3.0 kb. In some embodiments, the RHA comprises a nucleotide sequence homologous or substantially homologous to a region downstream of an E6V mutation in exon 1 of the HBB gene and is about 0.5 kb to about 3.0 kb. In some embodiments, the RHA comprises a nucleotide sequence homologous or substantially homologous to a region downstream of a double-strand break (DSB) effected by a gRNA and endonuclease, and is about 0.5 kb to about 3.0 kb In some embodiments, the RHA comprises a nucleotide sequence that spans the target site, and is about 0.5 kb to about 3.0 kb. In some embodiments, the RHA comprises a nucleotide sequence homologous or substantially homologous to all or a portion of intron 1-2 of the HBB gene and is about 0.5 kb to about 3.0 kb. In some embodiments, the RHA comprises a nucleotide sequence homologous or substantially homologous to all or a portion of exon 2 of the HBB gene and is about 0.5 kb to about 3.0 kb. In some embodiments, the RHA comprises a nucleotide sequence homologous or substantially homologous to all or a portion of intron 2-3 of the HBB gene and is about 0.5 kb to about 3.0 kb. In some embodiments, the RHA comprises a nucleotide sequence homologous or substantially homologous to all or a portion of exon 3 of the HBB gene and is about 0.5 kb to about 3.0 kb. In some embodiments, the RHA comprises a nucleotide sequence homologous or substantially homologous to a region downstream of the DSB in exon 1, intron 1-2, exon 2, and a portion of intron 2-3, inclusive and is about 0.5 kb to about 3.0 kb. In some embodiments, the RHA comprises a nucleotide sequence homologous or substantially homologous to a region downstream of the DSB in exon 1, intron 1-2, exon 2, intron 2-3, and a portion of exon 3, inclusive and is about 0.5 kb to about 3.0 kb. In some embodiments, the RHA comprises a nucleotide sequence homologous or substantially homologous to a region downstream of the DSB in exon 1, intron 1-2, exon 2, intron 2-3, and exon 3 inclusive and is about 0.5 kb to about 3.0 kb. In some embodiments, the RHA comprises the nucleotide sequence set forth in SEQ ID NO: 100. In some embodiments, the RHA comprises a nucleotide sequence having at least 80%, 85%, 90%, 95%, 96%, 97%, 98% or 99% identity to SEQ ID NO: 100.

In some embodiments, the disclosure provides a recombinant vector comprising a donor polynucleotide located between an LHA and an RHA, the recombinant vector having about 400 bases, about 500 bases, about 600 bases, about 700 bases, about 800 bases, about 900 bases, about 1 kb, about 1.5 kb, about 2 kb, about 2.5 kb, about 3 kb, about 3.5 kb, about 4 kb, or about 4.5 kb in length. In some embodiments, the nucleotide sequence is about 2.5 kb, about 2.6 kb, about 2.7 kb, about 2.8 kb, about 2.9 kb, about 3 kb, about 3.1 kb, about 3.2 kb, about 3.3 kb, about 3.4 kb, about 3.5 kb, about 3.6 kb, about 3.7 kb, about 3.8 kb, about 3.9 kb, about 4 kb, about 4.1 kb, about 4.2 kb, about 4.3 kb, about 4.4 kb or about 4.5 kb in length. In some embodiments, the recombinant vector is about 4.2 kb in length.

In some embodiments, the nucleotide sequence and/or recombinant vector comprising a donor polynucleotide located between an LHA and an RHA comprises the sequence set forth in SEQ ID NO: 98. In some embodiments, the nucleotide sequence and/or recombinant vector comprises a nucleotide sequence having at least 80%, 85%, 90%, 95%, 96%, 97%, 98% or 99% identity to SEQ ID NO: 98.

Methods of Making and Testing Donor Polynucleotides

The donor polynucleotides provided by the disclosure are produced by suitable DNA synthesis method or means known in the art. Recombinant vectors can also be produced by said methods. DNA synthesis is the natural or artificial creation of deoxyribonucleic acid (DNA) molecules. The term DNA synthesis refers to DNA replication, DNA biosynthesis (e.g., in vivo DNA amplification), enzymatic DNA synthesis (e.g., polymerase chain reaction (PCR); in vitro DNA amplification) or chemical DNA synthesis.

In some embodiments, each strand of the donor polynucleotide is produced by oligonucleotide synthesis. Oligonucleotide synthesis is the chemical synthesis of relatively short fragments or strands of single-stranded nucleic acids with a defined chemical structure (sequence). Methods of oligonucleotide synthesis are known in the art (see e.g., Reese (2005) Organic & Biomolecular Chemistry 3(21): 3851). The two strands can then be annealed together or duplexed to form a donor polynucleotide.

In some aspects, the insertion of a donor polynucleotide into a DSB is determined by a suitable method known in the art. For example, after the insertional event, the nucleotide sequence of PCR amplicons generated using PCR primer that flank the DSB site is analyzed for the presence of the nucleotide sequence comprising the donor polynucleotide. In some embodiments, next-generation sequencing (NGS) techniques are used to determine the extent of donor polynucleotide insertion into a DSB analyzing PCR amplicons for the presence or absence of the donor polynucleotide sequence. Further, since each donor polynucleotide is a linear, dsDNA molecule, which can insert in either of two orientations, NGS analysis can be used to determine the extent of insertion of the donor polynucleotide in either direction.

In some aspects, the insertion of the donor polynucleotide and its ability to correct a mutation is determined by nucleotide sequence analysis of mRNA transcribed from the gDNA into which the donor polynucleotide is inserted. An mRNA transcribed from gDNA containing an inserted donor polynucleotide is analyzed by a suitable method known in the art. For example, conversion of mRNA extracted from cells treated or contacted with a donor polynucleotide or system provided by the disclosure is enzymatically converted into cDNA, which is further by analyzed by NGS analysis to determine the extent of mRNA molecule comprising the corrected mutation.

In other aspects, the insertion of a donor polynucleotide and its ability to correct a mutation is determined by protein sequence analysis of a polypeptide translated from an mRNA transcribed from the gDNA into which the donor polynucleotide is inserted. In some embodiments, a donor polynucleotide corrects or induces a mutation by the incorporation of a codon into an exon that makes an amino acid change in a gene comprising a gDNA molecule, wherein translation of an mRNA from the gene containing the inserted donor polynucleotide generates a polypeptide comprising the amino acid change. The amino acid change in the polypeptide is determined by protein sequence analysis using techniques including, but not limited to, Sanger sequencing, mass spectrometry, functional assays that measure an enzymatic activity of the polypeptide, or immunoblotting using an antibody reactive to the amino acid change.

Use of Donor Polynucleotides to Correct or Induce a Mutation

In some embodiments, a donor polynucleotide provided by the disclosure is used to correct or induce a mutation in a gDNA in a cell by insertion of the donor polynucleotide into a target nucleic acid (e.g., gDNA) at a cleavage site (e.g., a DSB) induced by a site-directed nuclease, such as those described herein. In some embodiments, a donor polynucleotide provided by the disclosure is used to correct or induce a mutation in a gDNA in a cell by exchanging a region proximal to a cleavage site (e.g., a DSB) for the corresponding region provided by the donor polynucleotide in a target nucleic acid (e.g., gDNA), induced by a site-directed nuclease, such as those described herein. In some embodiments, HDR DNA repair mechanisms of the cell repair the DSB using the donor polynucleotide, thereby inserting the donor polynucleotide into the DSB and adding the nucleotide sequence of the donor polynucleotide to the gDNA. In some embodiments, HDR DNA repair mechanisms of the cell repair the DSB use the donor polynucleotide, thereby exchanging a region in the gDNA for the corresponding region provided by the donor polynucleotide, thus adding the nucleotide sequence of the donor polynucleotide to the gDNA. In some embodiments, the donor polynucleotide comprises a nucleotide sequence which corrects a disease-causing mutation in a gDNA in a cell. In some embodiments, the donor polynucleotide is inserted at a location proximal to the mutation, thereby correcting the mutation. In some embodiments, the donor polynucleotide is exchanged at a location proximal to the mutation, thereby correcting the mutation. In some embodiments, the mutation is a substitution, missense, nonsense, insertion, deletion or frameshift mutation. In some embodiments the mutation is in an exon. In some embodiments, the mutation is a substitution, insertion or deletion and is located in an intron. In some embodiments, the mutation is proximal to a cleavage site in a gDNA. In some embodiments, the mutation is a protein-coding mutation. In some embodiments, the mutation is associated with or causes a disease.

In some embodiments, the donor polynucleotide is inserted into the DSB by HDR DNA repair. In some embodiments, the donor polynucleotide is exchanged a location proximal to the DSB by HDR DNA repair. In some embodiments, the donor polynucleotide, a portion of the donor polynucleotide is inserted into the target nucleic acid cleavage site by HDR DNA repair. In some embodiments, the donor polynucleotide, a portion of the donor polynucleotide is exchanged proximal to a target nucleic acid cleavage site by HDR DNA repair. In certain aspects, insertion of a donor polynucleotide into the target nucleic acid via HDR repair can result in, for example, mutations, deletions, alterations, integrations, gene correction, gene replacement, gene tagging, transgene insertion, nucleotide deletion, gene disruption, translocations and/or gene mutation of the endogenous gene sequence. In certain aspects, exchange of a donor polynucleotide into the target nucleic acid via HDR repair can result in, for example, mutations, deletions, alterations, integrations, gene correction, gene replacement, gene tagging, transgene insertion, nucleotide deletion, gene disruption, translocations and/or gene mutation of the endogenous gene sequence.

In some embodiments, the disease-causing mutation in the HBB gene results in an E6V amino acid substitution in the human beta-globin protein. In some embodiments, the donor polynucleotide comprises a nucleotide sequence which corrects a E6V mutation encoded by an HBB gene in a gDNA in a cell. In some embodiments, the disclosure provides donor polynucleotides used to repair a DSB introduced into a target nucleic acid molecule (e.g., gDNA) by a site-directed nuclease (e.g., Cas9) in a cell. In some embodiments, the disclosure provides donor polynucleotides used to repair a DSB introduced into an HBB gene by Cas9 in a cell. In some embodiments, the donor polynucleotide is used by the HDR repair pathway of the cell to repair the DSB in the target nucleic acid molecule. In some embodiments, the donor polynucleotide is used by the HDR repair pathway of the cell to repair the DSB in the HBB gene. In some embodiments, the site-directed nuclease is a Cas nuclease. In some embodiments, the Cas nuclease is Cas9. The site-directed nucleases described herein can introduce DSB in target nucleic acids (e.g., genomic DNA) in a cell. The introduction of a DSB in the genomic DNA of a cell, induced by a site-directed nuclease, will stimulate the endogenous DNA repair pathways, such as those described herein. The HDR pathway can be used to insert a polynucleotide (e.g., a donor polynucleotide) into the DSB during repair.

Accordingly, in some embodiments, a single donor polynucleotide or multiple copies of the same donor polynucleotide are provided. In other embodiments, two or more donor polynucleotides are provided such that repair may occur at two or more target sites. For example, different donor polynucleotides are provided to repair a single gene in a cell, or two different genes in a cell. In some embodiments, the different donor polynucleotides are provided in independent copy numbers.

In some embodiments, the donor polynucleotide is incorporated into the target nucleic acid as an insertion mediated by HDR. In some embodiments, the donor polynucleotide sequence has no similarity to the nucleic acid sequence near the cleavage site. In some embodiments, a single donor polynucleotide or multiple copies of the same donor polynucleotide are provided. In other embodiments, two or more donor polynucleotides having different sequences are inserted at two or more sites by non-homologous end joining. In some embodiments, the different donor polynucleotides are provided in independent copy numbers.

Systems for Genome Editing

In some aspects, the disclosure provide systems for correcting a mutation in a genomic DNA molecule. In some embodiments, the system comprises a site-directed nuclease, such as a CRISPR/Cas system and optionally a gRNA, and a donor polynucleotide, such as those described herein. In some embodiments of the present disclosure, the system comprises an engineered nuclease. In some embodiments, the system comprises a site-directed nuclease. In some embodiments, the site-directed nuclease comprises a CRISPR/Cas nuclease system. In some embodiments, the Cas nuclease is Cas9. In some embodiments, the guide RNA comprising the CRISPR/Cas system is an sgRNA.

CRISPR/Cas Nuclease Systems

Naturally-occurring CRISPR/Cas systems are genetic defense systems that provides a form of acquired immunity in prokaryotes. CRISPR is an abbreviation for Clustered Regularly Interspaced Short Palindromic Repeats, a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA are used by the prokaryote to detect and destroy similar foreign DNA upon re-introduction, for example, from similar viruses during subsequent attacks. Transcription of the CRISPR locus results in the formation of an RNA molecule comprising the spacer sequence, which associates with and targets Cas (CRISPR-associated) proteins able to recognize and cut the foreign, exogenous DNA. Numerous types and classes of CRISPR/Cas systems have been described (see e.g., Koonin et al., (2017) Curr Opin Microbiol 37:67-78).

Engineered versions of CRISPR/Cas systems has been developed in numerous formats to mutate or edit genomic DNA of cells from other species. The general approach of using the CRISPR/Cas system involves the heterologous expression or introduction of a site-directed nuclease (e.g.: Cas nuclease) in combination with a guide RNA (gRNA) into a cell, resulting in a DNA cleavage event (e.g., the formation a single-strand or double-strand break (SSB or DSB)) in the backbone of the cell's genomic DNA at a precise, targetable location. The manner in which the DNA cleavage event is repaired by the cell provides the opportunity to edit the genome by the addition, removal, or modification (substitution) of DNA nucleotide(s) or sequences (e.g., genes).

Guide RNAs (2RNAs)

Engineered CRISPR/Cas systems comprise at least two components: 1) a guide RNA (gRNA) molecule and 2) a Cas nuclease, which interact to form a gRNA/Cas nuclease complex. A gRNA comprises at least a user-defined targeting domain termed a "spacer" comprising a nucleotide sequence and a CRISPR repeat sequence. In engineered CRISPR/Cas systems, a gRNA/Cas nuclease complex is targeted to a specific target sequence of interest within a target nucleic acid (e.g., a genomic DNA molecule) by generating a gRNA comprising a spacer with a nucleotide sequence that is able to bind to the specific target sequence in a complementary fashion (See Jinek et al., Science, 337, 816-821 (2012) and Deltcheva et al., Nature, 471, 602-607 (2011)). Thus, the spacer provides the targeting function of the gRNA/Cas nuclease complex.

In naturally-occurring type II-CRISPR/Cas systems, the "gRNA" is comprised of two RNA strands: 1) a CRISPR RNA (crRNA) comprising the spacer and CRISPR repeat sequence, and 2) a trans-activating CRISPR RNA (tracrRNA). In Type II-CRISPR/Cas systems, the portion of the crRNA comprising the CRISPR repeat sequence and a portion of the tracrRNA hybridize to form a crRNA: tracrRNA duplex, which interacts with a Cas nuclease (e.g., Cas9). As used herein, the terms "split gRNA" or "modular gRNA" refer to a gRNA molecule comprising two RNA strands, wherein the first RNA strand incorporates the crRNA function(s) and/or structure and the second RNA strand incorporates the tracrRNA function(s) and/or structure, and wherein the first and second RNA strands partially hybridize.

Accordingly, in some embodiments, a gRNA provided by the disclosure comprises two RNA molecules. In some embodiments, the gRNA comprises a CRISPR RNA (crRNA) and a trans-activating CRISPR RNA (tracrRNA). In some embodiments, the gRNA is a split gRNA. In some embodiments, the gRNA is a modular gRNA. In some embodiments, the split gRNA comprises a first strand comprising, from 5' to 3', a spacer, and a first region of complementarity; and a second strand comprising, from 5' to 3', a second region of complementarity; and optionally a tail domain.

In some embodiments, the crRNA comprises a spacer comprising a nucleotide sequence that is complementary to and hybridizes with a sequence that is complementary to the target sequence on a target nucleic acid (e.g., a genomic DNA molecule). In some embodiments, the crRNA comprises a region that is complementary to and hybridizes with a portion of the tracrRNA.

In some embodiments, the tracrRNA may comprise all or a portion of a wild-type tracrRNA sequence from a naturally-occurring CRISPR/Cas system. In some embodiments, the tracrRNA may comprise a truncated or modified variant of the wild-type tracr RNA. The length of the tracr RNA may depend on the CRISPR/Cas system used. In some embodiments, the tracrRNA may comprise 5, 6, 7, 8, 9, 10, 11, 12, 13, 14, 15, 16, 17, 18, 19, 20, 25, 30, 40, 50, 60, 70, 80, 90, 100, or more than 100 nucleotides in length. In certain embodiments, the tracrRNA is at least 26 nucleotides in length. In additional embodiments, the tracrRNA is at least 40 nucleotides in length. In some embodiments, the tracrRNA may comprise certain secondary structures, such as, e.g., one or more hairpins or stem-loop structures, or one or more bulge structures.

Single Guide RNA (sgRNA)

Engineered CRISPR/Cas nuclease systems often combine a crRNA and a tracrRNA into a single RNA molecule, referred to herein as a "single guide RNA" (sgRNA), by adding a linker between these components. Without being bound by theory, similar to a duplexed crRNA and tracrRNA, an sgRNA will form a complex with a Cas nuclease (e.g., Cas9), guide the Cas nuclease to a target sequence and activate the Cas nuclease for cleavage the target nucleic acid (e.g., genomic DNA). Accordingly, in some embodiments, the gRNA may comprise a crRNA and a tracrRNA that are operably linked. In some embodiments, the sgRNA may comprise a crRNA covalently linked to a tracrRNA. In some embodiments, the crRNA and the tracrRNA is covalently linked via a linker. In some embodiments, the sgRNA may comprise a stem-loop structure via base pairing between the crRNA and the tracrRNA. In some embodiments, a sgRNA comprises, from 5' to 3', a spacer, a first region of complementarity, a linking domain, a second region of complementarity, and, optionally, a tail domain.

The sgRNA can comprise a 20 nucleotide spacer sequence at the 5' end of the sgRNA sequence. The sgRNA can comprise a less than 20 nucleotide spacer sequence at the 5' end of the sgRNA sequence. The sgRNA can comprise a more than 20 nucleotide spacer sequence at the 5' end of the sgRNA sequence. The sgRNA can comprise a variable length spacer sequence with 17-30 nucleotides at the 5' end of the sgRNA sequence as set forth by SEQ ID NO: 1.

The sgRNA can comprise no uracil at the 3' end of the sgRNA sequence. The sgRNA can comprise one or more uracil at the 3' end of the sgRNA sequence. For example, the sgRNA can comprise 1 uracil (U) at the 3' end of the sgRNA sequence. The sgRNA can comprise 2 uracil (UU) at the 3' end of the sgRNA sequence. The sgRNA can comprise 3 uracil (UUU) at the 3' end of the sgRNA sequence. The sgRNA can comprise 4 uracil (UUUU) at the 3' end of the sgRNA sequence. The sgRNA can comprise 5 uracil (UUUUU) at the 3' end of the sgRNA sequence. The sgRNA can comprise 6 uracil (UUUUUU) at the 3' end of the sgRNA sequence. The sgRNA can comprise 7 uracil (UUUUUUU) at the 3' end of the sgRNA sequence. The sgRNA can comprise 8 uracil (UUUUUU) at the 3' end of the sgRNA sequence.

The sgRNA can be unmodified or modified. For example, modified sgRNAs can comprise one or more 2'-O-methyl phosphorothioate nucleotides.

In some embodiments, the sgRNA comprises a spacer sequence comprising SEQ ID NO: 16. In some embodiments, the sgRNA comprises SEQ ID NO: 17. In some embodiments, the sgRNA comprises a nucleotide sequence at least 90%, 91%, 92%, 93%, 94%, 95%, 96%, 97%, 98% or 99% identical to SEQ ID NO 17.

By way of illustration, guide RNAs used in the CRISPR/Cas system, or other smaller RNAs can be readily synthesized by chemical means, as illustrated herein and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

Spacers

In some embodiments, the gRNAs provided by the disclosure comprise a spacer sequence. A spacer sequence is a sequence that defines the target site of a target nucleic acid (e.g.: DNA). The target nucleic acid is a double-stranded molecule: one strand comprises the target sequence adjacent to a PAM sequence and is referred to as the "PAM strand," and the second strand is referred to as the "non-PAM strand" and is complementary to the PAM strand and target sequence. Both gRNA spacer and the target sequence are complementary to the non-PAM strand of the target nucleic acid. In some embodiments, a spacer sequence corresponding to a target sequence adjacent to a PAM sequence is complementary to the non-PAM strand of the target nucleic acid. Thus, in some embodiments, a spacer sequence which corresponds to a target sequence adjacent to a PAM sequence is identical to the PAM strand. The gRNA spacer sequence hybridizes to the complementary strand (e.g.: the non-PAM strand of the target nucleic acid/target site). In some embodiments, the spacer is sufficiently complementary to the complementary strand of the target sequence (e.g.: non-PAM strand), as to target a Cas nuclease to the target nucleic acid. In some embodiments, the spacer is at least 80%, 85%, 90% or 95% complementary to the non-PAM strand of the target nucleic acid. In some embodiments, the spacer is 100% complementary to the non-PAM strand of the target nucleic acid. In some embodiments, the spacer comprises 1, 2, 3, 4, 5, 6 or more nucleotides that are not complementary with the non-PAM strand of the target nucleic acid. In some embodiments, the spacer comprises 1 nucleotide that is not complementary with the non-PAM strand of the target nucleic acid. In some embodiments, the spacer comprises 2 nucleotides that are not complementary with the non-PAM strand of the target nucleic acid.

In some embodiments, the 5' most nucleotide of gRNA comprises the 5' most nucleotide of the spacer. In some embodiments, the spacer is located at the 5' end of the crRNA. In some embodiments, the spacer is located at the 5' end of the sgRNA. In some embodiments, the spacer is about 15-50, about 20-45, about 25-40 or about 30-35 nucleotides in length. In some embodiments, the spacer is about 19-22 nucleotides in length. In some embodiments the spacer is about 15, 16, 17, 18, 19, 20, 21, 22, 23, 24, 25, 26, 27, 28, 29 or 30 nucleotides in length. In some embodiments the spacer is 19 nucleotides in length. In some embodiments, the spacer is 20 nucleotides in length, in some embodiments, the spacer is 21 nucleotides in length.

In some embodiments, the nucleotide sequence of the target sequence and the PAM comprises the formula 5' $N_{19-21}$-N-R-G-3' (SEQ ID NO: 63), wherein N is any nucleotide, and wherein R is a nucleotide comprising the nucleobase adenine (A) or guanine (G), and wherein the three 3' terminal nucleic acids, N-R-G represent the *S. pyogenes* PAM (SEQ ID NO: 64). In some embodiments, the nucleotide sequence of the spacer is designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, and/or presence of SNPs.

In some embodiments, the spacer comprise at least one or more modified nucleotide(s) such as those described herein. The disclosure provides gRNA molecules comprising a spacer which may comprise the nucleobase uracil (U), while any DNA encoding a gRNA comprising a spacer comprising the nucleobase uracil (U) will comprise the nucleobase thymine (T) in the corresponding position(s).

In some embodiments, the spacer sequence corresponds to a target sequence comprising SEQ ID NO: 15. In some embodiments, the spacer sequence corresponds to a target sequence comprising SEQ ID NO: 15 and comprises 1, 2, 3, 4, 5, 6 or more nucleotides that are not complementary with the non-PAM strand of the target nucleic acid.

In some embodiments, the spacer sequence comprises SEQ ID NO: 16. In some embodiments, the spacer sequence comprises a sequence at least 90%, 91%, 92%, 93%, 94%, 95%, 96%, 97%, 98% or 99% identical to SEQ ID NO: 16.

Methods of Making gRNAs

The gRNAs of the present disclosure is produced by a suitable means available in the art, including but not limited to in vitro transcription (IVT), synthetic and/or chemical synthesis methods, or a combination thereof. Enzymatic (IVT), solid-phase, liquid-phase, combined synthetic methods, small region synthesis, and ligation methods are utilized. In one embodiment, the gRNAs are made using IVT enzymatic synthesis methods. Methods of making polynucleotides by IVT are known in the art and are described in International Application PCT/US2013/30062.

Accordingly, the present disclosure also includes polynucleotides, e.g., DNA, constructs and vectors are used to in vitro transcribe a gRNA described herein.

In some aspects, non-natural modified nucleobases are introduced into polynucleotides, e.g., gRNA, during synthesis or post-synthesis. In certain embodiments, modifications are on internucleoside linkages, purine or pyrimidine bases, or sugar. In particular embodiments, the modification is introduced at the terminal of a polynucleotide; with chemical synthesis or with a polymerase enzyme. Examples of modified nucleic acids and their synthesis are disclosed in PCT application No. PCT/US2012/058519. Synthesis of modified polynucleotides is also described in Verma and Eckstein, Annual Review of Biochemistry, vol. 76, 99-134 (1998).

In some aspects, enzymatic or chemical ligation methods are used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990).

Certain embodiments of the invention also provide nucleic acids, e.g., vectors, encoding gRNAs described herein. In some embodiments, the nucleic acid is a DNA molecule. In other embodiments, the nucleic acid is an RNA molecule. In some embodiments, the nucleic acid comprises a nucleotide sequence encoding a crRNA. In some embodiments, the nucleotide sequence encoding the crRNA comprises a spacer flanked by all or a portion of a repeat sequence from a naturally-occurring CRISPR/Cas system. In some embodiments, the nucleic acid comprises a nucleotide sequence encoding a tracrRNA. In some embodiments, the crRNA and the tracrRNA is encoded by two separate nucleic acids. In other embodiments, the crRNA and the tracrRNA is encoded by a single nucleic acid. In some embodiments, the crRNA and the tracrRNA is encoded by opposite strands of a single nucleic acid. In other embodiments, the crRNA and the tracrRNA is encoded by the same strand of a single nucleic acid.

In some embodiments, the gRNAs provided by the disclosure are chemically synthesized by any means described in the art (see e.g., WO/2005/01248). While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together.

In some embodiments, the gRNAs provided by the disclosure are synthesized by enzymatic methods (e.g., in vitro transcription, IVT).

Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

In certain embodiments, more than one guide RNA can be used with a CRISPR/Cas nuclease system. Each guide RNA may contain a different targeting sequence, such that the CRISPR/Cas system cleaves more than one target nucleic acid. In some embodiments, one or more guide RNAs may have the same or differing properties such as activity or stability within the Cas9 RNP complex. Where more than one guide RNA is used, each guide RNA can be encoded on the same or on different vectors. The promoters used to drive expression of the more than one guide RNA is the same or different.

The guide RNA may target any sequence of interest via the targeting sequence (e.g. spacer sequence) of the crRNA. In some embodiments, the degree of complementarity between the targeting sequence of the guide RNA and the target sequence on the target nucleic acid molecule is about 60%, 65%, 70%, 75%, 80%, 85%, 90%, 95%, 97%, 98%, 99%, or 100%. In some embodiments, the targeting sequence of the guide RNA and the target sequence on the target nucleic acid molecule is 100% complementary. In other embodiments, the targeting sequence of the guide RNA and the target sequence on the target nucleic acid molecule may contain at least one mismatch. For example, the targeting sequence of the guide RNA and the target sequence on the target nucleic acid molecule may contain 1, 2, 3, 4, 5, 6, 7, 8, 9, or 10 mismatches. In some embodiments, the targeting sequence of the guide RNA and the target sequence on the target nucleic acid molecule may contain 1-6 mismatches. In some embodiments, the targeting sequence of the guide RNA and the target sequence on the target nucleic acid molecule may contain 5 or 6 mismatches.

The length of the targeting sequence may depend on the CRISPR/Cas9 system and components used. For example, different Cas9 proteins from different bacterial species have varying optimal targeting sequence lengths. Accordingly, the targeting sequence may comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the targeting sequence may comprise 18-24 nucleotides in length. In some embodiments, the targeting sequence may comprise 19-21 nucleotides in length. In some embodiments, the targeting sequence may comprise 20 nucleotides in length.

In some embodiments of the present disclosure, a CRISPR/Cas nuclease system includes at least one guide RNA. In some embodiments, the guide RNA and the Cas protein may form a ribonucleoprotein (RNP), e.g., a CRISPR/Cas complex. The guide RNA may guide the Cas protein to a target sequence on a target nucleic acid molecule (e.g., a genomic DNA molecule), where the Cas protein cleaves the target nucleic acid. In some embodiments, the CRISPR/Cas complex is a Cpf1/guide RNA complex. In some embodiments, the CRISPR complex is a Type-II CRISPR/Cas9 complex. In some embodiments, the Cas protein is a Cas9 protein. In some embodiments, the CRISPR/Cas9 complex is a Cas9/guide RNA complex.

Cas Nuclease

In some embodiments, the disclosure provides compositions and systems (e.g., an engineered CRISPR/Cas system) comprising a site-directed nuclease, wherein the site-directed nuclease is a Cas nuclease. The Cas nuclease may comprise at least one domain that interacts with a guide RNA (gRNA). Additionally, the Cas nuclease are directed to a target sequence by a guide RNA. The guide RNA interacts with the Cas nuclease as well as the target sequence such that, once directed to the target sequence, the Cas nuclease is capable of cleaving the target sequence. In some embodiments, the guide RNA provides the specificity for the cleavage of the target sequence, and the Cas nuclease are universal and paired with different guide RNAs to cleave different target sequences.

In some embodiments, the CRISPR/Cas system comprise components derived from a Type-I, Type-II, or Type-III system. Updated classification schemes for CRISPR/Cas loci define Class 1 and Class 2 CRISPR/Cas systems, having Types I to V or VI (Makarova et al., (2015) Nat Rev Microbiol, 13(11):722-36; Shmakov et al., (2015) Mol Cell, 60:385-397). Class 2 CRISPR/Cas systems have single protein effectors. Cas proteins of Types II, V, and VI are single-protein, RNA-guided endonucleases, herein called "Class 2 Cas nucleases." Class 2 Cas nucleases include, for example, Cas9, Cpf1, C2c1, C2c2, and C2c3 proteins. The Cpf1 nuclease (Zetsche et al., (2015) Cell 163:1-13) is homologous to Cas9, and contains a RuvC-like nuclease domain.

In some embodiments, the Cas nuclease are from a Type-II CRISPR/Cas system (e.g., a Cas9 protein from a CRISPR/Cas9 system). In some embodiments, the Cas nuclease are from a Class 2 CRISPR/Cas system (a single-protein Cas nuclease such as a Cas9 protein or a Cpf1 protein). The Cas9 and Cpf1 family of proteins are enzymes with DNA endonuclease activity, and they can be directed to cleave a desired nucleic acid target by designing an appropriate guide RNA, as described further herein.

A Type-II CRISPR/Cas system component are from a Type-IIA, Type-IIB, or Type-IIC system. Cas9 and its orthologs are encompassed. Non-limiting exemplary species that the Cas9 nuclease or other components are from include *Streptococcus pyogenes, Streptococcus thermophilus, Streptococcus* sp., *Staphylococcus aureus, Listeria innocua, Lactobacillus gasseri, Francisella novicida, Wolinella succinogenes, Sutterella wadsworthensis, Gamma proteobacterium, Neisseria meningitidis, Campylobacter jejuni, Pasteurella multocida, Fibrobacter succinogene, Rhodospirillum rubrum, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Lactobacillus buchneri, Treponema denticola, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonfex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Streptococcus pasteurianus, Neisseria cinerea, Campylobacter lari, Parvibaculum lavamentivorans, Corynebacterium diphtheria*, or *Acaryochloris marina*. In some embodiments, the Cas9 protein are from *Streptococcus pyogenes* (SpCas9). In some embodiments, the Cas9 protein are from *Streptococcus thermophilus* (StCas9). In some embodiments, the Cas9 protein are from *Neisseria meningitides* (NmCas9). In some embodiments, the Cas9 protein are from *Staphylococcus aureus* (SaCas9). In some embodiments, the Cas9 protein are from *Campylobacter jejuni* (CjCas9).

In some embodiments, a Cas nuclease may comprise more than one nuclease domain. For example, a Cas9 nuclease may comprise at least one RuvC-like nuclease domain (e.g., Cpf1) and at least one HNH-like nuclease domain (e.g., Cas9). In some embodiments, the Cas9 nuclease introduces a DSB in the target sequence. In some embodiments, the Cas9 nuclease is modified to contain only one functional nuclease domain. For example, the Cas9 nuclease is modified such that one of the nuclease domains is mutated or fully or partially deleted to reduce its nucleic acid cleavage activity. In some embodiments, the Cas9 nuclease is modified to contain no functional RuvC-like nuclease domain. In other embodiments, the Cas9 nuclease is modified to contain no functional HNH-like nuclease domain. In some embodiments in which only one of the nuclease domains is functional, the Cas9 nuclease is a nickase that is capable of introducing a single-stranded break (a "nick") into the target sequence. In some embodiments, a conserved amino acid within a Cas9 nuclease nuclease domain is substituted to reduce or alter a nuclease activity. In some embodiments, the Cas nuclease nickase comprises an amino acid substitution in the RuvC-like nuclease domain. Exemplary amino acid substitutions in the RuvC-like nuclease domain include D10A (based on the *S. pyogenes* Cas9 nuclease). In some embodiments, the nickase comprises an amino acid substitution in the HNH-like nuclease domain. Exemplary amino acid substitutions in the HNH-like nuclease domain include E762A, H840A, N863A, H983A, and D986A (based on the *S. pyogenes* Cas9 nuclease). In some embodiments, the nuclease system described herein comprises a nickase and a pair of guide RNAs that are complementary to the sense and antisense strands of the target sequence, respectively. The guide RNAs directs the nickase to target and introduce a DSB by generating a nick on opposite strands of the target sequence (i.e., double nicking). Chimeric Cas9 nucleases are used, where one domain or region of the protein is replaced by a portion of a different protein. For example, a Cas9 nuclease domain is replaced with a domain from a different nuclease such as Fok1. A Cas9 nuclease is a modified nuclease.

In alternative embodiments, the Cas nuclease is from a Type-I CRISPR/Cas system. In some embodiments, the Cas nuclease is a component of the Cascade complex of a Type-I CRISPR/Cas system. For example, the Cas nuclease is a Cas3 nuclease. In some embodiments, the Cas nuclease is derived from a Type-III CRISPR/Cas system. In some embodiments, the Cas nuclease is derived from Type-IV CRISPR/Cas system. In some embodiments, the Cas nuclease is derived from a Type-V CRISPR/Cas system. In some embodiments, the Cas nuclease is derived from a Type-VI CRISPR/Cas system.

High Fidelity Endonucleases

In some embodiments, the disclosure provides a CRISPR/Cas system comprising a Cas nuclease engineered for increased fidelity. As used herein, the term "fidelity" when used in reference to a CRISPR/Cas system comprising a Cas nuclease and gRNA refers to the specificity of the system for a target site in a DNA molecule (e.g., genomic DNA molecule) that is homologous (e.g., perfect match) to the gRNA spacer sequence. In some embodiments, a CRISPR/Cas system with increased fidelity has reduced activity at off-target sites in the DNA molecule, i.e., sites that are an imperfect match to the gRNA spacer sequence.

In some embodiments, a CRISPR/Cas system of the disclosure comprises a Cas variant comprising one or more mutations for increased fidelity. In some embodiments, the one or more mutations result in reduced activity of the CRISPR/Cas system at off-target sites in the DNA molecule, for example, compared to a system comprising an unmodified version of the Cas nuclease (e.g., wild-type Cas nuclease). In some embodiments, the CRISPR/Cas system has substantially equivalent activity for inducing cleavage at an on-target site in the DNA molecule, for example, as compared to the system comprising an unmodified version of the Cas nuclease.

Methods of making Cas variants with increased fidelity are known in the art. For example, in some embodiments, a method of structure-guided engineering is used to make a Cas variant with increased fidelity.

In some embodiments, a CRISPR/Cas system described herein comprises a Cas9 nuclease comprising one or more mutations for increased fidelity. In some embodiments, the Cas9 nuclease is derived from *S. pyogenes*, wherein the Cas nuclease comprises one or more mutations relative to wild-type SpCas9 for increased fidelity.

A suitable Cas9 nuclease with increased fidelity for use in the present disclosure includes any one described US2019/0010471; US2018/0142222; U.S. Pat. No. 9,944,912; WO2020/057481; US2019/0177710; US2018/0100148; U.S. Pat. No. 10,526,591; and US20200149020; each of which is incorporated herein by reference in their entirety.

In some embodiments, a Cas nuclease engineered for increased fidelity reduces cleavage of one or more predicted off-target sites by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 115%, at least about 120%, at least about 125%, at least about 30%, at least about 135%, at least about 140%, at least about 145%, at least about 150%, at least about 155%, at least about 160%, at least about 165%, at least about 170%, at least about 175%, at least about 180%, at least about 185%, at least about 190%, at least about 195%, or at least about 200%, relative to a Cas nuclease not engineered for increased fidelity (e.g., wild-type Cas nuclease). In some embodiments, a Cas nuclease engineered for increased fidelity reduces cleavage of one or more predicted off-target sites by about 10% to about 200%, about 20% to about 190%, about 30% to about 180%, about 40% to about 170%, about 50% to about 160%, about 60% to about 150%, about 70% to about 140%, about 80% to about 130%, about 90% to about 120%, about 100% to about 110%, relative to a Cas nuclease not engineered for increased fidelity (e.g., wild-type Cas nuclease).

In some embodiments, cleavage of an off-target or on-target site is determined based on the percentage of INDELs. In some embodiments, the percentage of INDELs generated at one or more off-target sites by a Cas nuclease engineered for increased fidelity is decreased relative to the percentage of INDELs generated by a Cas nuclease not engineered for increased fidelity (e.g., wild-type Cas nuclease).

In some embodiments, a Cas nuclease engineered for increased fidelity maintains the same level of cleavage of the on-target site, and reduces the cleavage of one or more predicted off-target sites compared to a Cas nuclease not engineered for increased fidelity (e.g., wild-type Cas nuclease).

Engineered Nucleases

In additional embodiments, the donor polynucleotides provided by the disclosure are used in combination with a site-directed nuclease, wherein the site-directed nuclease is an engineered nuclease. Exemplary engineered nucleases are meganuclease (e.g., homing endonucleases), ZFN, TALEN, and megaTAL.

Naturally-occurring meganucleases may recognize and cleave double-stranded DNA sequences of about 12 to 40 base pairs and are commonly grouped into five families. In some embodiments, the meganuclease are chosen from the LAGLIDADG family, the GIY-YIG family, the HNH family, the His-Cys box family, and the PD-(D/E)XK family. In some embodiments, the DNA binding domain of the meganuclease are engineered to recognize and bind to a sequence other than its cognate target sequence. In some embodiments, the DNA binding domain of the meganuclease are fused to a heterologous nuclease domain. In some embodiments, the meganuclease, such as a homing endonuclease, are fused to TAL modules to create a hybrid protein, such as a "megaTAL" protein. The megaTAL protein have improved DNA targeting specificity by recognizing the target sequences of both the DNA binding domain of the meganuclease and the TAL modules.

ZFNs are fusion proteins comprising a zinc-finger DNA binding domain ("zinc fingers" or "ZFs") and a nuclease domain. Each naturally-occurring ZF may bind to three consecutive base pairs (a DNA triplet), and ZF repeats are combined to recognize a DNA target sequence and provide sufficient affinity. Thus, engineered ZF repeats are combined to recognize longer DNA sequences, such as, e.g., 9-, 12-, 15-, or 18-bp, etc. In some embodiments, the ZFN comprise ZFs fused to a nuclease domain from a restriction endonuclease. For example, the restriction endonuclease is FokI. In some embodiments, the nuclease domain comprises a dimerization domain, such as when the nuclease dimerizes to be active, and a pair of ZFNs comprising the ZF repeats and the nuclease domain is designed for targeting a target sequence, which comprises two half target sequences recognized by each ZF repeats on opposite strands of the DNA molecule, with an interconnecting sequence in between (which is sometimes called a spacer in the literature). For example, the interconnecting sequence is 5 to 7 bp in length. When both ZFNs of the pair bind, the nuclease domain may dimerize and introduce a DSB within the interconnecting sequence. In some embodiments, the dimerization domain of the nuclease domain comprises a knob-into-hole motif to promote dimerization. For example, the ZFN comprises a knob-into-hole motif in the dimerization domain of FokI.

The DNA binding domain of TALENs usually comprises a variable number of 34 or 35 amino acid repeats ("modules" or "TAL modules"), with each module binding to a single DNA base pair, A, T, G, or C. Adjacent residues at positions 12 and 13 (the "repeat-variable di-residue" or RVD) of each module specify the single DNA base pair that the module binds to. Though modules used to recognize G may also have affinity for A, TALENs benefit from a simple code of recognition—one module for each of the 4 bases-which greatly simplifies the customization of a DNA-binding domain recognizing a specific target sequence. In some embodiments, the TALEN may comprise a nuclease domain from a restriction endonuclease. For example, the restriction endonuclease is FokI. In some embodiments, the nuclease domain may dimerize to be active, and a pair of TALENS is designed for targeting a target sequence, which comprises two half target sequences recognized by each DNA binding domain on opposite strands of the DNA molecule, with an interconnecting sequence in between. For example, each half target sequence is in the range of 10 to 20 bp, and the interconnecting sequence is 12 to 19 bp in length. When both TALENs of the pair bind, the nuclease domain may dimerize and introduce a DSB within the interconnecting sequence. In some embodiments, the dimerization domain of the nuclease domain may comprise a knob-into-hole motif to promote dimerization. For example, the TALEN may comprise a knob-into-hole motif in the dimerization domain of FokI.

Modified Nucleases

In certain embodiments, the nuclease is optionally modified from its wild-type counterpart. In some embodiments, the nuclease is fused with at least one heterologous protein domain. At least one protein domain is located at the N-terminus, the C-terminus, or in an internal location of the nuclease. In some embodiments, two or more heterologous protein domains are at one or more locations on the nuclease.

In some embodiments, the protein domain may facilitate transport of the nuclease into the nucleus of a cell. For example, the protein domain is a nuclear localization signal (NLS). In some embodiments, the nuclease is fused with 1-10 NLS(s). In some embodiments, the nuclease is fused with 1-5 NLS(s). In some embodiments, the nuclease is fused with one NLS. In other embodiments, the nuclease is fused with more than one NLS. In some embodiments, the nuclease is fused with 2, 3, 4, or 5 NLSs. In some embodiments, the nuclease is fused with 2 NLSs. In some embodiments, the nuclease is fused with 3 NLSs. In some embodiments, the nuclease is fused with no NLS. In some embodiments, the NLS may be a monopartite sequence, such as, e.g., the SV40 NLS, PKKKRKV (SEQ ID NO: 65) or PKKKRRV (SEQ ID NO: 66). In some embodiments, the NLS is a bipartite sequence, such as, e.g., the NLS of nucleoplasmin, KRPAATKKAGQAKKKK (SEQ ID NO: 67). In some embodiments, the NLS is genetically modified from its wild-type counterpart.

In some embodiments, the protein domain is capable of modifying the intracellular half-life of the nuclease. In some embodiments, the half-life of the nuclease may be increased. In some embodiments, the half-life of the nuclease is reduced. In some embodiments, the entity is capable of increasing the stability of the nuclease. In some embodiments, the entity is capable of reducing the stability of the nuclease. In some embodiments, the protein domain act as a signal peptide for protein degradation. In some embodiments, the protein degradation is mediated by proteolytic enzymes, such as, e.g., proteasomes, lysosomal proteases, or calpain proteases. In some embodiments, the protein domain comprises a PEST sequence. In some embodiments, the nuclease is modified by addition of ubiquitin or a polyubiquitin chain. In some embodiments, the ubiquitin is a ubiquitin-like protein (UBL). Non-limiting examples of ubiquitin-like proteins include small ubiquitin-like modifier (SUMO), ubiquitin cross-reactive protein (UCRP, also known as interferon-stimulated gene-15 (ISG15)), ubiquitin-related modifier-1 (URM1), neuronal-precursor-cell-expressed developmentally downregulated protein-8 (NEDD8, also called Rub 1 in *S. cerevisiae*), human leukocyte antigen F-associated (FAT10), autophagy-8 (ATG8) and -12 (ATG12), Fau ubiquitin-like protein (FUB1), membrane-anchored UBL (MUB), ubiquitin fold-modifier-1 (UFM1), and ubiquitin-like protein-5 (UBLS).

In some embodiments, the protein domain is a marker domain. Non-limiting examples of marker domains include fluorescent proteins, purification tags, epitope tags, and reporter gene sequences. In some embodiments, the marker domain is a fluorescent protein. Non-limiting examples of suitable fluorescent proteins include green fluorescent proteins (e.g., GFP, GFP-2, tagGFP, turboGFP, sfGFP, EGFP, Emerald, Azami Green, Monomeric Azami Green, CopGFP, AceGFP, ZsGreenl), yellow fluorescent proteins (e.g., YFP, EYFP, Citrine, Venus, YPet, PhiYFP, ZsYellowl), blue fluorescent proteins (e.g., EBFP, EBFP2, Azurite, mKalamal, GFPuv, Sapphire, T-sapphire,), cyan fluorescent proteins (e.g., ECFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In other embodiments, the marker domain is a purification tag and/or an epitope tag. Non-limiting exemplary tags include glutathione-S-transferase (GST), chitin binding protein (CBP), maltose binding protein (MBP), thioredoxin (TRX), poly (NANP), tandem affinity purification (TAP) tag, myc, AcV5, AUl, AU5, E, ECS, E2, FLAG (SEQ ID NO: 95), HA, nus, Softag 1, Softag 3, Strep, SBP, Glu-Glu, HSV, KT3, S, S1, T7, V5, VSV-G, 6×His (SEQ ID NO: 94), biotin carboxyl carrier protein (BCCP), and calmodulin. Non-limiting exemplary reporter genes include glutathione-S-transferase (GST), horseradish peroxidase (HRP), chloramphenicol acetyltransferase (CAT), beta-galactosidase, beta-glucuronidase, luciferase, or fluorescent proteins.

In additional embodiments, the protein domain may target the nuclease to a specific organelle, cell type, tissue, or organ.

In further embodiments, the protein domain is an effector domain. When the nuclease is directed to its target nucleic acid, e.g., when a Cas9 protein is directed to a target nucleic acid by a guide RNA, the effector domain may modify or affect the target nucleic acid. In some embodiments, the effector domain is chosen from a nucleic acid binding domain, a nuclease domain, an epigenetic modification domain, a transcriptional activation domain, or a transcriptional repressor domain. In some embodiments, the effector domain can be a nucleobase deaminase domain.

Certain embodiments of the invention also provide nucleic acids encoding the nucleases (e.g., a Cas9 protein) described herein provided on a vector. In some embodiments, the nucleic acid is a DNA molecule. In other embodiments, the nucleic acid is an RNA molecule. In some embodiments, the nucleic acid encoding the nuclease is an mRNA molecule. In certain embodiments, the nucleic acid is an mRNA encoding a Cas9 protein.

In some embodiments, the nucleic acid encoding the nuclease is codon optimized for efficient expression in one or more eukaryotic cell types. In some embodiments, the nucleic acid encoding the nuclease is codon optimized for efficient expression in one or more mammalian cells.

In some embodiments, the nucleic acid encoding the nuclease is codon optimized for efficient expression in human cells. Methods of codon optimization including codon usage tables and codon optimization algorithms are available in the art.

Target Sites

In some embodiments, the site-directed nucleases described herein are directed to and cleave (e.g., introduce a DSB) a target nucleic acid molecule. In some embodiments, the target nucleic acid molecule is an HBB gene. In some embodiments, a Cas nuclease is directed by a guide RNA to a target site of a target nucleic acid molecule (gDNA), where the guide RNA hybridizes with the complementary strand of the target sequence and the Cas nuclease cleaves the target nucleic acid at the target site. In some embodiments, a Cas nuclease is directed by a gRNA to a target site of an HBB gene. In some embodiments, the Cas nuclease is directed by a gRNA to a target site comprising SEQ ID NO: 15 or 20. In some embodiments, the complementary strand of the target sequence is complementary to the targeting sequence (e.g.: spacer sequence) of the guide RNA. In some embodiments, the degree of complementarity between a targeting sequence of a guide RNA and its corresponding complementary strand of the target sequence is about 50%, 55%, 60%, 65%, 70%, 75%, 80%, 85%, 90%, 95%, 97%, 98%, 99%, or 100%. In some embodiments, the complementary strand of the target sequence and the targeting sequence of the guide RNA is 100% complementary. In other embodiments, the complementary strand of the target sequence and the targeting sequence of the guide RNA contains at least one mismatch. For example, the complementary strand of the target sequence and the targeting sequence of the guide RNA contain 1, 2, 3, 4, 5, 6, 7, 8, 9, or 10 mismatches. In some embodiments, the complementary strand of the target sequence and the targeting sequence of the guide RNA contain 1-6 mismatches. In some embodiments, the complementary strand of the target sequence and the targeting sequence of the guide RNA contain 5 or 6 mismatches.

The length of the target sequence may depend on the nuclease system used. For example, the target sequence for a CRISPR/Cas system comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the target sequence comprise 18-24 nucleotides in length. In some embodiments, the target sequence comprises 19-21 nucleotides in length. In some embodiments, the target sequence comprises 20 nucleotides in length. When nickases are used, the target sequence comprises a pair of target sequences recognized by a pair of nickases on opposite strands of the DNA molecule.

In some embodiments, the target sequence for a meganuclease comprises 12-40 or more nucleotides in length. When ZFNs are used, the target sequence comprises two half target sequences recognized by a pair of ZFNs on opposite strands of the DNA molecule, with an interconnecting sequence in between. In some embodiments, each half target sequence for ZFNs independently comprise 9, 12, 15, 18, or more nucleotides in length. In some embodiments, the interconnecting sequence for ZFNs comprise 4-20 nucleotides in length. In some embodiments, the interconnecting sequence for ZFNs comprise 5-7 nucleotides in length.

When TALENs are used, the target sequence may similarly comprise two half target sequences recognized by a pair of TALENs on opposite strands of the DNA molecule, with an interconnecting sequence in between. In some embodiments, each half target sequence for TALENs may independently comprise 10-20 or more nucleotides in length. In some embodiments, the interconnecting sequence for TALENs may comprise 4-20 nucleotides in length. In some embodiments, the interconnecting sequence for TALENs may comprise 12-19 nucleotides in length.

The target nucleic acid molecule is any DNA molecule that is endogenous or exogenous to a cell. As used herein, the term "endogenous sequence" refers to a sequence that is native to the cell. In some embodiments, the target nucleic acid molecule is a genomic DNA (gDNA) molecule or a chromosome from a cell or in the cell. In some embodiments, the target sequence of the target nucleic acid molecule is a genomic sequence from a cell or in the cell. In other embodiments, the cell is a eukaryotic cell. In some embodiments, the eukaryotic cell is a mammalian cell. In some embodiments, the eukaryotic cell may be a rodent cell. In some embodiments, the eukaryotic cell may be a human cell. In further embodiments, the target sequence may be a viral sequence. In yet other embodiments, the target sequence may be a synthesized sequence. In some embodiments, the target sequence may be on a eukaryotic chromosome, such as a human chromosome.

In some embodiments, the target sequence may be located in a coding sequence of a gene, an intron sequence of a gene, a transcriptional control sequence of a gene, a translational control sequence of a gene, or a non-coding sequence between genes. In some embodiments, the gene may be a protein coding gene. In other embodiments, the gene may be a non-coding RNA gene. In some embodiments, the target sequence may comprise all or a portion of a disease-associated gene.

In some embodiments, the target sequence may be located in a non-genic functional site in the genome that controls aspects of chromatin organization, such as a scaffold site or locus control region. In some embodiments, the target sequence may be a genetic safe harbor site, i.e., a locus that facilitates safe genetic modification.

In some embodiments, the target sequence may be adjacent to a protospacer adjacent motif (PAM), a short sequence recognized by a CRISPR/Cas9 complex. In some embodiments, the PAM may be adjacent to or within 1, 2, 3, or 4, nucleotides of the 3' end of the target sequence. In some embodiments, the target sequence may include the PAM. The length and the sequence of the PAM may depend on the Cas9 protein used. For example, the PAM may be selected from a consensus or a particular PAM sequence for a specific Cas9 nuclease or Cas9 ortholog, including those disclosed in FIG. 1 of Ran et al., (2015) Nature, 520:186-191 (2015), which is incorporated herein by reference. In some embodiments, the PAM may comprise 2, 3, 4, 5, 6, 7, 8, 9, or 10 nucleotides in length. Non-limiting exemplary PAM sequences include NGG (SpCas9 WT, SpCas9 nickase, dimeric dCas9-Fok1, SpCas9-HF1, SpCas9 K855A, eSpCas9 (1.0), eSpCas9 (1.1)), NGAN or NGNG (SpCas9 VQR variant), NGAG (SpCas9 EQR variant), NGCG (SpCas9 VRER variant), NAAG (SpCas9 QQR1 variant), NNGRRT or NNGRRN (SaCas9), NNNRRT (KKH SaCas9), NNNNRYAC (CjCas9), NNAGAAW (St1Cas9), NAAAAC (TdCas9), NGGNG (St3Cas9), NG (FnCas9), NAAAAN (TdCas9), NNAAAAW (StCas9), NNNNACA (CjCas9), GNNNCNNA (PmCas9), and NNNNGATT (NmCas9) (see e.g., Cong et al., (2013) Science 339:819-823; Kleinstiver et al., (2015) Nat Biotechnol 33:1293-1298; Kleinstiver et al., (2015) Nature 523:481-485; Kleinstiver et al., (2016) Nature 529:490-495; Tsai et al., (2014) Nat Biotechnol 32:569-576; Slaymaker et al., (2016) Science 351:84-88; Anders et al., (2016) Mol Cell 61:895-902; Kim et al., (2017) Nat Comm 8:14500; Fonfara et al., (2013) Nucleic Acids Res 42:2577-2590; Garneau et al., (2010) Nature 468:67-71; Magadan et al., (2012) PLoS ONE 7:e40913; Esvelt et al., (2013) Nat Methods 10(11):1116-1121(wherein N is defined as any nucleotide, W is defined as either A or T, R is defined as a purine (A) or (G), and Y is defined as a pyrimidine (C) or (T)). In some embodiments, the PAM sequence is NGG. In some embodiments, the PAM sequence is NGAN. In some embodiments, the PAM sequence is NGNG. In some embodiments, the PAM is NNGRRT. In some embodiments, the PAM sequence is NGGNG. In some embodiments, the PAM sequence may be NNAAAAW.

Modified Donor Polynucleotides

In some embodiments, donor polynucleotides are provided with chemistries suitable for delivery and stability within cells. Furthermore, in some embodiments, chemistries are provided that are useful for controlling the pharmacokinetics, biodistribution, bioavailability and/or efficacy of the donor polynucleotides described herein. Accordingly, in some embodiments, donor polynucleotides described herein may be modified, e.g., comprise a modified sugar moiety, a modified internucleoside linkage, a modified nucleoside, a modified nucleotide and/or combinations thereof. In addition, the modified donor polynucleotides may exhibit one or more of the following properties: are not immune stimulatory; are nuclease resistant; have improved cell uptake compared to unmodified donor polynucleotides; and/or are not toxic to cells or mammals.

Nucleotide and nucleoside modifications have been shown to make a polynucleotide (e.g., a donor polynucleotide) into which they are incorporated more resistant to nuclease digestion than the native polynucleotide and these modified polynucleotides have been shown to survive intact for a longer time than unmodified polynucleotides. Specific examples of modified oligonucleotides include those comprising modified backbones (i.e. modified internucleoside linkage), for example, phosphorothioates, phosphotriesters, methyl phosphonates, short chain alkyl or cycloalkyl intersugar linkages or short chain heteroatomic or heterocyclic intersugar linkages. In some embodiments, oligonucleotides may have phosphorothioate backbones; heteroatom backbones, such as methylene(methylimino) or MMI backbones; amide backbones (see e.g., De Mesmaeker et al., Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the polynucleotide is replaced with a polyamide backbone, the nucleotides being bound directly or indirectly to the aza nitrogen atoms of the polyamide backbone, see Nielsen et al., Science 1991, 254, 1497). Phosphorus-containing modified linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,031,272.1, 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010).

Cyclohexenyl nucleic acid oligonucleotide mimetics are described in Wang et al., J. Am. Chem. Soc, 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623, 070; 5,663,312; 5,633,360; 5,677,437; and 5,677,439, each of which is herein incorporated by reference.

In some embodiments, the donor polynucleotides of the disclosure are stabilized against nucleolytic degradation such as by the incorporation of a modification (e.g., a nucleotide modification). In some embodiments, donor polynucleotides of the disclosure include a phosphorothioate at least the first, second, and/or third internucleotide linkage at the 5' and/or 3' end of the nucleotide sequence. In some embodiments, donor polynucleotides of the disclosure include one or more 2'-modified nucleotides, e.g., 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In some embodiments, donor polynucleotides of the disclosure include a phosphorothioate and a 2'-modified nucleotide as described herein.

Any of the modified chemistries described herein can be combined with each other, and that one, two, three, four, five, or more different types of modifications can be included within the same molecule. In some embodiments, the donor polynucleotide comprises 1, 2, 3, 4, 5, 6, 7, 8, 9, 10 or modifications.

mRNA Components

In some embodiments, the systems provided by the disclosure comprise an engineered nuclease encoded by an mRNA. In some embodiments, the compositions provided by the disclosure comprise a nuclease system, wherein the nuclease comprising the nuclease system is encoded by an mRNA. In some embodiments, the mRNA may be a naturally or non-naturally occurring mRNA. In some embodiments, the mRNA may include one or more modified nucleobases, nucleosides, or nucleotides, as described below, in which case it may be referred to as a "modified mRNA". In some embodiments, the mRNA may include a 5' untranslated region (5'-UTR), a 3' untranslated region (3'-UTR), and/or a coding region (e.g., an open reading frame).

An mRNA may include any suitable number of base pairs, including tens (e.g., 10, 20, 30, 40, 50, 60, 70, 80, 90 or 100), hundreds (e.g., 200, 300, 400, 500, 600, 700, 800, or 900) or thousands (e.g., 1000, 2000, 3000, 4000, 5000, 6000, 7000, 8000, 9000, 10,000) of base pairs. Any number (e.g., all, some, or none) of nucleobases, nucleosides, or nucleotides may be an analog of a canonical species, substituted, modified, or otherwise non-naturally occurring. In certain embodiments, all of a particular nucleobase type may be modified. In some embodiments, an mRNA as described herein may include a 5' cap structure, a chain terminating nucleotide, optionally a Kozak or Kozak-like sequence (also known as a Kozak consensus sequence), a stem-loop, a polyA sequence, and/or a polyadenylation signal.

A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., $m^7G(5')ppp(5')G$, commonly written as $m^7GpppG$.

A cap species may also be an anti-reverse cap analog. A non-limiting list of possible cap species includes $m^7GpppG$, $m^7Gpppm^7G$, $m^73'dGpppG$, $m_2^{7,O3'}GpppG$, $m_2^{7,O3'}GppppG$, $m_2^{7,O2'}GppppG$, $m^7Gpppm^7G$, $m^73'dGpppG$, $m_2^{7,O3'}GpppG$, $m_2^{7,O3'}GppppG$, and $m_2^{7,O2'}GppppG$.

An mRNA may instead or additionally include a chain terminating nucleoside. For example, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxythymine. In some embodiments, incorporation of a chain terminating nucleotide into an mRNA, for example at the 3'-terminus, may result in stabilization of the mRNA, as described, for example, in International Patent Publication No. WO 2013/103659.

An mRNA may instead or additionally include a stem loop, such as a histone stem loop. A stem loop may include 2, 3, 4, 5, 6, 7, 8, or more nucleotide base pairs. For example, a stem loop may include 4, 5, 6, 7, or 8 nucleotide base pairs. A stem loop may be located in any region of an mRNA. For example, a stem loop may be located in, before, or after an untranslated region (a 5' untranslated region or a 3' untranslated region), a coding region, or a polyA sequence or tail.

In some embodiments, a stem loop may affect one or more function(s) of an mRNA, such as initiation of translation, translation efficiency, and/or transcriptional termination.

An mRNA may instead or additionally include a polyA sequence and/or polyadenylation signal. A polyA sequence may be comprised entirely or mostly of adenine nucleotides or analogs or derivatives thereof. A polyA sequence may be a tail located adjacent to a 3' untranslated region of an mRNA. In some embodiments, a polyA sequence may affect the nuclear export, translation, and/or stability of an mRNA.

Modified RNA

In some embodiments, an RNA of the disclosure (e.g.: gRNA or mRNA) comprises one or more modified nucleobases, nucleosides, nucleotides or internucleoside linkages. In some embodiments, modified mRNAs and/or gRNAs may have useful properties, including enhanced stability, intracellular retention, enhanced translation, and/or the lack of a substantial induction of the innate immune response of a cell into which the mRNA and/or gRNA is introduced, as compared to a reference unmodified mRNA and/or gRNA. Therefore, use of modified mRNAs and/or gRNAs may enhance the efficiency of protein production, intracellular retention of nucleic acids, as well as possess reduced immunogenicity.

In some embodiments, an mRNA and/or gRNA includes one or more (e.g., 1, 2, 3 or 4) different modified nucleobases, nucleosides, nucleotides or internucleoside linkages. In some embodiments, an mRNA and/or gRNA includes one or more (e.g., 1, 2, 3, 4, 5, 6, 7, 8, 9, 10, 20, 30, 40, 50, 60, 70, 80, 90, 100, or more) different modified nucleobases, nucleosides, or nucleotides. In some embodiments, the modified gRNA may have reduced degradation in a cell into which the gRNA is introduced, relative to a corresponding unmodified gRNA. In some embodiments, the modified mRNA may have reduced degradation in a cell into which the mRNA is introduced, relative to a corresponding unmodified mRNA.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine($\tau m^5s^2U$), 1-taurinomethyl-4-thio-pseudouridine, 5-methyl-uridine ($m^5U$, i.e., having the nucleobase deoxythymine), 1-methyl-pseudouridine ($m^1ψ$), 5-methyl-2-thio-uridine ($M^5s^2U$), 1-methyl-4-thio-pseudouridine ($m^1s^4ψ$), 4-thio-1-methyl-pseudouridine, 3-methyl-pseudouridine ($m^3ψ$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3$ ψ), 5-(isopentenylaminomethyl)uridine ($inm^5U$), 5-(isopentenylaminomethyl)-2-thio-uridine (inm$^5$s$^2$U), α-thio-uridine, 2'-O-methyl-uridine (Um), 5,2'-O-dimethyl-uridine (m$^5$Um), 2'-O-methyl-pseudouridine (ψm), 2-thio-2'-O-methyl-uridine (s$^2$Um), 5-methoxycarbonylmethyl-2'-O-methyl-uridine (mcm$^5$Um), 5-carbamoylmethyl-2'-O-methyl-uridine (ncm$^5$Um), 5-carboxymethylaminomethyl-2'-O-methyl-uridine (cmnm$^5$Um), 3,2'-O-dimethyl-uridine (m$^3$Um), and 5-(isopentenylaminomethyl)-2'-O-methyl-uridine (inm$^5$Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m$^3$C), N4-acetyl-cytidine (ac$^4$C), 5-formyl-cytidine (f$^5$C), N4-methyl-cytidine (m$^4$C), 5-methyl-cytidine (m$^5$C), 5-halo-cytidine (e.g., 5-iodo-cytidine), 5-hydroxymethyl-cytidine (hm$^5$C), 1-methyl-pseudoisocytidine, pyrrolo-cytidine, pyrrolo-pseudoisocytidine, 2-thio-cytidine (s$^2$C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k$_2$C), α-thio-cytidine, 2'-O-methyl-cytidine (Cm), 5,2'-O-dimethyl-cytidine (m$^5$Cm), N4-acetyl-2'-O-methyl-cytidine (ac$^4$Cm), N4,2'-O-dimethyl-cytidine (m$^4$Cm), 5-formyl-2'-O-methyl-cytidine (f$^5$Cm), N4,N4,2'-O-trimethyl-cytidine (m$^4$2Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include α-thio-adenosine, 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2, 6-diaminopurine, 7-deaza-8-aza-2,6-diaminopurine, 1-methyl-adenosine (m$^1$A), 2-methyl-adenine (m$^2$A), N6-methyl-adenosine (m$^6$A), 2-methylthio-N6-methyl-adenosine (ms$^2$m$^6$A), N6-isopentenyl-adenosine (i$^6$A), 2-methylthio-N6-isopentenyl-adenosine (ms$^2$i6A), N6-(cis-hydroxyisopentenyl)adenosine (io$^6$A), 2-methylthio-N6-(cis-hydroxyisopentenyl)adenosine (ms$^2$io$^6$A), N6-glycinylcarbamoyl-adenosine (g$^6$A), N6-threonylcarbamoyl-adenosine (t$^6$A), N6-methyl-N6-threonylcarbamoyl-adenosine (m$^6$t$^6$A), 2-methylthio-N6-threonylcarbamoyl-adenosine (ms$^2$g$^6$A), N6,N6-dimethyl-adenosine (m$^6$2A), N6-hydroxynorvalylcarbamoyl-adenosine (hn$^6$A), 2-methylthio-N6-hydroxynorvalylcarbamoyl-adenosine (ms$^2$hn$^6$A), N6-acetyl-adenosine (ac$^6$A), 7-methyl-adenine, 2-methylthio-adenine, 2-methoxy-adenine, α-thio-adenosine, 2'-O-methyl-adenosine (Am), N6,2'-O-dimethyl-adenosine (m$^6$Am), N6,N6,2'-O-trimethyl-adenosine (m$^6{}_2$Am), 1,2'-O-dimethyl-adenosine (m$^1$Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include α-thio-guanosine, inosine (I), 1-methyl-inosine (m$^1$I), wyosine (imG), methylwyosine (mimG), 4-demethyl-wyosine (imG-14), isowyosine (imG2), wybutosine (yW), peroxywybutosine (o$_2$yW), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQ$_0$), 7-aminomethyl-7-deaza-guanosine (preQ$_1$), archaeosine (G$^+$), 7-deaza-8-aza-guanosine, 6-thio-guanosine, 6-thio-7-deaza-guanosine, 6-thio-7-deaza-8-aza-guanosine, 7-methyl-guanosine (m$^7$G), 6-thio-7-methyl-guanosine, 7-methyl-inosine, 6-methoxy-guanosine, 1-methyl-guanosine (m$^1$G), N2-methyl-guanosine (m$^2$G), N2,N2-dimethyl-guanosine (m$^2$2G), N2,7-dimethyl-guanosine (m$^2$,7G), N2, N2,7-dimethyl-guanosine (m$^{2,2,7}$G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m$^2$Gm), N2,N2-dimethyl-2'-O-methyl-guanosine (m$^2$2Gm), 1-methyl-2'-O-methyl-guanosine (m$^1$Gm), N2,7-dimethyl-2'-O-methyl-guanosine (m$^2$,7Gm), 2'-O-methyl-inosine (Im), 1,2'-O-dimethyl-inosine (m$^1$Im), 2'-O-ribosylguanosine (phosphate) (Gr(p)), 1-thio-guanosine, 06-methyl-guanosine, 2'-F-ara-guanosine, and 2'-F-guanosine.

In some embodiments, an mRNA and/or gRNA of the disclosure includes a combination of one or more of the aforementioned modified nucleobases (e.g., a combination of 2, 3 or 4 of the aforementioned modified nucleobases.) In some embodiments, the modified nucleobase is pseudouridine (W), N1-methylpseudouridine (m$^1$W), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, an mRNA of the disclosure includes a combination of one or more of the aforementioned modified nucleobases (e.g., a combination of 2, 3 or 4 of the aforementioned modified nucleobases.) In one embodiment, the modified nucleobase is N1-methylpseudouridine (m$^1$ψ) and the mRNA of the disclosure is fully modified with N1-methylpseudouridine (m$^1$ψ). In some embodiments, N1-methylpseudouridine (m$^1$ψ) represents from 75-100% of the uracils in the mRNA. In some embodiments, N1-methylpseudouridine (m$^1$ψ) represents 100% of the uracils in the mRNA.

In some embodiments, the modified nucleobase is a modified cytosine. Exemplary nucleobases and nucleosides having a modified cytosine include N4-acetyl-cytidine (ac$^4$C), 5-methyl-cytidine (m$^5$C), 5-halo-cytidine (e.g., 5-iodo-cytidine), 5-hydroxymethyl-cytidine (hm$^5$C), 1-methyl-pseudoisocytidine, 2-thio-cytidine (s$^2$C), 2-thio-5-methyl-cytidine. In some embodiments, an mRNA of the disclosure includes a combination of one or more of the aforementioned modified nucleobases (e.g., a combination of 2, 3 or 4 of the aforementioned modified nucleobases.) In some embodiments, the modified nucleobase is a modified adenine. Exemplary nucleobases and nucleosides having a modified adenine include 7-deaza-adenine, 1-methyl-adenosine (m$^1$A), 2-methyl-adenine (m$^2$A), N6-methyl-adenosine (m$^6$A). In some embodiments, an mRNA of the disclosure includes a combination of one or more of the aforementioned modified nucleobases (e.g., a combination of 2, 3 or 4 of the aforementioned modified nucleobases.) In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 7-deaza-guanosine, 7-cyano-7-deaza-guanosine ($preQ_0$), 7-aminomethyl-7-deaza-guanosine ($preQ_1$), 7-methyl-guanosine ($m^7G$), 1-methyl-guanosine ($m^1G$), 8-oxo-guanosine, 7-methyl-8-oxo-guanosine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is 1-methyl-pseudouridine ($m^1W$), 5-methoxy-uridine ($mo^5U$), 5-methyl-cytidine ($m^5C$), pseudouridine ($\psi$), $\alpha$-thio-guanosine, or $\alpha$-thio-adenosine. In some embodiments, an mRNA of the disclosure includes a combination of one or more of the aforementioned modified nucleobases (e.g., a combination of 2, 3 or 4 of the aforementioned modified nucleobases.)

In certain embodiments, an mRNA and/or a gRNA of the disclosure is uniformly modified (i.e., fully modified, modified through-out the entire sequence) for a particular modification. For example, an mRNA can be uniformly modified with N1-methylpseudouridine ($m^1\psi$) or 5-methyl-cytidine ($m^5C$), meaning that all uridines or all cytosine nucleosides in the mRNA sequence are replaced with N1-methylpseudouridine ($m^1\psi$) or 5-methyl-cytidine ($m^5C$). Similarly, mRNAs of the disclosure can be uniformly modified for any type of nucleoside residue present in the sequence by replacement with a modified residue such as those set forth above.

In some embodiments, an mRNA of the disclosure may be modified in a coding region (e.g., an open reading frame encoding a polypeptide). In other embodiments, an mRNA may be modified in regions besides a coding region. For example, in some embodiments, a 5'-UTR and/or a 3'-UTR are provided, wherein either or both may independently contain one or more different nucleoside modifications. In such embodiments, nucleoside modifications may also be present in the coding region.

Ribonucleoproteins

In certain aspects, the site-directed polypeptide (e.g., Cas nuclease) and genome-targeting nucleic acid (e.g., gRNA or sgRNA) may each be administered separately to a cell or a subject. In certain aspects, the site-directed polypeptide may be pre-complexed with one or more guide RNAs, or one or more sgRNAs. Such pre-complexed material is known as a ribonucleoprotein particle (RNP). In some embodiments, the nuclease system comprises a ribonucleoprotein (RNP). In some embodiments, the nuclease system comprises a Cas9 RNP comprising a purified Cas9 protein in complex with a gRNA. Cas9 protein can be expressed and purified by any means known in the art. Ribonucleoproteins are assembled in vitro and can be delivered directly to cells using standard electroporation or transfection techniques known in the art.

Vectors

In some embodiments, the site-directed nuclease (e.g., Cas nuclease) and the donor polynucleotide may be provided by one or more vectors. In some embodiments, the vector may be a DNA vector. In some embodiments, the vector may be circular. In other embodiments, the vector may be linear. Non-limiting exemplary vectors include plasmids, phagemids, cosmids, artificial chromosomes, minichromosomes, transposons, viral vectors, and expression vectors.

In some embodiments, the vector may be a viral vector. In some embodiments, the viral vector may be genetically modified from its wild-type counterpart. For example, the viral vector may comprise an insertion, deletion, or substitution of one or more nucleotides to facilitate cloning or such that one or more properties of the vector is changed. Such properties may include packaging capacity, transduction efficiency, immunogenicity, genome integration, replication, transcription, and translation. In some embodiments, a portion of the viral genome may be deleted such that the virus is capable of packaging exogenous sequences having a larger size. In some embodiments, the viral vector may have an enhanced transduction efficiency. In some embodiments, the immune response induced by the virus in a host may be reduced. In some embodiments, viral genes (such as, e.g., integrase) that promote integration of the viral sequence into a host genome may be mutated such that the virus becomes non-integrating. In some embodiments, the viral vector may be replication defective. In some embodiments, the viral vector may comprise exogenous transcriptional or translational control sequences to drive expression of coding sequences on the vector. In some embodiments, the virus may be helper-dependent. For example, the virus may need one or more helper virus to supply viral components (such as, e.g., viral proteins) required to amplify and package the vectors into viral particles. In such a case, one or more helper components, including one or more vectors encoding the viral components, may be introduced into a host cell along with the vector system described herein. In other embodiments, the virus may be helper-free. For example, the virus may be capable of amplifying and packaging the vectors without any helper virus. In some embodiments, the vector system described herein may also encode the viral components required for virus amplification and packaging.

Non-limiting exemplary viral vectors include adeno-associated virus (AAV) vector, lentivirus vectors, adenovirus vectors, herpes simplex virus (HSV-1) vectors, bacteriophage T4, baculovirus vectors, and retrovirus vectors. In some embodiments, the viral vector may be an AAV vector. In other embodiments, the viral vector may a lentivirus vector. In some embodiments, the lentivirus may be non-integrating. In some embodiments, the viral vector may be an adenovirus vector. In some embodiments, the adenovirus may be a high-cloning capacity or "gutless" adenovirus, where all coding viral regions apart from the 5' and 3' inverted terminal repeats (ITRs) and the packaging signal ($\psi$) are deleted from the virus to increase its packaging capacity. In yet other embodiments, the viral vector may be an HSV-1 vector. In some embodiments, the HSV-1-based vector is helper dependent, and in other embodiments it is helper independent. For example, an amplicon vector that retains only the packaging sequence requires a helper virus with structural components for packaging, while a 30 kb-deleted HSV-1 vector that removes non-essential viral functions does not require helper virus. In additional embodiments, the viral vector may be bacteriophage T4. In some embodiments, the bacteriophage T4 may be able to package any linear or circular DNA or RNA molecules when the head of the virus is emptied. In further embodiments, the viral vector may be a baculovirus vector. In yet further embodiments, the viral vector may be a retrovirus vector. In embodiments using AAV or lentiviral vectors, which have smaller cloning capacity, it may be necessary to use more than one vector to deliver all the components of a vector system as disclosed herein. For example, one AAV vector may contain sequences encoding a Cas9 protein, while a second AAV vector may contain one or more guide sequences and one or more copies of donor polynucleotide.

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived, and may be from a different AAV serotype than the rAAV genome ITRs, including, but not limited to, AAV serotypes AAV-1, AAV-2,AAV-3, AAV-4, AAV-5, AAV-6, AAV-7, AAV-8, AAV-9, AAV-10, AAV-11, AAV-12,AAV-13 and AAV rh.74. Production of pseudotyped rAAV is disclosed in, for example, international patent application publication number WO 01/83692. In some embodiments, the vector is AAV6.

A method of generating a packaging cell involves creating a cell line that stably expresses all of the necessary components for AAV particle production. For example, a plasmid (or multiple plasmids)comprising a rAAV genome lacking AAV rep and cap genes, AAV rep and cap genes separate from the rAAV genome, and a selectable marker, such as aneomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus orbaculovirus, rather than plasmids, to introduce rAAV genomes and/or rep and cap genes into packaging cells.

In certain embodiments, a viral vector may be modified to target a particular tissue or cell type. For example, viral surface proteins may be altered to decrease or eliminate viral protein binding to its natural cell surface receptor(s). The surface proteins may also be engineered to interact with a receptor specific to a desired cell type. Viral vectors may have altered host tropism, including limited or redirected tropism. Certain engineered viral vectors are described, for example, in WO2011130749, WO2015009952, U.S. Pat. No. 5,817,491, WO2014135998, and WO2011125054. In some embodiments, the vector may be capable of driving expression of one or more coding sequences in a cell. In some embodiments, the cell may be a eukaryotic cell, such as, e.g., a yeast, plant, insect, or mammalian cell. In some embodiments, the eukaryotic cell may be a mammalian cell. In some embodiments, the eukaryotic cell may be a rodent cell. In some embodiments, the eukaryotic cell may be a human cell. Suitable promoters to drive expression in different types of cells are known in the art. In some embodiments, the promoter may be wild-type. In other embodiments, the promoter may be modified for more efficient or efficacious expression. In yet other embodiments, the promoter may be truncated yet retain its function. For example, the promoter may have a normal size or a reduced size that is suitable for proper packaging of the vector into a virus.

In some embodiments, the vector may comprise a nucleotide sequence encoding the nuclease described herein. In some embodiments, the vector system may comprise one copy of the nucleotide sequence encoding the nuclease. In other embodiments, the vector system may comprise more than one copy of the nucleotide sequence encoding the nuclease. In some embodiments, the nucleotide sequence encoding the nuclease may be operably linked to at least one transcriptional or translational control sequence. In some embodiments, the nucleotide sequence encoding the nuclease may be operably linked to at least one promoter. In some embodiments, the nucleotide sequence encoding the nuclease may be operably linked to at least one transcriptional or translational control sequence.

In some embodiments, the promoter may be constitutive, inducible, or tissue-specific. In some embodiments, the promoter may be a constitutive promoter. Non-limiting exemplary constitutive promoters include cytomegalovirus immediate early promoter (CMV), simian virus (SV40) promoter, adenovirus major late (MLP) promoter, Rous sarcoma virus (RSV) promoter, mouse mammary tumor virus (MMTV) promoter, phosphoglycerate kinase (PGK) promoter, elongation factor-alpha (EF1α) promoter, ubiquitin promoters, actin promoters, tubulin promoters, immunoglobulin promoters, a functional fragment thereof, or a combination of any of the foregoing. In some embodiments, the promoter may be a CMV promoter. In some embodiments, the promoter may be a truncated CMV promoter. In other embodiments, the promoter may be an EF1α promoter. In some embodiments, the promoter may be an inducible promoter. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech). In some embodiments, the promoter may be a tissue-specific promoter. In some embodiments, the tissue-specific promoter is exclusively or predominantly expressed in liver tissue. Non-limiting exemplary tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, Nphsl promoter, OG-2 promoter, SP-B promoter, SYN1 promoter, and WASP promoter.

In some embodiments, the nuclease encoded by the vector may be a Cas protein, such as a Cas9 protein or Cpf1 protein. The vector system may further comprise a vector comprising a nucleotide sequence encoding the guide RNA described herein. In some embodiments, the vector system may comprise one copy of the guide RNA. In other embodiments, the vector system may comprise more than one copy of the guide RNA. In embodiments with more than one guide RNA, the guide RNAs may be non-identical such that they target different target sequences, or have other different properties, such as activity or stability within the Cas9 RNP complex. In some embodiments, the nucleotide sequence encoding the guide RNA may be operably linked to at least one transcriptional or translational control sequence. In some embodiments, the nucleotide sequence encoding the guide RNA may be operably linked to at least one promoter. In some embodiments, the promoter may be recognized by RNA polymerase III (Pol III). Non-limiting examples of Pol III promoters include U6, H1 and tRNA promoters. In some embodiments, the nucleotide sequence encoding the guide RNA may be operably linked to a mouse or human U6 promoter. In other embodiments, the nucleotide sequence encoding the guide RNA may be operably linked to a mouse or human H1 promoter. In some embodiments, the nucleotide sequence encoding the guide RNA may be operably linked to a mouse or human tRNA promoter. In embodiments with more than one guide RNA, the promoters used to drive expression may be the same or different. In some embodiments, the nucleotide encoding the crRNA of the guide RNA and the nucleotide encoding the tracr RNA of the guide RNA may be provided on the same vector. In some embodiments, the nucleotide encoding the crRNA and the nucleotide encoding the tracr RNA may be driven by the same promoter. In some embodiments, the crRNA and tracr RNA may be transcribed into a single transcript. For example, the crRNA and tracr RNA may be processed from the single transcript to form a double-molecule guide RNA. Alternatively, the crRNA and tracr RNA may be transcribed into a single-molecule guide RNA. In other embodiments, the crRNA and the tracr RNA may be driven by their corresponding promoters on the same vector. In yet other embodiments, the crRNA and the tracr RNA may be encoded by different vectors.

In some embodiments, the nucleotide sequence encoding the guide RNA may be located on the same vector comprising the nucleotide sequence encoding a Cas9 protein. In some embodiments, expression of the guide RNA and of the Cas9 protein may be driven by different promoters. In some embodiments, expression of the guide RNA may be driven by the same promoter that drives expression of the Cas9 protein. In some embodiments, the guide RNA and the Cas9 protein transcript may be contained within a single transcript. For example, the guide RNA may be within an untranslated region (UTR) of the Cas9 protein transcript. In some embodiments, the guide RNA may be within the 5' UTR of the Cas9 protein transcript. In other embodiments, the guide RNA may be within the 3' UTR of the Cas9 protein transcript. In some embodiments, the intracellular half-life of the Cas9 protein transcript may be reduced by containing the guide RNA within its 3' UTR and thereby shortening the length of its 3' UTR. In additional embodiments, the guide RNA may be within an intron of the Cas9 protein transcript. In some embodiments, suitable splice sites may be added at the intron within which the guide RNA is located such that the guide RNA is properly spliced out of the transcript. In some embodiments, expression of the Cas9 protein and the guide RNA in close proximity on the same vector may facilitate more efficient formation of the CRISPR complex.

In some embodiments, the vector system may further comprise a vector comprising the donor polynucleotide described herein. In some embodiments, the vector system may comprise one copy of the donor polynucleotide. In other embodiments, the vector system may comprise more than one copy of the donor polynucleotide. In some embodiments, the vector system may comprise 2, 3, 4, 5, 6, 7, 8, 9, 10, or more copies of the donor polynucleotide. The multiple copies of the donor polynucleotide may be located on the same or different vectors. The multiple copies of the donor polynucleotide may also be adjacent to one another, or separated by other nucleotide sequences or vector elements.

A vector system may comprise 1-3 vectors. In some embodiments, the vector system may comprise one single vector. In other embodiments, the vector system may comprise two vectors. In additional embodiments, the vector system may comprise three vectors. When different guide RNAs or donor polynucleotides are used for multiplexing, or when multiple copies of the guide RNA or the donor polynucleotide are used, the vector system may comprise more than three vectors.

In some embodiments, the nucleotide sequence encoding a Cas9 protein, a nucleotide sequence encoding the guide RNA, and a donor polynucleotide may be located on the same or separate vectors. In some embodiments, all of the sequences may be located on the same vector. In some embodiments, two or more sequences may be located on the same vector. The sequences may be oriented in the same or different directions and in any order on the vector. In some embodiments, the nucleotide sequence encoding the Cas9 protein and the nucleotide sequence encoding the guide RNA may be located on the same vector. In some embodiments, the nucleotide sequence encoding the Cas9 protein and the donor polynucleotide may be located on the same vector. In some embodiments, the nucleotide sequence encoding the guide RNA and the donor polynucleotide may be located on the same vector. In some embodiments, the vector system may comprise a first vector comprising the nucleotide sequence encoding the Cas9 protein, and a second vector comprising the nucleotide sequence encoding the guide RNA and the donor polynucleotide.

Methods of Increasing Homology Directed Repair

The repair of DNA breaks (e.g., DSBs) in cells is accomplished primarily through two DNA repair pathways, namely the non-homologous end joining (NHEJ) repair pathway and homology-directed repair (HDR) pathway.

During NHEJ, the Ku70/80 heterodimers bind to DNA ends and recruit the DNA protein kinase (DNA-PK) (Cannan & Pederson (2015) J Cell Physiol 231:3-14). Once bound, DNA-PK activates its own catalytic subunit (DNA-PKcs) and further enlists the endonuclease Artemis (also known as SNM1c). At a subset of DSBs, Artemis removes excess single-strand DNA (ssDNA) and generates a substrate that will be ligated by DNA ligase IV. DNA repair by NHEJ involves blunt-end ligation mechanism independent of sequence homology via the canonical DNA-PKcs/Ku70/80 complex.

During DNA repair by HDR, DSB ends are resected to expose 3' ssDNA tails, primarily by the MRE11-RAD50-NBS1 (URN) complex (Heyer et al., (2010) Annu Rev Genet 44: 113-139). Under physiological conditions, the adjacent sister chromatid will be used as a repair template, providing a homologous sequence, and the ssDNA will invade the template mediated by the recombinase Rad51, displacing an intact strand to form a D-loop. D-loop extension is followed by branch migration to produce double-Holliday junctions, the resolution of which completes the repair cycle. HDR often requires error-prone polymerases yet is typically viewed as error-free (Li and Xu (2016) Acta Biochim Biophys Sin 48(7):641-646).

The NHEJ pathway limits HDR first by being a fast-acting repair pathway that seals the broken DNA ends through a DNA ligase IV-dependent mechanism. Secondly, in NHEJ the Ku70/Ku80 heterodimer binds to the DNA ends with high affinity to block their processing by the nucleases that generate the single-stranded DNA tails that are necessary for initiation of HDR (Lieber, M. et al. (2010) *Annu Rev Biochem* 79:181-211; Symington, L. et al. (2011) *Annu Review Genetics* 45:247-271). Thirdly, 53BP1 is actively recruited to sites of damaged chromatin present at a DNA DSB where it functions to suppress the formation of 3' ssDNA tails and antagonize the action of BRCA1, a factor involved in HDR (Escribano-Diaz, C. (2013) *Molecular cell* 49:872-883; Feng, L. et al. (2013) *J. Biol Chem.* 288:11135-11143).

During the cell cycle, NHEJ occurs predominantly during G0/G1 and G2 (Chiruvella et al., (2013) Cold Spring Harb Perspect Biol 5:a012757). Current studies have shown that NHEJ is the only DSB repair pathway active during G0 and G1, while HDR functions primarily during the S and G2 phases, playing a major role in the repair of replication-associated DSBs (Karanam et al., (2012) Mol Cell 47:320-329; Li and Xu (2016) Acta Biochim Biophys Sin 48(7): 641-646). NHEJ, unlike HDR, is active in both dividing and non-dividing cells, not just dividing cells, which enables the development of therapies based on genome editing for non-dividing adult cells, such as, for example, cells of the eye, brain, pancreas, or heart.

A third repair mechanism is microhomology-mediated end joining (MMEJ), also referred to as "Alternative NHEJ", in which the genetic outcome is similar to NHEJ in that small deletions and insertions can occur at the cleavage site. MMEJ makes use of homologous sequences of a few nucleotides flanking the DNA break site to drive a more favored DNA end joining repair outcome, and recent reports have further elucidated the molecular mechanism of this process (Cho and Greenberg, (2015) Nature 518:174-176; Mateos-Gomez et al., (2015) Nature 518, 254-257; Ceccaldi et al., (2015) Nature 528, 258-262). The key mechanistic steps are resection of DSB ends, annealing of microhomologous regions, removal of heterologous flaps, fill-in synthesis and ligation. PARP1 plays a key role in binding to DNA blunt ends and initiating the MMEJ pathway by recruiting DNA polymerase theta (Polθ). Polθ enables the formation of resected DNA ends, as well as enabling the fill-in synthesis (Wang. H. et al. (2017) *Cell Biosci* 7:6).

Inhibition of 53BP1

In some embodiments, the disclosure provides methods for increasing HDR of a DSB mediated by a site-directed nuclease in a target gene in a cell or population of cells, such as a quiescent cell that has been induced to divide or a population of quiescent cells that has been induced to divide, e.g., CD34+HSCs, by inhibition of 53BP1. In some embodiments, the disclosure provides methods for increasing HDR of a DSB mediated by a site-directed nuclease in a cell or population of cells expressing an E6V mutation in HBB, by inhibition of 53BP1.

The p53-binding protein 1 (53BP1) is a key regulator of cellular response to DNA damage. The choice of repair pathway for repair of a DNA DSB is largely controlled by an antagonism between 53BP1, a pro-NHEJ factor, and BRCA1, a pro-HDR factor (Chapman, J. et al. (2012) *Molecular cell* 47:497-510). 53BP1 promotes NHEJ repair over HDR repair by suppressing formation of 3' single-stranded DNA tails, which is the rate-limiting step in the initiation of the HDR pathway, and by inhibiting BRCA1 recruitment to DSB sites (Escribano-Diaz, C. et al. (2013) Mol Cell. 49:872-883; Feng, L. et al (2013) J Biol Chem 288:11135-11143). Loss of 53BP1 has been shown to increase HDR efficiency, (Canny, M. et al. (2018) *Nat Biotechnol.* 36(1):95-102). Thus, inhibition of 53BP1 is expected to reduce DSB repair by the NHEJ pathway and favor repair by the HDR pathway.

Distinct protein domains in the 53BP1 structure are required to enable its function as a pro-NHEJ factor (Zimmermann et al (2014) Trends Cell Biol 24:108-117). Human 53BP1 is a large (e.g., 200 kDa, 1972 amino acids) multi-domain protein that enables recruitment to DSB sites and binding of protein factors involved in DNA repair. The 53BP1 N-terminus is comprised of a large subunit that is heavily phosphorylated following DNA damage and facilitates binding interactions with DNA repair machinery. The central portion of 53BP1 comprises a focus-forming region that is essential for binding to damaged chromatin, which allows recruitment to DSB sites. It comprises a nuclear localization signal (NLS), a tandem Tudor domain that binds to di-methylated histone H4 lysine 20 (e.g., $H4K20^{Me2}$), and a ubiquitin-dependent recruitment (UDR) motif that recognizes histone H2A/H2AX ubquitinated on lysine 15 (e.g., $H2A(X)K15^{Ub}$) (Botuyan, M. (2006) Cell 127:1361-1373; Fradet-Turcotte et al (2013) Nature 499:50-54). The focus-forming region extends from amino acids 1220-1711 of human 53BP1, with the tandem Tudor domain extending from amino acids 1484-1603 and the UDR extending from amino acids 1604-1631. The 53BP1 C-terminus is comprised of repeating BRCA1 C-terminus (BRCT) domains that are important for DNA repair in heterochromatin (Noon et al (2010) Nat Cell Biol 12:177-184) and mediate interactions with the tumor suppressor p53 that guides cellular response to DNA damage (Iwabuchi, et al (1994) PNAS 91:6098-6102).

The functionality of 53BP1 for promoting the NHEJ pathway requires recruitment to damaged chromatin through its tandem Tudor and UDR domains and binding to repair machinery through phosphorylation of the 53BP1 N-terminus.

Accordingly, the present disclosure provides 53BP1 inhibitors that inhibit NHEJ and promote HDR repair of a DSB in a target gene. In some embodiments, a 53BP1 inhibitor of the disclosure inhibits 53BP1 recruitment to DSB sites. In some embodiments, a 53BP1 inhibitor of the disclosure inhibits 53BP1 recruitment by inhibiting, reducing, disrupting or blocking an interaction of 53BP1 with damaged chromatin. In some embodiments, a 53BP1 inhibitor of the disclosure inhibits, reduces, disrupts or blocks an interaction of the 53BP1 focus forming region (amino acids 1220-1711) with DSB sites. In some embodiments, a 53BP1 inhibitor of the disclosure inhibits, reduces, disrupts or blocks an interaction of the 53BP1 focus forming region (amino acids 1220-1711) with damaged chromatin. In some embodiments, a 53BP1 inhibitor of the disclosure inhibits, reduces, disrupts or blocks an interaction of the 53BP1 tandem Tudor domain with damaged chromatin (e.g., with methylated histone, $H4K20^{Me2}$). In some embodiments, a 53BP1 inhibitor of the disclosure inhibits, reduces, disrupts or blocks the interaction of the 53BP1 UDR motif with damaged chromatin (e.g., with ubquitinylated histone, $H2A(X)K15^{Ub}$).

In some embodiments, a 53BP1 inhibitor of the disclosure inhibits, reduces, disrupts or blocks protein-protein interactions with the 53BP1 BRCT domain. In some embodiments, a 53BP1 inhibitor of the disclosure inhibits, reduces, disrupts or blocks the interactions of the 53BP1 BRCT domain with the tumor suppressor p53.

In some embodiments, a 53BP1 inhibitor of the disclosure inhibits, reduces, disrupts or blocks the ability of 53BP1 to bind to DNA repair factors. In some embodiments, a 53BP1 inhibitor of the disclosure inhibits, reduces, disrupts or blocks phosphorylation of the 53BP1 N-terminus, thus inhibiting, reducing or preventing binding of DNA repair factors. In some embodiments, a 53BP1 inhibitor of the disclosure binds to phosphorylated sites on the 53BP1 N-terminus, thus inhibiting, reducing or preventing DNA repair factors from recognizing and binding to phosphorylated sites on the 53BP1 N-terminus. In some embodiments, a 53BP1 inhibitor of the disclosure reduces, eliminates or removes phosphorylated sites on the 53BP1 N-terminus (e.g., by promoting or catalyzing a dephosphorylation mechanism), thus reducing, eliminating or removing sites required for binding of DNA repair factors. In some embodiments, a 53BP1 inhibitor that binds to phosphorylated sites on 53BP1 and facilitates HDR is suppressor of cancer cell invasion (SCAI) or a fragment thereof. In some embodiments, binding of SCAI or a fragment thereof prevents binding of the DNA repair factor RAP1-interacting factor homolog (RIF1). In some embodiments, blocking RIF1 binding to 53BP1 results in increased HDR repair of a DNA DSB.

In some embodiments, the 53BP1 inhibitor of the disclosure inhibits, disrupts or blocks 53BP1 recruitment to DSB sites in the cell. In some embodiments, the 53BP1 inhibitor of the disclosure inhibits, disrupts or blocks an interaction of 53BP1 with damaged chromatin in the cell. In some embodiments, the 53BP1 inhibitor of the disclosure inhibits, disrupts or blocks binding of DNA repair factors to sites of phosphorylation on the 53BP1 N-terminus. In some embodiments, the 53BP1 inhibitor of the disclosure is a small molecule. In some embodiments, the 53BP1 inhibitor of the disclosure is a polypeptide. In some embodiments, the 53BP1 inhibitor of the disclosure is a nucleic acid.

In some embodiments, recruitment of 53BP1 to a DSB site occurs via recognition of damaged chromatin. In some embodiments, recruitment of 53BP1 to damaged chromatin occurs through recognition of H4K20me2 through the 53BP1 UDR motif. In some embodiments, recognition of damaged chromatin by 53BP1 is dependent upon ubiquitination of histones. In some embodiments, inhibition of histone ubiquitination results in inhibition of 53BP1 recruitment to DSB sites.

Acetylation of 53BP1 has been shown to inhibit 53BP1 binding to damaged chromatin (Guo et al (2018) Nucleic Acids Res 46:689-703). In some embodiments, an inhibitor of 53BP1 promotes post-translational modification of 53BP1. In some embodiments, an inhibitor of 53BP1 promotes post-translation modification of 53BP1 that prevents 53BP1 binding to damaged chromatin. In some embodiments, an inhibitor of 53BP1 promotes acetylation of 53BP1. In some embodiments, an inhibitor of 53BP1 promotes acetylation of the 53BP1 UDR motif. In some embodiments, acetylation of 53BP1 prevents 53BP1 recruitment to DSB sites.

In some embodiments, a 53BP1 inhibitor is identified by binding affinity for the 53BP1 polypeptide. Methods of measuring binding affinity of an inhibitor to a protein are known in the art. Non-limiting examples include measuring inhibitor affinity by enzyme-linked immunosorbent assay (e.g., ELISA), immunoblot, immunoprecipitation-based assay, fluorescence polarization assay, fluorescence resonance energy transfer assay, fluorescence anisotropy assay, yeast surface display (Gai (2007) Curr Opin Struct Biol 17:467-473), kinetic exclusion assay, surface plasmon resonance, or isothermal titration calorimetry. In some embodiments, a method of measuring binding affinity is an ELISA wherein an inhibitor is measured for affinity to the 53BP1 polypeptide. In some embodiments, binding affinity is evaluated by a competition-based ELISA wherein binding of an inhibitor to the 53BP1 polypeptide is measured in the presence of increasing concentrations of a known 53BP1 binding partner (e.g., a histone methyl-lysine peptide with affinity for 53BP1).

In some embodiments, a 53BP1 inhibitor is identified by binding affinity for a fragment of the 53BP1 polypeptide. In some embodiments, a fragment is a domain of the 53BP1 polypeptide. In some embodiments, the domain is the Tudor domain. In some embodiments, the domain is the UDR motif. In some embodiments, the domain comprises the N-terminus of the 53BP1 polypeptide.

In some embodiments, a 53BP1 inhibitor of the disclosure binds to the 53BP1 polypeptide. Methods of determining the structural interactions that enable binding of the inhibitor with the 53BP1 polypeptide are known in the art. Non-limiting examples include X-ray crystallography, nuclear magnetic resonance (NMR) spectroscopy, electron microscopy, small-angle X-ray scattering (SAXS), and small-angle neutron scattering (SANS). In some embodiments, the structural interactions are determined by a mutagenesis experiment wherein residues of the 53BP1 polypeptide are mutated and the effect on inhibitor binding are evaluated. Such methods enable identification of key residues that contribute to binding.

In some embodiments, the 53BP1 inhibitor of the disclosure is a 53BP1 binding polypeptide that inhibits 53BP1 recruitment to the DSB in the cell. In some embodiments, a 53BP1 binding polypeptide of the disclosure inhibits, disrupts or blocks binding of 53BP1 to damaged chromatin in the cell. In some embodiments, a 53BP1 binding polypeptide of the disclosure inhibits, disrupts or blocks the 53BP1 tandem Tudor domain from binding to damaged chromatin in the cell. In some embodiments, a 53BP1 binding polypeptide of the disclosure inhibits, disrupts or blocks the 53BP1 UDR motif from binding to damaged chromatin in the cell.

In some embodiments, an inhibitor of 53BP1 is a polypeptide identified from a phage-display library or a variant thereof as described by US 2019/0010196A, which is incorporated by reference herein. In some embodiments, a polypeptide inhibitor of 53BP1 has binding affinity for the 53BP1 Tudor domain. The 53BP1 Tudor domain is involved in recognition of methylated residues on the histone core that facilitates recruitment of 53BP1 to a DNA DSB site. In some embodiments, a 53BP1 polypeptide inhibitor of the disclosure inhibits, reduces or prevents recruitment of 53BP1 to a DNA DSB by binding to the 53BP1 Tudor domain.

In some embodiments, a 53BP1 polypeptide inhibitor of the disclosure is modified, by, for example, substitution of one or more amino acid residues, insertion of one or more amino acid residues, or deletion of one or more amino acid residues. In some embodiments, a 53BP1 polypeptide inhibitor of the disclosure is modified by chemical modifications. Techniques for modification of one or more amino acid residues are known to one skilled in the art. In some embodiments, a modification is substitution of one or more amino acid residues. In one embodiment, a modification increases binding affinity of the 53BP1 polypeptide inhibitor for the 53BP1 polypeptide or a fragment thereof.

In some embodiments, a modified polypeptide inhibitor of 53BP1 is identified by affinity for the 53BP1 Tudor domain. Affinity for the 53BP1 Tudor domain may be assessed by suitable assays known to one skilled in the art. In some embodiments, affinity is measured by a competitive immunoprecipitation assay against an endogenous polypeptide that binds 53BP1, for example, dimethylated histone H4 Lys20. In some embodiments, affinity is measured by isothermal calorimetry using recombinant 53BP1. In some embodiments, affinity is determined by assessing 53BP1 recruitment to DSB sites. In some embodiments, a 53BP1 polypeptide inhibitor of the disclosure has a quantifiable binding affinity for the 53BP1 Tudor domain of approximately 0.5 to $15\times10^{-9}$ M, 0.5 to $25\times10^{-9}$, 0.5 to $50\times10^{-9}$ M, 0.5 to $100\times10^{-9}$ M, 0.5 to $200\times10^{-9}$ M, 1 to $200\times10^{-9}$ M, 1 to $300\times10^{-9}$ M, 1 to $400\times10^{-9}$ M, 1 to $500\times10^{-9}$ M, 100 to $250\times10^{-9}$ M, 100 to $500\times10^{-9}$ M, or 200 to $500\times10^{-9}$ M. In some embodiments, a 53BP1 polypeptide inhibitor of the disclosure has a quantifiable binding affinity for the 53BP1 Tudor domain of approximately 200 to $500\times10^{-9}$ M. In some embodiments, a 53BP1 polypeptide inhibitor of the disclosure has a quantifiable binding affinity for the 53BP1 Tudor domain of approximately $250\times10^{-9}$ M.

In some embodiments, a 53BP1 polypeptide inhibitor of the disclosure comprises a polypeptide sequence of SEQ ID NO: 70. In some embodiments, a 53BP1 polypeptide inhibitor of the disclosure comprises a polypeptide sequence that is at least about 50%, 60%, 70% or 80% identical to the polypeptide sequence of SEQ ID NO: 70. In some embodiments, a 53BP1 polypeptide inhibitor comprises a polypeptide sequence that is at least about 90%, 95%, 96%, 97%, 98% or 99% identical to the polypeptide sequence of SEQ ID NO: 70. In some embodiments, a 53BP1 polypeptide inhibitor of the disclosure comprises a polypeptide sequence that is at least about 95% identical to the polypeptide sequence of SEQ ID NO: 70. In some embodiments, a 53BP1 polypeptide inhibitor of the disclosure comprises a polypeptide sequence that is at least about 96% identical to the polypeptide sequence of SEQ ID NO: 70. In some embodiments, a 53BP1 polypeptide inhibitor of the disclosure comprises a polypeptide sequence that is at least about 97% identical to the polypeptide sequence of SEQ ID NO: 70. In some embodiments, a 53BP1 polypeptide inhibitor of the disclosure comprises a polypeptide sequence that is at least about 98% identical to the polypeptide sequence of SEQ ID NO: 70. In some embodiments, a 53BP1 polypeptide inhibitor of the disclosure comprises a polypeptide sequence that is at least about 99% identical to the polypeptide sequence of SEQ ID NO: 70. In some embodiments, percent identity is made by a comparison that is performed by a BLAST algorithm wherein the parameters of the algorithm are selected to encompass the largest match between the respective polypeptide sequences over the entire length of the polypeptide sequence as set forth by SEQ ID NO: 70. BLAST algorithms are often used for sequence analysis and are well known by one skilled in the art (Altschul, S., et al. (1990) *J. Mol. Biol* 215:403-410; Gish, W. et al. (1993) *Nat. Genet.* 3:266-272; Madden, T. et al. (1996) *Meth. Enzymol.* 266:131-141; Altschul, S. et al. (1997) *Nucleic Acids Res.* 25:3389-3402; Zhang, J. et al. (1997) *Genome Res.* 7:649-656; Wootton, J. et al., (1993) *Comput. Chem.* 17:149-163; Hancock, J. et al. (1994) *Comput. Appl. Biosci.* 10:67-70).

In some embodiments, a 53BP1 polypeptide inhibitor of the disclosure comprises a fragment of a polypeptide comprising the polypeptide sequence of SEQ ID NO: 70 that retains binding to the 53BP1 Tudor domain. In some embodiments, a fragment has at least 1-5, at least 1-10, at least 5-15, at least 10-20, at least 15-30, at least 15-40 fewer amino acid residues than a polypeptide comprising a polypeptide sequence as set forth by SEQ ID NO: 70.

In some embodiments, a 53BP1 polypeptide inhibitor of the disclosure comprises a fusion polypeptide comprising a polypeptide comprising the polypeptide sequence of SEQ ID NO: 70 that retains binding to the 53BP1 Tudor domain. In some embodiments, a fusion polypeptide is obtained by addition of amino acids or peptides or by substitutions of individual amino acids or peptides that enable by chemical coupling with suitable reagents to a fusion partner. In some embodiments, a fusion is prepared by preparation and expression of a vector comprising a gene encoding a polypeptide described herein and a gene encoding a fusion partner.

In some embodiments, a fusion partner is a polypeptide, non-limiting examples include an enzyme, a fluorescent tag, a purification tag, a toxin, an antibody fragment, or an albumin fragment. In some embodiments, a fusion partner is a chemical label, non-limiting examples include a fluorescent dye, biotin, a radioactive label, a saccharide, or a phosphate.

In some embodiments, a 53BP1 polypeptide inhibitor as described herein is encoded by a polynucleotide. In some embodiments, a 53BP1 polypeptide inhibitor as described herein is provided as a nucleic acid comprising a nucleotide sequence encoding the 53BP1 polypeptide inhibitor. In some embodiments, the nucleic acid is a DNA molecule. In some embodiments, the nucleic acid is an RNA molecule. In some embodiments, the nucleic acid is a messenger RNA (mRNA). Methods of preparing mRNA or high expression of an encoded polypeptide are known in the art. In some embodiments, an mRNA comprises an open-reading frame (ORF) encoding an inhibitor of 53BP1. In some embodiments, the nucleic acid encoding a 53BP1 polypeptide inhibitor comprises an mRNA comprising an ORF encoding the amino acid sequence of SEQ ID NO: 70.

In some embodiments, a nucleic acid comprising a nucleotide sequence encoding a 53BP1 polypeptide inhibitor is delivered to a cell by a vector. Methods of delivering nucleic acids to a cell using a vector are known in the art and are described herein.

In some embodiments, a 53BP1 inhibitor of the disclosure comprises a gene-editing system for disrupting a gene encoding 53BP1. In some embodiments, the 53BP1 inhibitor comprises a CRISPR/Cas9 gene editing system. Methods of using CRISPR-Cas gene editing technology to create a genomic deletion in a cell (e.g., a knock-out in a gene of a cell) are known (e.g., Bauer (2015) Vis Exp 95:e52118). In some embodiments, a knock-out of a gene encoding 53BP1 using CRISPR-Cas gene editing comprises contacting a cell with Cas9 polypeptide and a gRNA targeting the 53BP1 gene locus. In some embodiments, gRNA sequence targeting the 53BP1 gene locus is designed using the 53BP1 gene sequence using methods known in the art (see e.g., Briner (2014) Molecular Cell 56:333-339). In some embodiments, gRNAs targeting the 53BP1 gene locus create indels in the region of the 53BP1 gene that disrupt expression of 53BP1 in the cell. In some embodiments, 50-100%, 50-90%, 50-80%, 50-70%, 50-60%, 60-100%, 60-90%, 60-80%, 60-70%, 70-100%, 70-90%, 70-80%, 80-100%, 80-90%, or 90-100% of cells in the edited population lack detectable expression of 53BP1.

In some embodiments, a 53BP1 inhibitor of the disclosure comprises a small interfering RNA (siRNA) which silences 53BP1 expression. Methods of silencing 53BP1 expression using siRNA are taught by US 2019/0010196 which is incorporated by reference herein. Methods of delivering siRNA can be performed using non-viral or viral delivery methods as described in the art (e.g., Gao (2009) Mol Pharm 6:651-658; Oliveira (2006) J Biomed Biotechnol 2006:63675; Tatiparti (2017) Nanomaterials 7:77). In some embodiments, a cell is transfected with siRNA targeting 53BP1 mRNAs. In some embodiments, expression of 53BP1 is decreased by about 50%, by about 60%, by about 70%, by about 80%, by about 90%, or by about 100% following transfection with siRNA targeting 53BP1 mRNA.

Inhibition of DNA-PKcs

In some embodiments, the disclosure provides methods for increasing HDR of a DSB mediated by a site-directed nuclease in a target gene in a cell or population of cells, such as a quiescent cell that has been induced to divide or a population of quiescent cells that has been induced to divide, e.g., CD34+HSCs, by inhibition of DNA-PKcs. In some embodiments, the disclosure provides methods for increasing HDR of a DSB mediated by a site-directed nuclease in a cell or population of cells expressing an E6V mutation in HBB by inhibition of DNA-PKcs. In some embodiments, the disclosure provides methods for increasing HDR of a DSB mediated by a site-directed nuclease in a target gene in a cell or population of cells, such as a quiescent cell that has been induced to divide or a population of quiescent cells that has been induced to divide, e.g., CD34+HSCs, by inhibition of 53BP1 and DNA-PKcs. In some embodiments, the disclosure provides methods for increasing HDR of a DSB mediated by a site-directed nuclease in a cell or population of cells expressing an E6V mutation in HBB by inhibition of 53BP1 and DNA-PKcs.

The DNA-PKcs is a member of the phosphatidylinositol-3 (PI-3) kinase-like kinase family (PIKK) and is a key kinase involved in NHEJ repair. DNA-PKcs is directed to DSB sites by binding to the Ku70/80 heterodimer that has high-affinity for broken dsDNA ends and is first recruited to DSB sites. The complex formed at the DSB comprising DNA, Ku70/80 and DNA-PKcs is referred to as "DNA-PK" (Gottlieb (1993) Cell 72:131-142). The large DNA-PK complex is responsible for holding the two ends of a broken DNA molecule together. Additionally, binding of DNA-PKcs to the DNA-Ku70/80 complex results in activation of DNA-PKcs kinase activity (Yoo et al (1999) Nucleic Acids Res 27:4679-4686; Calsou (1999) J Biol Chem 274:7848-7856). DNA-PKcs phosphorylates numerous NHEJ repair factors, thus enabling their function in NHEJ repair.

Accordingly, the present disclosure provides DNA-PKcs inhibitors that inhibit NHEJ and promote HDR repair of a DSB in a target gene. In some embodiments, a DNA-PKcs inhibitor of the disclosure inhibits, reduces, disrupts, or blocks the ability of DNA-PKcs to a DSB site. In some embodiments, a DNA-PKcs inhibitor of the disclosure inhibits, reduces, disrupts, or blocks the ability of DNA-PKcs to bind to Ku70/80 to form a DNA-PK complex. In some embodiments, a DNA-PKcs inhibitor of the disclosure inhibits, reduces, disrupts, or blocks the function of the DNA-PKcs kinase domain. In some embodiments, a DNA-PKcs inhibitor of the disclosure inhibits, reduces, disrupts, or blocks phosphorylation of NHEJ factors by the DNA-PKcs kinase domain. In some embodiments, a DNA-PKcs inhibitor of the disclosure is a polypeptide. In some embodiments, a DNA-PKcs inhibitor is a nucleic acid. In some embodiments, a DNA-PKcs inhibitor is a small molecule. In some embodiments, a DNA-PKcs inhibitor of the disclosure is a small molecule that inhibits, disrupts or blocks the DNA-PKcs kinase domain.

In some embodiments, a DNA-PKcs inhibitor of the disclosure is identified by binding affinity for DNA-PKcs or a fragment thereof (e.g., a functional domain of DNA-PKs). Methods of measuring binding affinity of an inhibitor for a protein domain are known in the art. Non-limiting examples include measuring inhibitor affinity by enzyme-linked immunosorbent assay (e.g., ELISA), immunoblot, immunoprecipitation-based assay, fluorescence polarization assay, fluorescence resonance energy transfer assay, fluorescence anisotropy assay, yeast surface display (Gai (2007) Curr Opin Struct Biol 17:467-473), kinetic exclusion assay, surface plasmon resonance, or isothermal titration calorimetry.

In some embodiments, a DNA-PKcs inhibitor of the disclosure binds to the DNA-PKcs polypeptide. Methods of determining the structural interactions that enable binding of the inhibitor with the DNA-PKcs polypeptide are known in the art. Non-limiting examples include X-ray crystallography, nuclear magnetic resonance (NMR) spectroscopy, electron microscopy, small-angle X-ray scattering (SAXS), and small-angle neutron scattering (SANS). In some embodiments, the structural interactions are determined by a mutagenesis experiment wherein residues of the DNA-PKcs polypeptide are mutated and the effect on inhibitor binding are evaluated. Such methods enable identification of key residues that contribute to binding.

In some embodiments, a method of inhibition of DNA-PKcs function in a cell comprises contacting the cell with a small molecule inhibitor of DNA-PKcs. In some embodiments, the DNA-PKCs inhibitor of the disclosure is a small molecule inhibitor Nu7441 (e.g., Leahy (2004) Bioorg Med Chem Lett 14:6083-6087). In some embodiments, the DNA-PKcs inhibitor of the disclosure is a PI 3-kinase inhibitor LY294002, which has been found to inhibit DNA-PKcs function in vitro (Izzard (1999) Cancer Res 59:2581-2586). In some embodiments, the DNA-PKCs inhibitor of the disclosure is a small molecule inhibitor capable of selectively inhibiting the activity of DNA-PKcs compared to PI 3-kinase. Non-limiting examples include 2-amino-chromen-4-ones that are described by WO 03/024949, which is incorporated by reference herein. In some embodiments, the DNA-PKCs inhibitor of the disclosure is a small molecule inhibitor of DNA-PKcs function, including 1 (2-hydroxy-4-morpholin-4-yl-phenyl)-ethanone (e.g., Kashishian (2003) Mol Cancer Ther 2:1257-1264). In some embodiments, the DNA-PKCs inhibitor of the disclosure is a small molecule inhibitor of DNA-PKcs function SU11752 (e.g., Ismail (2004) Oncogene 23:873-882). In some embodiments, the DNA-PKCs inhibitor of the disclosure is a small molecule inhibitor of DNA-PKcs function described in U.S. Pat. No. 9,592,232, incorporated herein by reference. In some embodiments, the DNA-PKcs inhibitor of the disclosure is a small molecule inhibitor of DNA-PKcs function described in U.S. Pat. No. 7,402,607, incorporated herein by reference. In some embodiments, the DNA-PKCs inhibitor of the disclosure is a small molecule inhibitor of DNA-PKcs function described in U.S. Pat. No. 6,893,821, incorporated herein by reference. In some embodiments, the DNA-PKcs inhibitor of the disclosure is a small molecule inhibitor of DNA-PKcs function described in US 2018/0194782.

In some embodiments, the DNA-PKcs inhibitor of the disclosure is Compound 984 or Compound 296 described in U.S. Pat. No. 9,592,232. The structures of Compound 984 and Compound 296 are provided below:

Compound 984

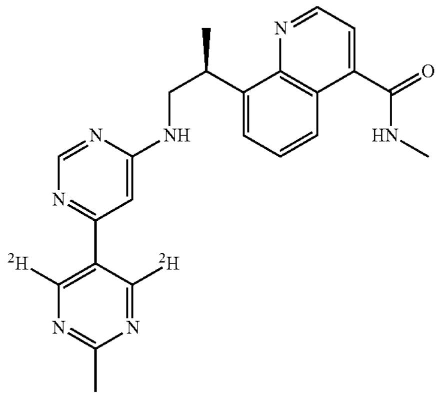 [SMILES: [2H]c1nc(C)nc([2H])c1-c1cc(NC[C@@H](C)c2cccc3c(C(=O)NC)ccnc23)ncn1]

-continued

Compound 296

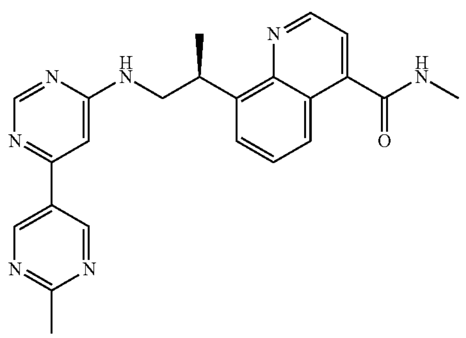 [SMILES: CNC(=O)c1ccnc2c([C@H](C)CNc3cc(-c4cnc(C)nc4)ncn3)cccc12]

Inhibition of Other Targets

In some embodiments, the disclosure provides methods for increasing HDR of a DSB mediated by a site-directed nuclease in a target gene in a cell or population of cells, such as a quiescent cell that has been induced to divide or a population of quiescent cells that has been induced to divide, e.g., CD34+ HSCs, by inhibition of the NHEJ pathway, alone or in combination with inhibition of 53BP1 and/or DNA-PKcs. In some embodiments, the disclosure provides methods for increasing HDR of a DSB mediated by a site-directed nuclease in a target gene in a cell or population of cells expressing an E6V mutation in the HBB gene, by inhibition of the NHEJ pathway, alone or in combination with inhibition of 53BP1 and/or DNA-PKcs. In some embodiments, the disclosure provides a method of inhibiting the NHEJ pathway by inhibition of key NHEJ enzymes. For example, in some embodiments, the disclosure provides a method of inhibiting the NHEJ pathway by inhibition of Ku70/80. In some embodiments, the disclosure provides inhibitors of Ku70/80 including CYREN (e.g., Arnoult (2017) Nature 549:548-552). In some embodiments, the disclosure provides a method of inhibiting the NHEJ pathway by inhibition of DNA Ligase IV. In some embodiments, the disclosure provides inhibitors of DNA Ligase IV, including Scr7 (Maruyama (2015) Nat Biotechnol 33:538-542).

In some embodiments, the disclosure provides methods of increasing or improving repair of a DNA DSB by HDR by inhibition of the MMEJ pathway (e.g., methods of MMEJ inhibition reviewed in Sfeir (2015) 40:701-714). In some embodiments, the disclosure provides methods of inhibition of the MMEJ pathway by inhibition of DNA polymerase theta (Pol θ). In some embodiments, the disclosure provides method of inhibition of the MMEJ pathway by inhibition of PARP. In some embodiments, the disclosure provides PARP inhibitors, including molecules developed for the treatment of cancer, including Veliparib and Olaparib. In some embodiments, inhibition of the MMEJ pathway comprises inhibition of MRE11. In some embodiments, the disclosure provides MRE11 inhibitors, including Mirin and derivatives (e.g., Shibata (2014) Molec Cell 53:7-18).

In some embodiments, the disclosure provides methods for increasing HDR of a DSB mediated by a site-directed nuclease in a target gene in a cell or population of cells, such as a quiescent cell that has been induced to divide or a population of quiescent cells that has been induced to divide, e.g., CD34+HSCs, by treatment of a cell or population of cells with a compound that stimulates HDR efficiency. In some embodiments, the disclosure provides methods for increasing HDR of a DSB mediated by a site-directed nuclease in a target gene in a cell or population expressing an E6V mutation in the HBB gene, by treatment of a cell or population of cells with a compound that stimulates HDR efficiency. In some embodiments, the disclosure provides a stimulator of HDR, wherein the stimulator of HDR is an agonist that promotes the function of a factor in the HDR pathway. In some embodiments, the disclosure provides a stimulator of an HDR factor, wherein the HDR factor is RAD51. In some embodiments, the disclosure provides agonists of RAD51, including RS-1 (e.g., Jayathilaka (2008) PNAS 105:15848-15853).

Combination of Inhibitors

In some embodiments, the disclosure provides methods for increasing HDR of a DSB mediated by a site-directed nuclease in a target gene in a cell or population of cells, such as a quiescent cell that has been induced to divide or a population of quiescent cells that has been induced to divide, e.g., CD34+HSCs, by treatment with an inhibitor of 53BP1 in combination with an inhibitor of the NHEJ pathway. In some embodiments, the disclosure provides methods for increasing HDR of a DSB mediated by a site-directed nuclease in a target gene in a cell or population of cells expressing an E6V mutation in the HBB gene, by treatment with an inhibitor of 53BP1 in combination with an inhibitor of the NHEJ pathway. In some embodiments, a method of increasing HDR is treatment with an inhibitor of 53BP1 in combination with an inhibitor of DNA-PKcs. In some embodiments, a method of increasing HDR is treatment with a polypeptide inhibitor of 53BP1 in combination with an inhibitor of DNA-PKcs. In some embodiments, a method of increasing HDR is treatment with a polypeptide inhibitor of 53BP1 comprising the amino acid sequence identified by SEQ ID NO: 70 in combination with a small molecule inhibitor of DNA-PKcs. In some embodiments, a method of increasing HDR is treatment with a polypeptide inhibitor of 53BP1 comprising the amino acid sequence identified by SEQ ID NO: 70 in combination with Compound 984 or Compound 296.

In some embodiments, a method of increasing HDR is treatment with an inhibitor of 53BP1 in combination with an inhibitor of Ku70/80. In some embodiments, a method of increasing HDR is treatment with a polypeptide inhibitor of 53BP1 comprising the amino acid sequence identified by SEQ ID NO: 70 in combination with an inhibitor of Ku70/80. In some embodiments, a method of increasing HDR is treatment with an inhibitor of 53BP1 in combination with an inhibitor of DNA Ligase IV. In some embodiments, a method of increasing HDR is treatment with a polypeptide inhibitor of 53BP1 comprising the amino acid sequence identified by SEQ ID NO: 70 in combination with an inhibitor of DNA Ligase IV.

In some embodiments, a method of increasing HDR is treatment with an inhibitor of 53BP1 in combination an inhibitor of the MMEJ pathway. In some embodiments, a method of increasing HDR is treatment with a polypeptide inhibitor of 53BP1 comprising the amino acid sequence identified by SEQ ID NO: 70 in combination with an inhibitor of the MMEJ pathway.

In some embodiments, a method of increasing HDR is treatment with a polypeptide inhibitor of 53BP1 comprising the amino acid sequence identified by SEQ ID NO: 70 in combination with an inhibitor of PARP. In some embodiments, a method of increasing HDR is treatment with a polypeptide inhibitor of 53BP1 comprising the amino acid sequence identified by SEQ ID NO: 70 in combination with an inhibitor of DNA polymerase theta.

Engineered Human Cells

Provided herein are methods of gene-editing within an HBB gene by repair of a DNA DSB in the HBB gene by the HDR pathway using a donor polynucleotide. In some embodiments, the HBB gene is edited to correct a mutation (e.g., an E6V mutation). In some embodiments, the HBB gene is edited by replacement with a different polynucleotide sequence, such as a polynucleotide sequence encoding a different gene (e.g., a transgene) or a variant version of the HBB gene. In some embodiments, the HBB gene is edited by deletion and insertion of a different gene (e.g., a transgene). In some embodiments, the HBB gene is edited by insertion of a transgene comprising one or more exons and one or more introns. In some embodiments, the HBB gene is edited by insertion of insertion of a transgene comprising only exons.

In some embodiments, an HBB gene is edited using methods herein to correct a genetic mutation that results in a monogenic disease. A monogenic disease is characterized by a mutation in a single gene. Non-limiting examples of gene mutations that result in monogenic disease include mutation of the beta-globin (e.g., hemoglobin beta, HBB) gene that results in hemoglobinopathies. Non-limiting examples of disorders associated with the HBB that are edited using methods described herein are detailed in Table 1.

TABLE 1

Disorders Associated with Mutations in HBB Gene

| Monogenic Disorder | Target Gene |
|---|---|
| Sickle Cell Disease | Hemoglobin subunit beta (HBB) |
| Beta-Thalassemia | Hemoglobin subunit beta (HBB) |

In some embodiments, a monogenic disease is treated by administering gene-edited human cells to a patient. In some embodiments, human cells are taken from the patient and edited to correct a genetic mutation prior to being reintroduced to the patient for treatment of a monogenic disorder. In some embodiments, cells from a patient are somatic cells that are reprogrammed to generated induced pluripotent stem cells (iPSCs). In some embodiments, iPSCs are gene-edited to correct a mutation and then differentiated prior to administration to a patient. In some embodiments, cells from a patient are hematopoietic stem cells (HSCs) or hematopoietic progenitor cells (HPCs). In some embodiments, HSCs and HPCs are gene-edited and introduced to a patient for treatment of a monogenic disease.

In some embodiments, HSCs are engineered (e.g., gene-edited) for treatment of a hemoglobinopathy. Hemoglobinopathies encompass a number of anemias that are associated with changes in the genetically determined structure or expression of hemoglobin. These include changes to the molecule structure of the hemoglobin chain, such as occurs with sickle cell anemia, as well as changes in which synthesis of one or more chains is reduced or absent, such as occurs with various thalassemias.

Disorders specifically associated with the β-globin protein are referred to generally as β-hemoglobinopathies. For example, β-thalassemias result from a partial or complete defect in the expression of the β-globin gene, leading to deficient or absent hemoglobin A (HbA). HbA is the most common human hemoglobin tetramer and consists of two α-chains and two β-chains (a202). β-thalassemias are due to mutations on the adult β-globin gene (HBB) on chromosome 11, and are inherited in an autosomal, recessive fashion.

Sickle cell disease (SCD) includes SCA, sickle hemoglobin C disease, sickle beta-plus-thalassemia, and sickle beta-zero-thalassemia. All forms of SCD are caused by mutations within the HBB gene. SCA is caused by a single missense mutation in the sixth codon (e.g., seventh codon when including the start codon) of the HBB gene (e.g., A to T), resulting in a substitution of glutamic acid by valine (e.g., Glu to Val). The mutant protein, when incorporated into hemoglobin, results in unstable hemoglobin HbS ($\alpha_2\beta_2^S$) in contrast to normal adult hemoglobin HbA ($\alpha_2\beta_2^A$). When HbS is the predominant form of hemoglobin, it results in red blood cells (RBCs) with distorted sickle shape. Sickled RBCs are less flexible than normal RBCs, and tend to get stuck in small blood vessels, resulting in vaso-occlusive events. These events are associated with tissue ischemia leading to acute and chronic pain.

In some embodiments, a patient is treated with gene-edited human cells to ameliorate a hemoglobinopathy (e.g., de Montalembert (2008) *BMJ,* 337:a1397; Sheth, et al. (2013) *British J. Haematology* 162:455-464). Methods towards treatment of hemoglobinopathies by production of genome-edited stem cells, including hematopoietic stem cells (HSCs), are taught by US 2018/0030438 and US 2018/0200387 which are incorporated by reference herein. In some embodiments, a method of treating a patient with hemoglobinopathy comprises administering gene-edited stem cells to the patient that give rise to a population of circulating RBCs that will be effective in ameliorating one or more clinical conditions associated with the patient's disease. In some embodiments, a gene-edited stem cell is an HSC, long-term repopulating hematopoietic cell or an LT-HSPC. In some embodiments, a gene-edited HSC or HPC administered for treatment of a hemoglobinopathy comprises a gene-edit within the HBB locus for correction of a mutation.

Engineered Hematopoietic Stem Cells

In some embodiments, stem cells are engineered (e.g., gene-edited) using methods of the disclosure. In some embodiments, stem cells are engineered to correct a gene mutation and/or replace a target gene. In some embodiments, stem cells are engineered to correct an E6V mutation in an HBB gene. In some embodiments, engineered stem cells are administered to a patient for treatment of a monogenic disease. In some embodiments, a stem cell comprises an HSC. In some embodiments, a stem cell comprises an HSC comprising an HBB gene encoding an E6V mutation. HSCs are defined by their pluripotency (e.g., capacity of a single HSC to generate any type of blood cell) and ability to self-renew. HSCs are comprised of two populations: short-term HSCs and long-term HSCs. Short term HSCs are capable of self-renewal for a short period of time, while LT-HSPCs are capable of indefinite self-renewal. LT-HSPCs are largely in a quiescent state, dividing only once every 145 days (Wilson, A. et al. (2008) Cell 135:1118-1129). In some embodiments, an HSC divides asymmetrically wherein one daughter cell remains in a stem state and one daughter cell expresses a distinct function or phenotype. In some embodiments, an HSC divides symmetrically wherein both daughter cells retain a stem state.

Early descendants of an HSC are termed hematopoietic progenitor cells. Hematopoietic progenitor cells (HPCs) retain the ability to differentiate into other cell types, but are not capable of self-renewal. In some embodiments, progenitor cells of an HSC are differentiated cells. In some embodiments, progenitor cells of an HSC comprise the same differentiation state. In some embodiments, progenitor cells of an HSC comprise different differentiation states. In some embodiments, progenitor cells of an HSC are lineage restricted precursor cells (e.g., a common myeloid progenitor cell, a common lymphoid progenitor cell). In some embodiments, lineage restricted precursor cells further differentiate. In some embodiments, an HSC differentiates into a common lymphoid progenitor cell that further differentiates into cell types comprising B cells, natural killer (NK) cells, and T cells. In some embodiments, an HSC differentiates into a common myeloid progenitor cell that further differentiates into cell types comprising dendritic cells (DCs), monocytes, myeloblasts, monocyte-derived DCs, macrophages, neutrophils, eosinophils, basophils, megakaryocyte-erythroid progenitor cells, erythrocytes, megakaryocytes, and platelets.

In some embodiments, an HSC of the disclosure has positive expression for the cell surface marker CD34. In some embodiments, an HSC of the disclosure has positive expression for cell surface markers comprising CD38, CD45RA, CD90, c-Kit tyrosine kinase receptor, stem cell antigen-1 (Sca-1), CD133 and CD49f. In some embodiments, an HSC of the disclosure has negative or low expression for cell surface markers comprising CD38, CD45RA, CD90, Thy-1.1 cell surface antigen and CD49f. In some embodiments, an HSC of the disclosure has negative or low expression of lineage cell surface markers comprising CD2, CD3, CD11b, CD11c, CD14, CD16, CD19, CD24, CD56, CD66b, CD235. In some embodiments, an HSC of the disclosure is an LT-HSC. In some embodiments, an LT-HSC has negative or low expression of lineage cell surface markers comprising CD2, CD3, CD11b, CD11c, CD14, CD16, CD19, CD24, CD56, CD66b, CD235. In some embodiments, an LT-HSC has negative or low expression of cell surface markers comprising CD45RA and CD38. In some embodiments, an LT-HSC has positive expression for cell surface markers comprising CD34 and CD90.

Methods for isolation of HSCs are known in the art as taught by U.S. Pat. Nos. 5,643,741, 5,087,570, 5,677,136, 7,790,458, 10,006,004, 10,086,045, 7,939,057, 10,058,573 that are incorporated by reference herein. In some embodiments, a population of cells comprising HSCs is derived from the patient (e.g., an autologous HSC). In some embodiments, a population of cells comprising HSCs is derived from a healthy donor (e.g., an allogenic HSC). In some embodiments, a population of cells comprising HSCs is derived from human cord blood. In some embodiments, a population of cells comprising HSCs is derived from bone marrow. In some embodiments, a population of cells comprising HSCs is derived from human peripheral blood.

In some embodiments, a population of cells comprising HSCs is derived following treatment of a subject (e.g., a patient, a healthy donor) with a stem cell mobilizer. In some embodiments, a stem cell mobilizer comprises a CXCR4 antagonist. The chemokine stromal cell derived factor-1 (e.g., CXCL12) is a chemokine that binds to CXCR4 on HSCs and HPCs and signals for retention in the bone marrow. By blocking this interaction with a CXCR4 antagonist, HSCs and HPCs rapidly mobilize to the blood (Broxmeyer, et al. (2005) *J. Exp Med* 18:1307-1318; Devine, S. et al (2008) *Blood* 112:990-998). Non-limiting examples of a CXCR4 antagonist include TG-0054 (TaiGen Biotechnology, Co., Ltd. (Taipei, Taiwan)), AMD3465, AMD3100 (e.g., wherein AMD or AMD3100 is used interchangeably with plerixafor, rINN, USAN, JM3100, and its trade name, Mozobil™, see U.S. Pat. Nos. 6,835,731 and 6,825,351), and NIBR1816 (Novartis, Basil, Switzerland). In some embodiments, a stem-cell mobilizer is plerixafor.

In some embodiments, a stem cell mobilizer comprises a colony stimulating factor. Non-limiting examples of a colony stimulating factor include, but are not limited to, granulocyte colony stimulating factor (G-CSF), granulocyte-macrophage colony stimulating factor (GM-CSF), macrophage colony stimulating factor (M-CSF), stem cell factor (SCF), FLT-3 ligand, or a combination thereof. Use of G-CSF as a stem cell mobilizing factor has demonstrated increased yield of stem cells from peripheral blood (Morton, et al (2001) Blood 98:3186; Smith, T. et al. (1997) J. Clin. Oncol. 15:5-10) In some embodiments, a stem cell mobilizer is a combination of a CXCR4 antagonist and a colony stimulating factor. In some embodiments, a stem cell mobilizer is a combination of Plerixafor and G-CSF.

In some embodiments, CD34+HSCs are enriched following isolation from a subject (e.g., a patient, a healthy donor). In some embodiments, CD34+HSCs are enriched from human blood, bone marrow, or cord blood. Methods of enriching CD34+HSCs are known in the art. In some embodiments, CD34+HSCs are enriched using a magnetic cell separator. In some embodiments, CD34+HSCs are enriched by fluorescent activated cell sorting (FACS). In some embodiments, CD34+HSCs are enriched by magnetic bead sorting for cells expressing CD34.

In some embodiments, an enriched population of CD34+ cells has a purity of at least 40%, at least 50%, at least 60%, at least 70%, at least 80%, at least 90%, or at least 100%. In some embodiments, an enriched population of CD34+ cells has a purity of at least 90%, at least 91%, at least 92%, at least 93%, at least 94%, at least 95%, at least 96%, at least 97%, at least 98%, at least 99%, or at least 100%. In some embodiments, an enriched population of CD34+ cells has a purity of at least about 90%. In some embodiments, an enriched population of CD34+ cells has a purity of at least about 91%. In some embodiments, an enriched population of CD34+ cells has a purity of at least about 92%. In some embodiments, an enriched population of CD34+ cells has a purity of at least about 93%. In some embodiments, an enriched population of CD34+ cells has a purity of at least about 94%. In some embodiments, an enriched population of CD34+ cells has a purity of at least about 95%. In some embodiments, an enriched population of CD34+ cells has a purity of at least about 96%. In some embodiments, an enriched population of CD34+ cells has a purity of at least about 97%. In some embodiments, an enriched population of CD34+ cells has a purity of at least about 98%. In some embodiments, an enriched population of CD34+ cells has a purity of at least about 99%. In some embodiments, an enriched population of CD34+ cells has a purity of at least about 100%.

In some embodiments, an enriched population of CD34+ cells comprises LT-HSPCs. In some embodiments, the proportion of the CD34+ population that is LT-HSPCs is 0.01-0.05%, 0.01-0.1%, 0.05-0.1%, 0.05-1%, 0.1-0.5%, 0.1-0.7%, 0.1-1.0%, 0.1-1.5%, 0.1-2.0%, 0.5-1.5%, 0.5-2.0%, or 1-2%. In some embodiments, the proportion of the CD34+ population that is LT-HSPCs is 0.05-1%. In some embodiments, the proportion of the CD34+ population that is LT-HSPCs is 0.1-1%. In some embodiments, the proportion of the CD34+ population that is LT-HSPCs is 0.1-2%. In some embodiments, the proportion of the CD34+ population that is LT-HSPCs is at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, or at least about 1.0% of the population.

In some embodiments, gene-editing of HSCs is performed prior to enrichment of CD34+HSCs. In some embodiments, gene-editing of HSCs is performed following enrichment of CD34+HSCs. In some embodiments, following gene-editing, a method is used to selected for gene-edited HSCs from a population comprising CD34+HSCs. In some embodiments, a method of isolating gene-edited HSCs enrichment of HSCs expressing truncated nerve growth factor (tNGFR) as described in the art (Dever et al (2016) *Nature* 539:384-389).

For ex vivo therapy, transplantation requires clearance of bone-marrow niches for donor HSCs to engraft. Methods are known in the art for depletion of the bone-marrow niche, including methods of treating with radiation, chemotherapy or a combination thereof.

Engineered Induced Pluripotent Stem Cells

In some embodiments, genetically engineered human cells of the disclosure are derived from induced pluripotent stem cells (iPSCs). iPSCs are reprogrammed from somatic cells to a pluripotent state wherein they can differentiate into all three germ layers. An advantage of using iPSCs is that the cell can be derived from the same subject to which the progenitor cells are to be administered. That is, a somatic cell can be obtained from a subject, reprogrammed to an iPSC, and then re-differentiated into a progenitor cell to be administered to the subject for treatment of a disorder (e.g., an autologous progenitor). Since the progenitors are derived from an autologous source, the risk of engraftment rejection or allergic responses is reduced compared to the use of cells form another subject or group of subjects. Thus, an iPSC can be gene-edited and reintroduced into a patient for correction of a disease resulting from a somatic genetic mutation.

Briefly, human iPSCs can be obtained by transducing somatic cells with stem cell associated transcription factors that include OCT4, SOX2, and NANOG (Budniatzky et al. (2014) Stem Cells Transl Med 3:448-457; Barret et al. Stem Cells Trans Med (2014) 3:1-6; Focosi et al. (2014) Blood Cancer Journal 4:e211). Exemplary methods for reprogramming somatic cells to generate iPSCs are known in the art as described by US 2019/0038771 which is incorporated by reference herein.

Pharmaceutical Compositions

The present disclosure includes pharmaceutical compositions comprising a donor polynucleotide, a gRNA, and a Cas9 protein, in combination with one or more pharmaceutically acceptable excipient, carrier or diluent. In some embodiments, the disclosure provides pharmaceutical compositions comprising a donor polynucleotide or recombinant vector, a gRNA, a Cas9 protein, and a 53BP1 inhibitor and/or DNA-PKcs inhibitor, in combination with one or more pharmaceutically acceptable excipient, carrier or diluent. In particular embodiments, the donor polynucleotide is encapsulated in a nanoparticle, e.g., a lipid nanoparticle. In some embodiments, the gRNA is encapsulated in a nanoparticle. In some embodiments, a Cas nuclease (e.g., SpCas9) is encapsulated in a nanoparticle. In some embodiments, the 53BP1 inhibitor is encapsulated in a nanoparticle, e.g., a lipid nanoparticle. In some embodiments, the DNA-PKcs inhibitor is encapsulated in a nanoparticle, e.g., a lipid nanoparticle. In some embodiments, the donor polynucleotide, gRNA, Cas9 protein, 53BP1 inhibitor and/or DNAK-PKcs inhibitor are encapsulated in the same or different nanoparticle, e.g., lipid nanoparticle. In particular embodiments, an mRNA encoding a Cas nuclease or nanoparticle encapsulating a Cas nuclease is present in a pharmaceutical composition. In various embodiments, the one or more mRNA present in the pharmaceutical composition is encapsulated in a nanoparticle, e.g., a lipid nanoparticle. In particular embodiments, the molar ratio of the first mRNA to the second mRNA is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1.

In some embodiments, the ratio between the lipid composition and the donor polynucleotide can be about 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide is about 20:1 or about 15:1.

In one embodiment, the lipid nanoparticles described herein can comprise polynucleotides (e.g., donor polynucleotide) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1,from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

Methods of Treatment

Provided herein are methods of treating a patient with a disease by gene-editing a genomic DNA molecule, such as correcting a mutation in a genomic DNA molecule. In some embodiments, the method may comprise introducing a donor polynucleotide, system, vector, or pharmaceutical composition described herein into a cell. In some embodiments, the method may comprise administering a donor polynucleotide or recombinant vector, system, vector, or pharmaceutical composition to a subject in need thereof (e.g., a patient having a disease caused by a mutation).

In some embodiments, the disclosure provides methods of treating a patient with a disease associated with a mutation in the HBB gene. In some embodiments, the mutation in the HBB gene is E6V. In some embodiments, the disease associated with a mutation in the HBB gene is a sickle cell disease (SCD, also referred to as sickle cell anemia or SCA). In some embodiments, the disease associated with a mutation in the HBB gene is a β-thalassemia.

Embodiments of the disclosure encompass methods for editing a target nucleic acid molecule (a genomic DNA) in a cell. In some embodiments, the method comprises introducing a donor polynucleotide described herein into a cell. In some embodiments, the method comprises contacting the cell with a pharmaceutical composition described herein. In some embodiments, the method comprises generating a stable cell line comprising a targeted edited nucleic acid molecule.

In some embodiments, the cell is a eukaryotic cell. Non-limiting examples of eukaryotic cells include yeast cells, plant cells, insect cells, cells from an invertebrate animal, cells from a vertebrate animal, mammalian cells, rodent cells, mouse cells, rat cells, and human cells. In some embodiments, the eukaryotic cell may be a mammalian cell. In some embodiments, the eukaryotic cell may be a rodent cell. In some embodiments, the eukaryotic cell may be a human cell. Similarly, the target sequence may be from any such cells or in any such cells.

The donor polynucleotide, system, vector, or pharmaceutical composition described herein may be introduced into the cell via any methods known in the art, such as, e.g., viral or bacteriophage infection, transfection, conjugation, protoplast fusion, lipofection, electroporation, calcium phosphate precipitation, polyethyleneimine (PEI)-mediated transfection, DEAE-dextran-mediated transfection, liposome-mediated transfection, particle gun technology, calcium phosphate precipitation, shear-driven cell permeation, fusion to a cell-penetrating peptide followed by cell contact, microinjection, and nanoparticle-mediated delivery. In some embodiments, the vector system may be introduced into the cell via viral infection. In some embodiments, the vector system may be introduced into the cell via bacteriophage infection.

Embodiments of the invention also encompass treating a patient with donor polynucleotide or recombinant vector, system, vector, or pharmaceutical composition described herein. In some embodiments, the patient has a mutation in the HBB gene. In some embodiments, the patient has an E6V mutation in the HBB gene. In some embodiments, the method may comprise administering the donor polynucleotide, system, vector, or pharmaceutical composition described herein to the patient. The method may be used as a single therapy or in combination with other therapies available in the art. In some embodiments, the patient may have a mutation (such as, e.g., insertion, deletion, substitution, chromosome translocation) in a disease-associated gene. In some embodiments, administration of the donor polynucleotide, system, vector, or pharmaceutical composition may result in a mutation comprising an insertion, deletion, or substitution of one or more nucleotides of the disease-associated gene in the patient. Certain embodiments may include methods of repairing the patient's mutation in the disease-associated gene. In some embodiments, the mutation may result in one or more amino acid changes in a protein expressed from the disease-associated gene. In some embodiments, the mutation may result in one or more nucleotide changes in an RNA expressed from the disease-associated gene. In some embodiments, the mutation may alter the expression level of the disease-associated gene. In some embodiments, the mutation may result in increased or decreased expression of the gene. In some embodiments, the mutation may result in gene knockdown in the patient. In some embodiments, the administration of the donor polynucleotide, system, vector, or pharmaceutical composition may result in the correction of the patient's mutation in the disease-associated gene. In some embodiments, the administration of the donor polynucleotide, system, vector, or pharmaceutical composition may result in gene knockout in the patient. In some embodiments, the administration of the donor polynucleotide, system, vector, or pharmaceutical composition system may result in replacement of an exon sequence, an intron sequence, a transcriptional control sequence, a translational control sequence, or a non-coding sequence of the disease-associated gene.

In some embodiments, the administration of the donor polynucleotide, system, vector, or pharmaceutical composition may result in integration of an exogenous sequence (e.g., the donor polynucleotide sequence) into the patient's genomic DNA. In some embodiments, the administration of the donor polynucleotide, system, vector, or pharmaceutical composition results in integration of an exogenous sequence encoding wild-type HBB (e.g., lacking the E6V mutation) into the patient's genomic DNA. In some embodiments, the administration of the donor polynucleotide, system, vector or pharmaceutical composition results in exchanging a region of the HBB gene correcting an E6V mutation for a region encoding the E6V mutation. In some embodiments, the exogenous sequence may comprise a protein or RNA coding sequence operably linked to an exogenous promoter sequence such that, upon integration of the exogenous sequence into the patient's genomic DNA, the patient is capable of expressing the protein or RNA encoded by the integrated sequence. The exogenous sequence may provide a supplemental or replacement protein coding or non-coding sequence. For example, the administration of the donor polynucleotide, system, vector, or pharmaceutical composition may result in the replacement of the mutant portion of the disease-associated gene in the patient. In some embodiments, the mutant portion may include an exon of the disease-associated gene. In other embodiments, the integration of the exogenous sequence may result in the expression of the integrated sequence from an endogenous promoter sequence present on the patient's genomic DNA. For example, the administration of the donor polynucleotide, system, vector, or pharmaceutical composition may result in supply of a functional gene product of the disease-associated gene to rectify the patient's mutation. In yet other embodiments, the administration of the donor polynucleotide, system, vector, or pharmaceutical composition may result in integration of an exon sequence, an intron sequence, a transcriptional control sequence, a translational control sequence, or a non-coding sequence into the patient's genomic DNA.

Additional embodiments of the invention also encompass methods of treating the patient in a tissue-specific manner. In some embodiments, the method may comprise administering the donor polynucleotide, system, vector, or pharmaceutical composition comprising a tissue-specific promoter as described herein to the patient. Non-limiting examples of suitable tissues for treatment by the methods include the immune system, neuron, muscle, pancreas, blood, kidney, bone, lung, skin, liver, and breast tissues.

In some embodiments, the disclosure provides a method to correct a mutation in a genomic DNA molecule (gDNA) in a cell, the method comprising contacting the cell with a donor polynucleotide described herein, a system comprising a donor polynucleotide, a gRNA, and a site-directed nuclease, according to the disclosure, or a pharmaceutical composition described herein, wherein when the donor polynucleotide, system or composition contacts the cell, an HDR DNA repair pathway inserts the donor polynucleotide into a double-stranded DNA break introduced into the gDNA at a location proximal to the mutation, thereby correcting the mutation.

In some embodiments, the disclosure provides a method to correct a mutation in a genomic DNA molecule (gDNA) in a cell, the method comprising contacting the cell with a donor polynucleotide or recombinant vector described herein, a system comprising a donor polynucleotide or recombinant vector, a gRNA, and a site-directed nuclease, according to the disclosure, or a pharmaceutical composition described herein, wherein when the donor polynucleotide, recombinant vector, system or composition contacts the cell, an HDR DNA repair pathway exchanges the donor polynucleotide or recombinant vector for a corresponding nucleic acid region in the HBB gene at a location proximal to the mutation, thereby correcting the mutation.

In some embodiments, the disclosure provides a method to correct a mutation in a genomic DNA molecule (gDNA) in a cell, the method comprising contacting the cell with a donor polynucleotide or recombinant vector described herein, a system comprising a donor polynucleotide or recombinant vector, a gRNA, and a site-directed nuclease, according to the disclosure, or a pharmaceutical composition described herein, wherein when the donor polynucleotide, recombinant vector, system or composition contacts the cell, an HDR DNA repair pathway exchanges a region around a double-stranded DNA break introduced into the gDNA at a location proximal to the mutation, thereby correcting the mutation.

In some embodiments, the disclosure provides a method of treating a patient with a disease by correcting a mutation in a genomic DNA molecule (gDNA) in a cell, the method comprising isolating a cell from the patient, contacting the cell with a donor polynucleotide described herein, a system comprising a donor polynucleotide, a gRNA, and a site-directed nuclease, according to the disclosure, or a pharmaceutical composition described herein, wherein, when the donor polynucleotide, system or composition contacts the cell, an HDR DNA repair pathway inserts the donor polynucleotide into a double-stranded DNA break introduced into the gDNA at a location proximal to the mutation, thereby correcting the mutation.

In some embodiments, the disclosure provides a method of treating a patient with a disease by correcting a mutation in a genomic DNA molecule (gDNA) in a cell, the method comprising isolating a cell from the patient, contacting the cell with a donor polynucleotide or recombinant vector described herein, a system comprising a donor polynucleotide or recombinant vector, a gRNA, and a site-directed nuclease, according to the disclosure, or a pharmaceutical composition described herein, an HDR DNA repair pathway exchanges the donor polynucleotide or recombinant vector for a corresponding nucleic acid region in the HBB gene at a location proximal to the mutation, thereby correcting the mutation.

In some embodiments, the disclosure provides a method of treating a patient with a disease by correcting a mutation in a genomic DNA molecule (gDNA) in a cell, the method comprising isolating a cell from the patient, contacting the cell with a donor polynucleotide or recombinant vector described herein, a system comprising a donor polynucleotide or recombinant vector, a gRNA, and a site-directed nuclease, according to the disclosure, or a pharmaceutical composition described herein, an HDR DNA repair pathway exchanges a region around a double-stranded DNA break introduced into the gDNA at a location proximal to the mutation, thereby correcting the mutation.

In some embodiments, the disclosure provides a method of treating a patient with a disease by correcting a mutation in a genomic DNA molecule (gDNA) in a cell, the method comprising administering to the patient an effective amount of a donor polynucleotide described herein, a system comprising a donor polynucleotide, a gRNA, and a site-directed nuclease, according to the disclosure, or a pharmaceutical composition described herein, wherein, when the donor polynucleotide, system or composition is administered, an HDR DNA repair pathway inserts the donor polynucleotide into a double-stranded DNA break introduced into the gDNA at a location proximal to the mutation, thereby correcting the mutation.

In some embodiments, the disclosure provides a method of treating a patient with a disease by correcting a mutation in a genomic DNA molecule (gDNA) in a cell, the method comprising administering to the patient an effective amount of a donor polynucleotide or recombinant vector described herein, a system comprising a donor polynucleotide or recombinant vector, a gRNA, and a site-directed nuclease, according to the disclosure, or a pharmaceutical composition described herein, an HDR DNA repair pathway exchanges the donor or recombinant vector a corresponding nucleic acid region in the HBB gene at a location proximal to the mutation, thereby correcting the mutation.

In some embodiments, the disclosure provides a method of treating a patient with a disease by correcting a mutation in a genomic DNA molecule (gDNA) in a cell, the method comprising administering to the patient an effective amount of a donor polynucleotide or recombinant vector, a gRNA, and a site-directed nuclease, according to the disclosure, or a pharmaceutical composition described herein, an HDR DNA repair pathway exchanges a region around a double-stranded DNA break introduced into the gDNA at a location proximal to the mutation, thereby correcting the mutation.

In some embodiments, the disclosure provides a method to correct an E6V mutation in HBB in a cell comprising an HBB gene encoding the E6V mutation, the method comprising contacting the cell with a donor polynucleotide or recombinant vector described herein, a system comprising a donor polynucleotide or recombinant vector, a gRNA, and a site-directed nuclease, according to the disclosure, or a pharmaceutical composition described herein, wherein when the donor polynucleotide or recombinant vector, system or composition contacts the cell, an HDR DNA repair pathway inserts the donor polynucleotide or recombinant vector into a double-stranded DNA break introduced into the gDNA at a location proximal to the mutation, thereby correcting the mutation.

In some embodiments, the disclosure provides a method to correct an E6V mutation in HBB in a cell comprising an HBB gene encoding the E6V mutation, the method comprising contacting the cell with a donor polynucleotide or recombinant vector described herein, a system comprising a donor polynucleotide or recombinant vector, a gRNA, and a site-directed nuclease, according to the disclosure, or a pharmaceutical composition described herein, wherein when the donor polynucleotide, recombinant vector, system or composition contacts the cell, an HDR DNA repair pathway exchanges the donor polynucleotide or recombinant vector for a corresponding nucleic acid region in the HBB gene at a location proximal to the mutation, thereby correcting the mutation.

In some embodiments, the disclosure provides a method to correct an E6V mutation in HBB in a cell comprising an HBB gene encoding the E6V mutation, the method comprising contacting the cell with a donor polynucleotide or recombinant vector described herein, a system comprising a donor polynucleotide or recombinant vector, a gRNA, and a site-directed nuclease, according to the disclosure, or a pharmaceutical composition described herein, wherein when the donor polynucleotide, recombinant vector, system or composition contacts the cell, an HDR DNA repair pathway exchanges a region around a double-stranded DNA break introduced into the gDNA at a location proximal to the mutation, thereby correcting the mutation.

In some embodiments, the disclosure provides a method of treating a patient with a disease associated with an E6V mutation in HBB by correcting the E6V mutation in the HBB gene in a cell, the method comprising isolating a cell from the patient, contacting the cell with a donor polynucleotide or recombinant vector described herein, a system comprising a donor polynucleotide or recombinant vector, a gRNA, and a site-directed nuclease, according to the disclosure, or a pharmaceutical composition described herein, wherein, when the donor polynucleotide, recombinant vector, system or composition contacts the cell, an HDR DNA repair pathway inserts the donor polynucleotide or recombinant vector into a double-stranded DNA break introduced into the gDNA at a location proximal to the mutation, thereby correcting the E6V mutation and treating the patient.

In some embodiments, the disclosure provides a method of treating a patient with a disease associated with an E6V mutation in HBB by correcting the E6V mutation in the HBB gene in a cell, the method comprising isolating a cell from the patient, contacting the cell with a donor polynucleotide or recombinant vector described herein, a system comprising a donor polynucleotide or recombinant vector, a gRNA, and a site-directed nuclease, according to the disclosure, or a pharmaceutical composition described herein, an HDR DNA repair pathway exchanges the donor polynucleotide or recombinant vector for a corresponding nucleic acid region in the HBB gene at a location proximal to the mutation, thereby correcting the E6V mutation and treating the patient.

In some embodiments, the disclosure provides a method of treating a patient with a disease associated with an E6V mutation in HBB by correcting the E6V mutation in the HBB gene in a cell, the method comprising isolating a cell from the patient, contacting the cell with a donor polynucleotide or recombinant vector described herein, a system comprising a donor polynucleotide or recombinant vector, a gRNA, and a site-directed nuclease, according to the disclosure, or a pharmaceutical composition described herein, an HDR DNA repair pathway exchanges a region around a double-stranded DNA break introduced into the gDNA at a location proximal to the mutation, thereby correcting the E6V mutation and treating the patient.

In some embodiments, the disclosure provides a method of treating a patient with a disease associated with an E6V mutation in HBB by correcting the E6V mutation in the HBB gene in a cell, the method comprising administering to the patient an effective amount of a donor polynucleotide or recombinant vector described herein, a system comprising a donor polynucleotide or recombinant vector, a gRNA, and a site-directed nuclease, according to the disclosure, or a pharmaceutical composition described herein, wherein, when the donor polynucleotide, recombinant vector, system or composition is administered, an HDR DNA repair pathway inserts the donor polynucleotide or recombinant vector into a double-stranded DNA break introduced into the gDNA at a location proximal to the mutation, thereby correcting the E6V mutation and treating the patient.

In some embodiments, the disclosure provides a method of treating a patient with a disease associated with an E6V mutation in HBB by correcting the E6V mutation in the HBB gene in a cell, the method comprising administering to the patient an effective amount of a donor polynucleotide or recombinant vector described herein, a system comprising a donor polynucleotide or recombinant vector, a gRNA, and a site-directed nuclease, according to the disclosure, or a pharmaceutical composition described herein, an HDR DNA repair pathway exchanges the donor polynucleotide or recombinant vector for a corresponding nucleic acid region in the HBB gene at a location proximal to the mutation, thereby correcting the E6V mutation and treating the patient.

In some embodiments, the disclosure provides a method of treating a patient with a disease associated with an E6V mutation in HBB by correcting the E6V mutation in the HBB gene in a cell, the method comprising administering to the patient an effective amount of a donor polynucleotide or recombinant vector, a gRNA, and a site-directed nuclease, according to the disclosure, or a pharmaceutical composition described herein, an HDR DNA repair pathway exchanges a region around a double-stranded DNA break introduced into the gDNA at a location proximal to the mutation, thereby correcting the E6V mutation and treating the patient.

In some embodiments, the cell is a hematopoietic stem cell. In some embodiments, the cell is a hematopoietic stem cell comprising an HBB gene encoding an E6V mutation. In some embodiments, the cell is a patient-specific induced pluripotent stem cell (iPSC). In some embodiments, the cell is a patient-specific induced pluripotent stem cell (iPSC) comprising an HBB gene encoding an E6V mutation. In some embodiments, the method further comprises differentiating the iPSC comprising the corrected mutation into a differentiated cell; and implanting the differentiated cell into a patient. In some embodiments, treatment results in the translation of an mRNA transcribed from the genomic DNA molecule (gDNA) comprising the inserted donor polynucleotide, wherein the translation results in the formation of a translation product (protein) that alleviates the disease or that does not cause or contribute to the disease.

Definitions

Terms used in the claims and specification are defined as set forth below unless otherwise specified. In the case of direct conflict with a term used in a parent provisional patent application, the term used in the instant application shall control.

It must be noted that, as used in the specification and the appended claims, the singular forms “a,” “an” and “the” include plural referents unless the context clearly dictates otherwise.

Further, unless otherwise required by context, singular terms shall include pluralities and plural terms shall include the singular.

About: As used herein, the term “about” (alternatively “approximately”) will be understood by persons of ordinary skill and will vary to some extent depending on the context in which it is used. If there are uses of the term which are not clear to persons of ordinary skill given the context in which it is used, “about” will mean up to plus or minus 10% of the particular value.

Amino acid: As used herein, the term “amino acid” refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

Amino acid substitution: As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g., insertion of about three to about five or even up to about ten, fifteen, or twenty amino acid residues.

The inserted residue(s) may be naturally occurring or non-naturally occurring as disclosed above.

An "amino acid deletion" refers to the removal of at least one amino acid residue from a predetermined amino acid sequence.

Base Composition: As used herein, the term "base composition" refers to the proportion of the total bases of a nucleic acid consisting of guanine+cytosine or thymine (or uracil)+adenine nucleobases.

Base Pair: As used herein, the term "base pair" refers to two nucleobases on opposite complementary polynucleotide strands, or regions of the same strand, that interact via the formation of specific hydrogen bonds. As used herein, the term "Watson-Crick base pairing", used interchangeably with "complementary base pairing", refers to a set of base pairing rules, wherein a purine always binds with a pyrimidine such that the nucleobase adenine (A) forms a complementary base pair with thymine (T) and guanine (G) forms a complementary base pair with cytosine (C) in DNA molecules. In RNA molecules, thymine is replaced by uracil (U), which, similar to thymine (T), forms a complementary base pair with adenine (A). The complementary base pairs are bound together by hydrogen bonds and the number of hydrogen bonds differs between base pairs. As in known in the art, guanine (G)-cytosine (C) base pairs are bound by three (3) hydrogen bonds and adenine (A)-thymine (T) or uracil (U) base pairs are bound by two (2) hydrogen bonds.

Base pairing interactions that do not follow these rules can occur in natural, non-natural, and synthetic nucleic acids and are referred to herein as "non-Watson-Crick base pairing" or alternatively "non-canonical base pairing". A "wobble base pair" is a pairing between two nucleobases in RNA molecules that does not follow Watson-Crick base pair rules. For example, inosine is a nucleoside that is structurally similar to guanosine, but is missing the 2-amino group. Inosine is able to form two hydrogen bonds with each of the four natural nucleobases (Oda et al., (1991) Nucleic Acids Res 19:5263-5267) and it is often used by researchers as a "universal" base, meaning that it can base pair with all the naturally-occurring or canonical bases. The four main wobble base pairs are the guanine-uracil (G-U) base pair, the hypoxanthine-uracil (I-U) base pair, the hypoxanthine-adenine (I-A) base pair, and the hypoxanthine-cytosine (I-C) base pair. In order to maintain consistency of nucleic acid nomenclature, "I" is used for hypoxanthine because hypoxanthine is the nucleobase of inosine; nomenclature otherwise follows the names of nucleobases and their corresponding nucleosides (e.g., "G" for both guanine and guanosine—as well as for deoxyguanosine). The thermodynamic stability of a wobble base pair is comparable to that of a Watson-Crick base pair. Wobble base pairs play a role in the formation of secondary structure in RNA molecules.

Blunt-end: As used herein, the term "blunt-end" "blunt-ended" refers to the structure of an end of a duplexed or double-stranded nucleic acid (e.g., DNA), wherein both complementary strands comprising the duplex terminate, at least at one end, in a base pair. Hence, neither strand comprising the duplex extends further from the end than the other.

Codon: As used herein, the term "codon" refers to a sequence of three nucleotides that together form a unit of genetic code in a DNA or RNA molecule. A codon is operationally defined by the initial nucleotide from which translation starts and sets the frame for a run of successive nucleotide triplets, which is known as an "open reading frame" (ORF). For example, the string GGGAAACCC, if read from the first position, contains the codons GGG, AAA, and CCC; if read from the second position, it contains the codons GGA and AAC; and if read from the third position, GAA and ACC. Thus, every nucleic sequence read in its 5'→3' direction comprises three reading frames, each producing a possibly distinct amino acid sequence (in the given example, Gly-Lys-Pro, Gly-Asn, or Glu-Thr, respectively). DNA is double-stranded defining six possible reading frames, three in the forward orientation on one strand and three reverse on the opposite strand. Open reading frames encoding polypeptides are typically defined by a start codon, usually the first AUG codon in the sequence.

Corrects or induces a mutation: As used herein, the term "corrects or induces a mutation" refers to a function of a donor polynucleotide, such as those described herein, to incorporate a desired alteration into a nucleotide sequence comprising a genomic DNA (gDNA) molecule upon insertion of the donor polynucleotide into a double-strand break (DSB) induced in the gDNA molecule, thereby changing the nucleotide sequence of the gDNA.

The term "corrects a mutation" refers to an incorporation of a desired alteration by a donor polynucleotide that results in a change of one or more nucleotides in a gDNA that comprises a mutation (e.g., a deleterious or disease-causing mutation) such that the mutation is reverted or transmuted in a desired manner. The identification of a mutation to correct can be determined by comparison of the nucleotide sequence of a gDNA known, or suspected to, comprise the mutation to the nucleotide sequence of a wild-type gDNA.

The term "induces a mutation" refers to an incorporation of a desired alteration by a donor polynucleotide that results in a change of one or more nucleotides in a gDNA such that the gDNA is mutated in a desired manner. A mutation induced by a donor polynucleotide may be any type of mutation known in the art. In some embodiments, the induction of a mutation is for therapeutic purposes or results in a therapeutic effect.

Covalently linked: As used herein, the term "covalently linked" (alternatively "conjugated", "linked," "attached," "fused", or "tethered"), when used with respect to two or more moieties, means that the moieties are physically associated or connected with one another, by whatever means including chemical conjugation, recombinant techniques or enzymatic activity, either directly or via one or more additional moieties that serves as a linking agent, to form a structure that is sufficiently stable so that the moieties remain physically associated under the conditions in which the structure is used, e.g., physiological conditions.

Complementary: As used herein, the term "complementary" or "complementarity" refers to a relationship between the sequence of nucleotides comprising two polynucleotide strands, or regions of the same polynucleotide strand, and the formation of a duplex comprising the strands or regions, wherein the extent of consecutive base pairing between the two strands or regions is sufficient for the generation of a duplex structure. It is known that adenine (A) forms specific hydrogen bonds, or "base pairs", with thymine (T) or uracil (U). Similarly, it is known that a cytosine (C) base pairs with guanine (G). It is also known that non-canonical nucleobases (e.g., inosine) can hydrogen bond with natural bases. A sequence of nucleotides comprising a first strand of a polynucleotide, or a region, portion or fragment thereof, is said to be "sufficiently complementary" to a sequence of nucleotides comprising a second strand of the same or a different nucleic acid, or a region, portion, or fragment thereof, if, when the first and second strands are arranged in an antiparallel fashion, the extent of base pairing between the two strands maintains the duplex structure under the conditions in which the duplex structure is used (e.g., physiological conditions in a cell). It should be understood that complementary strands or regions of polynucleotides can include some base pairs that are non-complementary. Complementarity may be "partial," in which only some of the nucleobases comprising the polynucleotide are matched according to base pairing rules. Or, there may be "complete" or "total" complementarity between the nucleic acids. Although the degree of complementarity between polynucleotide strands or regions has significant effects on the efficiency and strength of hybridization between the strands or regions, it is not required for two complementary polynucleotides to base pair at every nucleotide position. In some embodiments, a first polynucleotide is 100% or "fully" complementary to a second polynucleotide and thus forms a base pair at every nucleotide position. In some embodiments, a first polynucleotide is not 100% complementary (e.g., is 90%, or 80% or 70% complementary) and contains mismatched nucleotides at one or more nucleotide positions. While perfect complementarity is often desired, some embodiments can include one or more but preferably 6, 5, 4, 3, 2, or 1 mismatches.

Contacting: As used herein, the term "contacting" means establishing a physical connection between two or more entities. For example, contacting a cell with an agent (e.g., an RNA, a lipid nanoparticle composition, or other pharmaceutical composition of the disclosure) means that the cell and the agent are made to share a physical connection. Methods of contacting cells with external entities both in vivo, in vitro, and ex vivo are well known in the biological arts. In exemplary embodiments of the disclosure, the step of contacting a mammalian cell with a composition (e.g., an isolated RNA, nanoparticle, or pharmaceutical composition of the disclosure) is performed in vivo. For example, contacting a lipid nanoparticle composition and a cell (for example, a mammalian cell) which may be disposed within an organism (e.g., a mammal) may be performed by any suitable administration route (e.g., parenteral administration to the organism, including intravenous, intramuscular, intradermal, and subcutaneous administration). For a cell present in vitro, a composition (e.g., a lipid nanoparticle or an isolated RNA) and a cell may be contacted, for example, by adding the composition to the culture medium of the cell and may involve or result in transfection. Moreover, more than one cell may be contacted by an agent.

Culture: As used herein, the term "culture" can be used interchangeably with the terms "culturing", "grow", "growing", "maintain", "maintaining", "expand", "expanding" when referring to a cell culture or the process of culturing. The term refers to a cell (e.g., a primary cell) that is maintained outside its normal environment (e.g., a tissue in a living organism) under controlled conditions. Cultured cells are treated in a manner that enables survival. Culturing conditions can be modified to alter cell growth, homeostasis, differentiation, division, or a combination thereof in a controlled and reproducible manner. The term does not imply that all cells in the culture survive, grow, or divide as some may die, enter a state of quiescence, or enter a state of senescence. Cells are typically cultured in media, which can be changed during the course of the culture. Components can be added to the media or environmental factors (e.g., temperature, humidity, atmospheric gas levels) to promote cell survival, growth, homeostasis, division, or a combination thereof.

Denaturation: As used herein, the term "denaturation" refers to the process by which the hydrogen bonding between base paired nucleotides in a nucleic acid is disrupted, resulting in the loss of secondary and/or tertiary nucleic acid structure (e.g., the separation of previously annealed strands). Denaturation can occur by the application of an external substance, energy, or biochemical process to a nucleic acid.

Double-strand break: As used herein the term, "double-strand break" (DSB) refers to a DNA lesion generated when the two complementary strands of a DNA molecule are broken or cleaved, resulting in two free DNA ends or termini. DSBs may occur via exposure to environmental insults (e.g., irradiation, chemical agents, or UV light) or generated deliberately (e.g., via a site-directed nuclease) and for a defined biological purpose (e.g., the insertion of a donor polynucleotide to correct a mutation).

Duplex: As used herein, the term "duplex" refers to a structure formed by complementary strands of a double-stranded polynucleotide, or complementary regions of a single-stranded polynucleotide that folds back on itself. The duplex structure of a nucleic acid arises as a consequence of complementary nucleotide sequences being bound together, or hybridizing, by base pairing interactions.

$EC_{50}$: As used herein, the term "$EC_{50}$" refers to the concentration of a composition which induces a response, either in an in vitro or an in vivo assay, which is 50% of the maximal response, i.e., halfway between the maximal response and the baseline.

Effective dose: As used herein, the term "effective dose" or "effective dosage" is defined as an amount sufficient to achieve or at least partially achieve the desired effect.

Engraftment: As used herein, the term "engraftment" is used interchangeably with the term "chimerism" and refers to the process wherein donor stem cells are administered to (e.g., transplanted) a host, traffic to a tissue compartment, and establish within that compartment by undergoing self-renewal and generating differentiated cells for reconstitution of the tissue compartment. Often the term engraftment refers to the success of a hematopoietic stem cell (HSC) transplant (e.g., a bone marrow transplant). The term "engraftment" in this context refers to the persistence of transplanted HSCs and their progenitors following administration. The term engraftment can also refer to the success of a T cell therapy wherein ex vivo manipulated T cells are administered to a host. The term "engraftment" in this context refers to the persistence of transplanted donor T cells and their progenitors following administration Genome editing: As used herein, the term genome editing generally refers to the process of editing or changing the nucleotide sequence of a genome, preferably in a precise or predetermined manner. Examples of methods of genome editing described herein include methods of using site-directed nucleases to cut genomic DNA at a precise target location or sequence within a genome, thereby creating a DNA break (e.g., a DSB) within the target sequence, and repairing the DNA break such that the nucleotide sequence of the repaired genome has been changed at or near the site of the DNA break.

Double-strand DNA breaks (DSBs) can be and regularly are repaired by natural, endogenous cellular processes such as homology-directed repair (HDR) and non-homologous end-joining (NHEJ) (see e.g., Cox et al., (2015) Nature Medicine 21(2):121-131).

DNA repair by HDR utilizes a polynucleotide (often referred to as a "repair template" or "donor template") with a nucleotide sequence that is homologous to the sequences flanking the DSB. DNA repair by HDR mechanisms involves homologous recombination between the repair template and the cut genomic DNA molecule. Repair templates may be designed such that they insert or delete nucleotides in the genomic DNA molecule or change the nucleotide sequence of the genomic DNA molecule.

NHEJ mechanisms can repair a DSB by directly joining or ligating together the DNA ends that result from the DSB. Repair of a DSB by NHEJ can involve the random insertion or deletion of one or more nucleotides (i.e. indels). This aspect of DNA repair by NHEJ is often leveraged in genome editing methods to disrupt gene expression. NHEJ can also repair a DSB by insertion of an exogenous polynucleotide into the cut site in a homology-independent manner.

A third repair mechanism is microhomology-mediated end joining (MMEJ), also referred to as "alternative NHEJ", in which the genetic outcome is similar to NHEJ in that small deletions and insertions can occur at the cleavage site. MMEJ makes use of homologous sequences of a few basepairs flanking the DNA break site to drive a more favored DNA end joining repair outcome (see e.g., Cho and Greenberg, (2015) Nature 518, 174-176); Mateos-Gomez et al., Nature 518, 254-57 (2015); Ceccaldi et al., Nature 528, 258-62 (2015). In some instances it may be possible to predict likely repair outcomes based on analysis of potential microhomologies at the site of the DNA break. Each of the aforementioned DNA repair mechanisms can be used in genome editing methods to create desired genomic alterations. The first step in the genome editing process is to create typically one or two DNA breaks in a target sequence as close as possible to the site of intended mutation or alteration. This can achieved via the use of a site-directed nuclease, as described and illustrated herein.

Hemoglobinopathy: As used herein, the term "hemoglobinopathy" refers to any defect in the structure, function, or expression of any hemoglobin of an individual, and includes defects in the primary, secondary, tertiary or quaternary structure of hemoglobin caused by any mutation, such as deletion mutations or substitution mutations in the coding regions of the β-globin gene, or mutations in, or deletions of, the promoters or enhancers of such genes that cause a reduction in the amount of hemoglobin produced as compared to a normal condition. The term further comprises any decrease in the amount or effectiveness of hemoglobin, whether normal or abnormal, caused by external factors such as disease, chemotherapy, toxins, poisons, or the like. B-hemoglobinopathies contemplated herein include, but are not limited to, sickle cell disease (SCD, also referred to as a sickle cell anemia or SCA), sickle cell trait, hemoglobin C disease, hemoglobin C trait, hemoglobin S/C disease, hemoglobin D disease, hemoglobin E disease, thalassemais, hemoglobins with increased oxygen affinity, hemoglobins with decreased oxygen affinity, unstable hemoglobin disease, and methemoglobinemia.

In need: As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment.

Insertion: As used herein, an "insertion" or an "addition" refers to a change in an amino acid or nucleotide sequence resulting in the addition of one or more amino acid residues or nucleotides, respectively, to a molecule as compared to a reference sequence, for example, the sequence found in a naturally-occurring molecule.

Intron: As used herein, the term "intron" refers to any nucleotide sequence within a gene that is removed by RNA splicing mechanisms during maturation of the final RNA product (e.g., an mRNA). An intron refers to both the DNA sequence within a gene and the corresponding sequence in a RNA transcript (e.g., a pre-mRNA). Sequences that are joined together in the final mature RNA after RNA splicing are "exons". As used herein, the term "intronic sequence" refers to a nucleotide sequence comprising an intron or a portion of an intron. Introns are found in the genes of most eukaryotic organisms and can be located in a wide range of genes, including those that generate proteins, ribosomal RNA (rRNA), and transfer RNA (tRNA). When proteins are generated from intron-containing genes, RNA splicing takes place as part of the RNA processing pathway that follows transcription and precedes translation.

Lipid: As used herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

Modified: As used herein "modified" or "modification" refers to a changed state or change in structure resulting from a modification of a polynucleotide, e.g., DNA. Polynucleotides may be modified in various ways including chemically, structurally, and/or functionally. For example, the DNA molecules of the present disclosure may be modified by the incorporation of a chemically-modified base that provides a biological activity. In one embodiment, the DNA is modified by the introduction of non-natural or chemically-modified bases, nucleosides and/or nucleotides, e.g., as it relates to the natural nucleobases adenine (A), guanine (G), cytosine (C), and thymine (T). mRNA: As used herein, an "mRNA" refers to a messenger ribonucleic acid. An mRNA may be naturally or non-naturally occurring or synthetic. For example, an mRNA may include modified and/or non-naturally occurring components such as one or more nucleobases, nucleosides, nucleotides, or linkers. An mRNA may include a cap structure, a 5' transcript leader, a 5' untranslated region, an initiator codon, an open reading frame, a stop codon, a chain terminating nucleoside, a stem-loop, a hairpin, a polyA sequence, a polyadenylation signal, and/or one or more cis-regulatory elements. An mRNA may have a nucleotide sequence encoding a polypeptide. Translation of an mRNA, for example, in vivo translation of an mRNA inside a mammalian cell, may produce a polypeptide. Traditionally, the basic components of a natural mRNA molecule include at least a coding region, a 5'-untranslated region (5'-UTR), a 3'UTR, a 5' cap and a polyA sequence.

Naturally occurring: As used herein, the term "naturally occurring" as applied to an object refers to the fact that an object can be found in nature. For example, a polypeptide or polynucleotide sequence (e.g., a splice site), or components thereof such as amino acids or nucleotides, that is present in an organism (including viruses) that can be isolated from a source in nature and which has not been intentionally modified by man in the laboratory is naturally occurring.

Non-homologous end joining: As used herein, the term "non-homologous end joining" refers to a pathway that repairs double-strand breaks (DSBs) in DNA. NHEJ is referred to as "non-homologous" because the DNA termini are directly ligated without the need for a homologous template, in contrast to homology directed repair (HDR), which requires a homologous sequence to guide repair.

Non-replicative: As used herein, the term "non-replicative" refers to the characteristic of a DNA molecule as being unable to replicate within a cell or an organism. Certain DNA molecules (e.g., plasmids, viral genomes) contain sequence elements (e.g., origins of replications) that impart the DNA molecule with the ability to be copied, or replicated, by a cell or organism. The term "non-replicative" connotes those DNA molecules that do not contain such sequence elements.

Nucleic acid: As used herein, the term "nucleic acid" refers to deoxyribonucleotides or ribonucleotides and polymers or oligomers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Polymers of nucleotides are referred to as "polynucleotides". Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

Polynucleotides used herein can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases. "Modified nucleosides" include, for example, as inosine and thymine, when the latter is found in or comprises RNA. A variety of modifications can be made to DNA and RNA; thus, "polynucleotide" embraces chemically, enzymatically, or metabolically modified forms.

Nucleobase: As used herein, the term "nucleobase" (alternatively "nucleotide base" or "nitrogenous base") refers to a purine or pyrimidine heterocyclic compound found in nucleic acids, including any derivatives or analogs of the naturally occurring purines and pyrimidines that confer improved properties (e.g., binding affinity, nuclease resistance, chemical stability) to a nucleic acid or a portion or segment thereof. Adenine, cytosine, guanine, thymine, and uracil are the primary or canonical nucleobases predominately found in natural nucleic acids. Other natural, non-natural, non-canonical and/or synthetic nucleobases, can be incorporated into nucleic acids, such as those disclosed herein.

Nucleoside Nucleotide: As used herein, the term "nucleoside" refers to a compound containing a sugar molecule (e.g., a ribose in RNA or a deoxyribose in DNA), or derivative or analog thereof, covalently linked to a nucleobase (e.g., a purine or pyrimidine), or a derivative or analog thereof. As used herein, the term "nucleotide" refers to a nucleoside covalently linked to a phosphate group. As used herein, the term "ribonucleoside" refers to a nucleoside that comprise a ribose and a nucleobase (e.g., adenosine (A), cytidine (C), guanosine (G), 5-methyluridine ($m^5U$), uridine (U), or inosine (I)).

Operably linked: As used herein, a nucleic acid, or fragment or portion thereof, such as a polynucleotide or oligonucleotide is "operably linked" when it is placed into a functional relationship with another nucleic acid sequence, or fragment or portion thereof.

Polynucleotide oligonucleotide: As used herein, the terms "polynucleotide" and "oligonucleotide" are used interchangeably and refer to a single-stranded or double-stranded polymer or oligomer of nucleotides or nucleoside monomers consisting of naturally-occurring bases, sugars and intersugar (backbone) linkages. The terms "polynucleotide" and "oligonucleotide" also includes polymers and oligomers comprising non-naturally occurring bases, sugars and intersugar (backbone) linkages, or portions thereof, which function similarly.

Polynucleotides are not limited to any particular length of nucleotide sequence, as the term "polynucleotides" encompasses polymeric forms of nucleotides of any length. Short polynucleotides are typically referred to in the art as "oligonucleotides". In the context of the present disclosure, such modified or substituted polynucleotides and oligonucleotides are often preferred over native forms because the modification increases one or more desirable or beneficial biological properties or activities including, but not limited to, enhanced cellular uptake and/or increased stability in the presence of nucleases. In some embodiments, the agonists of the disclosure comprise polynucleotides and oligonucleotides that contain at least one region of modified nucleotides that confers one or more beneficial properties or increases biological activity (e.g., increased nuclease resistance, increased uptake into cells, increased duplex stability, increased binding affinity to a target polypeptide).

Palindromic sequence: As used herein, the term "palindromic sequence" (alternatively "palindrome") refers to a sequence of nucleotides that is self-complementary; wherein the sequence of nucleotides in the 5' to 3' direction is the same as the sequence of nucleotides comprising the complementary strand, when read in the 5' to 3'. For example, the sequence 5'-ACCTAGGT-3' is a palindromic sequence because its complementary sequence, 3'-TGGATCCA-5', when read in the 5' to 3' direction, is the same as the original sequence. In contrast, the sequence 5'-AGTGGCTG-3' is not a palindromic sequence because its complementary sequence, 3'-TCACCGAC-5', when read in the 5' to 3' direction, is not the same as the original sequence.

Parenteral administration: As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

Percent identity: As used herein, the term "percent identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. The percent identity between two sequences is a function of the number of identical positions shared by the sequences (i.e., % homology=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website. The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See www.ncbi.nlm.nih.gov.

Pharmaceutically acceptable: As used herein, the term "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

Pharmaceutically acceptable carrier: As used herein, the term "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) J Pharm Sci 66:1-19).

Polypeptide: As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

Preventing: As used herein, the term "preventing" or "prevent" when used in relation to a condition, refers to administration of a composition which reduces the frequency of, or delays the onset of, symptoms of a medical condition in a subject relative to a subject which does not receive the composition.

Purified: As used herein, the term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

Reprogramming: As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells into culture can lead to some loss of fully differentiated characteristics. Thus, simply culturing such cells included in the term differentiated cells does not render these cells non-differentiated cells (e.g., undifferentiated) or pluripotent cells. The transition of a differentiated cell to pluripotency requires a reprogramming stimulus beyond the stimuli that lead to partial loss of differentiated character in culture. Reprogrammed cells also have the characteristic of the capacity of extending passaging without loss of growth potential, relative to primary cell parents, which generally have capacity for only a limited number of divisions in culture.

Sense strand: As used herein the term "sense strand" or "coding strand" refers to a segment within double-stranded DNA (e.g., genomic DNA) with a 5' to 3' directionality and has the same nucleotide sequence as an mRNA transcribed from the segment. The transcription product is pre-mRNA transcript, which contains a sequence of nucleotides that is identical to that of the sense strand, with the exception that uracil will be incorporated into the mRNA at those positions where thymine is located in the DNA. The sense strand is complementary to the antisense strand of DNA, or template strand, which runs from 3' to 5'.

Site-directed nuclease: As used herein, the term "site-directed nuclease" refers to one of several distinct classes of nucleases that can be programmed or engineered to recognize a specific target site (i.e., a target nucleotide sequence) in a DNA molecule (e.g., a genomic DNA molecule) and generate a DNA break (e.g., a DSB) within the DNA molecule at, near or within the specific site. Site-directed nucleases are useful in genome editing methods, such as those described herein.

Site-directed nucleases include, but are not limited to, the zinc finger nucleases (ZFNs), transcription activator-like effector (TALE) nucleases, CRISPR/Cas nucleases (e.g., Cas9), homing endonucleases (also termed meganucleases), and other nucleases (see, e.g., Hafez and Hausner, Genome 55, 553-69 (2012); Carroll, Ann. Rev. Biochem. 83, 409-39 (2014); Gupta and Musunuru, J. Clin. Invest. 124, 4154-61 (2014); and Cox et al., supra. These differ mainly in the way they bind DNA and create the targeted, site-specific DNA break. Site-directed nucleases known in the art may produce a single-strand break (SSB) or a DSB. For the purposes of the present invention, the disclosure's reference to a "site-directed nuclease" refers to those nucleases that produce a DSB. After creation of a DSB, essentially the same natural cellular DNA repair mechanisms of NHEJ or HDR are co-opted to achieve the desired genetic modification. Therefore, it is contemplated that genome editing technologies or systems using site-directed nucleases can be used to achieve genetic and therapeutic outcomes described herein.

Stem cell: As used herein, the term "stem cell" is used interchangeably with the term "hematopoietic stem cell" (HSC). Stem cells are distinguished from other cell types by two important characteristics. First, stem cells are unspecialized cells capable of renewing themselves through cell division, sometimes after periods of inactivity (e.g., quiescent state). Second, under certain physiologic or experimental conditions, stem cells can be induced to become tissue- or organ-specific cells with special functions. In some organs, such as the gut and bone marrow, stem cells regularly divide to repair and replace worn out or damaged tissues. In other tissues, such as the pancreas and heart, stem cells only differentiate under certain conditions.

The term "HSC" can refer to multipotent stem cell that is capable of differentiating into all blood cells including erythrocytes, leukocytes, and platelets. HSCs are contained not only in the bone marrow, but also in umbilical cord blood derived cells.

Stem cell mobilizer: As used herein, the term "stem cell mobilizer" is used interchangeably with the terms "mobilizer of hematopoietic stem or progenitor cells" or "mobilize" and refers to any agent, whether it is a small organic molecule, a polypeptide (e.g., a growth factor or colony stimulating factor or an active fragment or mimic thereof), a nucleic acid, a carbohydrate, an antibody, that acts to enhance the migration of stem cells from the bone marrow into the peripheral blood. A stem cell mobilizer may increase the number of HSCs or hematopoietic progenitor/precursor cells in the peripheral blood, thus allowing for a more accessible source of stem cells. In some embodiments, a stem cell mobilizer refers to any agent that mobilizes CD34+ stem cells. It is further understood that an agent may have stem cell mobilizing activity in addition to one or more other biological activities including, but not limited to, immunosuppression.

Subject: As used herein, the term "subject" includes any human or non-human animal. For example, the methods and compositions of the present invention can be used to treat a subject with a disorder (e.g.: a genetic disorder). The term "non-human animal" includes all vertebrates, e.g., mammals and non-mammals, such as non-human primates, sheep, dog, cow, chickens, amphibians, reptiles, etc.

Therapeutic agent: As used herein, the term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the terms "therapeutically effective amount" or "therapeutically effective dose," or similar terms used herein are intended to mean an amount of an agent that will elicit the desired biological or medical response, such as, for example, at least partially arresting the condition or disease and its complications in a patient already suffering from the disease (e.g., an improvement in one or more symptoms of a cancer). Amounts effective for this use will depend on the severity of the disorder being treated and the general state of the patient's own immune system.

Treat: The terms "treat," "treating," and "treatment," as used herein, refer to therapeutic measures described herein. The methods of "treatment" employ administration of a composition of the disclosure to a subject, in need of such treatment, in order to, cure, delay, reduce the severity of, or ameliorate one or more symptoms of the disorder or recurring disorder, or in order to prolong the survival of a subject beyond that expected in the absence of such treatment.

Wild-Type SpCas9: The terms "wild-type SpCas9 nuclease" and "wild-type SpCas9" refer to a polypeptide having the amino acid sequence of SEQ ID NO: 103 that has biochemical and biological activity when combined with a suitable gRNA to form an active CRISPR/Cas endonuclease system.

Wild-Type SaCas9: The terms "wild-type SaCas9 nuclease" and "wild-type SaCas9" refer to a polypeptide having the amino acid sequence of SEQ ID NO: 104 that has biochemical and biological activity when combined with a suitable gRNA to form an active CRISPR/Cas endonuclease system.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions.

EQUIVALENTS AND SCOPE

Those skilled in the art will recognize, or be able to ascertain using no more than routine experimentation, many equivalents to the specific embodiments, described herein. The scope of the present disclosure is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process. Furthermore, it is to be understood that the disclosure encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc.

For purposes of simplicity those embodiments have not been specifically set forth in haec verba herein.

It is also noted that the term "comprising" is intended to be open and permits but does not require the inclusion of additional elements or steps. When the term "comprising" is used herein, the term "consisting of" is thus also encompassed and disclosed Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

Example 1. In Vitro Screen of DNA DSB Repair Modulators for Improved HDR in T Cells Multiple pathways are used for repair of DNA double stranded breaks (DSBs). The homology directed repair (HDR) pathway uses homologous donor DNA (e.g., a sister chromatid or exogenous donor DNA) for high fidelity repair. The efficiency of HDR is generally low due to competition with other repair pathways, notably the non-homologous end-joining (NHEJ) pathway. HDR is predominantly active in the S/G2 phases of the cell cycle, whereas NHEJ repair is active in each phase of the cell cycle and is the predominant repair pathway in G1 cells.

Thus, HDR efficiency is poor in non-dividing or slowly dividing cells, for example, long-term repopulating hematopoietic cells (LT-HSPCs), lung progenitor cells, or hepatic cells. Given that NHEJ repair is error-prone, frequently resulting in small nucleotide insertions or deletions (indels) that can cause a frameshift mutation, it is undesirable for generating precise modification of a gene (i.e., specific nucleotide changes or knock-in of a gene).

An in vitro assay was conducted to determine the ability of various inhibitors and enhancers to improve the efficiency of HDR repair in HEK293 T cells. Specifically, a fluorescent reporter-based screening approach was developed to identify molecules that enhance gene-editing by HDR. A reporter system was generated in HEK293 T cells comprising a genomic AAVS1 locus that encoded either a blue fluorescent protein (BFP) or a green fluorescent protein (GFP) within the AAVS1 locus. A gene encoding BFP can be converted to a gene encoding GFP by substitution of cytosine at position 199 to uridine (e.g., a C to U transition at position 199). By introducing a DSB within the BFP gene using a CRISPR/Cas9 gene-editing system, a homology donor DNA encoding the nucleotide substitution can be used to edit the BFP gene to a GFP gene by HDR repair. Thus, a gene edit that induces a C to U transition at position 199 results in a change in cellular fluorescence. A change in the fluorescence of the cell measured by flow cytometry can be used to quantify efficiency of HDR repair. Additionally, the reverse gene edit can be performed for an AAVS1 locus encoding a GFP gene, wherein a GFP can be converted to BFP by substitution of uridine at position 199 to cytosine.

To create the reporter system, an AAV-based homology donor DNA encoding either BFP or GFP was created. The AAV-BFP or AAV-GFP donor was flanked by homology arms that were 1000 base pairs in length and expression of BFP or GFP was driven by the MND promoter (e.g., a synthetic promoter that contains the U3 region of a modified Moloney murine leukemia virus long term terminal repeat with myeloproliferative sarcoma virus enhancer and deleted negative control region, SEQ ID NO: 58). The viral DNA was packaged into capsids of adeno-associated virus serotype 6 (AAV6) vector. Either the BFP or GFP donor was introduced using the AAV6 vector into the AAVS1 locus in HEK293 T cells by homologous recombination using CRISPR-Cas9 as follows: purified Cas9 protein was complexed with two different single gRNAs (sgRNAs) targeting the AAVS1 locus at SEQ ID NO: 3 (spacer sequence identified by SEQ ID NO: 4; gRNA obtained from Maxcyte) or SEQ ID NO: 5 (spacer sequence identified by SEQ ID NO: 6; gRNA obtained from Thermo Fisher). Cas9 protein used in the Exemplary section provided herein refers to Cas9 polypeptide derived from *S pyogenes* (SpCas9), unless indicated otherwise.

The Cas9-sgRNA complex was electroporated into the HEK293 T cells using the Lonza Nucleofector program CM-130. Approximately, 2 hours after electroporation, the cells were infected with various viral doses of AAV6 encoding a BFP (SEQ ID NO: 44) or GFP homology donor (SEQ ID NO: 47). One week later, cells were analyzed by flow cytometry to verify integration and expression of BFP or GFP in the AAVS1 locus. HEK293 T cells expressing BFP or GFP were sorted into single cells in 96-well plates. After −2 weeks of growth, DNA extracted from individual cells was analyzed for precise integration of the respective BFP or GFP gene into the AAVS1 locus by long-range PCR. This PCR analysis allowed for determination of whether the BFP/GFP gene was integrated in one or both alleles of the AAVS1 locus.

To introduce a gene edit that converts BFP to GFP, cells were electroporated with ribonucleoprotein (RNP) comprised of Cas9 and sgRNA that targets the BFP gene encoded in the AAVS1 locus. The sgRNA targeted a sequence in the BFP gene identified by SEQ ID NO: 7 (sgRNA spacer sequence identified by SEQ ID NO: 8). The sgRNA were prepared using a standard sgRNA cassette specific to SpCas9, as indicated by SEQ ID NO: 2 (wherein a, c, g, u represent 2' O-methyl phosphorothioate nucleotides; s represents phosphorothioate nucleotides; and A, C, G, U, N represent canonical RNA nucleotides). The gRNAs used in the Exemplary section provided herein were sgRNAs prepared with the SpCas9 sgRNA cassette unless indicated otherwise.

The cells were also transfected with single-stranded oligodeoxynucleotide (ssODN) that encoded the gene correction necessary to convert BFP to GFP and homology arms complimentary to the sequence upstream and downstream of the target gene cut site. The efficiency of HDR repair was determined by measuring the level of cell GFP fluorescence.

Molecules that manipulate targets in DSB repair pathways were evaluated and are listed in Table 2. These included molecules that inhibit targets that facilitate repair by the NHEJ pathway, including i53 (polypeptide inhibitor of 53BP1), Nu7441 (DNA-PKcs inhibitor), SCR7 (DNA Ligase IV inhibitor), CYREN1 (Ku70/80 inhibitor), and CYREN2 (Ku70/80 inhibitor). Also evaluated were molecules that enhance repair by the HDR pathway, including RS-1 (Rad51 agonist). Additionally, molecules were evaluated that inhibit repair by the alternative end joining (A-EJ) pathway, including siRNA targeting DNA polymerase θ and veliparib (PARP inhibitor). Also evaluated were molecules that affect cell cycle, including XL 413 (CDC7 inhibitor). Finally, also tested was the P3 adrenergic receptor agonist L755,507 that was previously reported to improve HDR efficiency (Yu, C. et al. (2015) *Cell Stem Cell* 16:142-147).

TABLE 2

| Pathway | Molecule | Target | Reference |
|---|---|---|---|
| NHEJ | i53 | 53BP1 | SEQ ID NO: 70 |
| NHEJ | Nu7441 | DNA-PKcs | CAS 503468-95-9; Tocris 3712 |
| NHEJ | SCR7 | DNA Ligase IV | CAS 533426-72-0; Stemcell 74102 |
| NHEJ | CYREN1 and 2 | Ku70/80 | Arnoult et al *Nature* (2017) 549: 548-552 |
| HDR | RS-1 | Rad51 | CAS 312756-74-4 Sigma R9782 |
| MMEJ | siRNA | Pol θ | |
| MMEJ | Veliparib | PARP | CAS 912444-00-9 Santa Cruz 394457 |
| Unknown | L755,507 | β3-adrenergic receptor | CAS 159182-43-1 Tocris 2197 |
| Cell Cycle | XL 413 | CDC7 | CAS 1169562-71-3 Tocris 5493 |

Shown in FIG. 1A is a comparison of HDR editing efficiency for cells treated with Nu7441, SCR7, or RS-1. The cells were transfected with four different ssODNs. $2\times10^5$ cells were used per reaction, and treated with 100 μM of donor DNA. These included ssODN1 (SEQ ID NO: 21), ssODN2 (SEQ ID NO: 22) and ssODN4 (SEQ ID NO: 24) that are complimentary to the DNA strand containing the a PAM sequence and ssODN3 (SEQ ID NO: 23) that is complimentary to the DNA strand not containing the PAM sequence. A concentrated stock solution of each inhibitor was prepared in DMSO and diluted to a final concentration of 2.5 μM Nu7441, 1.25 μM SCR7, or 10 μM RS-1. HDR efficiency was compared relative to treatment with DMSO alone or to treatment with RNP-only. The cells were treated with RNP containing 1 μM Cas9 and 1.5 μM sgRNA.

Figure 1B:
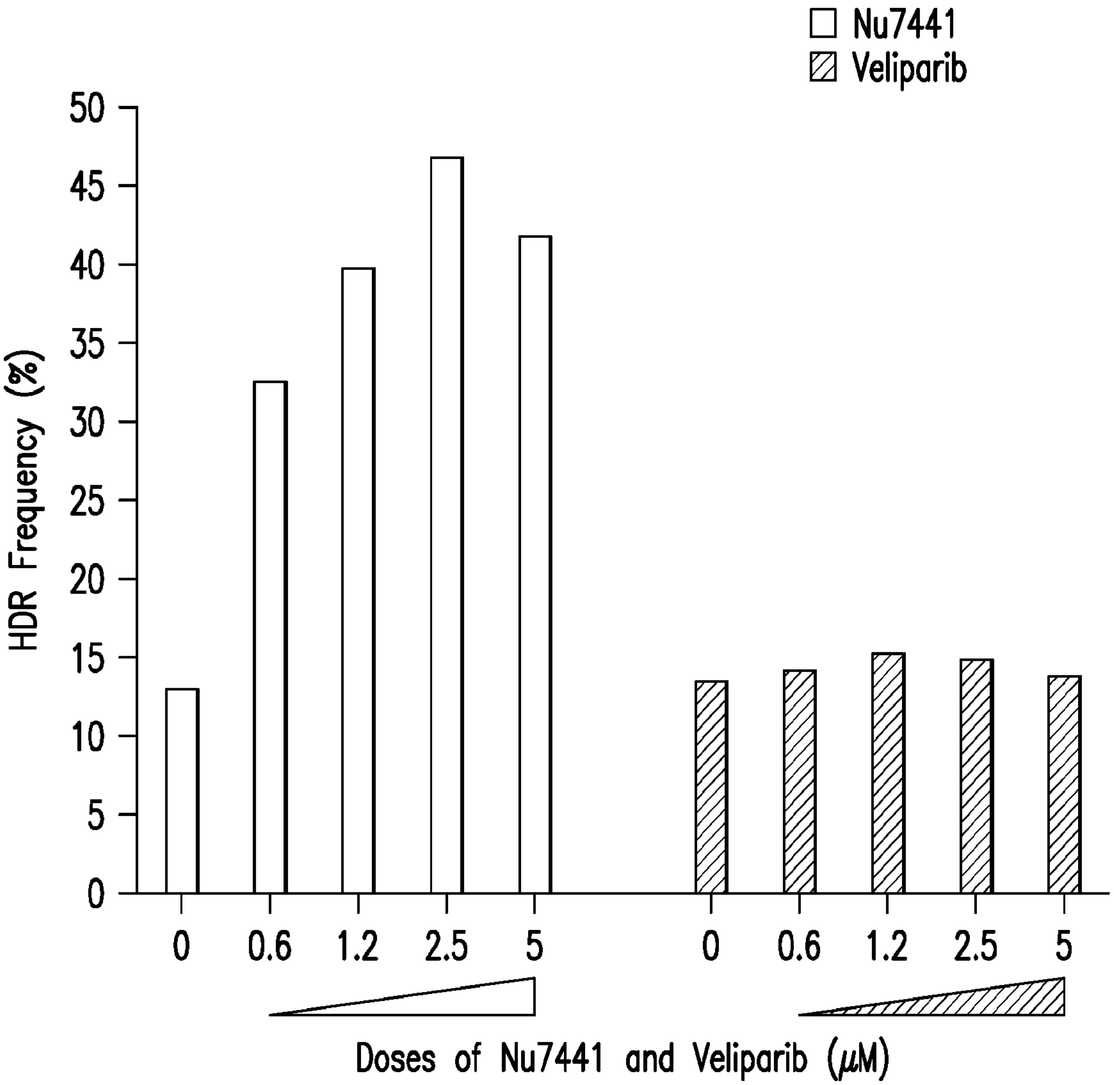
FIG. 1B shows HDR efficiency in the presence of Nu7441 or Veliparib (e.g., an inhibitor of PARP) with varied doses of inhibitor.
Figure 1C:
FIG. 1C shows HDR efficiency in the presence of Nu7441 or L755,507 (e.g., an inhibitor of β3-adrenergic receptor) using two different ssODN templates with varied doses of inhibitor.

As shown, no improvement in HDR efficiency was seen with treatment of SCR7 or RS-1 for any of the ssODN constructs tested. However, treatment with Nu7441 resulted in approximately 3-fold higher HDR efficiency for each of the ssODN constructs tested. The improvement in HDR efficiency for treatment with Nu7441 was dose-dependent as shown in FIG. 1B. Cells treated with high concentration of Nu7441 (2.5 μM) had an approximately 1.5-fold higher HDR efficiency than cells treated with low concentrations of Nu7441 (0.6 μM). This improvement with higher dose was seen for cells transfected with either ssODN 91-36 (SEQ ID NO: 26) or ssODN 91-61 (SEQ ID NO: 27) (FIG. 1C). In each case, treatment with concentrations of Nu7441 higher than 2.5 μM resulted in no further improvement in HDR efficiency.

Figure 1D:
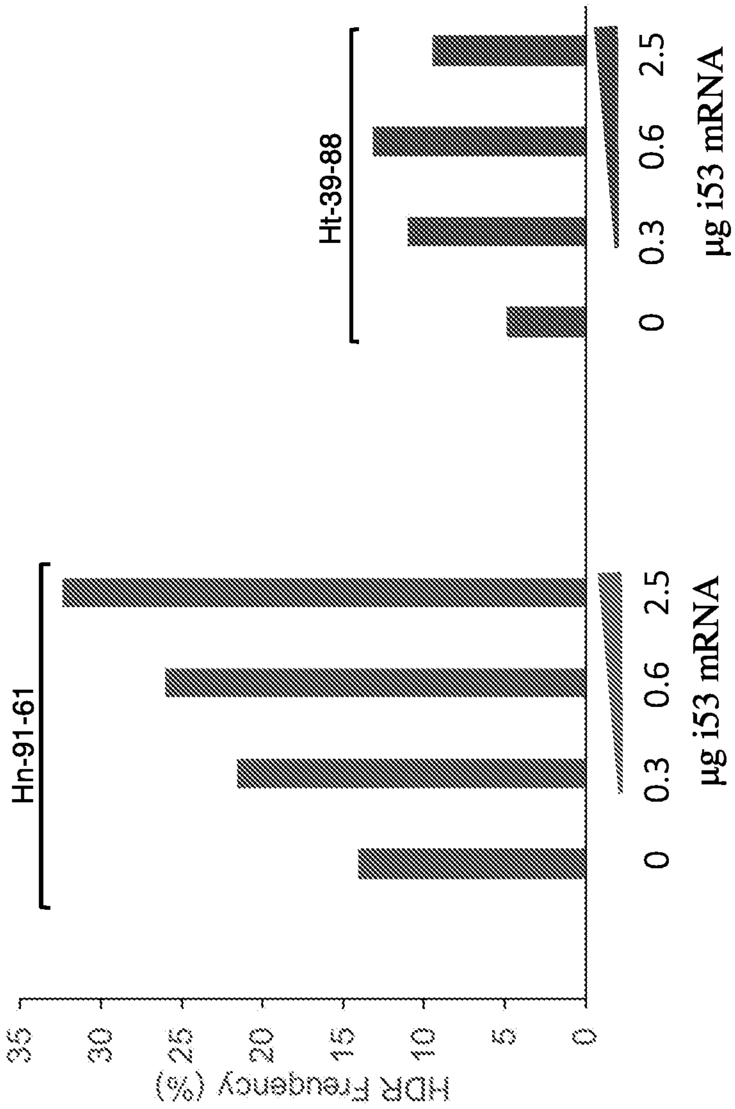
FIG. 1D shows HDR efficiency in the presence of the i53 polypeptide inhibitor of 53BP1 at varied doses using two different ssODN donors.

A protein inhibitor of 53BP1 was also evaluated for improved HDR efficiency. The choice of repair pathway for repair of a DNA DSB is largely controlled by an antagonism between p53-binding protein 1 (53BP1), a pro-NHEJ factor, and BRCA1, a pro-HDR factor (Chapman, J. et al. (2012) *Molecular cell* 47:497-510). 53BP1 promotes NHEJ repair over HDR repair by suppressing formation of 3' single-stranded DNA tails, which is the rate-limiting step in the initiation of the HDR pathway. Loss of 53BP1 has been shown to increase HDR efficiency, (Canny, M. et al. (2018) *Nat Biotechnol.* 36(1):95-102). Thus, inhibition of 53BP1 is expected to reduce DSB repair by the NHEJ pathway and favor repair by the HDR pathway. An inhibitor of 53BP1 is the i53 polypeptide (SEQ ID NO: 70). Using the same in vitro assay assessing increased HDR by a BFP to GFP gene conversion, the effect of inhibition of the i53 polypeptide inhibitor (SEQ ID NO: 70) was evaluated. HEK293 T cells were transfected with two different ssODNs homologous to the AAVS1 locus: Hn-91-61 (SEQ ID NO: 25) and Ht-39-88 (SEQ ID NO: 28). $2\times10^5$ cells were edited with 1 μM Cas9 and 1.5 μM sgRNA, and with 100 M ssODN. Cells were treated with different doses of an mRNA encoding the i53 polypeptide mRNA open reading frame encoding i53 polypeptide identified by SEQ ID NO: 69). HDR efficiency increased with treatment of mRNA encoding i53 as shown in FIG. 1D.

Additional molecules were tested for improved HDR efficiency by assessing a BFP to GFP gene edit that had no effect. Cells were treated with different concentrations of veliparib using ssODN identified by SEQ ID NO: 25, but no improvement in HDR efficiency was seen as shown in FIG. 1B. Cells were treated with different concentrations of L755,507 using either 91-36 ssODN (SEQ ID NO: 26) or 91-61 ssODN (SEQ ID NO: 27), but no improvement in HDR efficiency was seen as shown in FIG. 1C. Cells were treated with siRNA targeting DNA polymerase θ (Pol θ). However, no improvement in HDR efficiency was seen for any siRNA dose tested.

Example 2. Increased HDR and Decreased Indel Formation with Treatment by DNA PKcs Inhibitor Nu7441

The effect of DNA PK inhibition by Nu7441 correction of a DSB by the NHEJ pathway (e.g., introduce an indel at the DSB site) or HDR pathway (e.g., introduce a gene mutation encoded by a homology donor at the DSB site) was assessed using the reporter system described in Example 1. In this case gene-editing was evaluated in HEK293 T cells expressing GFP in the AAVS1 locus. To introduce a gene edit that converts GFP to BFP, cells were electroporated with ribonucleoprotein (RNP) comprised of Cas9 and gRNA1 (GFP target sequence identified by SEQ ID NO: 9; sgRNA spacer sequence identified by SEQ ID NO: 10) or gRNA2 (GFP target sequence identified by SEQ ID NO: 11; sgRNA spacer identified by SEQ ID NO: 12) that targets the GFP gene encoded in the AAVS1 locus. The cells were also transfected with ssODNs that encoded the gene correction necessary to convert GFP to BFP and homology arms complimentary to the sequence upstream and downstream of the target gene cut site. The efficiency of HDR repair was determined by measuring the level of cell BFP fluorescence. The efficiency of cutting (indel information) was monitored by TIDE analysis.

Figure 2A:
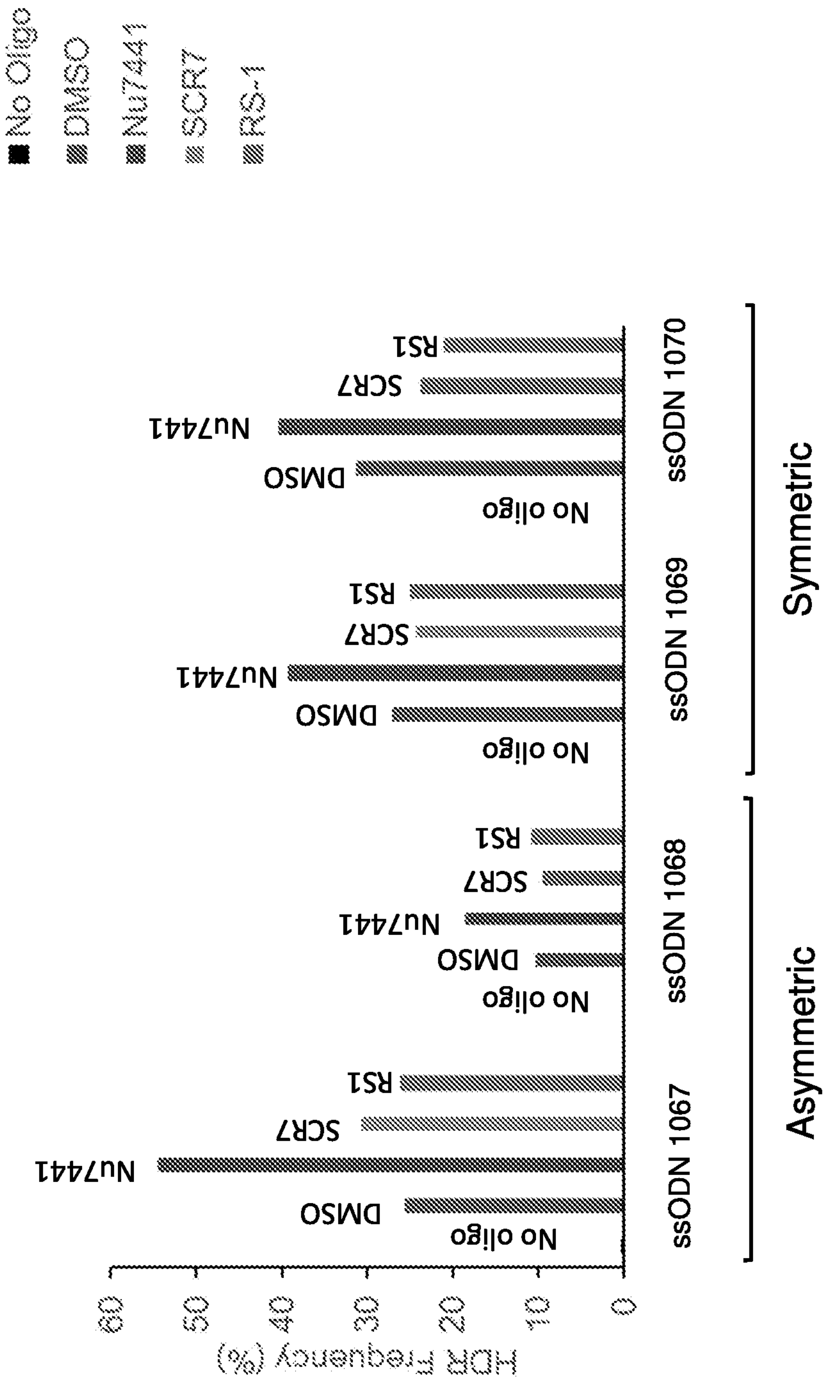
FIGS. 2A-2D include bar graphs showing editing in HEK293 T cells following electroporation with Cas9/sgRNA RNP using single-stranded oligodeoxynucleotide (ssODN) donor DNA that converts a gene in the AAVS1 locus encoding GFP to a gene encoding BFP in the presence of Nu7441, SCR7 or RS1.
Figure 2B:
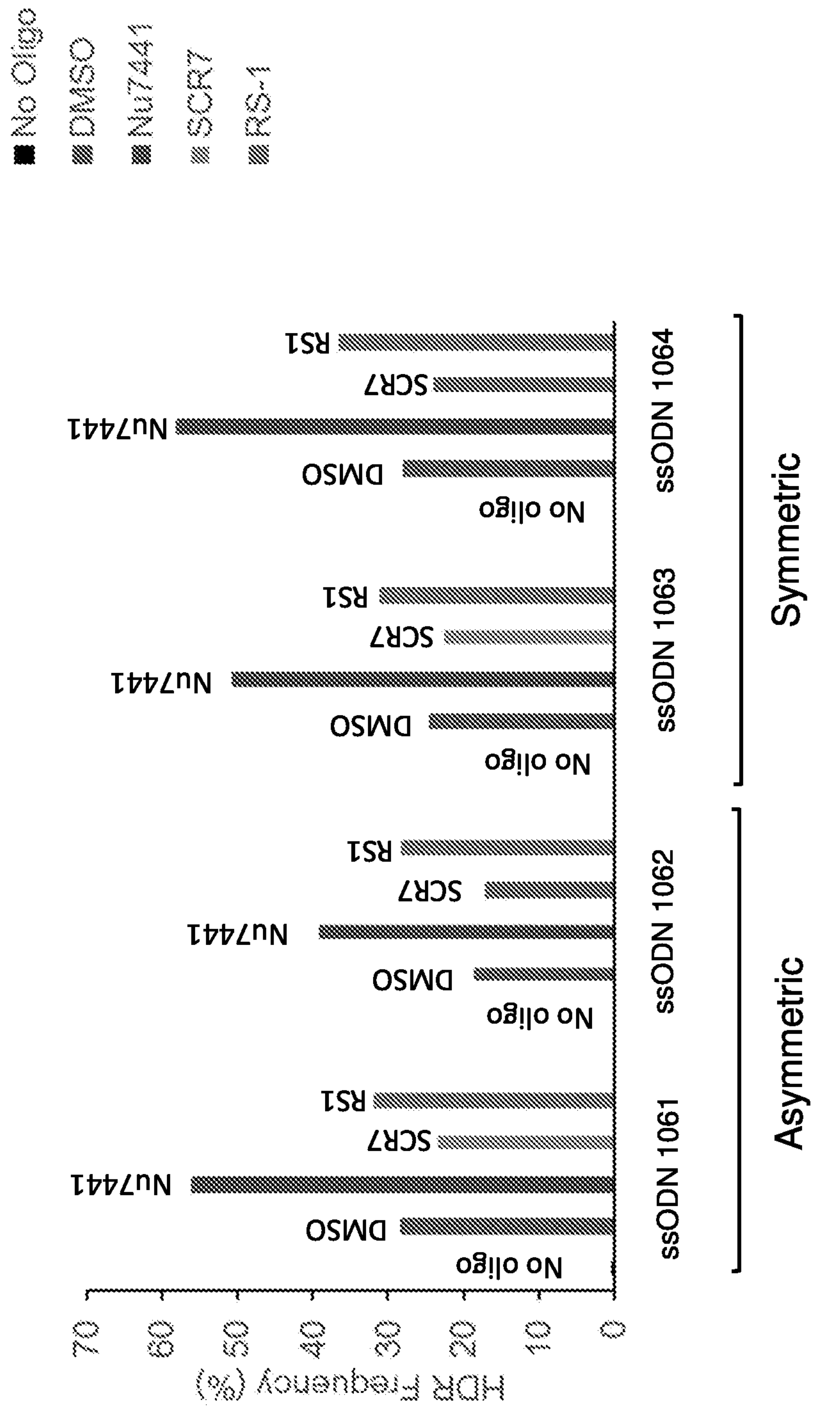

Shown in FIGS. 2A-2B is a comparison of HDR editing efficiency for cells treated with Nu7441, SCR7, or RS-1. Shown in FIG. 2A are cells were electroporated with RNP comprising Cas9 and gRNA1 (GFP target sequence shown in SEQ ID NO: 9; sgRNA spacer sequence identified by SEQ ID NO: 10). $2\times10^5$ cells were edited with 1 μM Cas9 and 1.5 μM gRNA1. The cells were transfected with four different ssODNs. These included ssODN 1067 (SEQ ID NO: 29) and ssODN 1069 (SEQ ID NO: 31) that are complimentary to the DNA strand containing the PAM sequence and ssODN 1068 (SEQ ID NO: 30) and ssODN 1070 (SEQ ID NO: 32) that are complimentary to the DNA strand not containing the PAM sequence. Cells were edited with 100 μM ssODN. A concentrated stock solution of each inhibitor was prepared in DMSO and diluted to a final concentration of 2.5 μM Nu7441, 1.25 μM SCR7, or 10 μM RS-1. HDR efficiency was compared relative to treatment with DMSO alone or to treatment with RNP-only. As shown, no improvement in HDR efficiency was seen with treatment of SCR7 or RS-1 for any of the ssODN constructs tested. However, treatment with Nu7441 resulted in improved HDR efficiency for each of the ssODN constructs tested FIG. 2A.

Shown in FIG. 2B are cells were electroporated with RNP comprising Cas9 and gRNA2 (GFP target sequence shown in SEQ ID NO: 11; sgRNA spacer sequence shown in SEQ ID NO: 12). The cells were transfected with four different ssODNs. These included ssODN 1061 (SEQ ID NO: 33) and ssODN 1063 (SEQ ID NO: 35) that are complimentary to the DNA strand containing the PAM sequence and ssODN 1062 (SEQ ID NO: 34) and ssODN 1064 (SEQ ID NO: 36) that are complimentary to the DNA strand not containing the PAM sequence. Similar to above, treatment with 2.5 μM Nu7441 resulted in improved HDR efficiency for each of the ssODN constructs tested FIG. 2A.

Figure 2C:
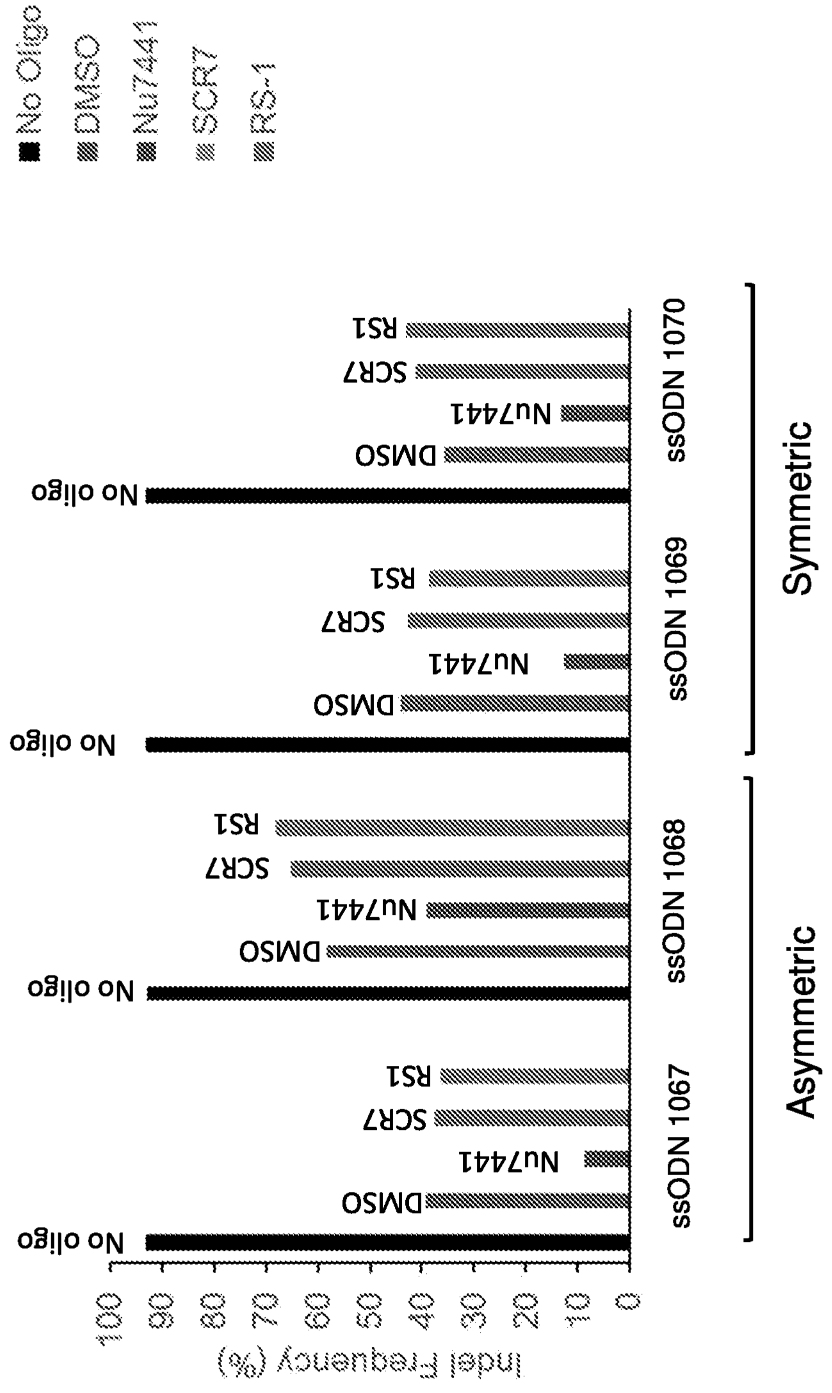
Figure 2D:
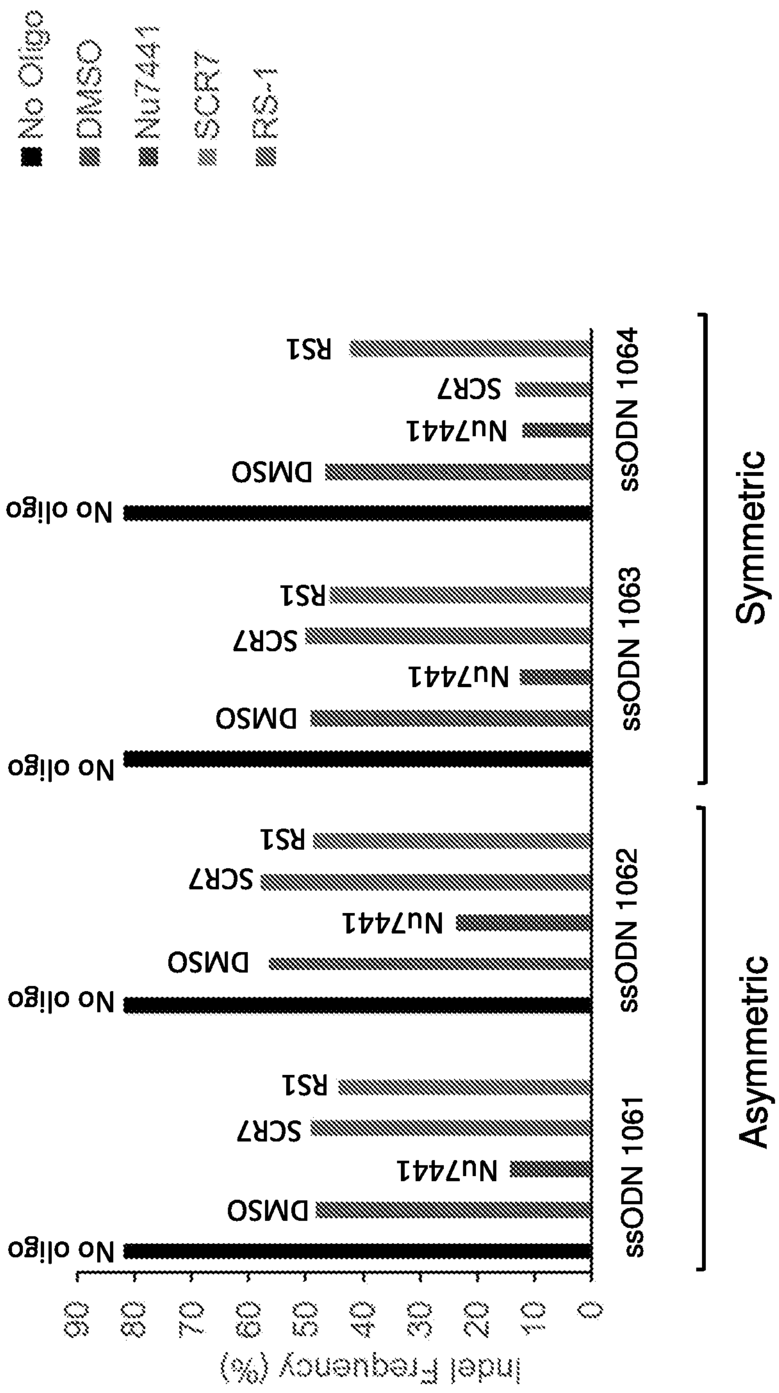

Shown in FIGS. 2C-2D is a measure of indel formation performed by TIDE analysis for the same edits that are described for FIGS. 2A-2B. Regardless of the ssODN or gRNA used, treatment with Nu7441 resulted in decreased indel formation at the DSB site, while treatment with SCR7 or RS-1 resulted in reduction compared to a DMSO control. Thus, the DNA PK inhibitor Nu7441 achieves reduced repair of a DSB by the NHEJ pathway when a homology donor is provided.

Figure 3:
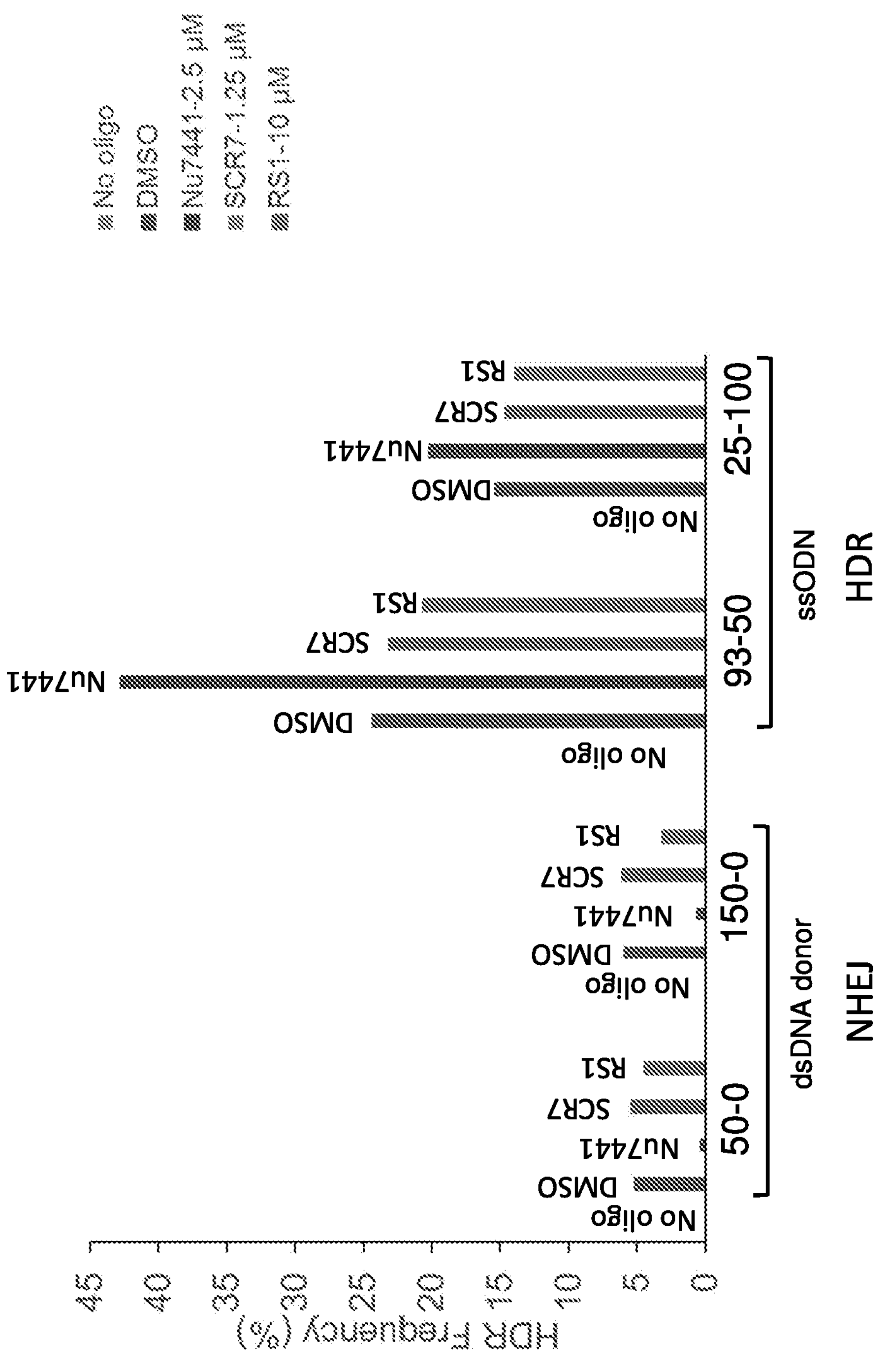
FIG. 3 includes a bar graph showing efficiency of gene insertion into the GSD1a locus in HEK293 T cells using either ssODNs as homology donors that facilitate HDR or dsDNA donors that facilitate NHEJ repair. Repair efficiency was evaluated in the presence of Nu7441, SCR7, or RS-1 using two different ssODN donor templates and two different dsDNA donor templates.

Having demonstrated improved HDR efficiency for a gene-edit in the AAV1 locus upon treatment with Nu7441, its effect on HDR for gene-editing at an additional gene locus was evaluated. HEK293 T cells were electroporated with RNP comprised of Cas9 and a gRNA targeting a sequence in the GSD1a locus shown in SEQ ID NO: 13 (spacer sequence identified by SEQ ID NO: 14). $2\times10^5$ cells were edited with 1 μM Cas9 and 1.5 μM gRNA. The cells were transfected with two different ssODNs homology donors: 93-50 (SEQ ID NO: 39) or 25-100 (SEQ ID NO: 40). These two ssODN donors contain homology arms spanning both sides of the double-stranded break induced by the Cas9-guide and facilitate correction of a point mutation in the G6PC gene sequence by HDR. Cells were edited with 100 μM ssODN. The cells were treated with 2.5 μM Nu7441, 1.25 μM SCR7, or 10 μM RS-1 and the effect on HDR efficiency was evaluated. While treatment with Nu7441 resulted in an approximately 1.7-fold increase in HDR efficiency over DMSO alone, treatment with SCR7 or RS-1 had no effect (FIG. 3).

The effect of Nu7441 treatment on gene correction by the NHEJ pathway was also evaluated. To do so, the cells were transfected with two different dsDNA donors: 50-0 (SEQ ID NO: 37) or 150-0 (SEQ ID NO: 38). Cells were edited with 1.5 g dsDNA donor. These dsDNA donors, lacking homology arms, introduce a second 3' splice site into exon 2 at the GSD1a locus when inserted into the cut site induced by the Cas9-guide complex by NHEJ repair. The cells were treated with 2.5 μM Nu7441, 1.25 μM SCR7, or 10 μM RS-1 and gene correction by NHEJ repair was evaluated. Treatment with Nu7441 resulted in a substantial decrease in gene correction for either dsDNA donor compared to treatment with DMSO alone, demonstrating that Nu7441 is inhibiting NHEJ repair following a Cas9/gRNA-mediated DNA DSB (FIG. 3). Treatment with SCR7 or RS-1 had no effect over DMSO alone.

Figure 4A:
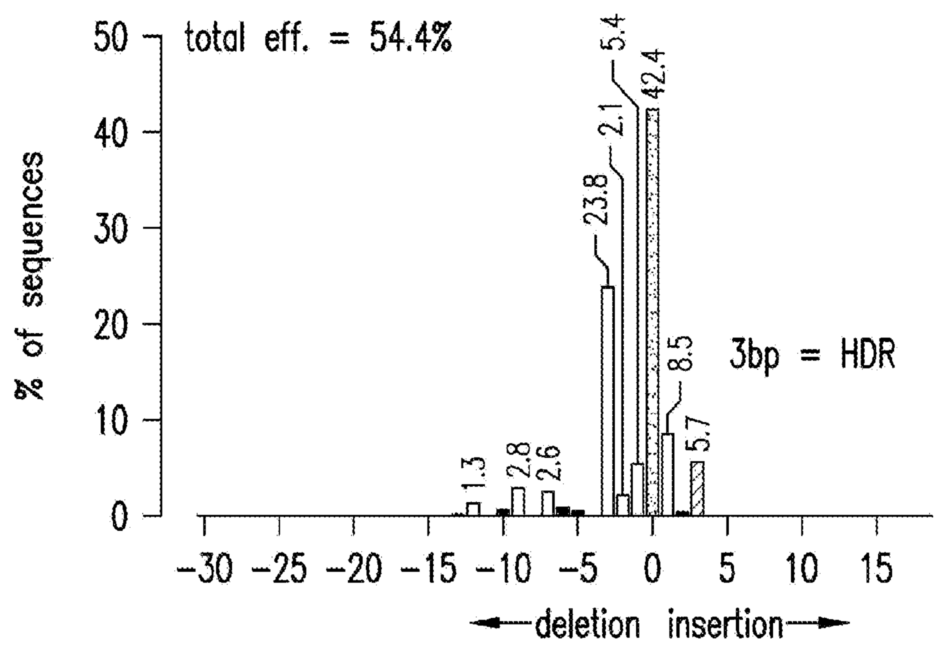
FIGS. 4A-4B include bar graphs showing mutations at the site of a DSB induced by Cas9/gRNA in the CFTR locus in HEK293 T cells resulting from DSB repair in the presence of a donor ssODN only (FIG. 4A) or donor ssODN and the DNA-PK inhibitor Nu7441 (FIG. 4B).
Figure 4B:
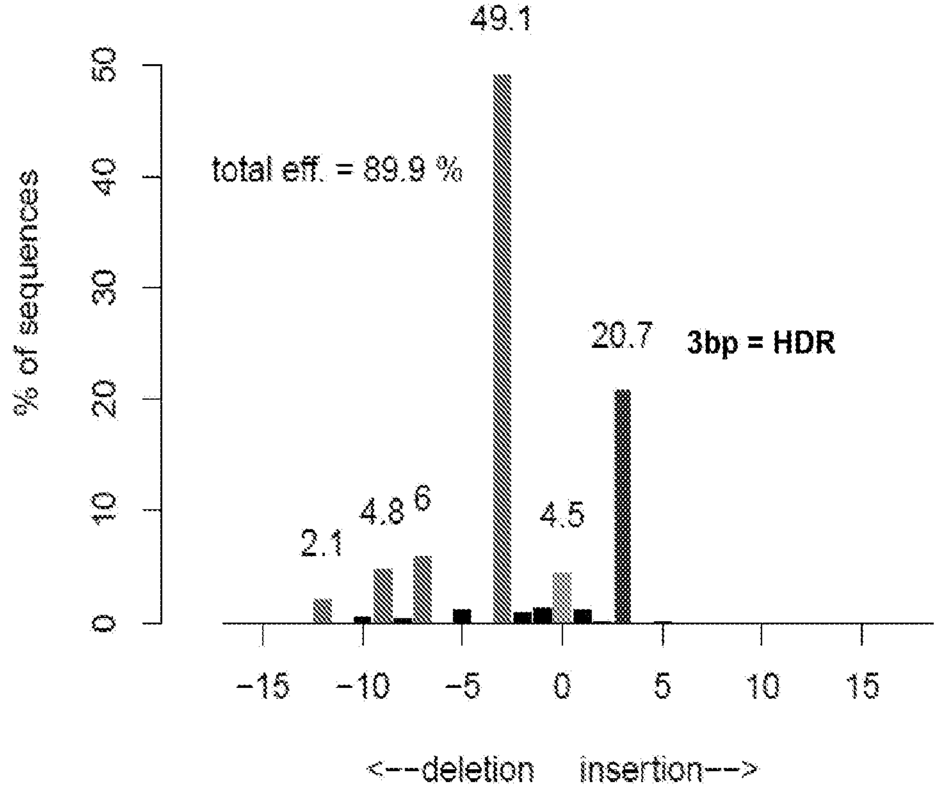
Figure 5:
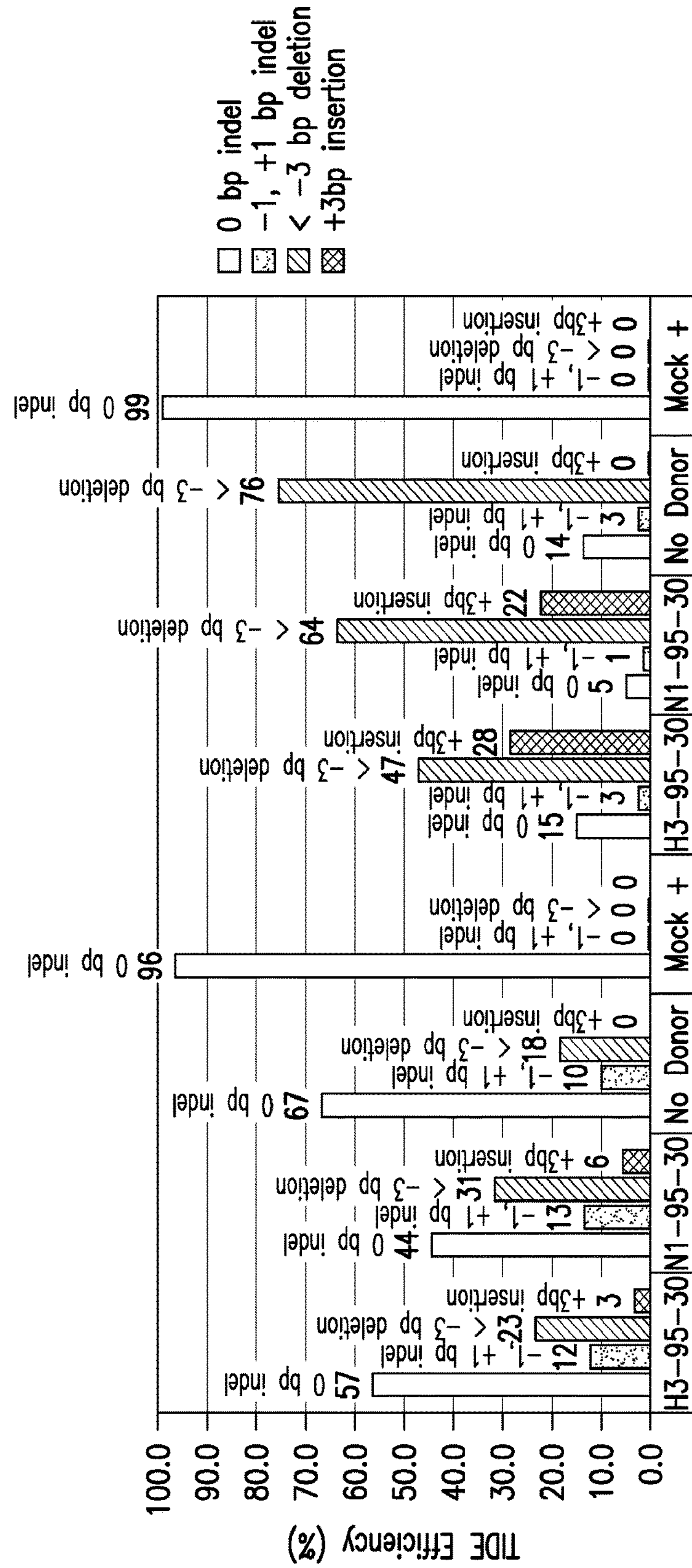
FIG. 5 include a bar graphs showing mutations at the site of DSB induced by Cas9/gRNA in the CFTR locus in HEK293 T cells resulting from DSB repair in the presence of donor ssODN H3-95-30 (SEQ ID NO: 41) or donor ssODN N1-95-30 (SEQ ID NO: 42) with treatment of Nu7441.Control cells are electroporated in the absence of gene-editing components or Nu7441 ("mock+DMSO").

The effect of Nu7441 treatment on HDR was also evaluated at the CFTR gene locus in HEK293 T cells. To do so cells were electroporated with RNP comprising Cas9 and a gRNA targeting the CFTR gene locus (SEQ ID NO: 18; sgRNA target sequence identified by SEQ ID NO: 19). $2\times10^5$ cells were edited with 1 μM Cas9 and 1.5 μM gRNA. The cells were transfected with a ssODN donor (SEQ ID NO: 42). Cells were edited with 100 μM ssODN. The ssODN contains homology arms spanning both sides of the DSB induced by the Cas9-guide and is designed to include 3 additional base pairs (GCA) into the CFTR gene to aid detection of HDR. Cells were also treated with 5 μM Nu7441. Gene correction was assessed by TIDE analysis. TIDE analysis uses a pair of PCR reactions and standard capillary sequencing runs to identify mutations induced at the site of a DSB (see e.g., Brinkman (2014) Nucleic Acids Res 42:e168). The type of mutation induced at the DSB was indicative of the pathway used to repair the DSB. Formation of an indel comprising either an insertion or a deletion of bases was considered due to NHEJ repair; a deletion of 2-3 base pairs was considered due to MMEJ repair; while an insertion of 3 base pairs was considered due to HDR repair. Shown in FIGS. 4A-4B are mutations introduced at the DSB for cells treated with Nu7441 (FIG. 4B) compared to a DMSO negative control (FIG. 4A). While indel formation (e.g., +1, 0, or −1 base pair) was high in the negative control (FIG. 4A), indicating high levels of NHEJ repair, indel formation was dramatically reduced in cells treated with Nu7441 (FIG. 4B). Additionally, cells treated with Nu7441 had much higher levels of HDR repair (+3 base pair insertion) at the DSB. This reduction in NHEJ repair in the presence of Nu7441 was evaluated with an additional ssODN donor (SEQ ID NO: 41). As shown in FIG. 5, treatment with either ssODN donor in the presence of Nu7441 resulted in decreased levels of indel formation due to NHEJ repair with a concurrent increase in HDR repair.

Together, these data demonstrate that treatment with Nu7441, a small molecule inhibitor of DNA PKcs, results in inhibition of NHEJ repair by CRISPR/Cas9 gene-editing and increased HDR editing efficiency at multiple gene loci.

Example 3. Efficient Gene Editing by HDR Using i53 at Multiple Gene Loci and in Multiple Cell Types Having demonstrated improved HDR efficiency with 53BP1 inhibition by the i53 polypeptide, its effect on HDR efficiency at the hemoglobin subunit beta (e.g., β-globin) (HBB) locus in CD34-expressing LT-HSPCs was investigated.

Frozen CD34-expressing LT-HSPCs derived from plerixafor (i.e., Mozibil®)+GCSF-dual mobilized peripheral blood obtained from healthy human donors were purchased from a commercial vendor. LT-HSPCs were maintained in culture media comprised of the reagents shown in Table 4 and were incubated at 37° C., 5% carbon dioxide, 4% oxygen. The cells were electroporated with RNP comprised of Cas9 and gRNA targeting the HBB locus (R02 gRNA, target sequence shown in SEQ ID NO: 15). $2\times10^5$ cells were edited with 3 g Cas9 and 3 g gRNA. The target gene sequence (including target sequence with PAM), R02 spacer sequence, and R02 sgRNA sequence are identified in Table 3.

TABLE 3

Sequences of R02 sgRNA

Figure 6A:
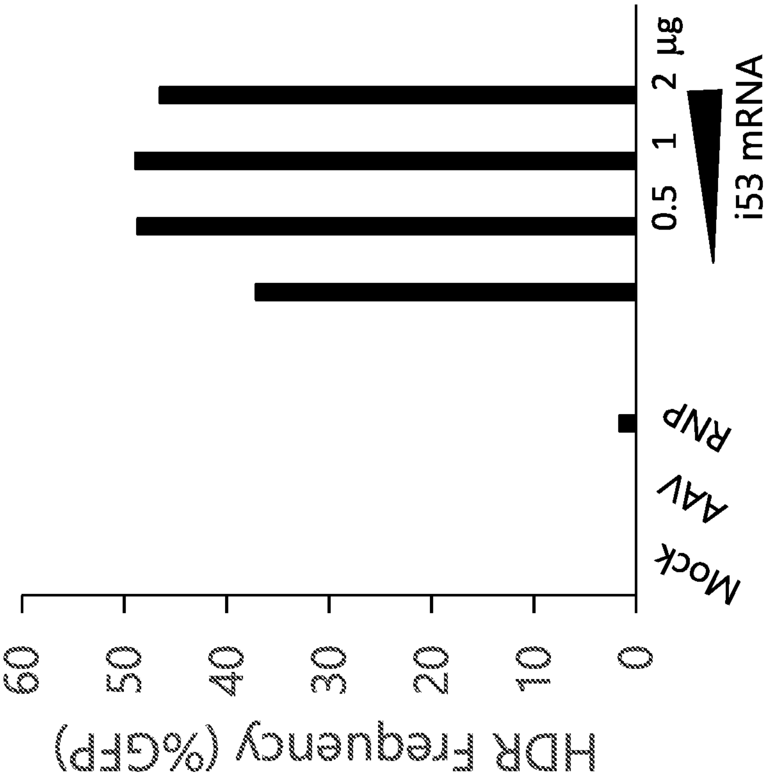
FIGS. 6A-6C include bar graphs showing HDR editing efficiency for insertion of donor DNA encoding GFP into the hemoglobin subunit beta (HBB) locus of CD34-expressing long-term repopulating hematopoietic stem cells (LT-HSPCs) using AAV-mediated delivery of donor DNA encoding GFP.

| Name/Description | Sequence | SEQ ID NO |
|---|---|---|
| HBB Target Sequence | CTTGCCCCACAGGGCAGTAA | 15 |
| HBB Target Sequence with PAM | CTTGCCCCACAGGGCAGTAACGG | 20 |
| R02 Spacer Sequence | CUUGCCCCACAGGGCAGUAA | 16 |
| R02 sgRNA (spacer in bold) | **csusus GCCCCACAGGGCAGUAA**GUUUUAGAGCUAGAAAUAGCAAGUUAAAAUAAGGCUAGUCCGUUAUCAACUUGAAAAAGUGGCACCGAGUCGGUGCusususU | 17 |

a, c, g, u: 2' O-methyl phosphorothioate nucleotides
s: phosphorothioate nucleotides
A, C, G, U, N: canonical RNA nucleotides The cells were transfected with a dsDNA homology donor encoding GFP under a SFFV promoter (SEQ ID NO: 60) that was delivered by AAV (SEQ ID NO: 56). Cells were edited with an AAV dose of 5,000 MOI. The HDR efficiency was determined by measuring the level of GFP fluorescence in the cells following electroporation. To determine the effect of 53BP1 inhibition on HDR efficiency, the 53BP1 inhibitor i53 was introduced as an mRNA-encoded protein to the cells during electroporation with Cas9/gRNA RNP and AAV DNA that serves as a donor for homology directed repair. As shown in FIG. 6A, treatment with mRNA encoding i53 polypeptide (SEQ ID NO: 70) resulted in an approximately 1.3-fold increase in HDR efficiency over cells treated with RNP+AAV-only. Additionally, improved HDR efficiency was seen at each dose of i53 mRNA tested (0.5, 1, and 2 g mRNA). No GFP expression over background was seen in cells treated with RNP-only or AAV-only.

TABLE 4

| Media components used to culture LT-HSPCs | |
|---|---|
| Component | Concentration |
| Thrombopoietin | 100 ng/mL |
| Fms-like tyrosine kinase 3 ligand | 100 ng/mL |
| Stem cell factor | 100 ng/mL |
| Interleukin-3 | 60 ng/mL |

Figure 6B:
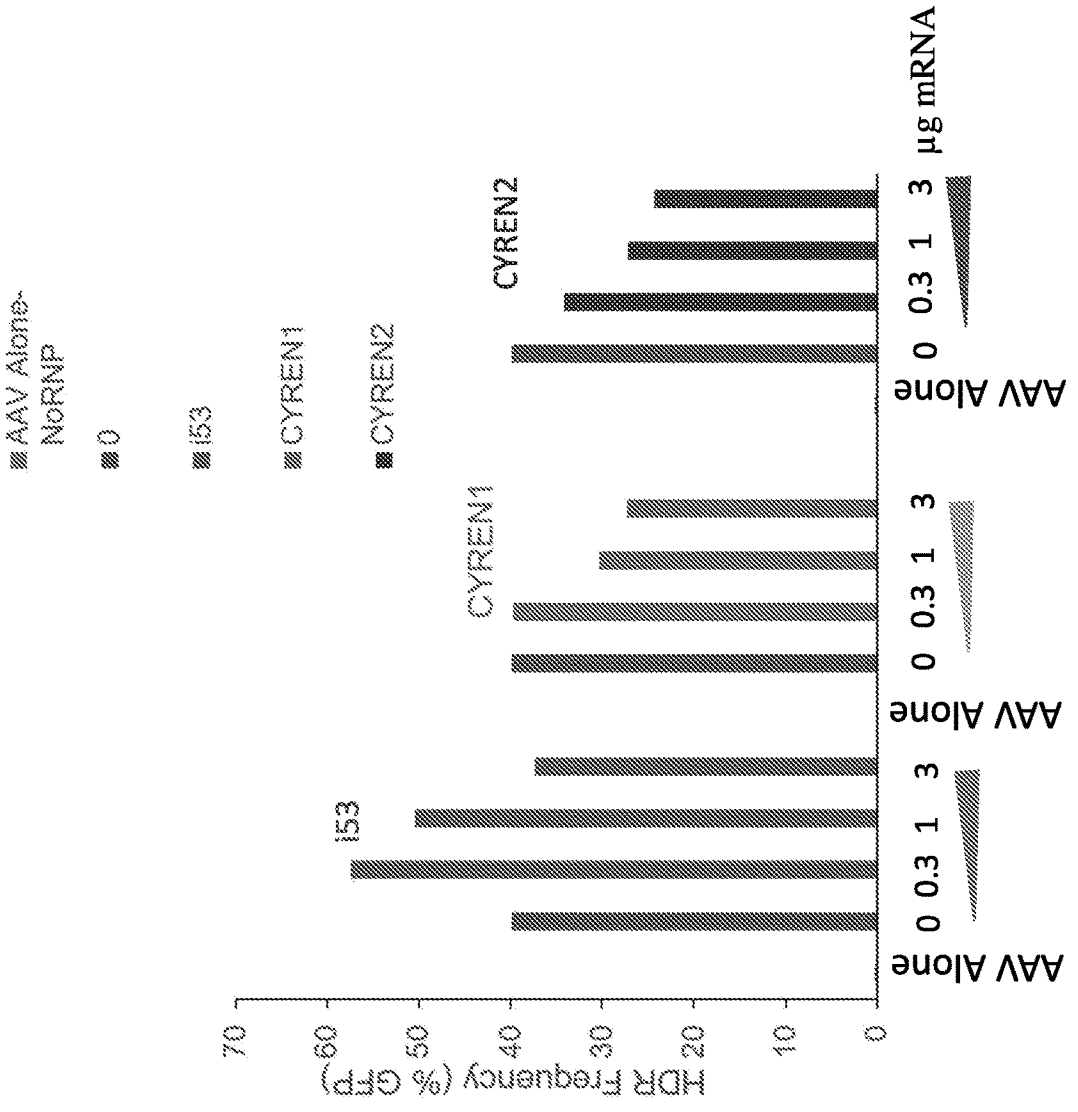

The effect of 53BP1 inhibition on HDR efficiency was compared to other mRNA-encoded proteins that inhibit the NHEJ pathway. These included the proteins CYREN1 and CYREN2 that inhibit Ku70/80, a heterodimer that binds DNA blunt ends to prevent processing of 3' single-stranded DNA tails necessary for HDR repair. Cells were electroporated with RNP, an AAV-GFP homology donor and mRNA encoding either i53 (mRNA ORF shown in SEQ ID NO: 69), CYREN1, or CYREN2. Treatment with i53 mRNA resulted in increased HDR efficiency when administered at 0.3 g or 1 g. Treatment with CYREN1 or CYREN2 mRNA resulted in no improvement in HDR efficiency over RNP+AAV-only (FIG. 6B).

An inhibitor of the cell division cycle7-related (CDC7) protein kinase was also evaluated for improved HDR editing of the HBB gene locus. CDC7 is an initiator of the G1/S transition. Inhibition of CDC7 using the small molecule XL413 has been shown to improve HDR efficiency by inducing an early S-phase cell cycle arrest (Wienert, B. et al. (2018) bioRxiv 500462). However, for gene-editing of the HBB locus in LT-HSPCs, no improvement in HDR efficiency was seen for any dose of XL413 tested (data not shown).

Figure 6C:
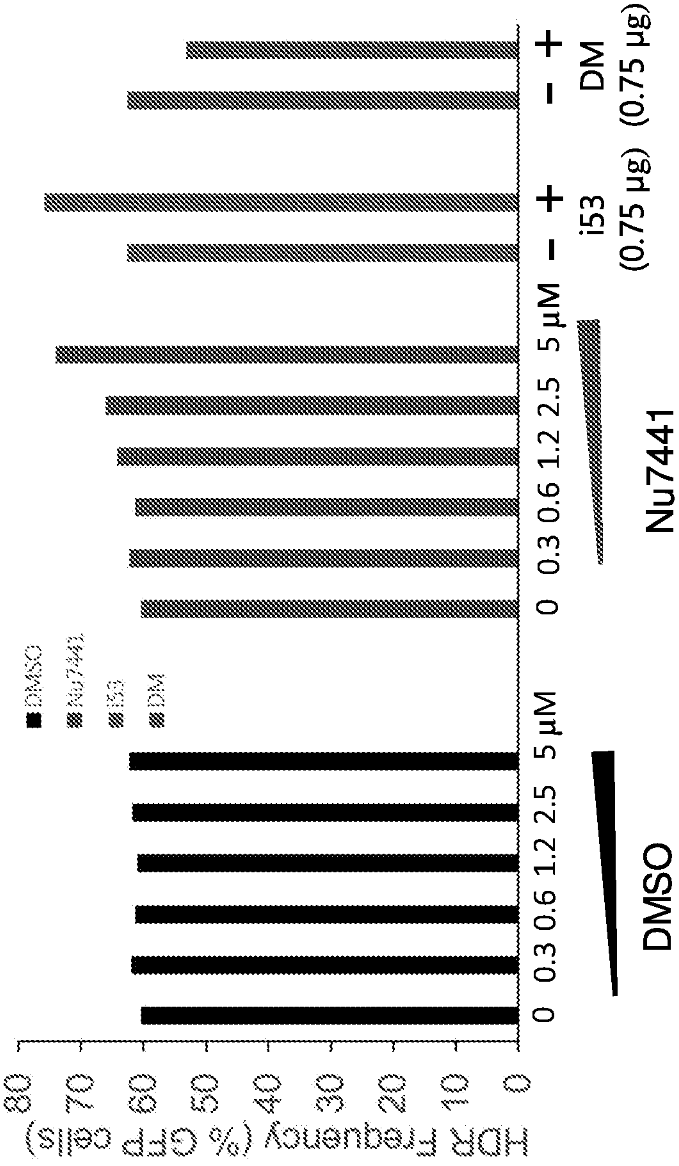

The effect of treatment with i53 and Nu7441 was compared for improving efficiency of HDR repair of the HBB locus. Cells were treated with different doses of Nu7441 or with mRNA encoding i53 (ORF shown by SEQ ID NO: 69). A comparable increase in HDR efficiency was seen upon treatment with 0.75 g of mRNA encoding i53 and 5 μM Nu7441 (FIG. 6C). No improvement in HDR efficiency was seen with treatment of a mRNA encoding a non-functional mutant i53 (e.g, DM, mRNA ORF shown by SEQ ID NO: 71).

Figure 7:
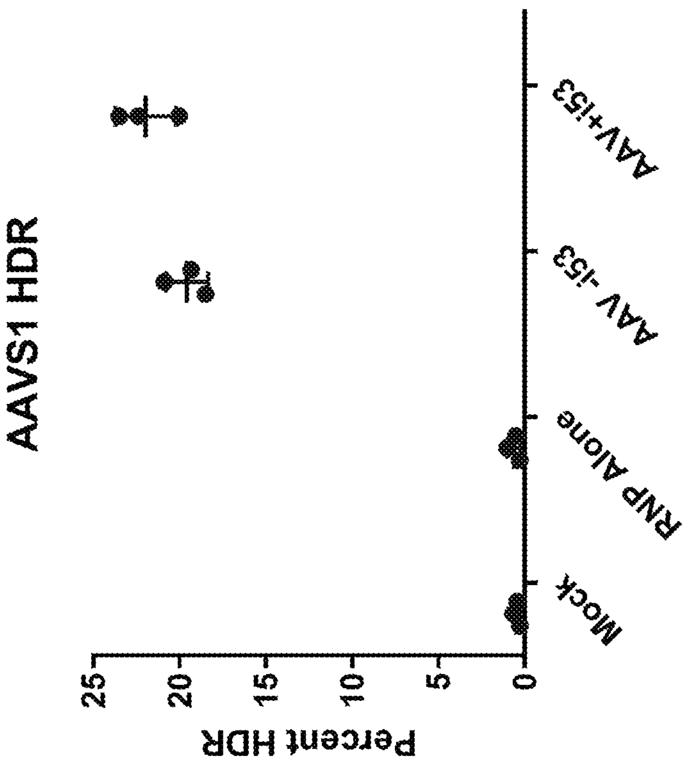
FIG. 7 includes a dot plot showing HDR editing efficiency with treatment of i53 for insertion of donor DNA encoding GFP delivered by AAV into the AAVS1 locus of hTERT RPE-1 cells.

The effect of treatment of i53 on HDR efficiency was evaluated in additional cell types, including editing of the AAVS1 locus in human epithelial cells immortalized with hTERT (hTERT RPE-1, ATCC CRL-4000) cells. RPE1 cells were lipofected with RNP comprised of Cas9 protein and gRNA targeting the AAVS1 locus (target sequence shown in SEQ ID NO: 3; spacer sequence shown in SEQ ID NO: 4). Cells were edited with 1 g Cas9 and 1 g gRNA. Cells were infected with AAV containing homology donor DNA encoding GFP (DJ serotype) as well as mRNA encoding i53 (mRNA ORF shown in SEQ ID NO: 69). Cells were edited with an AAV dose of 25,000 MOI. HDR efficiency was determined by measuring the level of GFP fluorescence in the cells following gene-editing. Treatment of cells with AAV and mRNA encoding i53 results in an increase in HDR efficiency over treatment with AAV alone (FIG. 7).

Figure 8:
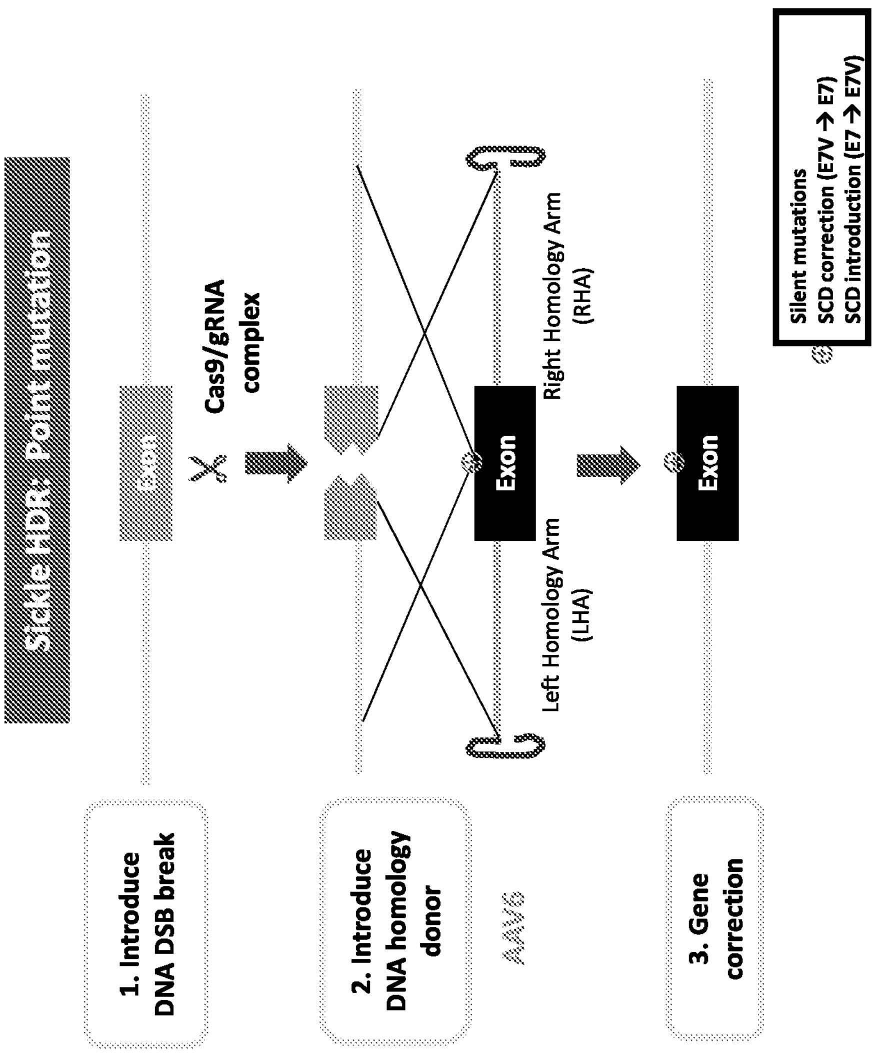
FIG. 8 includes a schematic showing editing of the HBB locus using a homology DNA donor to introduce a sickle cell correction mutation by HDR repair of a DNA DSB formed by Cas9/gRNA complex.

Example 4. Efficient Gene Editing of the Hemoglobin Beta Subunit (HBB) Locus in CD34-Expressing LT-HSPCs Using i53 In Vitro Improved HDR efficiency for CRISPR/Cas9 gene-editing of the HBB locus with i53 treatment in CD34-expressing LT-HSPCs was evaluated with donor DNA encoding a sickle cell mutation. A sickle mutation is a change of a GAG codon encoding Glu at position 7 of the beta-globin protein to a GUG codon encoding Val (codon 7 of the HBB open reading frame; E7V mutation). FIG. 8 shows editing of the HBB locus using a Cas9/gRNA complex to introduce a site-specific DSB into exon 1. The homology donor DNA provided introduces a gene correction into exon 1 when repair of the DSB occurs by the HDR pathway. For wild type cells, a homology donor DNA encoding a sickle cell mutation (E7V) can be provided to introduce the sickle mutation into the HBB gene. For cells with the sickle cell mutation, a homology donor DNA encoding a sickle cell correction (E7) can be provided to introduce a sickle correction to the HBB gene.

Figure 9:
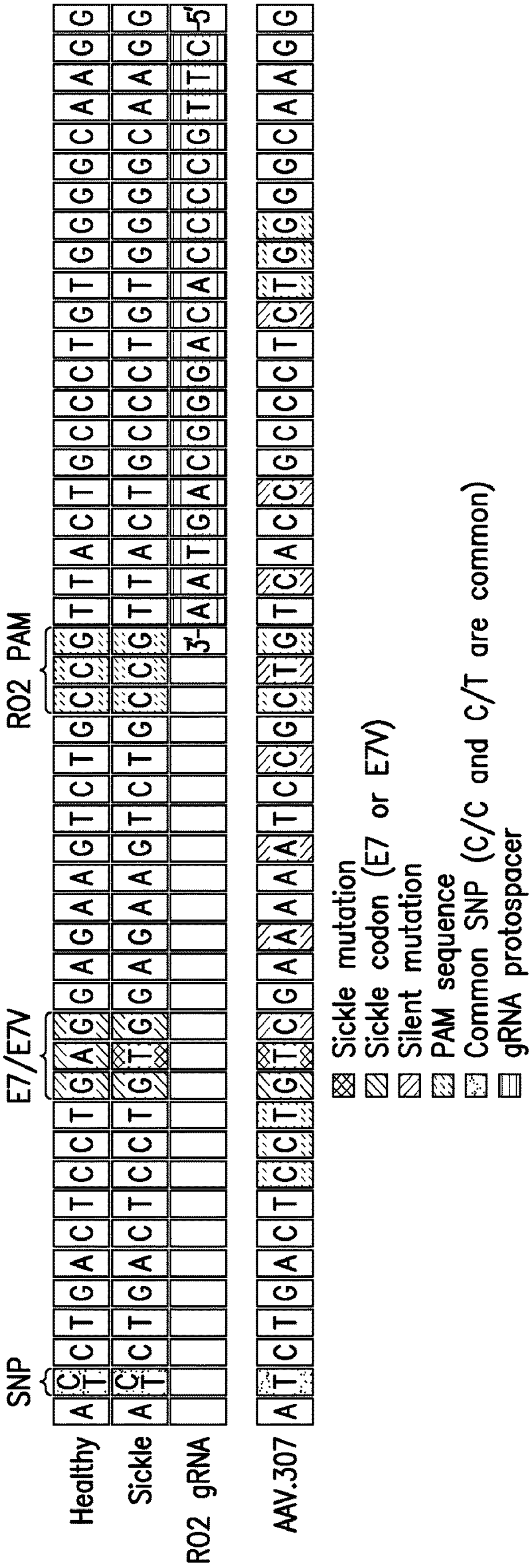
FIG. 9 includes a schematic showing the sequence near the site of Cas9/gRNA gene editing within the HBB locus. Included is the sequence for a wild type gene (SEQ ID NO: 113) and for a sickle cell mutant gene (SEQ ID NO: 114). The sequence targeted by the gRNA is highlighted (RO2 gRNA, SEQ ID NO: 115), as well as the sequence of the donor DNA that includes the sickle cell mutation (AAV.307 donor, SEQ ID NO: 116). Silent mutations encoded by the donor DNA are annotated.

LT-HSPCs were maintained in culture and gene-editing was performed following two days of culture. Cells were electroporated with RNP comprised of Cas9 and gRNA targeting the HBB locus (R02 gRNA, target sequence shown by SEQ ID NO: 15). $1\times10^6$ were edited per reaction using 20 g Cas9 and 20 g gRNA. The cells were electroporated with 1 g mRNA encoding i53. Electroporation was performed using the Maxcyte HSC-3 program. AAV encoding homology donor DNA (AAV.307) was administered prior to electroporation (pre-EP). Cells were edited with an AAV dose of 10,000 MOI. The donor DNA comprised homology arms to the HBB locus and encoded a sickle cell mutation (SEQ ID NO: 53). FIG. 9 shows the sequence of the HBB gene in the region of the gene edit as well as the sickle cell mutation that is introduced following gene editing. The downstream PAM recognition site on the HBB locus is indicated, as well as the sequence recognized by the R02 gRNA spacer. Additionally, a portion of the sequence of the AAV.307 homology donor DNA is shown, including gene changes that are incorporated into the HBB locus by HDR editing. The homology donor incorporates an edit to the PAM sequence to prevent re-cutting of the HBB locus by Cas9/gRNA following editing by HDR. Sequences of the AAV.307 donor are provided in Table 5.

TABLE 5

| Sequence of AAV.307 Homology Donor | |
|---|---|
| Name/Description | SEQ ID NO |
| 5' ITR | 112 |
| Left Homology Arm (LHA) | 52 |
| Gene-edit (E7 → E7V) | 53 |
| Right Homology Arm (RHA) | 54 |
| 3' ITR | 107 |
| LHA to RHA | 110 |
| AAV.307 | 111 |

Figure 10:
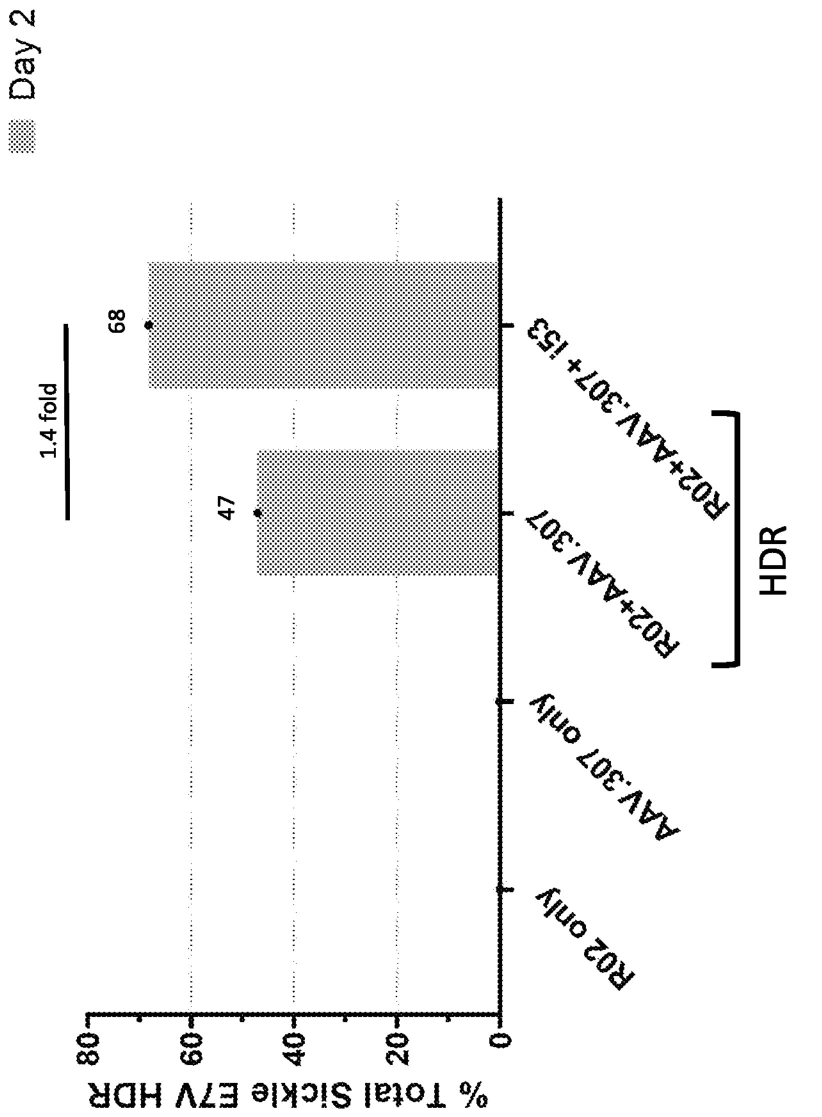
FIG. 10 includes a bar graph showing HDR editing efficiency for insertion of donor DNA encoding a sickle cell mutation into the HBB locus of CD34-expressing HSPCs using AAV-mediated delivery of donor DNA. Shown is a comparison of HDR efficiency in the presence of i53 relative to RNP+AAV-only, AAV-only, or RNP-only.

HDR efficiency at the HBB locus was evaluated upon treatment with i53. For assessing frequency of E7V modification of the HBB allele in samples of edited cells, a next-generating sequencing (NGS) assay using three PCR reactions was performed Cells were treated with AAV (e.g., AAV.307) and RNP (e.g., Cas9/R02 gRNA) and treated with 1 g of mRNA encoding the i53 polypeptide (SEQ ID NO: 70). Treatment with i53 resulted in 68% incorporation of the E7V gene edit, an increase of 1.4-fold over RNP+AAV alone (FIG. 10).

Figure 11:
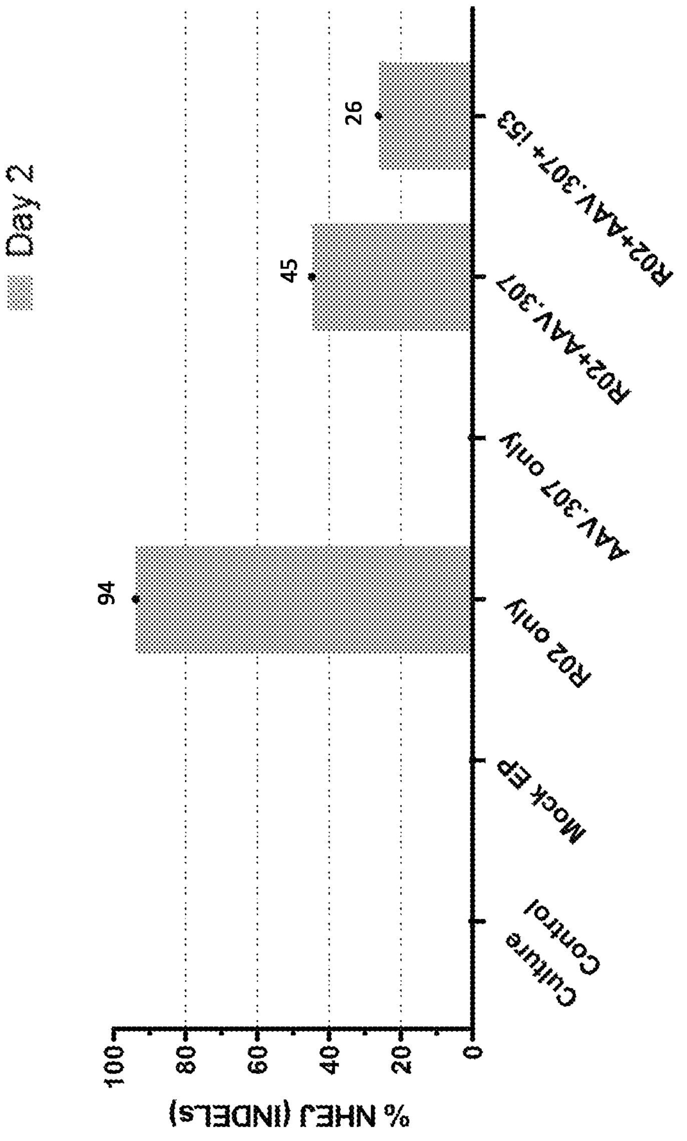
FIG. 11 includes a bar graph showing NHEJ editing efficiency within the HBB locus in CD34-expressing LT-HSPCs following electroporation with gRNA/Cas9 RNP and transfection with a homology DNA donor delivered by AAV. Treatment with i53 is compared to RNP+AAV-only, AAV-only, RNP-only, and mock electroporation (e.g., no RNP or AAV).
Figure 12A:
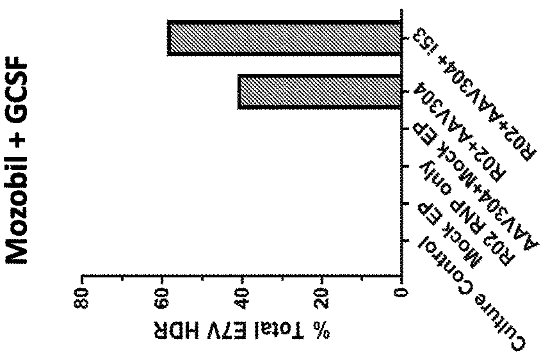
FIGS. 12A-12B include bar graphs showing HDR editing efficiency for insertion of donor DNA encoding a sickle cell mutation into the HBB locus of CD34-expressing LT-HSPCs using AAV-mediated delivery of donor DNA.
Figure 12B:
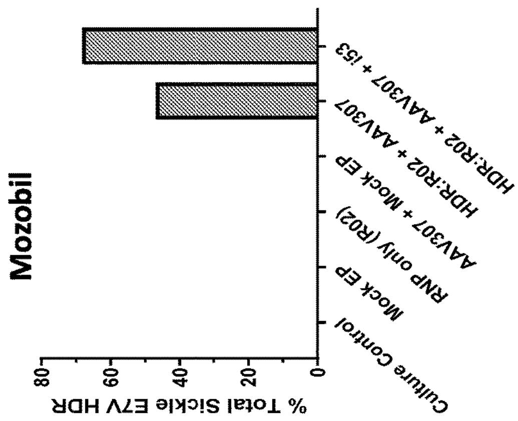

Editing efficiency at the HBB locus was evaluated by measuring indel formation by TIDE analysis. Electroporation of CD34-expressing LT-HSPCs with RNP comprised of Cas9 and R02 gRNA resulted in 94% indel formation, demonstrating the Cas9/gRNA yields high cutting efficiency within the desired target gene (FIG. 11). Notably, the level of indel formation decreased for cells treated with RNP+AAV. The lowest level of indel formation was seen for cells treated with RNP+AAV in the presence of i53, indicating that as the repair pathway shifts towards HDR, indel formation by the NHEJ pathway decreases. This group had 1.7-fold reduction in INDEL frequency relative to cells treated with RNP+AAV, The effect of i53 on HDR efficiency was evaluated for CD34-expressing LT-HSPCs isolated from human peripheral blood using different mobilization methods. HDR efficiency was evaluated for LT-HSPCs isolated from human donors following administration of either Mozobil+GCSF or Mozobil-alone and gene-edited with AAV+RNP with or without inclusion of mRNA encoding the i53 polypeptide (SEQ ID NO: 70). Editing was performed by electroporation with RNP containing 20 g Cas9 and 20 μg R02 gRNA and homology donor with a E7V mutation encoded by AAV (AAV.307 or AAV.304 comprising a gene-edit identified by SEQ ID NO: 50) at a dose of 10,000 MOI. Treatment with i53 resulted in approximately 60% incorporation of the sickle cell gene-edit by HDR in cells isolated by Mozobil+GCSF, approximately 1.5-fold increase in HDR efficiency over treatment with RNP+AAV alone (FIG. 12A). HDR efficiency in LT-HSPCs isolated using Mozobil and treated with i53 was even higher, with approximately 70% of cells incorporating the sickle cell gene-edit (FIG. 12B). These results demonstrate that by isolating LT-HSPCs from healthy donors using mobilization by Mozobil, along with editing in the presence of i53, high levels of HDR efficiency are achieved.

Figure 13:
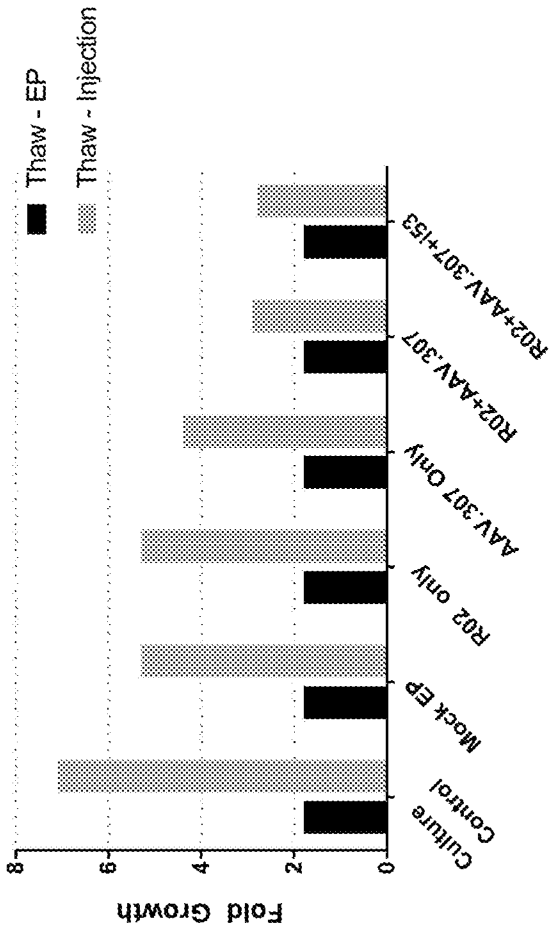
FIG. 13 includes a bar graph showing growth of CD34-expressing LT-HSPCs during ex vivo culture following gene editing with Cas9/gRNA RNP and AAV, either with or without treatment of i53.

The growth of CD34+ cells from the time the cells were thawed to right before they were subjected to editing conditions (black bars) was evaluated and no changes in cell growth were observed. Manipulations of the cells by the addition of CRISPR reagents used for editing caused a decrease in the fold growth between when they were thawed and injected into mice (blue bars) (FIG. 13).

Example 5. Evaluation of LT-HSPCs Edited with i53 Following Administered In Vivo As described above, HDR efficiency for editing the HBB locus in CD34-expressing LT-HSPCs is improved in the presence of i53. The effect of gene-editing with i53 was evaluated on the ability of the cells to engraft and retain the gene-edit following administration in vivo. Also evaluated was the effect of LT-HSPC dose on engraftment following administration in vivo.

Figure 14:
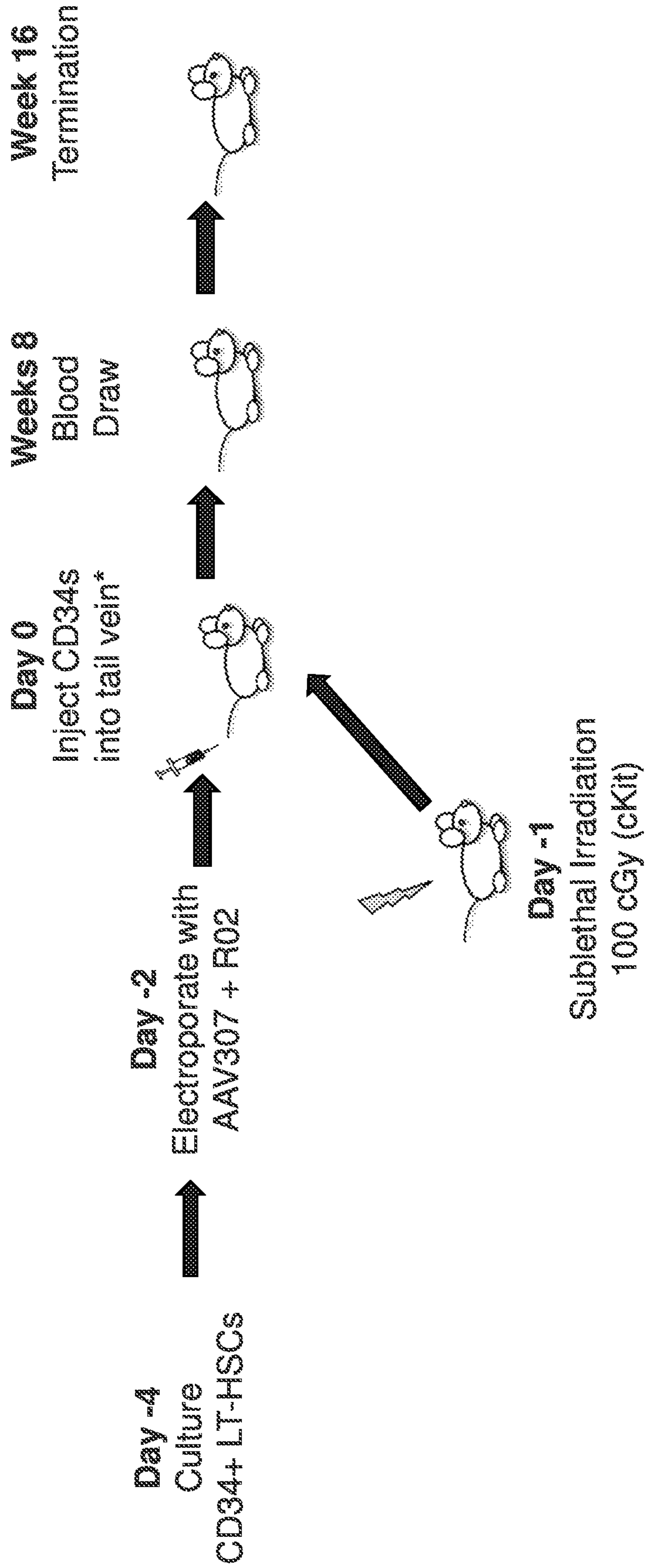
FIG. 14 includes a schematic showing a schedule for administration of gene-edited CD34-expressing LT-HSPCs into irradiated mice and subsequent analysis of mouse tissues for engraftment and HDR editing efficiency.

Human LT-HSPCs were administered to mice following electroporation with Cas9/gRNA (R02 gRNA, target sequence identified in SEQ ID NO: 15) and AAV encoding a sickle cell mutation (E7V) as shown in FIG. 14. Briefly, LT-HSPCs were mobilized from healthy donors using plerixafor. LT-HSPCs were gene-edited following 2 days in culture under conditions described in Example 3. To perform the gene-edit, cells were electroporated with RNP comprised of Cas9 and gRNA targeting the HBB locus (e.g., R02 gRNA, target sequence SEQ ID NO: 15) and homology donor DNA encoding a sickle cell mutation delivered by AAV (e.g., AAV.307). $1\times10^6$ cells were edited with 20 g Cas9, 20 g gRNA and an AAV dose of 10,000 MOI. The cells were incubated with AAV.307 for 1 hour prior to electroporation. Effect of gene-editing with i53 was determined by treating cells with mRNA encoding i53 polypeptide (SEQ ID NO: 70) during electroporation. Cells were edited with 1 g mRNA.

The cells were administered by intravenous injection to cKit mice at 2 days following electroporation. Recipient mice were treated with sublethal irradiation (100 cGy) at 1 day prior to administration of LT-HSPCs to eliminate hematopoietic cells in the bone marrow and enable engraftment of the donor cells. Animals were evaluated for presence of human hematopoietic cells in peripheral blood at 8 and 16 weeks following LT-HSPC administration. The bone marrow was also evaluated for engraftment and maintenance of the HBB gene-edit at 16 weeks following LT-HSPC administration.

Figure 15:
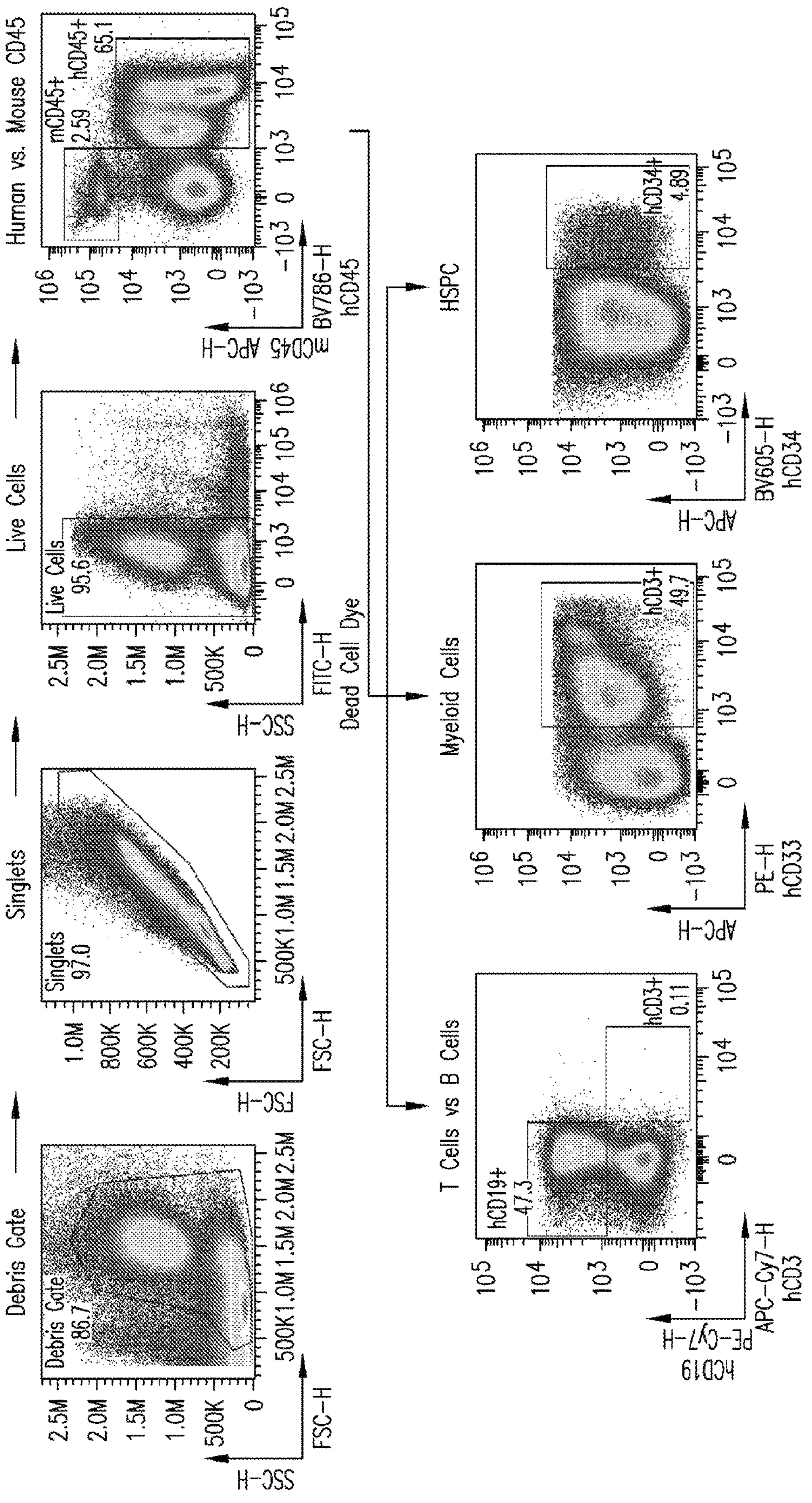
FIG. 15 includes scatter plots showing a flow cytometry gating strategy for quantification and lineage analysis of mouse tissue samples for cells derived from engrafted human LT-HSPCs.

Presence of human hematopoietic cells was measured by flow cytometry in mouse blood or bone marrow samples. The antibodies used for labeling cell-surface markers are shown in Table 6. The gating strategy used to quantify cells by flow cytometry is shown in FIG. 15. Cells were gated on singlet, live cells. Mouse and human CD45-expressing hematopoietic cells were distinguished by antibodies targeting mouse or human CD45. Engraftment was measured as percent chimerism which was defined as the quantity of human CD45 positive cells divided by the total number of CD45 positive cells (e.g., human and mouse CD45 expressing cells combined). The lineage of human CD45 positive cells was determined using markers for CD19 (e.g., B cells), CD3 (e.g., T cells), CD33 (e.g., myeloid cells), and CD34 (hematopoietic stem/progenitor cells (HSPCs)).

TABLE 6

| Antibody | Clone | Fluorophore | Catalog # |
|---|---|---|---|
| Anti-mouse CD45 | 30-F11 | APC | 103112 |
| Anti-human CD45 | HI30 | BV786 | 563716 |
| Anti-human CD19 | HIB19 | PE-Cy7 | 302216 |
| Anti-human CD3 | UCHT1 | APC-Cy7 | 300426 |
| Anti-human CD33 | P67.6 | PE | 366608 |
| Anti-human CD34 | 581 | BV421 | 562577 |

Figure 16:
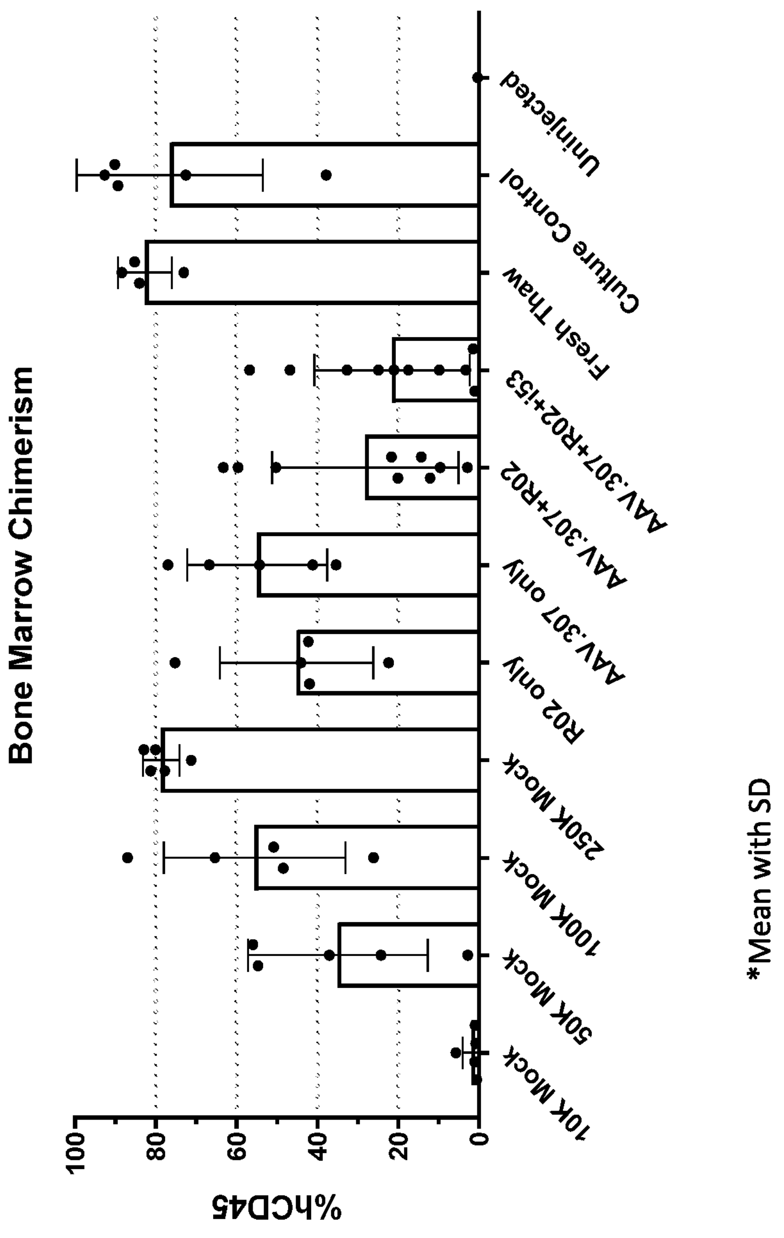
FIG. 16 includes a bar graph showing % chimerism of human cells derived from engrafted LT-HSPCs in mouse bone marrow samples isolated at 16 weeks post-engraftment. CD34-expressing LT-HSPCs were administered to mice according to FIG. 14

The effect of titrating the dose of LT-HSPCs on percent chimerism was evaluated in mouse bone marrow samples collected at 16 weeks following administration of LT-HSPCs. Animals received a dose of $0.01\times10^6$, $0.05\times10^6$, $0.1\times10^6$, or $0.25\times10^6$ LT-HSPCs that were treated with electroporation, but neither AAV or RNP. As shown in FIG. 16, increasing the dose of LT-HSPCs administered to the animals resulted in increased levels of chimerism. Administration of $0.25\times10^6$ LT-HSPCs resulted in approximately 80% human cells within all CD45-expressing cells in the bone marrow. The effect of treatment of i53 on percent chimerism was also evaluated in mouse bone marrow collected at 16 weeks following administration of LT-HSPCs. Animals received a dose of $0.25\times10^6$ LT-HSPCs that were gene-edited with RNP+AAV either with or without i53. Percent chimerism for cells treated with RNP+AAV was lower than for cells treated with RNP-only or AAV-only (FIG. 16). Inclusion of i53 resulted in no further decrease in chimerism compared to AAV+RNP alone.

Figure 17:
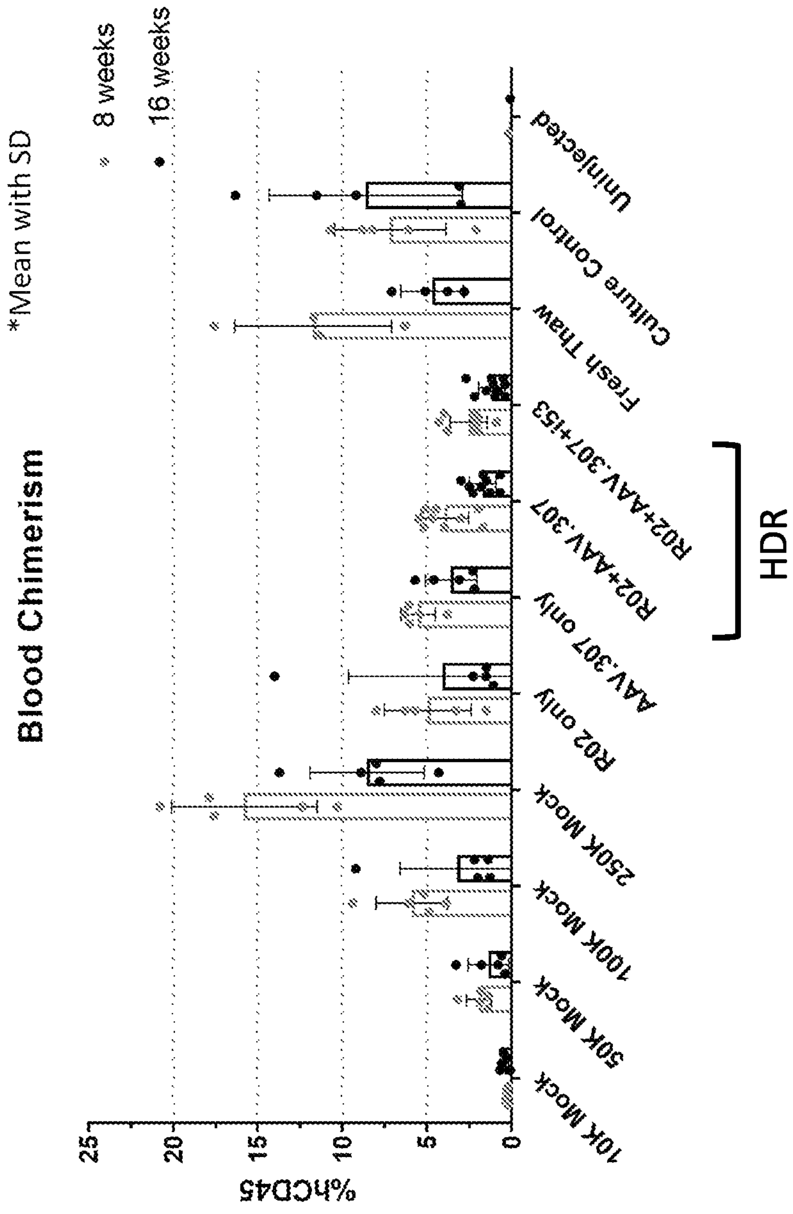
FIG. 17 includes a bar graph showing % chimerism of human cells derived from engrafted LT-HSPCs in mouse blood samples isolated at 8 and 16 weeks post-engraftment. CD34-expressing LT-HSPCs were administered to mice according to FIG. 14

The effect of titrating the dose of LT-HSPCs on percent chimerism was also evaluated in mouse blood samples collected at 8 and 16 weeks following administration of LT-HSPCs. As seen in the bone marrow, increasing the dose of LT-HSPCs resulted in higher proportion of human cells among CD45-expressing in the blood (FIG. 17). Additionally, the proportion of human CD45-expressing cells among total CD45-expressing cells in the blood was lower for LT-HSPCs gene-edited with RNP+AAV alone or in combination with i53, with approximately 2-3% human CD45-expressing cells present. These data indicate that cells edited by HDR repair exhibit lower levels of engraftment than unedited cells or cells edited with RNP only.

Figure 18A:
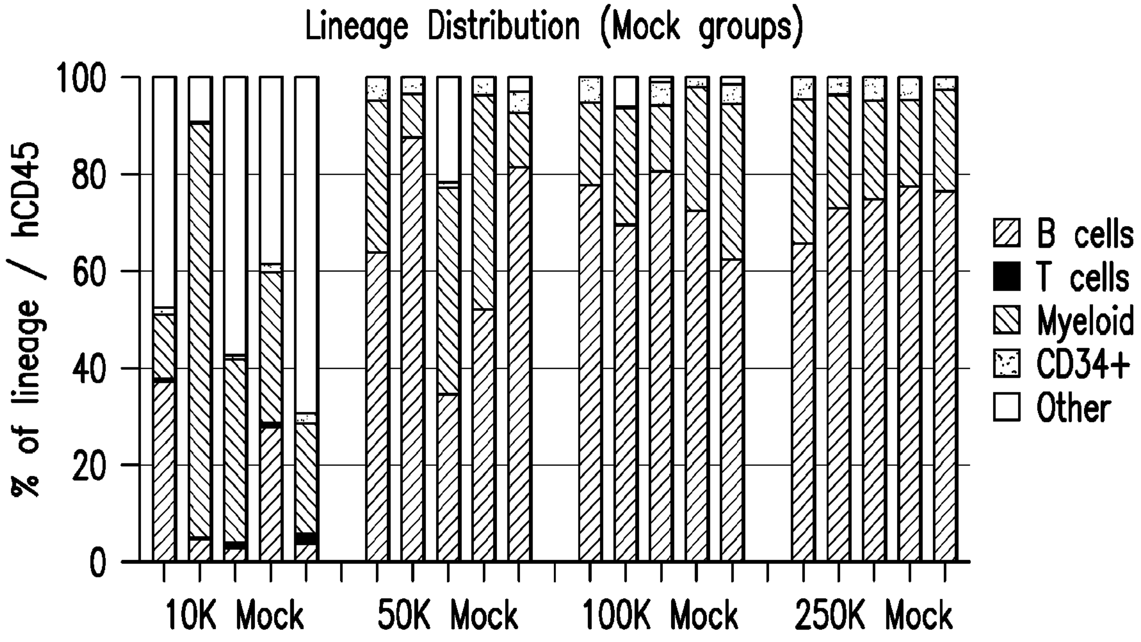
FIG. 18A-18B include bar graphs showing lineage distribution in mouse bone marrow isolated at 16 weeks post-engraftment of LT-HSPCs. Shown is the percentage of human CD45-expressing cells that are B cells, T cells, myeloid cells, or CD34-expressing hematopoietic stem/progenitor cells (HSPCs). CD34-expressing LT-HSPCs were administered to mice according to FIG. 14
Figure 18B:
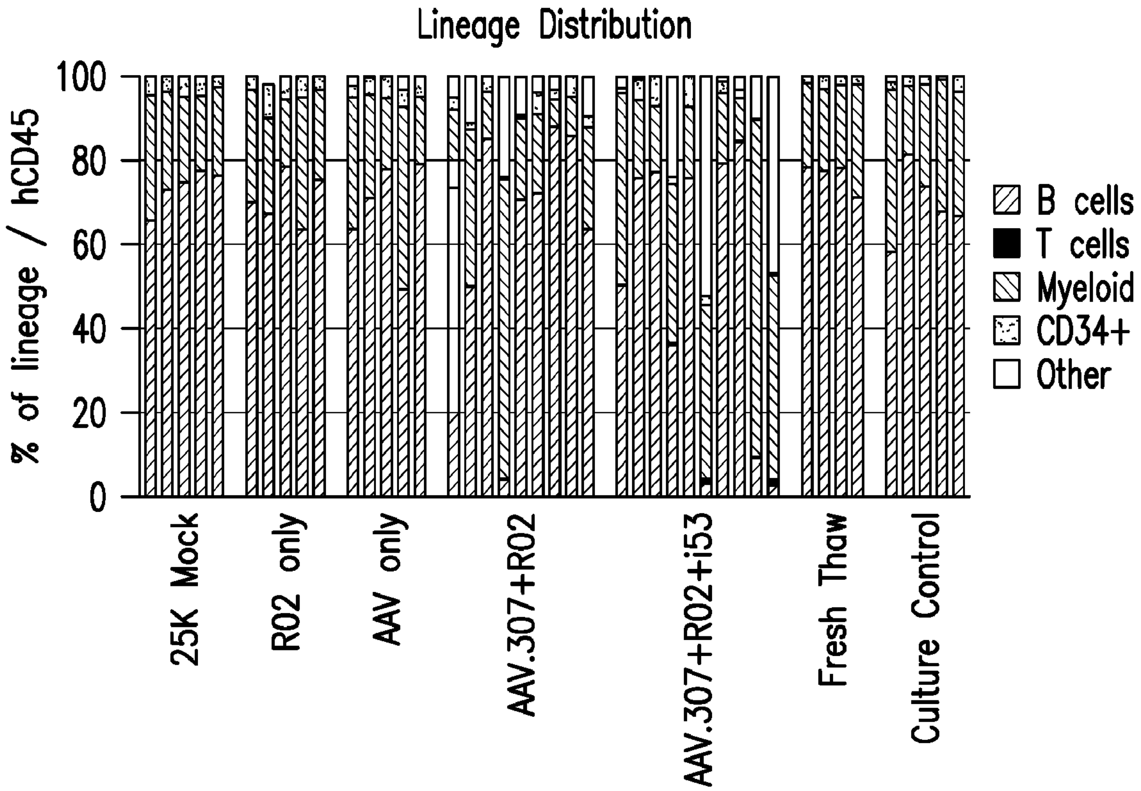

Shown in FIGS. 18A-18B is lineage analysis of engrafted CD45-expressing human cells in mouse bone marrow samples collected at 16 weeks post administration of LT-HSPCs. The lineage of CD45-expressing human leukocytes was evaluated for unedited LT-HSPCs administered at a dose of $0.01\times10^6$, $0.05\times10^6$, $0.1\times10^6$, or $0.25\times10^6$ cells (FIG. 18A). The lineage of CD45-expressing human leukocytes was also evaluated for LT-HSPCs edited with AAV+RNP either in the presence or absence of i53 (FIG. 18B). In both cases no gross changes in lineage distribution were observed for engrafted cells that were edited LT-HSPCs compared to un-edited LT-HSPCs.

Figure 19:
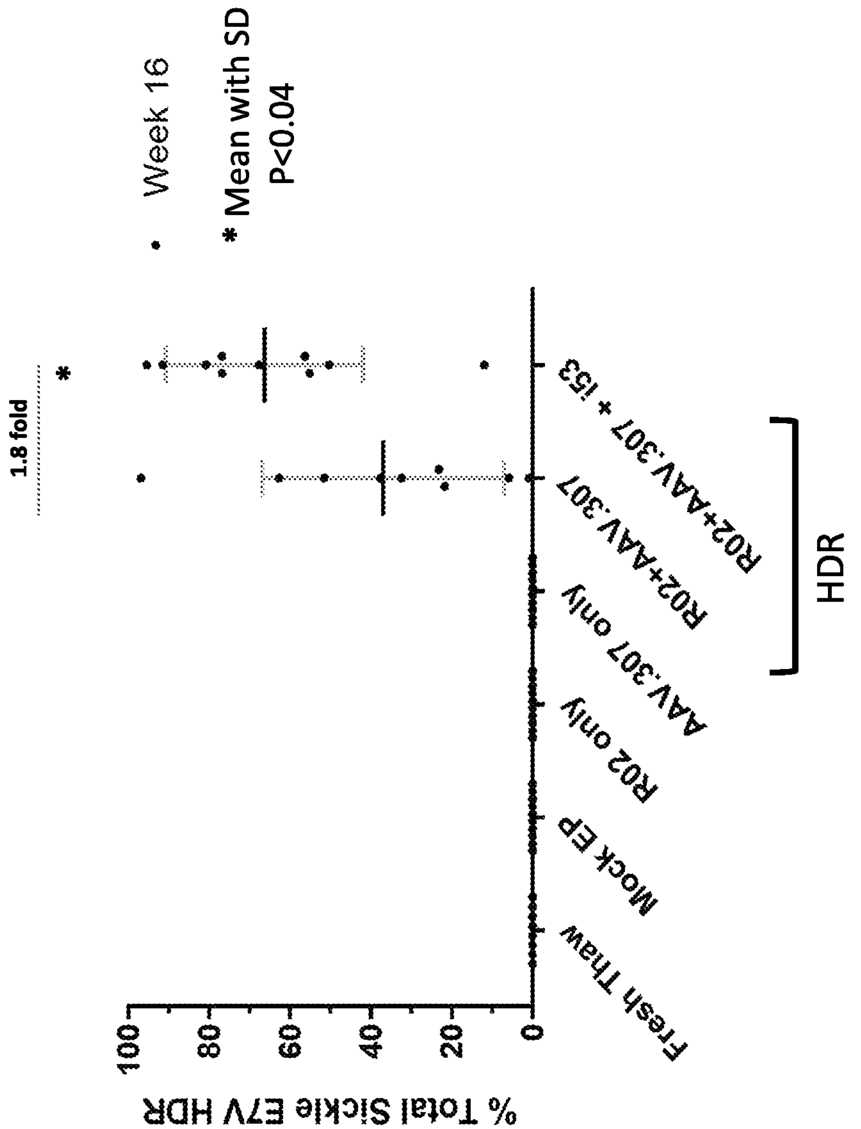
FIG. 19 includes a dot plot showing HDR editing efficiency for insertion of donor DNA encoding a sickle cell mutation into the HBB locus, measured in mouse bone marrow isolated at 16 weeks post-engraftment of LT-HSPCs.

Maintenance of gene-editing was evaluated in mouse bone marrow collected at 16 weeks post-administration of LT-HSPCs. Incorporation of a sickle mutation (E7V) in the HBB locus was evaluated in DNA isolated from mouse bone marrow samples using the next generation sequencing assay described in Example 4. Shown in FIG. 19 is a comparison of HDR efficiency for LT-HSPCs edited either with or without i53. LT-HSPCs were electroporated with Cas9/gRNA and treated with AAV. Administration of LT-HSPCs edited with i53 produced a bone marrow compartment with levels of gene-editing in the HBB locus that were substantially higher than AAV+RNP alone, with 65% incorporation of the gene edit by HDR. LT-HSPCs edited in the presence of i53 had 1.8-fold higher HDR frequency in the bone marrow compared to cells edited with AAV+RNP alone. These results demonstrate that LT-HSPCs edited with i53 have higher levels of HDR efficiency and the gene-edit is maintained in cells derived from these progenitor cells following administration in vivo.

Figure 20:
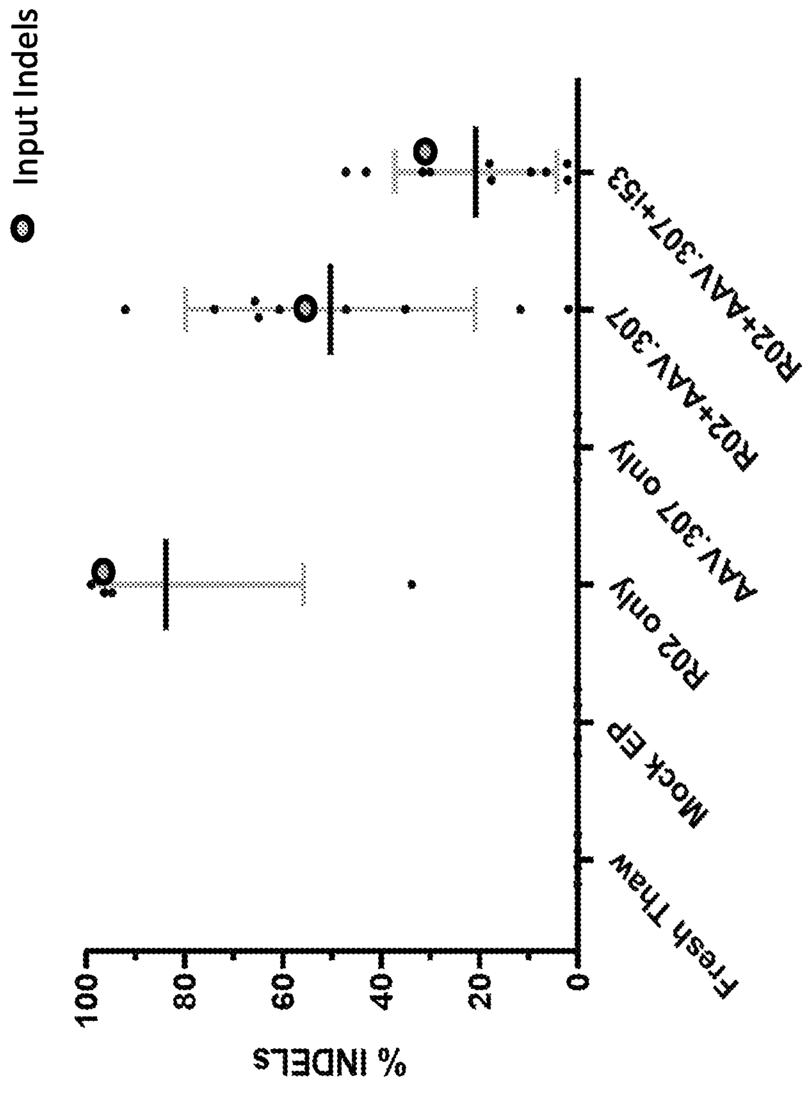
FIG. 20 includes a dot plot showing indel frequency in mouse bone marrow isolated at 16 weeks post-engraftment of LT-HSPCs relative to the indel frequency of LT-HSPCs prior to engraftment (e.g., input indels).

NHEJ editing of the HBB locus was also evaluated in mouse bone marrow collected at 16 weeks post engraftment. Indel formation at the site of Cas9/gRNA cutting was evaluated by TIDE analysis in bone marrow samples and compared to indel formation of LT-HSPCs prior to administration. Regardless of the method used to edit the LT-HSPCs, indel formation was similar at 16 weeks post-engraftment to the level present prior to administration, demonstrating persistence of gene-editing following engraftment of LT-HSPCs (FIG. 20). Interestingly, the level of indel formation was lowest for LT-HSPCs gene-edited in the presence of i53, demonstrating that i53 is an effective inhibitor of the NHEJ pathway.

Example 6. Evaluation of Gene Editing of the Hemoglobin Beta Subunit (HBB) Locus in CD34-Expressing LT-HSPCs In Vitro in the Presence of i53 or Nu7441

A direct comparison was made of the effect of i53 and Nu7441 on HDR efficiency for CRISPR/Cas9 gene-editing at the HBB locus in CD34-expressing LT-HSPCs using a homology donor DNA encoding a sickle cell mutation. LT-HSPCs were maintained in culture as described in Example 3 and gene-editing was performed following two days in culture as described in Example 4. Cells were electroporated with RNP comprised of Cas9 and gRNA targeting the HBB locus (R02 gRNA, target sequence shown by SEQ ID NO: 15). AAV encoding homology donor DNA (SEQ ID NO: 50) was administered either prior to electroporation (pre-EP) or post electroporation (post-EP). Additionally, where indicated, cells were treated with 5 μM Nu7441 or 1 μg of mRNA encoding i53 polypeptide (SEQ ID NO: 70) during electroporation.

Figure 21:
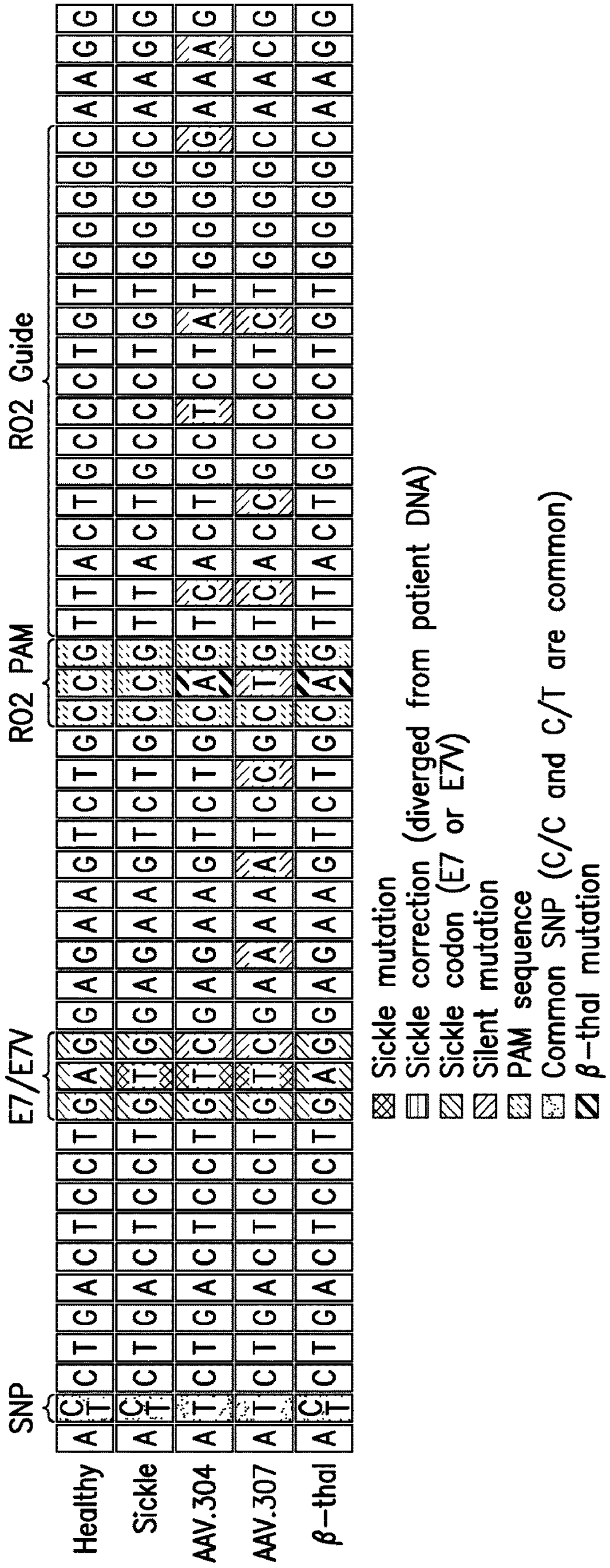
FIG. 21 includes a schematic showing the sequence near the site of Cas9/gRNA gene editing within the HBB locus. Included is the sequence for a wild type gene (SEQ ID NO: 113) and for a sickle cell mutant gene (SEQ ID NO:114). The sequence of different homology donor DNA templates that include either a sickle mutation or a sickle cell correction are shown (AAV.304 donor: SEQ ID NO: 117, AAV.307 donor: SEQ ID NO: 116). The donor DNA template with a sickle cell correction includes a β-thalassemia mutation (SEQ ID NO: 118).

The donor DNA comprised homology arms to the HBB locus and encoded a sickle cell mutation. FIG. 21 shows the sequence of the HBB gene in the region of the gene edit as well as the sickle cell mutation that is introduced following gene editing. The downstream PAM recognition site on the HBB locus is indicated, as well as the sequence of the homology donor DNA (AAV.304), including gene changes that are incorporated into the HBB locus by HDR editing. The homology donor incorporates an edit to the PAM sequence to prevent re-cutting of the HBB locus by Cas9/gRNA following editing by HDR. Sequences of the AAV.304 donor are provided in Table 7.

TABLE 7

Sequence of AAV.304 Homology Donor

| Name/Description | SEQ ID NO |
|---|---|
| 5' ITR | 112 |
| Left Homology Arm (LHA) | 49 |
| Gene-edit (E7 → E7V) | 50 |
| Right Homology Arm (RHA) | 51 |
| 3' ITR | 107 |
| LHA to RHA | 108 |
| AAV.304 | 109 |

Figure 22A:
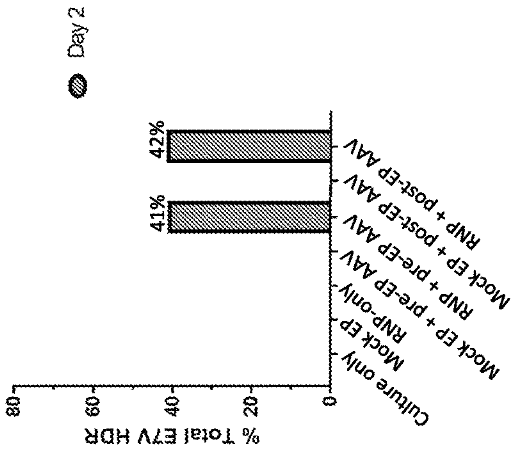
FIGS. 22A-22B include bar graphs showing HDR editing efficiency for insertion of donor DNA encoding a sickle cell mutation into the HBB locus of CD34-expressing LT-HSPCs using AAV-mediated delivery of donor DNA.

HDR efficiency was evaluated for AAV administered either pre-EP or post-EP following gene-editing of LT-HSPCs in vitro. For pre-EP, cells were incubated with AAV for 1 hour prior to electroporation. For post-EP, cells were incubated with AAV for 1 hour immediately following electroporation. HDR efficiency was evaluated by NGS assay as described in Example 4. Treatment with RNP and AAV administered either before or after electroporation resulted in a comparable level of incorporation of the gene edit by HDR, approximately 40% (FIG. 22A). Treatment with AAV-only either pre- or post-EP resulted in no incorporation of the donor DNA in the HBB locus.

Figure 22B:
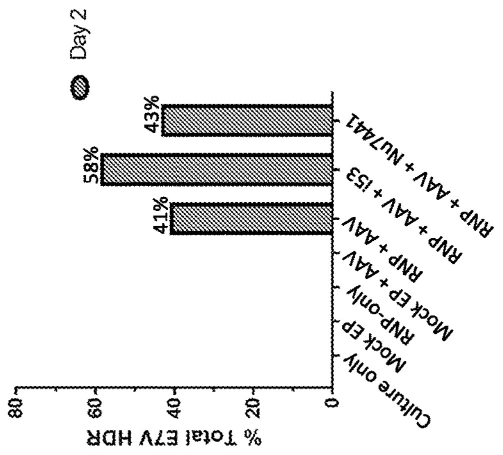

HDR efficiency at the HBB locus was evaluated upon treatment with either i53 or Nu7441 following gene-editing of LT-HSPCs in vitro. Cells were treated with pre-EP AAV and RNP and treated with either Nu7441 or mRNA encoding i53. Treatment with Nu7441 resulted in no improvement of HDR efficiency over RNP+AAV alone. However, treatment with i53 resulted in 58% incorporation of the E7V gene edit, an increase of 1.4-fold over RNP+AAV alone (FIG. 22B).

Example 7. Evaluation of LT-HSPCs Edited with i53 or Nu7441 Following Administered In Vivo As described in Example 6, HDR efficiency for editing the HBB locus in CD34-expressing LT-HSPCs is improved in the presence of i53, but not in the presence of Nu7441. The effect of gene-editing with either i53 or Nu7441 was evaluated on the ability of the cells to engraft and retain the gene-edit following administration in vivo. Also evaluated was the effect of gene-editing with treatment of AAV prior to electroporation or following electroporation on the ability of the edited cells to engraft and maintain the gene edit following administration in vivo.

Human LT-HSPCs were administered to mice following electroporation with Cas9/gRNA and AAV encoding a sickle cell mutation (E7V) as shown in FIG. 21. LT-HSPCs were mobilized from healthy donors using plerixafor. LT-HSPCs were gene-edited following 2 days in culture. To perform the gene-edit, cells were electroporated with RNP comprised of Cas9 and gRNA targeting the HBB locus (e.g., R02 gRNA, target sequence shown by SEQ ID NO: 15) and AAV encoding a sickle cell mutation (AAV.304). $1\times10^6$ cells were edited with 20 g Cas9 and 20 g gRNA. The AAV was administered either prior to electroporation (pre-EP) or following electroporation (post-EP). Cells were edited with an AAV dose of 10,000 MOI. Effect of gene-editing with i53 or Nu7441 was determined by treating cells with 1 g of mRNA encoding i53 polypeptide (SEQ ID NO: 70) or 5 μM Nu7441 during electroporation.

A dose of $0.5\times10^6$ cells was administered by intravenous injection to cKit mice at 2 days following electroporation. Recipient mice were treated with sublethal irradiation (100 cGy) at 1 day prior to administration of LT-HSPCs to eliminate hematopoietic cells in the bone marrow and enable engraftment of the donor cells. Animals were evaluated for presence of human hematopoietic cells in peripheral blood at 8 and 16 weeks following LT-HSPC administration. The bone marrow was also evaluated for engraftment and maintenance of the HBB gene-edit at 16 weeks following LT-HSPC administration.

Figure 23A:
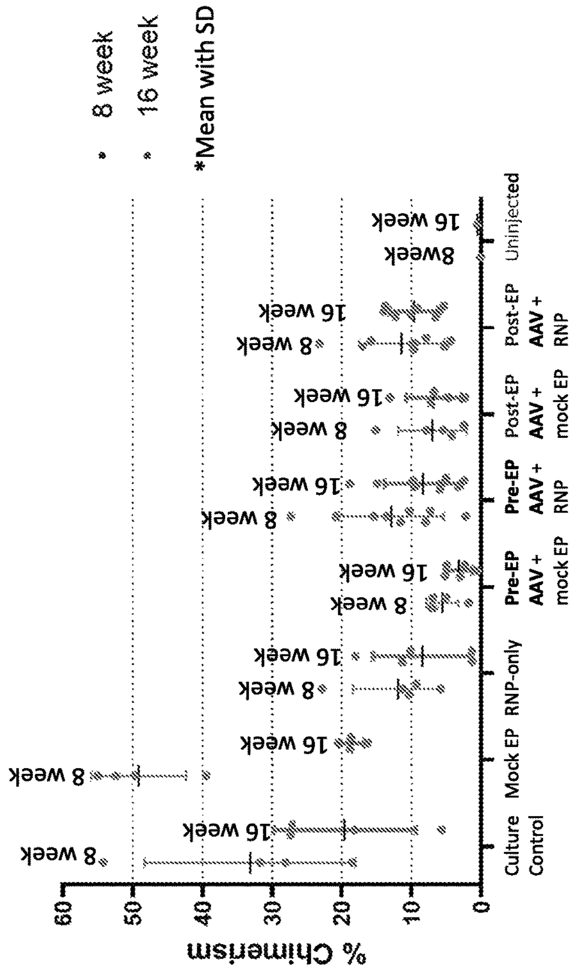
FIGS. 23A-23B include dot plots showing % chimerism of human cells derived from engrafted LT-HSPCs in mouse blood samples isolated at 8 weeks and 16 weeks post-engraftment.
Figure 23B:
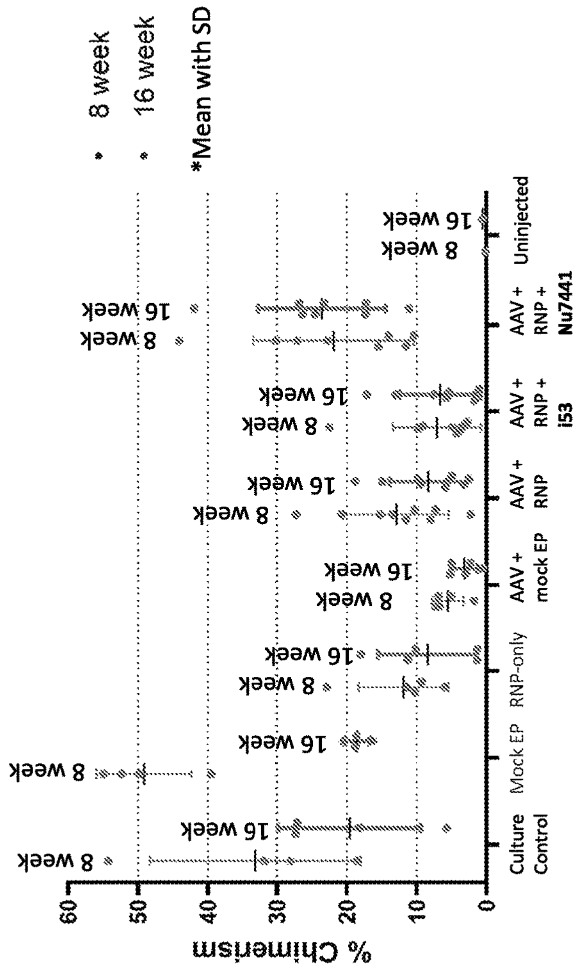

Percent chimerism was evaluated as described in Example 5 in mouse blood samples collected at 8 and 16 weeks post-administration of LT-HSPCs and compared for LT-HSPCs edited under different conditions. Shown in FIG. 23A is a comparison of LT-HSPCs edited with AAV administered either pre-EP or post-EP. LT-HSPCs were electroporated with Cas9/gRNA and treated with AAV prior to electroporation or following electroporation. LT-HSPCs electroporated with RNP demonstrated decreased chimerism relative to cells that were not electroporated. Treatment with AAV either pre-EP or post-EP resulted in no improvement in chimerism relative to treatment with RNP alone. Shown in FIG. 23B is a comparison of LT-HSPCs edited with pre-EP AAV and RNP in the presence of either i53 or Nu7441. Treatment with i53 resulted in levels of chimerism comparable to RNP+AAV alone. However, treatment with Nu7441 resulted in improved chimerism of approximately 25% at both 8 and 16 weeks, a 2.5-fold increase over RNP+AAV alone.

Figure 24A:
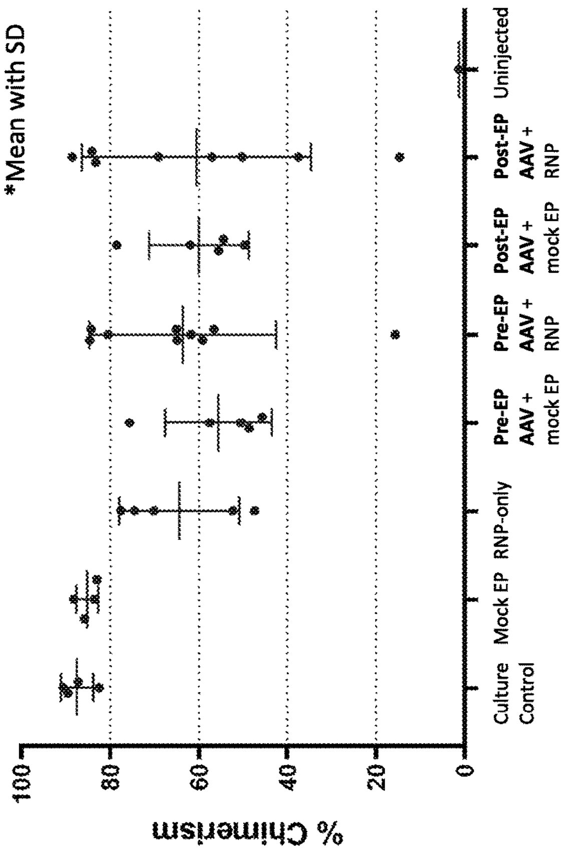
FIGS. 24A-24B include dot plots showing % chimerism of human cells derived from engrafted LT-HSPCs in mouse bone marrow samples isolated at 16 weeks post-engraftment.
Figure 24B:
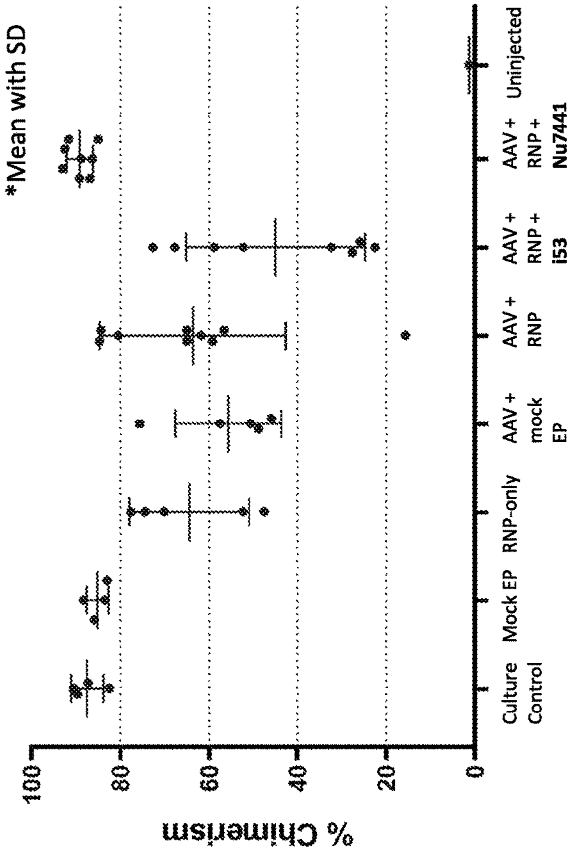

Additionally, percent chimerism was evaluated in mouse bone marrow samples collected at 16 weeks following administration of LT-HSPCs. Shown in FIG. 24A is a comparison of LT-HSPCs edited with AAV administered either pre-EP or post-EP. Similar to the chimerism seen in mouse blood samples as described above, LT-HSPCs electroporated with RNP demonstrated decreased chimerism relative to LT-HSPCs that were not electroporated. Furthermore, treatment with AAV either pre-EP or post-EP resulted in no improvement in chimerism relative to treatment with RNP alone. The chimerism in bone marrow at 16 weeks for LT-HSPCs edited in the presence of i53 or Nu7441 was also evaluated (FIG. 24B). Treatment with i53 resulted in levels of chimerism comparable to RNP+AAV alone. However, treatment with Nu7441 resulted in chimerism that was higher than RNP+AAV alone and comparable to culture LT-HSPCs that were not electroporated prior to engraftment. Combined, these results demonstrate an unexpected improvement in engraftment for LT-HSPCs gene-edited with treatment of Nu7441.

Figure 25:
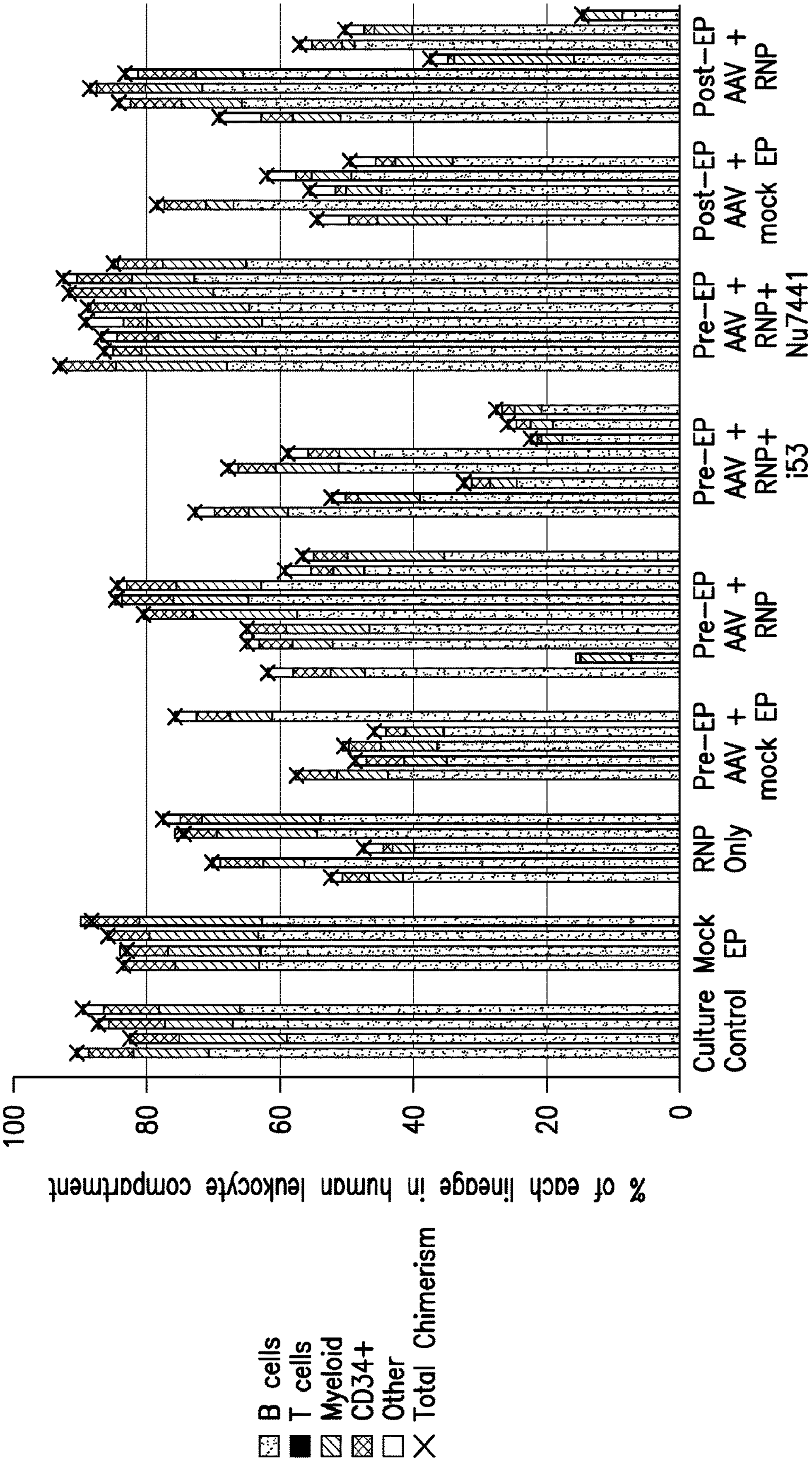
FIG. 25 includes a bar graph showing lineage distribution in mouse bone marrow isolated at 16 weeks post-engraftment of LT-HSPCs. Shown is total chimerism and percentage of human CD45-expressing cells that are B cells, T cells, myeloid cells, or CD34-expressing hematopoietic stem/progenitor cells (HSPCs). Lineage distribution is shown for LT-HSPCs edited with gRNA/Cas9 RNP and AAV given either pre-EP or post-EP. Also shown is lineage distribution for LT-HSPCs edited with AAV and gRNA/Cas9 RNP in the presence of i53 or Nu7441 compared to RNP+AAV-only.

Shown in FIG. 25 is lineage analysis of engrafted CD45-expressing human cells in mouse bone marrow samples collected at 16 weeks post administration of LT-HSPCs. The lineage of CD45-expressing human leukocytes was compared for LT-HSPCs that were gene-edited in the presence of i53 or Nu7441. In addition to providing higher levels of engraftment, treatment with Nu7441 resulted in a greater proportion of CD34-expressing cells and myeloid cells among human leukocytes in the bone marrow compared to treatment with i53.

Figure 26A:
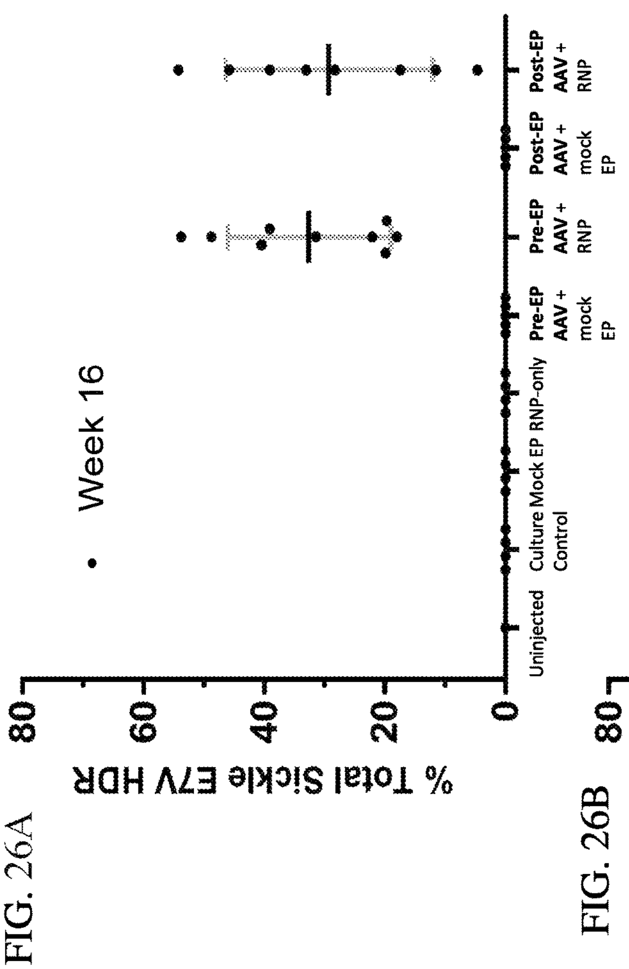
FIGS. 26A-26B include dot plots showing HDR editing efficiency for insertion of donor DNA encoding a sickle cell mutation into the HBB locus, measured in mouse bone marrow isolated at 16 weeks post-engraftment of LT-HSPCs.
Figure 26B:
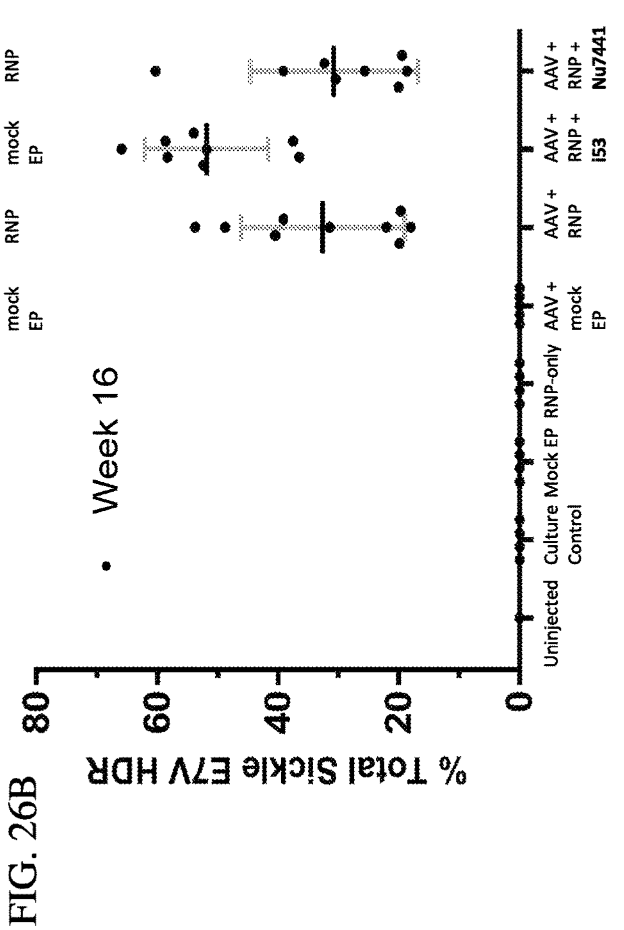

Maintenance of gene-editing was evaluated in mouse bone marrow collected at 16 weeks post-administration of LT-HSPCs. Incorporation of a sickle mutation (E7V) in the HBB locus was evaluated in DNA isolated from mouse bone marrow samples using the next generation sequencing assay described in Example 4. Shown in FIG. 26A is a comparison of HDR efficiency for LT-HSPCs edited with AAV administered either pre-EP or post-EP. LT-HSPCs were electroporated with Cas9/gRNA and treated with AAV prior to electroporation or following electroporation. Incorporation of the gene-edit in bone marrow samples was similar for LT-HSPCs edited with RNP and AAV given either pre-EP or post-EP. Additionally, incorporation of the gene edit in the HBB locus by HDR was compared for LT-HSPCs edited in the presence of i53 or Nu7441 (FIG. 26B). Administration of LT-HSPCs edited with Nu7441 produced a bone marrow compartment with levels of gene-editing in the HBB locus comparable to AAV+RNP alone. However, administration of LT-HSPCs edited with i53 produced levels of gene-editing in the HBB locus that were substantially higher than AAV+RNP alone. These results demonstrate that LT-HSPCs edited with i53 have higher levels of HDR efficiency and the gene-edit is maintained in cells derived from these progenitor cells following administration in vivo.

Figure 27:
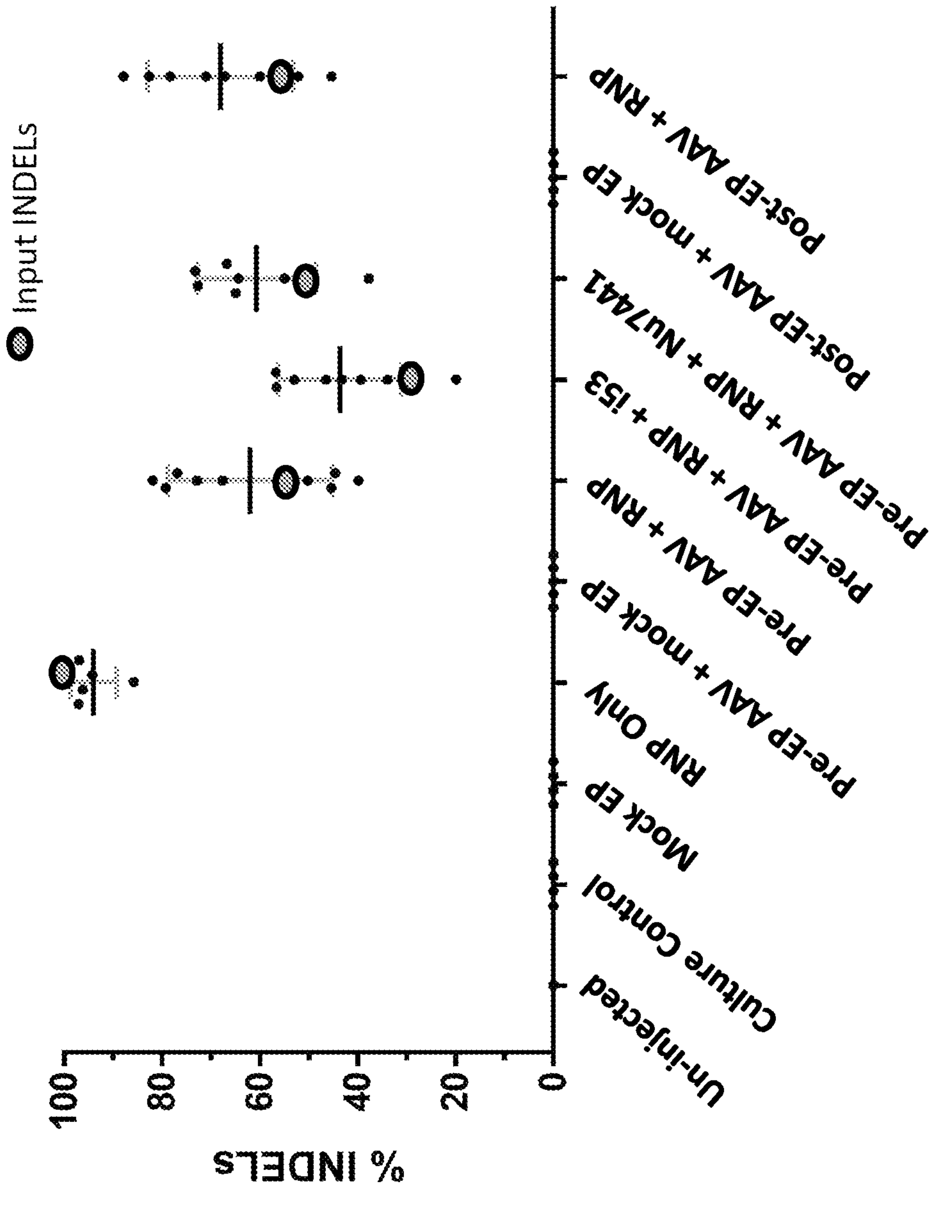
FIG. 27 includes a dot plot showing indel frequency in mouse bone marrow isolated at 16 weeks post-engraftment of LT-HSPCs relative to the indel frequency of LT-HSPCs prior to engraftment (e.g., input indels). Shown is indel frequency for LT-HSPCs edited with gRNA/Cas9 RNP and AAV given either pre-EP or post-EP. Also shown is indel frequency for LT-HSPCs edited with AAV and gRNA/Cas9 RNP in the presence of i53 or Nu7441 compared to RNP+AAV-only.

NHEJ editing of the HBB locus was also evaluated in mouse bone marrow collected at 16 weeks post engraftment. Indel formation at the site of Cas9/gRNA cutting was evaluated by TIDE analysis in bone marrow samples and compared to indel formation of LT-HSPCs prior to administration. Regardless of the method used to edit the LT-HSPCs, indel formation was similar at 16 weeks post-engraftment to the level present prior to administration (FIG. 27). Interestingly, the level of indel formation was lowest for LT-HSPCs gene-edited in the presence of i53, demonstrating that i53 is an effective inhibitor of the NHEJ pathway.

Figure 28:
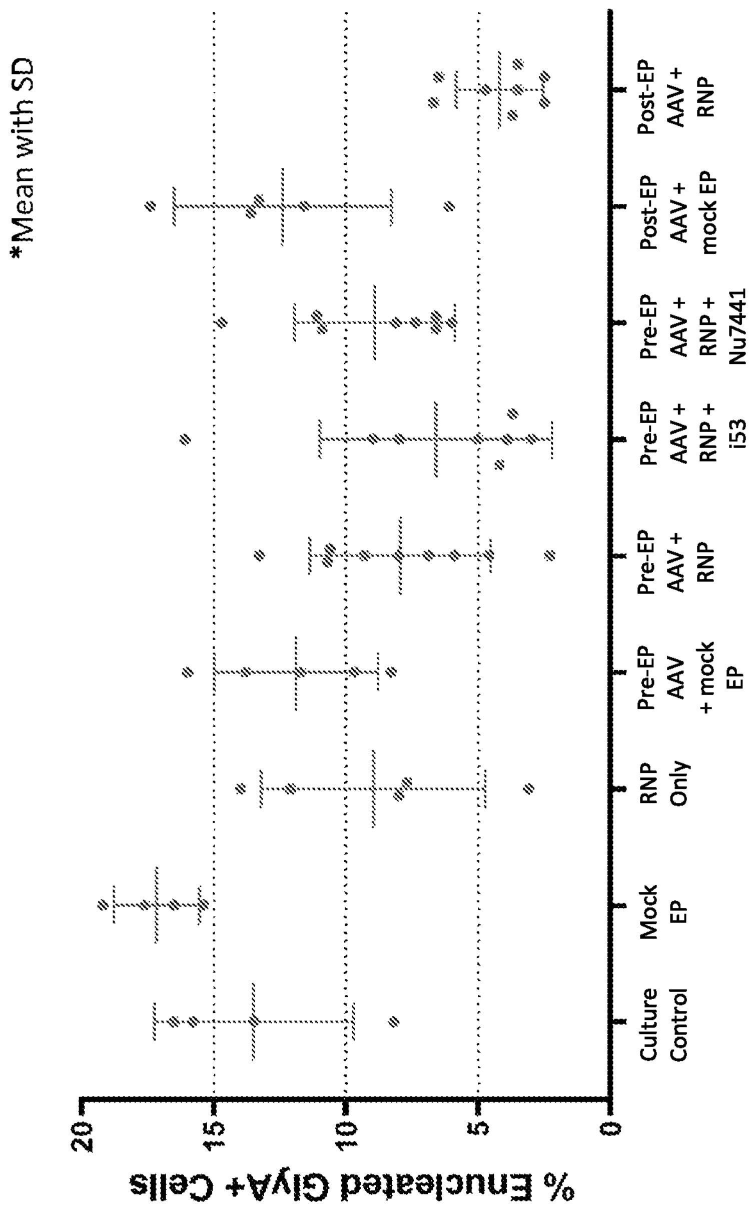
FIG. 28 includes a dot plot showing erythroid cell enucleation in mouse bone marrow isolated at 16 weeks post-engraftment of LT-HSPCs. Shown is enucleation for LT-HSPCs edited with gRNA/Cas9 RNP and AAV given either pre-EP or post-EP. Also shown is enucleation for LT-HSPCs edited with AAV and gRNA/Cas9 RNP in the presence of i53 or Nu7441 compared to RNP+AAV-only.

The functionality of the hematopoietic compartment in recipient mice was evaluated by measuring erythroid cell enucleation in bone marrow collected at 16 weeks post-engraftment. Mammalian erythrocytes extrude their nucleus prior to entering circulation. Human CD34-expressing LT-HSPCs are expected to differentiate into erythrocytes following engraftment, however the efficiency of enucleation can be low. Assessment of erythroid cell enucleation provides a measure of the ability of edited CD34 expressing cells to differentiate into erythroid cells compared to the unedited controls (i.e., ability to differentiate into functional cell types). Percent enucleation was compared for LT-HSPCs gene edited with Cas9/gRNA RNP and AAV given pre-EP or post-EP. Levels of enucleation were similar to cells treated with RNP-only or AAV-only (FIG. 28). Additionally, levels of enucleation were compared for LT-HSPCs gene edited with RNP+AAV in the presence of i53 or Nu7441. Levels of enucleation were also similar to cells treated with RNP-only or AAV-only.

Figure 29:
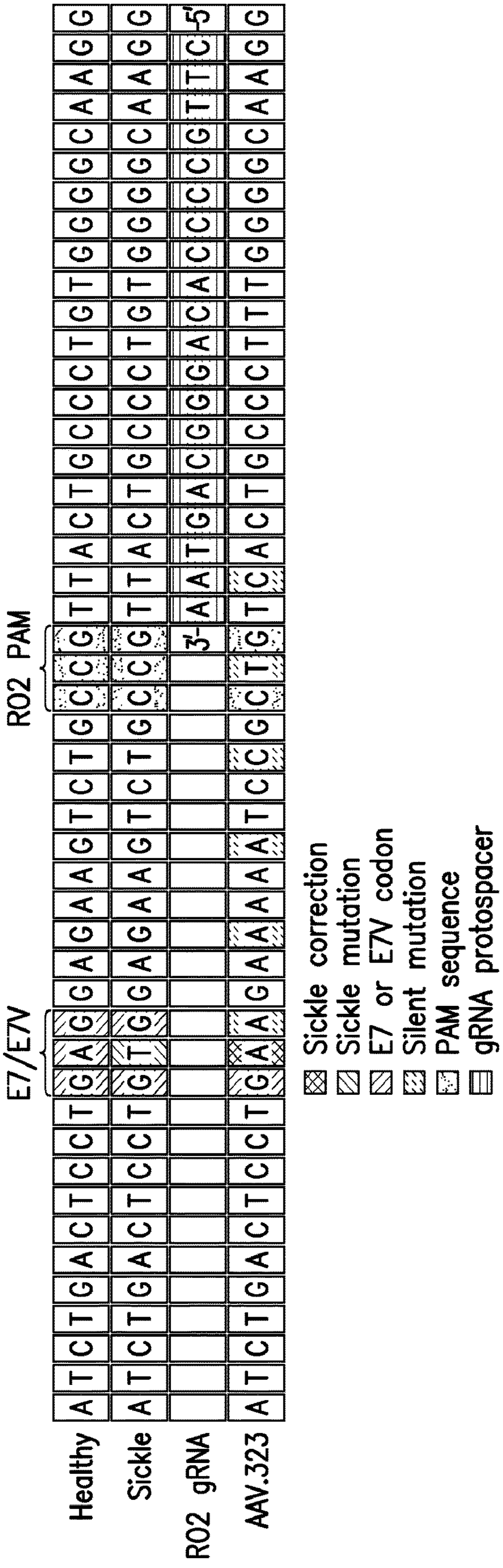
FIG. 29 includes a schematic showing the sequence near the site of Cas9/gRNA gene editing within the HBB locus. Included is the sequence for wild type HBB (healthy, SEQ ID NO: 113), for HBB encoding an E6V mutation (sickle, SEQ ID NO: 114), spacer sequence of R02 gRNA (SEQ ID NO: 115), and sequence of homology donor DNA encoded by AAV.323 (AAV.323 donor: SEQ ID NO: 119) to provide correction of the E6V sickle cell disease (SCD) mutation.

Example 8. Evaluation of i53 for In Vitro Correction of Sickle Cell Mutation in Human Patient-Derived Cells The effect of i53 on HDR efficiency was evaluated in cells derived from patients with a sickle cell mutation in the HBB gene. Specifically, CD34-expressing LT-HSPCs derived from human patients with sickle cell disease were edited with SpCas9, R02 guide, and a homology donor DNA encoding a correction to the sickle cell mutation in the HBB gene (i.e., E6V to E6) delivered by AAV. The AAV-encoded homology donor used for correction is referred to as "AAV.323" and is identified by sequence in Table 8. As shown in FIG. 29, AAV.323 encodes glutamate at position 6 of the HBB open reading frame (i.e., E6). However, the codon for E6 is "GAA" rather than wild-type "GAG", allowing the correction encoded by the AAV.323 to be detected in wild-type cells or cells encoding the E6V mutation in the HBB gene.

TABLE 8

Sequence of AAV323 Homology Donor Encoding SCD Correction

| Name/Description | SEQ ID NO |
|---|---|
| 5' ITR | 106 |
| Left Homology Arm (LHA) | 99 |
| Gene-edit (E6V → E6) | 102 |
| Right Homology Arm (RHA) | 100 |
| 3' ITR | 107 |
| LHA to RHA | 98 |
| AAV.323 | 105 |

Briefly, CD34-expressing LT-HSPCs were derived from plerixafor+GCSF-dual mobilized peripheral blood obtained from a human donor with sickle cell disease. The cells were seeded in Phase I media at a cell density of $2\times10^5$ cells/mL. Cells were cultured at 37° C. under normoxic conditions (i.e., oxygen 20%).

Editing of cells was performed following two days of in vitro culture. Briefly, $5\times10^5$ cells were electroporated with RNP containing 20 g SpCas9 and 20 μg R02 sgRNA, AAV.323 at a dose of 10,000 MOI, and 1 g mRNA encoding i53. The cells were incubated with AAV.323 for 1 hour prior to electroporation. The cells were edited by electroporation with R02+AAV.323+i53 mRNA and compared to control cells edited with R02 only, R02+AAV.323, or cells exposed to electroporation without RNP or AAV editing components (mock EP).

Following editing, the cells were differentiated to erythrocytes. Briefly, edited cells were plated in fresh Phase I media at a density of $2\times10^5$ cells/mL, and re-plated at similar density in fresh Phase I media on days 3 and 5 post-editing. On day 7 post-editing, the cells were incubated in Phase II media at a density of $2.5\times10^5$ cells/mL. On day 10 post-editing, the cells were incubated in Phase III media at a density of $1.2\times10^6$ cells/mL. Cell expansion during culture was monitored over time and cells electroporated with R02+AAV.323+i53 mRNA grew similarly to control cells (R02 only, R02+AAV.323, or mock EP cells) (data not shown). Additionally, cell viability was monitored at frequent time points beginning day 3 post-editing, and remained greater than 80% for each treatment group through approximately day 13 of culture.

Efficiency of Gene Edits

Figure 30A:
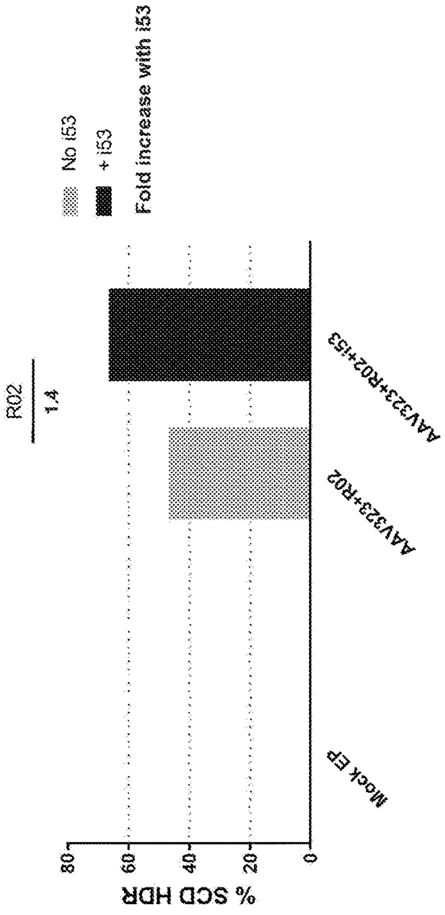
FIGS. 30A-30B provide bar graphs quantifying the frequency of a SCD gene correction (E6V to E6) in HBB by HDR repair (FIG. 30A) and frequency of INDELs in the HBB gene (FIG. 30B) in CD34-expressing LT-HSPCs derived from a patient donor with SCD mutation that were subsequently edited by electroporation with R02 gRNA/Cas9 RNP+AAV.323 in the presence of i53. Control cells were edited by electroporation with R02 gRNA/Cas9 RNP+AAV.323 only, R02 gRNA/Cas9 RNP only, or without AAV or RNP (mock EP).
Figure 30B:
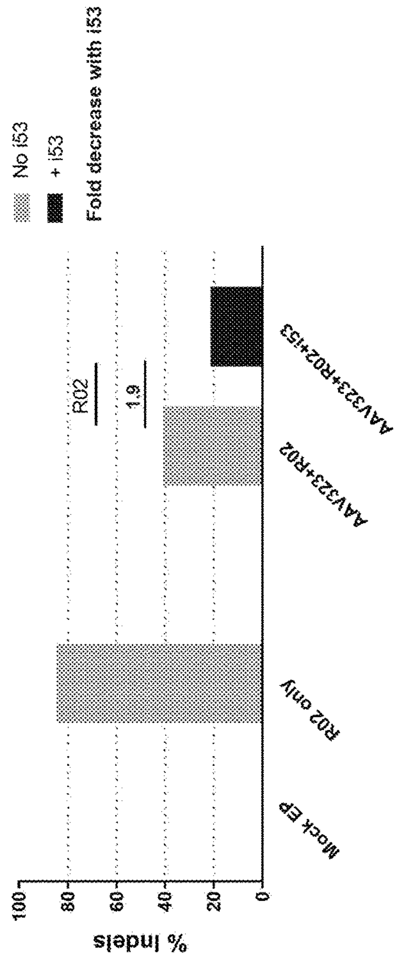
Figure 31A:
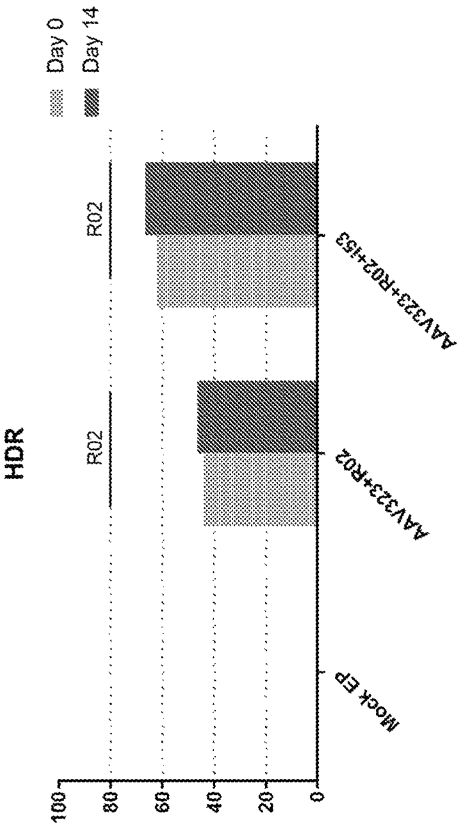
FIGS. 31A-31B provide bar graphs quantifying the frequency of SCD gene correction by HDR repair (FIG. 31A) and frequency of INDELs in HBB (FIG. 31B) measured either the same day as gene-editing (Day 0) or at 14 days following gene-editing and maintenance by in vitro culture (Day 14) for cells edited as in FIGS. 30A-30B.
Figure 31B:
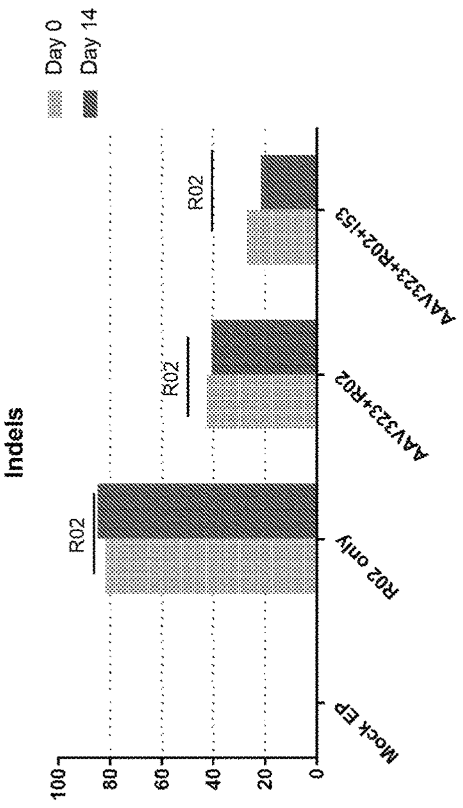

The efficiency of gene correction by HDR repair at the HBB gene locus was evaluated by NGS assay as described in Example 3. Frequency of INDELs at the R02 cut site was evaluated by NGS analysis. Treatment with i53 resulted in 66% incorporation of the E6V→E6 gene correction, an increase of 1.4-fold over RNP+AAV.323 alone (FIG. 30A). Additionally, frequency of INDELs at the R02 cut site was 1.9-fold lower for cells edited in the presence of i53 compared to cells edited with RNP+AAV.323 alone (FIG. 30B). Additionally, HDR repair and INDEL formation were compared at day 0 and day 14 post-editing. As shown in FIGS. 31A-31B, edit incorporated by HDR repair (FIG. 31A) and frequency of INDELs at the R02 cut site (FIG. 31B) was similar at day 0 and day 14 for each treatment group, indicating the edits were retained throughout in vitro differentiation to erythrocytes.

Hemoglobin Expression

Hemoglobin expressed by edited cells that were differentiated to erythrocytes was assessed. Hemoglobin A (HbA) is composed of 2 alpha-globin and 2 beta-globin units and is the dominant hemoglobin in adult humans. In human carriers of the HBB E6V mutation, a high proportion of total hemoglobin is hemoglobin S (HbS), which is composed of 2 alpha-globin units and 2 beta-globin units with E6V. Thus, proportion of HbS to HbA produced by edited cells was assessed using an HPLC-based quantification to determine if editing resulted in decreased levels of hemoglobin associated with sickle cell disease.

Figure 32A:
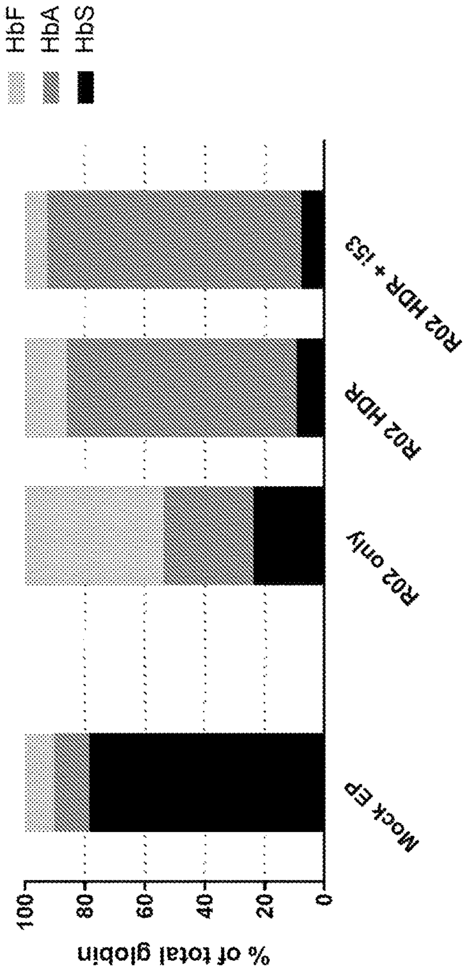
FIG. 32A provides a bar graph quantifying the proportion of total hemoglobin expressed by patient-derived CD34-expressing LT-HSPCs edited as in FIGS. 31A-31B that was HbF, HbA, or HbS as measured by HPLC analysis.
Figure 32B:
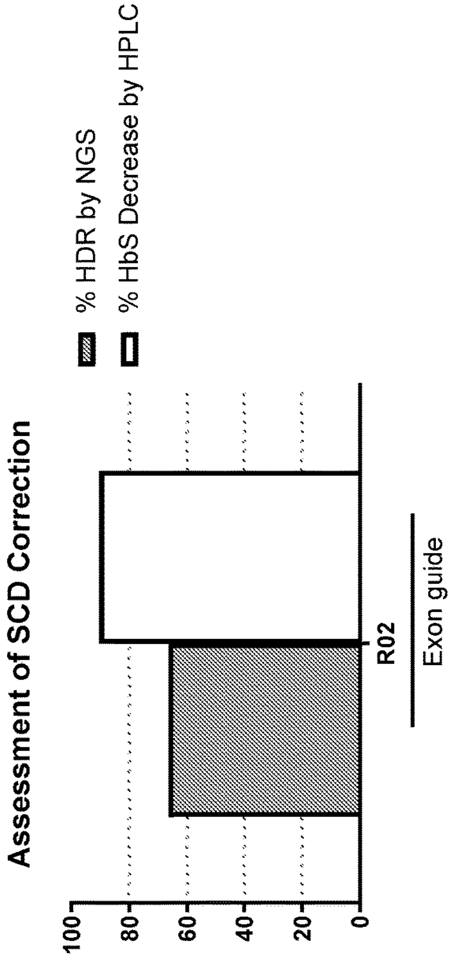
FIG. 32B provides an assessment of SCD correction for patient-derived CD34-expressing LT-HSPCs edited with R02 gRNA/Cas9 RNP+AAV.323+i53 that is comparison of the frequency of SCD gene correction by HDR repair ("% HDR by NGS") and percent decrease in HbS expression relative to mock EP (no RNP or AAV) control cells ("% HbS decrease by HPLC").

Briefly, on day 18 post-editing, $1\times10^6$ cells were harvested, centrifuged, and washed with PBS. The cells were prepared for HPLC analysis. Hemoglobin variants were quantified in cell samples using reverse-phase HPLC chromatography and gradient elution. As shown in FIG. 32A, HbS levels were dramatically reduced and HbA levels increased for cells edited with R02+AAV.332 or R02+AAV.332+i53 compared to mock EP control cells. As shown in FIG. 32B, cells edited in the presence of i53 had 66% correction of HBB gene locus by HDR, but a 90% decrease in HbS levels relative to mock EP control cells. Thus, high levels of HDR achieved with i53 contribute to normalization of hemoglobin expression products.

Erythrocyte Functionality

The ability of edited cells to differentiate to functional erythrocytes was assessed by determining expression of erythrocyte-associated cell surface markers and enucleation using flow cytometry on day 18 post editing.

Briefly, $4\times10^5$ cells were obtained, and half were stained for erythrocyte cell-surface markers and half were used for detection of enucleation. For staining cell-surface markers, the cells were incubated in PBS containing 1% human serum albumin (PBS-A) and an antibody cocktail of anti-CD233 (BRIC6-Band3)-FITC, anti-CD71-PE, anti-CD235a(GlyA)-PE/Cy7, and anti-CD49d (α4)-VioBlue. For detection of enucleation, 2 drops of NucRed nuclear staining reagent was added to 1 mL PBS-A, and 100 μL was added to plated cells. Following incubation, both cell samples were labeled with Sytox Blue solution (1:1000 dilution in PBS-A) for live/dead analysis. Samples were then assessed by flow cytometry. Cells edited with R02 only, R02+AAV.332, or R02+AAV.332+i53 each demonstrated levels of enucleation comparable to mock EP control cells (>30% of cell population having enucleation). Additionally, the proportion of the population that was $CD71^-GlyA^+$ erythrocytes was similar for cells edited with R02+AAV.332 or R02+AAV.332+i53 compared to mock EP control cells (>30% of cell population $CD71^-GlyA^+$).

Editing Patient-Derived PBMCs

It was further evaluated if editing of patient-derived PBMCs in the presence of i53 would yield high levels of correction of the HBB gene. PBMCs were obtained from a human donor with sickle cell disease. The PBMCs were expanded in StemSpan SFEM II (1×)+StemSpan CC100 (1×)+Dexamethasone 1 M+hEPO 2IU/mL at 37° C. under normoxic conditions (20% $O_2$ concentration). The cells were edited following five days of in vitro culture. Patient-derived PBMCs were edited with R02, R02+AAV.332, or R02+AAV.332+i53 as described above. On day 8, the cells were transferred to Phase 1 media, and differentiation to erythrocytes was performed through day 18 as described above.

Efficiency of HDR at the HBB gene locus was evaluated on day 12 using the NGS assay described in Example 4. Also evaluated was the frequency of INDELs at the R02 cut-site as measured by NGS.

Figure 33A:
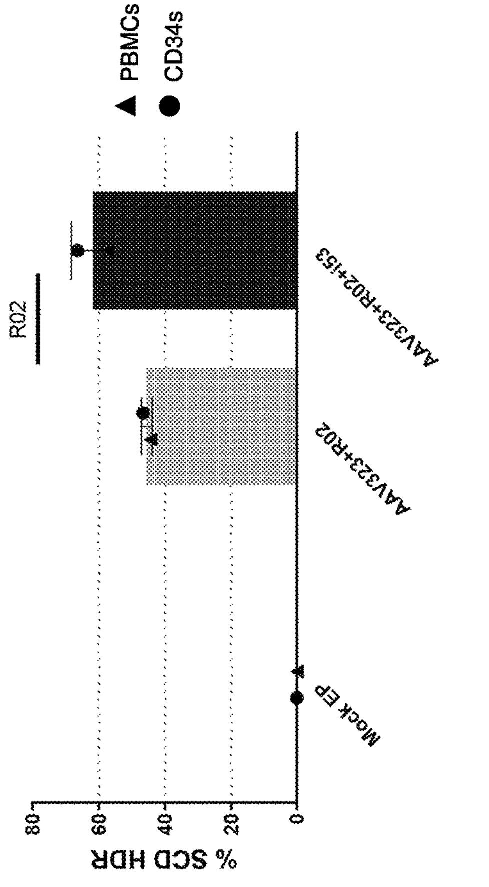
FIGS. 33A-33B provide bar graphs quantifying the frequency of SCD gene correction by HDR repair (FIG. 33A) and frequency of INDELs in HBB (FIG. 33B) measured in PBMCSs or CD34-expressing LT-HSPCs isolated from a patient donor with SCD mutation that were subsequently edited by electroporation with R02 gRNA/Cas9 RNP+AAV.323 in the presence of i53. Control cells were edited by electroporation with R02 gRNA/Cas9 RNP+AAV.323 only, R02 gRNA/Cas9 RNP only, or without AAV or RNP (mock EP).
Figure 33B:
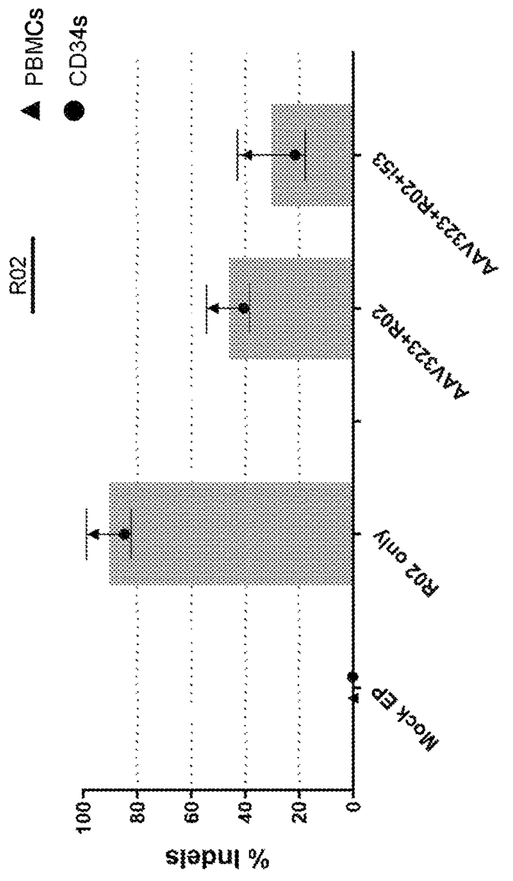

As shown in FIG. 33A, the frequency of correction of the HBB gene by HDR repair in the presence of i53 was approximately 60% in patient-derived PBMCs. Additionally, the frequency of INDELs was reduced in patient-derived PBMCs edited in the presence of i53 compared to control cells (FIG. 33B). The level of HDR repair and the frequency of INDELs in HBB were comparable in PBMCs and CD34-expressing LT-HSPCs edited in the presence of i53.

Figure 34:
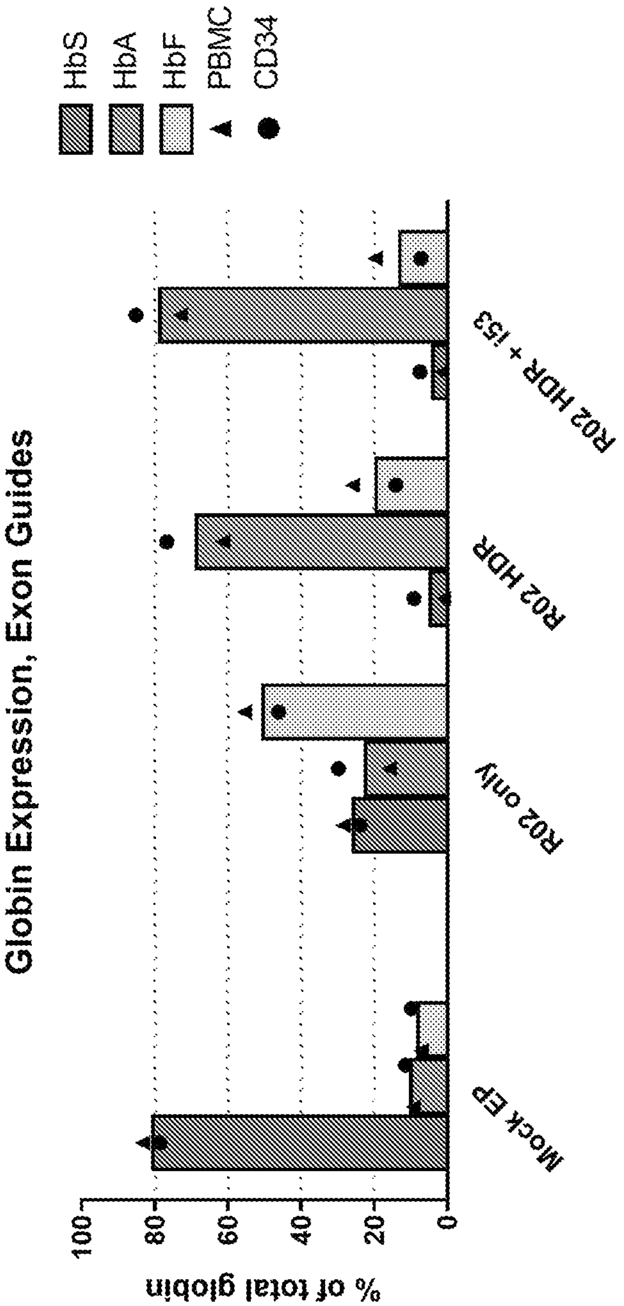
FIG. 34 provides a bar graph quantifying the proportion of total hemoglobin expressed by patient-derived PBMCs or CD34-expressing LT-HSPCs edited as in FIGS. 33A-33B that was HbF, HbA, or HbS as measured by HPLC analysis.

Hemoglobin expression was measured by HPLC analysis for edited PBMCs as described above. As shown in FIG. 34, PBMCs edited in the presence of i53 had significant reduction in expression of HbS and increased expression of HbA compared to mock EP control cells. The ratio of HbS to HbA was comparable for PBMCs edited in the presence of i53 to CD34-expressing LT-HSPCs edited with i53.

Additionally, the functionality of erythrocytes differentiated from edited PBMCs was evaluated by measuring cell-surface markers using flow cytometry as described above. PBMCs edited with either R02+AAV.323 or R02+AAV.232+i53 had similar levels of $CD71^{-}GlyA^{+}$ erythrocytes to control cells (R02 only or Mock EP cells), indicating edited cells undergoing HDR repair of the HBB locus properly differentiate to mature erythrocytes (data not shown).

Example 9. Analysis of Off-Target Genomic Editing with R02 gRNA

Off-target sites were investigated that hybridize and are edited by the R02 gRNA when provided as an RNP complex with wild-type SpCas9 polypeptide. Briefly, an analysis to identify putative off-target sites was performed using two approaches. The first approach was to screen the human genome to identify genomic sequences complementary to the R02 spacer sequence with i) up to 3 mismatches, or ii) 2 mismatches and 1 gap. The homology computation off-target prediction was performed using CCTOP, CRISPOR, and COSMID algorithms. Using this approach, 179 off-target sequences were predicted to have homology to the R02 spacer sequence.

The second approach was to screen candidate off-target sites using GUIDE-Seq (see, e.g., Tsai et al (2015) NAT BIOTECHNOL. 33:187). Based on this approach, 36 sites in the genomic DNA were identified as undergoing off-target CRISPR/Cas9 cleavage using the R02 gRNA.

Candidate off-target sequences were screened using a quantitative hybrid capture assay.

Briefly, $5\times10^{5}$ CD34-expressing LT-HSPCs were thawed and electroporated with RNP containing 15 μg SpCas9 polypeptide and 15 μg R02 sgRNA. Edited cells were treated with RNP containing SpCas9 polypeptide obtained from two separate commercial vendors (referred to as WT SpCas9_1 and WT SpCas9_2). Control cells were electroporated without RNP.

Edited and control cells were harvested, and genomic DNA was extracted using a DNeasy kit (Qiagen). The genomic DNA samples were hybridized with short probes that were prepared to overlay the region of the genomic DNA that included the putative off-target sequences. Bound genomic DNA was then enriched using a pull-down purification targeting the hybridization probe. The genomic DNA was then sequenced for frequency of INDELs by NGS analysis. The ratio of total number of reads with INDELs to the total number of reads was quantified for each putative target site for genomic DNA isolated from edited cells and control cells. For putative off-target sites with a frequency of INDELs exceeding 0.2% in edited cells compared to control cells, the target site was evaluated by statistical testing. A paired, on-sided T test was used to identify sites with significant difference in frequency of INDELs between edited and control cells (i.e., $p<0.05$).

Based on this analysis, two sites were identified as having a statistically significant level of off-target editing with the R02 gRNA/Cas9 complex using either WT SpCas9_1 or WT SpCas9_2. The sites identified were OT1 located at chr9:101,833,575-101,833,624 and OT2 located at chr12:124,319,275-124,319,308, each location relative to human reference genome hg38.

It was evaluated whether gene-editing at off-target sites would be reduced by combining R02 with a SpCas9 variant engineered for increased fidelity, while retaining on-target cutting efficiency.

SpCas9 variants having a R691A mutation have been reported to have increased fidelity (i.e., high fidelity or HiFi) by reducing Cas9 nuclease activity at sites with gRNA mismatches, while maintaining cutting efficiency at on-target sites (see, e.g., Vakulskas, et al (2018) *NAT MED* 24:1216). Accordingly, RNP complex containing R02 sgRNA and an SpCas9 variant having a R691A mutant were evaluated for frequency of edits at on-target and off-target sites in CD34-expressing LT-HSPCs. Specifically, two SpCas9 R691A HiFi variants were evaluated, a first variant having an N-terminal and C-terminal sv40 NLS (referred to as HF SpCas9_1) and a second variant having three N-terminal NLS sequences (referred to as HF SpCas9_2).

For editing, $5\times10^{5}$ CD34-expressing LT-HSPCs were electroporated with RNP containing 15 μg of R02 sgRNA and 15 g of either HF_SpCas9_1 or HF_SpCas9_2. Additionally, the cells were electroporated with 10,000 MOI of AAV.307. Control cells were edited under the same conditions using RNP containing either WT SpCas9_1 or WT SpCas9_2.

Figure 35A:
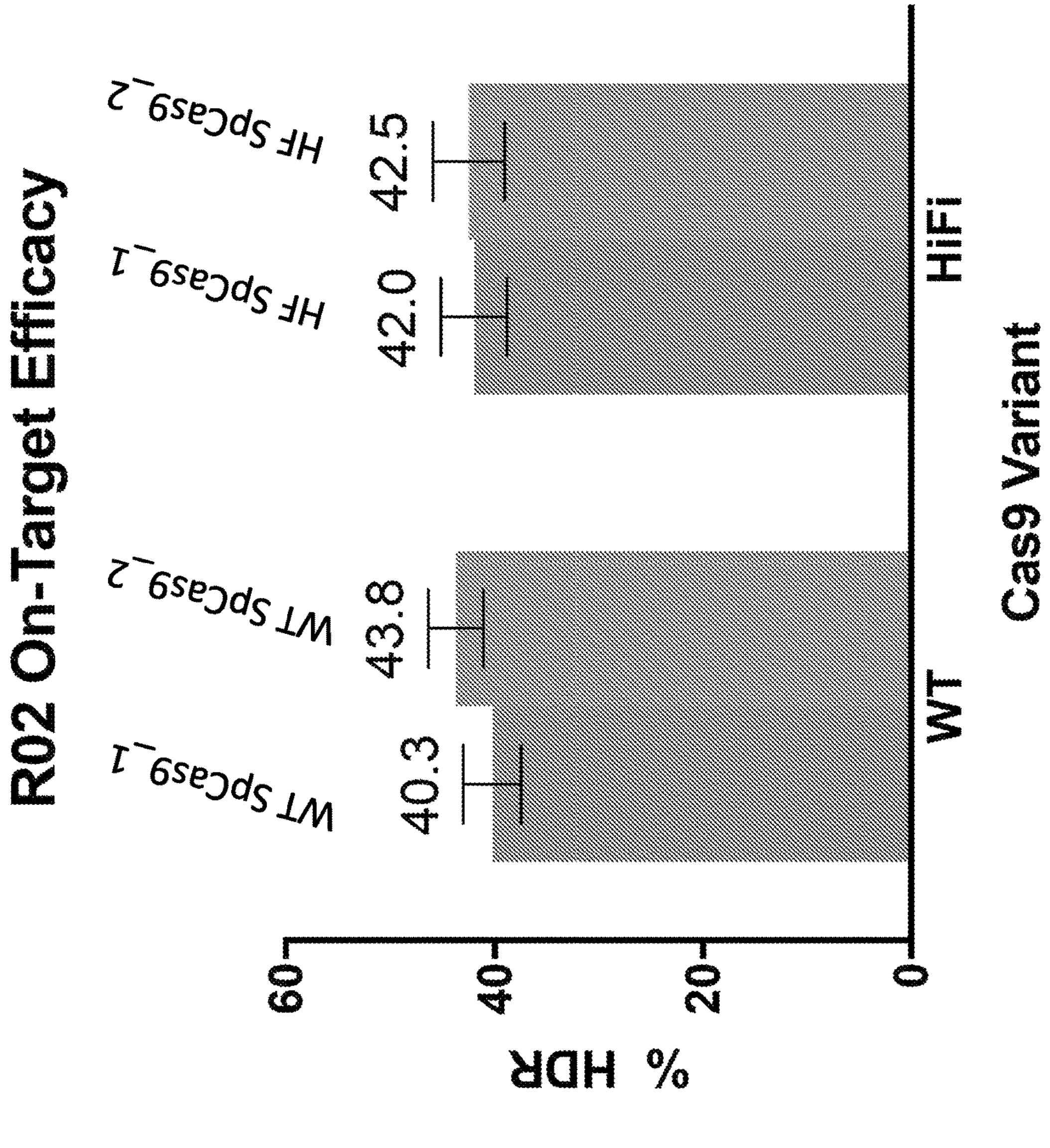
FIGS. 35A-35C provide bar graphs quantifying HDR editing efficiency at the R02 target site in the HBB gene (FIG. 35A) and the frequency of INDELs at R02 off-target sites OT1 (FIG. 35B) and OT2 (FIG. 35C) for CD34-expressing LT-HSPCs edited with RNP containing wild-type (WT) Cas9 or high fidelity (HiFi) Cas9 and R02 gRNA and AAV.307.

The efficiency of gene-editing at the HBB gene by HDR was evaluated using the NGS sequencing assay described in Example 4 on day 2 post-editing. As shown in FIG. 35A, the level of HDR using either HiFi SpCas9 variant was comparable to the level of HDR for editing using wild-type SpCas9. The level of HDR for each SpCas9 is shown in Table 9.

Figure 35B:
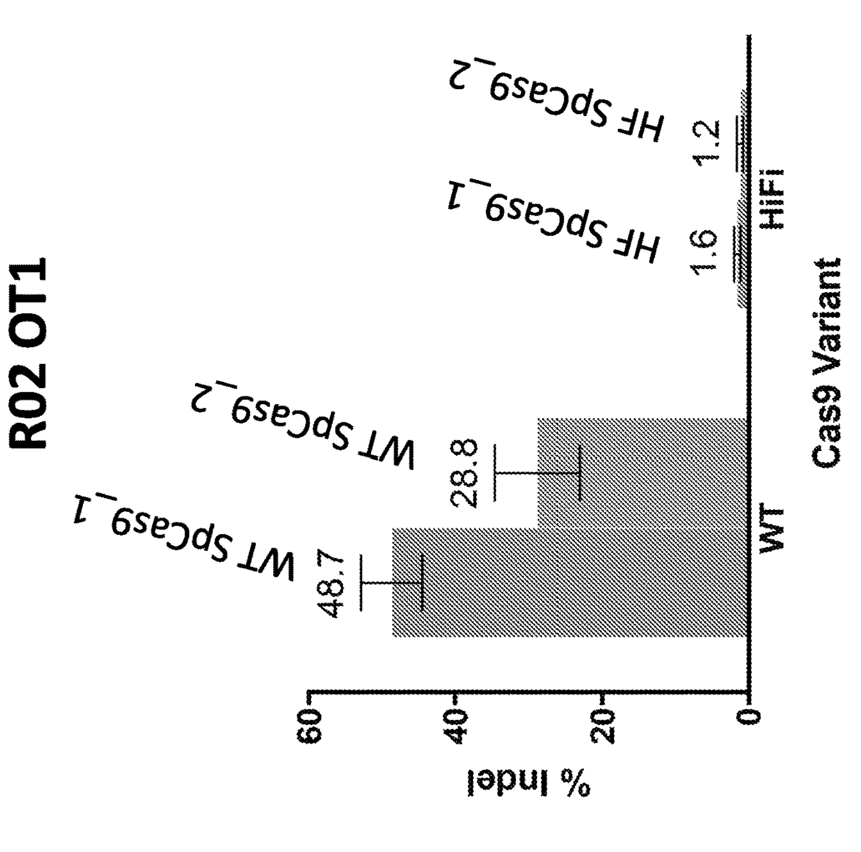
Figure 35C:
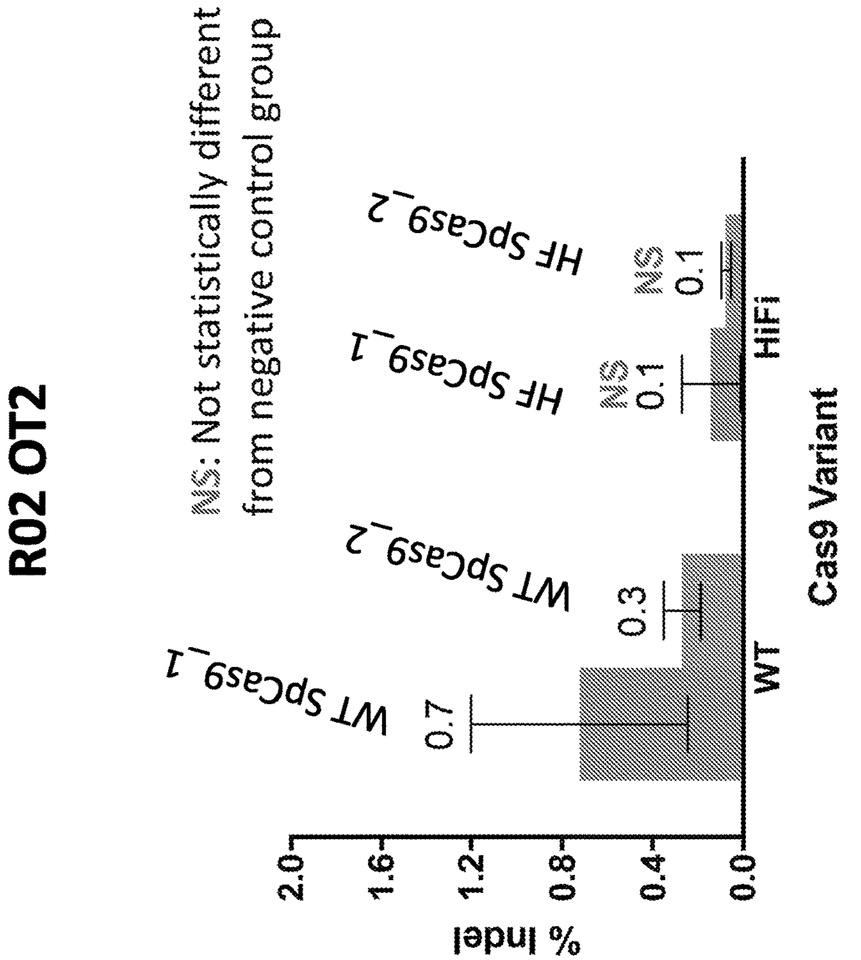

The frequency of INDELs at the OT1 and OT2 cut-sites was evaluated using genomic DNA extracted from edited cells. Primers flanking the OT1 and OT2 sites were used to amplify regions of the genomic DNA encompassing these sites by PCR. The PCR products were purified and sequenced using NGS. The sequencing data was analyzed to determine the frequency of INDELs at the OT1 and OT2 sites. As shown in FIG. 35B, the frequency of INDELs at the OT1 site was substantially reduced using either HiFi SpCas9 variant compared to that induced using wild-type SpCas9. As shown in FIG. 35C, frequency of INDELs at the OT2 site was negligible with use of either HiFi SpCas9 variants.

Quantification of INDEL frequency at the OT1 and OT2 for each SpCas9 variant is further shown in Table 9.

TABLE 9

On-Target and Off-Target Editing by SpCas9/R02 gRNA RNP

| SpCas9 | % HDR | OT1 % INDEL | OT2 % INDEL |
|---|---|---|---|
| WT SpCas9_1 | 40.3 | 48.7 | 0.7 |
| WT SpCas9_2 | 43.8 | 28.8 | 0.3 |

TABLE 9-continued

| On-Target and Off-Target Editing by SpCas9/R02 gRNA RNP | | | |
|---|---|---|---|
| SpCas9 | % HDR | OT1 % INDEL | OT2 % INDEL |
| HF SpCas9_1 | 42.0 | 1.6 | 0.1 |
| HF SpCas9_2 | 42.5 | 1.2 | 0.1 |

Example 10. Analysis of Hemoglobin Monomers in Edited CD34-Expressing LT-HSPCs

The hemoglobin monomers produced by CD34-expressing LT-HSPCs following CRISPR/Cas editing with R02 gRNA and subsequent in vitro differentiation was investigated. Briefly, CD34-expressing LT-HSPCs derived from healthy human patient donors and human patient donors with a SCD mutation (E6V) were isolated and seeded in culture as described in Example 8.

Editing of cells was performed following two days of in vitro culture. Briefly, $5\times10^5$ cells were electroporated with RNP containing 20 g SpCas9 and 20 μg R02 sgRNA and 10,000 MOI AAV.323. The cells were incubated with AAV.323 for 1 hour prior to electroporation. The cells were edited by electroporation with R02 RNP+AAV.323 or R02 RNP only and compared to control cells electroporated without RNP or AAV (mock EP). Subsequently, the cells were differentiated by in vitro culture as described in Example 8.

Hemoglobin monomers produced by differentiated cells was assessed on day 18 post-editing. Briefly, approximately $1\times10^6$ cells were harvested, centrifuged, and prepared for HPLC analysis. Hemoglobin monomers expressed by edited cells were detected using LC-MS with separation by reverse phase chromatography. The chromatography enabled separation and quantification of hemoglobin variants (e.g., beta-globin, delta-globin, alpha-globin, gamma2-globin, and gamma1-globin). Beta-globin variants were further differentiated based on elution time. These included wild-type beta globin (B), beta globin with SCD mutation (S) and unknown beta-globin monomers (U). The unknown beta-globing monomers were further characterized based upon analysis by mass spectrometry.

Editing with R02 RNP alone induces a high frequency of INDELs in the HBB gene. Such INDELs can introduce frameshift mutations in HBB that disrupt gene expression. Thus, LT-HSPCs edited with R02 RNP and differentiated to erythrocytes are expected to produce decreased levels of beta-globin monomers (i.e., B+S+U) relative to total hemoglobin. It was evaluated if editing using R02 RNP+AAV would prevent this phenotype by reducing frequency of INDELs in the HBB gene.

Figure 36A:
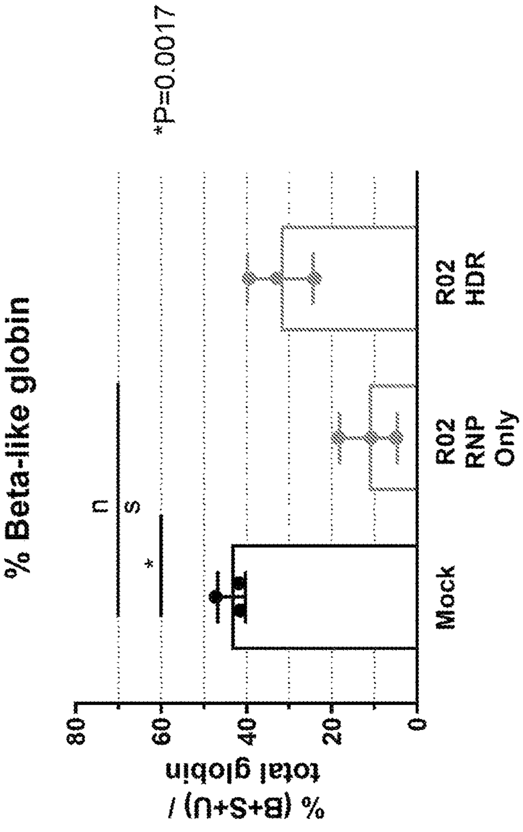
FIG. 36A provides a bar graph quantifying the ratio of beta globin monomers (beta-globin (B), beta-globin with SCD mutation (S), and unknown beta-globin mutants (U)) to total hemoglobin expressed by SCD patient and healthy donor-derived CD34+LT-HSPCs following editing and in vitro differentiation. Cells were edited by electroporation with R02 RNP and AAV.323 or with R02 RNP only. Control cells were electroporated without RNP or AAV (mock).

As shown in FIG. 36A, CD34-expressing LT-HSPCs edited with R02 RNP alone had an approximately 1.8-fold decrease in beta-globin monomers (B+S+U) relative to total hemoglobin compared to mock EP control cells, indicating overall reduced expression of beta-globin monomers. In contrast, cells edited with R02 RNP+AAV had no significant difference compared to mock EP control cells in the level of beta-globin monomers (B+S+U) relative to total hemoglobin.

Figure 36B:
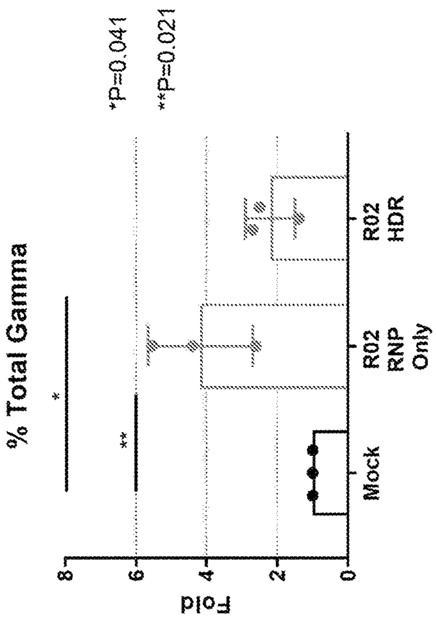
FIG. 36B provides a bar graph quantifying fold-change in total gamma-globin expression by cells edited as in FIG. 36A compared to expression by mock control cells.

Furthermore, the level of gamma globin expressed by edited cells following in vitro differentiation was also assessed using the LCMS assay. As shown in FIG. 36B, the level of total gamma-globin relative to total hemoglobin was increased in cells edited with either R02 RNP alone or R02+AAV relative to mock EP control cells. These data indicate upregulation of gamma-globin in edited cells can contribute to production of functional hemoglobin (i.e., HbF), potentially off-setting any decrease in beta-globin production.

Figure 36C:
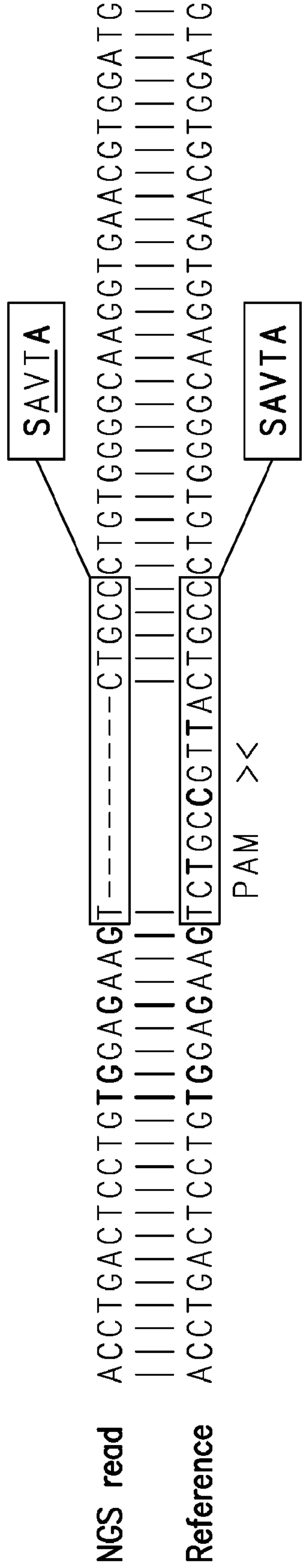
FIG. 36C provides a schematic showing a 9nt deletion in the HBB gene induced by repair of an R02-induced DSB (NGS Read, SEQ ID NO: 123) as compared to the wild-type HBB gene (reference, SEQ ID NO: 124) and corresponding polypeptide sequence (SEQ ID NO: 122) encoded by the NGS and reference reads.

The beta globin monomers produced by edited cells were compared to sequence reads from NGS analysis of the region surrounding the R02 cut site. CD34-expressing LT-HSPCs derived from either a patient donor with SCD or a healthy donor were edited with R02 RNP or R02 RNP+AAV as described above. INDELs induced at the R02 cut site were evaluated by NGS analysis, and the sequence reads were used to identify the most common INDELs induced in the HBB gene following editing in both the wild-type HBB gene and the HBB gene with a E6V mutation. Based on this analysis, a deletion of 9 nucleotides surrounding the R02 cut site as shown in FIG. 36C was determined as occurring in both LT-HSPCs derived from healthy or SCD patient donors. Indeed, 20-30% of sequence reads from the cells edited with R02 RNP and 3-9% of sequence reads from the cells edited with R02 RNP+AAV corresponded to the −9 nucleotide INDEL.

Example 11. Increased HDR Efficiency with DNA-PK Inhibitors for Editing the HBB Gene in CD34-Expressing LT-HSPCs Potent inhibitors of the DNA-PK enzyme complex that functions in the NHEJ repair machinery were evaluated for blocking NHEJ repair and improving HDR efficiency when used with CRISPR/Cas components for editing the HBB gene locus. Specifically, compounds 984 and 296 have been reported as reversible inhibitors of the DNA-PK catalytic subunit (DNA-PKcs), for example, see U.S. Pat. No. 9,592,232 which is herein incorporated by reference. The compounds have high affinity and selectivity for DNA-PK.

Structure of compounds 984 and 296 are provided in Table 10.

TABLE 10

Structures of DNA-PK Inhibitors

Compound 984

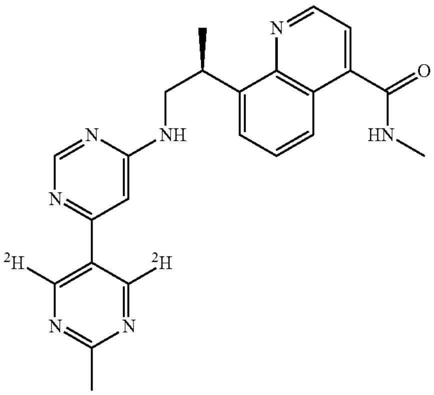

TABLE 10-continued

Structures of DNA-PK Inhibitors

Compound 296

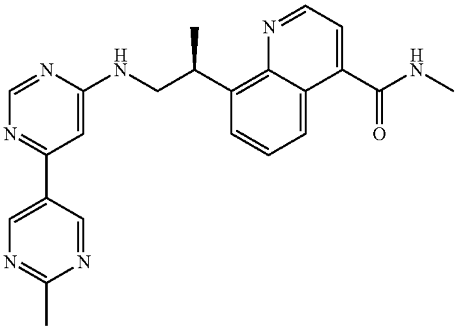

The effect of DNA-PK inhibition using Compound 296 was compared to the effect of 53BP1 inhibition using i53 for increased HDR repair of the HBB gene locus with donor DNA encoding GFP. Specifically, frozen CD34-expressing LT-HSPCs isolated from plerixafor-mobilized or plerixafor/GCSF-dual mobilized peripheral blood obtained from healthy human donors were thawed and seeded in media with components as described in Example 3. The cells were maintained in culture, and gene-editing was performed following two days of culture.

For editing, $5\times10^5$ CD34-expressing LT-HSPCs were electroporated with RNP containing 20 μg SpCas9 and 20 μg R02 gRNA. Electroporation was performed using the CA-137 program of the Lonza Amaza™ 4D-Nucleofector™. The cells were electroporated with a dsDNA homology donor encoding GFP under a SFFV promoter that was delivered by AAV at a dose of 10,000 MOI. The AAV donor was administered 1 hour prior to electroporation. The cells were electroporated with compound 296 at a concentration ranging from 0.014 μM to 10 μM. For comparison, positive control cells were electroporated with 1 g i53 mRNA and negative control cells were electroporated with RNP+AAV only.

The efficiency of HDR for repair of the HBB gene with donor encoding GFP was determined by measuring the percentage of cells expressing GFP following electroporation.

Edited cells were evaluated for GFP fluorescence on day 2 post-editing using flow cytometry, and viability was determined via staining with Tryphan Blue.

Figure 37A:
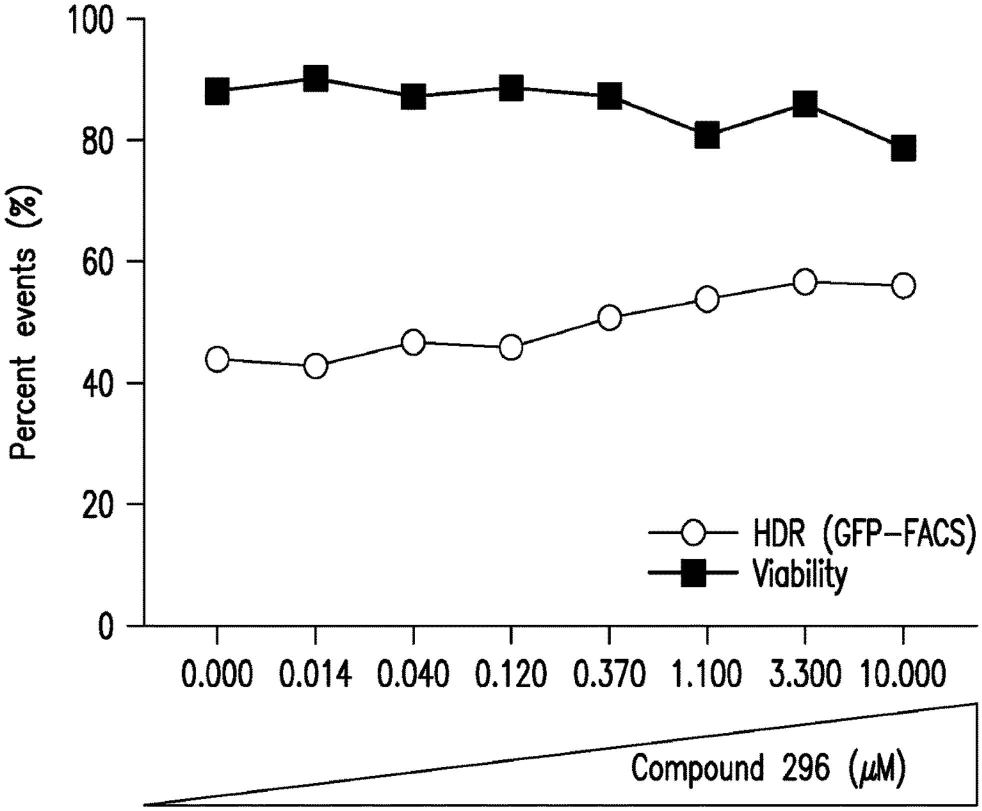
FIGS. 37A-37B provide graphs showing HDR editing efficiency for insertion of donor DNA encoding GFP in the HBB gene locus of CD34-expressing LT-HSPCs following editing with R02 RNP+AAV-delivered donor DNA encoding GFP either alone or in combination with a DNA-PK inhibitor (compound 296) provided at indicated concentrations.
Figure 37B:
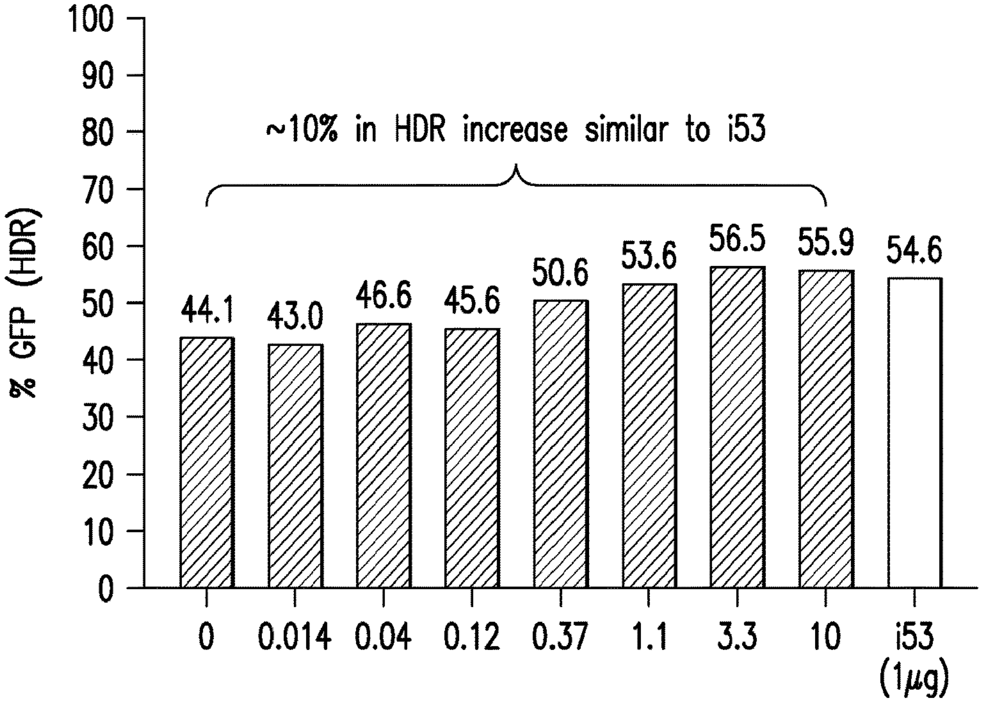

As shown in FIG. 37A, the level of HDR repair for cells edited with treatment of 1.1 μM, 3.3 μM, or 10 μM of compound 296 (53.5%, 56.5%, and 55.9% respectively) was significantly higher than for negative control cells edited without compound 296 (44.1%). Additionally, viability of edited cells was high for each concentration of compound 296 evaluated (>80%). As shown in FIG. 37B, the level of HDR repair for cells edited with treatment of 1.1 μM, 3.3 μM, or 10 μM of compound 296 was comparable to cells edited with i53 mRNA.

The DNA-PK inhibitors were evaluated in combination with R02 RNP and AAV.307 for increasing HDR efficiency at the HBB gene locus, and compared to effect of editing with i53. Editing was performed as described above. However, the cells were electroporated with AAV.307 administered 1 hour prior to electroporation at a dose of 10,000 MOI. The cells were electroporated with compound 296 at a concentration ranging from 0.005 μM to 10 μM, with compound 984 at a concentration ranging from 0.005 μM to 10 PM, or with 1 μg i53 mRNA. Negative control cells were electroporated with RNP+AAV only or RNP only.

Edited cells were evaluated for viability as described above, and for incorporation of gene-edits at 2 days post-electroporation. The efficiency of HDR repair for insertion of an E6V mutation in the HBB gene was quantified by NGS assay as described in Example 4. The frequency of INDELs induced at the R02 cut site was also evaluated by NGS analysis.

Figure 38A:
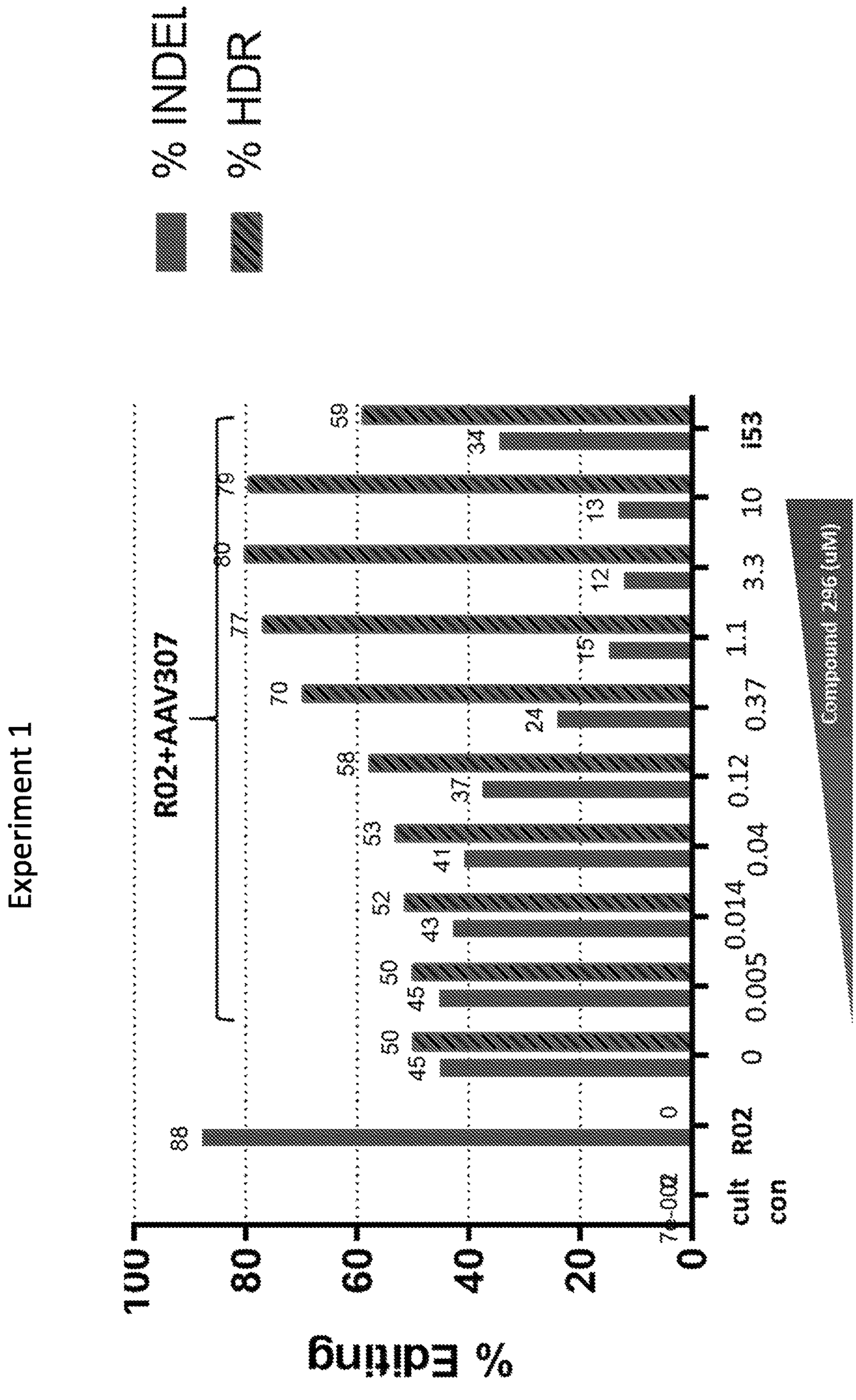
FIGS. 38A-38C provide graphs quantifying HDR editing efficiency and frequency of INDELs in the HBB gene for CD34-expressing LT-HSPCs edited with R02 RNP+AAV.307 either alone or in combination with compound 296 at indicated concentrations. Comparison is made to cells edited with R02 RNP+AAV.307+i53 and control cells edited with R02 RNP only.
Figure 38B:
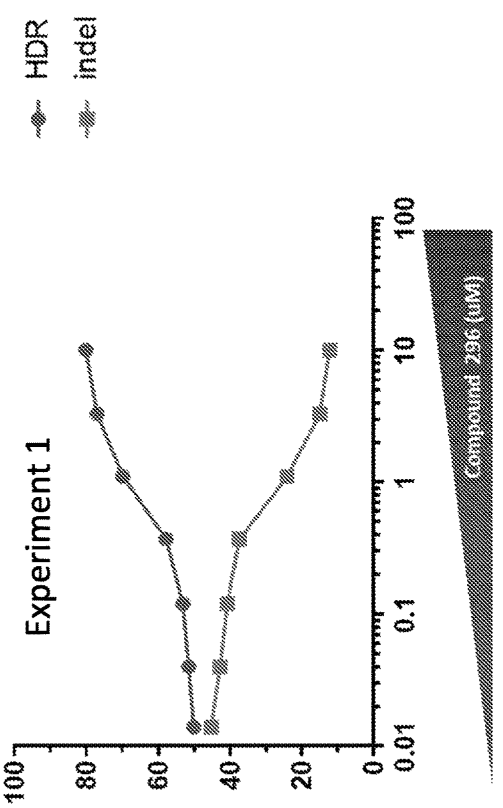

As shown in FIGS. 38A-38B, the level of HDR repair for cells edited with 0.37-10 M of compound 296 was 70% or higher. Indeed, treatment with 3.3 μM of compound 296 resulted in editing with 80% HDR efficiency. HDR efficiency at these concentrations was at least 1.6-fold higher than for control cells edited with R02 RNP+AAV only. Moreover, the frequency of INDELs at these concentrations was reduced by at least 4.6 fold compared to control cells edited with R02 RNP only.

Figure 38C:
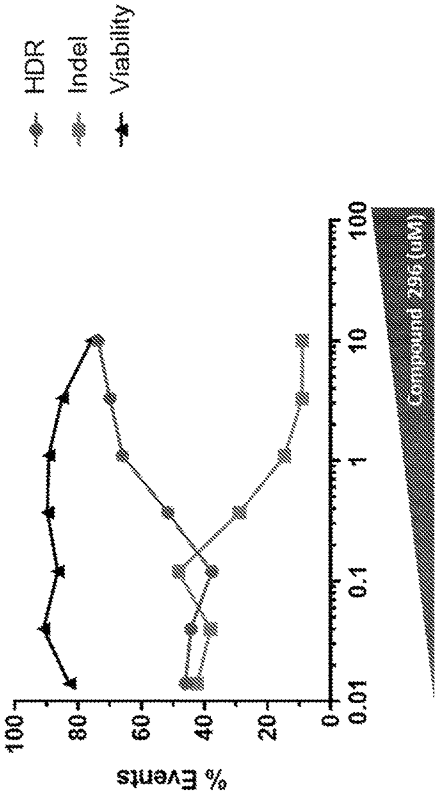

The level of HDR repair for cells edited with i53 was also high (59%), with reduced frequency of INDELs relative to control cells. In an independent experiment testing equivalent conditions ("Experiment 2"), levels of HDR and INDEL frequency were similar for each of the concentrations of compound 296 evaluated (FIG. 38C). Moreover, viability of edited cells was high at each concentration of compound 296 used for editing (>80%).

Figure 38D:
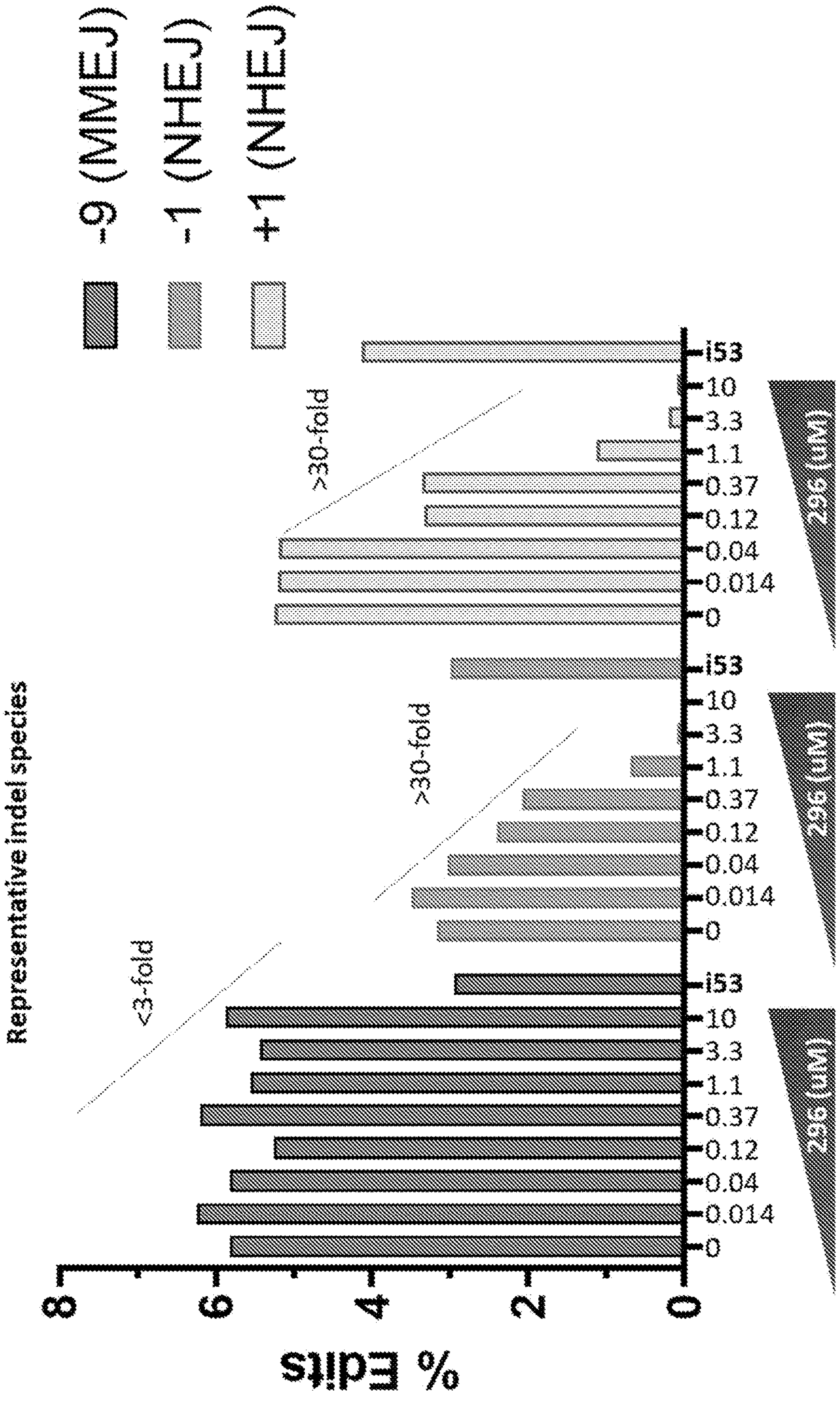
FIG. 38D provides a bar graph quantifying the percentage of total sequence reads having a deletion in HBB of 9 nt (corresponding to repair by the MMEJ pathway) or an INDEL in HBB of 1 nt (corresponding to repair by NHEJ) for cells edited as in FIGS. 38A-38C. The fold-reduction in INDEL frequency is indicated for cells edited with 10 M compound 296 as compared to no editing with compound 296.

The INDELs species identified for cells edited in Experiment 2 were further evaluated to determine frequency of repair by NHEJ or MMEJ repair pathways. An INDEL of 1 nt was considered due to NHEJ repair; a deletion of −9 nt was considered due to MMEJ repair based on the microhomology present on either side of the R02 cut site. Based on percentage of total reads corresponding to these INDEL species, the ratio of gene edits due to NHEJ and MMEJ repair was evaluated. As shown in FIG. 38D, cells edited in the presence of compound 296 had up to a 30-fold decrease in INDELs due to NHEJ repair, with only a modest reduction in INDEL species due to MMEJ repair. Thus, reduced frequency of INDELs with treatment of compound 296 is largely due to suppression of the NHEJ repair pathway.

Figure 39A:
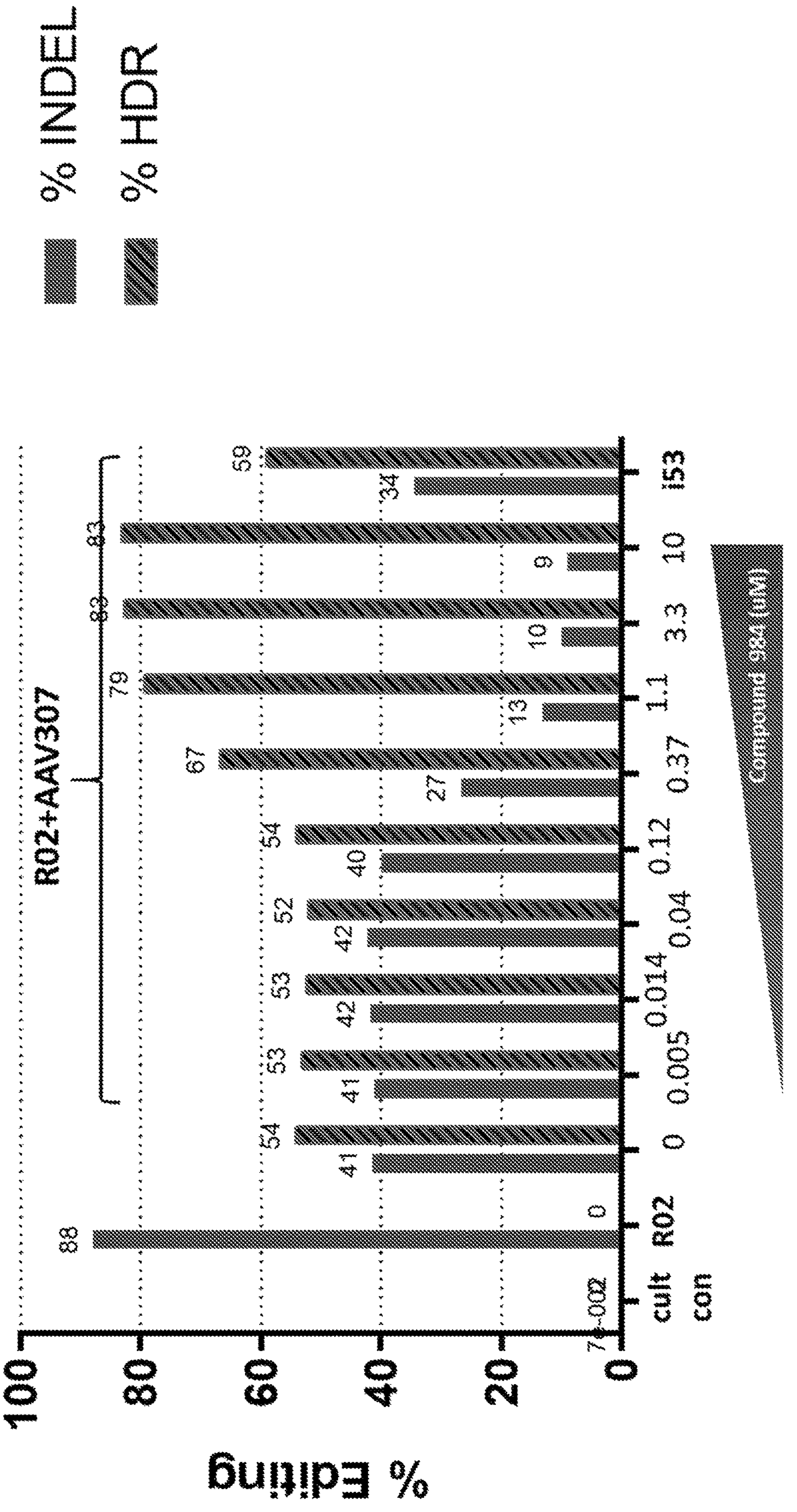
FIGS. 39A-39B provide graphs quantifying HDR editing efficiency and frequency of INDELs in the HBB gene for CD34-expressing LT-HSPCs edited with R02 RNP+AAV.307 either alone or in combination with the DNA-PK inhibitor compound 984 at indicated concentrations. Comparison is made to control cells edited R02 RNP+AAV.307+i53 and control cells edited with R02 RNP only.
Figure 39B:
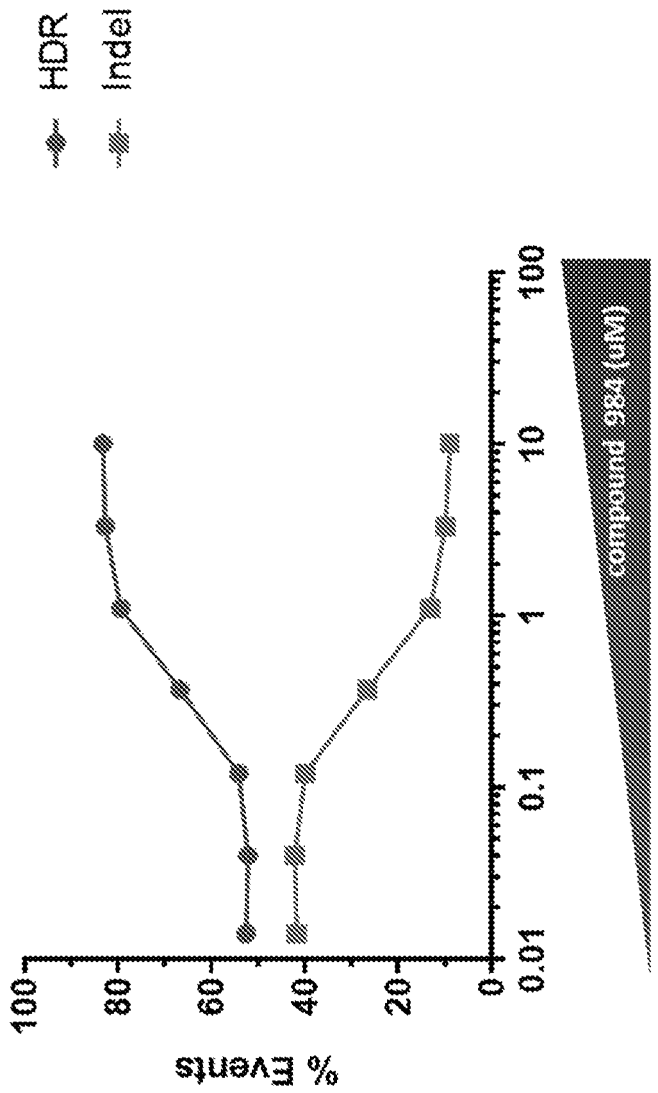

Evaluation of cells edited with compound 984 also demonstrated high levels of HDR editing and decreased frequency of INDELs in the HBB gene. As shown in FIGS. 39A-39B, the level of HDR repair for cells edited with treatment of 0.37-10 μM of compound 984 was high, with treatment of 3.3 μM or 10 μM in particular resulting in >80% HDR efficiency compared to 54% HDR efficiency in cells edited with R02 RNP+AAV only. The frequency of INDELs at these concentrations were also significantly reduced compared to control cells edited with R02 RNP only (i.e., by approximately 8-fold). Additionally, good viability was observed for cells following editing with compound 984, particularly at minimal concentrations that were identified as effective for editing.

Together these data demonstrate a substantial improvement in HDR editing efficiency and decreased frequency of INDELs in the HBB gene locus when DNA-PK inhibitors compound 296 or 984 are combined with RNP containing R02 gRNA.

Sequence Listing

| SEQ ID NO: | Identifier | Name/ Description | Sequence |
|---|---|---|---|
| 1 | gRNA-related | sgRNA 1 | $n_{(17-30)}$guuuuagagcuagaaauagcaaguuaaaauaaggcuaguccguuaucaacuugaaaaaguggcaccgagucggugcu$_{(1-8)}$ |
| 2 | gRNA-related | SpCas9 sgRNA | csususN$_{(17-30)}$ GUUUUAGAGCUAGAAAUAGCAAGUUAAAAUAAGGCUAGUC CGUUAUCAACUUGAAAAAGUGGCACCGAGUCGGUGCususus U |
| 3 | gRNA-related | AAVS1 target sequence A | GGGGCCACTAGGGACAGGAT |
| 4 | gRNA-related | AAVS1 sgRNA spacer A | GGGGCCACUAGGGACAGGAU |
| 5 | gRNA-related | AAVS1 target sequence B | GCCAGTAGCCAGCCCCGTCC |
| 6 | gRNA-related | AAVS1 sgRNA spacer B | GCCAGUAGCCAGCCCCGUCC |
| 7 | gRNA-related | BFP target sequence | TGAAGCACTGCACGCCAT |
| 8 | gRNA-related | BFP sgRNA spacer | UGAAGCACUGCACGCCAU |
| 9 | gRNA-related | GFP target sequence A | GCTGAAGCACTGCACGCCGT |
| 10 | gRNA-related | GFP sgRNA spacer A | GCUGAAGCACUGCACGCCGU |
| 11 | gRNA-related | GFP target sequence B | CTCGTGACCACCCTGACCTA |
| 12 | gRNA-related | GFP sgRNA spacer B | CUCGUGACCACCCUGACCUA |
| 13 | gRNA-related | GSD1a target sequence | TCTTTGGACAGCGTCCATAC |
| 14 | gRNA-related | GSD1a Ch32 gRNA spacer | UCUUUGGACAGCGUCCAUAC |
| 15 | gRNA-related | HBB target sequence | CTTGCCCCACAGGGCAGTAA |
| 16 | gRNA-related | HBB RO2 sgRNA spacer | CUUGCCCCACAGGGCAGUAA |
| 17 | gRNA-related | HBB sgRNA | csususGCCCCACAGGGCAGUAAGUUUUAGAGCUAGAAAUAG CAAGUUAAAAUAAGGCUAGUCCGUUAUCAACUUGAAAAAG UGGCACCGAGUCGGUGCususus U |
| 18 | gRNA-related | CFTR target sequence | TCTGTATCTATATTCATCAT |
| 19 | gRNA-related | CFTR sgRNA spacer | UCUGUAUCUAUAUUCAUCAU |
| 20 | gRNA-related | HBB Target Sequence (PAM in bold) | CTTGCCCCACAGGGCAGTAA**CGG** |
| 21 | Donor DNA | ssODN1 (Ht-CR282) | GCCACCTACGGCAAGCTGACCCTGAAGTTCATCTGCACCACC GGCAAGCTGCCCGTGCCCTGGCCCACCCTCGTGACCACCCTG ACGTACGGCGTGCAGTGCTTCAGCCGCTACCCCGACCACATG A |
| 22 | Donor DNA | ssODN2 (Hn-CR283) | TCATGTGGTCGGGGTAGCGGCTGAAGCACTGCACGCCGTACG TCAGGGTGGTCACGAGGGTGGGCCAGGGCACGGGCAGCTTG CCGGTGGTGCAGATGAACTTCAGGGTCAGCTTGCCGTAGGTG GC |

-continued

Sequence Listing

| SEQ ID NO: | Identifier | Name/ Description | Sequence |
| --- | --- | --- | --- |
| 23 | Donor DNA | ssODN3 (Hn-39-88) | CGCTCCTGGACGTAGCCTTCGGGCATGGCGGACTTGAAGAAGTCGTGCTGCTTCATGTGGTCGGGGTAGCGGCTGAAGCACTGCACGCCGTACGTCAGGGTGGTCACGAGGGTGGGCCAGGGCACGG |
| 24 | Donor DNA | ssODN4 (Ht-91-61) | GCCACCTACGGCAAGCTGACCCTGAAGTTCATCTGCACCACCGGCAAGCTGCCCGTGCCCTGGCCCACCCTCGTGACCACCCTGACGTACGGCGTGCAGTGCTTCAGCCGCTACCCCGACCACATGAAGCAGCACGACTTCTTCAAGTCCGC |
| 25 | Donor DNA | ssODN (Hn-91-61) | GCGGACTTGAAGAAGTCGTGCTGCTTCATGTGGTCGGGGTAGCGGCTGAAGCACTGCACGCCGTACGTCAGGGTGGTCACGAGGGTGGGCCAGGGCACGGGCAGCTTGCCGGTGGTGCAGATGAACTTCAGGGTCAGCTTGCCGTAGGTGGC |
| 26 | Donor DNA | ssODN (Hn-91-36) | TCATGTGGTCGGGGTAGCGGCTGAAGCACTGCACGCCGTACGTCAGGGTGGTCACGAGGGTGGGCCAGGGCACGGGCAGCTTGCCGGTGGTGCAGATGAACTTCAGGGTCAGCTTGCCGTAGGTGGC |
| 27 | Donor DNA | ssODN (Ht-91-61) | GCCACCTACGGCAAGCTGACCCTGAAGTTCATCTGCACCACCGGCAAGCTGCCCGTGCCCTGGCCCACCCTCGTGACCACCCTGACGTACGGCGTGCAGTGCTTCAGCCGCTACCCCGACCACATGAAGCAGCACGACTTCTTCAAGTCCGC |
| 28 | Donor DNA | ssODN (Ht-39-88) | CGCTCCTGGACGTAGCCTTCGGGCATGGCGGACTTGAAGAAGTCGTGCTGCTTCATGTGGTCGGGGTAGCGGCTGAAGCACTGCACGCCGTACGTCAGGGTGGTCACGAGGGTGGGCCAGGGCACGG |
| 29 | Donor DNA | ssODN 1067 | GCCACCTACGGCAAGCTGACCCTGAAGTTCATCTGCACCACCGGCAAGCTGCCCGTGCCCTGGCCCACCCTCGTGACCACCCTGAGCcACGGGGTGCAGTGCTTCAGCCGCTACCCCGACCACATGA |
| 30 | Donor DNA | ssODN 1068 | TCATGTGGTCGGGGTAGCGGCTGAAGCACTGCACCCCGTGGCTCAGGGTGGTCACGAGGGTGGGCCAGGGCACGGGCAGCTTGCCGGTGGTGCAGATGAACTTCAGGGTCAGCTTGCCGTAGGTGGC |
| 31 | Donor DNA | ssODN 1069 | TCATCTGCACCACCGGCAAGCTGCCCGTGCCCTGGCCCACCCTCGTGACCACCCTGAGCcACGGGGTGCAGTGCTTCAGCCGCTACCCCGACCACATGAAGCAGCACGACTTCTTCAAGTCCGCCAT |
| 32 | Donor DNA | ssODN 1070 | ATGGCGGACTTGAAGAAGTCGTGCTGCTTCATGTGGTCGGGGTAGCGGCTGAAGCACTGCACCCCGTGGCTCAGGGTGGTCACGAGGGTGGGCCAGGGCACGGGCAGCTTGCCGGTGGTGCAGATGA |
| 33 | Donor DNA | ssODN 1061 | CTCCTGGACGTAGCCTTCGGGCATGGCGGACTTGAAGAAGTCGTGCTGCTTCATGTGGTCGGGGTAGCGGCTGAAGCACTGCACCCCGTGGCTCAGGGTGGTCACGAGGGTGGGCCAGGGCACGGGC |
| 34 | Donor DNA | ssODN 1062 | GCCCGTGCCCTGGCCCACCCTCGTGACCACCCTGAGCCACGGGGTGCAGTGCTTCAGCCGCTACCCCGACCACATGAAGCAGCACGACTTCTTCAAGTCCGCCATGCCCGAAGGCTACGTCCAGGAG |
| 35 | Donor DNA | ssODN 1063 | GACTTGAAGAAGTCGTGCTGCTTCATGTGGTCGGGGTAGCGGCTGAAGCACTGCACCCCGTGGCTCAGGGTGGTCACGAGGGTGGGCCAGGGCACGGGCAGCTTGCCGGTGGTGCAGATGAACTTCA |
| 36 | Donor DNA | ssODN 1064 | TGAAGTTCATCTGCACCACCGGCAAGCTGCCCGTGCCCTGGCCCACCCTCGTGACCACCCTGAGCcACGGGGTGCAGTGCTTCAGCCGCTACCCCGACCACATGAAGCAGCACGACTTCTTCAAGTC |

-continued

Sequence Listing

| SEQ ID NO: | Identifier | Name/ Description | Sequence |
| --- | --- | --- | --- |
| 37 | Donor DNA | 50-0 dsDNA | CCCAGAAACTTGTTCTGTTTTTCCATAGGATTCTCTTTGGACA GTGCCCT |
| 38 | Donor DNA | 150-0 dsDNA | AGGGCACTGTCCAAAGAGAATCCTATGGAAAAACAGAACAA GTTTCTGGGGTTACTGAATGAATGCTTTTGCCCAAAGCCTAC ACCTTCAAGAAGAGTGTAGCCTGAGAAGGATTTCACATGTTG CCTCTAGAAGGGAGAACTGGGTGGC |
| 39 | Donor DNA | 93-50 ssODN | TCTTGAAGGTGTAGGCTTTGGGCAAAAGCATTCATTCAGTAA CCCCAGAAACTTGTTCTGTTTTTCCATAGGATTCTCTTTGGAC AGTGCCCTTACTGGTGGGTCCTGGATACTGACTACTACAGCA ACACTTCCGTGCCCT |
| 40 | Donor DNA | 25-100 ssODN | TAGGATTCTCTTTGGACAGTGCCCTTACTGGTGGGTCCTGGAT ACTGACTACTACAGCAACACTTCCGTGCCCCTGATAAAGCAG TTCCCTGTAACCTGTGAGACTGGACCAGGTAAGCGTCCCA |
| 41 | Donor DNA | H3-95-30 ssODN | TAAGCACAGTGGAAGAATTTCATTCTGTTCTCAGTTTTCCTGG ATTATGCCTGGCACCATTAAAGAAAATATCATAAGCTTTGGT GTTTGCTATGATGAATATAGATACAGAAGCGTCATCAAAG |
| 42 | Donor DNA | N1-95-30 ssODN | AATTAAGCACAGTGGAAGAATTTCATTCTGTTCTCAGTTTTCC TGGATTATGCCTGGCACCATTAAAGAAAATATCATCTTTGGT GTTTGCTAGCATGATGAATATAGATACAGAAGCGTCATCA |
| 43 | Donor DNA | AAVS1 locus LHA (used for BFP donor) | CCCCAGCTCTTCTCTGTTCAGCCCTAAGAATCCTGGCTCCAGC CCCTCCTACTCTAGCCCCCAACCCCCTAGCCACTAAGGCAAT TGGGGTGCAGGAATGGGGGCAGGGTACCAGCCTCACCAAGT GGTTGATAAACCCACGTGGGGTACCCTAAGAACTTGGGAACA GCCACAGCAGGGGGGCGATGCTTGGGGACCTGCCTGGAGAA GGATGCAGGACGAGAAACACAGCCCCAGGTGGAGAAACTGG CCGGGAATCAAGAGTCACCCAGAGACAGTGACCAACCATCC CTGTTTTCCTAGGACTGAGGGTTTCAGTGCTAAAACTAGGCT GTCCTGGGCAAACAGCATAAGCTGGTCACCCCACACCCAGAC CTGACCCAAACCCAGCTCCCCTGCTTCTTGGCCACGTAACCT GAGAAGGGAATCCCTCCTCTCTGAACCCCAGCCCACCCCAAT GCTCCAGGCCTCCTGGGATACCCCGAAGAGTGAGTTTGCCAA GCAGTCACCCCACAGTTGGAGGAGAATCCACCCAAAAGGCA GCCTGGTAGACAGGGCTGGGGTGGCCTCTCGTGGGGTCCAGG CCAAGTAGGTGGCCTGGGGCCTCTGGGGGATGCAGGGGAAG GGGGATGCAGGGGAACGGGGATGCAGGGGAACGGGGCTCAG TCTGAAGAGCAGAGCCAGGAACCCCTGTAGGGAAGGGGCAG GAGAGCCAGGGGCATGAGATGGTGGACGAGGAAGGGGGAC AGGGAAGCCTGAGCGCCTCTCCTGGGCTTGCCAAGGACTCAA ACCCAGAAGCCCAGAGCAGGGCCTTAGGGAAGCGGGACCCT GCTCTGGGCGGAGGAATATGTCCCAGATAGCACTGGGGACTC TTTAAGGAAAGAAGGATGGAGAAAGAGAAAGGGAGTAGAG GCGGCCACGACCTGGTGAACACCTAGGACGCACCATTCTCAC AAAGGGAGTTTTCCACACGGACACCCCCCTCCTCACCACAGC CCTG |
| 44 | Donor DNA | BFP locus donor | ATGGTGAGCAAGGGCGAGGAGCTGTTCACCGGGGTGGTGCC CATCCTGGTCGAGCTGGACGGCGACGTAAACGGCCACAAGTT CAGCGTGTCCGGCGAGGGCGAGGGCGATGCCACCTACGGCA AGCTGACCCTGAAGTTCATCTGCACCACCGGCAAGCTGCCCG TGCCCTGGCCCACCCTCGTGACCACCCTGACCCATGGCGTGC AGTGCTTCAGCCGCTACCCCGACCACATGAAGCAGCACGACT TCTTCAAGTCCGCCATGCCCGAAGGCTACGTCCAGGAGCGCA CCATCTTCTTCAAGGACGACGGCAACTACAAGACCCGCGCCG AGGTGAAGTTCGAGGGCGACACCCTGGTGAACCGCATCGAG CTGAAGGGCATCGACTTCAAGGAGGACGGCAACATCCTGGG GCACAAGCTGGAGTACAACTACAACAGCCACAACGTCTATAT CATGGCCGACAAGCAGAAGAACGGCATCAAGGTGAACTTCA AGATCCGCCACAACATCGAGGACGGCAGCGTGCAGCTCGCC GACCACTACCAGCAGAACACCCCCATCGGCGACGGCCCCGTG CTGCTGCCCGACAACCACTACCTGAGCACCCAGTCCAAGCTG AGCAAAGACCCCAACGAGAAGCGCGATCACATGGTCCTGCT GGAGTTCGTGACCGCCGCCGGGATCACTCTCGGCATGGACGA GCTGTACAAG |
| 45 | Donor DNA | AAVS1 locus RHA (used for BFP donor) | ACTGTGGGGTGGAGGGGACAGATAAAAGTACCCAGAACCAG AGCCACATTAACCGGCCCTGGGAATATAAGGTGGTCCCAGCT CGGGGACACAGGATCCCTGGAGGCAGCAAACATGCTGTCCT GAAGTGGACATAGGGGCCCGGGTTGGAGGAAGAAGACTAGC |

-continued

Sequence Listing

| SEQ ID NO: | Identifier | Name/ Description | Sequence |
|---|---|---|---|
| | | | TGAGCTCTCGGACCCCTGGAAGATGCCATGACAGGGGGCTGG<br>AAGAGCTAGCACAGACTAGAGAGGTAAGGGGGGTAGGGGAG<br>CTGCCCAAATGAAAGGAGTGAGAGGTGACCCGAATCCACAG<br>GAGAACGGGGTGTCCAGGCAAAGAAAGCAAGAGGATGGAG<br>AGGTGGCTAAAGCCAGGGAGACGGGGTACTTTGGGGTTGTCC<br>AGAAAAACGGTGATGATGCAGGCCTACAAGAAGGGGAGGCG<br>GGACGCAAGGGAGACATCCGTCGGAGAAGGCCATCCTAAGA<br>AACGAGAGATGGCACAGGCCCCAGAAGGAGAAGGAAAAGG<br>GAACCCAGCGAGTGAAGACGGCATGGGGTTGGGTGAGGGAG<br>GAGAGATGCCCGGAGAGGACCCAGACACGGGGAGGATCCGC<br>TCAGAGGACATCACGTGGTGCAGCGCCGAGAAGGAAGTGCT<br>CCGGAAAGAGCATCCTTGGGCAGCAACACAGCAGAGAGCAA<br>GGGGAAGAGGGAGTGGAGGAAGACGGAACCTGAAGGAGGC<br>GGCAGGGAAGGATCTGGGCCAGCCGTAGAGGTGACCCAGGC<br>CACAAGCTGCAGACAGAAAGCGGCACAGGCCCAGGGGAGAG<br>AATGCAGGTCAGAGAAAGCAGGACCTGCCTGGGAAGGGGAA<br>ACAGTGGGCCAGAGGCGGCGCAGAAGCCAGTAGAGCTCAAA<br>GTGGTCCGGACTCAGGAGAGAGACGGCAGCGTTAGAGGGCA<br>GAGTTCCGGCGGCACAGCAAGGGCACTCGGGGGCGAGAGGA<br>GGGCAGCGCAAAGTGACAATGGCCAGGGCCAGGCAGATAGA<br>CCAGACTGAGCTATGG |
| 46 | Donor DNA | AAVS1 locus LHA (used for GFP donor) | CCCCAGCTCTTCTCTGTTCAGCCCTAAGAATCCTGGCTCCAGC<br>CCCTCCTACTCTAGCCCCCAACCCCCTAGCCACTAAGGCAAT<br>TGGGGTGCAGGAATGGGGGCAGGGTACCAGCCTCACCAAGT<br>GGTTGATAAACCCACGTGGGGTACCCTAAGAACTTGGGAACA<br>GCCACAGCAGGGGGGCGATGCTTGGGGACCTGCCTGGAGAA<br>GGATGCAGGACGAGAAACACAGCCCCAGGTGGAGAAACTGG<br>CCGGGAATCAAGAGTCACCCAGAGACAGTGACCAACCATCC<br>CTGTTTTCCTAGGACTGAGGGTTTCAGTGCTAAAACTAGGCT<br>GTCCTGGGCAAACAGCATAAGCTGGTCACCCCACACCCAGAC<br>CTGACCCAAACCCAGCTCCCCTGCTTCTTGGCCACGTAACCT<br>GAGAAGGGAATCCCTCCTCTCTGAACCCCAGCCCACCCCAAT<br>GCTCCAGGCCTCCTGGGATACCCCGAAGAGTGAGTTTGCCAA<br>GCAGTCACCCCACAGTTGGAGGAGAATCCACCCAAAAGGCA<br>GCCTGGTAGACAGGGCTGGGGTGGCCTCTCGTGGGGTCCAGG<br>CCAAGTAGGTGGCCTGGGGCCTCTGGGGGATGCAGGGGAAG<br>GGGGATGCAGGGGAACGGGGATGCAGGGGAACGGGGCTCAG<br>TCTGAAGAGCAGAGCCAGGAACCCCTGTAGGGAAGGGGCAG<br>GAGAGCCAGGGGCATGAGATGGTGGACGAGGAAGGGGGAC<br>AGGGAAGCCTGAGCGCCTCTCCTGGGCTTGCCAAGGACTCAA<br>ACCCAGAAGCCCAGAGCAGGGCCTTAGGGAAGCGGGACCCT<br>GCTCTGGGCGGAGGAATATGTCCCAGATAGCACTGGGGACTC<br>TTTAAGGAAAGAAGGATGGAGAAAGAGAAAGGGAGTAGAG<br>GCGGCCACGACCTGGTGAACACCTAGGACGCACCATTCTCAC<br>AAAGGGAGTTTTCCACACGGACACCCCCCTCCTCACCACAGC<br>CCTG |
| 47 | Donor DNA | GFP donor to AAVS1 locus | ATGGTGAGCAAGGGCGAGGAGCTGTTCACCGGGGTGGTGCC<br>CATCCTGGTCGAGCTGGACGGCGACGTAAACGGCCACAAGTT<br>CAGCGTGTCCGGCGAGGGCGAGGGCGATGCCACCTACGGCA<br>AGCTGACCCTGAAGTTCATCTGCACCACCGGCAAGCTGCCCG<br>TGCCCTGGCCCACCCTCGTGACCACCCTGACCTACGGCGTGC<br>AGTGCTTCAGCCGCTACCCCGACCACATGAAGCAGCACGACT<br>TCTTCAAGTCCGCCATGCCCGAAGGCTACGTCCAGGAGCGCA<br>CCATCTTCTTCAAGGACGACGGCAACTACAAGACCCGCGCCG<br>AGGTGAAGTTCGAGGGCGACACCCTGGTGAACCGCATCGAG<br>CTGAAGGGCATCGACTTCAAGGAGGACGGCAACATCCTGGG<br>GCACAAGCTGGAGTACAACTACAACAGCCACAACGTCTATAT<br>CATGGCCGACAAGCAGAAGAACGGCATCAAGGTGAACTTCA<br>AGATCCGCCACAACATCGAGGACGGCAGCGTGCAGCTCGCC<br>GACCACTACCAGCAGAACACCCCCATCGGCGACGGCCCCGTG<br>CTGCTGCCCGACAACCACTACCTGAGCACCCAGTCCGCCCTG<br>AGCAAAGACCCCAACGAGAAGCGCGATCACATGGTCCTGCT<br>GGAGTTCGTGACCGCCGCCGGGATCACTCTCGGCATGGACGA<br>GCTGTACAAGTAA |
| 48 | Donor DNA | AAVS1 locus RHA (used for GFP donor) | ACTGTGGGGTGGAGGGGACAGATAAAAGTACCCAGAACCAG<br>AGCCACATTAACCGGCCCTGGGAATATAAGGTGGTCCCAGCT<br>CGGGGACACAGGATCCCTGGAGGCAGCAAACATGCTGTCCT<br>GAAGTGGACATAGGGGCCCGGGTTGGAGGAAGAAGACTAGC<br>TGAGCTCTCGGACCCCTGGAAGATGCCATGACAGGGGGCTGG<br>AAGAGCTAGCACAGACTAGAGAGGTAAGGGGGGTAGGGGAG<br>CTGCCCAAATGAAAGGAGTGAGAGGTGACCCGAATCCACAG |

-continued

Sequence Listing

| SEQ ID NO: | Identifier | Name/ Description | Sequence |
|---|---|---|---|
| | | | GAGAACGGGGTGTCCAGGCAAAGAAAGCAAGAGGATGGAG<br>AGGTGGCTAAAGCCAGGGAGACGGGGTACTTTGGGGTTGTCC<br>AGAAAAACGGTGATGATGCAGGCCTACAAGAAGGGGAGGCG<br>GGACGCAAGGGAGACATCCGTCGGAGAAGGCCATCCTAAGA<br>AACGAGAGATGGCACAGGCCCCAGAAGGAGAAGGAAAAGG<br>GAACCCAGCGAGTGAAGACGGCATGGGGTTGGGTGAGGGAG<br>GAGAGATGCCCGGAGAGGACCCAGACACGGGGAGGATCCGC<br>TCAGAGGACATCACGTGGTGCAGCGCCGAGAAGGAAGTGCT<br>CCGGAAAGAGCATCCTTGGGCAGCAACACAGCAGAGAGCAA<br>GGGGAAGAGGGAGTGGAGGAAGACGGAACCTGAAGGAGGC<br>GGCAGGGAAGGATCTGGGCCAGCCGTAGAGGTGACCCAGGC<br>CACAAGCTGCAGACAGAAAGCGGCACAGGCCCAGGGGAGAG<br>AATGCAGGTCAGAGAAAGCAGGACCTGCCTGGGAAGGGGAA<br>ACAGTGGGCCAGAGGCGGCGCAGAAGCCAGTAGAGCTCAAA<br>GTGGTCCGGACTCAGGAGAGAGACGGCAGCGTTAGAGGGCA<br>GAGTTCCGGCGGCACAGCAAGGGCACTCGGGGGCGAGAGGA<br>GGGCAGCGCAAAGTGACAATGGCCAGGGCCAGGCAGATAGA<br>CCAGACTGAGCTATGG |
| 49 | Donor DNA | HBB locus LHA (used for E7 to E7V AAV.304) | CTTGCTTTGACAATTTTGGTCTTTCAGAATACTATAAATATAA<br>CCTATATTATAATTTCATAAAGTCTGTGCATTTTCTTTGACCC<br>AGGATATTTGCAAAAGACATATTCAAACTTCCGCAGAACACT<br>TTATTTCACATATACATGCCTCTTATATCAGGGATGTGAAACA<br>GGGTCTTGAAAACTGTCTAAATCTAAAACAATGCTAATGCAG<br>GTTTAAATTTAATAAAATAAAATCCAAAATCTAACAGCCAAG<br>TCAAATCTGCATGTTTTAACATTTAAAATATTTTAAAGACGTC<br>TTTTCCCAGGATTCAACATGTGAAATCTTTTCTCAGGGATACA<br>CGTGTGCCTAGATCCTCATTGCTTTAGTTTTTTACAGAGGAAT<br>GAATATAAAAAGAAAATACTTAAATTTTATCCCTCTTACCTCT<br>ATAATCATACATAGGCATAATTTTTTAACCTAGGCTCCAGAT<br>AGCCATAGAAGAACCAAACACTTTCTGCGTGTGTGAGAATAA<br>TCAGAGTGAGATTTTTTCACAAGTACCTGATGAGGGTTGAGA<br>CAGGTAGAAAAAGTGAGAGATCTCTATTTATTTAGCAATAAT<br>AGAGAAAGCATTTAAGAGAATAAAGCAATGGAAATAAGAAA<br>TTTGTAAATTTCCTTCTGATAACTAGAAATAGAGGATCCAGTT<br>TCTTTTGGTTAACCTAAATTTTATTTCATTTTATTGTTTTATTT<br>TATTTTATTTTATTTTATTTTGTGTAATCGTAGTTTCAGAGTGT<br>TAGAGCTGAAAGGAAGAAGTAGGAGAAACATGCAAAGTAAA<br>AGTATAACACTTTCCTTACTAAACCGACATGGGTTTCCAGGT<br>AGGGGCAGGATTCAGGATGACTGACAGGGCCCTTAGGGAAC<br>ACTGAGACCCTACGCTGACCTCATAAATGCTTGCTACCTTTGC<br>TGTTTTAATTACATCTTTTAATAGCAGGAAGCAGAACTCTGC<br>ACTTCAAAAGTTTTTCCTCACCTGAGGAGTTAATTTAGTACAA<br>GGGGAAAAAGTACAGGGGGATGGGAGAAAGGCGATCACGTT<br>GGGAAGCTATAGAGAAAGAAGAGTAAATTTTAGTAAAGGAG<br>GTTTAAACAAACAAAATATAAAGAGAAATAGGAACTTGAAT<br>CAAGGAAATGATTTTAAAACGCAGTATTCTTAGTGGACTAGA<br>GGAAAAAAATAATCTGAGCCAAGTAGAAGACCTTTTCCCCTC<br>CTACCCCTACTTTCTAAGTCACAGAGGCTTTTTGTTCCCCCAG<br>ACACTCTTGCAGATTAGTCCAGGCAGAAACAGTTAGATGTCC<br>CCAGTTAACCTCCTATTTGACACCACTGATTACCCCATTGATA<br>GTCACACTTTGGGTTGTAAGTGACTTTTTATTTATTTGTATTTT<br>TGACTGCATTAAGAGGTCTCTAGTTTTTTATCTCTTGTTTCCC<br>AAAACCTAATAAGTAACTAATGCACAGAGCACATTGATTTGT<br>ATTTATTCTATTTTTAGACATAATTTATTAGCATGCATGAGCA<br>AATTAAGAAAAACAACAACAAATGAATGCATATATATGTAT<br>ATGTATGTGTGTATATATACACACATATATATATATATTTTTT<br>CTTTTCTTACCAGAAGGTTTTAATCCAAATAAGGAGAAGATA<br>TGCTTAGAACCGAGGTAGAGTTTTCATCCATTCTGTCCTGTAA<br>GTATTTTGCATATTCTGGAGACGCAGGAAGAGATCCATCTAC<br>ATATCCCAAAGCTGAATTATGGTAGACAAAACTCTTCCACTT<br>TTAGTGCATCAACTTCTTATTTGTGTAATAAGAAAATTGGGA<br>AAACGATCTTCAATATGCTTACCAAGCTGTGATTCCAAATAT<br>TACGTAAATACACTTGCAAAGGAGGATGTTTTTAGTAGCAAT<br>TTGTACTGATGGTATGGGGCCAAGAGATATATCTTAGAGGGA<br>GGGCTGAGGGTTTGAAGTCCAACTCCTAAGCCAGTGCCAGAA<br>GAGCCAAGGACAGGTACGGCTGTCATCACTTAGACCTCACCC<br>TGTGGAGCCACACCCTAGGGTTGGCCAATCTACTCCCAGGAG<br>CAGGGAGGGCAGGAGCCAGGGCTGGGCATAAAAGTCAGGGC<br>AGAGCCATCTATTGCTTACATTTGCTTCTGACACAACTGTGTT<br>CACTAGCAACCTCAAACAGACACCATGGTGCA |
| 50 | Donor DNA | E7 to E7V AAV.304 | TCTGACTCCTGTCGAGAAGTCTGCAGTCACTGCTCTATGGGG<br>GAAA |

-continued

Sequence Listing

| SEQ ID NO: | Identifier | Name/ Description | Sequence |
|---|---|---|---|
| 51 | Donor DNA | HBB locus RHA (used for E7 to E7V AAV.304) | GTGAACGTGGATGAAGTTGGTGGTGAGGCCCTGGGCAGGTTG GTATCAAGGTTACAAGACAGGTTTAAGGAGACCAATAGAAA CTGGGCATGTGGAGACAGAGAAGACTCTTGGGTTTCTGATAG GCACTGACTCTCTCTGCCTATTGGTCTATTTTCCCACCCTTAG GCTGCTGGTGGTCTACCCTTGGACCCAGAGGTTCTTTGAGTCC TTTGGGGATCTGTCCACTCCTGATGCTGTTATGGGCAACCCTA AGGTGAAGGCTCATGGCAAGAAAGTGCTCGGTGCCTTTAGTG ATGGCCTGGCTCACCTGGACAACCTCAAGGGCACCTTTGCCA CACTGAGTGAGCTGCACTGTGACAAGCTGCACGTGGATCCTG AGAACTTCAGGGTGAGTCTATGGGACGCTTGATGTTTTCTTTC CCCTTCTTTTCTATGGTTAAGTTCATGTCATAGGAAGGGGATA AGTAACAGGGTACAGTTTAGAATGGGAAACAGACGAATGAT TGCATCAGTGTGGAAGTCTCAGGATCGTTTTAGTTTCTTTTAT TTGCTGTTCATAACAATTGTTTTCTTTTGTTTAATTCTTGCTTT CTTTTTTTTTCTTCTCCGCAATTTTTACTATTATACTTAATGCC TTAACATTGTGTATAACAAAAGGAAATATCTCTGAGATACAT TAAGTAACTTAAAAAAAAACTTTACACAGTCTGCCTAGTACA TTACTATTTGGAATATATGTGTGCTTATTTGCATATTCATAAT CTCCCTACTTTATTTTCTTTTATTTTTAATTGATACATAATCAT TATACATATTTATGGGTTAAAGTGTAATGTTTTAATATGTGTA CACATATTGACCAAATCAGGGTAATTTTGCATTTGTAATTTTA AAAAATGCTTTCTTCTTTTAATATACTTTTTTGTTTATCTTATT TCTAATACTTTCCCTAATCTCTTTCTTTCAGGGCAATAATGAT ACAATGTATCATGCCTCTTTGCACCATTCTAAAGAATAACAG TGATAATTTCTGGGTTAAGGCAATAGCAATATCTCTGCATAT AAATATTTCTGCATATAAATTGTAACTGATGTAAGAGGTTTC ATATTGCTAATAGCAGCTACAATCCAGCTACCATTCTGCTTTT ATTTTATGGTTGGGATAAGGCTGGATTATTCTGAGTCCAAGC TAGGCCCTTTTGCTAATCATGTTCATACCTCTTATCTTCCTCCC ACAGCTCCTGGGCAACGTGCTGGTCTGTGTGCTGGCCCATCA CTTTGGCAAAGAATTCACCCCACCAGTGCAGGCTGCCTATCA GAAAGTGGTGGCTGGTGTGGCTAATGCCCTGGCCCACAAGTA TCACTAAGCTCGCTTTCTTGCTGTCCAATTTCTATTAAAGGTT CCTTTGTTCCCTAAGTCCAACTACTAAACTGGGGGATATTATG AAGGGCCTTGAGCATCTGGATTCTGCCTAATAAAAAACATTT ATTTTCATTGCAATGATGTATTTAAATTATTTCTGAATATTTT ACTAAAAAGGGAATGTGGGAGGTCAGTGCATTTAAAACATA AAGAAATGAAGAGCTAGTTCAAACCTTGGGAAAATACACTA TATCTTAAACTCCATGAAAGAAGGTGAGGCTGCAAACAGCTA ATGCACATTGGCAACAGCCCCTGATGCATATGCCTTATTCAT CCCTCAGAAAAGGATTCAAGTAGAGGCTTGATTTGGAGGTTA AAGTTTTGCTATGCTGTATTTTACATTACTTATTGTTTTAGCTG TCCTCATGAATGTCTTTTCACTACCCATTTGCTTATCCTGCAT CTCTCAGCCTTGACTCCACTCAGTTCTCTTGCTTAGAGATACC ACCTTTCCCCTGAAGTGTTCCTTCCATGTTTTACGGCGAGATG GTTTCTCCTCGCCTGGCCACTCAGCCTTAGTTGTCTCTGTTGT CTTATAGAGGTCTACTTGAAGAAGGAAAAACAGGGGTCATG GTTTGACTGTCCTGTGAGCCCTTCTTCCCTGCCTCCCCCACTC ACAGTGACCCGGAATCTGCAGTGCTAGTCTCCCGGAACTATC ACTCTTTCACAGTCTGCTTTGGAAGGACTGGGCTTAGTATGA AAAGTTAGGACTGAGAAGAATTTGAAAGGCGGCTTTTTGTAG CTTGATATTCACTACTGTCTTATTACCCTGTC |
| 52 | Donor DNA | HBB locus LHA (used for E7 to E7V AAV.307) | CTTGCTTTGACAATTTTGGTCTTTCAGAATACTATAAATATAA CCTATATTATAATTTCATAAAGTCTGTGCATTTTCTTTGACCC AGGATATTTGCAAAAGACATATTCAAACTTCCGCAGAACACT TTATTTCACATATACATGCCTCTTATATCAGGGATGTGAAACA GGGTCTTGAAAACTGTCTAAATCTAAAACAATGCTAATGCAG GTTTAAATTTAATAAAATAAAATCCAAAATCTAACAGCCAAG TCAAATCTGCATGTTTTAACATTTAAAATATTTTAAAGACGTC TTTTCCCAGGATTCAACATGTGAAATCTTTTCTCAGGGATACA CGTGTGCCTAGATCCTCATTGCTTTAGTTTTTTACAGAGGAAT GAATATAAAAAGAAAATACTTAAATTTTATCCCTCTTACCTCT ATAATCATACATAGGCATAATTTTTTAACCTAGGCTCCAGAT AGCCATAGAAGAACCAAACACTTTCTGCGTGTGTGAGAATAA TCAGAGTGAGATTTTTTCACAAGTACCTGATGAGGGTTGAGA CAGGTAGAAAAAGTGAGAGATCTCTATTTATTTAGCAATAAT AGAGAAAGCATTTAAGAGAATAAAGCAATGGAAATAAGAAA TTTGTAAATTTCCTTCTGATAACTAGAAATAGAGGATCCAGTT TCTTTTGGTTAACCTAAATTTTATTTCATTTTATTGTTTTATTT TATTTTATTTTATTTTATTTTGTGTAATCGTAGTTTCAGAGTGT TAGAGCTGAAAGGAAGAAGTAGGAGAAACATGCAAAGTAAA AGTATAACACTTTCCTTACTAAACCGACATGGGTTTCCAGGT |

Sequence Listing

| SEQ ID NO: | Identifier | Name/ Description | Sequence |
|---|---|---|---|
| | | | AGGGGCAGGATTCAGGATGACTGACAGGGCCCTTAGGGAAC ACTGAGACCCTACGCTGACCTCATAAATGCTTGCTACCTTTGC TGTTTTAATTACATCTTTTAATAGCAGGAAGCAGAACTCTGC ACTTCAAAAGTTTTTCCTCACCTGAGGAGTTAATTTAGTACAA GGGGAAAAAGTACAGGGGGATGGGAGAAAGGCGATCACGTT GGGAAGCTATAGAGAAAGAAGAGTAAATTTTAGTAAAGGAG GTTTAAACAAACAAAATATAAAGAGAAATAGGAACTTGAAT CAAGGAAATGATTTTAAAACGCAGTATTCTTAGTGGACTAGA GGAAAAAAATAATCTGAGCCAAGTAGAAGACCTTTTCCCCTC CTACCCCTACTTTCTAAGTCACAGAGGCTTTTTGTTCCCCCAG ACACTCTTGCAGATTAGTCCAGGCAGAAACAGTTAGATGTCC CCAGTTAACCTCCTATTTGACACCACTGATTACCCCATTGATA GTCACACTTTGGGTTGTAAGTGACTTTTTATTTATTTGTATTTT TGACTGCATTAAGAGGTCTCTAGTTTTTTATCTCTTGTTTCCC AAAACCTAATAAGTAACTAATGCACAGAGCACATTGATTTGT ATTTATTCTATTTTTAGACATAATTTATTAGCATGCATGAGCA AATTAAGAAAAACAACAACAAATGAATGCATATATATGTAT ATGTATGTGTGTATATATACACACATATATATATATATTTTT CTTTTCTTACCAGAAGGTTTTAATCCAAATAAGGAGAAGATA TGCTTAGAACCGAGGTAGAGTTTTCATCCATTCTGTCCTGTAA GTATTTTGCATATTCTGGAGACGCAGGAAGAGATCCATCTAC ATATCCCAAAGCTGAATTATGGTAGACAAAACTCTTCCACTT TTAGTGCATCAACTTCTTATTTGTGTAATAAGAAAATTGGGA AAACGATCTTCAATATGCTTACCAAGCTGTGATTCCAAATAT TACGTAAATACACTTGCAAAGGAGGATGTTTTTAGTAGCAAT TTGTACTGATGGTATGGGGCCAAGAGATATATCTTAGAGGGA GGGCTGAGGGTTTGAAGTCCAACTCCTAAGCCAGTGCCAGAA GAGCCAAGGACAGGTACGGCTGTCATCACTTAGACCTCACCC TGTGGAGCCACACCCTAGGGTTGGCCAATCTACTCCCAGGAG CAGGGAGGGCAGGAGCCAGGGCTGGGCATAAAAGTCAGGGC AGAGCCATCTATTGCTTACATTTGCTTCTGACACAACTGTGTT CACTAGCAACCTCAAACAGACACCATGGTGCA |
| 53 | Donor DNA | E7 to E7V AAV.307 | TCTGACTCCTGTCGAAAAATCCGCTGTCACCGCCCTCTGGGG CAAG |
| 54 | Donor DNA | HBB locus RHA (used for E7 to E7V AAV.307) | GTGAACGTGGATGAAGTTGGTGGTGAGGCCCTGGGCAGGTTG GTATCAAGGTTACAAGACAGGTTTAAGGAGACCAATAGAAA CTGGGCATGTGGAGACAGAGAAGACTCTTGGGTTTCTGATAG GCACTGACTCTCTCTGCCTATTGGTCTATTTTCCCACCCTTAG GCTGCTGGTGGTCTACCCTTGGACCCAGAGGTTCTTTGAGTCC TTTGGGGATCTGTCCACTCCTGATGCTGTTATGGGCAACCCTA AGGTGAAGGCTCATGGCAAGAAAGTGCTCGGTGCCTTTAGTG ATGGCCTGGCTCACCTGGACAACCTCAAGGGCACCTTTGCCA CACTGAGTGAGCTGCACTGTGACAAGCTGCACGTGGATCCTG AGAACTTCAGGGTGAGTCTATGGGACGCTTGATGTTTTCTTTC CCCTTCTTTTCTATGGTTAAGTTCATGTCATAGGAAGGGGATA AGTAACAGGGTACAGTTTAGAATGGGAAACAGACGAATGAT TGCATCAGTGTGGAAGTCTCAGGATCGTTTTAGTTTCTTTTAT TTGCTGTTCATAACAATTGTTTTCTTTTGTTTAATTCTTGCTTT CTTTTTTTTTCTTCTCCGCAATTTTTACTATTATACTTAATGCC TTAACATTGTGTATAACAAAAGGAAATATCTCTGAGATACAT TAAGTAACTTAAAAAAAAACTTTACACAGTCTGCCTAGTACA TTACTATTTGGAATATATGTGTGCTTATTTGCATATTCATAAT CTCCCTACTTTATTTTCTTTTATTTTTAATTGATACATAATCAT TATACATATTTATGGGTTAAAGTGTAATGTTTTAATATGTGTA CACATATTGACCAAATCAGGGTAATTTTGCATTTGTAATTTTA AAAAATGCTTTCTTCTTTTAATATACTTTTTTGTTTATCTTATT TCTAATACTTTCCCTAATCTCTTTCTTTCAGGGCAATAATGAT ACAATGTATCATGCCTCTTTGCACCATTCTAAAGAATAACAG TGATAATTTCTGGGTTAAGGCAATAGCAATATCTCTGCATAT AAATATTTCTGCATATAAATTGTAACTGATGTAAGAGGTTTC ATATTGCTAATAGCAGCTACAATCCAGCTACCATTCTGCTTTT ATTTTATGGTTGGGATAAGGCTGGATTATTCTGAGTCCAAGC TAGGCCCTTTTGCTAATCATGTTCATACCTCTTATCTTCCTCCC ACAGCTCCTGGGCAACGTGCTGGTCTGTGTGCTGGCCCATCA CTTTGGCAAAGAATTCACCCCACCAGTGCAGGCTGCCTATCA GAAAGTGGTGGCTGGTGTGGCTAATGCCCTGGCCCACAAGTA TCACTAAGCTCGCTTTCTTGCTGTCCAATTTCTATTAAAGGTT CCTTTGTTCCCTAAGTCCAACTACTAAACTGGGGGATATTATG AAGGGCCTTGAGCATCTGGATTCTGCCTAATAAAAAACATTT ATTTTCATTGCAATGATGTATTTAAATTATTTCTGAATATTTT ACTAAAAAGGGAATGTGGGAGGTCAGTGCATTTAAAACATA AAGAAATGAAGAGCTAGTTCAAACCTTGGGAAAATACACTA |

-continued

Sequence Listing

| SEQ ID NO: | Identifier | Name/ Description | Sequence |
|---|---|---|---|
| | | | TATCTTAAACTCCATGAAAGAAGGTGAGGCTGCAAACAGCTA ATGCACATTGGCAACAGCCCCTGATGCATATGCCTTATTCAT CCCTCAGAAAAGGATTCAAGTAGAGGCTTGATTTGGAGGTTA AAGTTTTGCTATGCTGTATTTTACATTACTTATTGTTTTAGCTG TCCTCATGAATGTCTTTTCACTACCCATTTGCTTATCCTGCAT CTCTCAGCCTTGACTCCACTCAGTTCTCTTGCTTAGAGATACC ACCTTTCCCCTGAAGTGTTCCTTCCATGTTTTACGGCGAGATG GTTTCTCCTCGCCTGGCCACTCAGCCTTAGTTGTCTCTGTTGT CTTATAGAGGTCTACTTGAAGAAGGAAAAACAGGGGTCATG GTTTGACTGTCCTGTGAGCCCTTCTTCCCTGCCTCCCCCACTC ACAGTGACCCGGAATCTGCAGTGCTAGTCTCCCGGAACTATC ACTCTTTCACAGTCTGCTTTGGAAGGACTGGGCTTAGTATGA AAAGTTAGGACTGAGAAGAATTTGAAAGGCGGCTTTTTGTAG CTTGATATTCACTACTGTCTTATTACCCTGTC |
| 55 | Donor DNA | HBB locus LHA (used for GFP AAV) | GACTGCATTAAGAGGTCTCTAGTTTTTTACCTCTTGTTTCCCA AAACCTAATAAGTAACTAATGCACAGAGCACATTGATTTGTA TTTATTCTATTTTTAGACATAATTTATTAGCATGCATGAGCAA ATTAAGAAAAACAACAACAAATGAATGCATATATATGTATAT GTATGTGTGTACATATACACATATATATATATTTTTTTTCTTTT CTTACCAGAAGGTTTTAATCCAAATAAGGAGAAGATATGCTT AGAACTGAGGTAGAGTTTTCATCCATTCTGTCCTGTAAGTATT TTGCATATTCTGGAGACGCAGGAAGAGATCCATCTACATATC CCAAAGCTGAATTATGGTAGACAAAACTCTTCCACTTTTAGT GCATCAATTTCTTATTTGTGTAATAAGAAAATTGGGAAAACG ATCTTCAATATGCTTACCAAGCTGTGATTCCAAATATTACGTA AATACACTTGCAAAGGAGGATGTTTTTAGTAGCAATTTGTAC TGATGGTATGGGGCCAAGAGATATATCTTAGAGGGAGGGCT GAGGGTTTGAAGTCCAACTCCTAAGCCAGTGCCAGAAGAGCC AAGGACAGGTACGGCTGTCATCACTTAGACCTCACCCTGTGG AGCCACACCCTAGGGTTGGCCAATCTACTCCCAGGAGCAGGG AGGGCAGGAGCCAGGGCTGGGCATAAAAGTCAGGGCAGAGC CATCTATTGCTTACATTTGCTTCTGACACAACTGTGTTCACTA GCAACCTCAAACAGACACCATGGTGCATCTGACTCCTGAGGA |
| 56 | Donor DNA | GFP | ATGGTGAGCAAGGGCGAGGAGCTGTTCACCGGGGTGGTGCC CATCCTGGTCGAGCTGGACGGCGACGTAAACGGCCACAAGTT CAGCGTGTCCGGCGAGGGCGAGGGCGATGCCACCTACGGCA AGCTGACCCTGAAGTTCATCTGCACCACCGGCAAGCTGCCCG TGCCCTGGCCCACCCTCGTGACCACCCTGACCTACGGCGTGC AGTGCTTCAGCCGCTACCCCGACCACATGAAGCAGCACGACT TCTTCAAGTCCGCCATGCCCGAAGGCTACGTCCAGGAGCGCA CCATCTTCTTCAAGGACGACGGCAACTACAAGACCCGCGCCG AGGTGAAGTTCGAGGGCGACACCCTGGTGAACCGCATCGAG CTGAAGGGCATCGACTTCAAGGAGGACGGCAACATCCTGGG GCACAAGCTGGAGTACAACTACAACAGCCACAACGTCTATAT CATGGCCGACAAGCAGAAGAACGGCATCAAGGTGAACTTCA AGATCCGCCACAACATCGAGGACGGCAGCGTGCAGCTCGCC GACCACTACCAGCAGAACACCCCCATCGGCGACGGCCCCGTG CTGCTGCCCGACAACCACTACCTGAGCACCCAGTCCGCCCTG AGCAAAGACCCCAACGAGAAGCGCGATCACATGGTCCTGCT GGAGTTCGTGACCGCCGCCGGGATCACTCTCGGCATGGACGA GCTGTACAAGTAA |
| 57 | Donor DNA | HBB locus RHA (used for GFP AAV) | CTGCCCTGTGGGGCAAGGTGAACGTGGATGAAGTTGGTGGTG AGGCCCTGGGCAGGTTGGTATCAAGGTTACAAGACAGGTTTA AGGAGACCAATAGAAACTGGGCATGTGGAGACAGAGAAGAC TCTTGGGTTTCTGATAGGCACTGACTCTCTCTGCCTATTGGTC TATTTTCCCACCCTTAGGCTGCTGGTGGTCTACCCTTGGACCC AGAGGTTCTTTGAGTCCTTTGGGGATCTGTCCACTCCTGATGC TGTTATGGGCAACCCTAAGGTGAAGGCTCATGGCAAGAAAGT GCTCGGTGCCTTTAGTGATGGCCTGGCTCACCTGGACAACCT CAAGGGCACCTTTGCCACACTGAGTGAGCTGCACTGTGACAA GCTGCACGTGGATCCTGAGAACTTCAGGGTGAGTCTATGGGA CGCTTGATGTTTTCTTTCCCCTTCTTTTCTATGGTTAAGTTCAT GTCATAGGAAGGGGATAAGTAACAGGGTACAGTTTAGAATG GGAAACAGACGAATGATTGCATCAGTGTGGAAGTCTCAGGA TCGTTTTAGTTTCTTTTATTTGCTGTTCATAACAATTGTTTTCT TTTGTTTAATTCTTGCTTTCTTTTTTTTTCTTCTCCGCAATTTTT ACTATTATACTTAATGCCTTAACATTGTGTATAACAAAAGGA AATATCTCTGAGATACATTAAGTAACTTAAAAAAAAACTTTA |

-continued

Sequence Listing

| SEQ ID NO: | Identifier | Name/ Description | Sequence |
|---|---|---|---|
| | | | CACAGTCTGCCTAGTACATTACTATTTGGAATATATGTGTGCT TATTTGCATATTCATAATCTCCCTACTTTATTTTCTTTTATTTT TAATTGATACATAATCATTATACATATTTATGGGTTAAAGTGT AATGTTTTAATATGTGTACACATATTGACCAAATCAGGGTAA TTTTGCATTTGTAATTTTAAAAAATGC |
| 58 | | MND promoter | GGCCGCCAGTGTGATGGATATCTGCAGAATTCGCCCTTATGG GGATCCGAACAGAGAGACAGCAGAATATGGGCCAAACAGGA TATCTGTGGTAAGCAGTTCCTGCCCCGGCTCAGGGCCAAGAA CAGTTGGAACAGCAGAATATGGGCCAAACAGGATATCTGTG GTAAGCAGTTCCTGCCCCGGCTCAGGGCCAAGAACAGATGGT CCCCAGATGCGGTCCCGCCCTCAGCAGTTTCTAGAGAACCAT CAGATGTTTCCAGGGTGCCCCAAGGACCTGAAATGACCCTGT GCCTTATTTGAACTAACCAATCAGTTCGCTTCTCGCTTCTGTT CGCGCGCTTCTGCTCCCCGAGCTCTATATAAGCAGAGCTCGT TTAGTGAACCGTCAGATCGCCTGGAGACGCCATCCACGCTGT TTTGACCTCCATAGAAGACACCGACTCTAGAG |
| 59 | | EF1α promoter | GGCTCCGGTGCCCGTCAGTGGGCAGAGCGCACATCGCCCACA GTCCCCGAGAAGTTGGGGGGAGGGGTCGGCAATTGAACCGG TGCCTAGAGAAGGTGGCGCGGGGTAAACTGGGAAAGTGATG TCGTGTACTGGCTCCGCCTTTTTCCCGAGGGTGGGGGAGAAC CGTATATAAGTGCAGTAGTCGCCGTGAACGTTCTTTTTCGCA ACGGGTTTGCCGCCAGAACACAGGTAAGTGCCGTGTGTGGTT CCCGCGGGCCTGGCCTCTTTACGGGTTATGGCCCTTGCGTGCC TTGAATTACTTCCACTGGCTGCAGTACGTGATTCTTGATCCCG AGCTTCGGGTTGGAAGTGGGTGGGAGAGTTCGAGGCCTTGCG CTTAAGGAGCCCCTTCGCCTCGTGCTTGAGTTGAGGCCTGGC CTGGGCGCTGGGGCCGCCGCGTGCGAATCTGGTGGCACCTTC GCGCCTGTCTCGCTGCTTTCGATAAGTCTCTAGCCATTTAAAA TTTTTGATGACCTGCTGCGACGCTTTTTTTCTGGCAAGATAGT CTTGTAAATGCGGGCCAAGATCTGCACACTGGTATTTCGGTT TTTGGGGCCGCGGGCGGCGACGGGGCCCGTGCGTCCCAGCGC ACATGTTCGGCGAGGCGGGGCCTGCGAGCGCGGCCACCGAG AATCGGACGGGGGTAGTCTCAAGCTGGCCGGCCTGCTCTGGT GCCTGGCCTCGCGCCGCCGTGTATCGCCCCGCCCTGGGCGGC AAGGCTGGCCCGGTCGGCACCAGTTGCGTGAGCGGAAAGAT GGCCGCTTCCCGGCCCTGCTGCAGGGAGCTCAAAATGGAGGA CGCGGCGCTCGGGAGAGCGGGCGGGTGAGTCACCCACACAA AGGAAAAGGGCCTTTCCGTCCTCAGCCGTCGCTTCATGTGAC TCCACGGAGTACCGGGCGCCGTCCAGGCACCTCGATTAGTTC TCGAGCTTTTGGAGTACGTCGTCTTTAGGTTGGGGGGAGGGG TTTTATGCGATGGAGTTTCCCCACACTGAGTGGGTGGAGACT GAAGTTAGGCCAGCTTGGCACTTGATGTAATTCTCCTTGGAA TTTGCCCTTTTTGAGTTTGGATCTTGGTTCATTCTCAAGCCTC AGACAGTGGTTCAAAGTTTTTTTCTTCCATTTCAGGTGTCGTG A |
| 60 | | SFFV promoter | GTAACGCCATTTTGCAAGGCATGGAAAAATACCAAACCAAG AATAGAGAAGTTCAGATCAAGGGCGGGTACATGAAAATAGC TAACGTTGGGCCAAACAGGATATCTGCGGTGAGCAGTTTCGG CCCCGGCCCGGGGCCAAGAACAGATGGTCACCGCAGTTTCGG CCCCGGCCCGAGGCCAAGAACAGATGGTCCCCAGATATGGC CCAACCCTCAGCAGTTTCTTAAGACCCATCAGATGTTTCCAG GCTCCCCCAAGGACCTGAAATGACCCTGCGCCTTATTTGAAT TAACCAATCAGCCTGCTTCTCGCTTCTGTTCGCGCGCTTCTGC TTCCCGAGCTCTATAAAAGAGCTCACAACCCCTCACTCGGCG CGCCAGTCCTCCGACAGACTGAGTCG |
| 61 | | 2A peptide from porcine teschovirus | GCCACGAACTTCTCTCTGTTAAAGCAAGCAGGAGACGTGGA AGAAAACCCCGGTCCT |
| 62 | | Synthetic poly(A) signal | AATAAAATCGCTATCCATCGAAGATGGATGTGTGTTGGTTTT TTGTGTG |
| 63 | PAM | Canonical PAM | $N_x$NRG (N = any nucleotide; R = A or G; x = 19-21) |
| 64 | PAM | SpCas9 PAM | NRG (N = any nucleotide, R = A or G) |

-continued

Sequence Listing

| SEQ ID NO: | Identifier | Name/ Description | Sequence |
|---|---|---|---|
| 65 | Nuclear localization signal (NLS) | SV40 NLS 1 | PKKKRKV |
| 66 | NLS | SV40 NLS 2 | PKKKRRV |
| 67 | NLS | Nucleoplasmin NLS | KRPAATKKAGQAKKKK |
| 68 | I53 | i53 (DNA) | ATGCTGATCTTCGTGAAGACCCTGACCGGCAAGACCATCACC CTGGAGGTGGAGCCCAGCGACACCATCGAGAACGTGAAGGC CAAGATCCAGGACAAGGAGGGCATCCCCCCCGACCAGCAGA GGCTGGCCTTCGCCGGCAAGAGCCTGGAGGACGGCAGGACC CTGAGCGACTACAACATCCTGAAGGACAGCAAGCTGCACCC CCTGCTGAGGCTGAGGTGA |
| 69 | I53 mRNA | i53 (RNA) | AUGCUGAUCUUCGUGAAGACCCUGACCGGCAAGACCAUCA CCCUGGAGGUGGAGCCCAGCGACACCAUCGAGAACGUGAA GGCCAAGAUCCAGGACAAGGAGGGCAUCCCCCCCGACCAGC AGAGGCUGGCCUUCGCCGGCAAGAGCCUGGAGGACGGCAG GACCCUGAGCGACUACAACAUCCUGAAGGACAGCAAGCUG CACCCCCUGCUGAGGCUGAGGUGA |
| 70 | I53 | i53 (aa) | MLIFVKTLTGKTITLEVEPSDTIENVKAKIQDKEGIPPDQQRLAF AGKSLEDGRTLSDYNILKDSKLHPLLRLR |
| 71 | DM mRNA | I53-DM (RNA) | AUGUUGAUUUUCGUGAAAACCCUUACCGGGAAAACCAUCA CCCUCGAGGUUGAACCCUCGGAUACGAUAGAAAAUGUAAA GGCCAAGAUCCAGGAUAAGGAAGGAAUUCCUCCUGAUCAG CAGAGACUGGCCUUUGCUGGCAAAUCGCUGGAAGAUGGAC GUACUUUGUCUGACUACAAUAUUCUAAAGGACUCUAAACU UCAUCUAGUGUUGAGACUUCGU |
| 72 | | A10 (DNA) | ATGCAGATTTACGTGAAGACCTTTGCCCGGAAGCCCATCACC CTCGAGGTTGAACCCTCGGATACGATAGAAAATGTAAAGGC CAAGATCCAGGATAAGGAAGGAATTCCTCCTGATCAGCAGC GACTGATCTTTGCTGAAATGCGGCTGGAAGATGGACGTACTT TGTCTGACTACAATATTAAAAACGACTCTACTCTTTTTCTTGT GTTGAAAAATAGTGTTACT |
| 73 | | A10 (RNA) | AUGCAGAUUUACGUGAAGACCUUUGCCCGGAAGCCCAUCA CCCUCGAGGUUGAACCCUCGGAUACGAUAGAAAAUGUAAA GGCCAAGAUCCAGGAUAAGGAAGGAAUUCCUCCUGAUCAG CAGCGACUGAUCUUUGCUGAAAUGCGGCUGGAAGAUGGAC GUACUUUGUCUGACUACAAUAUUAAAAACGACUCUACUCU UUUUCUUGUGUUGAAAAAUAGUGUUACU |
| 74 | | A10 (aa) | MQIYVKTFARKPITLEVEPSDTIENVKAKIQDKEGIPPDQQRLIFA EMRLEDGRTLSDYNIKNDSTLFLVLKNSVT |
| 75 | | A11 (DNA) | ATGCTGATTTTCGTGACCACCGATATGGGGATGACAATCTCA CTCGAGGTTGAACCCTCGGATACGATAGAAAATGTAAAGGC CAAGATCCAGGATAAGGAAGGAATTCCTCCTGATCAGCAGA GACTGATCTTTGGTGACAAGGATCTGGAAGATGGACGTACTT TGTCTGACTACAATATTCAAAAGGAGTCTAGCCTTAATCTTG TGCTGAAACTTCGTGGTGGT |
| 76 | | A11 (RNA) | AUGCUGAUUUUCGUGACCACCGAUAUGGGGAUGACAAUCU CACUCGAGGUUGAACCCUCGGAUACGAUAGAAAAUGUAAA GGCCAAGAUCCAGGAUAAGGAAGGAAUUCCUCCUGAUCAG CAGAGACUGAUCUUUGGUGACAAGGAUCUGGAAGAUGGAC GUACUUUGUCUGACUACAAUAUUCAAAAGGAGUCUAGCCU UAAUCUUGUGCUGAAACUUCGUGGUGGU |
| 77 | | A11 (aa) | MLIFVTTDMGMTISLEVEPSDTIENVKAKIQDKEGIPPDQQRLIF GDKDLEDGRTLSDYNIQKESSLNLVLKLRGG |
| 78 | | C08 (DNA) | ATGCAGATTTTCGTGACCACCGATATGTGGATGAGAATCTCA CTCGAGGTTGAACCCTCGGATACGATAGAAAATGTAAAGGC CAAGATCCAGGATAAGGAAGGAATTCCTCCTGATCAGCAGA GACTGATCTTTGGTGACAAGGATCTGGAAGATGGACGTACTT TGTCTGACTACAATATTCAAAAGGAGTCTAGCCTTAATCTTG TGCTGAACCTTCGTGGTGGT |

-continued

| SEQ ID NO: | Identifier | Name/ Description | Sequence |
|---|---|---|---|
| 79 | | C08 (RNA) | AUGCAGAUUUUCGUGACCACCGAUAUGUGGAUGAGAAUCU CACUCGAGGUUGAACCCUCGGAUACGAUAGAAAAUGUAAA GGCCAAGAUCCAGGAUAAGGAAGGAAUUCCUCCUGAUCAG CAGAGACUGAUCUUUGGUGACAAGGAUCUGGAAGAUGGAC GUACUUUGUCUGACUACAAUAUUCAAAAGGAGUCUAGCCU UAAUCUUGUGCUGAACCUUCGUGGUGGU |
| 80 | | C08 (aa) | MQIFVTTDMWMRISLEVEPSDTIENVKAKIQDKEGIPPDQQRLIF GDKDLEDGRTLSDYNIQKESSLNLVLNLRGG |
| 81 | | G08 (DNA) | ATGTTGATTTTCGTGAAAACCCTTACCGGGAAAACCATCACC CTCGAGGTTGAACCCTCGGATACGATAGAAAATGTAAAGGC CAAGATCCAGGATAAGGAAGGAATTCCTCCTGATCAGCAGA GACTGATCTTTGCTGGCAAATCGCTGGAAGATGGACGTACTT TGTCTGACTACAATATTCTAAAGGACTCTAAACTTCATCCTCT GTTGAGACTTCGTGGTGGT |
| 82 | | G08 (RNA) | AUGUUGAUUUUCGUGAAAACCCUUACCGGGAAAACCAUCA CCCUCGAGGUUGAACCCUCGGAUACGAUAGAAAAUGUAAA GGCCAAGAUCCAGGAUAAGGAAGGAAUUCCUCCUGAUCAG CAGAGACUGAUCUUUGCUGGCAAAUCGCUGGAAGAUGGAC GUACUUUGUCUGACUACAAUAUUCUAAAGGACUCUAAACU UCAUCCUCUGUUGAGACUUCGUGGUGGU |
| 83 | | G08 (aa) | MLIFVKTLTGKTITLEVEPSDTIENVKAKIQDKEGIPPDQQRLIFA GKSLEDGRTLSDYNILKDSKLHPLLRLRGG |
| 84 | | H04 (DNA) | ATGCGAATTATCGTGAAAACCTTTATGCGGAAGCCGATCACG CTCGAGGTTGAACCCTCGGATACGATAGAAAATGTAAAGGC CAAGATCCAGGATAAGGAAGGAATTCCTCCTGATCAGCAGA GACTGTATTTTGCGGCCAGTCAGCTGGAAGATGGACGTACTT TGTCTGACTACAATATTCAAAAGGAGTCTACTCTTCTTCTTGT GGTAAGGCTGCTCCGCGTT |
| 85 | | H04 (RNA) | AUGCGAAUUAUCGUGAAAACCUUUAUGCGGAAGCCGAUCA CGCUCGAGGUUGAACCCUCGGAUACGAUAGAAAAUGUAAA GGCCAAGAUCCAGGAUAAGGAAGGAAUUCCUCCUGAUCAG CAGAGACUGUAUUUUGCGGCCAGUCAGCUGGAAGAUGGAC GUACUUUGUCUGACUACAAUAUUCAAAAGGAGUCUACUCU UCUUCUUGUGGUAAGGCUGCUCCGCGUU |
| 86 | | H04 (aa) | MRIIVKTFMRKPITLEVEPSDTIENVKAKIQDKEGIPPDQQRLYF AASQLEDGRTLSDYNIQKESTLLLVVRLLRV |
| 87 | | I53 alt (DNA) | ATGTTGATTTTCGTGAAAACCCTTACCGGGAAAACCATCACC CTCGAGGTTGAACCCTCGGATACGATAGAAAATGTAAAGGC CAAGATCCAGGATAAGGAAGGAATTCCTCCTGATCAGCAGA GACTGGCCTTTGCTGGCAAATCGCTGGAAGATGGACGTACTT TGTCTGACTACAATATTCTAAAGGACTCTAAACTTCATCCTCT GTTGAGACTTCGT |
| 88 | | I53 alt (RNA) | AUGUUGAUUUUCGUGAAAACCCUUACCGGGAAAACCAUCA CCCUCGAGGUUGAACCCUCGGAUACGAUAGAAAAUGUAAA GGCCAAGAUCCAGGAUAAGGAAGGAAUUCCUCCUGAUCAG CAGAGACUGGCCUUUGCUGGCAAAUCGCUGGAAGAUGGAC GUACUUUGUCUGACUACAAUAUUCUAAAGGACUCUAAACU UCAUCCUCUGUUGAGACUUCGU |
| 89 | | FLAG-tagged i53 DNA | ATGGACTACAAAGACGATGACGATAAAGCCGCCAGTTTAAA CGGCGCGCCATTAATTAAGGATCCAATGTTGATTTTCGTGAA AACCCTTACCGGGAAAACCATCACCCTCGAGGTTGAACCCTC GGATACGATAGAAAATGTAAAGGCCAAGATCCAGGATAAGG AAGGAATTCCTCCTGATCAGCAGAGACTGGCCTTTGCTGGCA AATCGCTGGAAGATGGACGTACTTTGTCTGACTACAATATTC TAAAGGACTCTAAACTTCATCCTCTGTTGAGACTTCGTTGA |

-continued

Sequence Listing

| SEQ ID NO: | Identifier | Name/ Description | Sequence |
|---|---|---|---|
| 90 | | FLAG-tagged i53 RNA | AUGGACUACAAAGACGAUGACGAUAAAGCCGCCAGUUUAA ACGGCGCGCCAUUAAUUAAGGAUCCAAUGUUGAUUUUCGU GAAAACCCUUACCGGGAAAACCAUCACCCUCGAGGUUGAA CCCUCGGAUACGAUAGAAAAUGUAAAGGCCAAGAUCCAGG AUAAGGAAGGAAUUCCUCCUGAUCAGCAGAGACUGGCCUU UGCUGGCAAAUCGCUGGAAGAUGGACGUACUUUGUCUGAC UACAAUAUUCUAAAGGACUCUAAACUUCAUCCUCUGUUGA GACUUCGUUGA |
| 91 | | Linker (DNA) | GCCGCCAGTTTAAACGGCGCGCCATTAATTAAGGATCCA |
| 92 | | Linker (RNA) | GCCGCCAGUUUAAACGGCGCGCCAUUAAUUAAGGAUCCA |
| 93 | | Linker | AASLNGAPLIKDP |
| 94 | Protein tag | 6xHis | HHHHHH |
| 95 | Protein tag | Flag | MDYKDDDDK |
| 96 | Protein tag | FLAG (DNA) | GACTACAAAGACGATGACGATAAA |
| 97 | Protein tag | FLAG (RNA) | GACUACAAAGACGAUGACGAUAAA |
| 98 | Donor DNA | HBB locus LHA to RHA (used for E6V to E6, AAV.323) | CTTGCTTTGACAATTTTGGTCTTTCAGAATACTATAAATATAA CCTATATTATAATTTCATAAAGTCTGTGCATTTTCTTTGACCC AGGATATTTGCAAAAGACATATTCAAACTTCCGCAGAACACT TTATTTCACATATACATGCCTCTTATATCAGGGATGTGAAAC AGGGTCTTGAAAACTGTCTAAATCTAAAACAATGCTAATGCA GGTTTAAATTTAATAAAATAAAATCCAAAATCTAACAGCCAA GTCAAATCTGCATGTTTTAACATTTAAAATATTTTAAAGACG TCTTTTCCCAGGATTCAACATGTGAAATCTTTTCTCAGGGATA CACGTGTGCCTAGATCCTCATTGCTTTAGTTTTTTACAGAGGA ATGAATATAAAAAGAAAATACTTAAATTTTATCCCTCTTACC TCTATAATCATACATAGGCATAATTTTTTAACCTAGGCTCCA GATAGCCATAGAAGAACCAAACACTTTCTGCGTGTGTGAGA ATAATCAGAGTGAGATTTTTTCACAAGTACCTGATGAGGGTT GAGACAGGTAGAAAAAGTGAGAGATCTCTATTTATTTAGCA ATAATAGAGAAAGCATTTAAGAGAATAAAGCAATGGAAATA AGAAATTTGTAAATTTCCTTCTGATAACTAGAAATAGAGGAT CCAGTTTCTTTTGGTTAACCTAAATTTTATTTCATTTTATTGTT TTATTTTATTTTATTTTATTTTATTTTGTGTAATCGTAGTTTCA GAGTGTTAGAGCTGAAAGGAAGAAGTAGGAGAAACATGCAA AGTAAAAGTATAACACTTTCCTTACTAAACCGACATGGGTTT CCAGGTAGGGGCAGGATTCAGGATGACTGACAGGGCCCTTA GGGAACACTGAGACCCTACGCTGACCTCATAAATGCTTGCTA CCTTTGCTGTTTTAATTACATCTTTTAATAGCAGGAAGCAGA ACTCTGCACTTCAAAAGTTTTTCCTCACCTGAGGAGTTAATTT AGTACAAGGGGAAAAAGTACAGGGGGATGGGAGAAAGGCG ATCACGTTGGGAAGCTATAGAGAAAGAAGAGTAAATTTTAG TAAAGGAGGTTTAAACAAACAAAATATAAAGAGAAATAGGA ACTTGAATCAAGGAAATGATTTTAAAACGCAGTATTCTTAGT GGACTAGAGGAAAAAAATAATCTGAGCCAAGTAGAAGACCT TTTCCCCTCCTACCCCTACTTTCTAAGTCACAGAGGCTTTTTG TTCCCCCAGACACTCTTGCAGATTAGTCCAGGCAGAAACAGT TAGATGTCCCCAGTTAACCTCCTATTTGACACCACTGATTACC CCATTGATAGTCACACTTTGGGTTGTAAGTGACTTTTTATTTA TTTGTATTTTTGACTGCATTAAGAGGTCTCTAGTTTTTTATCT CTTGTTTCCCAAAACCTAATAAGTAACTAATGCACAGAGCAC ATTGATTTGTATTTATTCTATTTTTAGACATAATTTATTAGCA TGCATGAGCAAATTAAGAAAAACAACAACAAATGAATGCAT ATATATGTATATGTATGTGTGTATATATACACACATATATAT ATATATTTTTTCTTTTCTTACCAGAAGGTTTTAATCCAAATAA GGAGAAGATATGCTTAGAACCGAGGTAGAGTTTTCATCCATT CTGTCCTGTAAGTATTTTGCATATTCTGGAGACGCAGGAAGA GATCCATCTACATATCCCAAAGCTGAATTATGGTAGACAAAA CTCTTCCACTTTTAGTGCATCAACTTCTTATTTGTGTAATAAG AAAATTGGGAAAACGATCTTCAATATGCTTACCAAGCTGTGA TTCCAAATATTACGTAAATACACTTGCAAAGGAGGATGTTTT TAGTAGCAATTTGTACTGATGGTATGGGGCCAAGAGATATAT CTTAGAGGGAGGGCTGAGGGTTTGAAGTCCAACTCCTAAGCC |

-continued

| SEQ ID NO: | Identifier | Name/ Description | Sequence |
|---|---|---|---|
| | | | AGTGCCAGAAGAGCCAAGGACAGGTACGGCTGTCATCACTT AGACCTCACCCTGTGGAGCCACACCCTAGGGTTGGCCAATCT ACTCCCAGGAGCAGGGAGGGCAGGAGCCAGGGCTGGGCATA AAAGTCAGGGCAGAGCCATCTATTGCTTACATTTGCTTCTGA CACAACTGTGTTCACTAGCAACCTCAAACAGACACCATGGTG CATCTGACTCCTGAAGAAAAATCCGCTGTCACTGCCCTGTGG GGCAAGGTGAACGTGGATGAAGTTGGTGGTGAGGCCCTGGG CAGGTTGGTATCAAGGTTACAAGACAGGTTTAAGGAGACCA ATAGAAACTGGGCATGTGGAGACAGAGAAGACTCTTGGGTT TCTGATAGGCACTGACTCTCTCTGCCTATTGGTCTATTTTCCC ACCCTTAGGCTGCTGGTGGTCTACCCTTGGACCCAGAGGTTC TTTGAGTCCTTTGGGGATCTGTCCACTCCTGATGCTGTTATGG GCAACCCTAAGGTGAAGGCTCATGGCAAGAAAGTGCTCGGT GCCTTTAGTGATGGCCTGGCTCACCTGGACAACCTCAAGGGC ACCTTTGCCACACTGAGTGAGCTGCACTGTGACAAGCTGCAC GTGGATCCTGAGAACTTCAGGGTGAGTCTATGGGACGCTTGA TGTTTTCTTTCCCCTTCTTTTCTATGGTTAAGTTCATGTCATAG GAAGGGGATAAGTAACAGGGTACAGTTTAGAATGGGAAACA GACGAATGATTGCATCAGTGTGGAAGTCTCAGGATCGTTTTA GTTTCTTTTATTTGCTGTTCATAACAATTGTTTTCTTTTGTTTA ATTCTTGCTTTCTTTTTTTTTCTTCTCCGCAATTTTTACTATTA TACTTAATGCCTTAACATTGTGTATAACAAAAGGAAATATCT CTGAGATACATTAAGTAACTTAAAAAAAAACTTTACACAGTC TGCCTAGTACATTACTATTTGGAATATATGTGTGCTTATTTGC ATATTCATAATCTCCCTACTTTATTTTCTTTTATTTTTAATTGA TACATAATCATTATACATATTTATGGGTTAAAGTGTAATGTTT TAATATGTGTACACATATTGACCAAATCAGGGTAATTTTGCA TTTGTAATTTTAAAAAATGCTTTCTTCTTTTAATATACTTTTTT GTTTATCTTATTTCTAATACTTTCCCTAATCTCTTTCTTTCAGG GCAATAATGATACAATGTATCATGCCTCTTTGCACCATTCTA AAGAATAACAGTGATAATTTCTGGGTTAAGGCAATAGCAAT ATCTCTGCATATAAATATTTCTGCATATAAATTGTAACTGATG TAAGAGGTTTCATATTGCTAATAGCAGCTACAATCCAGCTAC CATTCTGCTTTTATTTTATGGTTGGGATAAGGCTGGATTATTC TGAGTCCAAGCTAGGCCCTTTTGCTAATCATGTTCATACCTCT TATCTTCCTCCCACAGCTCCTGGGCAACGTGCTGGTCTGTGTG CTGGCCCATCACTTTGGCAAAGAATTCACCCCACCAGTGCAG GCTGCCTATCAGAAAGTGGTGGCTGGTGTGGCTAATGCCCTG GCCCACAAGTATCACTAAGCTCGCTTTCTTGCTGTCCAATTTC TATTAAAGGTTCCTTTGTTCCCTAAGTCCAACTACTAAACTGG GGGATATTATGAAGGGCCTTGAGCATCTGGATTCTGCCTAAT AAAAAACATTTATTTTCATTGCAATGATGTATTTAAATTATTT CTGAATATTTTACTAAAAAGGGAATGTGGGAGGTCAGTGCAT TTAAAACATAAAGAAATGAAGAGCTAGTTCAAACCTTGGGA AAATACACTATATCTTAAACTCCATGAAAGAAGGTGAGGCTG CAAACAGCTAATGCACATTGGCAACAGCCCCTGATGCATATG CCTTATTCATCCCTCAGAAAAGGATTCAAGTAGAGGCTTGAT TTGGAGGTTAAAGTTTTGCTATGCTGTATTTTACATTACTTAT TGTTTTAGCTGTCCTCATGAATGTCTTTTCACTACCCATTTGC TTATCCTGCATCTCTCAGCCTTGACTCCACTCAGTTCTCTTGC TTAGAGATACCACCTTTCCCCTGAAGTGTTCCTTCCATGTTTT ACGGCGAGATGGTTTCTCCTCGCCTGGCCACTCAGCCTTAGT TGTCTCTGTTGTCTTATAGAGGTCTACTTGAAGAAGGAAAAA CAGGGGTCATGGTTTGACTGTCCTGTGAGCCCTTCTTCCCTGC CTCCCCCACTCACAGTGACCCGGAATCTGCAGTGCTAGTCTC CCGGAACTATCACTCTTTCACAGTCTGCTTTGGAAGGACTGG GCTTAGTATGAAAAGTTAGGACTGAGAAGAATTTGAAAGGC GGCTTTTTGTAGCTTGATATTCACTACTGTCTTATTACCCTGT C |
| 99 | Donor DNA | HBB locus LHA (used for E6V to E6, AAV.323) | CTTGCTTTGACAATTTTGGTCTTTCAGAATACTATAAATATAA CCTATATTATAATTTCATAAAGTCTGTGCATTTTCTTTGACCC AGGATATTTGCAAAAGACATATTCAAACTTCCGCAGAACACT TTATTTCACATATACATGCCTCTTATATCAGGGATGTGAAAC AGGGTCTTGAAAACTGTCTAAATCTAAAACAATGCTAATGCA GGTTTAAATTTAATAAAATAAAATCCAAAATCTAACAGCCAA GTCAAATCTGCATGTTTTAACATTTAAAATATTTTAAAGACG TCTTTTCCCAGGATTCAACATGTGAAATCTTTTCTCAGGGATA CACGTGTGCCTAGATCCTCATTGCTTTAGTTTTTTACAGAGGA ATGAATATAAAAAGAAAATACTTAAATTTTATCCCTCTTACC TCTATAATCATACATAGGCATAATTTTTTTAACCTAGGCTCCA GATAGCCATAGAAGAACCAAACACTTTCTGCGTGTGTGAGA ATAATCAGAGTGAGATTTTTCACAAGTACCTGATGAGGGTT GAGACAGGTAGAAAAAGTGAGAGATCTCTATTTATTTAGCA |

-continued

Sequence Listing

| SEQ ID NO: | Identifier | Name/ Description | Sequence |
|---|---|---|---|
| | | | ATAATAGAGAAAGCATTTAAGAGAATAAAGCAATGGAAATA AGAAATTTGTAAATTTCCTTCTGATAACTAGAAATAGAGGAT CCAGTTTCTTTTGGTTAACCTAAATTTTATTTCATTTTATTGTT TTATTTTATTTTATTTTATTTTATTTTGTGTAATCGTAGTTTCA GAGTGTTAGAGCTGAAAGGAAGAAGTAGGAGAAACATGCAA AGTAAAAGTATAACACTTTCCTTACTAAACCGACATGGGTTT CCAGGTAGGGGCAGGATTCAGGATGACTGACAGGGCCCTTA GGGAACACTGAGACCCTACGCTGACCTCATAAATGCTTGCTA CCTTTGCTGTTTTAATTACATCTTTTAATAGCAGGAAGCAGA ACTCTGCACTTCAAAAGTTTTTCCTCACCTGAGGAGTTAATTT AGTACAAGGGGAAAAAGTACAGGGGGATGGGAGAAAGGCG ATCACGTTGGGAAGCTATAGAGAAAGAAGAGTAAATTTTAG TAAAGGAGGTTTAAACAAACAAAATATAAAGAGAAATAGGA ACTTGAATCAAGGAAATGATTTTAAAACGCAGTATTCTTAGT GGACTAGAGGAAAAAAATAATCTGAGCCAAGTAGAAGACCT TTTCCCCTCCTACCCCTACTTTCTAAGTCACAGAGGCTTTTTG TTCCCCCAGACACTCTTGCAGATTAGTCCAGGCAGAAACAGT TAGATGTCCCCAGTTAACCTCCTATTTGACACCACTGATTACC CCATTGATAGTCACACTTTGGGTTGTAAGTGACTTTTTATTTA TTTGTATTTTTGACTGCATTAAGAGGTCTCTAGTTTTTTATCT CTTGTTTCCCAAAACCTAATAAGTAACTAATGCACAGAGCAC ATTGATTTGTATTTATTCTATTTTTAGACATAATTTATTAGCA TGCATGAGCAAATTAAGAAAAACAACAACAAATGAATGCAT ATATATGTATATGTATGTGTGTATATATACACACATATATAT ATATATTTTTTCTTTTCTTACCAGAAGGTTTTAATCCAAATAA GGAGAAGATATGCTTAGAACCGAGGTAGAGTTTTCATCCATT CTGTCCTGTAAGTATTTTGCATATTCTGGAGACGCAGGAAGA GATCCATCTACATATCCCAAAGCTGAATTATGGTAGACAAAA CTCTTCCACTTTTAGTGCATCAACTTCTTATTTGTGTAATAAG AAAATTGGGAAAACGATCTTCAATATGCTTACCAAGCTGTGA TTCCAAATATTACGTAAATACACTTGCAAAGGAGGATGTTTT TAGTAGCAATTTGTACTGATGGTATGGGGCCAAGAGATATAT CTTAGAGGGAGGGCTGAGGGTTTGAAGTCCAACTCCTAAGCC AGTGCCAGAAGAGCCAAGGACAGGTACGGCTGTCATCACTT AGACCTCACCCTGTGGAGCCACACCCTAGGGTTGGCCAATCT ACTCCCAGGAGCAGGGAGGGCAGGAGCCAGGGCTGGGCATA AAAGTCAGGGCAGAGCCATCTATTGCTTACATTTGCTTCTGA CACAACTGTGTTCACTAGCAACCTCAAACAGACACCATGGTG CATCTGACTCCT |
| 100 | Donor DNA | HBB locus RHA (used for E6V to E6, AAV.323) | ACTGCCCTGTGGGGCAAGGTGAACGTGGATGAAGTTGGTGG TGAGGCCCTGGGCAGGTTGGTATCAAGGTTACAAGACAGGTT TAAGGAGACCAATAGAAACTGGGCATGTGGAGACAGAGAAG ACTCTTGGGTTTCTGATAGGCACTGACTCTCTCTGCCTATTGG TCTATTTTCCCACCCTTAGGCTGCTGGTGGTCTACCCTTGGAC CCAGAGGTTCTTTGAGTCCTTTGGGGATCTGTCCACTCCTGAT GCTGTTATGGGCAACCCTAAGGTGAAGGCTCATGGCAAGAA AGTGCTCGGTGCCTTTAGTGATGGCCTGGCTCACCTGGACAA CCTCAAGGGCACCTTTGCCACACTGAGTGAGCTGCACTGTGA CAAGCTGCACGTGGATCCTGAGAACTTCAGGGTGAGTCTATG GGACGCTTGATGTTTTCTTTCCCCTTCTTTTCTATGGTTAAGTT CATGTCATAGGAAGGGGATAAGTAACAGGGTACAGTTTAGA ATGGGAAACAGACGAATGATTGCATCAGTGTGGAAGTCTCA GGATCGTTTTAGTTTCTTTTATTTGCTGTTCATAACAATTGTTT TCTTTTGTTTAATTCTTGCTTTCTTTTTTTTTCTTCTCCGCAATT TTTACTATTATACTTAATGCCTTAACATTGTGTATAACAAAAG GAAATATCTCTGAGATACATTAAGTAACTTAAAAAAAAACTT TACACAGTCTGCCTAGTACATTACTATTTGGAATATATGTGT GCTTATTTGCATATTCATAATCTCCCTACTTTATTTTCTTTTAT TTTTAATTGATACATAATCATTATACATATTTATGGGTTAAAG TGTAATGTTTTAATATGTGTACACATATTGACCAAATCAGGG TAATTTTGCATTTGTAATTTTAAAAAATGCTTTCTTCTTTTAA TATACTTTTTTGTTTATCTTATTTCTAATACTTTCCCTAATCTC TTTCTTTCAGGGCAATAATGATACAATGTATCATGCCTCTTTG CACCATTCTAAAGAATAACAGTGATAATTTCTGGGTTAAGGC AATAGCAATATCTCTGCATATAAATATTTCTGCATATAAATT GTAACTGATGTAAGAGGTTTCATATTGCTAATAGCAGCTACA ATCCAGCTACCATTCTGCTTTTATTTTATGGTTGGGATAAGGC TGGATTATTCTGAGTCCAAGCTAGGCCCTTTTGCTAATCATGT TCATACCTCTTATCTTCCTCCCACAGCTCCTGGGCAACGTGCT GGTCTGTGTGCTGGCCCATCACTTTGGCAAAGAATTCACCCC ACCAGTGCAGGCTGCCTATCAGAAAGTGGTGGCTGGTGTGGC TAATGCCCTGGCCCACAAGTATCACTAAGCTCGCTTTCTTGCT GTCCAATTTCTATTAAAGGTTCCTTTGTTCCCTAAGTCCAACT ACTAAACTGGGGGATATTATGAAGGGCCTTGAGCATCTGGAT |

-continued

Sequence Listing

| SEQ ID NO: | Identifier | Name/ Description | Sequence |
|---|---|---|---|
| | | | TCTGCCTAATAAAAAACATTTATTTTCATTGCAATGATGTATT<br>TAAATTATTTCTGAATATTTTACTAAAAAGGGAATGTGGGAG<br>GTCAGTGCATTTAAAACATAAAGAAATGAAGAGCTAGTTCA<br>AACCTTGGGAAAATACACTATATCTTAAACTCCATGAAAGAA<br>GGTGAGGCTGCAAACAGCTAATGCACATTGGCAACAGCCCC<br>TGATGCATATGCCTTATTCATCCCTCAGAAAAGGATTCAAGT<br>AGAGGCTTGATTTGGAGGTTAAAGTTTTGCTATGCTGTATTTT<br>ACATTACTTATTGTTTTAGCTGTCCTCATGAATGTCTTTTCAC<br>TACCCATTTGCTTATCCTGCATCTCTCAGCCTTGACTCCACTC<br>AGTTCTCTTGCTTAGAGATACCACCTTTCCCCTGAAGTGTTCC<br>TTCCATGTTTTACGGCGAGATGGTTTCTCCTCGCCTGGCCACT<br>CAGCCTTAGTTGTCTCTGTTGTCTTATAGAGGTCTACTTGAAG<br>AAGGAAAAACAGGGGTCATGGTTTGACTGTCCTGTGAGCCCT<br>TCTTCCCTGCCTCCCCCACTCACAGTGACCCGGAATCTGCAG<br>TGCTAGTCTCCCGGAACTATCACTCTTTCACAGTCTGCTTTGG<br>AAGGACTGGGCTTAGTATGAAAAGTTAGGACTGAGAAGAAT<br>TTGAAAGGCGGCTTTTTGTAGCTTGATATTCACTACTGTCTTA<br>TTACCCTGTC |
| 101 | Donor DNA | HBB exons 1-3 | ATGGTGCATCTGACTCCTGAAGAAAAATCCGCTGTCACTGCC<br>CTGTGGGGCAAGGTGAACGTGGATGAAGTTGGTGGTGAGGC<br>CCTGGGCAGGTTGGTATCAAGGTTACAAGACAGGTTTAAGG<br>AGACCAATAGAAACTGGGCATGTGGAGACAGAGAAGACTCT<br>TGGGTTTCTGATAGGCACTGACTCTCTCTGCCTATTGGTCTAT<br>TTTCCCACCCTTAGGCTGCTGGTGGTCTACCCTTGGACCCAG<br>AGGTTCTTTGAGTCCTTTGGGGATCTGTCCACTCCTGATGCTG<br>TTATGGGCAACCCTAAGGTGAAGGCTCATGGCAAGAAAGTG<br>CTCGGTGCCTTTAGTGATGGCCTGGCTCACCTGGACAACCTC<br>AAGGGCACCTTTGCCACACTGAGTGAGCTGCACTGTGACAAG<br>CTGCACGTGGATCCTGAGAACTTCAGGGTGAGTCTATGGGAC<br>GCTTGATGTTTTCTTTCCCCTTCTTTTCTATGGTTAAGTTCATG<br>TCATAGGAAGGGGATAAGTAACAGGGTACAGTTTAGAATGG<br>GAAACAGACGAATGATTGCATCAGTGTGGAAGTCTCAGGAT<br>CGTTTTAGTTTCTTTTATTTGCTGTTCATAACAATTGTTTTCTT<br>TTGTTTAATTCTTGCTTTCTTTTTTTTTCTTCTCCGCAATTTTTA<br>CTATTATACTTAATGCCTTAACATTGTGTATAACAAAAGGAA<br>ATATCTCTGAGATACATTAAGTAACTTAAAAAAAAACTTTAC<br>ACAGTCTGCCTAGTACATTACTATTTGGAATATATGTGTGCTT<br>ATTTGCATATTCATAATCTCCCTACTTTATTTTCTTTTATTTTT<br>AATTGATACATAATCATTATACATATTTATGGGTTAAAGTGT<br>AATGTTTTAATATGTGTACACATATTGACCAAATCAGGGTAA<br>TTTTGCATTTGTAATTTTAAAAAATGCTTTCTTCTTTTAATAT<br>ACTTTTTTGTTTATCTTATTTCTAATACTTTCCCTAATCTCTTT<br>CTTTCAGGGCAATAATGATACAATGTATCATGCCTCTTTGCA<br>CCATTCTAAAGAATAACAGTGATAATTTCTGGGTTAAGGCAA<br>TAGCAATATCTCTGCATATAAATATTTCTGCATATAAATTGTA<br>ACTGATGTAAGAGGTTTCATATTGCTAATAGCAGCTACAATC<br>CAGCTACCATTCTGCTTTTATTTTATGGTTGGGATAAGGCTGG<br>ATTATTCTGAGTCCAAGCTAGGCCCTTTTGCTAATCATGTTCA<br>TACCTCTTATCTTCCTCCCACAGCTCCTGGGCAACGTGCTGGT<br>CTGTGTGCTGGCCCATCACTTTGGCAAAGAATTCACCCCACC<br>AGTGCAGGCTGCCTATCAGAAAGTGGTGGCTGGTGTGGCTAA<br>TGCCCTGGCCCACAAGTATCAC |
| 102 | Donor DNA | E6V to E6 Insert (reverse complement of PAM underlined) | GAAGAAAAATCCGCTGTC |
| 103 | | Wild-type *S. pyogenes* Cas9 | MAPKKKRKVGSGGSGGSGDKKYSIGLDIGTNSVGWAVITDEYK<br>VPSKKFKVLGNTDRHSIKKNLIGALLFDSGETAEATRLKRTARR<br>RYTRRKNRICYLQEIFSNEMAKVDDSFFHRLEESFLVEEDKKHE<br>RHPIFGNIVDEVAYHEKYPTIYHLRKKLVDSTDKADLRLIYLAL<br>AHMIKFRGHFLIEGDLNPDNSDVDKLFIQLVQTYNQLFEENPIN<br>ASGVDAKAILSARLSKSRRLENLIAQLPGEKKNGLFGNLIALSLG<br>LTPNFKSNFDLAEDAKLQLSKDTYDDDLDNLLAQIGDQYADLF<br>LAAKNLSDAILLSDILRVNTEITKAPLSASMIKRYDEHHQDLTLL<br>KALVRQQLPEKYKEIFFDQSKNGYAGYIDGGASQEEFYKFIKPIL<br>EKMDGTEELLVKLNREDLLRKQRTFDNGSIPHQIHLGELHAILR<br>RQEDFYPFLKDNREKIEKILTFRIPYYVGPLARGNSRFAWMTRK<br>SEETITPWNFEEVVDKGASAQSFIERMTNFDKNLPNEKVLPKHS<br>LLYEYFTVYNELTKVKYVTEGMRKPAFLSGEQKKAIVDLLFKT<br>NRKVTVKQLKEDYFKKIECFDSVEISGVEDRFNASLGTYHDLLK |

-continued

Sequence Listing

| SEQ ID NO: | Identifier | Name/ Description | Sequence |
|---|---|---|---|
| | | | IIKDKDFLDNEENEDILEDIVLTLTLFEDREMIEERLKTYAHLFDD KVMKQLKRRRYTGWGRLSRKLINGIRDKQSGKTILDFLKSDGF ANRNFMQLIHDDSLTFKEDIQKAQVSGQGDSLHEHIANLAGSPA IKKGILQTVKVVDELVKVMGRHKPENIVIEMARENQTTQKGQK NSRERMKRIEEGIKELGSQILKEHPVENTQLQNEKLYLYYLQNG RDMYVDQELDINRLSDYDVDHIVPQSFLKDDSIDNKVLTRSDK NRGKSDNVPSEEVVKKMKNYWRQLLNAKLITQRKFDNLTKAE RGGLSELDKAGFIKRQLVETRQITKHVAQILDSRMNTKYDEND KLIREVKVITLKSKLVSDFRKDFQFYKVREINNYHHAHDAYLNA VVGTALIKKYPKLESEFVYGDYKVYDVRKMIAKSEQEIGKATA KYFFYSNIMNFFKTEITLANGEIRKRPLIETNGETGEIVWDKGRD FATVRKVLSMPQVNIVKKTEVQTGGFSKESILPKRNSDKLIARK KDWDPKKYGGFDSPTVAYSVLVVAKVEKGKSKKLKSVKELLG ITIMERSSFEKNPIDFLEAKGYKEVKKDLIIKLPKYSLFELENGRK RMLASAGELQKGNELALPSKYVNFLYLASHYEKLKGSPEDNEQ KQLFVEQHKHYLDEIIEQISEFSKRVILADANLDKVLSAYNKHR DKPIREQAENIIHLFTLTNLGAPAAFKYFDTTIDRKRYTSTKEVL DATLIHQSITGLYETRIDLSQLGGDGSAGSGGSGGSGPKKKRKV |
| 104 | | Wild-type *S. aureus* Cas9 | MHHHHHHHHGSGGSGGSGPKKKRKVGSGGSGGSGKRNYILGL DIGITSVGYGIIDYETRDVIDAGVRLFKEANVENNEGRRSKRGA RRLKRRRRHRIQRVKKLLFDYNLLTDHSELSGINPYEARVKGLS QKLSEEEFSAALLHLAKRRGVHNVNEVEEDTGNELSTKEQISRN SKALEEKYVAELQLERLKKDGEVRGSINRFKTSDYVKEAKQLL KVQKAYHQLDQSFIDTYIDLLETRRTYYEGPGEGSPFGWKDIKE WYEMLMGHCTYFPEELRSVKYAYNADLYNALNDLNNLVITRD ENEKLEYYEKFQIIENVFKQKKKPTLKQIAKEILVNEEDIKGYRV TSTGKPEFTNLKVYHDIKDITARKEIIENAELLDQIAKILTIYQSSE DIQEELTNLNSELTQEEIEQISNLKGYTGTHNLSLKAINLILDELW HTNDNQIAIFNRLKLVPKKVDLSQQKEIPTTLVDDFILSPVVKRS FIQSIKVINAIIKKYGLPNDIIIELAREKNSKDAQKMINEMQKRNR QTNERIEEIIRTTGKENAKYLIEKIKLHDMQEGKCLYSLEAIPLED LLNNPFNYEVDHIIPRSVSFDNSFNNKVLVKQEENSKKGNRTPF QYLSSSDSKISYETFKKHILNLAKGKGRISKTKKEYLLEERDINR FSVQKDFINRNLVDTRYATRGLMNLLRSYFRVNNLDVKVKSIN GGFTSFLRRKWKFKKERNKGYKHHAEDALIIANADFIFKEWKK LDKAKKVMENQMFEEKQAESMPEIETEQEYKEIFITPHQIKHIK DFKDYKYSHRVDKKPNRELINDTLYSTRKDDKGNTLIVNNLNG LYDKDNDKLKKLINKSPEKLLMYHHDPQTYQKLKLIMEQYGD EKNPLYKYYEETGNYLTKYSKKDNGPVIKKIKYYGNKLNAHLD ITDDYPNSRNKVVKLSLKPYRFDVYLDNGVYKFVTVKNLDVIK KENYYEVNSKCYEEAKKLKKISNQAEFIASFYNNDLIKINGELY RVIGVNNDLLNRIEVNMIDITYREYLENMNDKRPPRIIKTIASKT QSIKKYSTDILGNLYEVKSKKHPQIIKKGGSAGSGGSGGSGPKK KRKV |
| 105 | Donor template | Full AAV-323 | CCTGCAGGCAGCTGCGCGCTCGCTCGCTCACTGAGGCCGCCC GGGCGTCGGGCGACCTTTGGTCGCCCGGCCTCAGTGAGCGAG CGAGCGCGCAGAGAGGGAGTGGCCAACTCCATCACTAGGGG TTCCTGCGGCCGCACGCGTCTTGCTTTGACAATTTTGGTCTTT CAGAATACTATAAATATAACCTATATTATAATTTCATAAAGT CTGTGCATTTTCTTTGACCCAGGATATTTGCAAAAGACATATT CAAACTTCCGCAGAACACTTTATTTCACATATACATGCCTCTT ATATCAGGGATGTGAAACAGGGTCTTGAAAACTGTCTAAATC TAAAACAATGCTAATGCAGGTTTAAATTTAATAAAATAAAAT CCAAAATCTAACAGCCAAGTCAAATCTGCATGTTTTAACATT TAAAATATTTTAAAGACGTCTTTTCCCAGGATTCAACATGTG AAATCTTTTCTCAGGGATACACGTGTGCCTAGATCCTCATTG CTTTAGTTTTTTACAGAGGAATGAATATAAAAAGAAAATACT TAAATTTTATCCCTCTTACCTCTATAATCATACATAGGCATAA TTTTTTAACCTAGGCTCCAGATAGCCATAGAAGAACCAAACA CTTTCTGCGTGTGTGAGAATAATCAGAGTGAGATTTTTTCAC AAGTACCTGATGAGGGTTGAGAGAGGTAGAAAAAGTGAGAG ATCTCTATTTATTTAGCAATAATAGAGAAAGCATTTAAGAGA ATAAAGCAATGGAAATAAGAAATTTGTAAATTTCCTTCTGAT AACTAGAAATAGAGGATCCAGTTTCTTTTGGTTAACCTAAAT TTTATTTCATTTTATTGTTTTATTTTATTTTATTTTATTTTATTT TGTGTAATCGTAGTTTCAGAGTGTTAGAGCTGAAAGGAAGAA GTAGGAGAAACATGCAAAGTAAAAGTATAACACTTTCCTTAC TAAACCGACATGGGTTTCCAGGTAGGGGCAGGATTCAGGAT GACTGACAGGGCCCTTAGGGAACACTGAGACCCTACGCTGA CCTCATAAATGCTTGCTACCTTTGCTGTTTTAATTACATCTTT TAATAGCAGGAAGCAGAACTCTGCACTTCAAAAGTTTTTCCT CACCTGAGGAGTTAATTTAGTACAAGGGGAAAAAGTACAGG |

-continued

Sequence Listing

| SEQ ID NO: | Identifier | Name/ Description | Sequence |
|---|---|---|---|
| | | | GGGATGGGAGAAAGGCGATCACGTTGGGAAGCTATAGAGAA<br>AGAAGAGTAAATTTTAGTAAAGGAGGTTTAAACAAACAAAA<br>TATAAAGAGAAATAGGAACTTGAATCAAGGAAATGATTTTA<br>AAACGCAGTATTCTTAGTGGACTAGAGGAAAAAAATAATCT<br>GAGCCAAGTAGAAGACCTTTTCCCCTCCTACCCCTACTTTCTA<br>AGTCACAGAGGCTTTTTGTTCCCCCAGACACTCTTGCAGATT<br>AGTCCAGGCAGAAAGAGTTAGATGTCCCCAGTTAACCTCCTA<br>TTTGACACCACTGATTACCCCATTGATAGTCACACTTTGGGTT<br>GTAAGTGACTTTTTATTTATTTGTATTTTTGACTGCATTAAGA<br>GGTCTCTAGTTTTTTATCTCTTGTTTCCCAAAACCTAATAAGT<br>AACTAATGCACAGAGCACATTGATTTGTATTTATTCTATTTTT<br>AGACATAATTTATTAGCATGCATGAGCAAATTAAGAAAAAC<br>AACAACAAATGAATGCATATATATGTATATGTATGTGTGTAT<br>ATATACACACATATATATATATATTTTTTCTTTTCTTACCAGA<br>AGGTTTTAATCCAAATAAGGAGAAGATATGCTTAGAACCGA<br>GGTAGAGTTTTCATCCATTCTGTCCTGTAAGTATTTTGCATAT<br>TCTGGAGACGCAGGAAGAGATCCATCTACATATCCCAAAGCT<br>GAATTATGGTAGACAAAACTCTTCCACTTTTAGTGCATCAAC<br>TTCTTATTTGTGTAATAAGAAAATTGGGAAAACGATCTTCAA<br>TATGCTTACCAAGCTGTGATTCCAAATATTACGTAAATACAC<br>TTGCAAAGGAGGATGTTTTTAGTAGCAATTTGTACTGATGGT<br>ATGGGGCCAAGAGATATATCTTAGAGGGAGGGCTGAGGGTT<br>TGAAGTCCAACTCCTAAGCCAGTGCCAGAAGAGCCAAGGAC<br>AGGTACGGCTGTCATCACTTAGACCTCACCCTGTGGAGCCAC<br>ACCCTAGGGTTGGCCAATCTACTCCCAGGAGCAGGGAGGGC<br>AGGAGCCAGGGCTGGGCATAAAAGTCAGGGCAGAGCCATCT<br>ATTGCTTACATTTGCTTCTGACACAACTGTGTTCACTAGCAAC<br>CTCAAACAGACACCATGGTGCATCTGACTCCTGAAGAAAAAT<br>CCGCTGTCACTGCCCTGTGGGGCAAGGTGAACGTGGATGAA<br>GTTGGTGGTGAGGCCCTGGGCAGGTTGGTATCAAGGTTACAA<br>GACAGGTTTAAGGAGACCAATAGAAACTGGGCATGTGGAGA<br>CAGAGAAGACTCTTGGGTTTCTGATAGGCACTGACTCTCTCT<br>GCCTATTGGTCTATTTTCCCACCCTTAGGCTGCTGGTGGTCTA<br>CCCTTGGACCCAGAGGTTCTTTGAGTCCTTTGGGGATCTGTCC<br>ACTCCTGATGCTGTTATGGGCAACCCTAAGGTGAAGGCTCAT<br>GGCAAGAAAGTGCTCGGTGCCTTTAGTGATGGCCTGGCTCAC<br>CTGGACAACCTCAAGGGCACCTTTGCCACACTGAGTGAGCTG<br>CACTGTGACAAGCTGCACGTGGATCCTGAGAACTTCAGGGTG<br>AGTCTATGGGACGCTTGATGTTTTCTTTCCCCTTCTTTTCTAT<br>GGTTAAGTTCATGTCATAGGAAGGGGATAAGTAACAGGGTA<br>CAGTTTAGAATGGGAAACAGACGAATGATTGCATCAGTGTG<br>GAAGTCTCAGGATCGTTTTAGTTTCTTTTATTTGCTGTTCATA<br>ACAATTGTTTTCTTTTGTTTAATTCTTGCTTTCTTTTTTTTTCTT<br>CTCCGCAATTTTTACTATTATACTTAATGCCTTAACATTGTGT<br>ATAACAAAAGGAAATATCTCTGAGATACATTAAGTAACTTAA<br>AAAAAAACTTTACACAGTCTGCCTAGTACATTACTATTTGGA<br>ATATATGTGTGCTTATTTGCATATTCATAATCTCCCTACTTTA<br>TTTTCTTTTATTTTTAATTGATACATAATCATTATACATATTTA<br>TGGGTTAAAGTGTAATGTTTTAATATGTGTACACATATTGAC<br>CAAATCAGGGTAATTTTGCATTTGTAATTTTAAAAAATGCTTT<br>CTTCTTTTAATATACTTTTTTGTTTATCTTATTTCTAATACTTT<br>CCCTAATCTCTTTCTTTCAGGGCAATAATGATACAATGTATCA<br>TGCCTCTTTGCACCATTCTAAAGAATAACAGTGATAATTTCT<br>GGGTTAAGGCAATAGCAATATCTCTGCATATAAATATTTCTG<br>CATATAAATTGTAACTGATGTAAGAGGTTTCATATTGCTAAT<br>AGCAGCTACAATCCAGCTACCATTCTGCTTTTATTTTATGGTT<br>GGGATAAGGCTGGATTATTCTGAGTCCAAGCTAGGCCCTTTT<br>GCTAATCATGTTCATACCTCTTATCTTCCTCCCACAGCTCCTG<br>GGCAACGTGCTGGTCTGTGTGCTGGCCCATCACTTTGGCAAA<br>GAATTCACCCCACCAGTGCAGGCTGCCTATCAGAAAGTGGTG<br>GCTGGTGTGGCTAATGCCCTGGCCCACAAGTATCACTAAGCT<br>CGCTTTCTTGCTGTCCAATTTCTATTAAAGGTTCCTTTGTTCC<br>CTAAGTCCAACTACTAAACTGGGGGATATTATGAAGGGCCTT<br>GAGCATCTGGATTCTGCCTAATAAAAAACATTTATTTTCATT<br>GCAATGATGTATTTAAATTATTTCTGAATATTTTACTAAAAA<br>GGGAATGTGGGAGGTCAGTGCATTTAAAACATAAAGAAATG<br>AAGAGCTAGTTCAAACCTTGGGAAAATACACTATATCTTAAA<br>CTCCATGAAAGAAGGTGAGGCTGCAAACAGCTAATGCACAT<br>TGGCAACAGCCCCTGATGCATATGCCTTATTCATCCCTCAGA<br>AAAGGATTCAAGTAGAGGCTTGATTTGGAGGTTAAAGTTTTG<br>CTATGCTGTATTTTACATTACTTATTGTTTTAGCTGTCCTCAT<br>GAATGTCTTTTCACTACCCATTTGCTTATCCTGCATCTCTCAG<br>CCTTGACTCCACTCAGTTCTCTTGCTTAGAGATACCACCTTTC<br>CCCTGAAGTGTTCCTTCCATGTTTTACGGCGAGATGGTTTCTC |

-continued

Sequence Listing

| SEQ ID NO: | Identifier | Name/ Description | Sequence |
|---|---|---|---|
| | | | CTCGCCTGGCCACTCAGCCTTAGTTGTCTCTGTTGTCTTATAG AGGTCTACTTGAAGAAGGAAAAACAGGGGTCATGGTTTGAC TGTCCTGTGAGCCCTTCTTCCCTGCCTCCCCCACTCACAGTGA CCCGGAATCTGCAGTGCTAGTCTCCCGGAACTATCACTCTTT CACAGTCTGCTTTGGAAGGACTGGGCTTAGTATGAAAAGTTA GGACTGAGAAGAATTTGAAAGGCGGCTTTTTGTAGCTTGATA TTCACTACTGTCTTATTACCCTGTCGGTAACCACGTGCGGCCG AGGCTGCAGCGTCGTCCTCCCTAGGAACCCCTAGTGATGGAG TTGGCCACTCCCTCTCTGCGCGCTCGCTCGCTCACTGAGGCC GGGCGACCAAAGGTCGCCCGACGCCCGGGCTTTGCCCGGGC GGCCTCAGTGAGCGAGCGAGCGCGCAGCTGCCTGCAGGGGC GCCTGATGCGGTATTTTCTCCTTACGCATCTGTGCGGTATTTC ACACCGCATACGTCAAAGCAACCATAGTACGCGCCCTGTAGC GGCGCATTAAGCGCGGCGGGTGTGGTGGTTACGCGCAGCGT GACCGCTACACTTGCCAGCGCCCTAGCGCCCGCTCCTTTCGC TTTCTTCCCTTCCTTTCTCGCCACGTTCGCCGGCTTTCCCCGTC AAGCTCTAAATCGGGGGCTCCCTTTAGGGTTCCGATTTAGTG CTTTACGGCACCTCGACCCCAAAAAACTTGATTTGGGTGATG GTTCACGTAGTGGGCCATCGCCCTGATAGACGGTTTTTCGCC CTTTGACGTTGGAGTCCACGTTCTTTAATAGTGGACTCTTGTT CCAAACTGGAACAACACTCAACCCTATCTCGGGCTATTCTTT TGATTTATAAGGGATTTTGCCGATTTCGGCCTATTGGTTAAA AAATGAGCTGATTTAACAAAAATTTAACGCGAATTTTAACAA AATATTAACGTTTACAATTTTATGGTGCACTCTCAGTACAATC TGCTCTGATGCCGCATAGTTAAGCCAGCCCCGACACCCGCCA ACACCCGCTGACGCGCCCTGACGGGCTTGTCTGCTCCCGGCA TCCGCTTACAGACAAGCTGTGACCGTCTCCGGGAGCTGCATG TGTCAGAGGTTTTCACCGTCATCACCGAAACGCGCGAGACGA AAGGGCCTCGTGATACGCCTATTTTTATAGGTTAATGTCATG AACAATAAAACTGTCTGCTTACATAAACAGTAATACAAGGG GTGTTATGAGCCATATTCAACGGGAAACGTCGAGGCCGCGAT TAAATTCCAACATGGATGCTGATTTATATGGGTATAAATGGG CTCGCGATAATGTCGGGCAATCAGGTGCGACAATCTATCGCT TGTATGGGAAGCCCGATGCGCCAGAGTTGTTTCTGAAACATG GCAAAGGTAGCGTTGCCAATGATGTTACAGATGAGATGGTC AGACTAAACTGGCTGACGGAATTTATGCCTCTTCCGACCATC AAGCATTTTATCCGTACTCCTGATGATGCATGGTTACTCACC ACTGCGATCCCCGGAAAAACAGCATTCCAGGTATTAGAAGA ATATCCTGATTCAGGTGAAAATATTGTTGATGCGCTGGCAGT GTTCCTGCGCCGGTTGCATTCGATTCCTGTTTGTAATTGTCCT TTTAACAGCGATCGCGTATTTCGTCTCGCTCAGGCGCAATCA CGAATGAATAACGGTTTGGTTGATGCGAGTGATTTTGATGAC GAGCGTAATGGCTGGCCTGTTGAACAAGTCTGGAAAGAAAT GCATAAACTTTTGCCATTCTCACCGGATTCAGTCGTCACTCAT GGTGATTTCTCACTTGATAACCTTATTTTTGACGAGGGGAAA TTAATAGGTTGTATTGATGTTGGACGAGTCGGAATCGCAGAC CGATACCAGGATCTTGCCATCCTATGGAACTGCCTCGGTGAG TTTTCTCCTTCATTACAGAAACGGCTTTTTCAAAAATATGGTA TTGATAATCCTGATATGAATAAATTGCAGTTTCATTTGATGCT CGATGAGTTTTTCTAATCTCATGACCAAAATCCCTTAACGTG AGTTTTCGTTCCACTGAGCGTCAGACCCCGTAGAAAAGATCA AAGGATCTTCTTGAGATCCTTTTTTTCTGCGCGTAATCTGCTG CTTGCAAACAAAAAAACCACCGCTACCAGCGGTGGTTTGTTT GCCGGATCAAGAGCTACCAACTCTTTTTCCGAAGGTAACTGG CTTCAGCAGAGCGCAGATACCAAATACTGTCCTTCTAGTGTA GCCGTAGTTAGGCCACCACTTCAAGAACTCTGTAGCACCGCC TACATACCTCGCTCTGCTAATCCTGTTACCAGTGGCTGCTGCC AGTGGCGATAAGTCGTGTCTTACCGGGTTGGACTCAAGACGA TAGTTACCGGATAAGGCGCAGCGGTCGGGCTGAACGGGGGG TTCGTGCACACAGCCCAGCTTGGAGCGAACGACCTACACCGA ACTGAGATACCTACAGCGTGAGCTATGAGAAAGCGCCACGC TTCCCGAAGGGAGAAAGGCGGACAGGTATCCGGTAAGCGGC AGGGTCGGAACAGGAGAGCGCACGAGGGAGCTTCCAGGGGG AAACGCCTGGTATCTTTATAGTCCTGTCGGGTTTCGCCACCTC TGACTTGAGCGTCGATTTTTGTGATGCTCGTCAGGGGGGCGG AGCCTATGGAAAAACGCCAGCAACGCGGCCTTTTTACGGTTC CTGGCCTTTTGCTGGCCTTTTGCTCACATGT |
| 106 | | AAV2 ITR for LHA (AAV.323) | CCTGCAGGCAGCTGCGCGCTCGCTCGCTCACTGAGGCCGCCC GGGCGTCGGGCGACCTTTGGTCGCCCGGCCTCAGTGAGCGAG CGAGCGCGCAGAGAGGGAGTGGCCAACTCCATCACTAGGGG TTCCT |

-continued

Sequence Listing

| SEQ ID NO: | Identifier | Name/ Description | Sequence |
|---|---|---|---|
| 107 | | AAV2 ITR for RHA (AAV.323) | AGGAACCCCTAGTGATGGAGTTGGCCACTCCCTCTCTGCGCG CTCGCTCGCTCACTGAGGCCGGGCGACCAAAGGTCGCCCGAC GCCCGGGCTTTGCCCGGGCGGCCTCAGTGAGCGAGCGAGCG CGCAGCTGCCTGCAGG |
| 108 | Donor template | HBB Locus LHA to RHA (AAV.304) | CTTGCTTTGACAATTTTGGTCTTTCAGAATACTATAAATATAA CCTATATTATAATTTCATAAAGTCTGTGCATTTTCTTTGACCC AGGATATTTGCAAAAGACATATTCAAACTTCCGCAGAACACT TTATTTCACATATACATGCCTCTTATATCAGGGATGTGAAAC AGGGTCTTGAAAACTGTCTAAATCTAAAACAATGCTAATGCA GGTTTAAATTTAATAAAATAAAATCCAAAATCTAACAGCCAA GTCAAATCTGCATGTTTTAACATTTAAAATATTTTAAAGACG TCTTTTCCCAGGATTCAACATGTGAAATCTTTTCTCAGGGATA CACGTGTGCCTAGATCCTCATTGCTTTAGTTTTTTACAGAGGA ATGAATATAAAAAGAAAATACTTAAATTTTATCCCTCTTACC TCTATAATCATACATAGGCATAATTTTTTAACCTAGGCTCCA GATAGCCATAGAAGAACCAAACACTTTCTGCGTGTGTGAGA ATAATCAGAGTGAGATTTTTTCACAAGTACCTGATGAGGGTT GAGACAGGTAGAAAAAGTGAGAGATCTCTATTTATTTAGCA ATAATAGAGAAAGCATTTAAGAGAATAAAGCAATGGAAATA AGAAATTTGTAAATTTCCTTCTGATAACTAGAAATAGAGGAT CCAGTTTCTTTTGGTTAACCTAAATTTTATTTCATTTTATTGTT TTATTTTATTTTATTTTATTTTATTTTGTGTAATCGTAGTTTCA GAGTGTTAGAGCTGAAAGGAAGAAGTAGGAGAAACATGCAA AGTAAAAGTATAACACTTTCCTTACTAAACCGACATGGGTTT CCAGGTAGGGGCAGGATTCAGGATGACTGACAGGGCCCTTA GGGAACACTGAGACCCTACGCTGACCTCATAAATGCTTGCTA CCTTTGCTGTTTTAATTACATCTTTTAATAGCAGGAAGCAGA ACTCTGCACTTCAAAAGTTTTTCCTCACCTGAGGAGTTAATTT AGTACAAGGGGAAAAAGTACAGGGGGATGGGAGAAAGGCG ATCACGTTGGGAAGCTATAGAGAAAGAAGAGTAAATTTTAG TAAAGGAGGTTTAAACAAACAAAATATAAAGAGAAATAGGA ACTTGAATCAAGGAAATGATTTTAAAACGCAGTATTCTTAGT GGACTAGAGGAAAAAAATAATCTGAGCCAAGTAGAAGACCT TTTCCCCTCCTACCCCTACTTTCTAAGTCACAGAGGCTTTTTG TTCCCCCAGACACTCTTGCAGATTAGTCCAGGCAGAAACAGT TAGATGTCCCCAGTTAACCTCCTATTTGACACCACTGATTACC CCATTGATAGTCACACTTTGGGTTGTAAGTGACTTTTTATTTA TTTGTATTTTTGACTGCATTAAGAGGTCTCTAGTTTTTTATCT CTTGTTTCCCAAAACCTAATAAGTAACTAATGCACAGAGCAC ATTGATTTGTATTTATTCTATTTTTAGACATAATTTATTAGCA TGCATGAGCAAATTAAGAAAAACAACAACAAATGAATGCAT ATATATGTATATGTATGTGTGTATATATACACACATATATAT ATATATTTTTTCTTTTCTTACCAGAAGGTTTTAATCCAAATAA GGAGAAGATATGCTTAGAACCGAGGTAGAGTTTTCATCCATT CTGTCCTGTAAGTATTTTGCATATTCTGGAGACGCAGGAAGA GATCCATCTACATATCCCAAAGCTGAATTATGGTAGACAAAA CTCTTCCACTTTTAGTGCATCAACTTCTTATTTGTGTAATAAG AAAATTGGGAAAACGATCTTCAATATGCTTACCAAGCTGTGA TTCCAAATATTACGTAAATACACTTGCAAAGGAGGATGTTTT TAGTAGCAATTTGTACTGATGGTATGGGGCCAAGAGATATAT CTTAGAGGGAGGGCTGAGGGTTTGAAGTCCAACTCCTAAGCC AGTGCCAGAAGAGCCAAGGACAGGTACGGCTGTCATCACTT AGACCTCACCCTGTGGAGCCACACCCTAGGGTTGGCCAATCT ACTCCCAGGAGCAGGGAGGGCAGGAGCCAGGGCTGGGCATA AAAGTCAGGGCAGAGCCATCTATTGCTTACATTTGCTTCTGA CACAACTGTGTTCACTAGCAACCTCAAACAGACACCATGGTG CATCTGACTCCTGTCGAGAAGTCTGCAGTCACTGCTCTATGG GGGAAAGTGAACGTGGATGAAGTTGGTGGTGAGGCCCTGGG CAGGTTGGTATCAAGGTTACAAGACAGGTTTAAGGAGACCA ATAGAAACTGGGCATGTGGAGACAGAGAAGACTCTTGGGTT TCTGATAGGCACTGACTCTCTCTGCCTATTGGTCTATTTTCCC ACCCTTAGGCTGCTGGTGGTCTACCCTTGGACCCAGAGGTTC TTTGAGTCCTTTGGGGATCTGTCCACTCCTGATGCTGTTATGG GCAACCCTAAGGTGAAGGCTCATGGCAAGAAAGTGCTCGGT GCCTTTAGTGATGGCCTGGCTCACCTGGACAACCTCAAGGGC ACCTTTGCCACACTGAGTGAGCTGCACTGTGACAAGCTGCAC GTGGATCCTGAGAACTTCAGGGTGAGTCTATGGGACGCTTGA TGTTTTCTTTCCCCTTCTTTTCTATGGTTAAGTTCATGTCATAG GAAGGGGATAAGTAACAGGGTACAGTTTAGAATGGGAAACA GACGAATGATTGCATCAGTGTGGAAGTCTCAGGATCGTTTTA GTTTCTTTTATTTGCTGTTCATAACAATTGTTTTCTTTTGTTTA ATTCTTGCTTTCTTTTTTTTTCTTCTCCGCAATTTTTACTATTA TACTTAATGCCTTAACATTGTGTATAACAAAAGGAAATATCT |

-continued

Sequence Listing

| SEQ ID NO: | Identifier | Name/ Description | Sequence |
|---|---|---|---|
| | | | CTGAGATACATTAAGTAACTTAAAAAAAAACTTTACACAGTC TGCCTAGTACATTACTATTTGGAATATATGTGTGCTTATTTGC ATATTCATAATCTCCCTACTTTATTTTCTTTTATTTTTAATTGA TACATAATCATTATACATATTTATGGGTTAAAGTGTAATGTTT TAATATGTGTACACATATTGACCAAATCAGGGTAATTTTGCA TTTGTAATTTTAAAAAATGCTTTCTTCTTTTAATATACTTTTTT GTTTATCTTATTTCTAATACTTTCCCTAATCTCTTTCTTTCAGG GCAATAATGATACAATGTATCATGCCTCTTTGCACCATTCTA AAGAATAACAGTGATAATTTCTGGGTTAAGGCAATAGCAAT ATCTCTGCATATAAATATTTCTGCATATAAATTGTAACTGATG TAAGAGGTTTCATATTGCTAATAGCAGCTACAATCCAGCTAC CATTCTGCTTTTATTTTATGGTTGGGATAAGGCTGGATTATTC TGAGTCCAAGCTAGGCCCTTTTGCTAATCATGTTCATACCTCT TATCTTCCTCCCACAGCTCCTGGGCAACGTGCTGGTCTGTGTG CTGGCCCATCACTTTGGCAAAGAATTCACCCCACCAGTGCAG GCTGCCTATCAGAAAGTGGTGGCTGGTGTGGCTAATGCCCTG GCCCACAAGTATCACTAAGCTCGCTTTCTTGCTGTCCAATTTC TATTAAAGGTTCCTTTGTTCCCTAAGTCCAACTACTAAACTGG GGGATATTATGAAGGGCCTTGAGCATCTGGATTCTGCCTAAT AAAAAACATTTATTTTCATTGCAATGATGTATTTAAATTATTT CTGAATATTTTACTAAAAAGGGAATGTGGGAGGTCAGTGCAT TTAAAACATAAAGAAATGAAGAGCTAGTTCAAACCTTGGGA AAATACACTATATCTTAAACTCCATGAAAGAAGGTGAGGCTG CAAACAGCTAATGCACATTGGCAACAGCCCCTGATGCATATG CCTTATTCATCCCTCAGAAAAGGATTCAAGTAGAGGCTTGAT TTGGAGGTTAAAGTTTTGCTATGCTGTATTTTACATTACTTAT TGTTTTAGCTGTCCTCATGAATGTCTTTTCACTACCCATTTGC TTATCCTGCATCTCTCAGCCTTGACTCCACTCAGTTCTCTTGC TTAGAGATACCACCTTTCCCCTGAAGTGTTCCTTCCATGTTTT ACGGCGAGATGGTTTCTCCTCGCCTGGCCACTCAGCCTTAGT TGTCTCTGTTGTCTTATAGAGGTCTACTTGAAGAAGGAAAAA CAGGGGTCATGGTTTGACTGTCCTGTGAGCCCTTCTTCCCTGC CTCCCCCACTCACAGTGACCCGGAATCTGCAGTGCTAGTCTC CCGGAACTATCACTCTTTCACAGTCTGCTTTGGAAGGACTGG GCTTAGTATGAAAAGTTAGGACTGAGAAGAATTTGAAAGGC GGCTTTTTGTAGCTTGATATTCACTACTGTCTTATTACCCTGT C |
| 109 | Donor template | Full AAV (AAV.304) | CCTGCAGGCAGCTGCGCGCTCGCTCGCTCACTGAGGCCGCCC GGGCAAAGCCCGGGCGTCGGGCGACCTTTGGTCGCCCGGCCT CAGTGAGCGAGCGAGCGCGCAGAGAGGGAGTGGCCAACTCC ATCACTAGGGGTTCCTGCGGCCGCACGCGTCTTGCTTTGACA ATTTTGGTCTTTCAGAATACTATAAATATAACCTATATTATAA TTTCATAAAGTCTGTGCATTTTCTTTGACCCAGGATATTTGCA AAAGACATATTCAAACTTCCGCAGAACACTTTATTTCACATA TACATGCCTCTTATATCAGGGATGTGAAACAGGGTCTTGAAA ACTGTCTAAATCTAAAACAATGCTAATGCAGGTTTAAATTTA ATAAAATAAAATCCAAAATCTAACAGCCAAGTCAAATCTGC ATGTTTTAACATTTAAAATATTTTAAAGACGTCTTTTCCCAGG ATTCAACATGTGAAATCTTTTCTCAGGGATACACGTGTGCCT AGATCCTCATTGCTTTAGTTTTTTACAGAGGAATGAATATAA AAAGAAAATACTTAAATTTTATCCCTCTTACCTCTATAATCAT ACATAGGCATAATTTTTTAACCTAGGCTCCAGATAGCCATAG AAGAACCAAACACTTTCTGCGTGTGTGAGAATAATCAGAGTG AGATTTTTTCACAAGTACCTGATGAGGGTTGAGACAGGTAGA AAAAGTGAGAGATCTCTATTTATTTAGCAATAATAGAGAAAG CATTTAAGAGAATAAAGCAATGGAAATAAGAAATTTGTAAA TTTCCTTCTGATAACTAGAAATAGAGGATCCAGTTTCTTTTGG TTAACCTAAATTTTATTTCATTTTATTGTTTTATTTTATTTTAT TTTATTTTATTTTGTGTAATCGTAGTTTCAGAGTGTTAGAGCT GAAAGGAAGAAGTAGGAGAAACATGCAAAGTAAAAGTATA ACACTTTCCTTACTAAACCGACATGGGTTTCCAGGTAGGGGC AGGATTCAGGATGACTGACAGGGCCCTTAGGGAACACTGAG ACCCTACGCTGACCTCATAAATGCTTGCTACCTTTGCTGTTTT AATTACATCTTTTAATAGCAGGAAGCAGAACTCTGCACTTCA AAAGTTTTTCCTCACCTGAGGAGTTAATTTAGTACAAGGGGA AAAAGTACAGGGGGATGGGAGAAAGGCGATCACGTTGGGAA GCTATAGAGAAAGAAGAGTAAATTTTAGTAAAGGAGGTTTA AACAAACAAAATATAAAGAGAAATAGGAACTTGAATCAAGG AAATGATTTTAAAACGCAGTATTCTTAGTGGACTAGAGGAAA AAAATAATCTGAGCCAAGTAGAAGACCTTTTCCCCTCCTACC CCTACTTTCTAAGTCACAGAGGCTTTTTGTTCCCCCAGACACT CTTGCAGATTAGTCCAGGCAGAAACAGTTAGATGTCCCCAGT TAACCTCCTATTTGACACCACTGATTACCCCATTGATAGTCAC |

-continued

Sequence Listing

| SEQ ID NO: | Identifier | Name/ Description | Sequence |
|---|---|---|---|
| | | | ACTTTGGGTTGTAAGTGACTTTTTATTTATTTGTATTTTTGACT GCATTAAGAGGTCTCTAGTTTTTTATCTCTTGTTTCCCAAAAC CTAATAAGTAACTAATGCACAGAGCACATTGATTTGTATTTA TTCTATTTTTAGACATAATTTATTAGCATGCATGAGCAAATTA AGAAAAACAACAACAAATGAATGCATATATATGTATATGTA TGTGTGTATATATACACACATATATATATATATTTTTTCTTTT CTTACCAGAAGGTTTTAATCCAAATAAGGAGAAGATATGCTT AGAACCGAGGTAGAGTTTTCATCCATTCTGTCCTGTAAGTAT TTTGCATATTCTGGAGACGCAGGAAGAGATCCATCTACATAT CCCAAAGCTGAATTATGGTAGACAAAACTCTTCCACTTTTAG TGCATCAACTTCTTATTTGTGTAATAAGAAAATTGGGAAAAC GATCTTCAATATGCTTACCAAGCTGTGATTCCAAATATTACG TAAATACACTTGCAAAGGAGGATGTTTTTAGTAGCAATTTGT ACTGATGGTATGGGGCCAAGAGATATATCTTAGAGGGAGGG CTGAGGGTTTGAAGTCCAACTCCTAAGCCAGTGCCAGAAGA GCCAAGGACAGGTACGGCTGTCATCACTTAGACCTCACCCTG TGGAGCCACACCCTAGGGTTGGCCAATCTACTCCCAGGAGCA GGGAGGGCAGGAGCCAGGGCTGGGCATAAAAGTCAGGGCA GAGCCATCTATTGCTTACATTTGCTTCTGACACAACTGTGTTC ACTAGCAACCTCAAACAGACACCATGGTGCATCTGACTCCTG TCGAGAAGTCTGCAGTCACTGCTCTATGGGGGAAAGTGAAC GTGGATGAAGTTGGTGGTGAGGCCCTGGGCAGGTTGGTATCA AGGTTACAAGACAGGTTTAAGGAGACCAATAGAAACTGGGC ATGTGGAGACAGAGAAGACTCTTGGGTTTCTGATAGGCACTG ACTCTCTCTGCCTATTGGTCTATTTTCCCACCCTTAGGCTGCT GGTGGTCTACCCTTGGACCCAGAGGTTCTTTGAGTCCTTTGG GGATCTGTCCACTCCTGATGCTGTTATGGGCAACCCTAAGGT GAAGGCTCATGGCAAGAAAGTGCTCGGTGCCTTTAGTGATGG CCTGGCTCACCTGGACAACCTCAAGGGCACCTTTGCCACACT GAGTGAGCTGCACTGTGACAAGCTGCACGTGGATCCTGAGA ACTTCAGGGTGAGTCTATGGGACGCTTGATGTTTTCTTTCCCC TTCTTTTCTATGGTTAAGTTCATGTCATAGGAAGGGGATAAG TAACAGGGTACAGTTTAGAATGGGAAACAGACGAATGATTG CATCAGTGTGGAAGTCTCAGGATCGTTTTAGTTTCTTTTATTT GCTGTTCATAACAATTGTTTTCTTTTGTTTAATTCTTGCTTTCT TTTTTTTTCTTCTCCGCAATTTTTACTATTATACTTAATGCCTT AACATTGTGTATAACAAAAGGAAATATCTCTGAGATACATTA AGTAACTTAAAAAAAAACTTTACACAGTCTGCCTAGTACATT ACTATTTGGAATATATGTGTGCTTATTTGCATATTCATAATCT CCCTACTTTATTTTCTTTTATTTTTAATTGATACATAATCATTA TACATATTTATGGGTTAAAGTGTAATGTTTTAATATGTGTACA CATATTGACCAAATCAGGGTAATTTTGCATTTGTAATTTTAA AAAATGCTTTCTTCTTTTAATATACTTTTTTGTTTATCTTATTT CTAATACTTTCCCTAATCTCTTTCTTTCAGGGCAATAATGATA CAATGTATCATGCCTCTTTGCACCATTCTAAAGAATAACAGT GATAATTTCTGGGTTAAGGCAATAGCAATATCTCTGCATATA AATATTTCTGCATATAAATTGTAACTGATGTAAGAGGTTTCA TATTGCTAATAGCAGCTACAATCCAGCTACCATTCTGCTTTTA TTTTATGGTTGGGATAAGGCTGGATTATTCTGAGTCCAAGCT AGGCCCTTTTGCTAATCATGTTCATACCTCTTATCTTCCTCCC ACAGCTCCTGGGCAACGTGCTGGTCTGTGTGCTGGCCCATCA CTTTGGCAAAGAATTCACCCCACCAGTGCAGGCTGCCTATCA GAAAGTGGTGGCTGGTGTGGCTAATGCCCTGGCCCACAAGTA TCACTAAGCTCGCTTTCTTGCTGTCCAATTTCTATTAAAGGTT CCTTTGTTCCCTAAGTCCAACTACTAAACTGGGGGATATTAT GAAGGGCCTTGAGCATCTGGATTCTGCCTAATAAAAAACATT TATTTTCATTGCAATGATGTATTTAAATTATTTCTGAATATTT TACTAAAAAGGGAATGTGGGAGGTCAGTGCATTTAAAACAT AAAGAAATGAAGAGCTAGTTCAAACCTTGGGAAAATACACT ATATCTTAAACTCCATGAAAGAAGGTGAGGCTGCAAACAGC TAATGCACATTGGCAACAGCCCCTGATGCATATGCCTTATTC ATCCCTCAGAAAAGGATTCAAGTAGAGGCTTGATTTGGAGGT TAAAGTTTTGCTATGCTGTATTTTACATTACTTATTGTTTTAG CTGTCCTCATGAATGTCTTTTCACTACCCATTTGCTTATCCTG CATCTCTCAGCCTTGACTCCACTCAGTTCTCTTGCTTAGAGAT ACCACCTTTCCCCTGAAGTGTTCCTTCCATGTTTTACGGCGAG ATGGTTTCTCCTCGCCTGGCCACTCAGCCTTAGTTGTCTCTGT TGTCTTATAGAGGTCTACTTGAAGAAGGAAAAACAGGGGTC ATGGTTTGACTGTCCTGTGAGCCCTTCTTCCCTGCCTCCCCCA CTCACAGTGACCCGGAATCTGCAGTGCTAGTCTCCCGGAACT ATCACTCTTTCACAGTCTGCTTTGGAAGGACTGGGCTTAGTA TGAAAAGTTAGGACTGAGAAGAATTTGAAAGGCGGCTTTTTG TAGCTTGATATTCACTACTGTCTTATTACCCTGTCGGTAACCA CGTGCGGCCGAGGCTGCAGCGTCGTCCTCCCTAGGAACCCCT |

-continued

Sequence Listing

| SEQ ID NO: | Identifier | Name/ Description | Sequence |
|---|---|---|---|
| | | | AGTGATGGAGTTGGCCACTCCCTCTCTGCGCGCTCGCTCGCT<br>CACTGAGGCCGGGCGACCAAAGGTCGCCCGACGCCCGGGCT<br>TTGCCCGGGCGGCCTCAGTGAGCGAGCGAGCGCGCAGCTGC<br>CTGCAGGGGCGCCTGATGCGGTATTTTCTCCTTACGCATCTGT<br>GCGGTATTTCACACCGCATACGTCAAAGCAACCATAGTACGC<br>GCCCTGTAGCGGCGCATTAAGCGCGGCGGGTGTGGTGGTTAC<br>GCGCAGCGTGACCGCTACACTTGCCAGCGCCCTAGCGCCCGC<br>TCCTTTCGCTTTCTTCCCTTCCTTTCTCGCCACGTTCGCCGGCT<br>TTCCCCGTCAAGCTCTAAATCGGGGGCTCCCTTTAGGGTTCC<br>GATTTAGTGCTTTACGGCACCTCGACCCCAAAAAACTTGATT<br>TGGGTGATGGTTCACGTAGTGGGCCATCGCCCTGATAGACGG<br>TTTTTCGCCCTTTGACGTTGGAGTCCACGTTCTTTAATAGTGG<br>ACTCTTGTTCCAAACTGGAACAACACTCAACCCTATCTCGGG<br>CTATTCTTTTGATTTATAAGGGATTTTGCCGATTTCGGCCTAT<br>TGGTTAAAAAATGAGCTGATTTAACAAAAATTTAACGCGAAT<br>TTTAACAAAATATTAACGTTTACAATTTTATGGTGCACTCTCA<br>GTACAATCTGCTCTGATGCCGCATAGTTAAGCCAGCCCCGAC<br>ACCCGCCAACACCCGCTGACGCGCCCTGACGGGCTTGTCTGC<br>TCCCGGCATCCGCTTACAGACAAGCTGTGACCGTCTCCGGGA<br>GCTGCATGTGTCAGAGGTTTTCACCGTCATCACCGAAACGCG<br>CGAGACGAAAGGGCCTCGTGATACGCCTATTTTTATAGGTTA<br>ATGTCATGAACAATAAAACTGTCTGCTTACATAAACAGTAAT<br>ACAAGGGGTGTTATGAGCCATATTCAACGGGAAACGTCGAG<br>GCCGCGATTAAATTCCAACATGGATGCTGATTTATATGGGTA<br>TAAATGGGCTCGCGATAATGTCGGGCAATCAGGTGCGACAA<br>TCTATCGCTTGTATGGGAAGCCCGATGCGCCAGAGTTGTTTC<br>TGAAACATGGCAAAGGTAGCGTTGCCAATGATGTTACAGAT<br>GAGATGGTCAGACTAAACTGGCTGACGGAATTTATGCCTCTT<br>CCGACCATCAAGCATTTTATCCGTACTCCTGATGATGCATGG<br>TTACTCACCACTGCGATCCCCGGAAAAACAGCATTCCAGGTA<br>TTAGAAGAATATCCTGATTCAGGTGAAAATATTGTTGATGCG<br>CTGGCAGTGTTCCTGCGCCGGTTGCATTCGATTCCTGTTTGTA<br>ATTGTCCTTTTAACAGCGATCGCGTATTTCGTCTCGCTCAGGC<br>GCAATCACGAATGAATAACGGTTTGGTTGATGCGAGTGATTT<br>TGATGACGAGCGTAATGGCTGGCCTGTTGAACAAGTCTGGAA<br>AGAAATGCATAAACTTTTGCCATTCTCACCGGATTCAGTCGT<br>CACTCATGGTGATTTCTCACTTGATAACCTTATTTTTGACGAG<br>GGGAAATTAATAGGTTGTATTGATGTTGGACGAGTCGGAATC<br>GCAGACCGATACCAGGATCTTGCCATCCTATGGAACTGCCTC<br>GGTGAGTTTTCTCCTTCATTACAGAAACGGCTTTTTCAAAAAT<br>ATGGTATTGATAATCCTGATATGAATAAATTGCAGTTTCATTT<br>GATGCTCGATGAGTTTTTCTAATCTCATGACCAAAATCCCTTA<br>ACGTGAGTTTTCGTTCCACTGAGCGTCAGACCCCGTAGAAAA<br>GATCAAAGGATCTTCTTGAGATCCTTTTTTTCTGCGCGTAATC<br>TGCTGCTTGCAAACAAAAAAACCACCGCTACCAGCGGTGGTT<br>TGTTTGCCGGATCAAGAGCTACCAACTCTTTTTCCGAAGGTA<br>ACTGGCTTCAGCAGAGCGCAGATACCAAATACTGTCCTTCTA<br>GTGTAGCCGTAGTTAGGCCACCACTTCAAGAACTCTGTAGCA<br>CCGCCTACATACCTCGCTCTGCTAATCCTGTTACCAGTGGCTG<br>CTGCCAGTGGCGATAAGTCGTGTCTTACCGGGTTGGACTCAA<br>GACGATAGTTACCGGATAAGGCGCAGCGGTCGGGCTGAACG<br>GGGGGTTCGTGCACACAGCCCAGCTTGGAGCGAACGACCTA<br>CACCGAACTGAGATACCTACAGCGTGAGCTATGAGAAAGCG<br>CCACGCTTCCCGAAGGGAGAAAGGCGGACAGGTATCCGGTA<br>AGCGGCAGGGTCGGAACAGGAGAGCGCACGAGGGAGCTTCC<br>AGGGGGAAACGCCTGGTATCTTTATAGTCCTGTCGGGTTTCG<br>CCACCTCTGACTTGAGCGTCGATTTTTGTGATGCTCGTCAGG<br>GGGGCGGAGCCTATGGAAAAACGCCAGCAACGCGGCCTTTT<br>TACGGTTCCTGGCCTTTTGCTGGCCTTTTGCTCACATGT |
| 110 | Donor template | HBB Locus LHA to RHA (AAV.307) | CTTGCTTTGACAATTTTGGTCTTTCAGAATACTATAAATATAA<br>CCTATATTATAATTTCATAAAGTCTGTGCATTTTCTTTGACCC<br>AGGATATTTGCAAAAGACATATTCAAACTTCCGCAGAACACT<br>TTATTTCACATATACATGCCTCTTATATCAGGGATGTGAAAC<br>AGGGTCTTGAAAACTGTCTAAATCTAAAACAATGCTAATGCA<br>GGTTTAAATTTAATAAAATAAAATCCAAAATCTAACAGCCAA<br>GTCAAATCTGCATGTTTTAACATTTAAAATATTTTAAAGACG<br>TCTTTTCCCAGGATTCAACATGTGAAATCTTTTCTCAGGGATA<br>CACGTGTGCCTAGATCCTCATTGCTTTAGTTTTTTACAGAGGA<br>ATGAATATAAAAAGAAAATACTTAAATTTTATCCCTCTTACC<br>TCTATAATCATACATAGGCATAATTTTTTAACCTAGGCTCCA<br>GATAGCCATAGAAGAACCAAACACTTTCTGCGTGTGTGAGA<br>ATAATCAGAGTGAGATTTTTTCACAAGTACCTGATGAGGGTT<br>GAGACAGGTAGAAAAAGTGAGAGATCTCTATTTATTTAGCA |

-continued

Sequence Listing

| SEQ ID NO: | Identifier | Name/ Description | Sequence |
|---|---|---|---|
| | | | ATAATAGAGAGAAAGCATTTAAGAGAATAAAGCAATGGAAATA AGAAATTTGTAAATTTCCTTCTGATAACTAGAAATAGAGGAT CCAGTTTCTTTTGGTTAACCTAAATTTTATTTCATTTTATTGTT TTATTTTATTTTATTTTATTTTATTTTGTGTAATCGTAGTTTCA GAGTGTTAGAGCTGAAAGGAAGAAGTAGGAGAAACATGCAA AGTAAAAGTATAACACTTTCCTTACTAAACCGACATGGGTTT CCAGGTAGGGGCAGGATTCAGGATGACTGACAGGGCCCTTA GGGAACACTGAGACCCTACGCTGACCTCATAAATGCTTGCTA CCTTTGCTGTTTTAATTACATCTTTTAATAGCAGGAAGCAGA ACTCTGCACTTCAAAAGTTTTTCCTCACCTGAGGAGTTAATTT AGTACAAGGGGAAAAAGTACAGGGGGATGGGAGAAAGGCG ATCACGTTGGGAAGCTATAGAGAAAGAAGAGTAAATTTTAG TAAAGGAGGTTTAAACAAACAAAATATAAAGAGAAATAGGA ACTTGAATCAAGGAAATGATTTTAAAACGCAGTATTCTTAGT GGACTAGAGGAAAAAAATAATCTGAGCCAAGTAGAAGACCT TTTCCCCTCCTACCCCTACTTTCTAAGTCACAGAGGCTTTTTG TTCCCCCAGACACTCTTGCAGATTAGTCCAGGCAGAAACAGT TAGATGTCCCCAGTTAACCTCCTATTTGACACCACTGATTACC CCATTGATAGTCACACTTTGGGTTGTAAGTGACTTTTTATTTA TTTGTATTTTTGACTGCATTAAGAGGTCTCTAGTTTTTTATCT CTTGTTTCCCAAAACCTAATAAGTAACTAATGCACAGAGCAC ATTGATTTGTATTTATTCTATTTTTAGACATAATTTATTAGCA TGCATGAGCAAATTAAGAAAAACAACAACAAATGAATGCAT ATATATGTATATGTATGTGTGTATATATACACACATATATAT ATATATTTTTTCTTTTCTTACCAGAAGGTTTTAATCCAAATAA GGAGAAGATATGCTTAGAACCGAGGTAGAGTTTTCATCCATT CTGTCCTGTAAGTATTTTGCATATTCTGGAGACGCAGGAAGA GATCCATCTACATATCCCAAAGCTGAATTATGGTAGACAAAA CTCTTCCACTTTTAGTGCATCAACTTCTTATTTGTGTAATAAG AAAATTGGGAAAACGATCTTCAATATGCTTACCAAGCTGTGA TTCCAAATATTACGTAAATACACTTGCAAAGGAGGATGTTTT TAGTAGCAATTTGTACTGATGGTATGGGGCCAAGAGATATAT CTTAGAGGGAGGGCTGAGGGTTTGAAGTCCAACTCCTAAGCC AGTGCCAGAAGAGCCAAGGACAGGTACGGCTGTCATCACTT AGACCTCACCCTGTGGAGCCACACCCTAGGGTTGGCCAATCT ACTCCCAGGAGCAGGGAGGGCAGGAGCCAGGGCTGGGCATA AAAGTCAGGGCAGAGCCATCTATTGCTTACATTTGCTTCTGA CACAACTGTGTTCACTAGCAACCTCAAACAGACACCATGGTG CATCTGACTCCTGTCGAAAAATCCGCTGTCACCGCCCTCTGG GGCAAGGTGAACGTGGATGAAGTTGGTGGTGAGGCCCTGGG CAGGTTGGTATCAAGGTTACAAGACAGGTTTAAGGAGACCA ATAGAAACTGGGCATGTGGAGACAGAGAAGACTCTTGGGTT TCTGATAGGCACTGACTCTCTCTGCCTATTGGTCTATTTTCCC ACCCTTAGGCTGCTGGTGGTCTACCCTTGGACCCAGAGGTTC TTTGAGTCCTTTGGGGATCTGTCCACTCCTGATGCTGTTATGG GCAACCCTAAGGTGAAGGCTCATGGCAAGAAAGTGCTCGGT GCCTTTAGTGATGGCCTGGCTCACCTGGACAACCTCAAGGGC ACCTTTGCCACACTGAGTGAGCTGCACTGTGACAAGCTGCAC GTGGATCCTGAGAACTTCAGGGTGAGTCTATGGGACGCTTGA TGTTTTCTTTCCCCTTCTTTTCTATGGTTAAGTTCATGTCATAG GAAGGGGATAAGTAACAGGGTACAGTTTAGAATGGGAAACA GACGAATGATTGCATCAGTGTGGAAGTCTCAGGATCGTTTTA GTTTCTTTTATTTGCTGTTCATAACAATTGTTTTCTTTTGTTTA ATTCTTGCTTTCTTTTTTTTTCTTCTCCGCAATTTTTACTATTA TACTTAATGCCTTAACATTGTGTATAACAAAAGGAAATATCT CTGAGATACATTAAGTAACTTAAAAAAAAACTTTACACAGTC TGCCTAGTACATTACTATTTGGAATATATGTGTGCTTATTTGC ATATTCATAATCTCCCTACTTTATTTTCTTTTATTTTTAATTGA TACATAATCATTATACATATTTATGGGTTAAAGTGTAATGTTT TAATATGTGTACACATATTGACCAAATCAGGGTAATTTTGCA TTTGTAATTTTAAAAAATGCTTTCTTCTTTTAATATACTTTTTT GTTTATCTTATTTCTAATACTTTCCCTAATCTCTTTCTTTCAGG GCAATAATGATACAATGTATCATGCCTCTTTGCACCATTCTA AAGAATAACAGTGATAATTTCTGGGTTAAGGCAATAGCAAT ATCTCTGCATATAAATATTTCTGCATATAAATTGTAACTGATG TAAGAGGTTTCATATTGCTAATAGCAGCTACAATCCAGCTAC CATTCTGCTTTTATTTTATGGTTGGGATAAGGCTGGATTATTC TGAGTCCAAGCTAGGCCCTTTTGCTAATCATGTTCATACCTCT TATCTTCCTCCCACAGCTCCTGGGCAACGTGCTGGTCTGTGTG CTGGCCCATCACTTTGGCAAAGAATTCACCCCACCAGTGCAG GCTGCCTATCAGAAAGTGGTGGCTGGTGTGGCTAATGCCCTG GCCCACAAGTATCACTAAGCTCGCTTTCTTGCTGTCCAATTTC TATTAAAGGTTCCTTTGTTCCCTAAGTCCAACTACTAAACTGG GGGATATTATGAAGGGCCTTGAGCATCTGGATTCTGCCTAAT |

-continued

Sequence Listing

| SEQ ID NO: | Identifier | Name/ Description | Sequence |
| --- | --- | --- | --- |
| | | | AAAAAACATTTATTTTCATTGCAATGATGTATTTAAATTATTT<br>CTGAATATTTTACTAAAAAGGGAATGTGGGAGGTCAGTGCAT<br>TTAAAACATAAAGAAATGAAGAGCTAGTTCAAACCTTGGGA<br>AAATACACTATATCTTAAACTCCATGAAAGAAGGTGAGGCTG<br>CAAACAGCTAATGCACATTGGCAACAGCCCCTGATGCATATG<br>CCTTATTCATCCCTCAGAAAAGGATTCAAGTAGAGGCTTGAT<br>TTGGAGGTTAAAGTTTTGCTATGCTGTATTTTACATTACTTAT<br>TGTTTTAGCTGTCCTCATGAATGTCTTTTCACTACCCATTTGC<br>TTATCCTGCATCTCTCAGCCTTGACTCCACTCAGTTCTCTTGC<br>TTAGAGATACCACCTTTCCCCTGAAGTGTTCCTTCCATGTTTT<br>ACGGCGAGATGGTTTCTCCTCGCCTGGCCACTCAGCCTTAGT<br>TGTCTCTGTTGTCTTATAGAGGTCTACTTGAAGAAGGAAAAA<br>CAGGGGTCATGGTTTGACTGTCCTGTGAGCCCTTCTTCCCTGC<br>CTCCCCCACTCACAGTGACCCGGAATCTGCAGTGCTAGTCTC<br>CCGGAACTATCACTCTTTCACAGTCTGCTTTGGAAGGACTGG<br>GCTTAGTATGAAAAGTTAGGACTGAGAAGAATTTGAAAGGC<br>GGCTTTTTGTAGCTTGATATTCACTACTGTCTTATTACCCTGT<br>C |
| ill | Donor template | Full AAV (AAV.307) | CCTGCAGGCAGCTGCGCGCTCGCTCGCTCACTGAGGCCGCCC<br>GGGCAAAGCCCGGGCGTCGGGCGACCTTTGGTCGCCCGGCCT<br>CAGTGAGCGAGCGAGCGCGCAGAGAGGGAGTGGCCAACTCC<br>ATCACTAGGGGTTCCTGCGGCCGCACGCGTCTTGCTTTGACA<br>ATTTTGGTCTTTCAGAATACTATAAATATAACCTATATTATAA<br>TTTCATAAAGTCTGTGCATTTTCTTTGACCCAGGATATTTGCA<br>AAAGACATATTCAAACTTCCGCAGAACACTTTATTTCACATA<br>TACATGCCTCTTATATCAGGGATGTGAAACAGGGTCTTGAAA<br>ACTGTCTAAATCTAAAACAATGCTAATGCAGGTTTAAATTTA<br>ATAAAATAAAATCCAAAATCTAACAGCCAAGTCAAATCTGC<br>ATGTTTTAACATTTAAAATATTTTAAAGACGTCTTTTCCCAGG<br>ATTCAACATGTGAAATCTTTTCTCAGGGATACACGTGTGCCT<br>AGATCCTCATTGCTTTAGTTTTTTACAGAGGAATGAATATAA<br>AAAGAAAATACTTAAATTTTATCCCTCTTACCTCTATAATCAT<br>ACATAGGCATAATTTTTTAACCTAGGCTCCAGATAGCCATAG<br>AAGAACCAAACACTTTCTGCGTGTGTGAGAATAATCAGAGTG<br>AGATTTTTTCACAAGTACCTGATGAGGGTTGAGACAGGTAGA<br>AAAAGTGAGAGATCTCTATTTATTTAGCAATAATAGAGAAAG<br>CATTTAAGAGAATAAAGCAATGGAAATAAGAAATTTGTAAA<br>TTTCCTTCTGATAACTAGAAATAGAGGATCCAGTTTCTTTTGG<br>TTAACCTAAATTTTATTTCATTTTATTGTTTTATTTTATTTTAT<br>TTTATTTTATTTTGTGTAATCGTAGTTTCAGAGTGTTAGAGCT<br>GAAAGGAAGAAGTAGGAGAAACATGCAAAGTAAAAGTATA<br>ACACTTTCCTTACTAAACCGACATGGGTTTCCAGGTAGGGGC<br>AGGATTCAGGATGACTGACAGGGCCCTTAGGGAACACTGAG<br>ACCCTACGCTGACCTCATAAATGCTTGCTACCTTTGCTGTTTT<br>AATTACATCTTTTAATAGCAGGAAGCAGAACTCTGCACTTCA<br>AAAGTTTTTCCTCACCTGAGGAGTTAATTTAGTACAAGGGGA<br>AAAAGTACAGGGGGATGGGAGAAAGGCGATCACGTTGGGAA<br>GCTATAGAGAAAGAAGAGTAAATTTTAGTAAAGGAGGTTTA<br>AACAAACAAAATATAAAGAGAAATAGGAACTTGAATCAAGG<br>AAATGATTTTAAAACGCAGTATTCTTAGTGGACTAGAGGAAA<br>AAAATAATCTGAGCCAAGTAGAAGACCTTTTCCCCTCCTACC<br>CCTACTTTCTAAGTCACAGAGGCTTTTTGTTCCCCCAGACACT<br>CTTGCAGATTAGTCCAGGCAGAAACAGTTAGATGTCCCCAGT<br>TAACCTCCTATTTGACACCACTGATTACCCCATTGATAGTCAC<br>ACTTTGGGTTGTAAGTGACTTTTTATTTATTTGTATTTTTGACT<br>GCATTAAGAGGTCTCTAGTTTTTTATCTCTTGTTTCCCAAAAC<br>CTAATAAGTAACTAATGCACAGAGCACATTGATTTGTATTTA<br>TTCTATTTTTAGACATAATTTATTAGCATGCATGAGCAAATTA<br>AGAAAAACAACAACAAATGAATGCATATATATGTATATGTA<br>TGTGTGTATATATACACACATATATATATATATTTTTTCTTTT<br>CTTACCAGAAGGTTTTAATCCAAATAAGGAGAAGATATGCTT<br>AGAACCGAGGTAGAGTTTTCATCCATTCTGTCCTGTAAGTAT<br>TTTGCATATTCTGGAGACGCAGGAAGAGATCCATCTACATAT<br>CCCAAAGCTGAATTATGGTAGACAAAACTCTTCCACTTTTAG<br>TGCATCAACTTCTTATTTGTGTAATAAGAAAATTGGGAAAAC<br>GATCTTCAATATGCTTACCAAGCTGTGATTCCAAATATTACG<br>TAAATACACTTGCAAAGGAGGATGTTTTTAGTAGCAATTTGT<br>ACTGATGGTATGGGGCCAAGAGATATATCTTAGAGGGAGGG<br>CTGAGGGTTTGAAGTCCAACTCCTAAGCCAGTGCCAGAAGA<br>GCCAAGGACAGGTACGGCTGTCATCACTTAGACCTCACCCTG<br>TGGAGCCACACCCTAGGGTTGGCCAATCTACTCCCAGGAGCA<br>GGGAGGGCAGGAGCCAGGGCTGGGCATAAAGTCAGGGCA<br>GAGCCATCTATTGCTTACATTTGCTTCTGACACAACTGTGTTC |

-continued

Sequence Listing

| SEQ ID NO: | Identifier | Name/ Description | Sequence |
|---|---|---|---|
| | | | ACTAGCAACCTCAAACAGACACCATGGTGCATCTGACTCCTG TCGAAAAATCCGCTGTCACCGCCCTCTGGGGCAAGGTGAACG TGGATGAAGTTGGTGGTGAGGCCCTGGGCAGGTTGGTATCAA GGTTACAAGACAGGTTTAAGGAGACCAATAGAAACTGGGCA TGTGGAGACAGAGAAGACTCTTGGGTTTCTGATAGGCACTGA CTCTCTCTGCCTATTGGTCTATTTTCCCACCCTTAGGCTGCTG GTGGTCTACCCTTGGACCCAGAGGTTCTTTGAGTCCTTTGGG GATCTGTCCACTCCTGATGCTGTTATGGGCAACCCTAAGGTG AAGGCTCATGGCAAGAAAGTGCTCGGTGCCTTTAGTGATGGC CTGGCTCACCTGGACAACCTCAAGGGCACCTTTGCCACACTG AGTGAGCTGCACTGTGACAAGCTGCACGTGGATCCTGAGAA CTTCAGGGTGAGTCTATGGGACGCTTGATGTTTTCTTTCCCCT TCTTTTCTATGGTTAAGTTCATGTCATAGGAAGGGGATAAGT AACAGGGTACAGTTTAGAATGGGAAACAGACGAATGATTGC ATCAGTGTGGAAGTCTCAGGATCGTTTTAGTTTCTTTTATTTG CTGTTCATAACAATTGTTTTCTTTTGTTTAATTCTTGCTTTCTT TTTTTTTCTTCTCCGCAATTTTTACTATTATACTTAATGCCTTA ACATTGTGTATAACAAAAGGAAATATCTCTGAGATACATTAA GTAACTTAAAAAAAAACTTTACACAGTCTGCCTAGTACATTA CTATTTGGAATATATGTGTGCTTATTTGCATATTCATAATCTC CCTACTTTATTTTCTTTTATTTTTAATTGATACATAATCATTAT ACATATTTATGGGTTAAAGTGTAATGTTTTAATATGTGTACA CATATTGACCAAATCAGGGTAATTTTGCATTTGTAATTTTAA AAAATGCTTTCTTCTTTTAATATACTTTTTTGTTTATCTTATTT CTAATACTTTCCCTAATCTCTTTCTTTCAGGGCAATAATGATA CAATGTATCATGCCTCTTTGCACCATTCTAAAGAATAACAGT GATAATTTCTGGGTTAAGGCAATAGCAATATCTCTGCATATA AATATTTCTGCATATAAATTGTAACTGATGTAAGAGGTTTCA TATTGCTAATAGCAGCTACAATCCAGCTACCATTCTGCTTTTA TTTTATGGTTGGGATAAGGCTGGATTATTCTGAGTCCAAGCT AGGCCCTTTTGCTAATCATGTTCATACCTCTTATCTTCCTCCC ACAGCTCCTGGGCAACGTGCTGGTCTGTGTGCTGGCCCATCA CTTTGGCAAAGAATTCACCCCACCAGTGCAGGCTGCCTATCA GAAAGTGGTGGCTGGTGTGGCTAATGCCCTGGCCCACAAGTA TCACTAAGCTCGCTTTCTTGCTGTCCAATTTCTATTAAAGGTT CCTTTGTTCCCTAAGTCCAACTACTAAACTGGGGGATATTAT GAAGGGCCTTGAGCATCTGGATTCTGCCTAATAAAAAACATT TATTTTCATTGCAATGATGTATTTAAATTATTTCTGAATATTT TACTAAAAAGGGAATGTGGGAGGTCAGTGCATTTAAAACAT AAAGAAATGAAGAGCTAGTTCAAACCTTGGGAAAATACACT ATATCTTAAACTCCATGAAAGAAGGTGAGGCTGCAAACAGC TAATGCACATTGGCAACAGCCCCTGATGCATATGCCTTATTC ATCCCTCAGAAAAGGATTCAAGTAGAGGCTTGATTTGGAGGT TAAAGTTTTGCTATGCTGTATTTTACATTACTTATTGTTTTAG CTGTCCTCATGAATGTCTTTTCACTACCCATTTGCTTATCCTG CATCTCTCAGCCTTGACTCCACTCAGTTCTCTTGCTTAGAGAT ACCACCTTTCCCCTGAAGTGTTCCTTCCATGTTTTACGGCGAG ATGGTTTCTCCTCGCCTGGCCACTCAGCCTTAGTTGTCTCTGT TGTCTTATAGAGGTCTACTTGAAGAAGGAAAAACAGGGGTC ATGGTTTGACTGTCCTGTGAGCCCTTCTTCCCTGCCTCCCCCA CTCACAGTGACCCGGAATCTGCAGTGCTAGTCTCCCGGAACT ATCACTCTTTCACAGTCTGCTTTGGAAGGACTGGGCTTAGTA TGAAAAGTTAGGACTGAGAAGAATTTGAAAGGCGGCTTTTTG TAGCTTGATATTCACTACTGTCTTATTACCCTGTCGGTAACCA CGTGCGGCCGAGGCTGCAGCGTCGTCCTCCCTAGGAACCCCT AGTGATGGAGTTGGCCACTCCCTCTCTGCGCGCTCGCTCGCT CACTGAGGCCGGGCGACCAAAGGTCGCCCGACGCCCGGGCT TTGCCCGGGCGGCCTCAGTGAGCGAGCGAGCGCGCAGCTGC CTGCAGGGGCGCCTGATGCGGTATTTTCTCCTTACGCATCTGT GCGGTATTTCACACCGCATACGTCAAAGCAACCATAGTACGC GCCCTGTAGCGGCGCATTAAGCGCGGCGGGTGTGGTGGTTAC GCGCAGCGTGACCGCTACACTTGCCAGCGCCCTAGCGCCCGC TCCTTTCGCTTTCTTCCCTTCCTTTCTCGCCACGTTCGCCGGCT TTCCCCGTCAAGCTCTAAATCGGGGGCTCCCTTTAGGGTTCC GATTTAGTGCTTTACGGCACCTCGACCCCAAAAAACTTGATT TGGGTGATGGTTCACGTAGTGGGCCATCGCCCTGATAGACGG TTTTTCGCCCTTTGACGTTGGAGTCCACGTTCTTTAATAGTGG ACTCTTGTTCCAAACTGGAACAACACTCAACCCTATCTCGGG CTATTCTTTTGATTTATAAGGGATTTTGCCGATTTCGGCCTAT TGGTTAAAAAATGAGCTGATTTAACAAAAATTTAACGCGAAT TTTAACAAAATATTAACGTTTACAATTTTATGGTGCACTCTCA GTACAATCTGCTCTGATGCCGCATAGTTAAGCCAGCCCCGAC ACCCGCCAACACCCGCTGACGCGCCCTGACGGGCTTGTCTGC TCCCGGCATCCGCTTACAGACAAGCTGTGACCGTCTCCGGGA |

-continued

Sequence Listing

| SEQ ID NO: | Identifier | Name/ Description | Sequence |
|---|---|---|---|
| | | | GCTGCATGTGTCAGAGGTTTTCACCGTCATCACCGAAACGCG CGAGACGAAAGGGCCTCGTGATACGCCTATTTTTATAGGTTA ATGTCATGAACAATAAAACTGTCTGCTTACATAAACAGTAAT ACAAGGGGTGTTATGAGCCATATTCAACGGGAAACGTCGAG GCCGCGATTAAATTCCAACATGGATGCTGATTTATATGGGTA TAAATGGGCTCGCGATAATGTCGGGCAATCAGGTGCGACAA TCTATCGCTTGTATGGGAAGCCCGATGCGCCAGAGTTGTTTC TGAAACATGGCAAAGGTAGCGTTGCCAATGATGTTACAGAT GAGATGGTCAGACTAAACTGGCTGACGGAATTTATGCCTCTT CCGACCATCAAGCATTTTATCCGTACTCCTGATGATGCATGG TTACTCACCACTGCGATCCCCGGAAAAACAGCATTCCAGGTA TTAGAAGAATATCCTGATTCAGGTGAAAATATTGTTGATGCG CTGGCAGTGTTCCTGCGCCGGTTGCATTCGATTCCTGTTTGTA ATTGTCCTTTTAACAGCGATCGCGTATTTCGTCTCGCTCAGGC GCAATCACGAATGAATAACGGTTTGGTTGATGCGAGTGATTT TGATGACGAGCGTAATGGCTGGCCTGTTGAACAAGTCTGGAA AGAAATGCATAAACTTTTGCCATTCTCACCGGATTCAGTCGT CACTCATGGTGATTTCTCACTTGATAACCTTATTTTTGACGAG GGGAAATTAATAGGTTGTATTGATGTTGGACGAGTCGGAATC GCAGACCGATACCAGGATCTTGCCATCCTATGGAACTGCCTC GGTGAGTTTTCTCCTTCATTACAGAAACGGCTTTTTCAAAAAT ATGGTATTGATAATCCTGATATGAATAAATTGCAGTTTCATTT GATGCTCGATGAGTTTTTCTAATCTCATGACCAAAATCCCTTA ACGTGAGTTTTCGTTCCACTGAGCGTCAGACCCCGTAGAAAA GATCAAAGGATCTTCTTGAGATCCTTTTTTTCTGCGCGTAATC TGCTGCTTGCAAACAAAAAAACCACCGCTACCAGCGGTGGTT TGTTTGCCGGATCAAGAGCTACCAACTCTTTTTCCGAAGGTA ACTGGCTTCAGCAGAGCGCAGATACCAAATACTGTCCTTCTA GTGTAGCCGTAGTTAGGCCACCACTTCAAGAACTCTGTAGCA CCGCCTACATACCTCGCTCTGCTAATCCTGTTACCAGTGGCTG CTGCCAGTGGCGATAAGTCGTGTCTTACCGGGTTGGACTCAA GACGATAGTTACCGGATAAGGCGCAGCGGTCGGGCTGAACG GGGGGTTCGTGCACACAGCCCAGCTTGGAGCGAACGACCTA CACCGAACTGAGATACCTACAGCGTGAGCTATGAGAAAGCG CCACGCTTCCCGAAGGGAGAAAGGCGGACAGGTATCCGGTA AGCGGCAGGGTCGGAACAGGAGAGCGCACGAGGGAGCTTCC AGGGGGAAACGCCTGGTATCTTTATAGTCCTGTCGGGTTTCG CCACCTCTGACTTGAGCGTCGATTTTTGTGATGCTCGTCAGG GGGGCGGAGCCTATGGAAAAACGCCAGCAACGCGGCCTTTT TACGGTTCCTGGCCTTTTGCTGGCCTTTTGCTCACATGT |
| 112 | Donor template | 5' ITR | CCTGCAGGCAGCTGCGCGCTCGCTCGCTCACTGAGGCCGCCC GGGCAAAGCCCGGGCGTCGGGCGACCTTTGGTCGCCCGGCCT CAGTGAGCGAGCGAGCGCGCAGAGAGGGAGTGGCCAACTCC ATCACTAGGGGTTCCT |

The invention claimed is:

1. A method for homology directed repair (HDR) of a double-strand break (DSB) in a target site in a human beta-globin (HBB) gene in a cell or population of cells, the method comprising contacting the cell or population of cells with:

(a) a *S. pyogenes* Cas9 endonuclease, an mRNA encoding the *S. pyogenes* Cas9 endonuclease, or a recombinant expression vector comprising a nucleotide sequence encoding the *S. pyogenes* Cas9 endonuclease, to generate a double-stranded break (DSB) at the target site in the HBB gene, wherein the *S. pyogenes* Cas9 endonuclease is a high fidelity Cas9 comprising a R691A mutation;

(b) a single guide RNA (sgRNA) targeting the target site in the HBB gene, the sgRNA comprising a spacer sequence corresponding to a target sequence in the HBB gene consisting of SEQ ID NO: 15;

(c) a recombinant vector comprising a nucleic acid, the nucleic acid comprising from 5' to 3' (i) a nucleotide sequence homologous with a region located upstream of the target site in the HBB gene, (ii) a nucleotide sequence homologous with a region of the HBB gene comprising the target site, the nucleotide sequence comprising the nucleotide sequence of SEQ ID NO: 102, and (iii) a nucleotide sequence homologous with a region located downstream of the target site in the HBB gene; and (d) a 53BP1 inhibitor; an inhibitor of DNA-PK; or both;

wherein the recombinant vector of (c) comprises the nucleotide sequence of SEQ ID NO: 98;

wherein the double-strand break (DSB) occurs at the target site in the HBB gene and the nucleic acid comprising the nucleotide sequence of SEQ ID NO: 98 is exchanged with a homologous nucleotide sequence of the HBB gene, thereby correcting an E6V mutation in the HBB gene in the cell or population of cells.

2. A method for correcting an E6V mutation in human beta-globin (HBB) in a cell or population of cells, the method comprising contacting the cell or population of cells comprising an HBB gene encoding the E6V mutation with:

(a) a *S. pyogenes* Cas9 endonuclease, an mRNA encoding the *S. pyogenes* Cas9 endonuclease, or a recombinant expression vector comprising a nucleotide sequence encoding the *S. pyogenes* Cas9 endonuclease to generate a double-stranded break (DSB) at a target site in the HBB gene;

(b) a single guide RNA (sgRNA) targeting the target site in the HBB gene, the sgRNA comprising a spacer sequence corresponding to a target sequence in the HBB gene consisting of SEQ ID NO: 15; and (c) a recombinant vector comprising a nucleic acid, the nucleic acid comprising from 5' to 3' (i) a nucleotide sequence homologous with a region located upstream of a site of the HBB gene encoding the E6V mutation, (ii) a nucleotide sequence which corrects the E6V mutation and is homologous with a site of the HBB gene encoding the E6V mutation, the nucleotide sequence set forth in SEQ ID NO: 102, and (iii) a nucleotide sequence homologous with a region located downstream of the site of the HBB gene encoding the E6V mutation in the HBB gene, (d) a 53BP1 inhibitor; an inhibitor of DNA-PK; or both;

wherein the recombinant vector of (c) comprises the nucleotide sequence of SEQ ID NO: 98; and wherein the double-strand break (DSB) occurs at the target site in the HBB gene and the nucleic acid comprising the nucleotide sequence of SEQ ID NO: 98 is exchanged with a homologous nucleotide sequence of the HBB gene, thereby correcting the E6V mutation in HBB in the cell or population of cells.

3. The method of claim 1, wherein cleavage of one or more predicted off-target sites in the cell or population of cells is reduced relative to a cell or population of cells contacted with a wild-type *S. pyogenes* Cas9.

4. The method of claim 1, wherein the nucleotide sequence of (c)(i) is homologous with a region located upstream of a mutation in the HBB gene that results in an E6V mutation in HBB and the nucleotide sequence of (c)(iii) is homologous with a region located downstream of the mutation in the HBB gene that results in the E6V mutation in HBB.

5. The method of claim 1 wherein the 53BP1 inhibitor and/or the inhibitor of DNA-PK increases HDR of the DSB, relative to HDR in a cell or population of cells without the 53BP1 inhibitor and/or inhibitor of DNA-PK.

6. The method of claim 1, wherein the high fidelity Cas9 endonuclease comprises at least one NLS.

7. The method of claim 1 wherein (i) the 53BP1 inhibitor and/or the inhibitor of DNA-PK increases HDR frequency in the cell population by at least 50% relative to a cell population without the 53BP1 inhibitor and/or the inhibitor of DNA-PK;

(ii) the 53BP1 inhibitor and/or the inhibitor of DNA-PK decreases indel frequency by 2-10 fold in the cell population; or (iii) both (i) and (ii).

8. The method of claim 1 wherein the 53BP1 inhibitor is a 53BP1 binding polypeptide that inhibits 53BP1 recruitment to the DSB in the cell, wherein the 53BP1 binding polypeptide comprises an amino acid sequence selected from a group consisting of: SEQ ID NOs: 70, 74, 77, 80, 83 and 86.

9. The method of claim 1 wherein (i) the 53BP1 inhibitor comprises a nucleic acid or a vector comprising a nucleotide sequence encoding a 53BP1 binding polypeptide that inhibits 53BP1 recruitment to the DSB site in the cell; or (ii) the 53BP1 inhibitor comprises a vector comprising a nucleotide sequence encoding the 53BP1 binding polypeptide, wherein the nucleotide sequence is selected from a group consisting of: SEQ ID NOs: 69, 73, 76, 79, 82, 85 and 88.

10. The method of claim 1 wherein the inhibitor of DNA-PK targets the catalytic subunit of DNA-PK (DNA-PKcs).

11. The method of claim 1 wherein the inhibitor of DNA-PK is Nu7441, Compound 984, or Compound 296.

12. The method of claim 1, wherein (i) the nucleotide sequence of (c)(i) is about 0.2 kb to about 3 kb in length;

(ii) the nucleotide sequence of (c)(iii) is about 0.2 kb to about 3 kb in length; or (iii) both (i) and (ii).

13. The method of claim 1, wherein the nucleotide sequence of (c)(i) and/or the nucleotide sequence of (c)(iii) is about 2.2 kb each.

14. The method of claim 1, wherein the recombinant vector is an AAV vector.

15. The method of claim 14, wherein the AAV vector is about 2.5 kb-4.6 kb in length.

16. The method of claim 14, wherein the AAV vector comprises AAV6.

17. The method of claim 14, wherein the AAV vector comprises 5' and 3' inverted terminal repeats (ITRs) derived from AAV2.

18. The method of claim 14, wherein the AAV vector comprises SEQ ID NO: 105.

19. The method of claim 1, wherein (i) the cell or population of cells is a hematopoietic stem or progenitor cell (HSPC) or a population of HSPCs;

(ii) the cell or population of cells is a CD34 expressing cell or a population of CD34 expressing cells; or (iii) both (i) and (ii).

20. The method of claim 19, wherein the cell or the population of cells is isolated from a tissue sample obtained from a human donor.

21. The method of claim 20, wherein the tissue sample is a peripheral blood sample.

22. The method of claim 20, wherein the human donor has a sickle cell disease.

23. A cell or population of cells generated by the method of claim 1.

* * * * *